United States Patent
Gray et al.

(10) Patent No.: US 12,233,128 B2
(45) Date of Patent: Feb. 25, 2025

(54) DEGRADERS THAT TARGET ALK AND THERAPEUTIC USES THEREOF

(71) Applicant: DANA-FARBER CANCER INSTITUTE, INC., Boston, MA (US)

(72) Inventors: Nathanael S. Gray, Boston, MA (US); John M. Hatcher, Boston, MA (US); Chelsea E. Powell, Brookline, MA (US); Pasi A. Janne, Needham, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 972 days.

(21) Appl. No.: 17/278,093

(22) PCT Filed: Sep. 26, 2019

(86) PCT No.: PCT/US2019/053125
§ 371 (c)(1),
(2) Date: Mar. 19, 2021

(87) PCT Pub. No.: WO2020/069106
PCT Pub. Date: Apr. 2, 2020

(65) Prior Publication Data
US 2022/0409731 A1 Dec. 29, 2022

Related U.S. Application Data

(60) Provisional application No. 62/895,693, filed on Sep. 4, 2019, provisional application No. 62/737,533, filed on Sep. 27, 2018.

(51) Int. Cl.
*A61K 47/54* (2017.01)
*A61K 47/55* (2017.01)

(52) U.S. Cl.
CPC ............ *A61K 47/555* (2017.08); *A61K 47/55* (2017.08)

(58) Field of Classification Search
CPC .............................. A61K 38/43; C07D 487/14
See application file for complete search history.

(56) References Cited

U.S. PATENT DOCUMENTS

2012/0083488 A1 4/2012 Kinoshita et al.

FOREIGN PATENT DOCUMENTS

| EP | 3725771 A1 | 10/2020 |
| EP | 4029499 A1 | 7/2022 |
| WO | 2018064589 A1 | 4/2018 |
| WO | 2019114770 A1 | 6/2019 |

OTHER PUBLICATIONS

Heuckmann et al., "Differential Protein Stability and ALK Inhibitor Sensitivity of EML4-ALK Fusion Variants", Clinical Cancer Research, Sep. 1, 2012, vol. 18, No. 17, pp. 4682-4690.
Lovly et al., "Rationale for Co-Targeting IGF-1R and ALK in ALK Fusion-Positive Lung Cancer", Clinical Cancer Research, Sep. 2014, vol. 20, No. 9, pp. 1027-1034.
Powell et al., "Chemically Induced Degradation of Anaplastic Lymphoma Kinase (ALK)", Journal of Medicinal Chemistry, Apr. 16, 2018, vol. 61, pp. 4249-4255.
Richards et al., "Crystal Structure of EML 1 reveals the basis for Hsp90 Dependence of Oncogenic EML4-ALK by Disruption of an ATypical ß-Propeller Domain" PNAS, Apr. 8, 2014, vol. 111, No. 14, pp. 5195-5200.
Taipale et al., "Quantitative Analysis of Hsp90-Client Interactions Reveals Principles of Substrate Recognition", Cell, Aug. 31, 2012, vol. 150, No. 5, pp. 987-1001.
Yan et al., "Discovery of a PROTAC Targeting ALK with in Vivo Activity", European Journal of Medicinal Chemistry, 2020, pp. 1-29.
Zhang et al., "Proteolysis TargetingChimeras (PROTACs) of Anaplastic Lymphoma Kinase (ALK)", European Journal of Medicinal Chemistry, Mar. 27, 2018, vol. 151, pp. 304-314.

*Primary Examiner* — Kamal A Saeed
(74) *Attorney, Agent, or Firm* — ArentFox Schiff LLP; Daniel W. Clarke; Shawn P. Foley

(57) ABSTRACT

Disclosed are bispecific compounds (degraders) that target ALK for degradation. Also disclosed are pharmaceutical compositions containing the degraders and methods of using the compounds to treat diseases and disorders characterized or mediated by aberrant ALK activity.

7 Claims, 7 Drawing Sheets

DEGRADERS THAT TARGET ALK AND THERAPEUTIC USES THEREOF

RELATED APPLICATIONS

This application is a national stage application, filed under 35 U.S.C. § 371, of International Application No. PCT/US2019/053125, filed Sep. 26, 2019, which claims the benefit of priority under 35 U.S.C. § 119(e) to U.S. Provisional Application No. 62/737,533, filed Sep. 27, 2018 and U.S. Provisional Application No. 62/895,693, filed Sep. 4, 2019, the entire contents of each of which are incorporated herein by reference in their entirety.

GOVERNMENT LICENSE RIGHTS

This invention was made with government support under grant number R01 CA136851-08 awarded by the National Institutes of Health and under grant number 1F31 CA210619-01A1 awarded by the National Institutes of Health. The government has certain rights in the invention.

BACKGROUND OF THE INVENTION

Anaplastic lymphoma kinase (ALK) is a member of the insulin receptor tyrosine kinase family (RTK). Other members of this family include α- and β-type platelet-derived growth factor (PDGF) receptors, epidermal growth factor (EGF) receptor, human epidermal growth factor receptor 2 (HER2)/neu, insulin and insulin like growth factor 1 (IGF-1) receptors. At an amino acid sequence level, ALK is most closely related to members such as Ros-1, leucocyte tyrosine kinase, the insulin receptor and cMet (hepatic growth factor receptor). As with all members of this gene family, it possesses an extracellular ligand binding domain, a transmembrane spanning sequence, and an intracellular kinase catalytic region/signaling domain.

The RTK family of receptors regulate cellular growth; they may also trigger neoplastic transformation when they are mutated, translocated, or otherwise expressed aberrantly (Orscheschek et al., Lancet 345(8942):87-90 (1995); Roskoski et al., Pharmacol. Res. 68(1):68-94 (2013); Ullrich et al., Cell 61(2):203-212 (1990)). Multiple mutations involving the ALK gene have been implicated in the pathogenesis of several cancers, including, for example, anaplastic large cell lymphoma (ALCL), rhabdomyosarcoma, inflammatory myofibroblastic pseudo tumor, neuro-blastoma and non-small cell lung cancer (NSCLC).

Deregulation of ALK was first identified in ALCL, a subtype of non-Hodgkin's lymphoma (Lebeau et al., Leukemia 3(12):866-870 (1989)). The deregulation of ALK was a result of a t(2;5)(p23;q35) chromosomal translocation. The altered form of the ALK gene encodes a fusion of nucleophosmin (NPM) to a truncated form of ALK—a chimeric receptor tyrosine kinase (RTK) that is de-regulated and constitutively activated leading to an "oncogene-addicted" state.

Aberrant ALK activity has also been identified in connection with non-small cell lung cancer (NSCLC) (Soda et al., Nature 448(7153):561-63 (2007)). Here, a mutation in ALK, which arises from inv(2)(p21p23), leads to the fusion of the echinoderm microtubule-associated protein like-4 (EML4) gene with the ALK gene. EML4 is a member of the EMAP-like (EML) protein family and plays an important role in the correct formation of microtubules which is a critical step in the cell growth cycle (Inamura et al., J. Thorac. Oncol. 3(1):13-17 (2008)). The EML4-ALK gene expresses an EML4-ALK fusion protein that exhibits abnormal kinase activity and which has been shown to play a pivotal role in the malignant transformation of susceptible lung parenchyma (Mano et al., Cancer Sci. 99(12):2349-2355 (2008)). Lung cancers with ALK rearrangements are highly sensitive to ALK tyrosine kinase inhibition, further underscoring the notion that such cancers are addicted to ALK kinase activity.

There are currently five FDA approved kinase inhibitors for the treatment of ALK-positive NSCLC: crizotinib, ceritinib (LDK378), alectinib, brigatinib, and lorlatinib. ALK-positive tumors are highly sensitive to ALK inhibition, indicating that these tumors addicted to ALK kinase activity. However despite initial dramatic responses of variable median duration, (10.9 months for crizotinib; 25.7 months for alectinib), resistance to therapy typically develops (Peters et al., N. Engl. J. Med. 377:829-838 (2017); Soria et al., Lancet 389:917-929 (2017); Katayama et al., Sci. Trans. Med. 4(120):120ra17 (2012); Cooper et al., Ann. Pharmacother. 49:107-112 (2015); Sullivan et al., Ther. Adv. Med. Oncl. 8:32-47 (2016)). Next-generation ALK inhibitors such as lorlatinib have been able to successfully target resistant tumors and have shown improvements in potency and overall response rates relative to approved inhibitors, resistance to these inhibitors still consistently arises in patients (Mologni et al., Transl. Lung Cancer Res. 4:5-7 (2015); Katayama et al., Clin. Cancer Res. 20:5686-5696 (2014); Qin et al., Targeted Oncology 12:709-718 (2017); Shaw et al., N. Engl. J. Med. 374:54-61 (2016)). The FDA approved the use of lorlatinib for the treatment of lung cancer in November 2018.

SUMMARY OF THE INVENTION

A first aspect of the present invention is directed to a bispecific compound of formula (I),

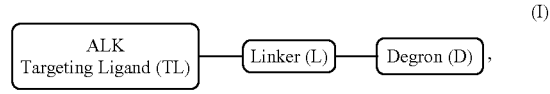

(I)

or a pharmaceutically acceptable salt or stereoisomer thereof. The ALK targeting ligand is an alectinib analog, a lorlatinib analog, TPX-005 or an analog thereof, 3-[1-[(3-fluorophenyl)methyl]pyrazol-4-yl]-5-(1-methylpyrazol-4-yl)-1H-pyrrolo[2,3-b]pyridine or an analog thereof, or ensartinib or an analog thereof.

A second aspect of the present invention is directed to bispecific compounds 9-12 or a pharmaceutically acceptable salt or stereoisomer thereof. These compounds may induce proteasome-mediated degradation of ALK.

Another aspect of the present invention is directed to a pharmaceutical composition containing a therapeutically effective amount of the bispecific compound of formula (I) or a pharmaceutically acceptable salt or stereoisomer thereof, and a pharmaceutically acceptable carrier.

In another aspect of the present invention, methods of making the bispecific compounds are provided.

A further aspect of the present invention is directed to a method of treating a disease or disorder involving (characterized or mediated by) aberrant ALK activity, that includes administering a therapeutically effective amount of the bispecific compound of formula (I) or a pharmaceutically acceptable salt or stereoisomer thereof, to a subject in need thereof.

Without intending to be bound by any particular theory of operation, the bispecific compounds of formula I (also referred to herein as PROTACs or degraders) are believed to promote the degradation of ALK via cells' Ubiquitin/Proteasome System, whose function is to routinely identify and remove damaged proteins. After destruction of an ALK molecule, the degrader is released and continues to be active. Thus, by engaging and exploiting the body's own natural protein disposal system, the bispecific compounds of the present invention may represent a potential improvement over current small molecule inhibitors of ALK. Thus, effective intracellular concentrations of the degraders may be significantly lower than for small molecule ALK inhibitors.

Accordingly, the bispecific compounds of the present invention may offer at least one additional advantage including improved pharmacodynamics effects. The degradation of ALK may decrease tyrosine kinase inhibitor resistance imparted by intrinsic scaffolding functions of kinases and may also decrease the likelihood of de novo resistance mutations to the degraders since efficient degradation of ALK may be achieved with targeting ligands that have relatively less affinity to ALK compared to known ALK inhibitors. Collectively, the present bispecific compounds may represent an advancement over known ALK inhibitors and may overcome one or more limitations regarding their use.

DETAILED DESCRIPTION OF THE INVENTION

Figure 1A:
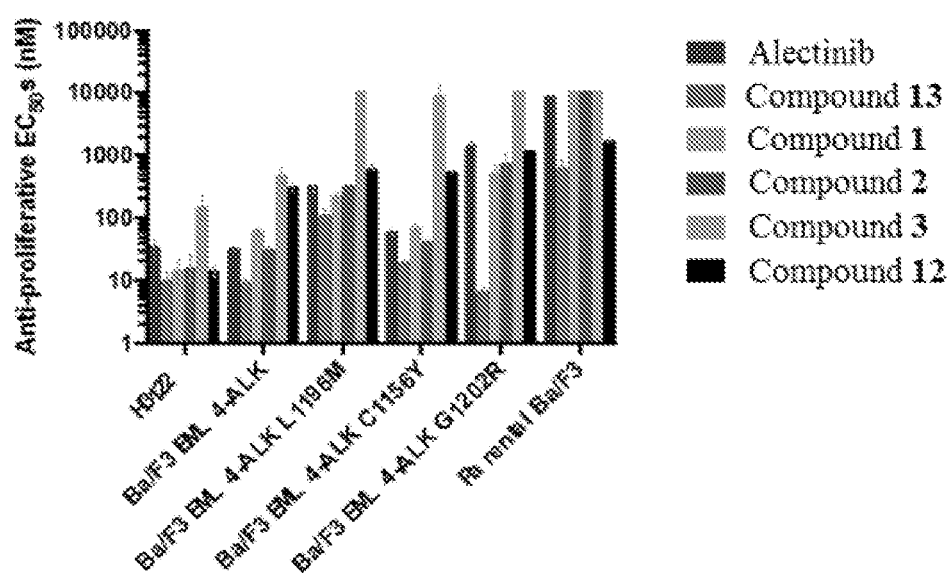
FIG. 1A is graph that shows the anti-proliferative activities of inventive compounds 1-3, 12 (ALK degraders), non-inventive compound 13 (Alectinib derivative), and Alectinib (ALK inhibitor) on H3122 cells, ALK-positive Ba/F3 cells, and parental (ALK-negative) Ba/F3 cells after 72 hours by CellTiter-Glo®.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "aliphatic" refers to a non-cyclic hydrocarbon group and includes branched and unbranched, alkyl, alkenyl, or alkynyl groups.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group, or a methyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

As used herein, the term "aldehyde" is represented by the formula —C(O)H. The terms "C(O)" and C=O are used interchangeably herein.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

Representative examples of substituents may include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-C6, C1-5, C1-4, C1-3, C1-2, C1), haloalkyl (e.g., CF3), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, sulfonyl, substituted sulfonyl, urea, substituted urea, carbamate, substituted carbamate, amino acid, and peptide groups.

The term "binding" as it relates to interaction between the targeting ligand and the targeted protein, refers to an inter-molecular interaction that is substantially specific in that binding of the targeting ligand with other proteinaceous entities present in the cell is functionally insignificant. The present bispecific compounds preferentially bind and recruit ALK for targeted degradation, including mutant forms thereof (e.g., EML4-ALK including the G1202R and L1196M mutants, and NPM-ALK) that manifest themselves in pathological states. The bispecific compounds may also bind and recruit one or more other kinases for degradation including, for example, c-ros oncogene 1 (ROS1), ret-proto oncogene (RET), insulin-like growth factor-1 receptor (IGF-1R), hepatocyte growth factor receptor (HGFR or c-MET), FLT-3, and tropomyosin receptor kinase A (TrkA), TrkB and TrkC.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bispecific compounds of the present invention have a structure represented by formula I:

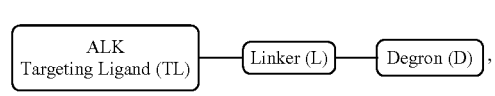

(I)

wherein the targeting ligand represents a moiety that binds ALK, the degron represents a moiety that binds an E3 ubiquitin ligase, and the linker represents a moiety that connects covalently the degron and the targeting ligand, or a pharmaceutically acceptable salt or stereoisomer thereof.

Targeting Ligands

In some embodiments, the ALK targeting ligand is an alectinib analog.

In some embodiments, the alectinib analog has a structure as represented by formula TL-1a:

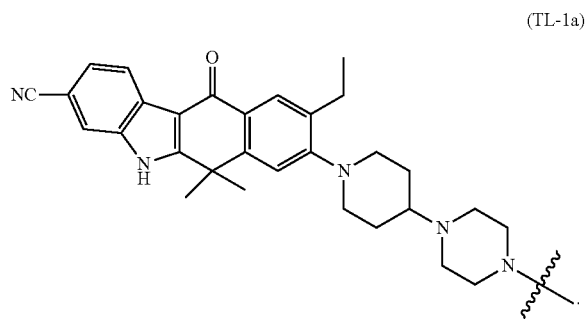 [SMILES: *N1CCN(C2CCN(c3cc4c(cc3CC)C(=O)c3c([nH]c5cc(C#N)ccc35)C4(C)C)CC2)CC1]

(TL-1a)

Thus, in some embodiments, the bispecific compounds of the present invention may have a structure as represented by formula I-1a:

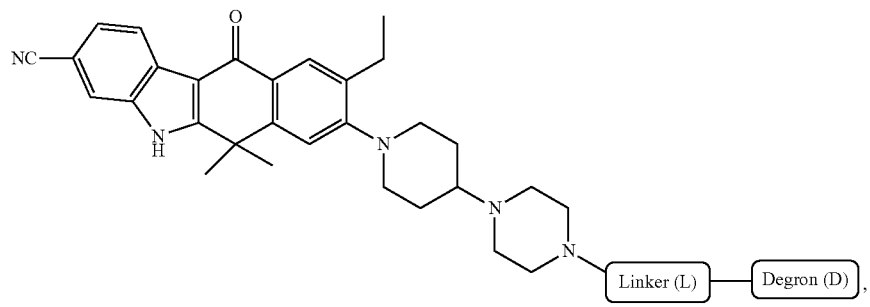

(I-1a)

or a pharmaceutically acceptable salt or stereoisomer thereof.

In some embodiments, the alectinib analog has a structure represented by formula TL-1b:

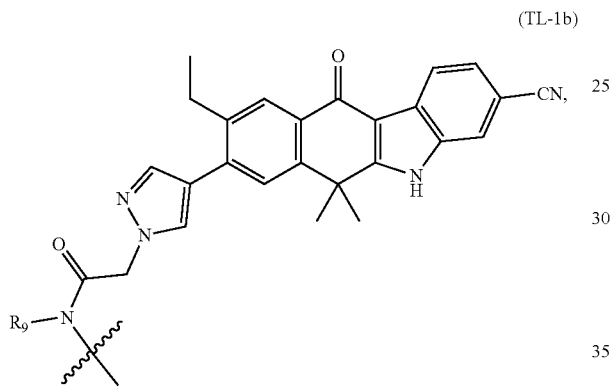

(TL-1b)

wherein $R_9$ is H or Me.

Thus, in some embodiments, the bispecific compounds of the present invention may have a structure as represented by formula I-1b:

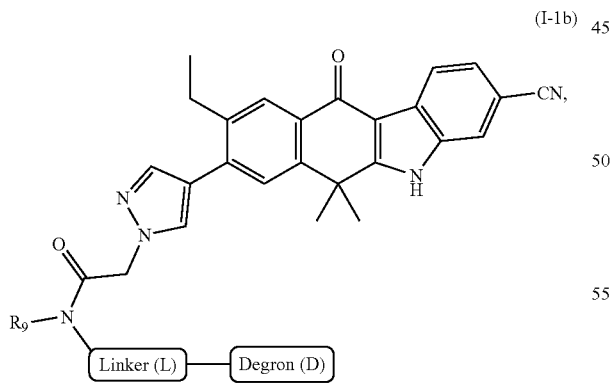

(I-1b)

wherein $R_9$ is H or Me, or a pharmaceutically acceptable salt or stereoisomer thereof.

In some embodiments, the targeting ligand is a lorlatinib analog.

In some embodiments, the ALK targeting ligand is a lorlatinib analog having any one of the following structures TL-2a1, TL-2a2, or TL-2a3:

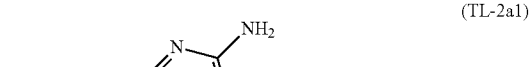
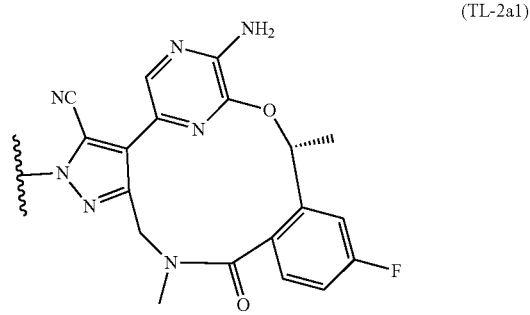

(TL-2a1)

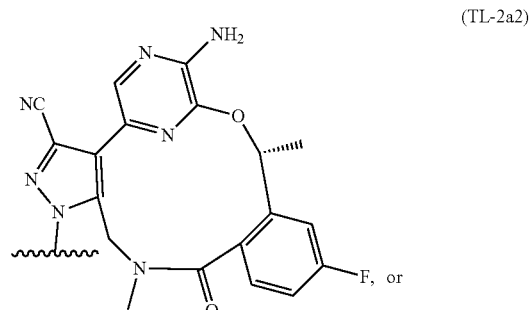

(TL-2a2)

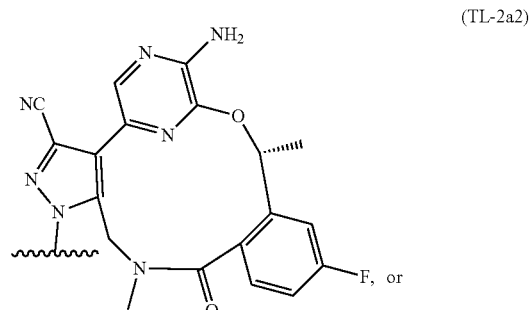

(TL-2a3)

Lorlatinib, also known as (10R)-7-amino-12-fluoro-2,10,16-trimethyl-15-oxo-10,15,16,17-tetrahydro-2H-8,4-(metheno)pyrazolo[4,3-h][2,5,11]benzoxadiaza-cyclotetradecine-3-carbonitrile, and analogs thereof, have been described in International Patent Publication WO 2013/132376 and in U.S. Pat. No. 8,680,111.

In some embodiments, the ALK targeting ligand is a lorlatinib analog and the bispecific compound has a structure of formula I-2b:

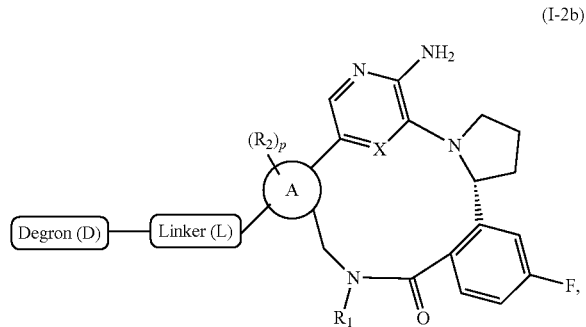

(I-2b)

or a pharmaceutically acceptable salt or stereoisomer thereof, wherein:

A is an optionally substituted $C_6$-$C_{12}$ aryl or optionally substituted 5-6 membered heteroaryl group;

X is CH or N;

$R_1$ represents hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic and 5-6 membered heteroaryl, wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic or 5-6 membered heteroaryl may be optionally substituted by halogen, —OH, —OR$_7$, —NH$_2$, —NO$_2$, —CN, —S(O)$_r$R$_7$, —S(O)$_2$NR$_7$R$_8$, —S(O)$_2$OR$_7$, —C(O)R$_7$, —OC(O)R$_7$, —NR$_7$C(O)R$_5$, —C(O)OR$_7$, —C(=NR$_7$)NR$_7$R$_8$, —NR$_7$C(O)NR$_7$R$_8$, —NR$_7$S(O)$_2$R$_8$ or —C(O)NR$_7$R$_8$;

each $R_2$ independently represents halogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic, 5-6 membered heteroaryl, —S(O)$_r$R$_5$, —S(O)$_2$NR$_5$R$_6$, —S(O)$_2$OR$_7$, —NO$_2$, —(CR$_3$R$_4$)$_q$NR$_5$R$_6$, —N(CR$_3$R$_4$)(CR$_3$R$_4$)$_q$NR$_5$R$_6$, —OR$_5$, —O(CR$_3$R$_4$)(CR$_3$R$_4$)$_q$OR$_5$, —O(CR$_3$R$_4$)(CR$_3$R$_4$)$_q$R$_5$, —CN, —CF$_3$, —CHF$_2$, —OCF$_3$, —OCHF$_2$, —C(O)R$_5$, —OC(O)R$_5$, —O(CR$_3$R$_4$)$_q$R$_5$, —NR$_5$C(O)R$_6$, —(CR$_3$R$_4$)$_q$C(O)OR$_5$, —(CR$_3$R$_4$)$_q$NR$_5$R$_6$, —C(=NR$_5$)NR$_5$R$_6$, —NR$_5$C(O)NR$_5$R$_6$, —NR$_5$S(O)$_2$R$_6$ and —(CR$_3$R$_4$)$_q$C(O)NR$_5$R$_6$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic, or 5-6 membered heteroaryl may be independently optionally substituted by halogen, —OH, —OR$_7$, —NH$_2$, —NO$_2$, —CN, —S(O)$_r$R$_7$, —S(O)$_2$NR$_7$R$_8$, —S(O)$_2$OR$_7$, —C(O)R$_7$, —OC(O)R$_7$, —NR$_7$C(O)R$_5$, —C(O)OR$_7$, —C(=NR$_7$)NR$_7$R$_8$, —NR$_7$C(O)NR$_7$R$_8$, —NR$_7$S(O)$_2$R$_8$ or —C(O)NR$_7$R$_8$;

each $R_3$ and $R_4$ independently represents hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic, 5-6 membered heteroaryl, —OH, —OR$_7$, —NH$_2$, —NO$_2$, —CN, —S(O)$_r$R$_7$, —S(O)$_2$NR$_7$R$_8$, —S(O)$_2$OR$_7$, —C(O)R$_7$, —OC(O)R$_7$, —NR$_7$C(O)R$_5$, —C(O)OR$_7$, —C(=NR$_7$)NR$_7$R$_8$, —NR$_7$C(O)NR$_7$R$_8$, —NR$_7$S(O)$_2$R$_8$ or —C(O)NR$_7$R$_8$; wherein each hydrogen on said $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic, or 5-6 membered heteroaryl may be independently optionally substituted by halogen, —OH, —OR$_7$, —NH$_2$, —NO$_2$, —CN, —S(O)$_r$R$_7$, —S(O)$_2$NR$_7$R$_8$, —S(O)$_2$OR$_7$, —C(O)R$_7$, —OC(O)R$_7$, —NR$_7$C(O)R$_5$, —C(O)OR$_7$, —C(=NR$_7$)NR$_7$R$_8$, —NR$_7$C(O)NR$_7$R$_8$, —NR$_7$S(O)$_2$R$_8$ or —C(O)NR$_7$R$_8$;

each $R_5$ and $R_6$ independently represents hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic, or 5-6 membered heteroaryl, any of which may be independently optionally substituted by halogen, —OH, —OR$_7$, —NH$_2$, —NO$_2$, —CN, —S(O)$_r$R$_7$, —S(O)$_2$NR$_7$R$_8$, —S(O)$_2$OR$_7$, —C(O)R$_7$, —OC(O)R$_7$, —NR$_7$C(O)R$_5$, —C(O)OR$_7$, —C(=NR$_7$)NR$_7$R$_8$, —NR$_7$C(O)NR$_7$R$_8$, —NR$_7$S(O)$_2$R$_8$ or —C(O)NR$_7$R$_8$;

each $R_7$ and $R_8$ independently represents hydrogen, $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 3-12 membered heterocyclic, or 5-6 membered heteroaryl;

p is 1, 2, 3 or 4;

each q is independently 0, 1, 2 or 3;

each r is independently 0, 1, 2 or 3; and each t is independently 0, 1 or 2.

In some embodiments, ring A is pyrazole;

$R_1$ is methyl or cyclopropyl;

$R_2$ is H, methyl, or methoxy; and p is 1.

In some embodiments, the targeting ligand is a lorlatinib analog having a structure represented by formula TL-2b1:

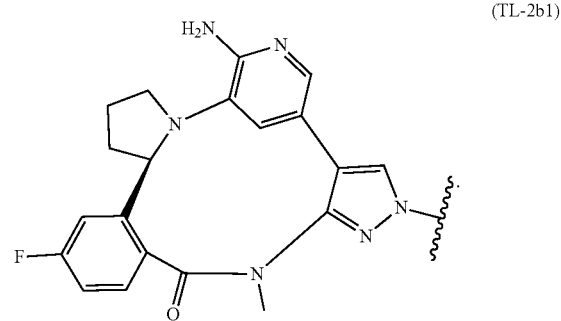 [SMILES: *n1cc2c(n1)N(C)C(=O)c1ccc(F)cc1[C@H]1CCCN1c1cc-2cnc1N]

(TL-2b1)

In some embodiments, the targeting ligand is a lorlatinib analog having a structure represented by formula TL-2b2:

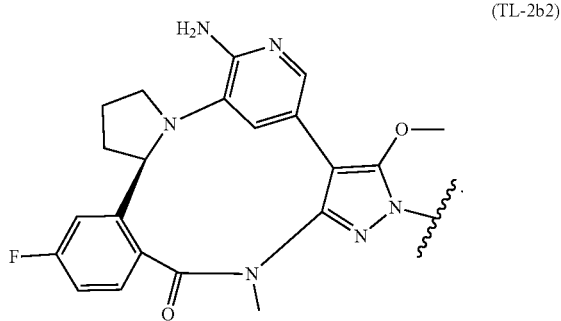 [SMILES: *n1nc2c(c1OC)-c1cnc(N)c(c1)N1CCC[C@@H]1c1cc(F)ccc1C(=O)N2C]

(TL-2b2)

In some embodiments, the targeting ligand is a lorlatinib analog having a structure represented by formula TL-2b3:

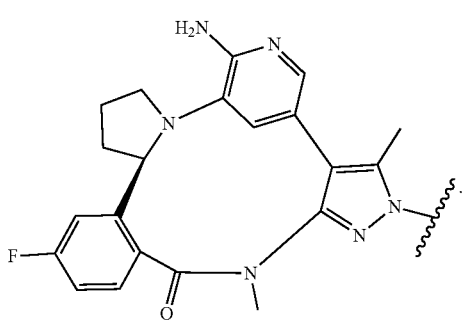
(TL-2b3)

In some embodiments, the targeting ligand is a lorlatinib analog having a structure represented by formula TL-2b4:

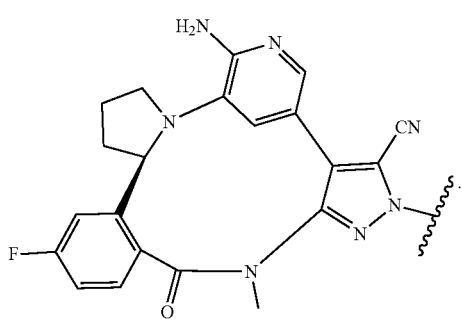
(TL-2b4)

In some embodiments, the targeting ligand is a lorlatinib analog having a structure represented by formula TL-2b5:

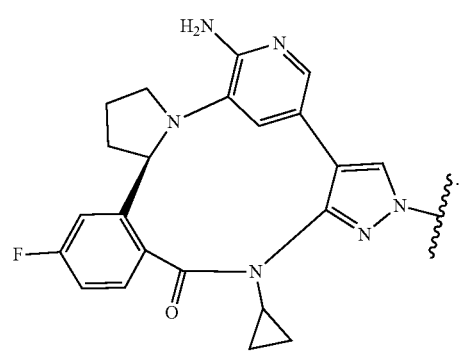
(TL-2b5)

In some embodiments, the targeting ligand is a lorlatinib analog having a structure represented by formula TL-2b6:

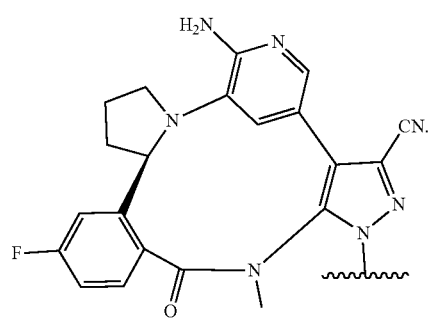
(TL-2b6)

In some embodiments, the targeting ligand is a lorlatinib analog having a structure represented by formula TL-2b7:

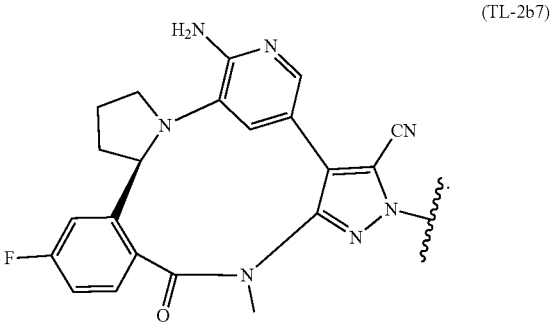
(TL-2b7)

In some embodiments, the targeting ligand is a lorlatinib analog having a structure represented by formula TL-2b8:

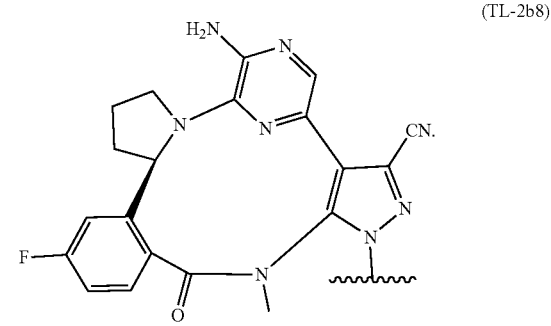 [SMILES: *n1nc(C#N)c2c1N(C)C(=O)c1ccc(F)cc1[C@H]1CCCN1c1nc-2cnc1N]
(TL-2b8)

Thus, in some embodiments, the bispecific compounds of the present invention may be represented by any one of the following structures:

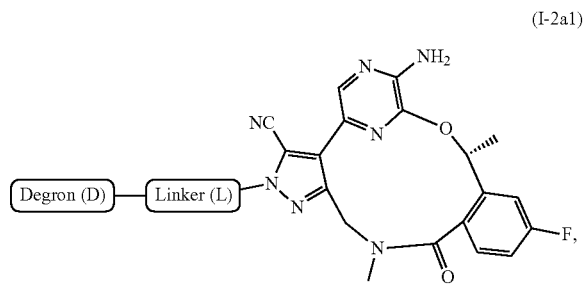
(I-2a1)

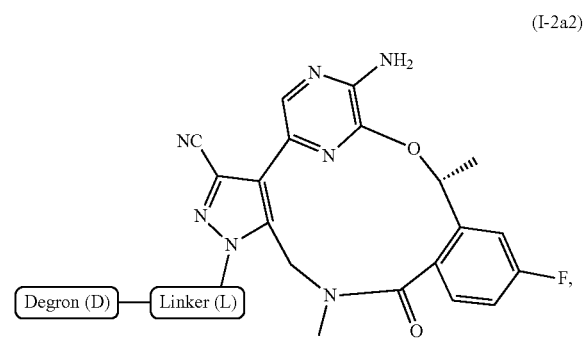
(I-2a2)

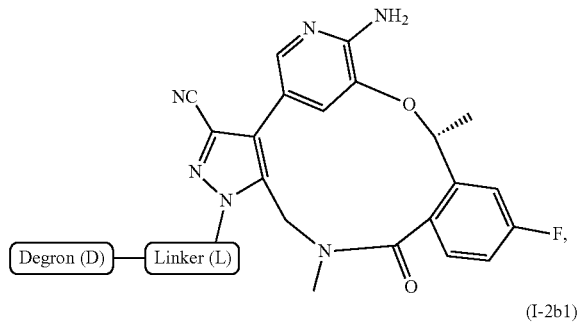
(I-2a3)

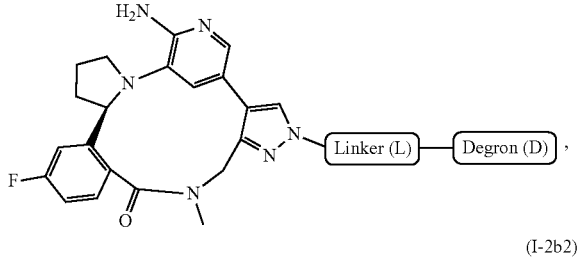
(I-2b1)

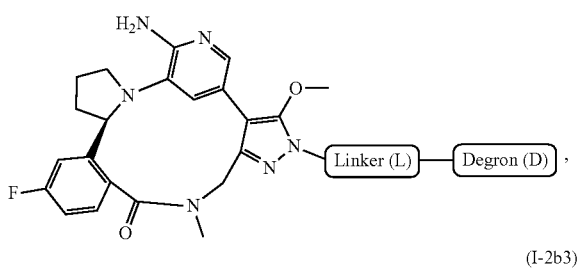
(I-2b2)

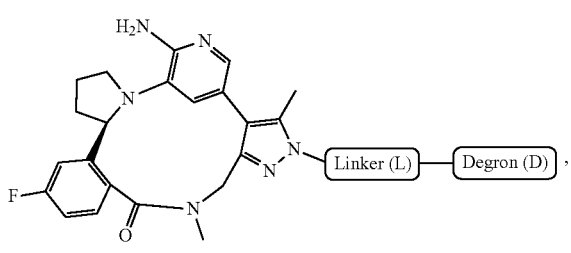
(I-2b3)

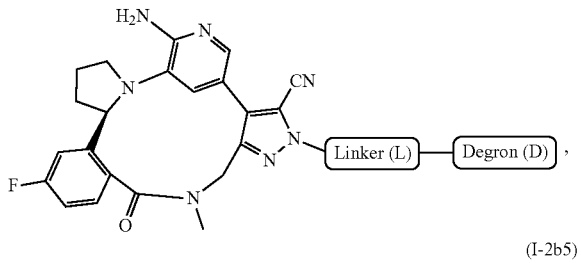
(I-2b4)

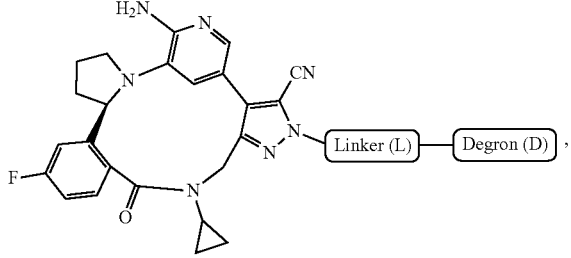
(I-2b5)

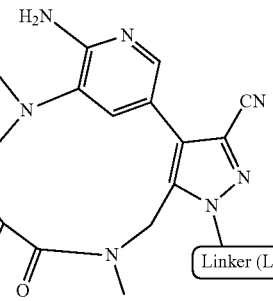
(I-2b6)

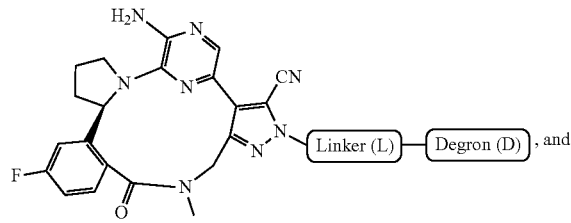
(I-2b7)

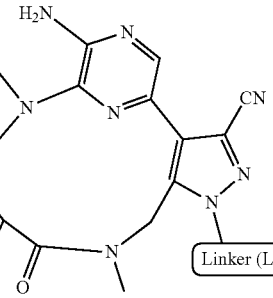
(I-2b8)

or a pharmaceutically acceptable salt or stereoisomer thereof.

Yet other lorlatinib analogs that may be suitable for use in the bispecific compounds of the present invention are also described in U.S. Pat. No. 8,680,111.

In some embodiments, the ALK targeting ligand is TPX-0005 (TL-3) or an analog thereof:

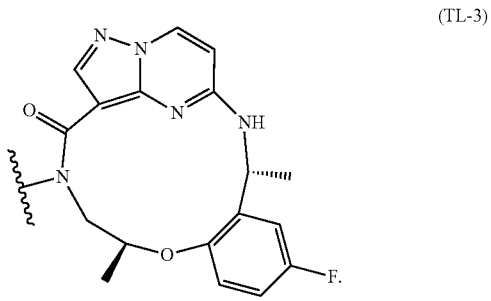 [SMILES: *N1C[C@H](C)Oc2ccc(F)cc2[C@@H](C)Nc2ccn3ncc(c3n2)C1=O]
(TL-3)

TPX-0005, also known as (13E,14E,3R,6S)-45-fluoro-3,6-dimethyl-5-oxa-2,8-diaza-1(5,3)-pyrazolo[1,5-a]pyrimidina-4(1,2)-benzenacyclononaphan-9-one, and analogs thereof are described, for example, in United States Patent Application Publication 2017/0002023 A1.

Thus, in some embodiments, the bispecific compounds of the present invention may have a structure as represented by following formula (I-3):

(I-3)

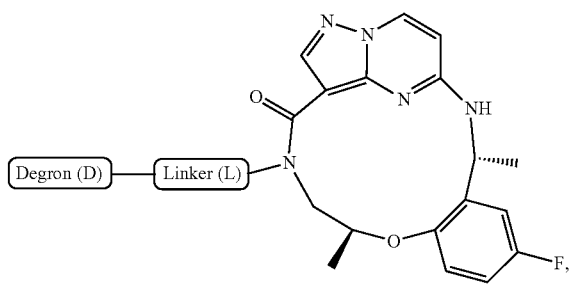

or a pharmaceutically acceptable salt or stereoisomer thereof.

In some embodiments, the ALK targeting ligand is 3-[1-[(3-fluorophenyl)methyl]pyrazol-4-yl]-5-(1-methylpyrazol-4-yl)-1H-pyrrolo[2,3-b]pyridine (TL-4), or an analog thereof.

(TL-4)

3-[1-[(3-fluorophenyl)methyl]pyrazol-4-yl]-5-(1-methylpyrazol-4-yl)-1H-pyrrolo[2,3-b]pyridine and analogs thereof are described, for example, in United States Patent Application Publication 2015/0183781 A1.

Thus, in some embodiments, the bispecific compounds of the present invention may have a structure as represented by following formula (I-4):

(I-4)

or a pharmaceutically acceptable salt or stereoisomer thereof.

In some embodiments, the ALK targeting ligand is ensartinib (TL-5), or an analog thereof:

(TL-5)

Thus, in some embodiments, the bispecific compounds of the present invention may have a structure as represented by following formula (I-5):

(I-5)

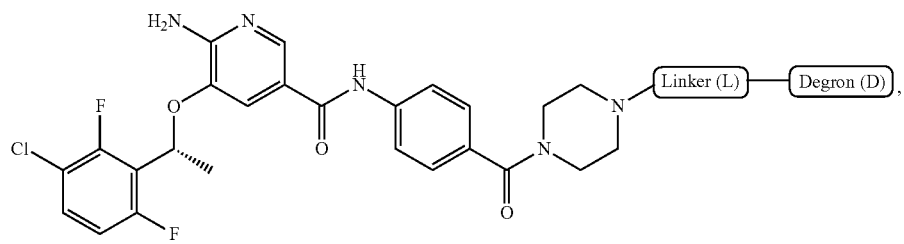

or a pharmaceutically acceptable salt or stereoisomer thereof.

Linkers

The linker ("L") provides a covalent attachment the targeting ligand and the degron. The structure of linker may not be critical, provided it does not substantially interfere with the activity of the targeting ligand or the degron. In some embodiments, the linker may be an alkylene chain or a bivalent alkylene chain, either of which may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker may be a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chain:

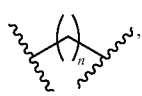
(L1)

wherein n is an integer of 1-10 ("of" meaning inclusive), e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10 examples of which include:

(L1-a)

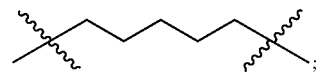
(L1-b)

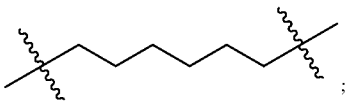
(L1-c)

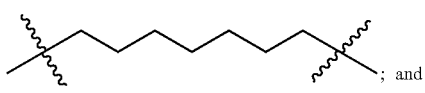
(L1-d)
; and

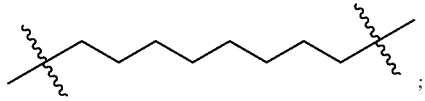
(L1-e)

alkylene chains terminating in various functional groups (as described above), examples of which are as follows:

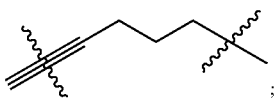
(L2-a)

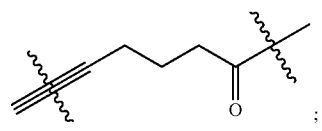
(L2-b)

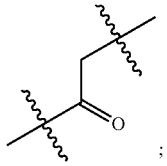
(L2-c)

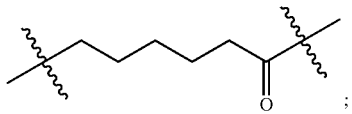
(L2-d)

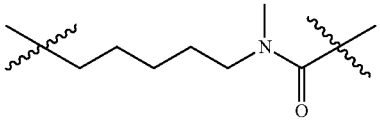
(L2-e)

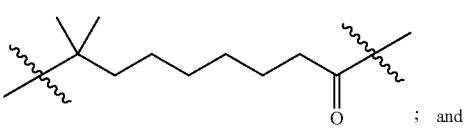
(L2-f)
; and

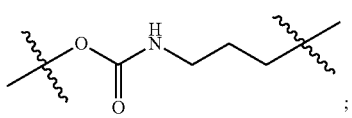
(L2-g)

alkylene chains interrupted with various functional groups (as described above), examples of which are as follows:

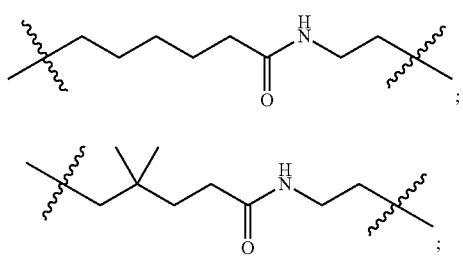
(L3-a);

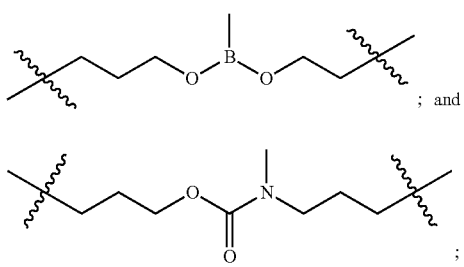
(L3-b);

(L3-c)
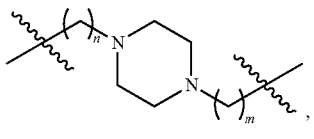 ; and (L3-d)

alkylene chains interrupted or terminating with heterocyclene groups, e.g., (L4)

wherein m and n are independently integers of 0-10, examples of which include:

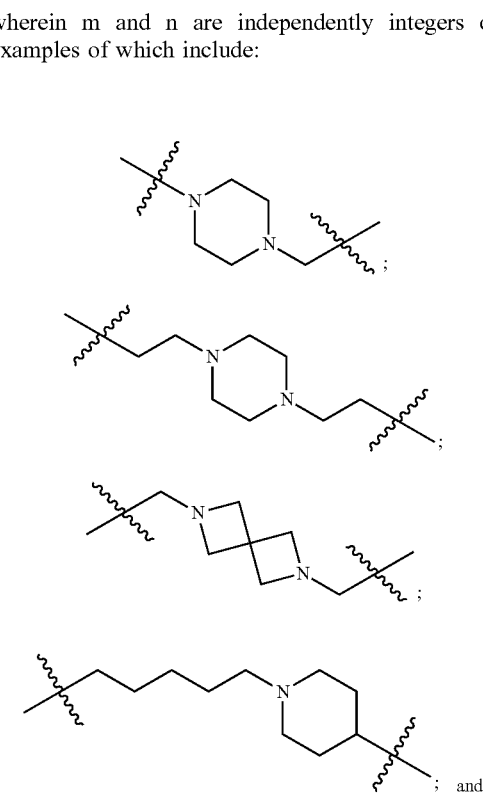

(L4-a); (L4-b); (L4-c); (L4-d); and (L4-e)
;

alkylene chains interrupted by amide, heterocyclene and/or aryl groups, examples of which include:

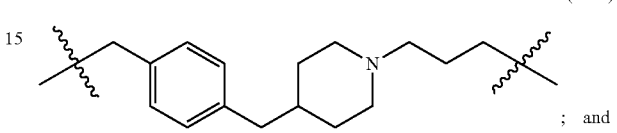
(L5-a); and (L5-b);

alkylene chains interrupted by heterocyclene and aryl groups, and a heteroatom, examples of which include:

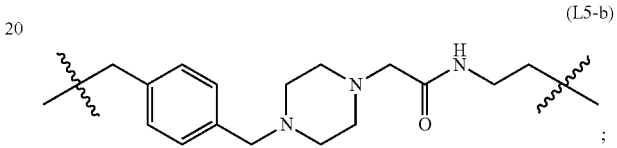
(L6-a);

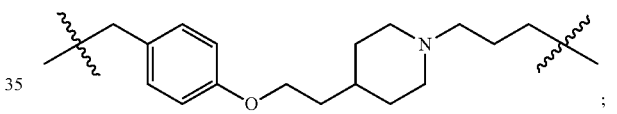
(L6-b); and

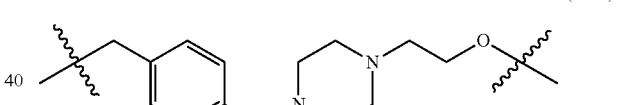
(L6-c);

and alkylene chains interrupted by a heteroatom such as N, O or B, e.g.,

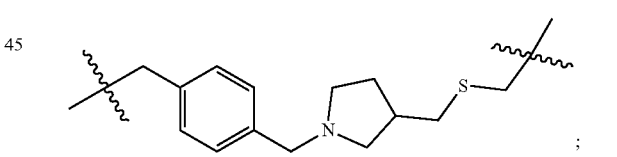
(L7)

wherein n is an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is

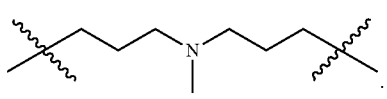
(L7-a)

In some embodiments, the linker is a polyethylene glycol chain, examples of which include:

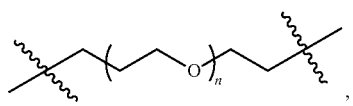
(L8)

wherein n is an integer of 2-10, examples of which include:

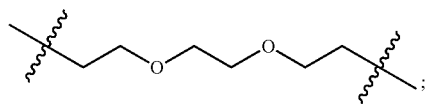
(L8-a)

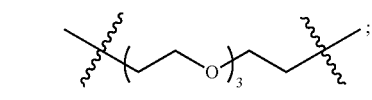
(L8-b)

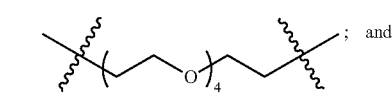
(L8-c)

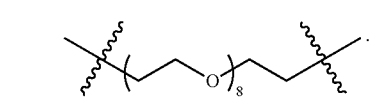
(L8-d)

In some embodiments, the polyethylene glycol linker may terminate in a functional group, examples of which are as follows:

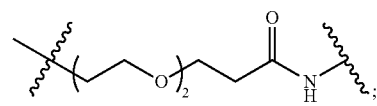
(L9-a)

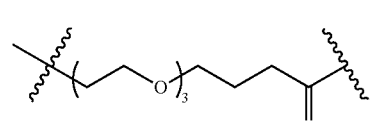
(L9-b)

(L9-c)

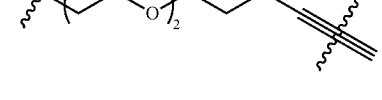
(L9-d)

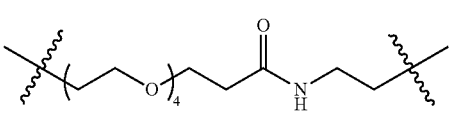
(L9-e)

In some embodiments, the compound of formula (I) includes a linker that is represented by any one of the following structures:

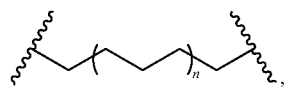
n = 1-6
(L10-a)

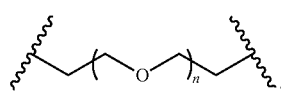
n = 1-6
(L10-b)

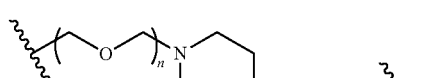
n = 1-3
(L10-c)

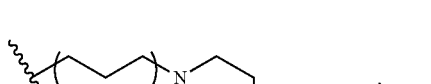
n = 1-3
(L10-d)

(L10-e)

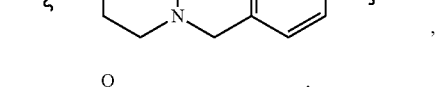
n = 1-6
, or
(L10-f)

n = 1-6
(L10-g)

In some embodiments, the compound of formula (I) includes a linker that is represented by any one of the following structures:

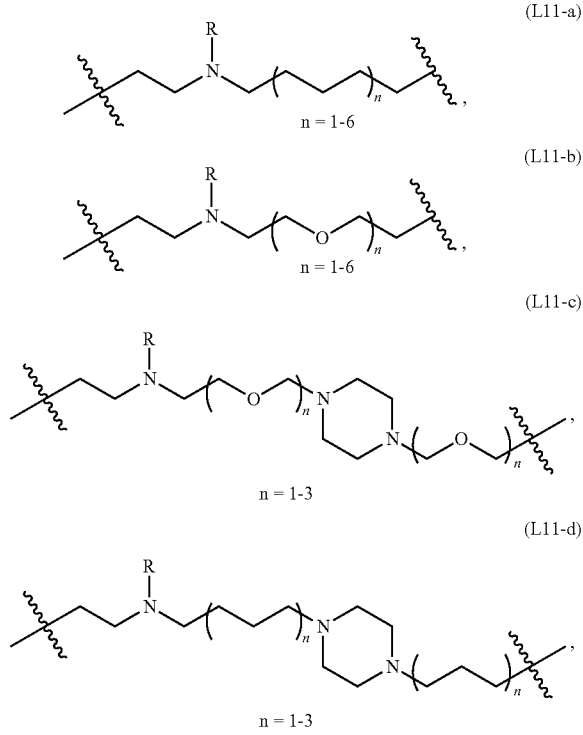
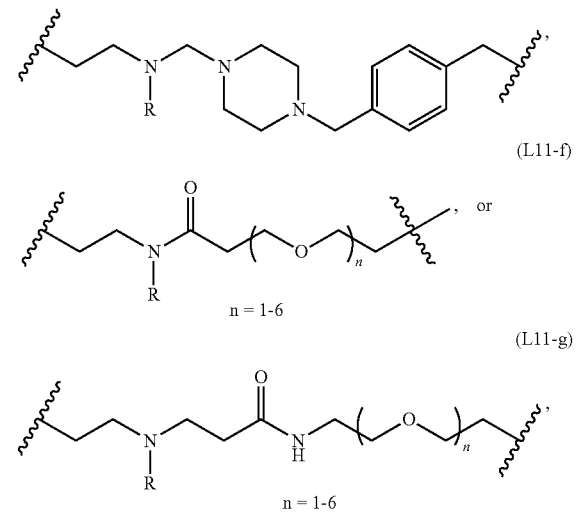
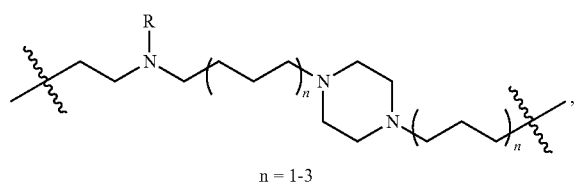
wherein R is H or Me.
In certain embodiments, linkers L11-a to L11-g are particularly suitable for use with lorlatinib and TPX-0005 targeting ligands and analogs thereof.
Thus, in some embodiments, the compounds of the present invention may have a structure as represented by any one of the following structures:
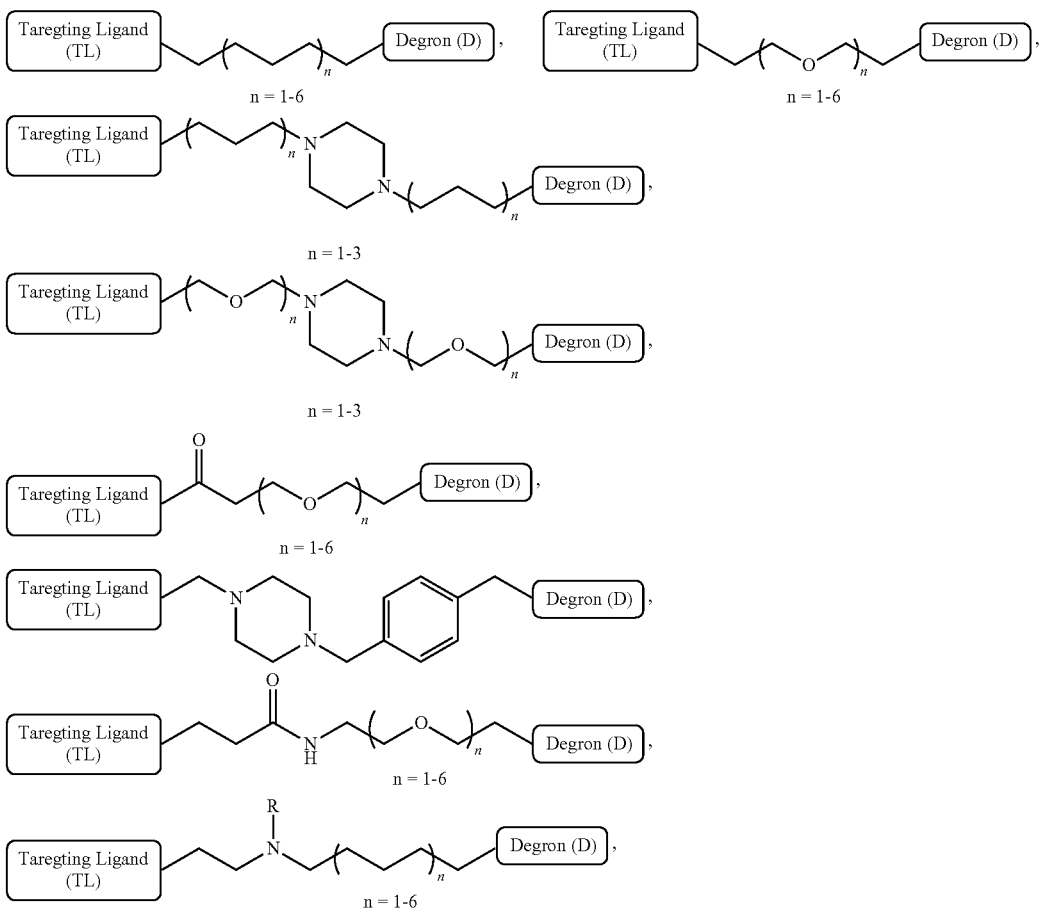

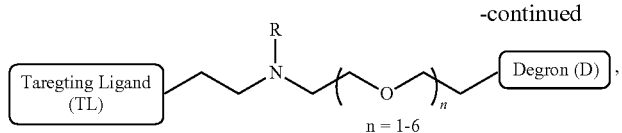
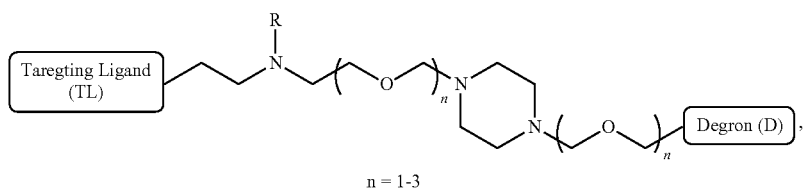
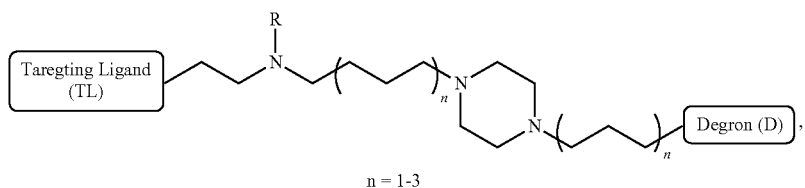
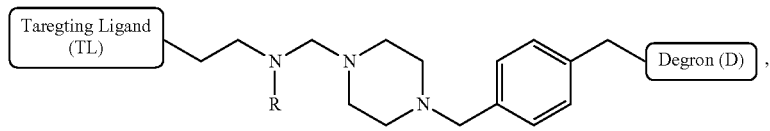
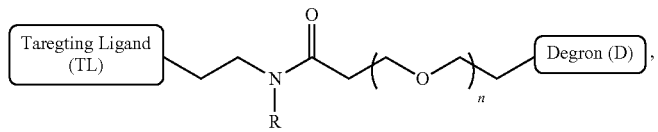
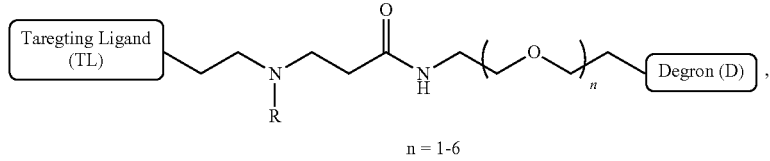
wherein R is H or Me, or a pharmaceutically acceptable salt or stereoisomer thereof.
In some embodiments, the bispecific compound of the present invention is represented by any one of the following structures:
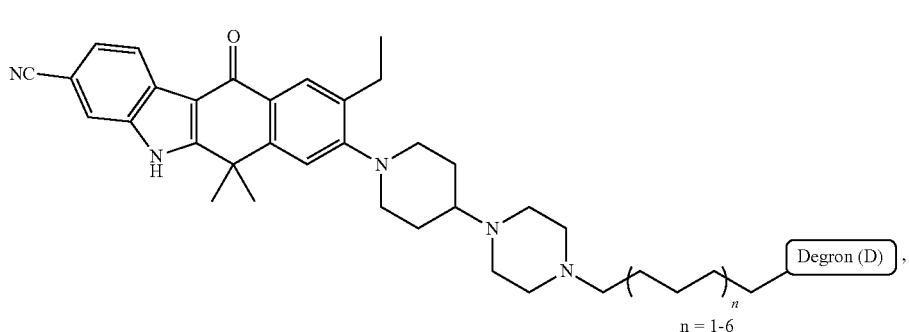

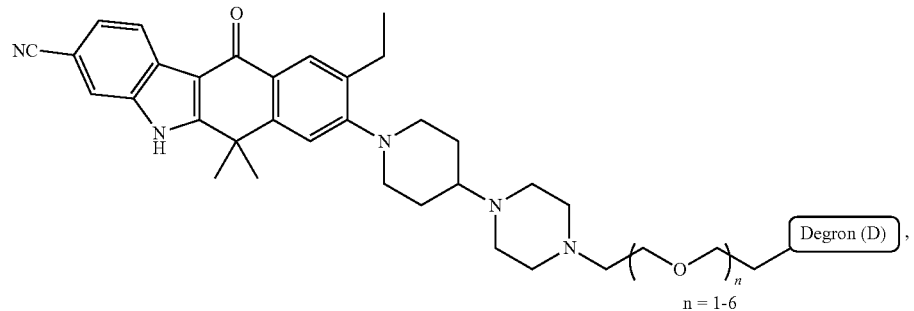
(TL1a-L10b)
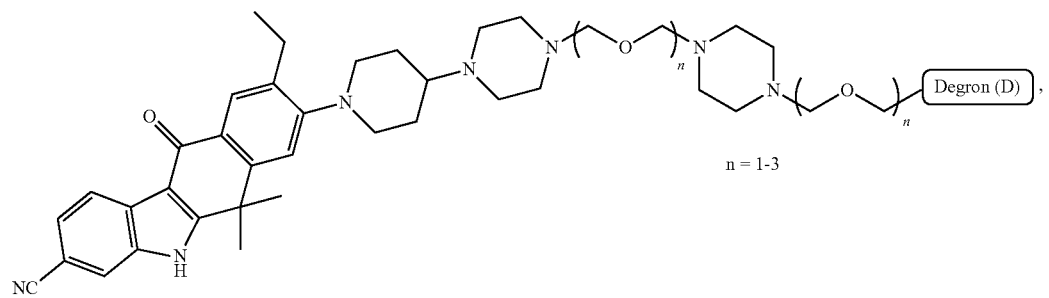
(TL1a-L10c)
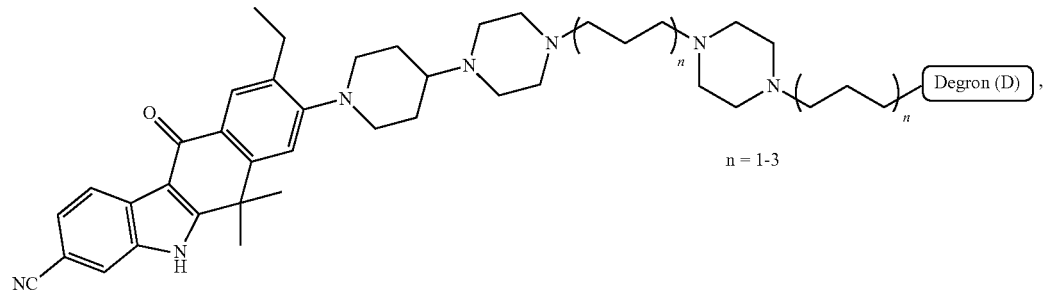
(TL1a-L10d)
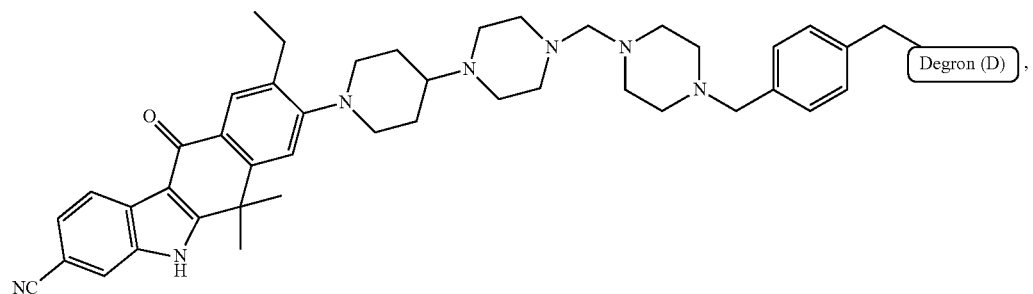
(TL1a-L10e)
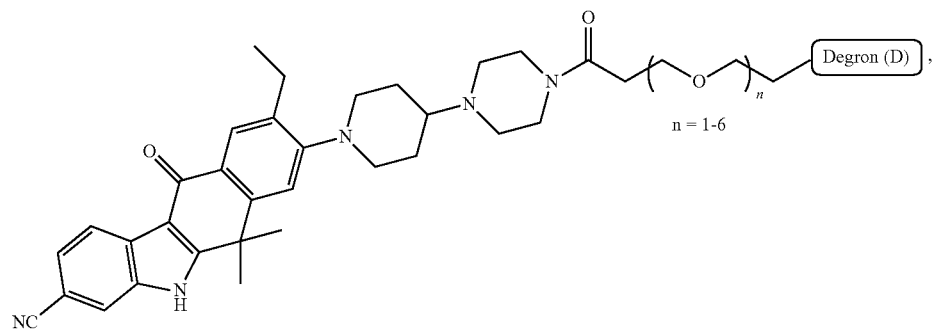
(TL1a-L10f)

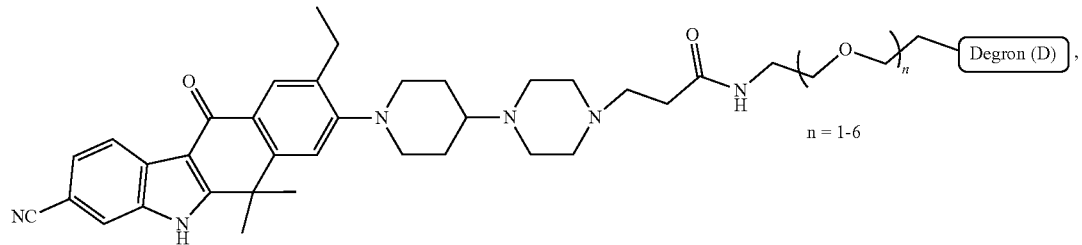
(TL1a-L10g)
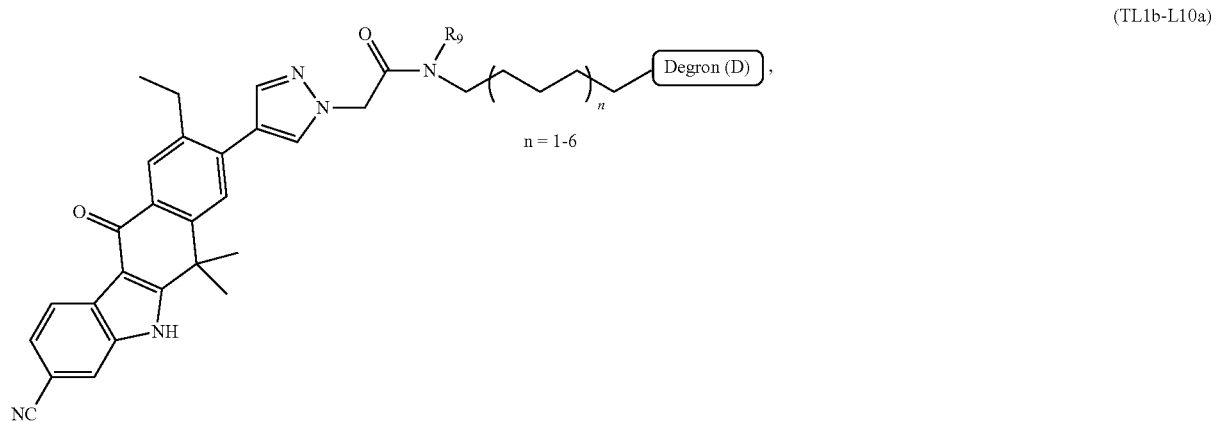
(TL1b-L10a)
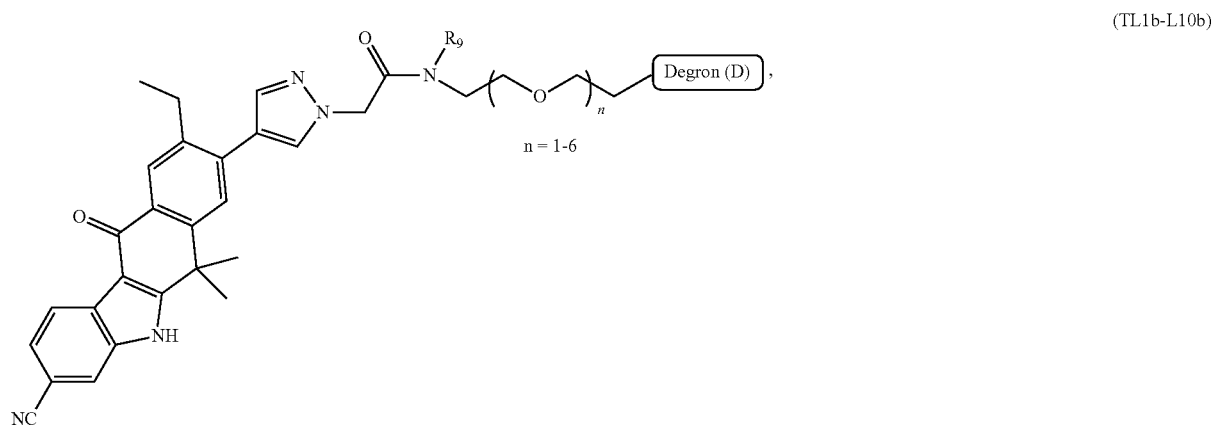
(TL1b-L10b)
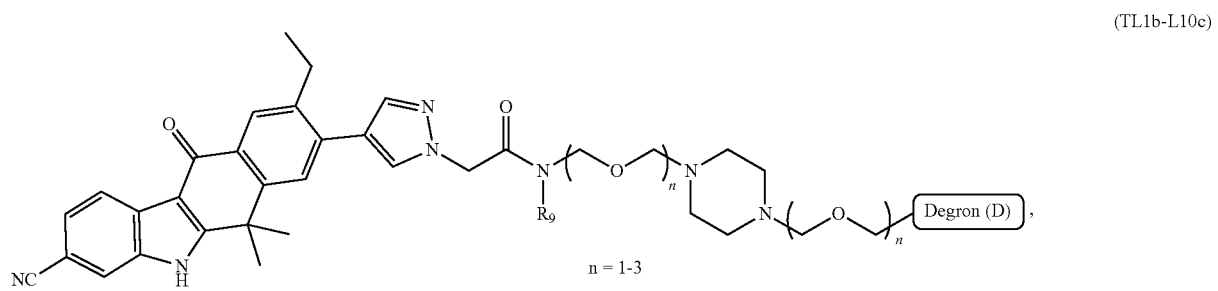
(TL1b-L10c)
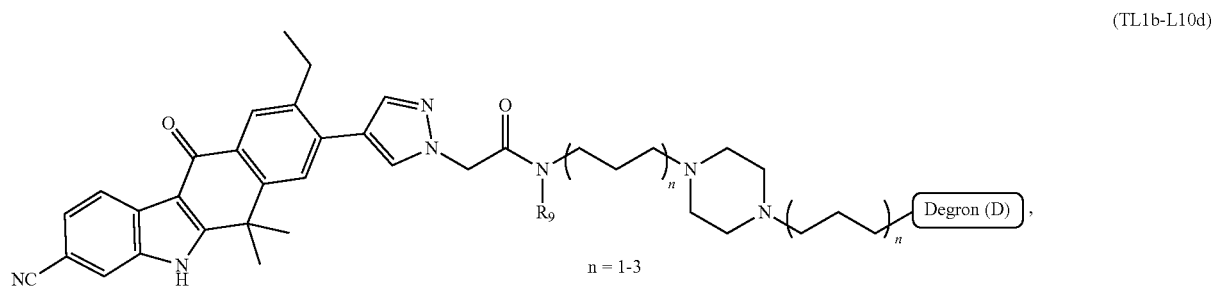
(TL1b-L10d)

(TL1b-L10e)
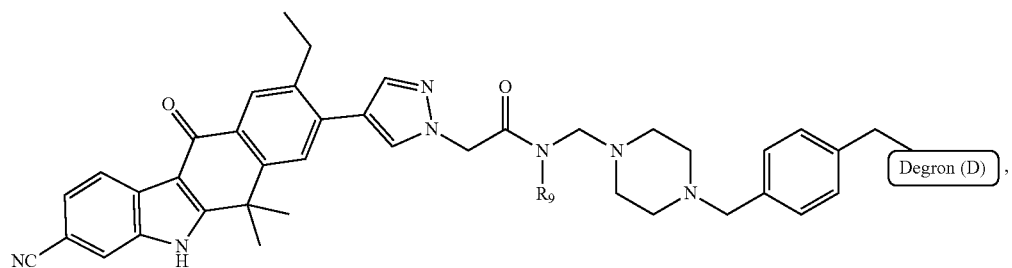
(TL1b-L10f)
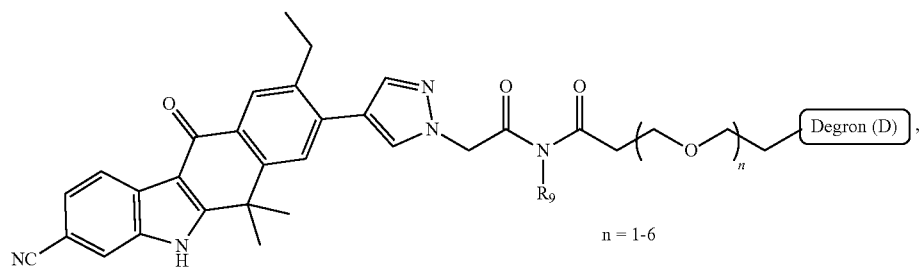
n = 1-6
(TL1b-L10g)
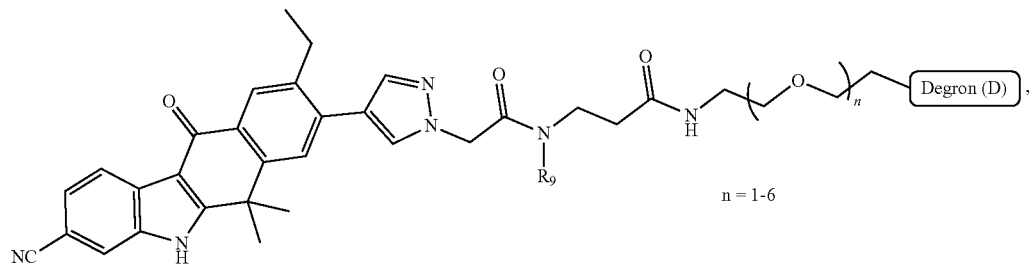
n = 1-6
(TL2a1-L10a)
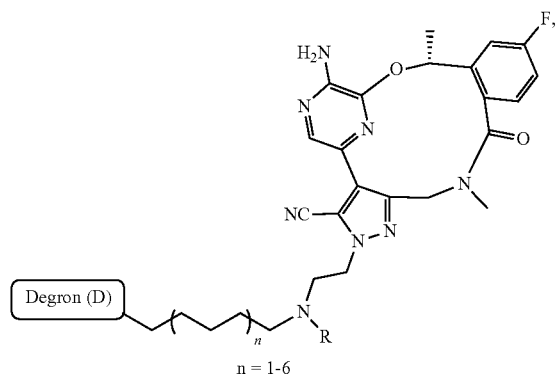
n = 1-6
(TL2a1-L10b)
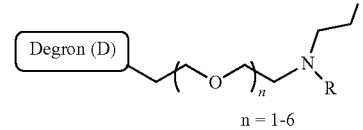
n = 1-6
(TL2a1-L10c)
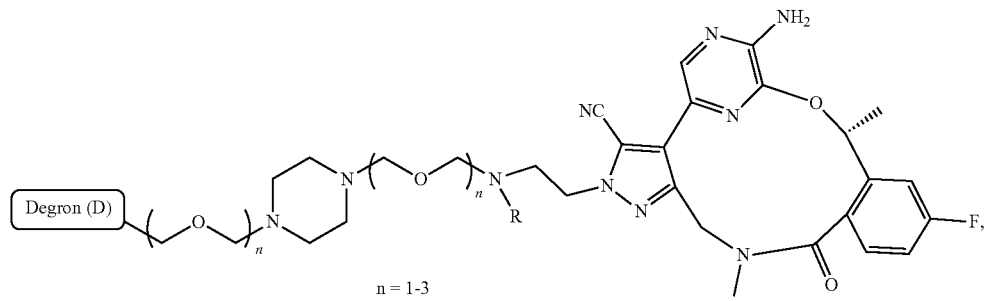
n = 1-3

-continued
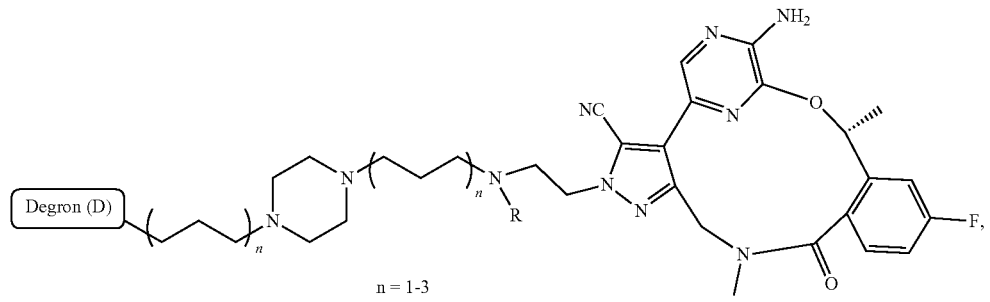
(TL2a1-L10d)
n = 1-3
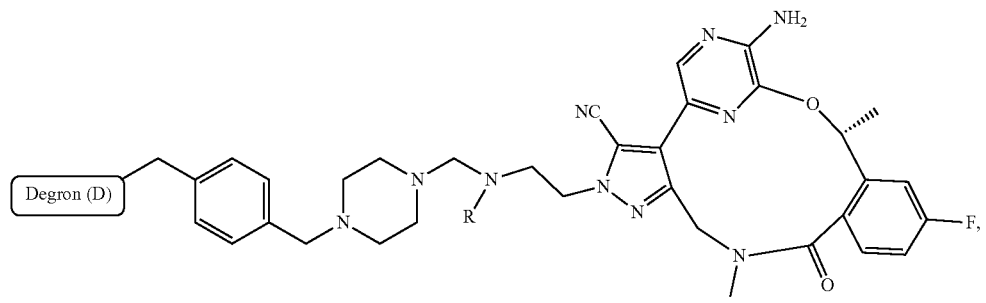
(TL2a1-L10e)
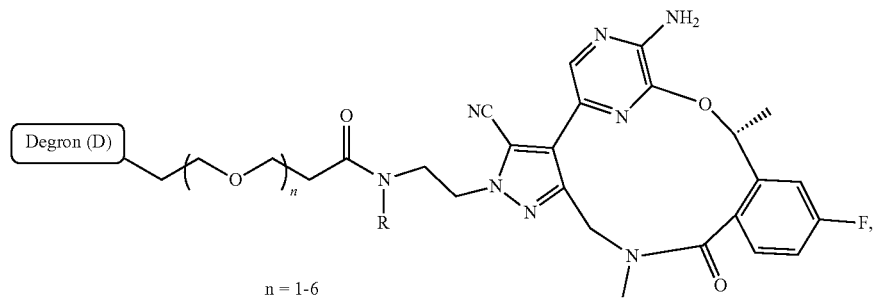
(TL2a1-L10f)
n = 1-6
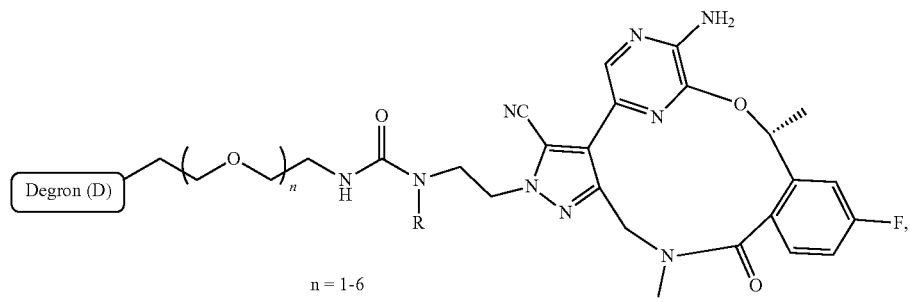
(TL2a1-L10g)
n = 1-6
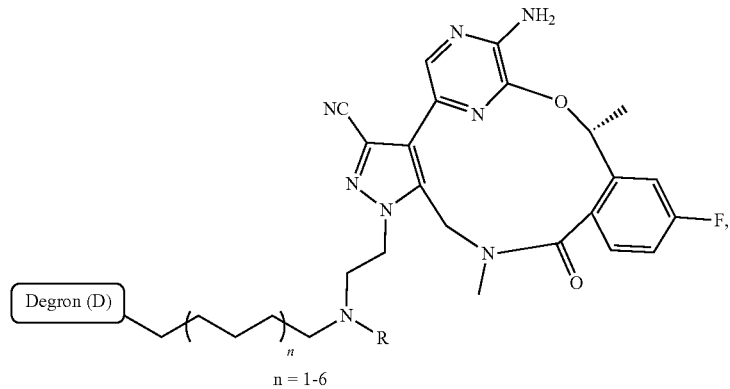
(TL2a2-L10a)
n = 1-6

-continued
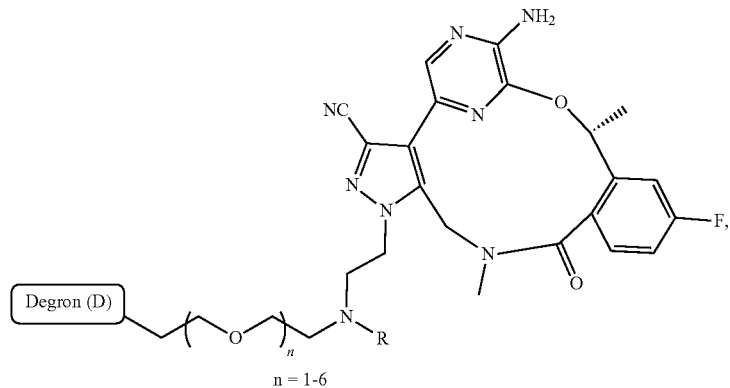
n = 1-6
(TL2a2-L10b)
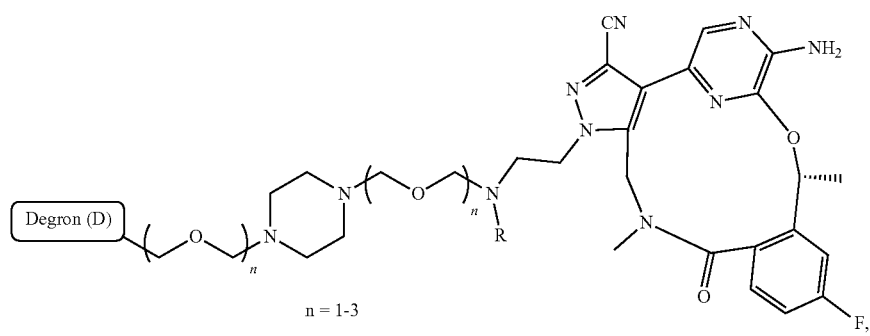
n = 1-3
(TL2a2-L10c)
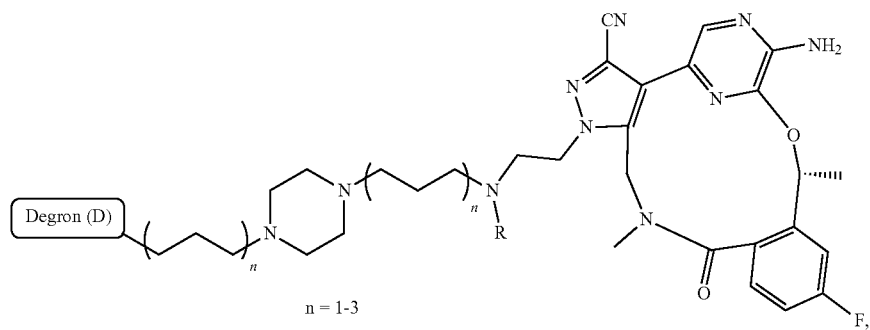
n = 1-3
(TL2a2-L10d)
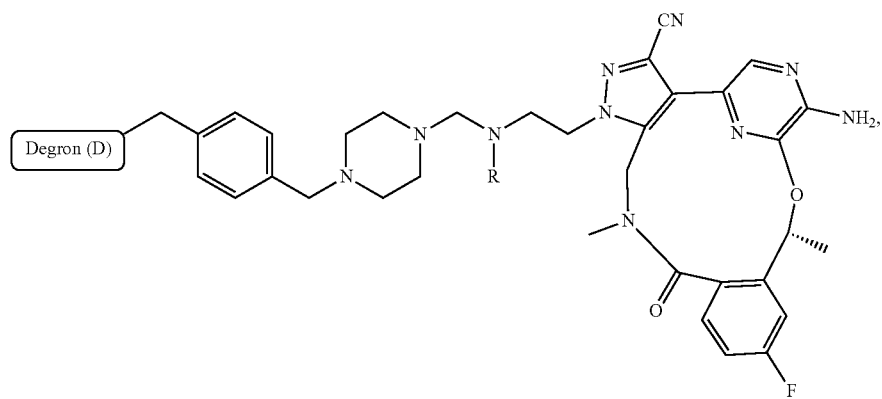
(TL2a2-L10e)

-continued
(TL2a2-L10f)
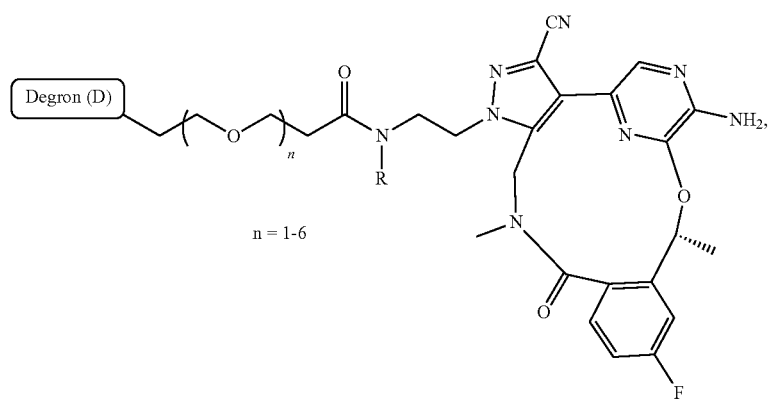
(TL2a2-L10g)
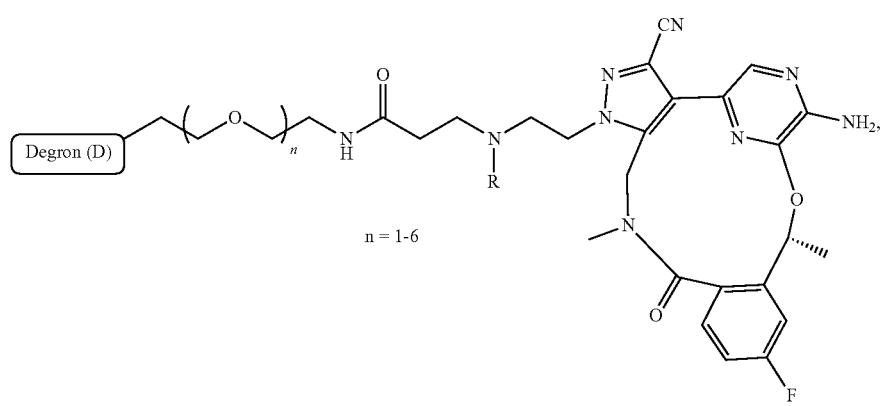
(TL2a3-L10a)
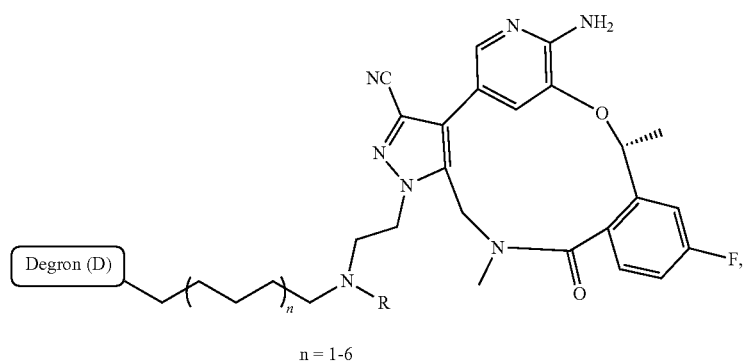
(TL2a3-L10b)
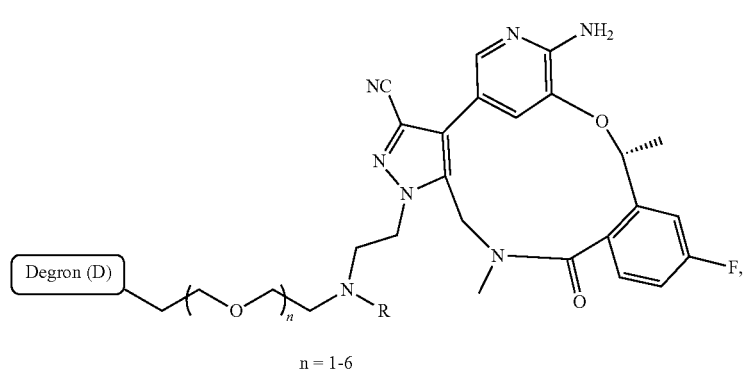

-continued
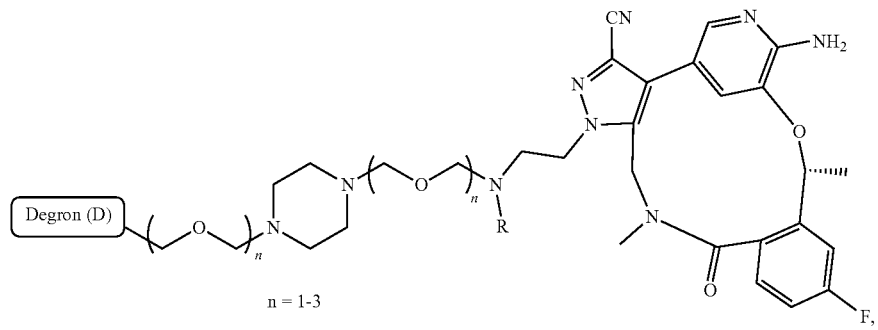
(TL2a3-L10c)
n = 1-3
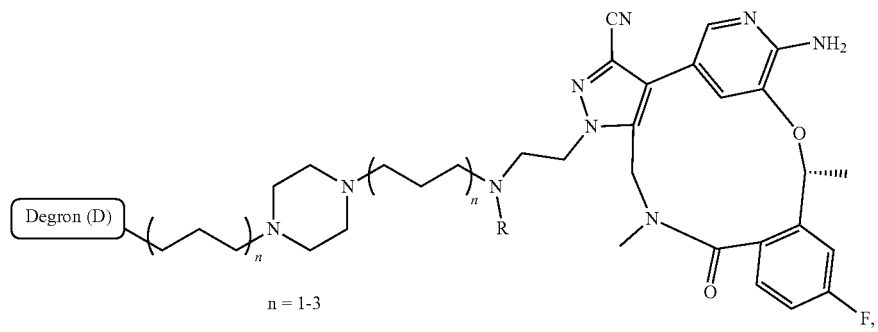
(TL2a3-L10d)
n = 1-3
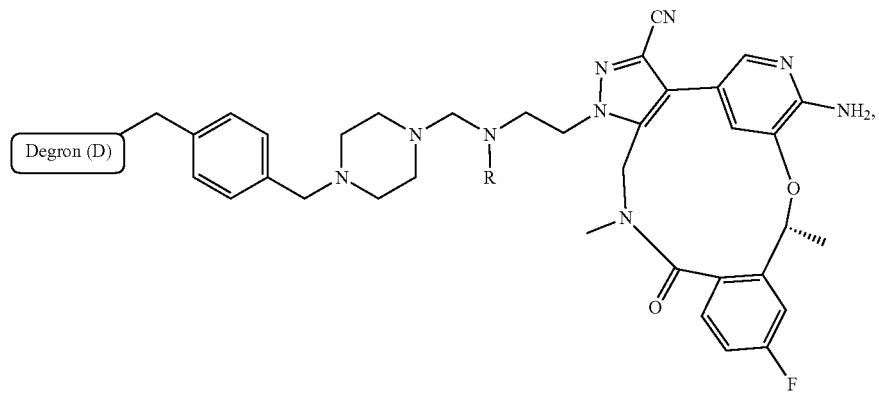
(TL2a3-L10e)
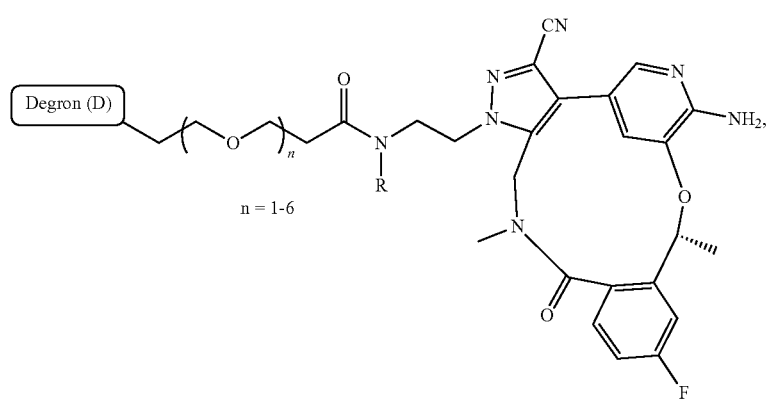
(TL2a3-L10f)
n = 1-6

-continued
(TL2a3-L10g)
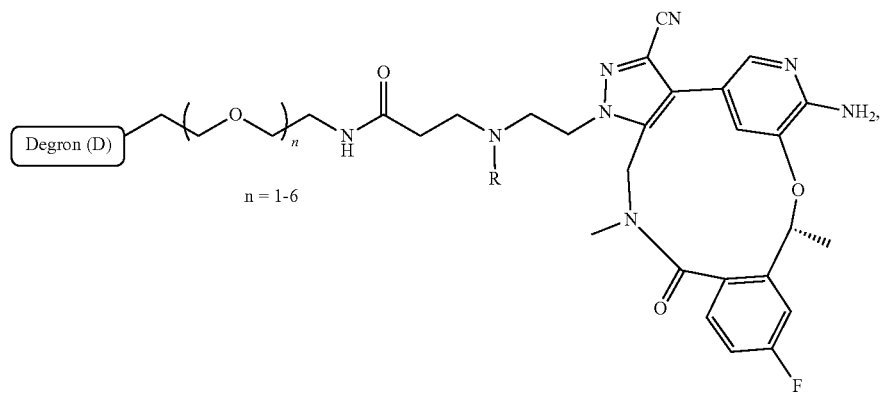
n = 1-6
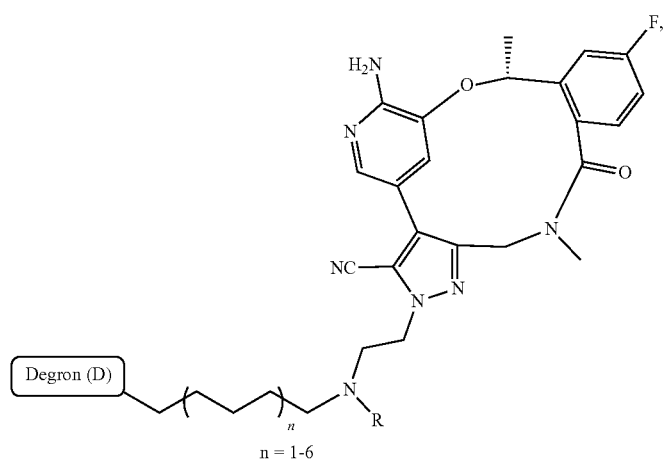
n = 1-6
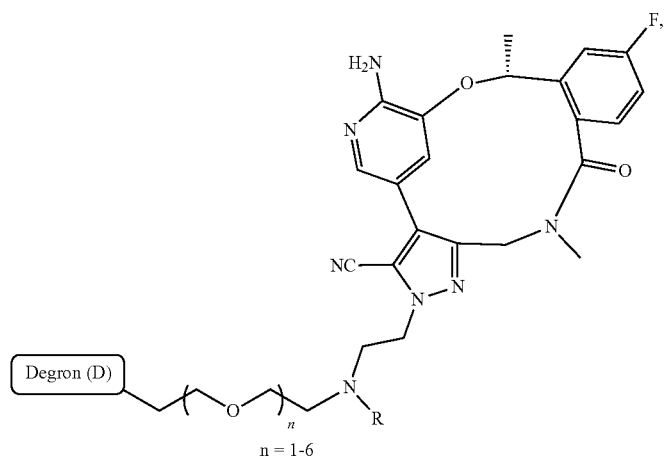
n = 1-6
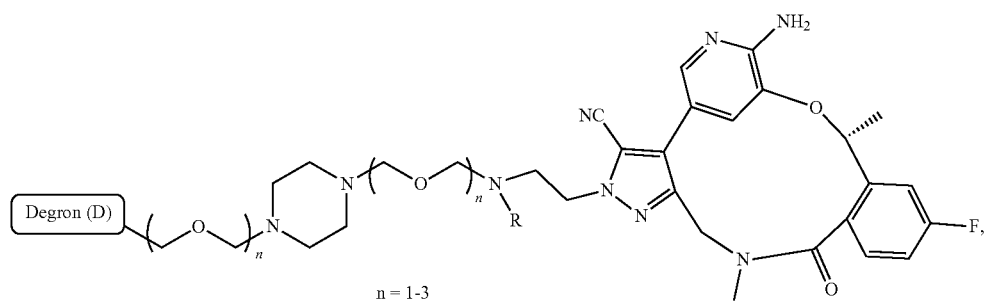
n = 1-3

-continued
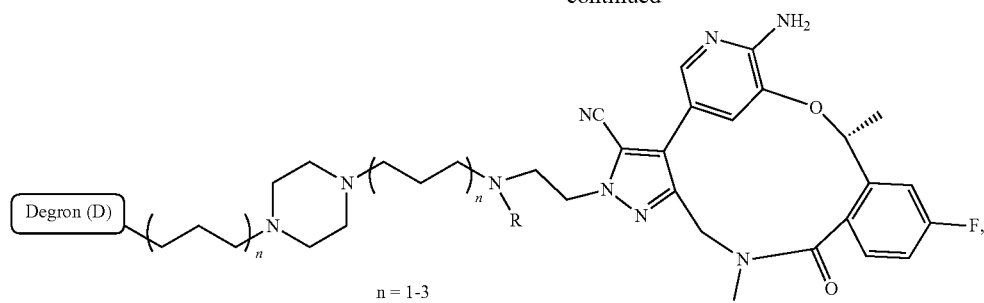
n = 1-3
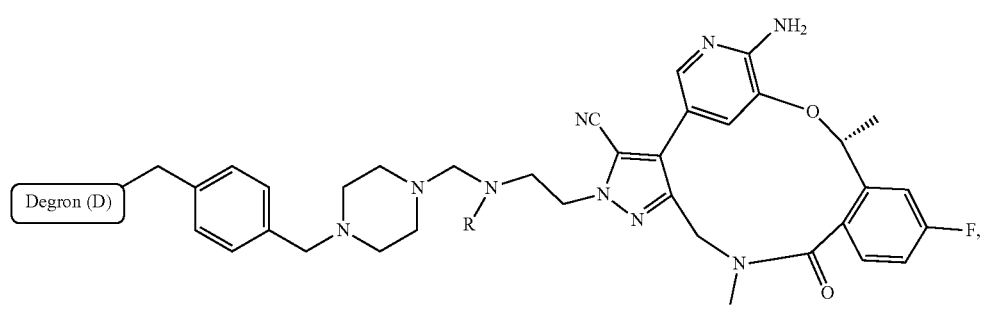
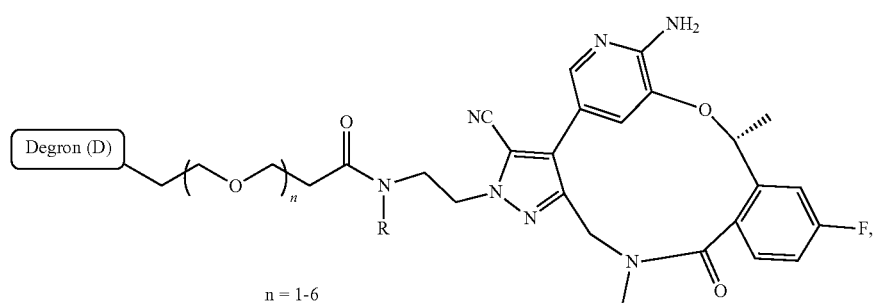
n = 1-6
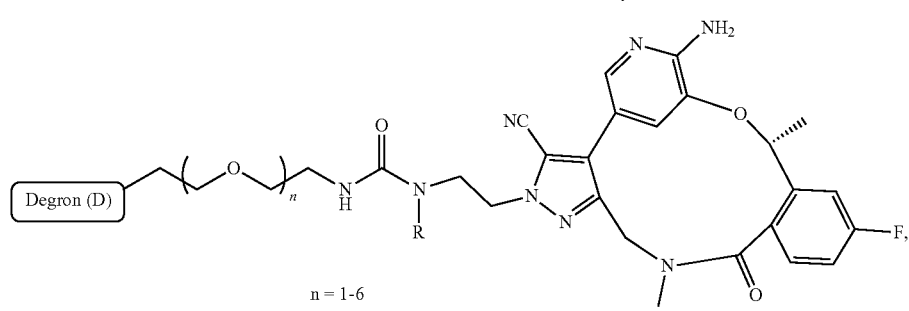
n = 1-6
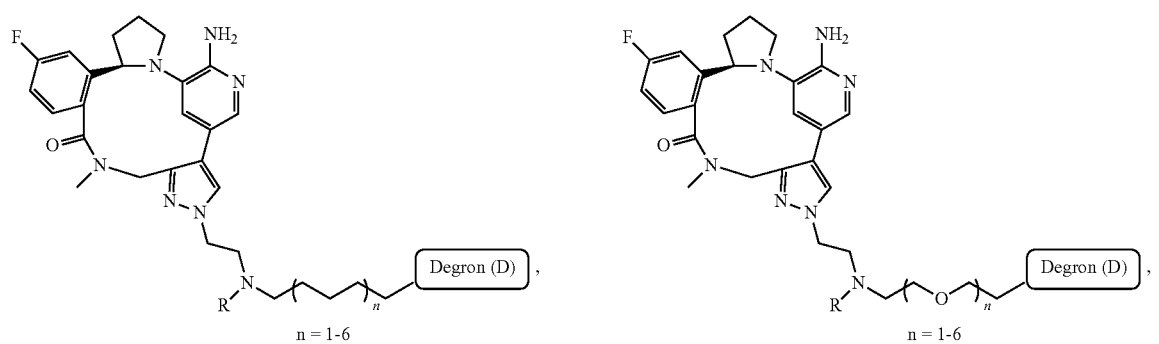
(TL2b1-L10a)    (TL2b1-L10b)
n = 1-6    n = 1-6

(TL2b1-L10c)
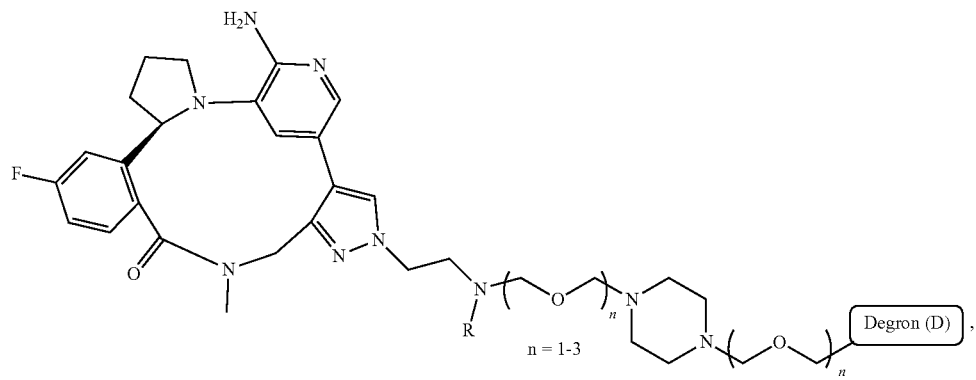
(TL2b1-L10d)
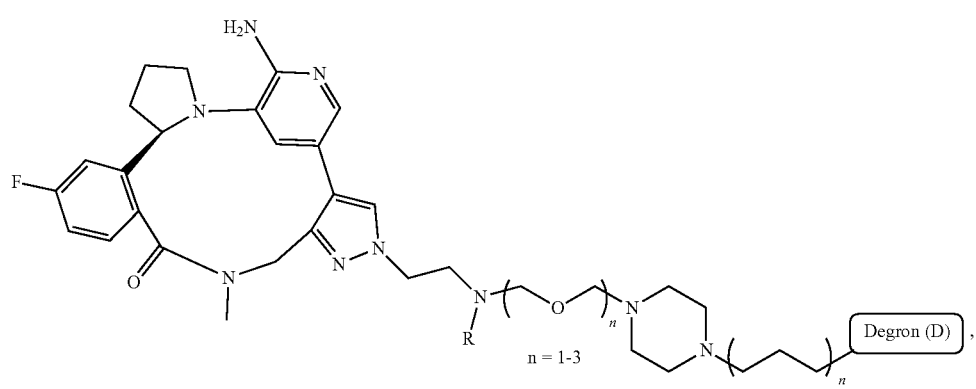
(TL2b1-L10e)
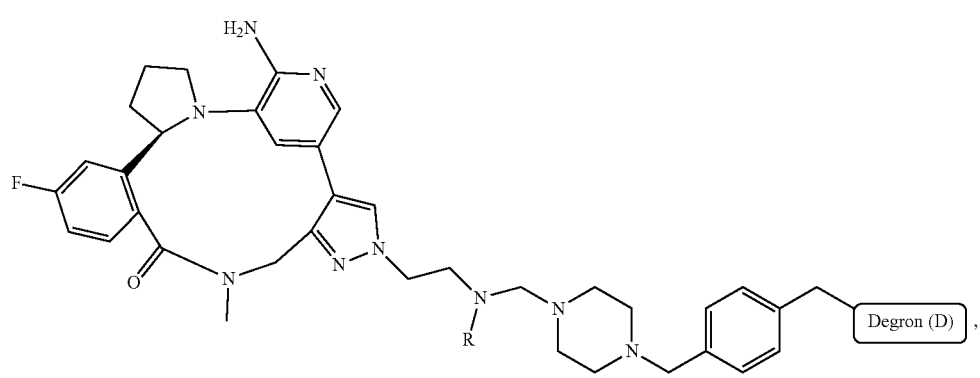
(TL2b1-L10f)
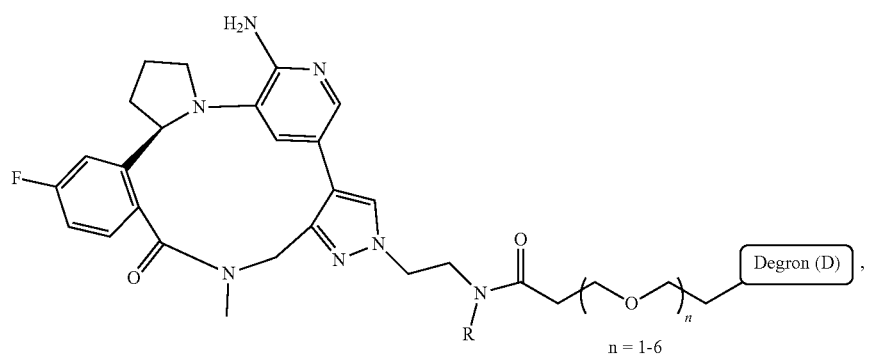

(TL2b1-L10g)
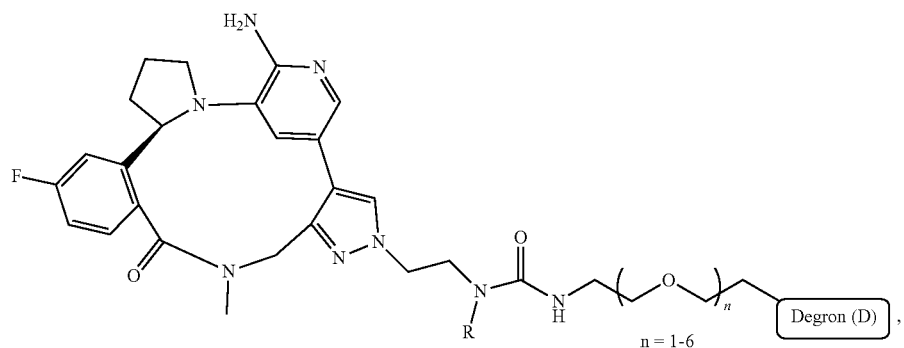
n = 1-6
(TL2b2-L10a)
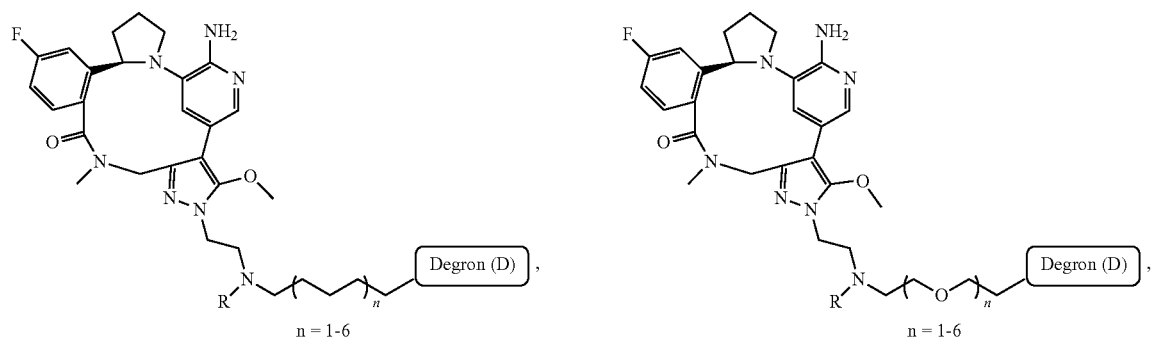
n = 1-6
(TL2b2-L10b)
n = 1-6
(TL2b2-L10c)
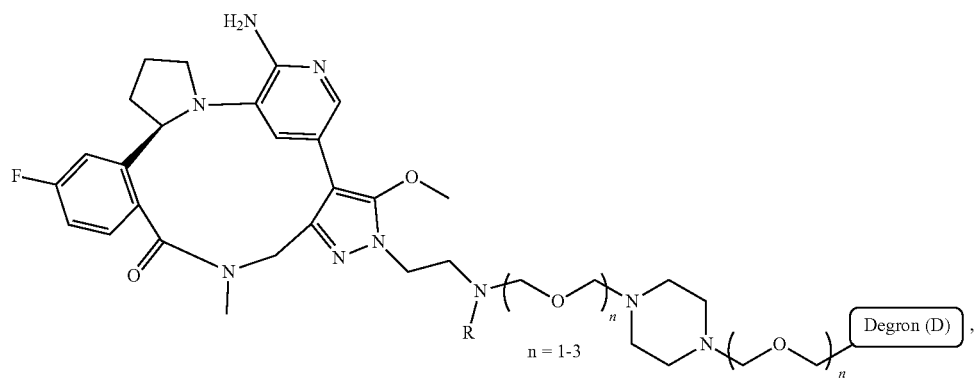
n = 1-3
(TL2b2-L10d)
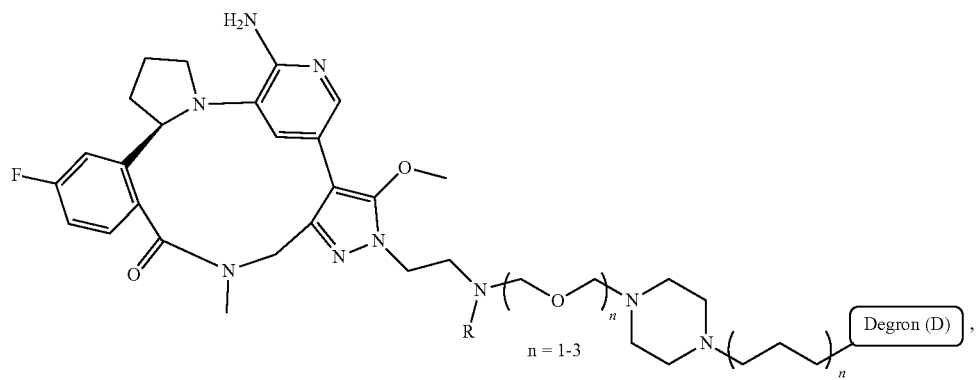
n = 1-3

-continued
(TL2b2-L10e)
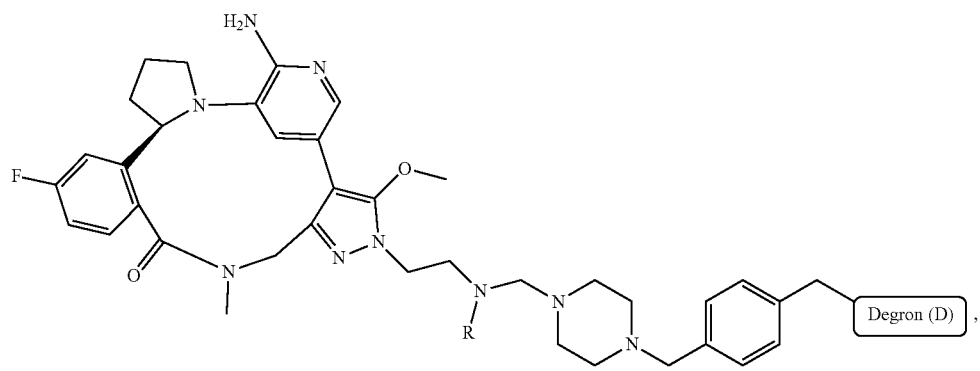
(TL2b2-L10f)
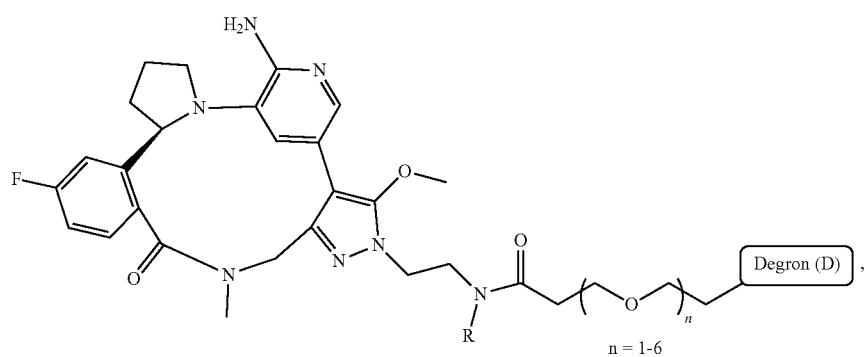
(TL2b2-L10g)
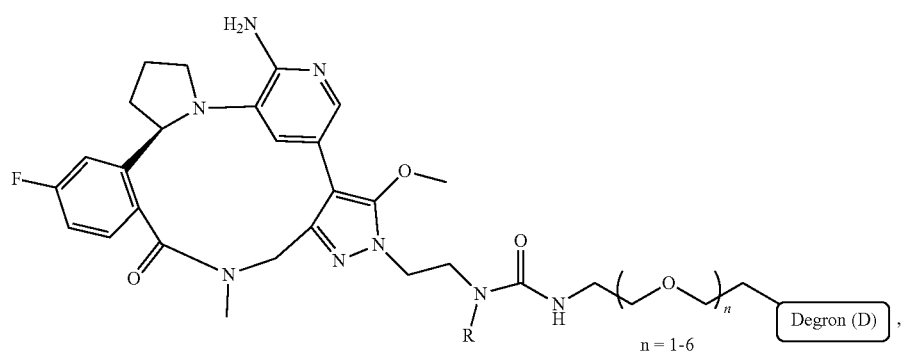
(TL2b3-L10a)
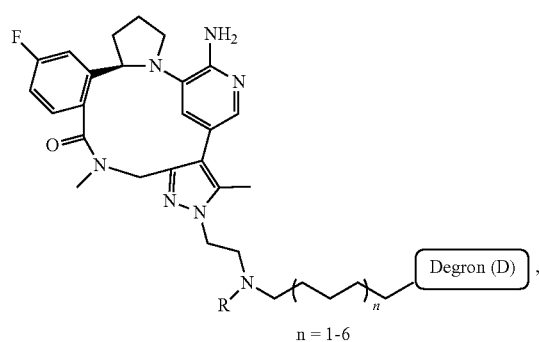
(TL2b3-L10b)
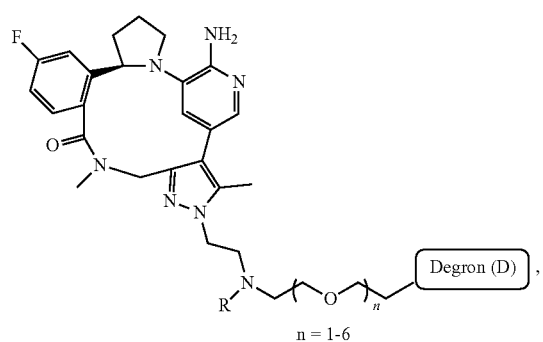

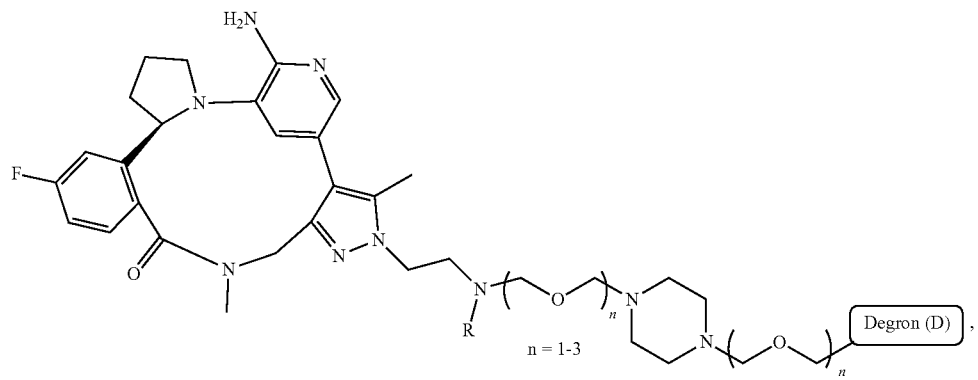
(TL2b3-L10c)
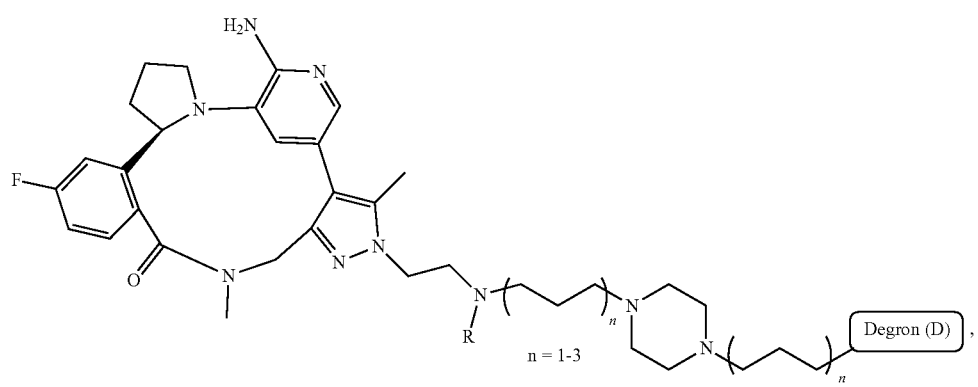
(TL2b3-L10d)
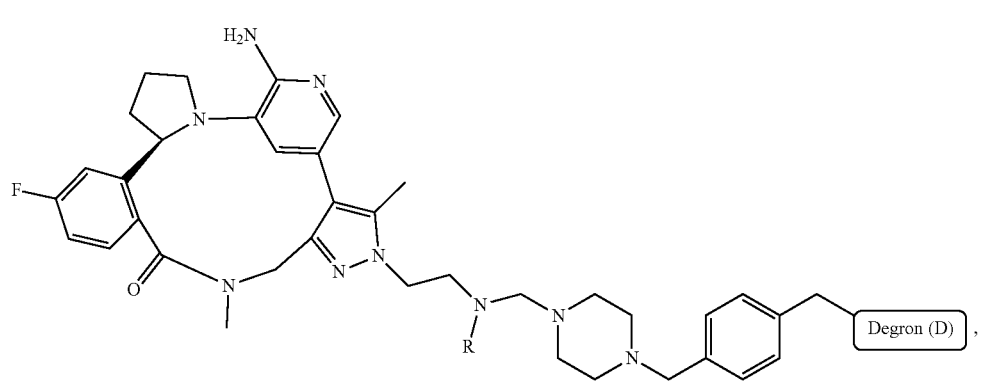
(TL2b3-L10e)
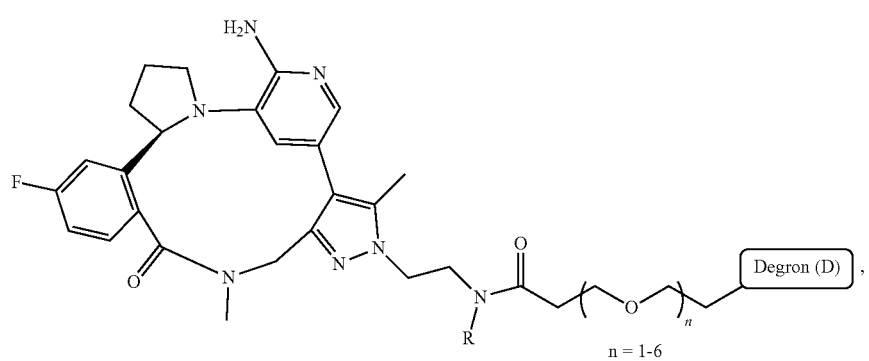
(TL2b3-L10f)

(TL2b3-L10g)
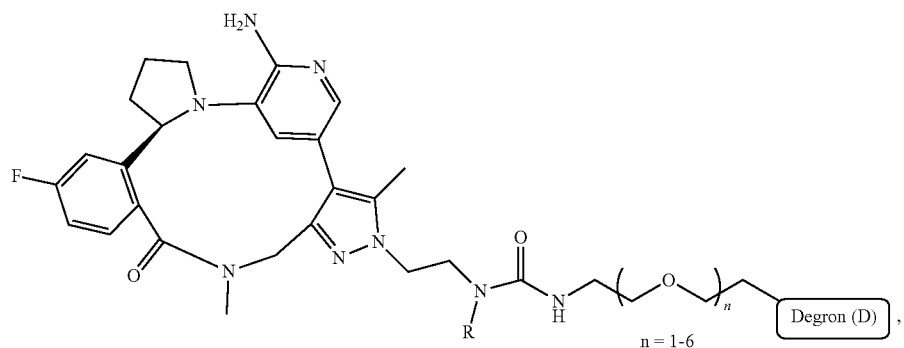
(TL2b4-L10a)
(TL2b4-L10b)
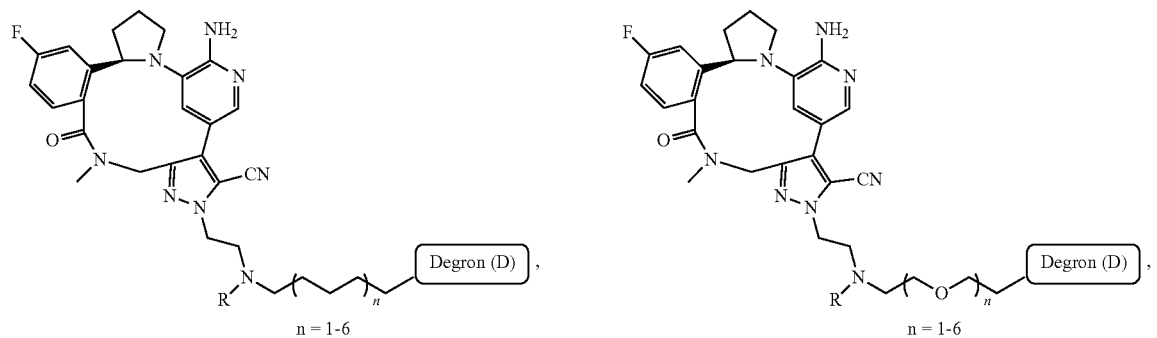
(TL2b4-L10c)
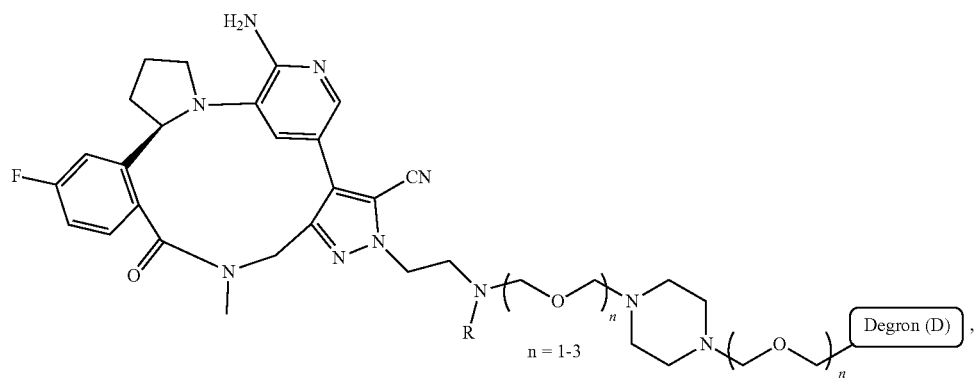
(TL2b4-L10d)
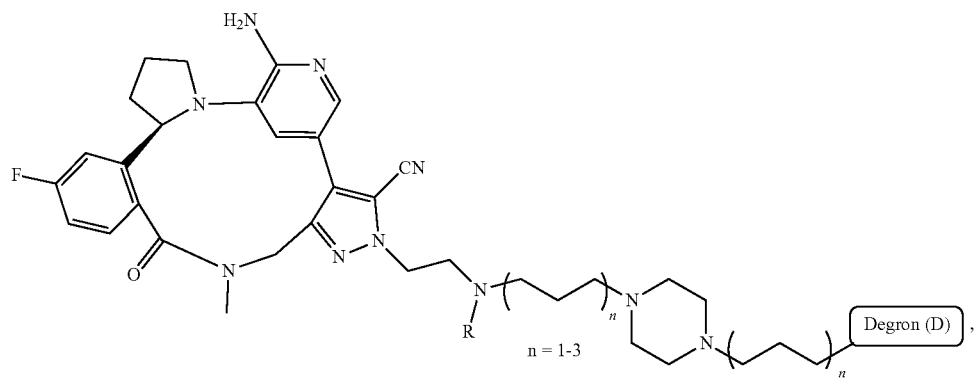

(TL2b4-L10e)
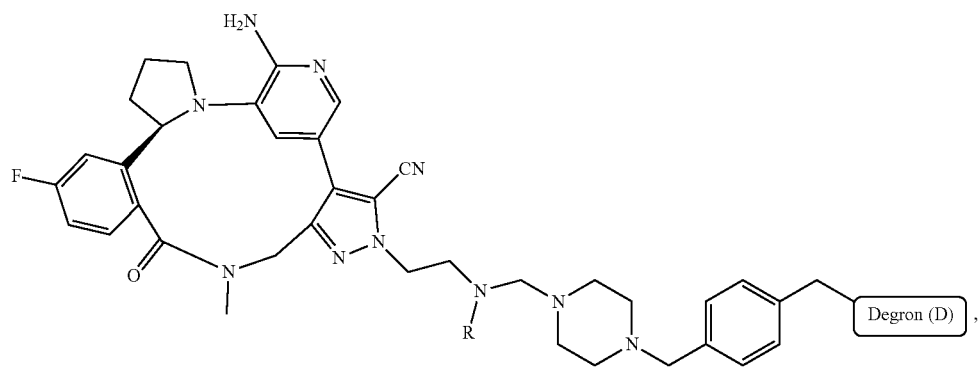
(TL2b4-L10f)
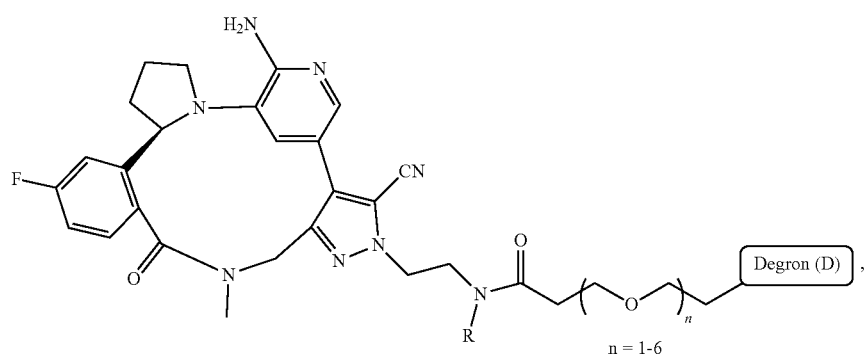
(TL2b4-L10g)
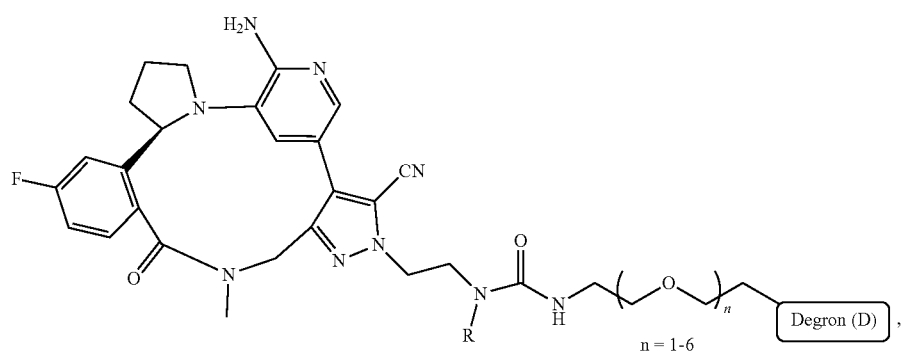
(TL2b5-L10a)
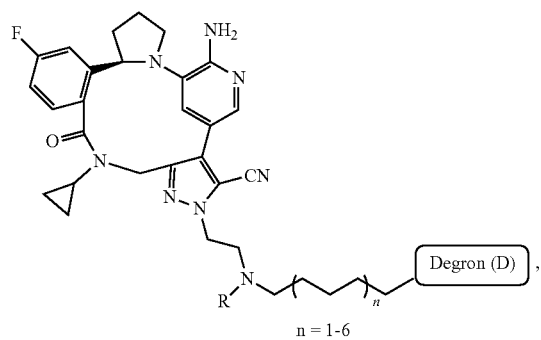
(TL2b5-L10b)
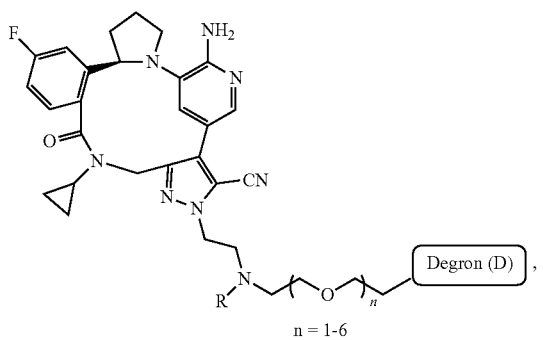

(TL2b5-L10c)
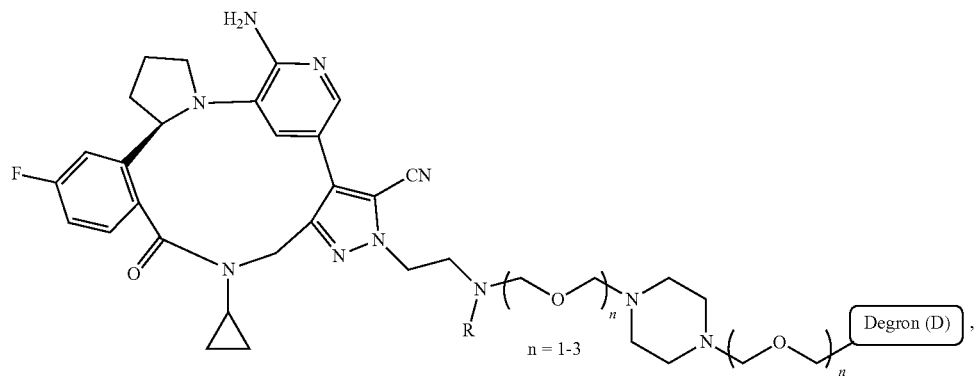
(TL2b5-L10d)
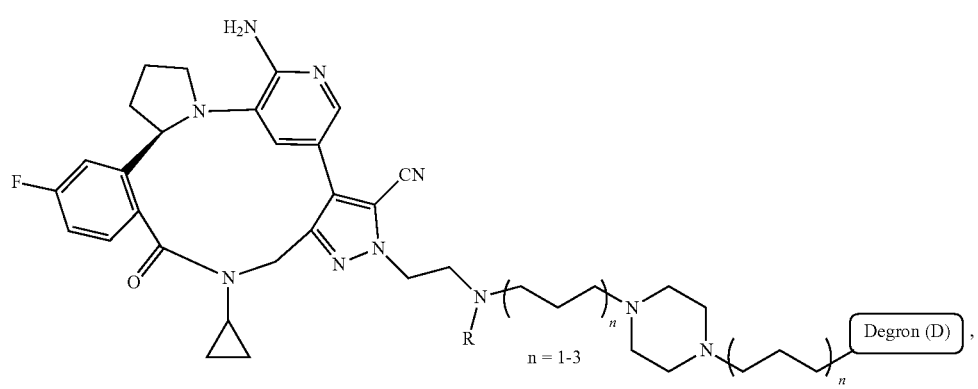
(TL2b5-L10e)
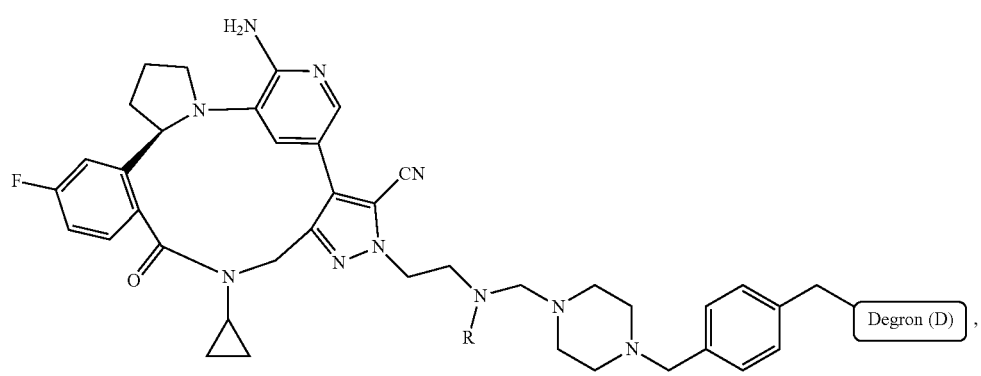
(TL2b5-L10f)
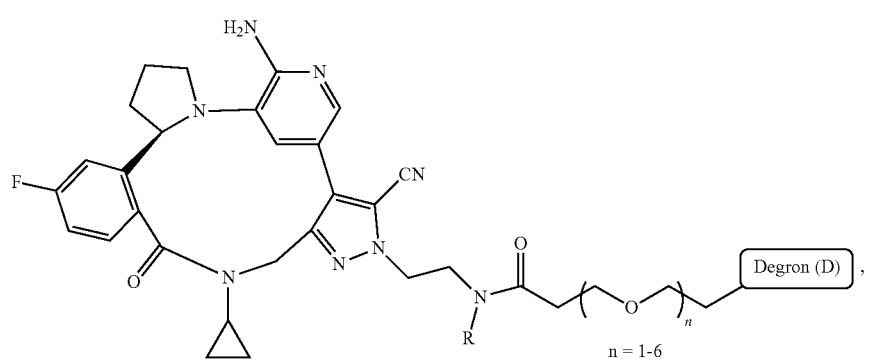

-continued
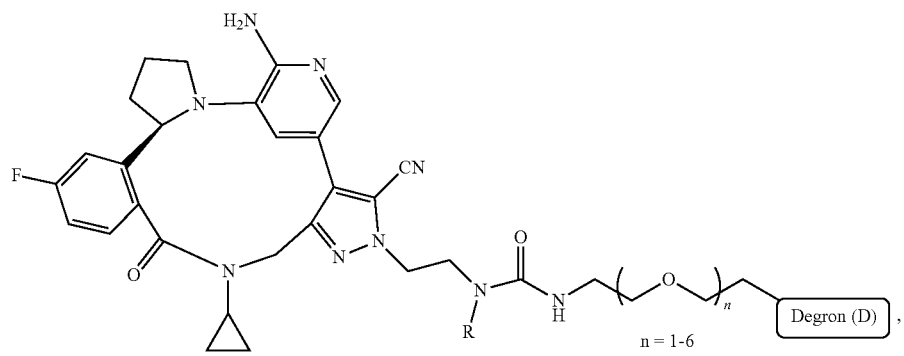
(TL2b5-L10g)
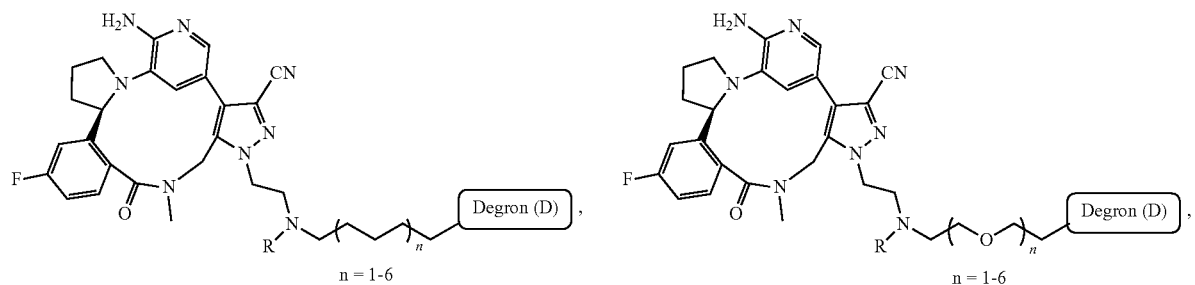
(TL2b6-L10a), (TL2b6-L10b)
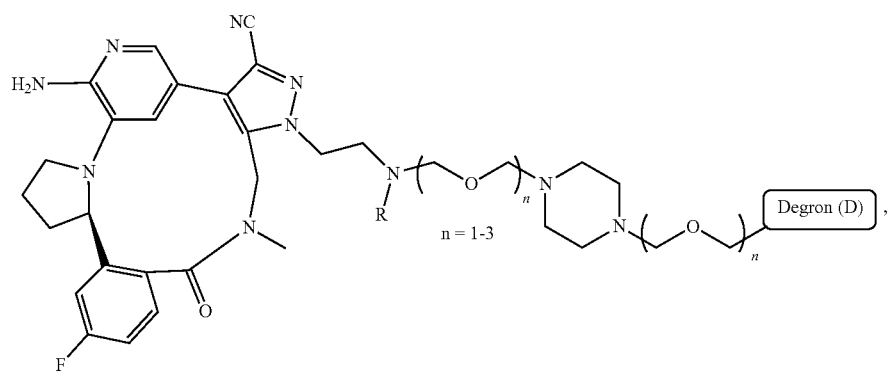
(TL2b6-L10c)
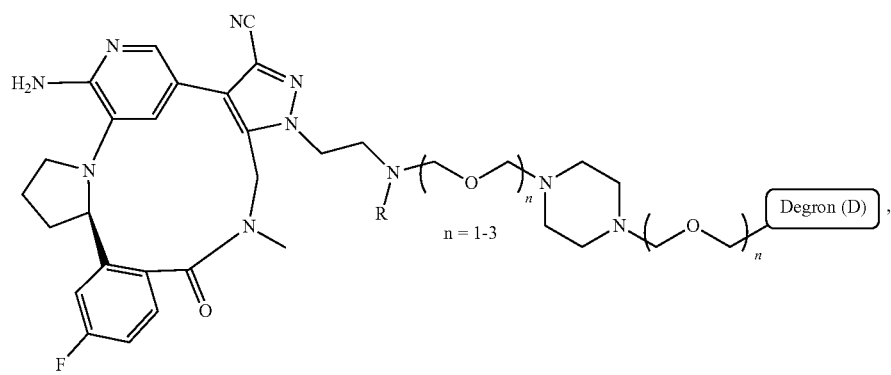
(TL2b6-L10d)

-continued
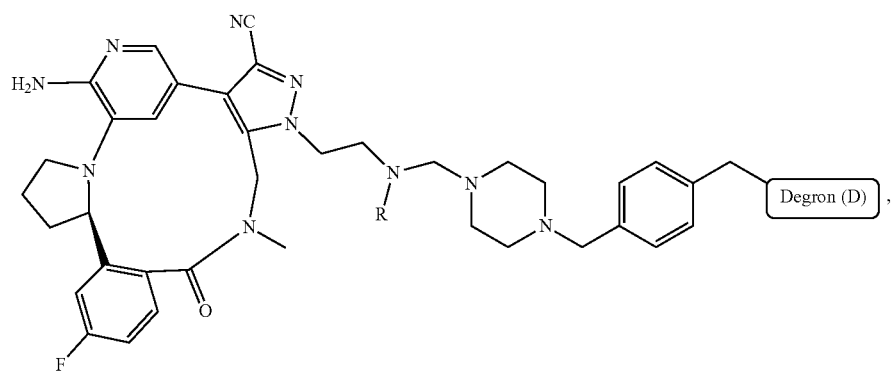
(TL2b6-L10e)
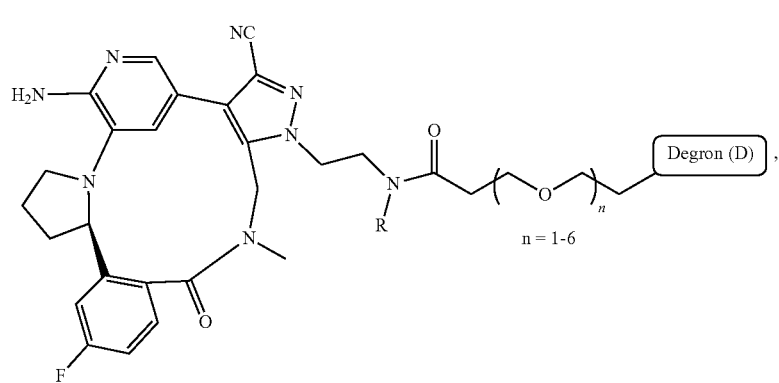
(TL2b6-L10f)
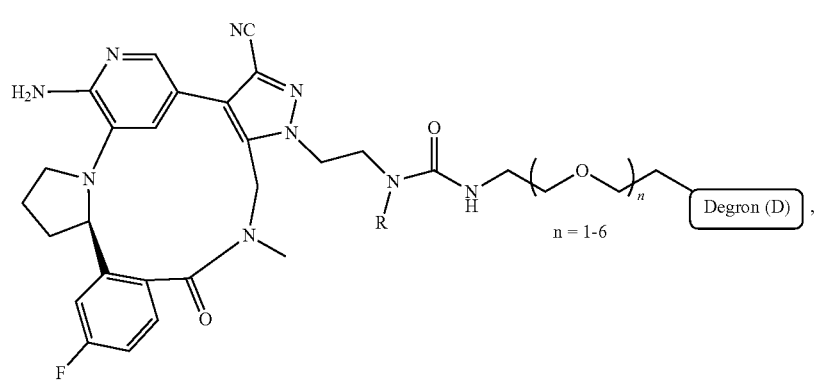
(TL2b6-L10g)
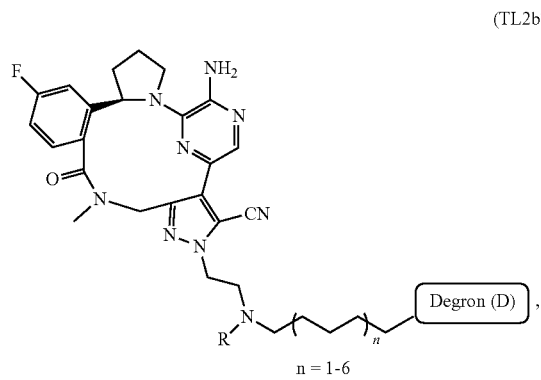
(TL2b7-L10a)
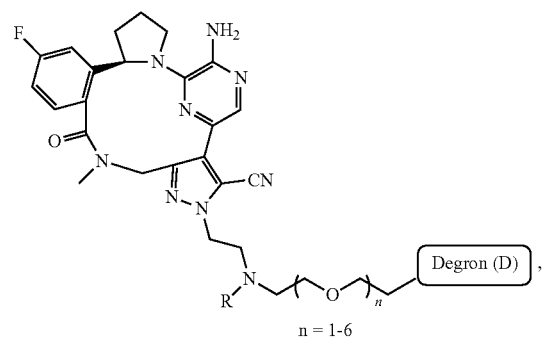
(TL2b7-L10b)

-continued
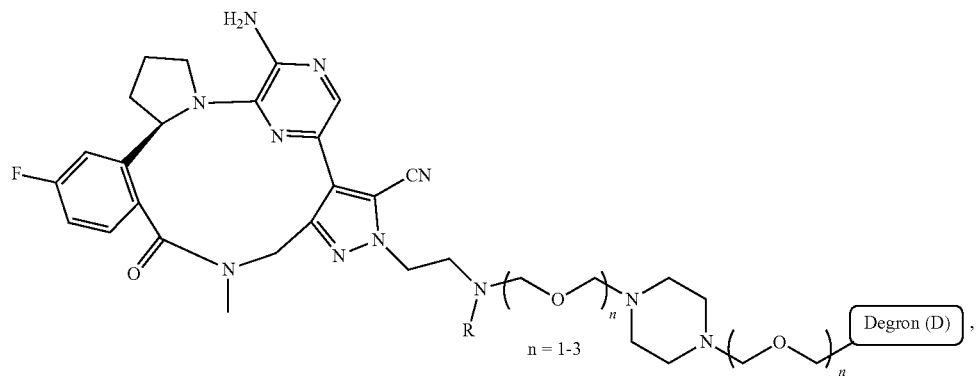
(TL2b7-L10c)
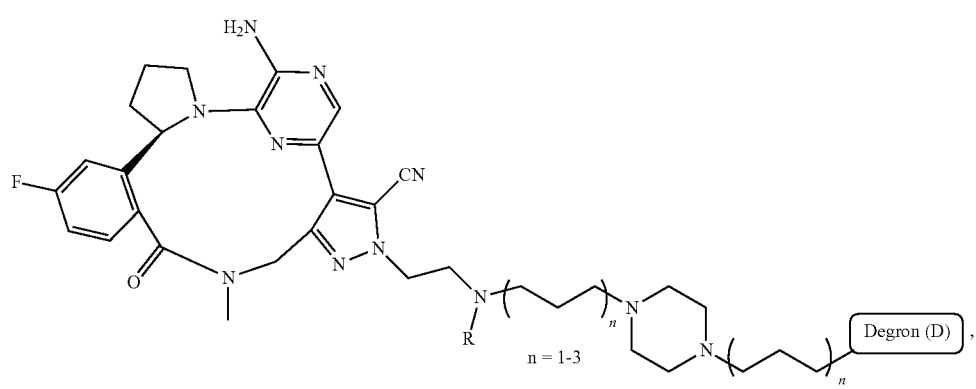
(TL2b7-L10d)
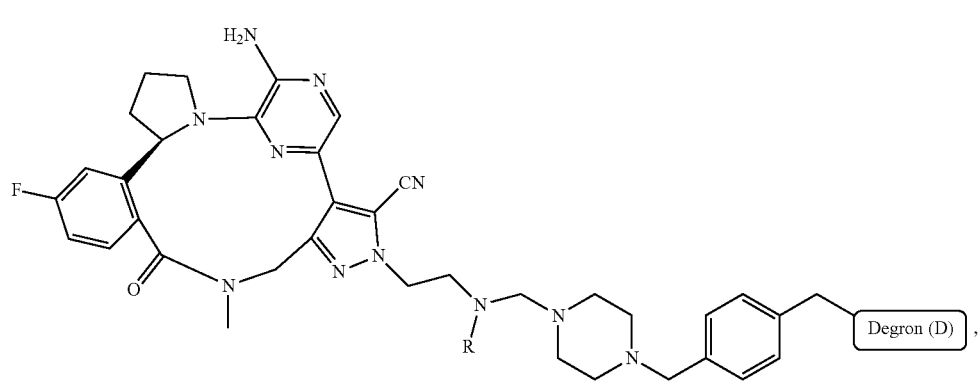
(TL2b7-L10e)
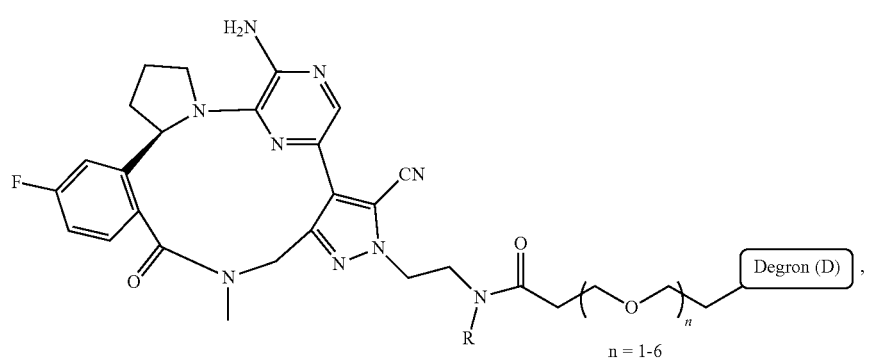
(TL2b7-L10f)

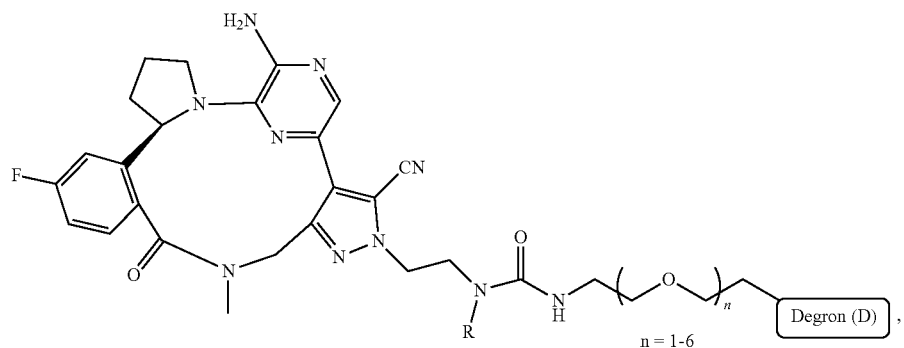
(TL2b7-L10g)
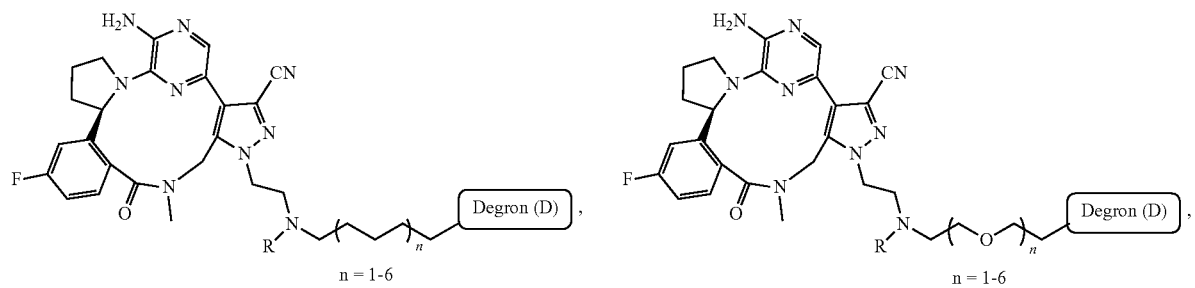
(TL2b8-L10a) (TL2b8-L10b)
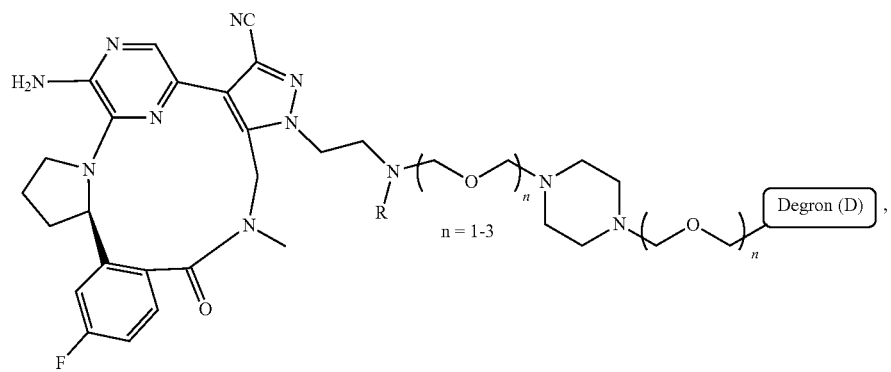
(TL2b8-L10c)
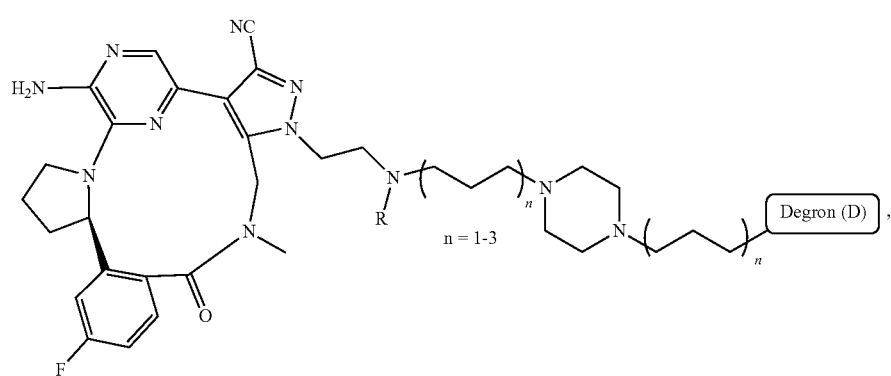
(TL2b8-L10d)

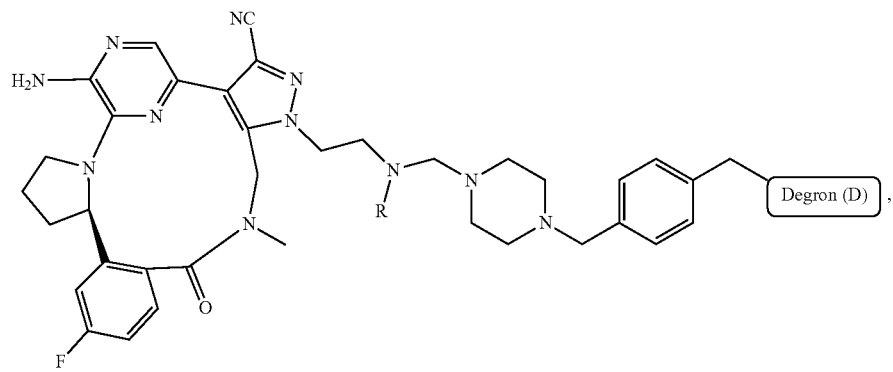
(TL2b8-L10e)
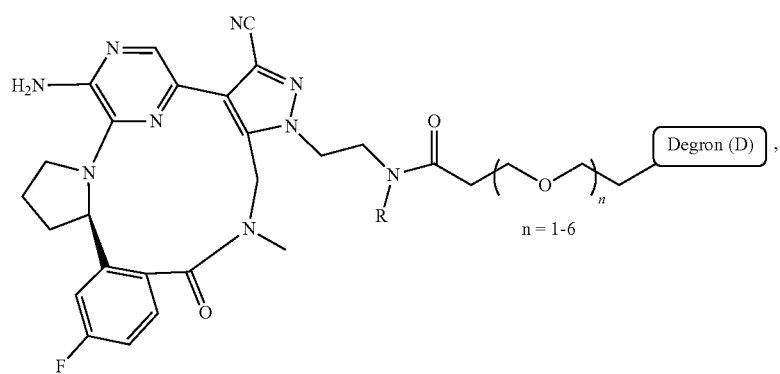
(TL2b8-L10f)
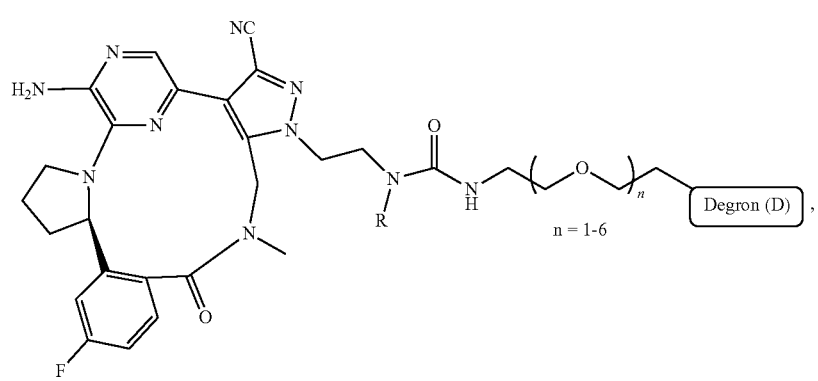
(TL2b8-L10g)
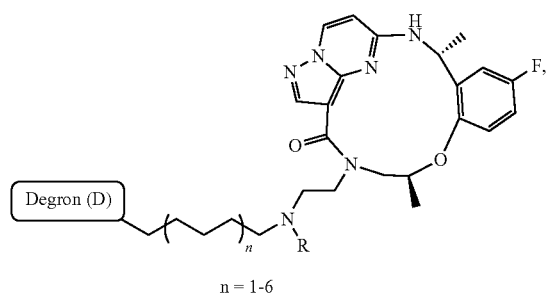
(TL3-L10a)
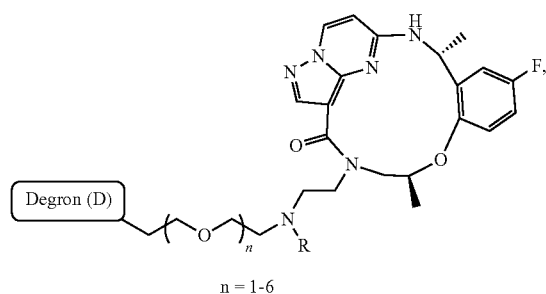
(TL3-L10b)

-continued
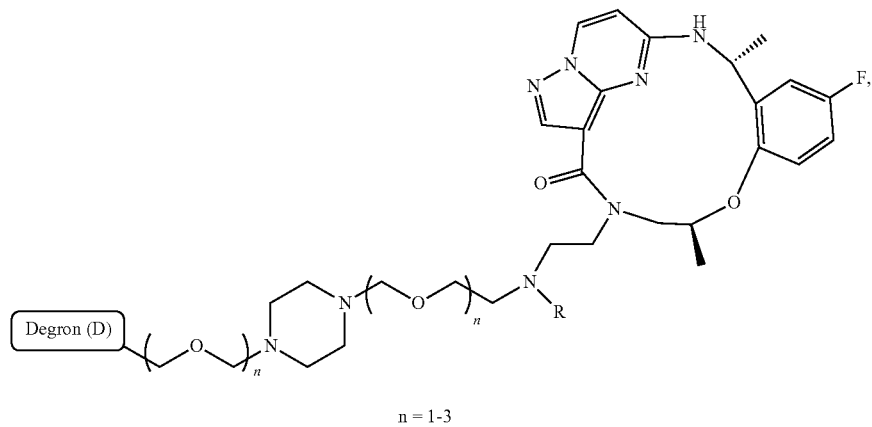
(TL3-L10c)
n = 1-3
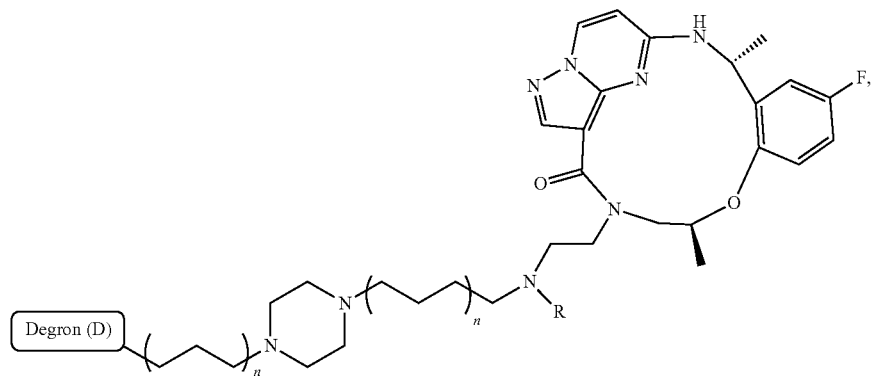
(TL3-L10d)
n = 1-3
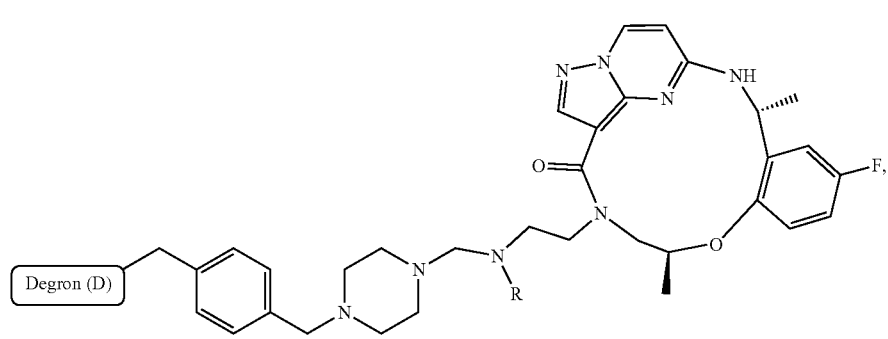
(TL3-L10e)
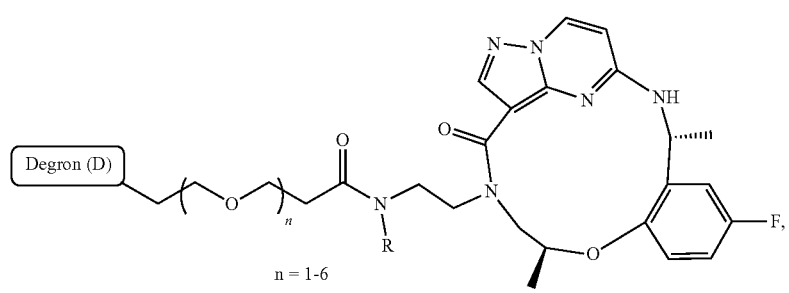
(TL3-L10f)
n = 1-6

(TL3-L10g)
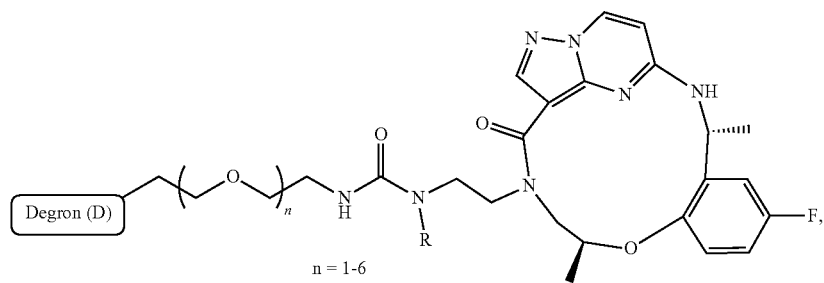
(TL4-L10a)
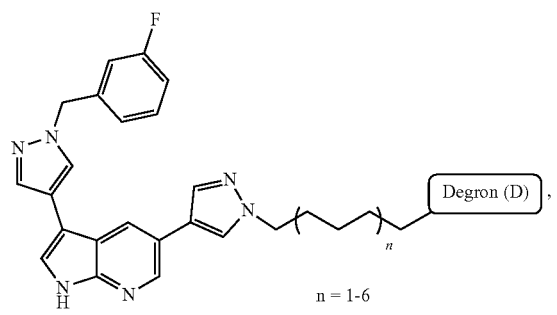
(TL4-L10b)
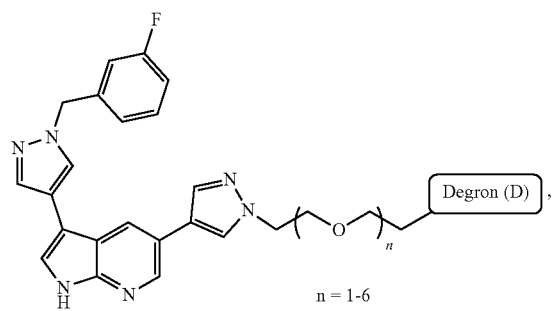
(TL4-L10c)
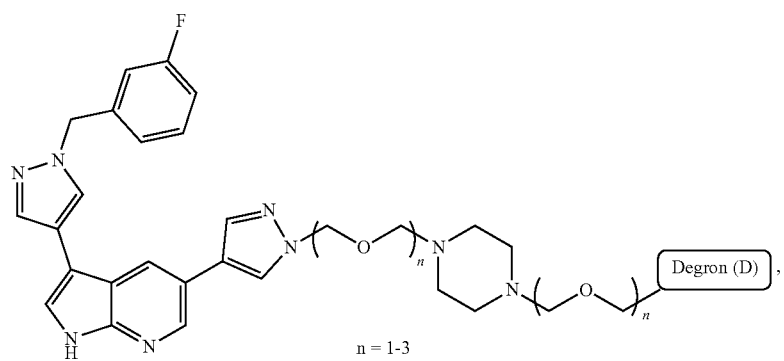
(TL4-L10d)
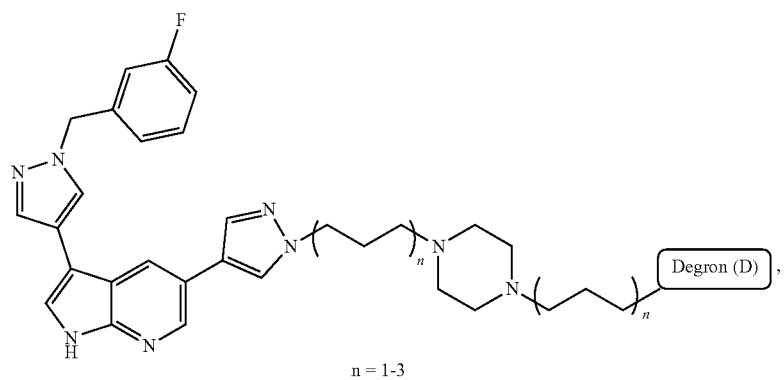

-continued
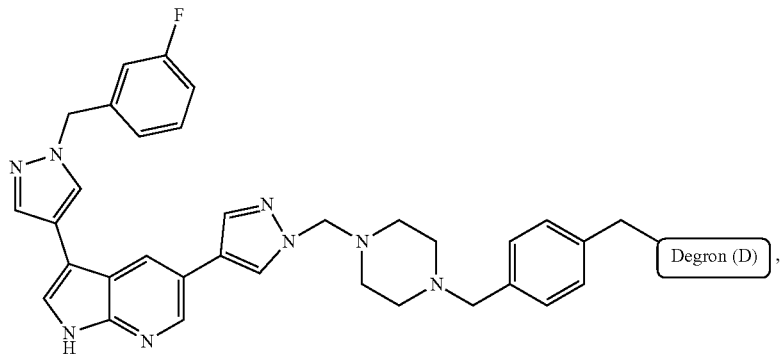
(TL4-L10e)
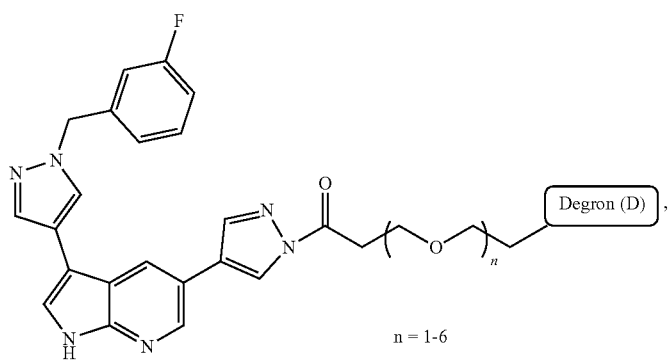
n = 1-6
(TL4-L10f)
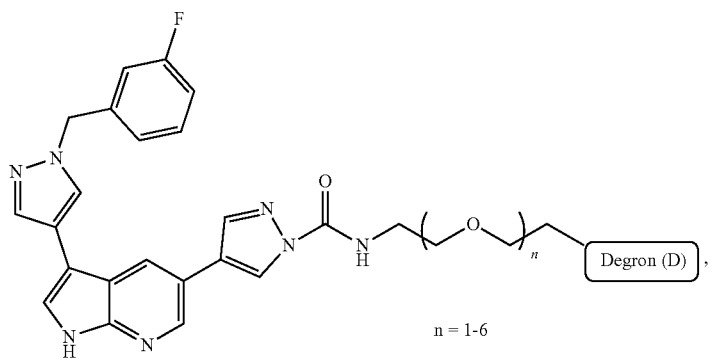
n = 1-6
(TL4-L10g)
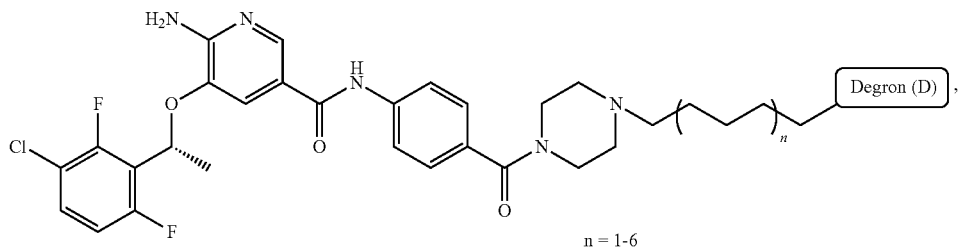
n = 1-6
(TL5-L10a)
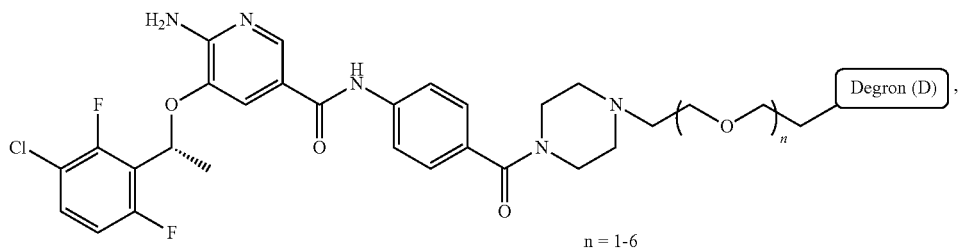
n = 1-6
(TL5-L10b)

-continued

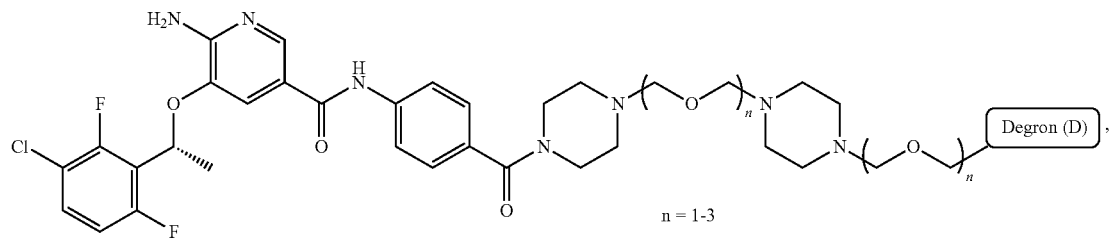
(TL5-L10c)

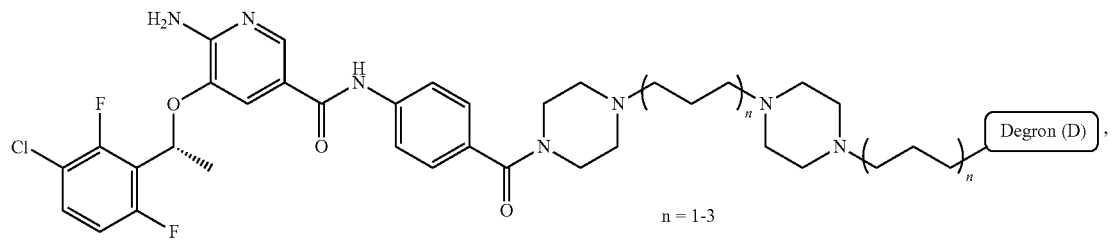
(TL5-L10d)

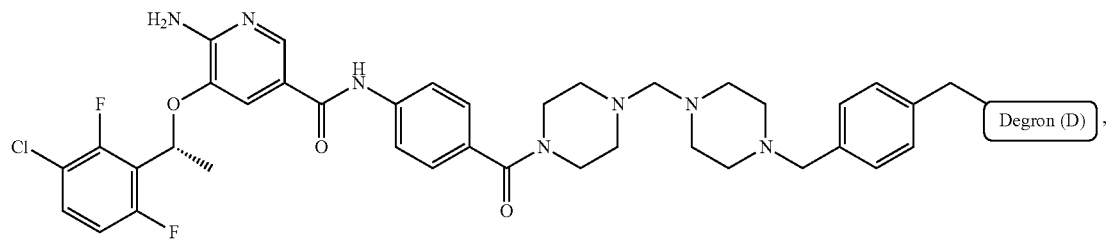
(TL5-L10e)

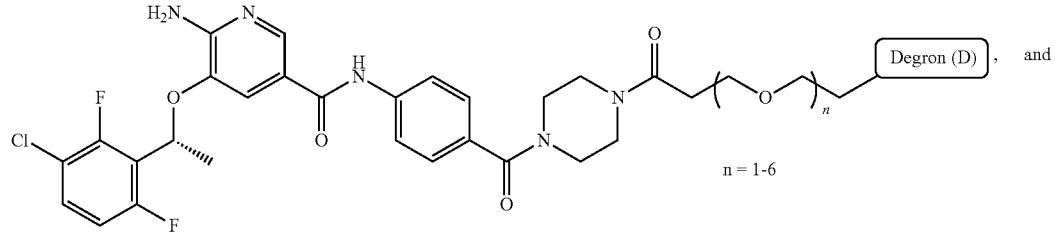
(TL5-L10f)

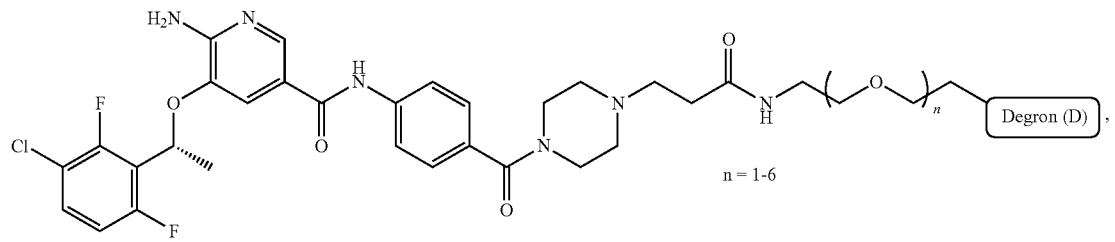
(TL5-L10g)

wherein
R is H or Me,
R₉ is H or Me,
or a pharmaceutically acceptable salt or stereoisomer thereof. In the above formulas where "n" appears twice, the "n" may be the same or different.

Degrons

The Ubiquitin-Proteasome Pathway (UPP) is a critical cellular pathway that regulates key regulator proteins and degrades misfolded or abnormal proteins. UPP is central to multiple cellular processes. The covalent attachment of ubiquitin to specific protein substrates is achieved through the action of E3 ubiquitin ligases. These ligases include over 500 different proteins and are categorized into multiple classes defined by the structural element of their E3 functional activity.

In some embodiments, the degron binds the E3 ubiquitin ligase which is cereblon (CRBN). Representative examples of degrons that bind CRBN are represented by any one of the following structures.

(D1-a) 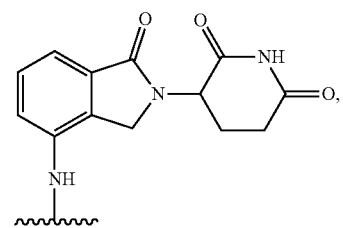
(D1-b) 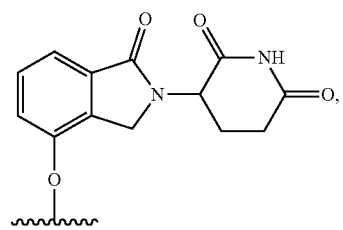
(D1-c) 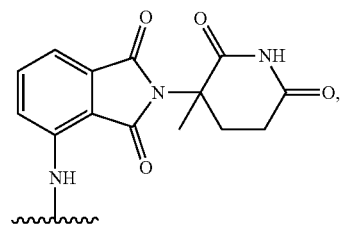
(D1-d) 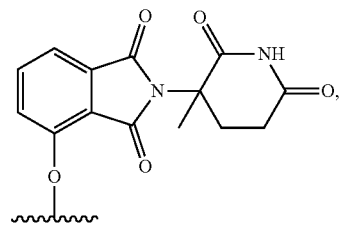
(D1-e) 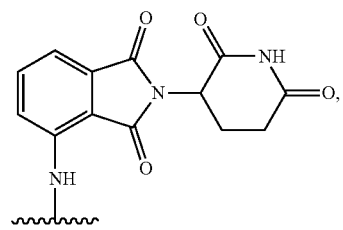
(D1-f) 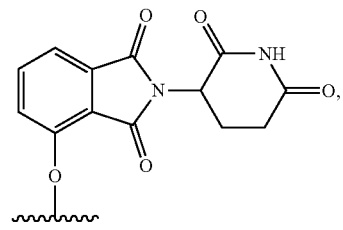
(D1-g) 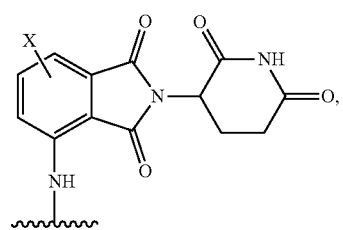
-continued
(D1-h) 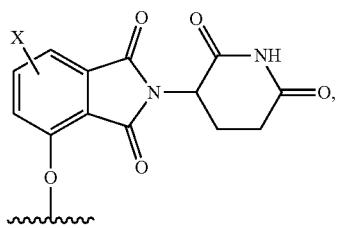
(D1-i) 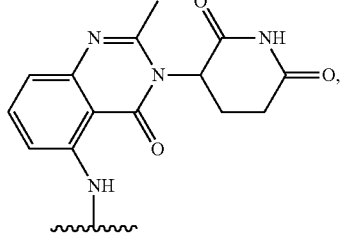
(D1-j) 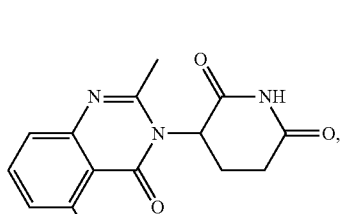
(D1-k) 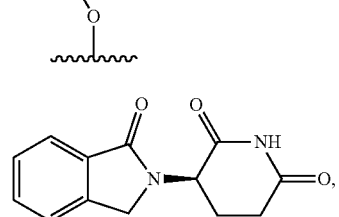
(D1-l) 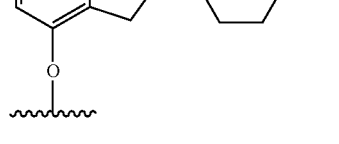
(D1-m) 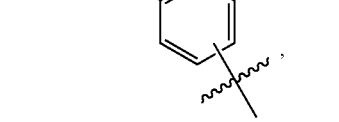

-continued
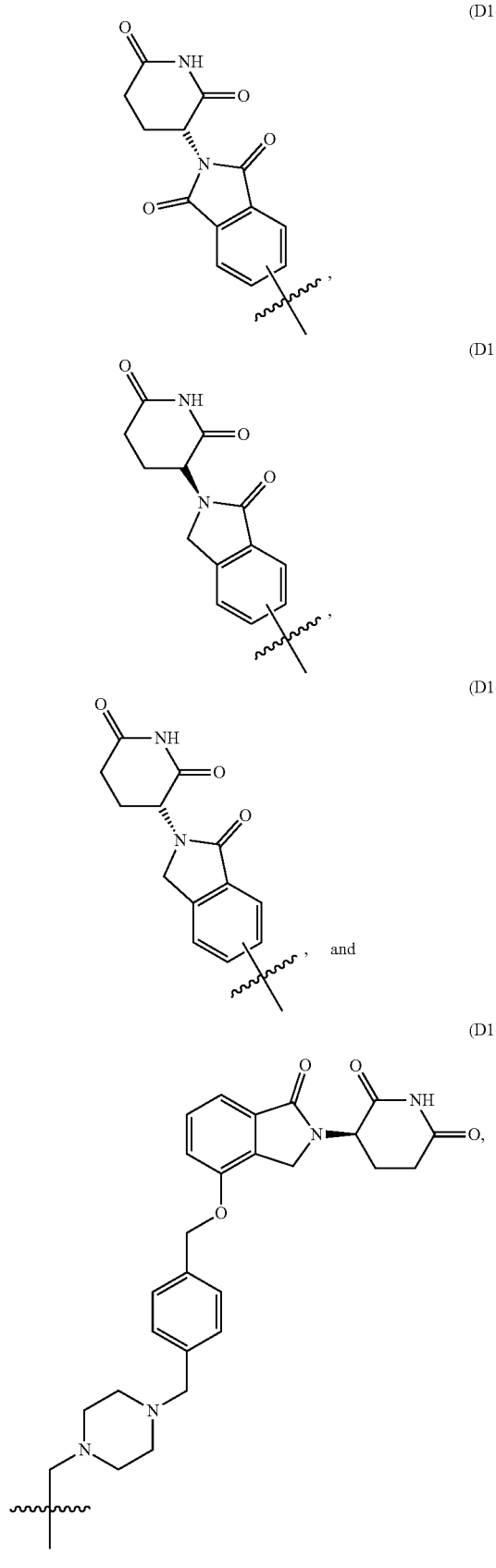
wherein X is alkyl, halo, CN, CF$_3$, OCHF$_2$ or OCF$_3$.
Thus, in some embodiments, the bispecific compounds of the present invention may be represented by any one of the following structures:
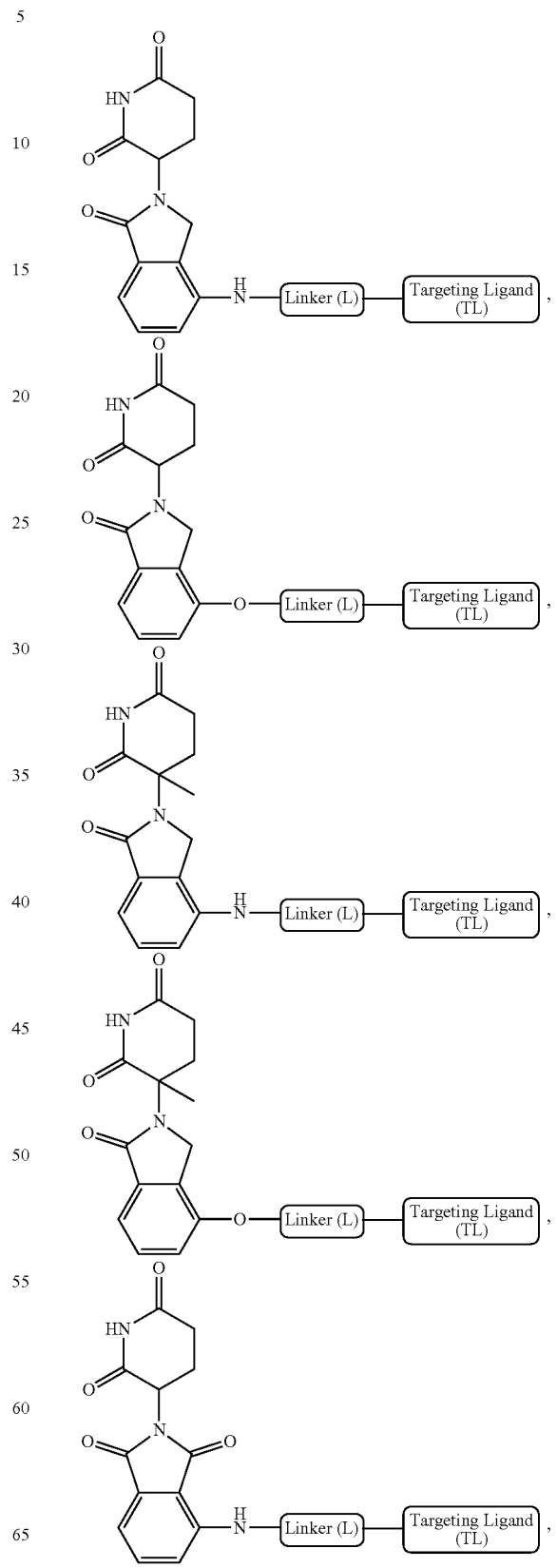

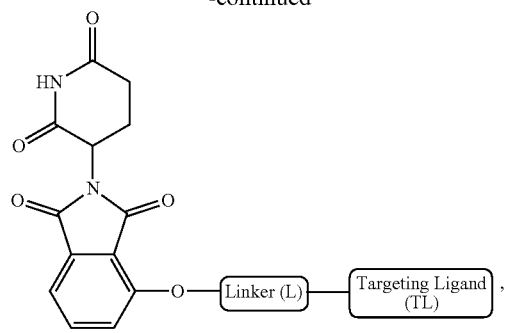
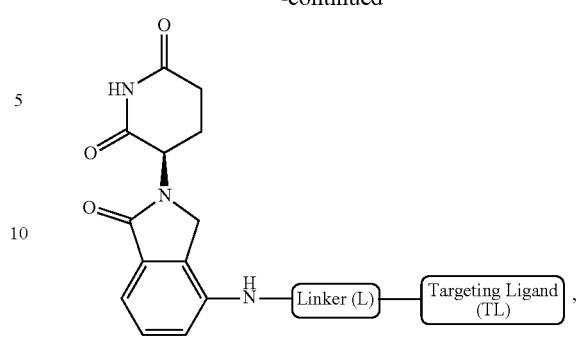
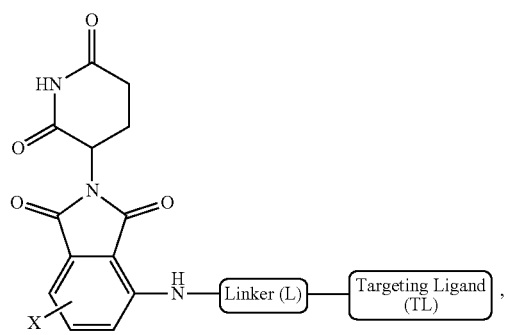
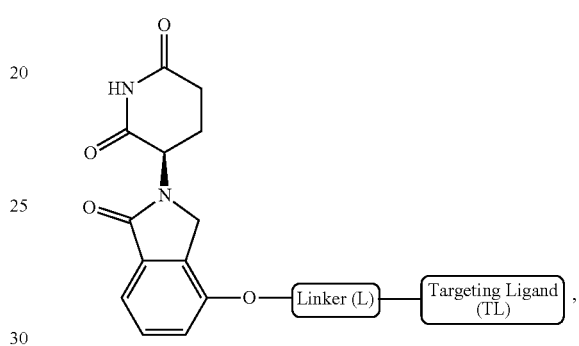
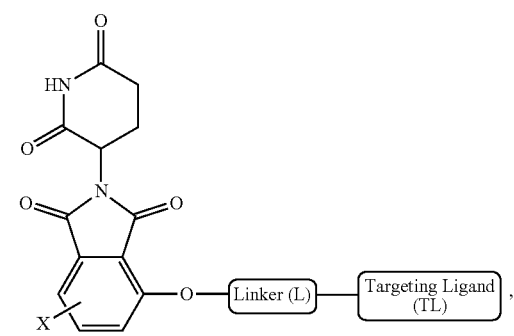
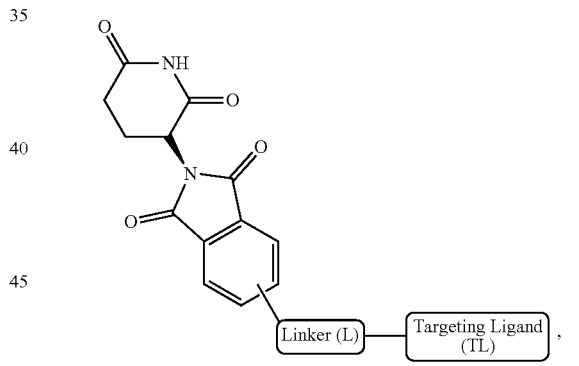
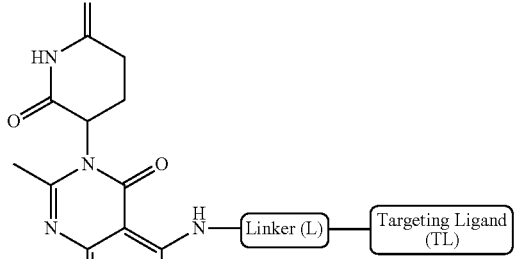
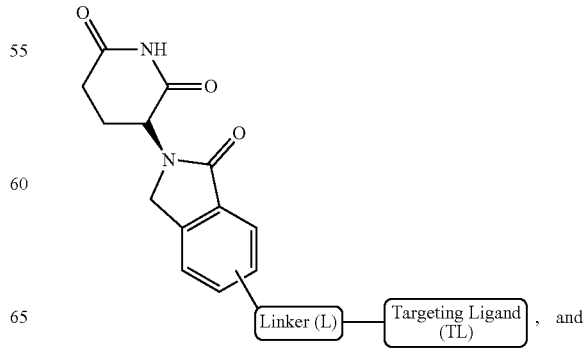, and
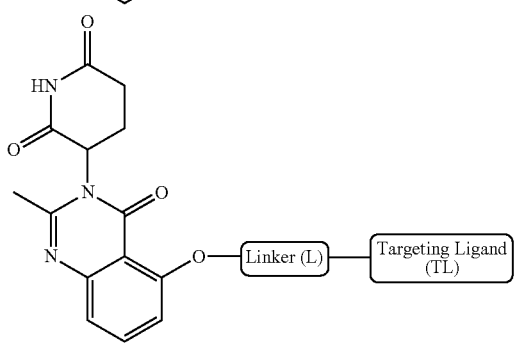

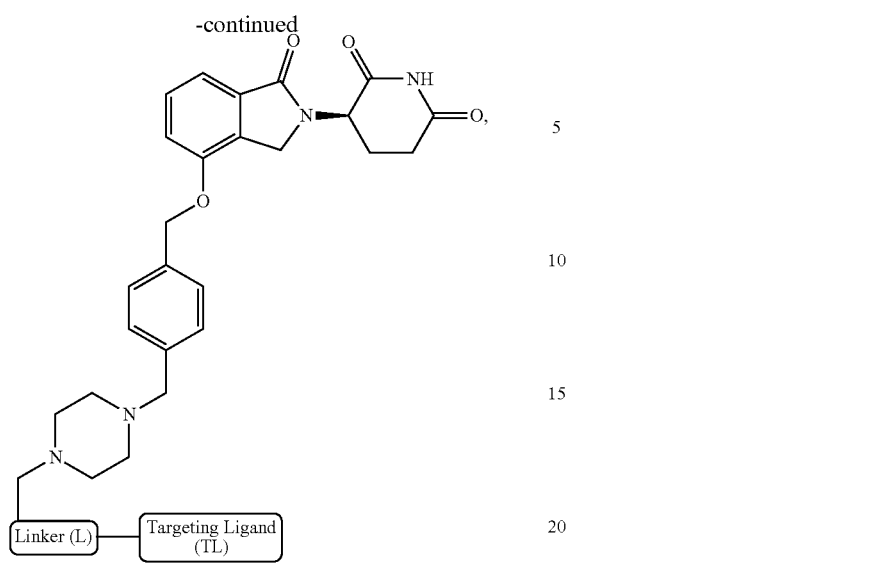
wherein X is alkyl, halo, CN, CF$_3$, OCHF$_2$ or OCF$_3$, or a pharmaceutically acceptable salt or stereoisomer thereof.
In some embodiments, the bispecific compounds of the present invention are represented by any one of the following structures:
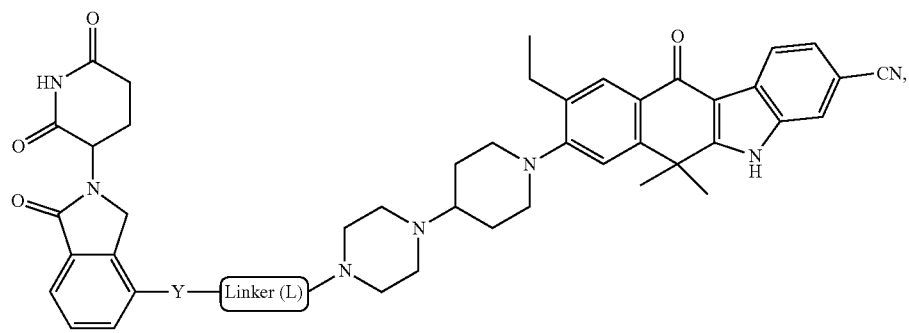
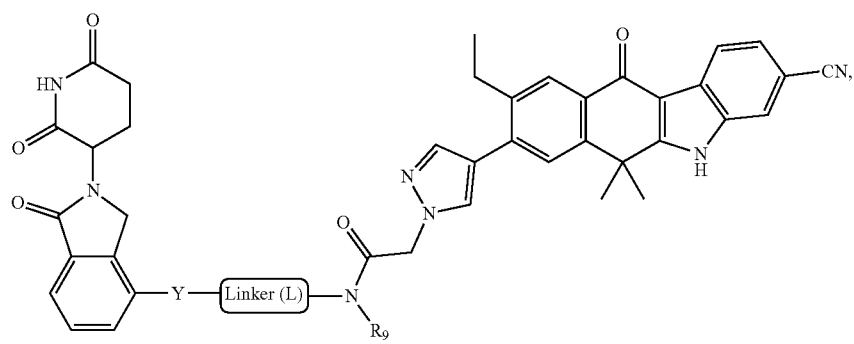

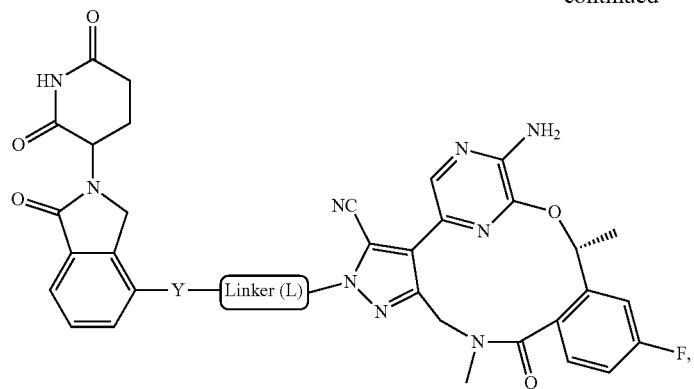
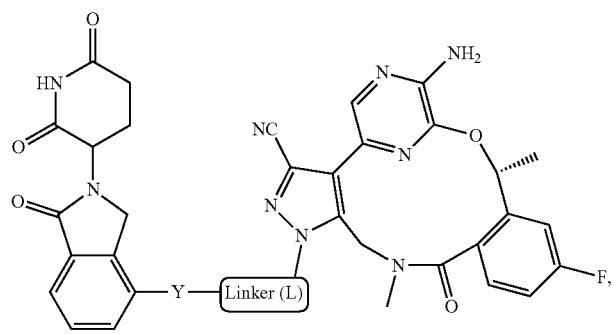
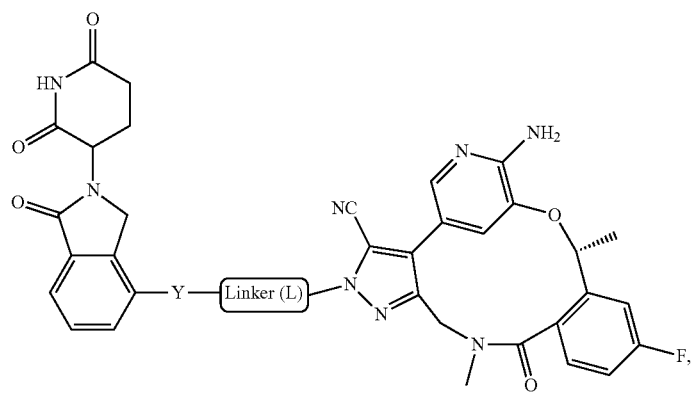
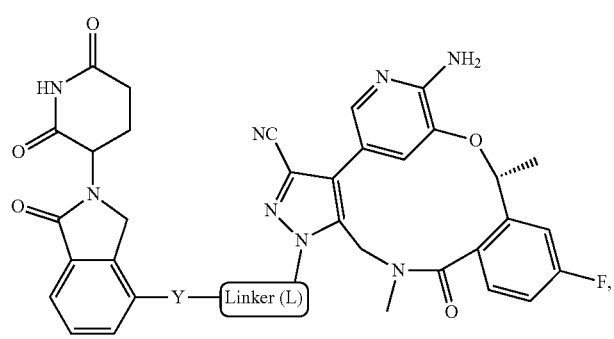

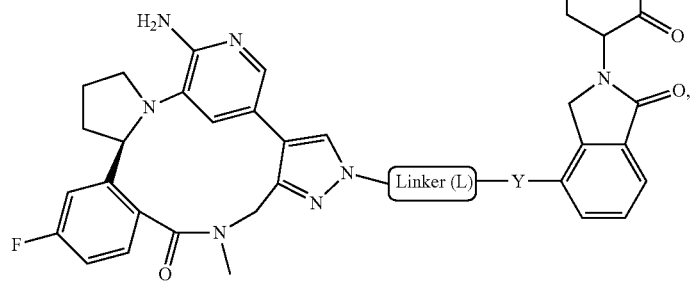
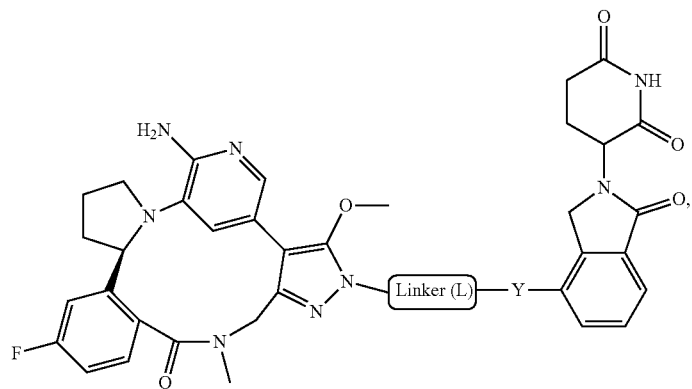
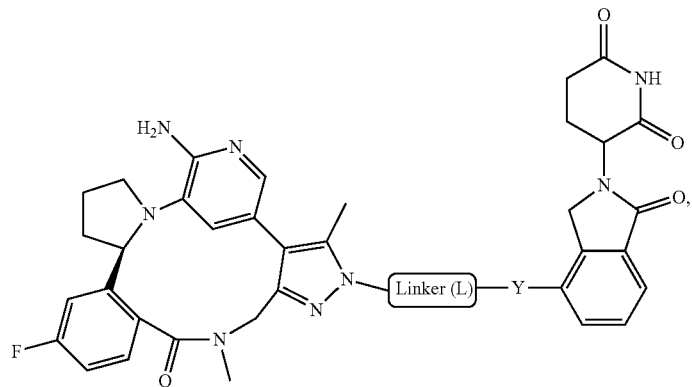
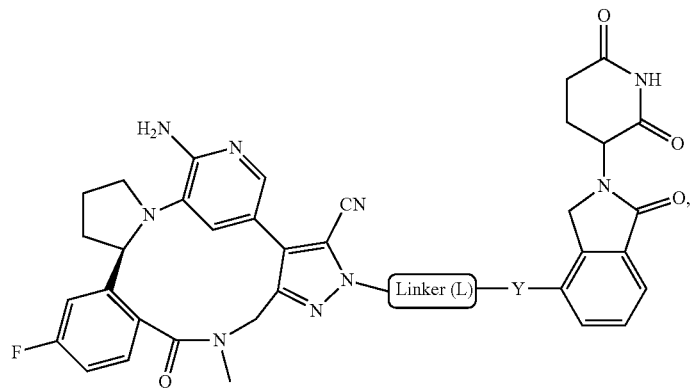

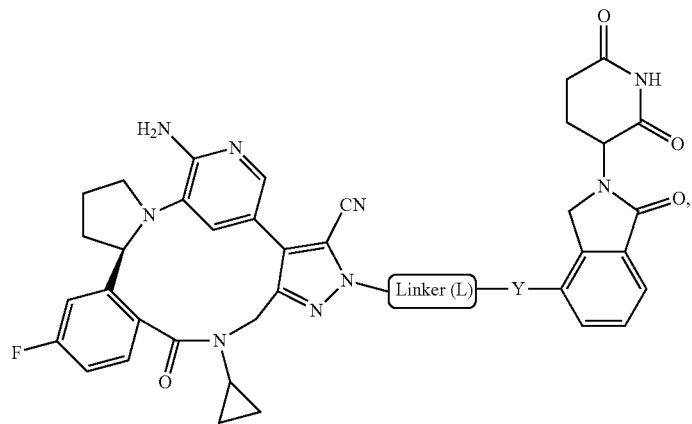
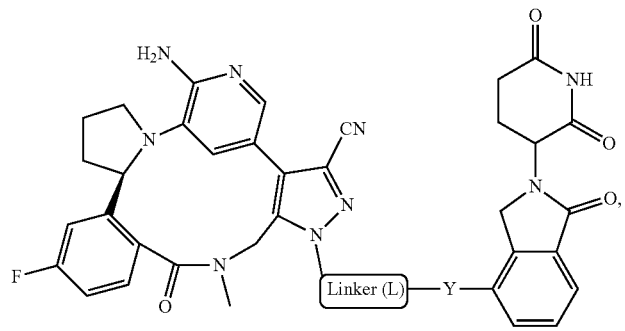
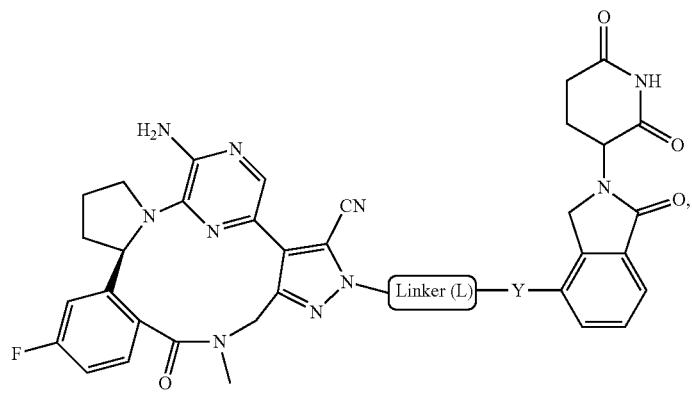
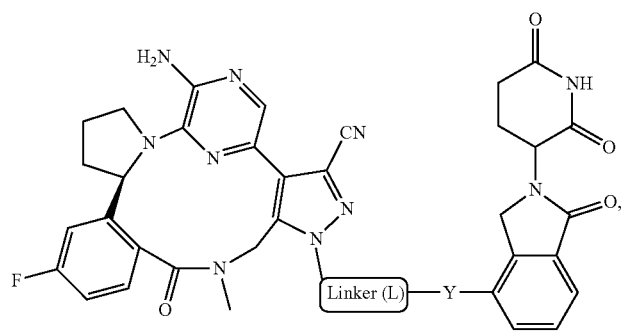

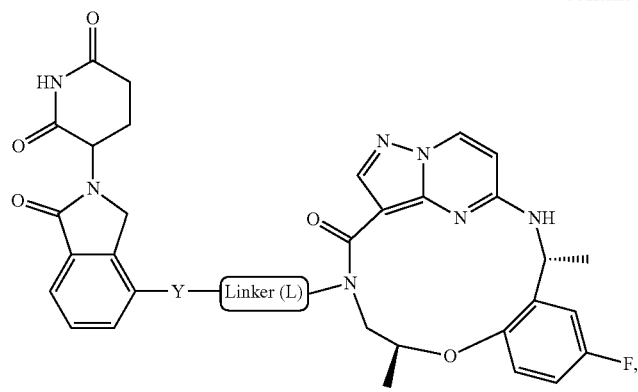
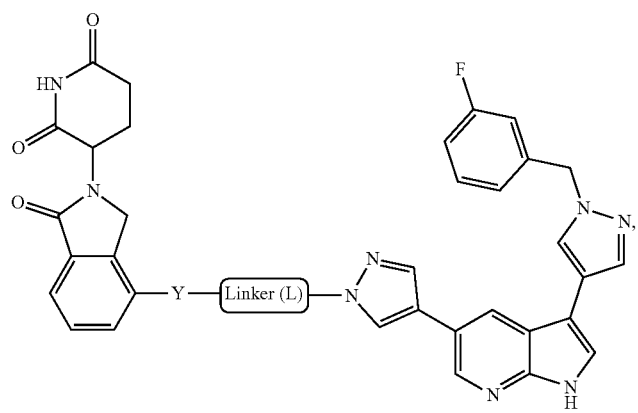
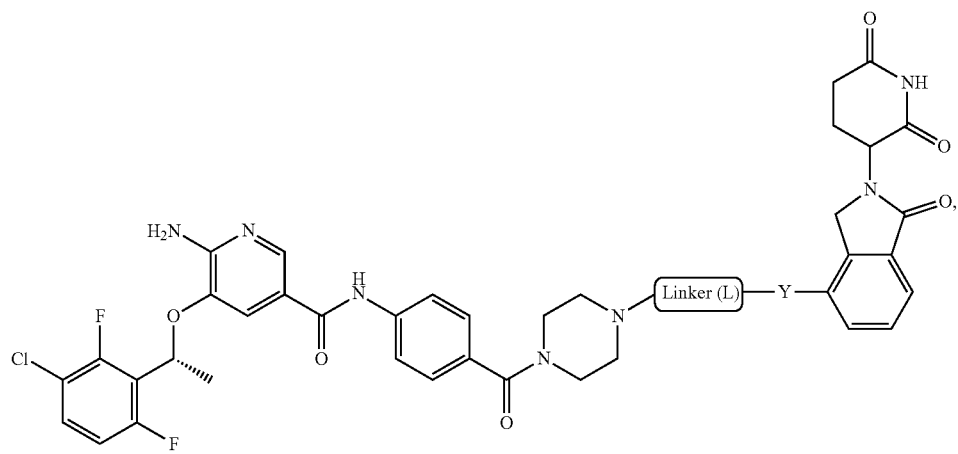
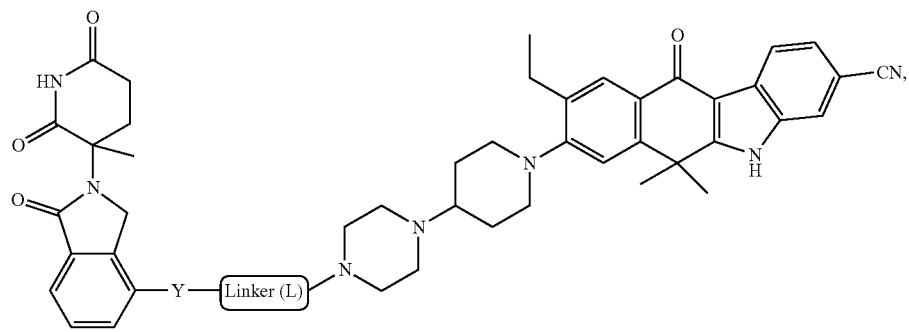

-continued
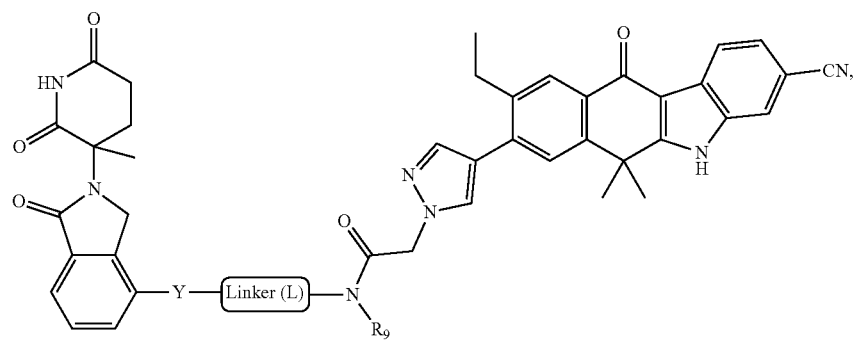
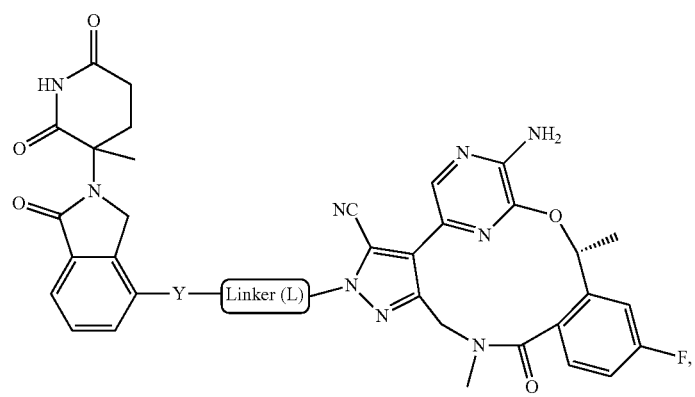
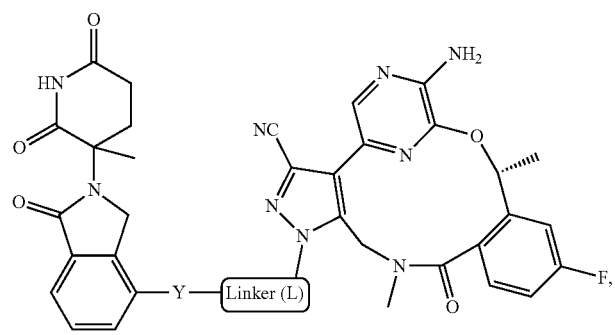
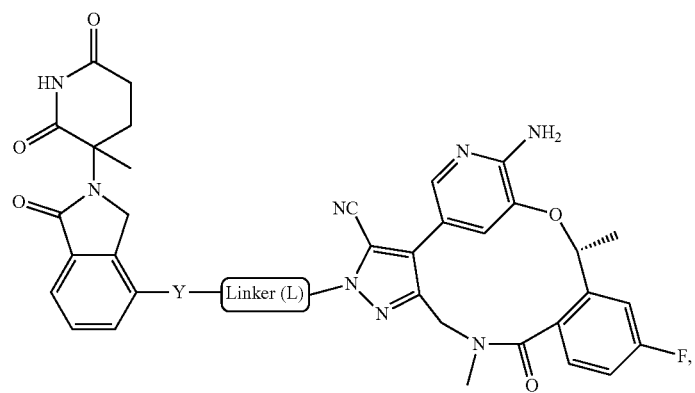

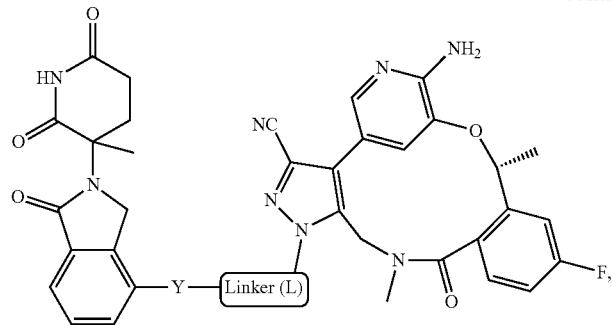
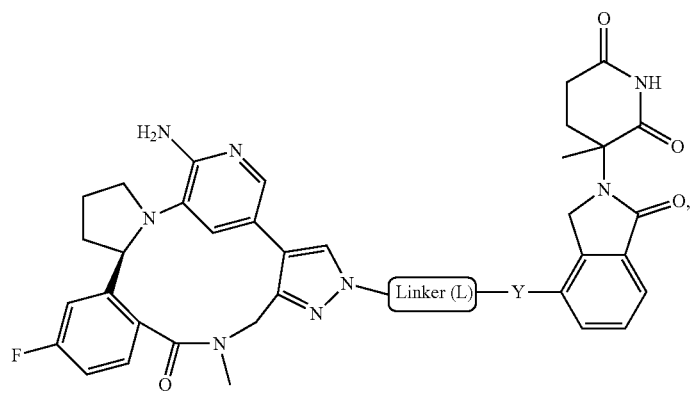
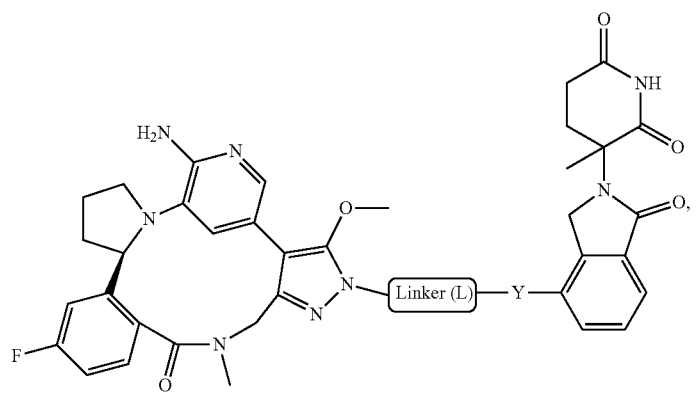
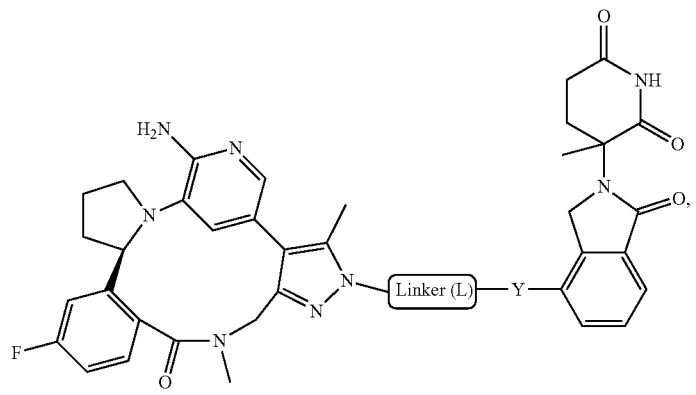

-continued
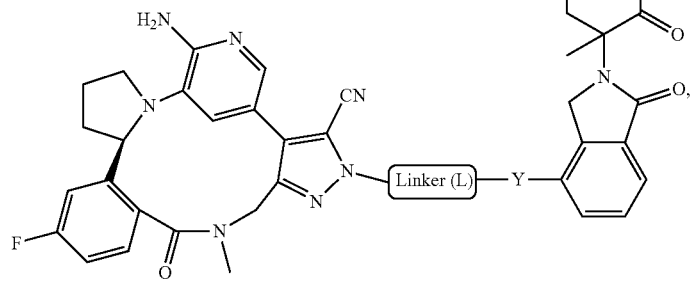
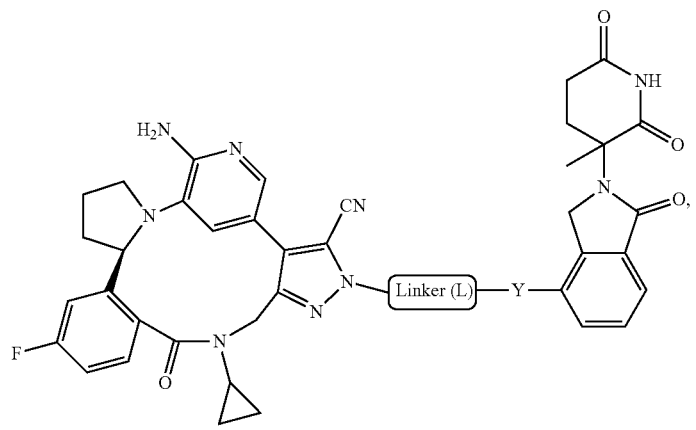
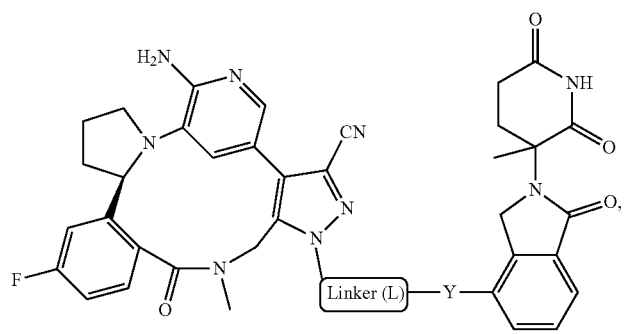
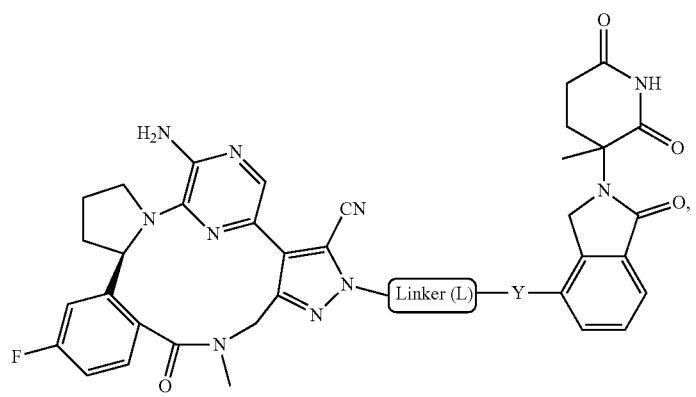

-continued
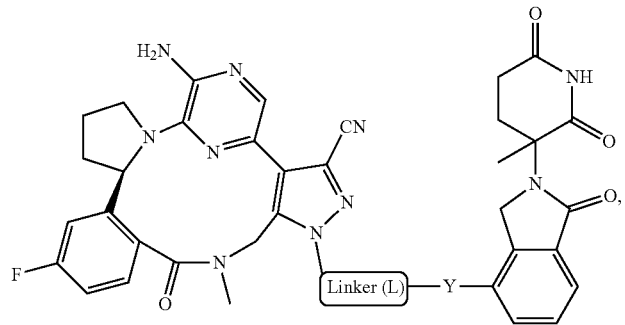
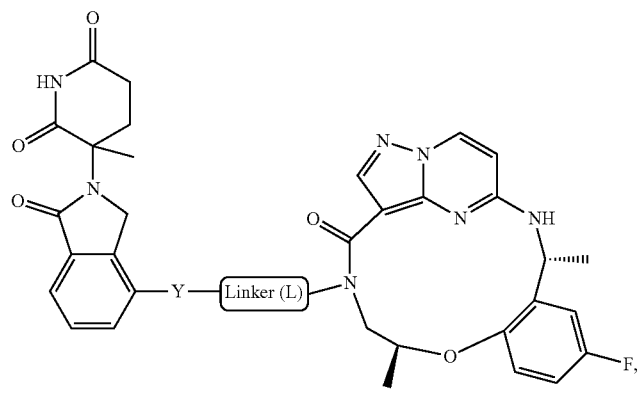
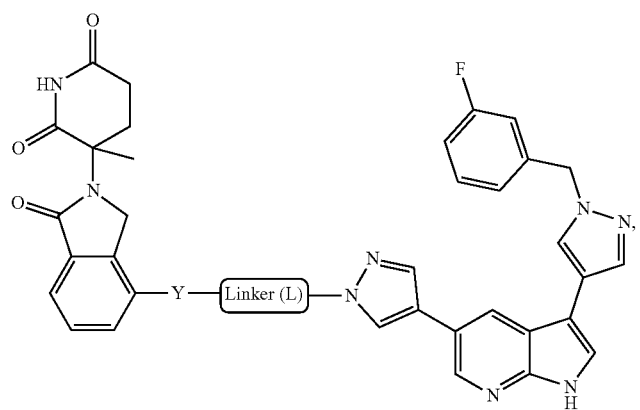
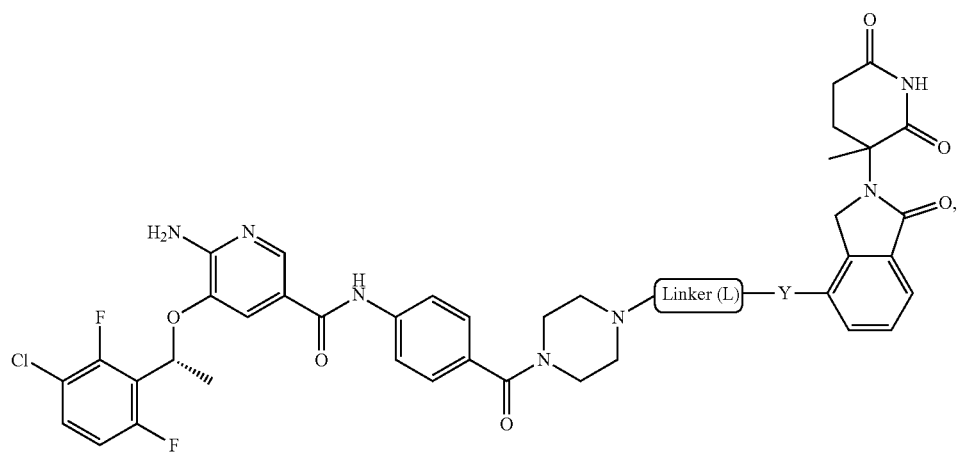

-continued
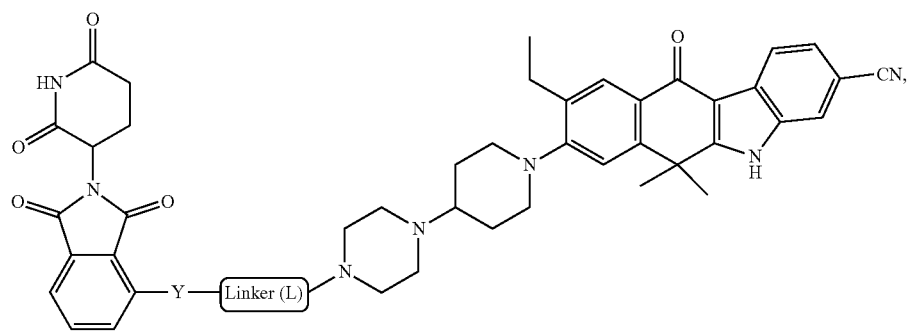
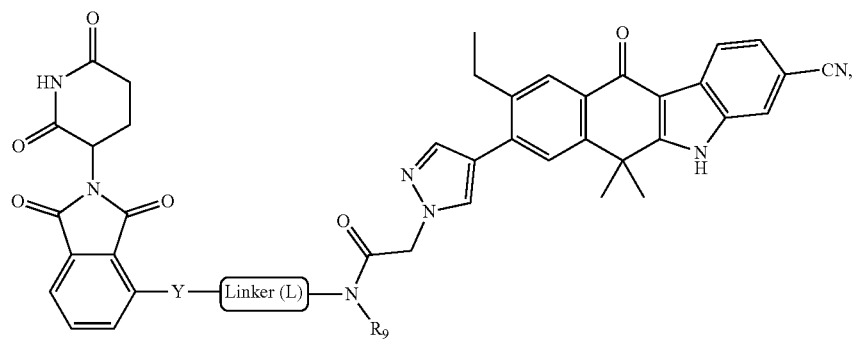
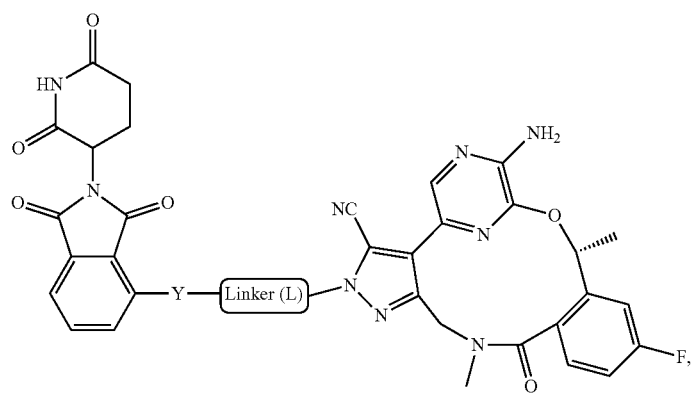
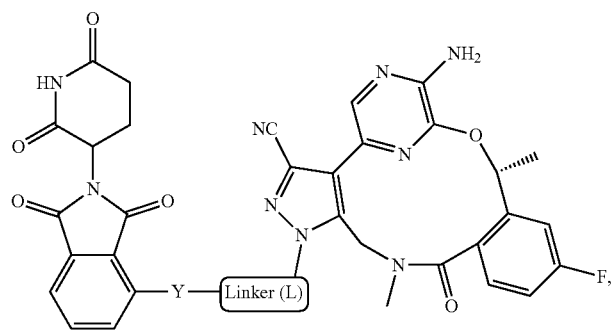

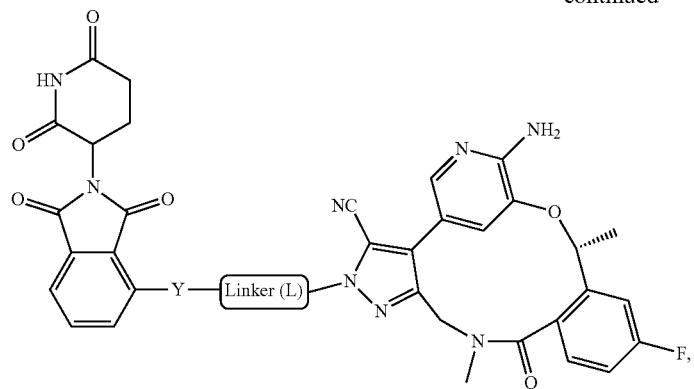
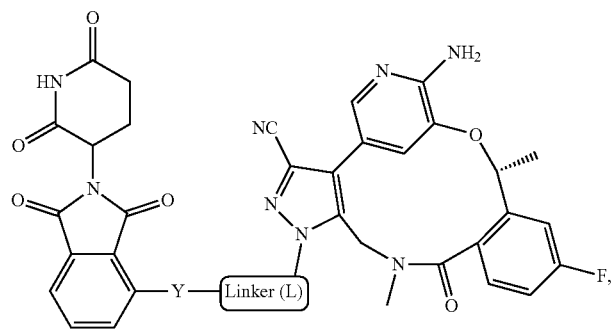
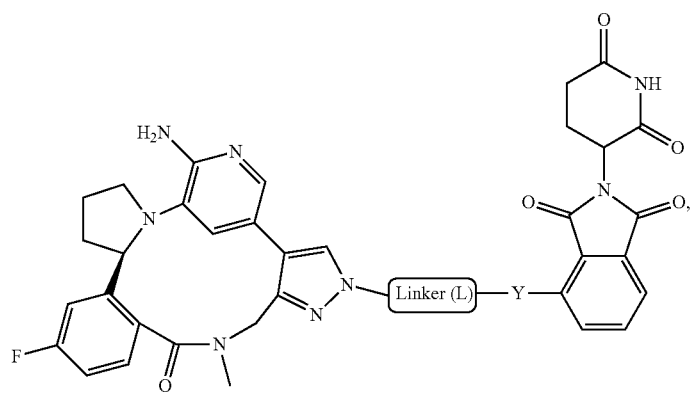
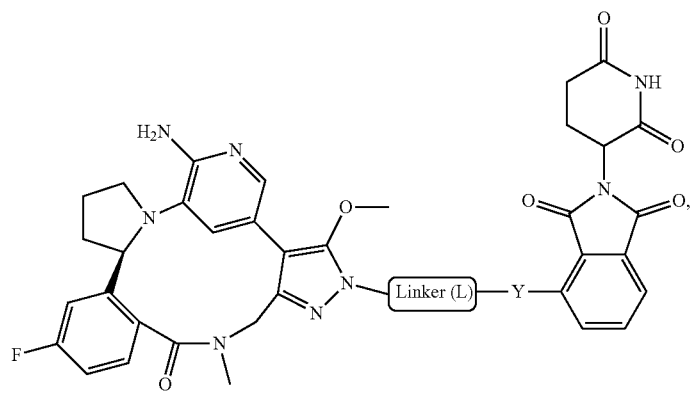

-continued
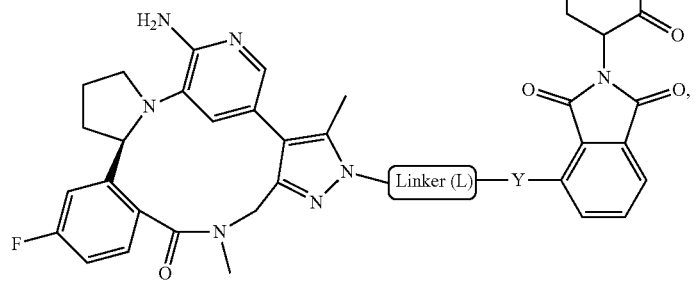
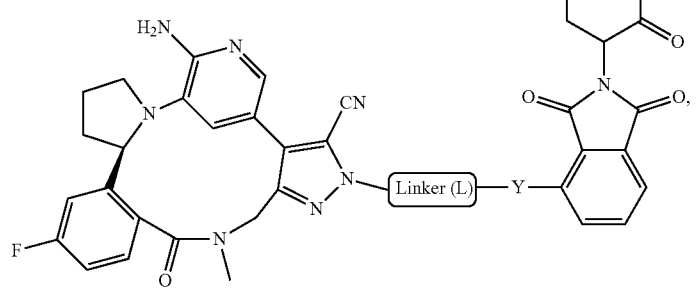
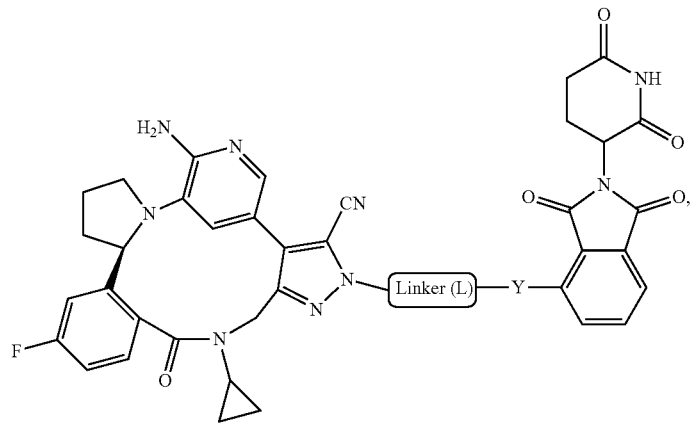
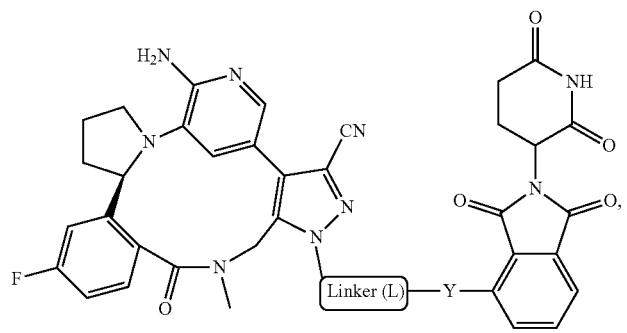

-continued
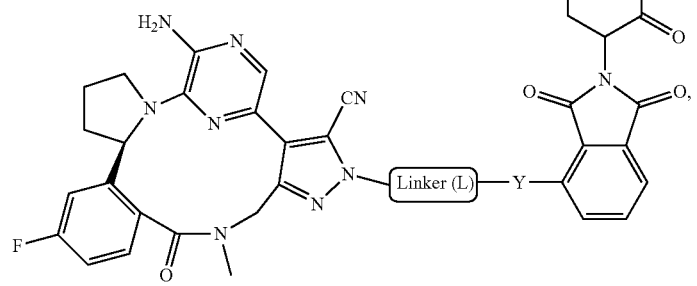
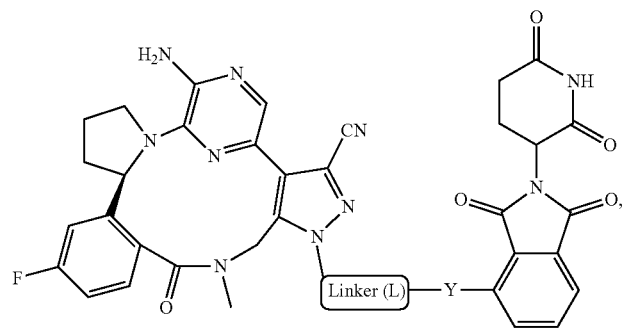
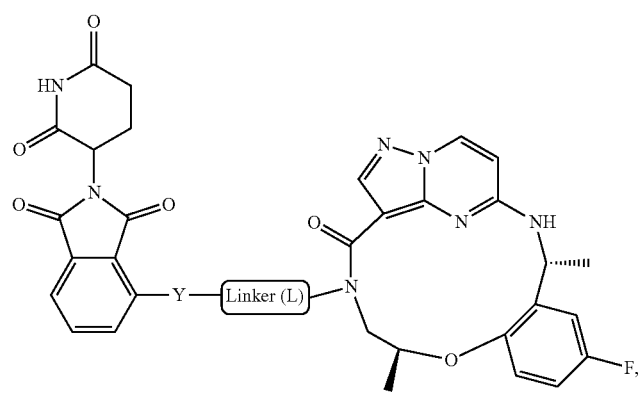
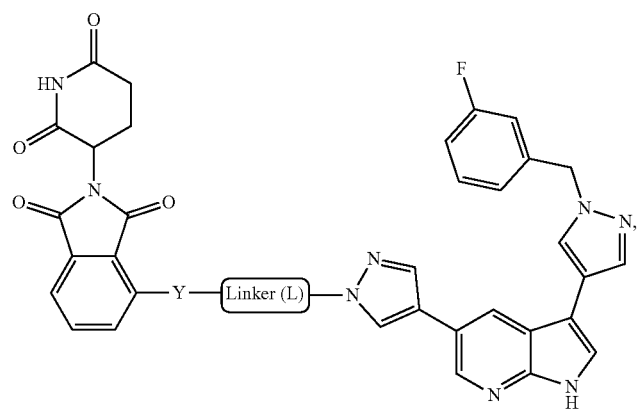

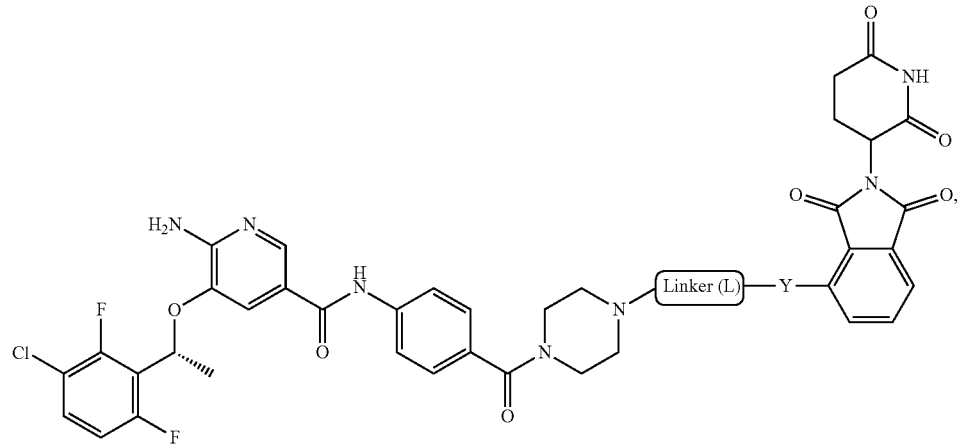
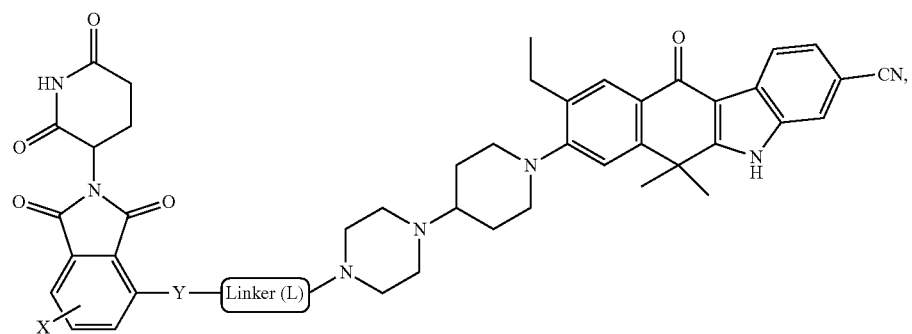
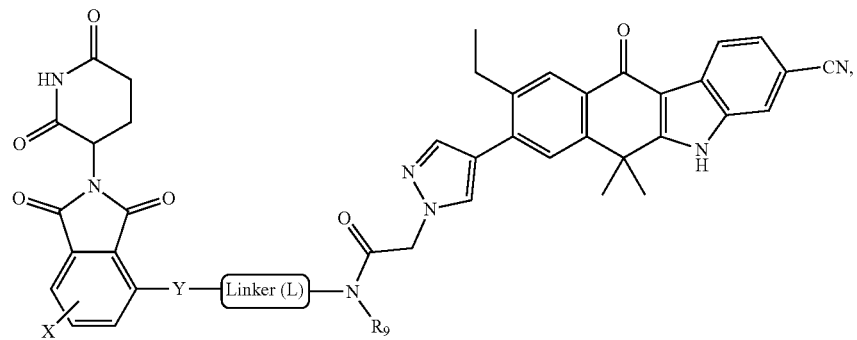
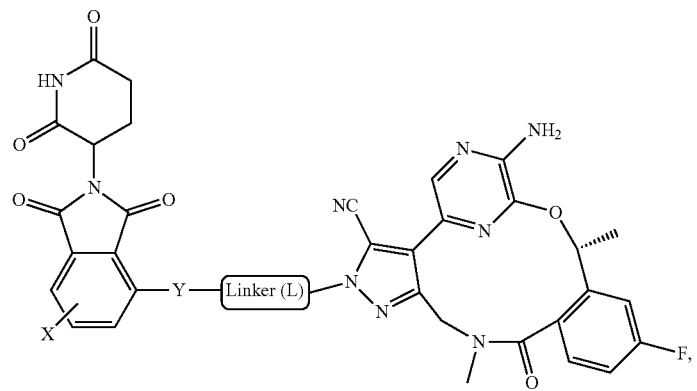

-continued
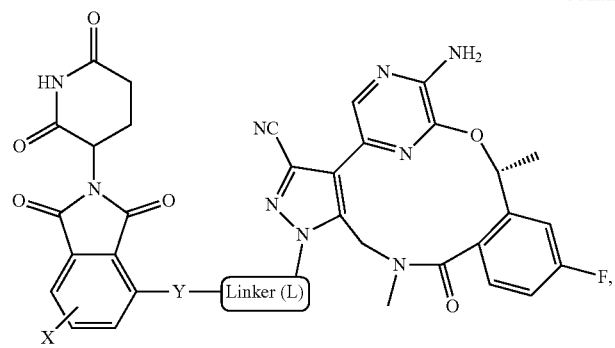
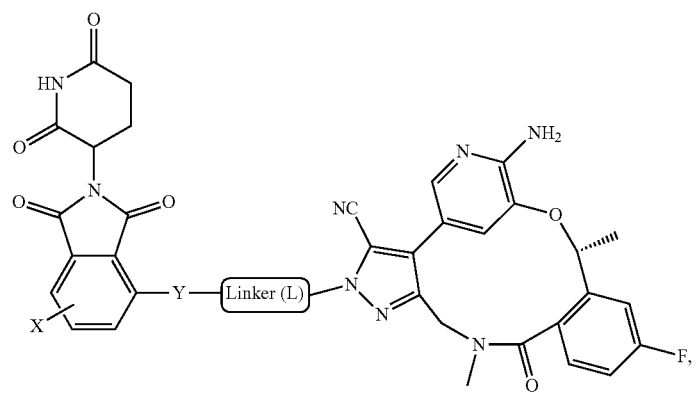
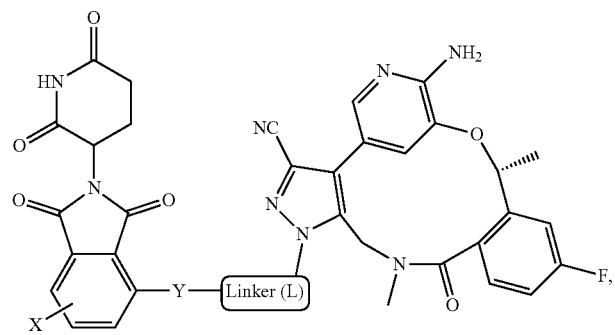
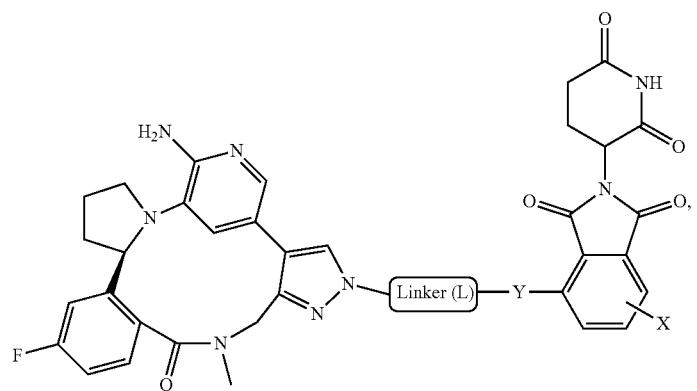

-continued
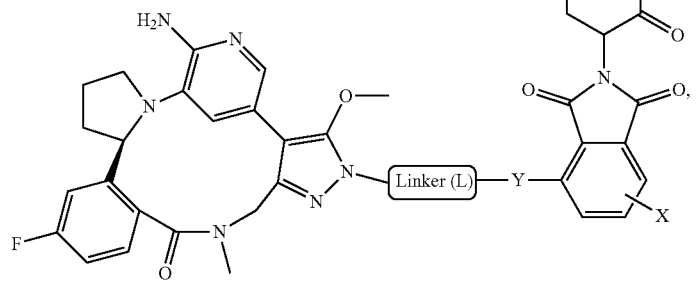
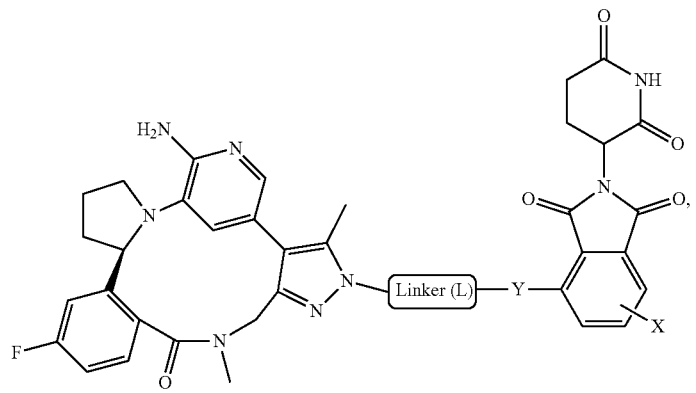
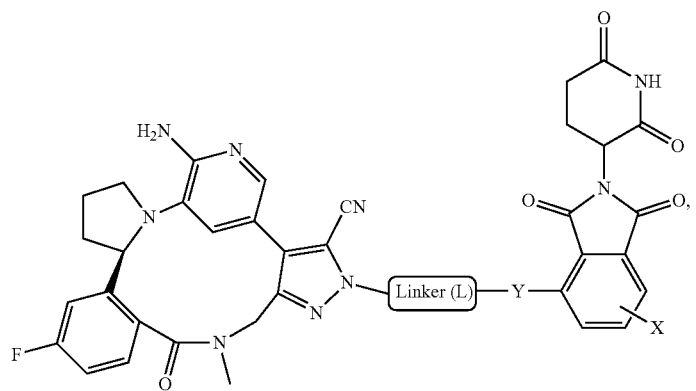
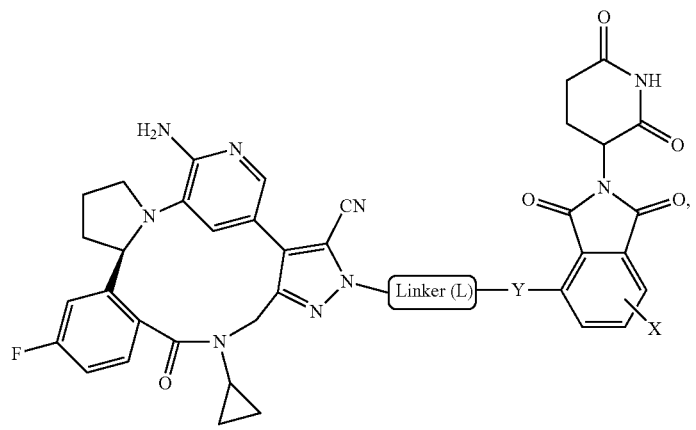

-continued
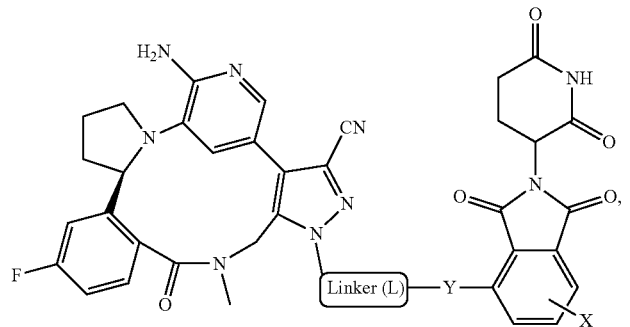
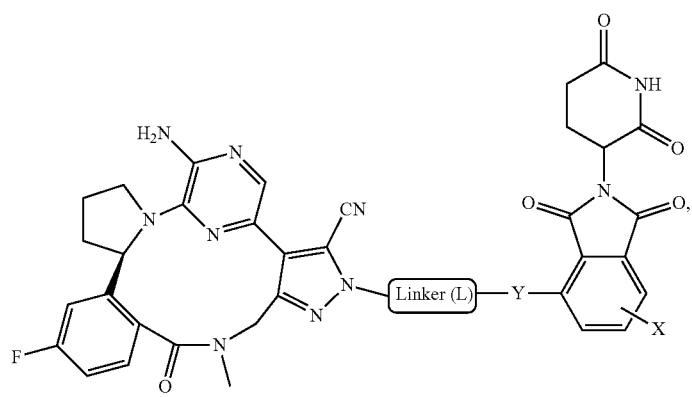
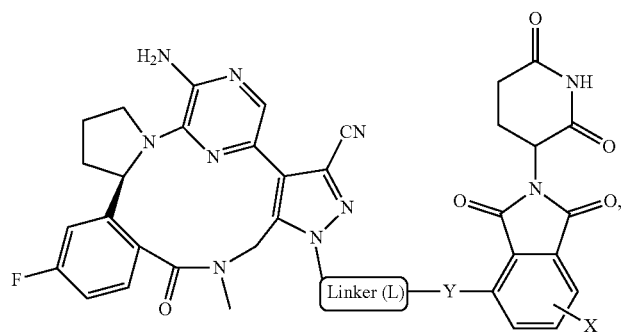
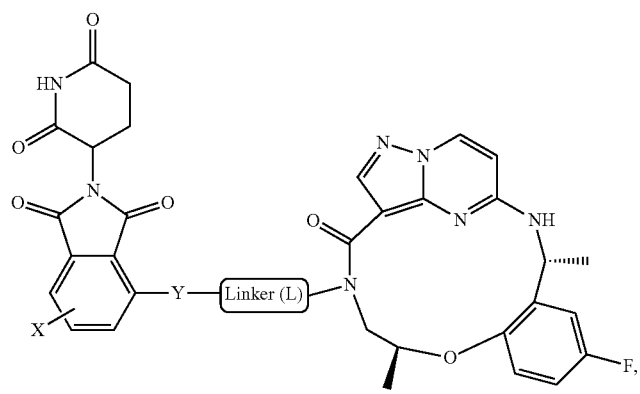

-continued
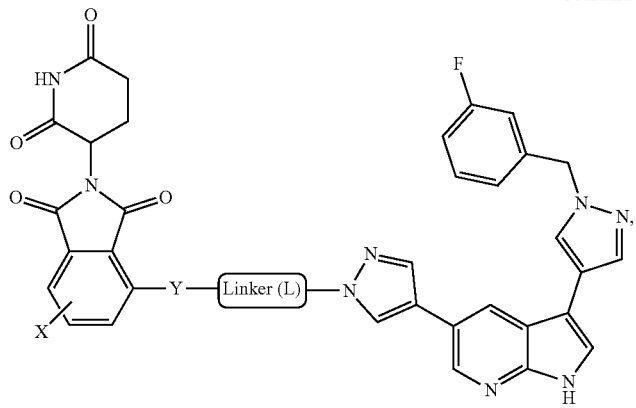
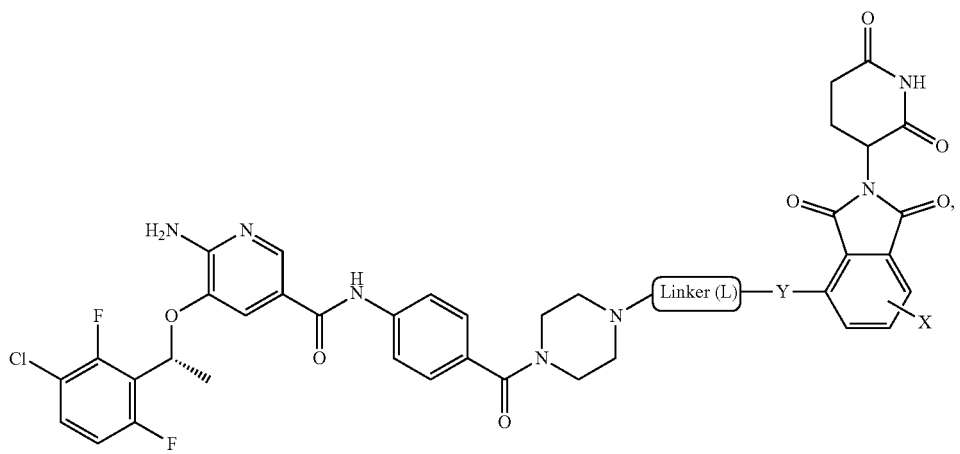
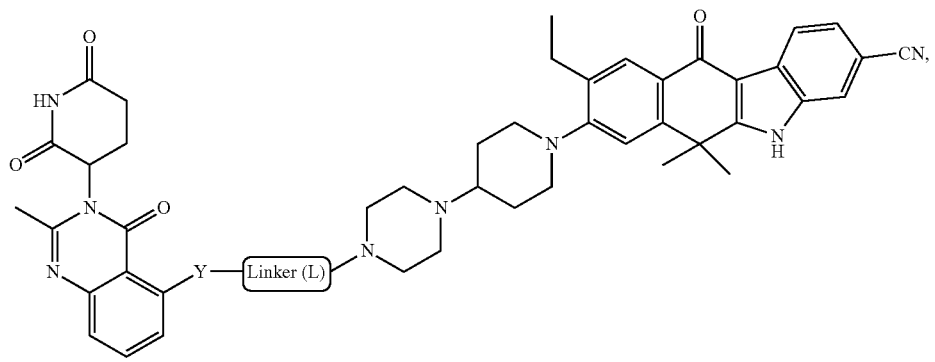
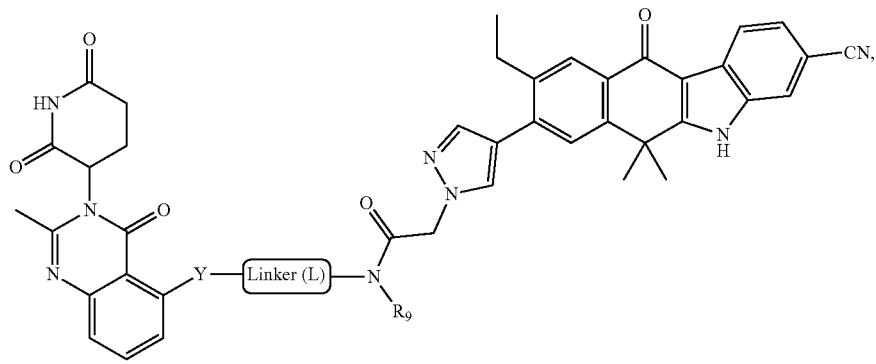

-continued
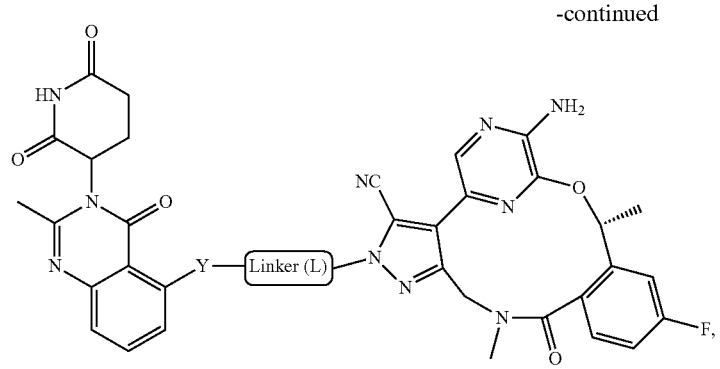
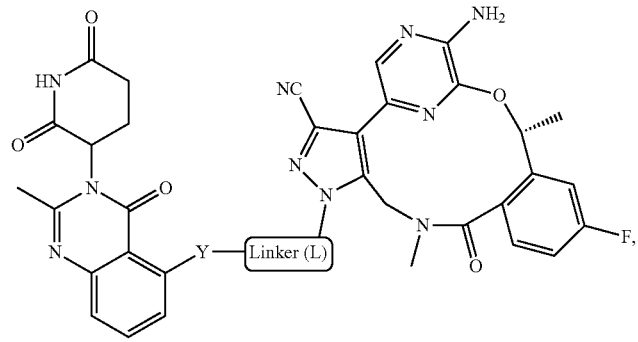
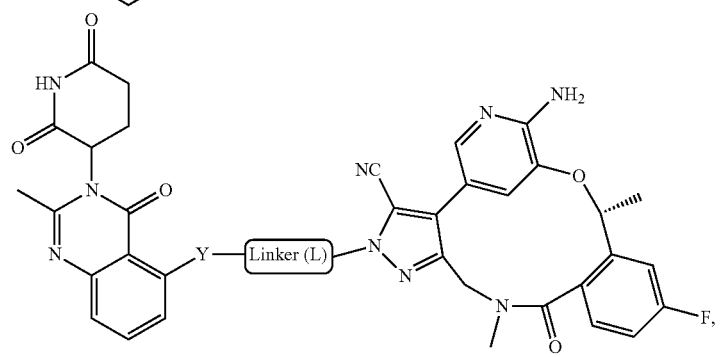
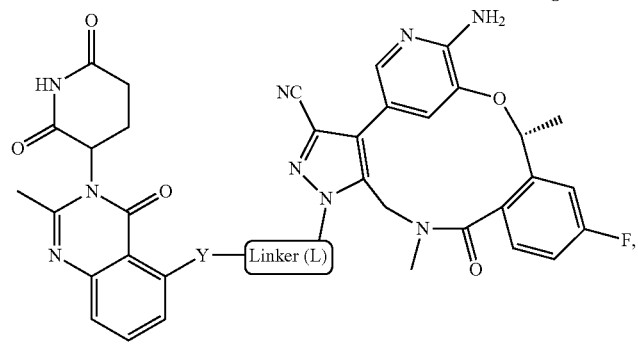
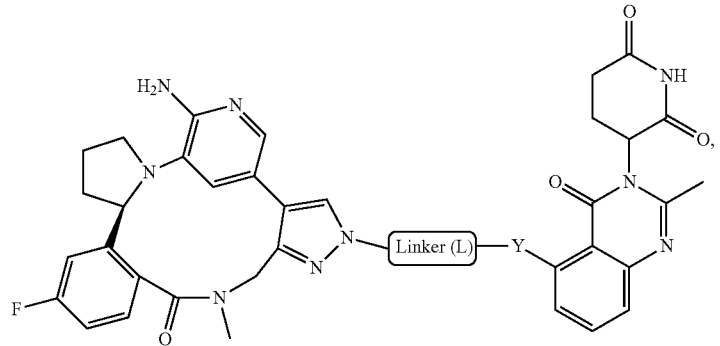

-continued
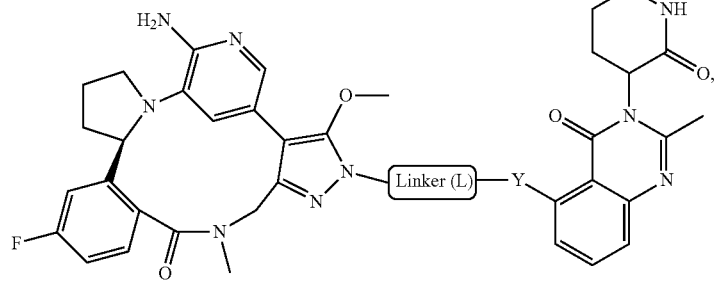
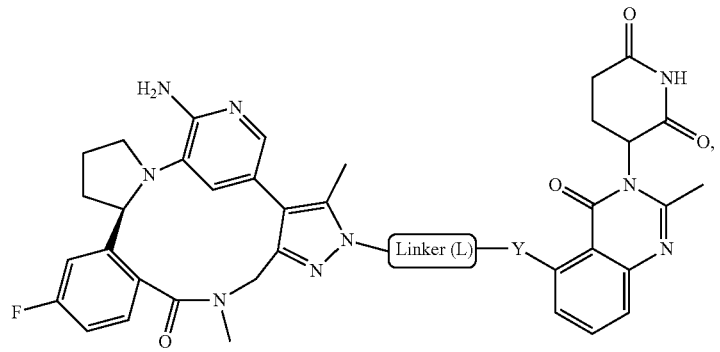
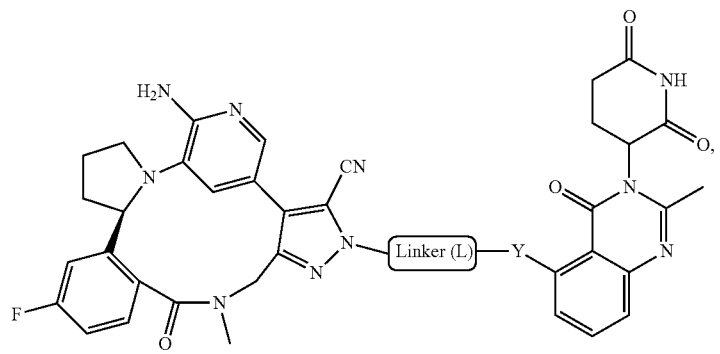
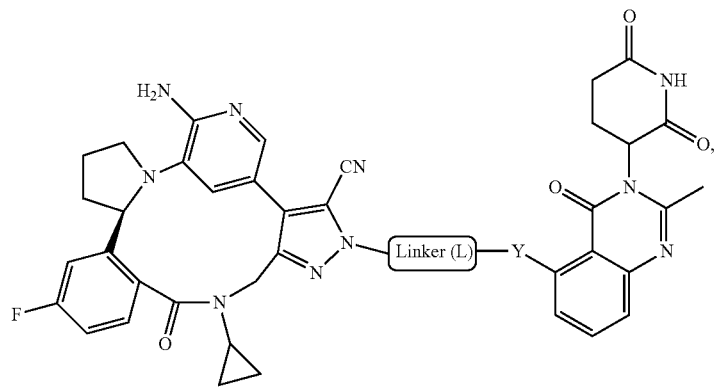

-continued
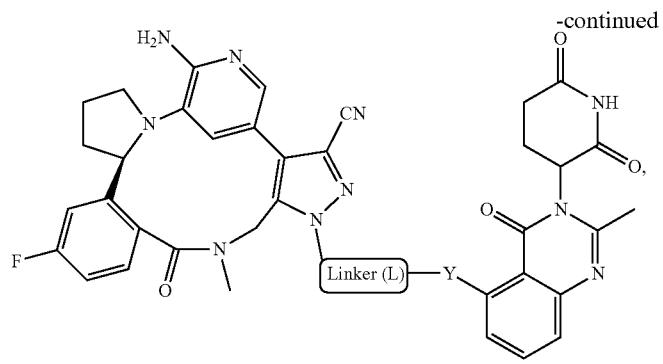
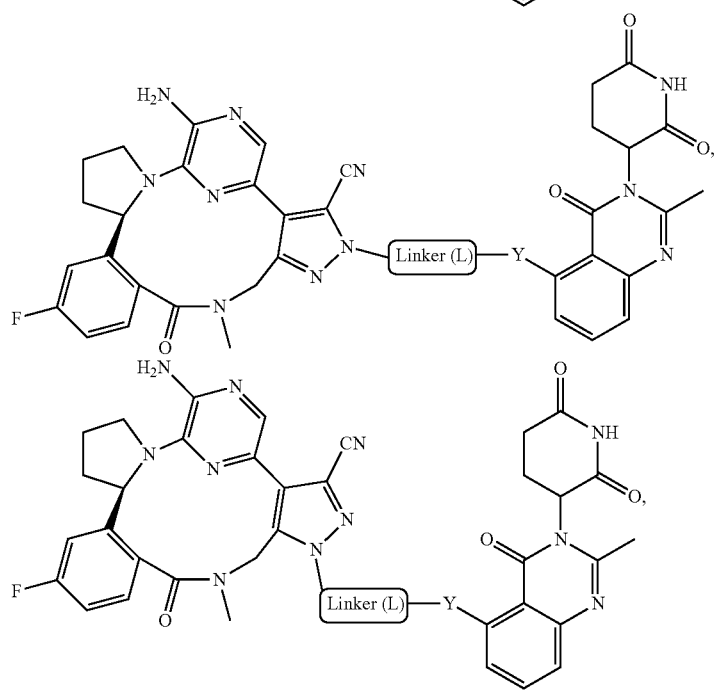
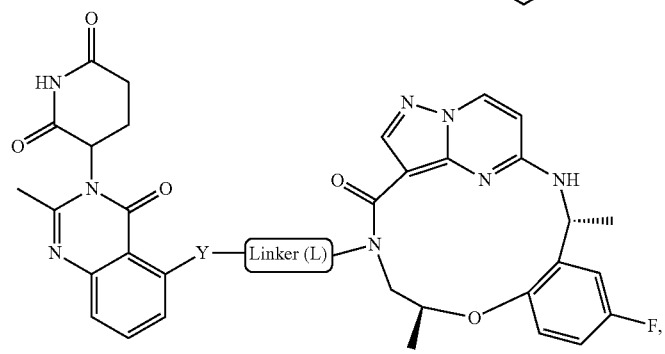
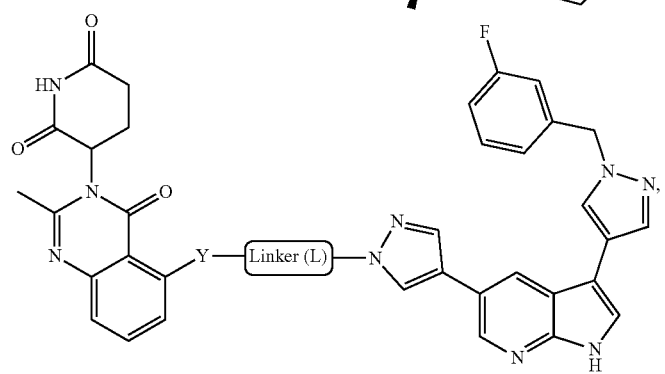

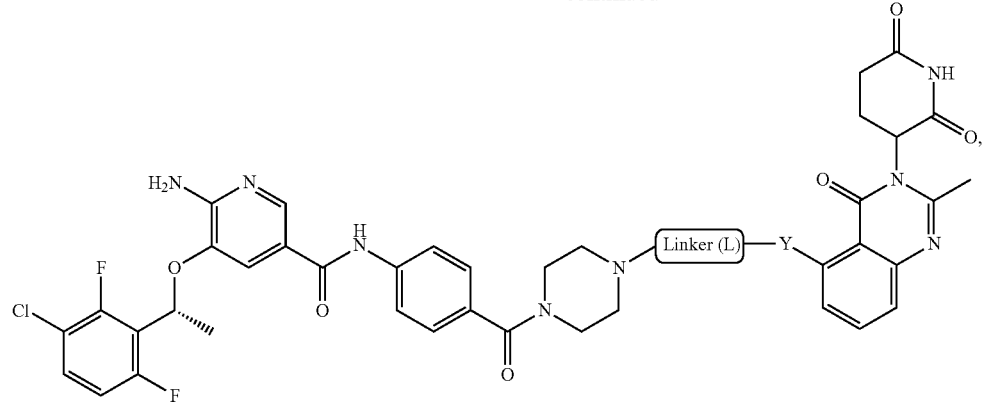
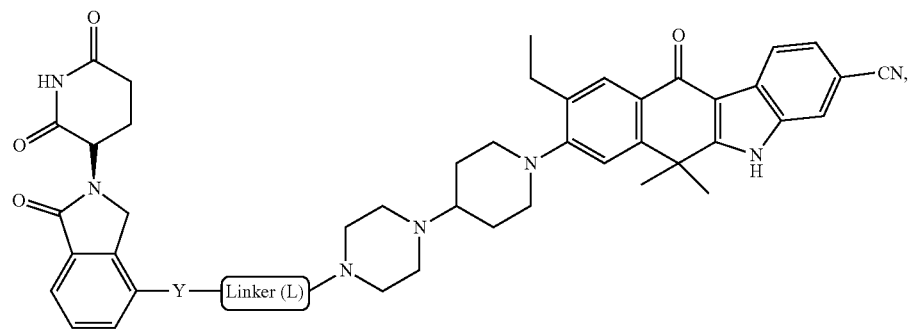
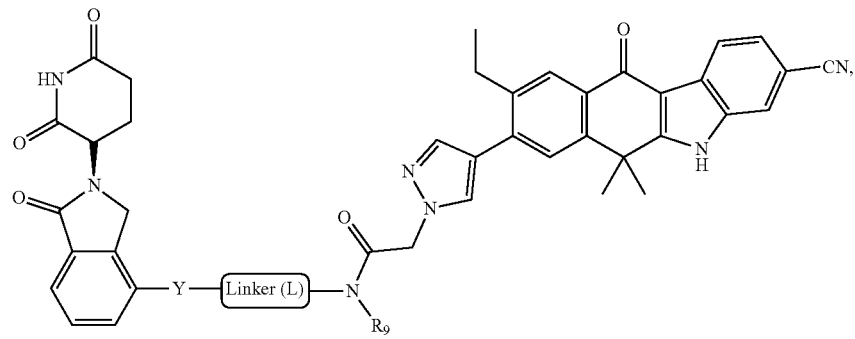
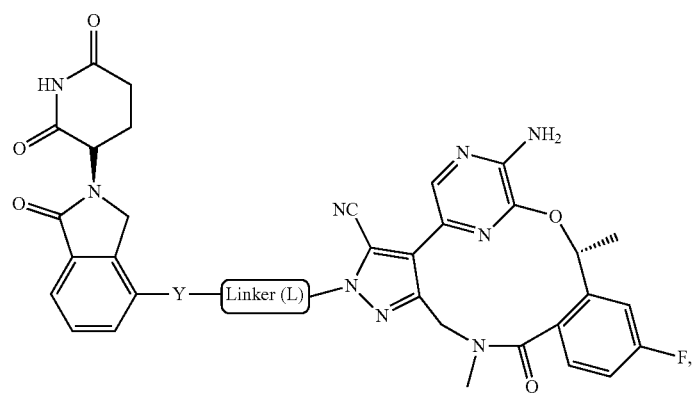

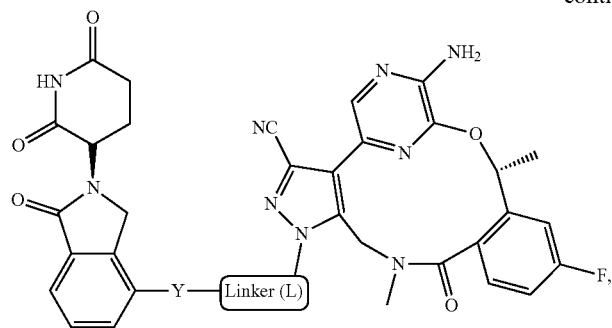
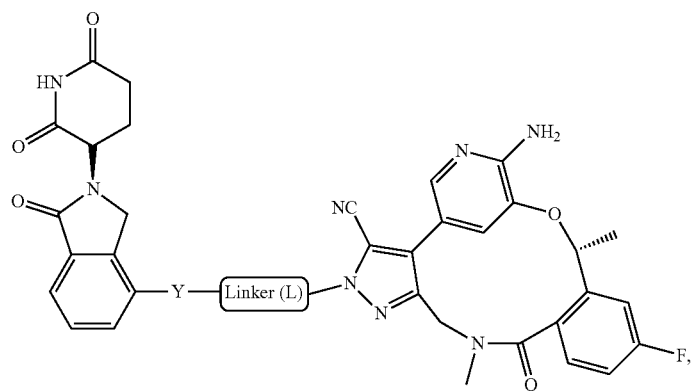
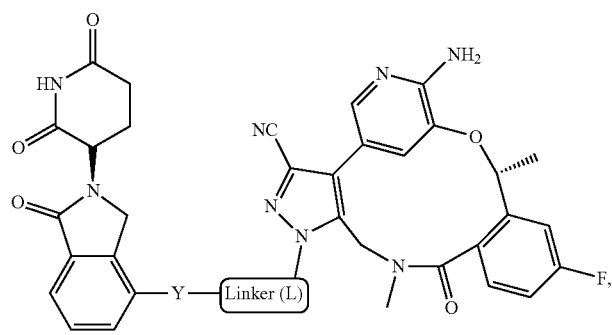
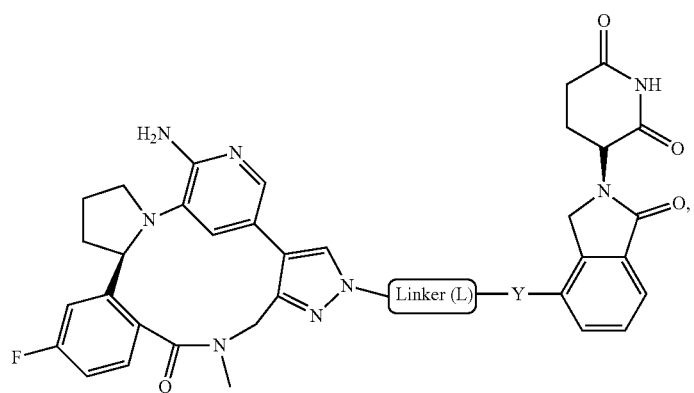

-continued
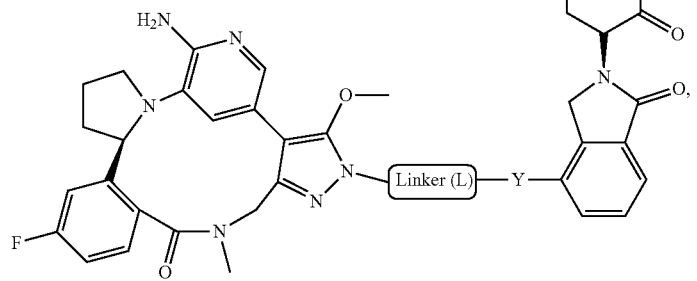
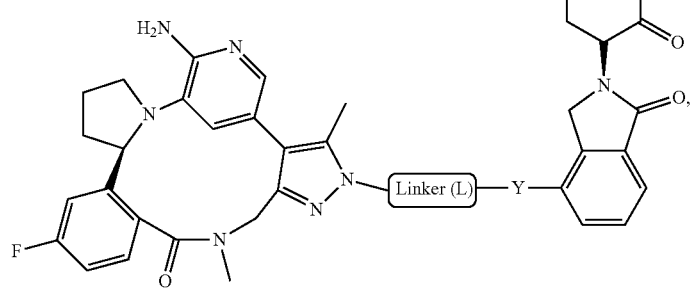
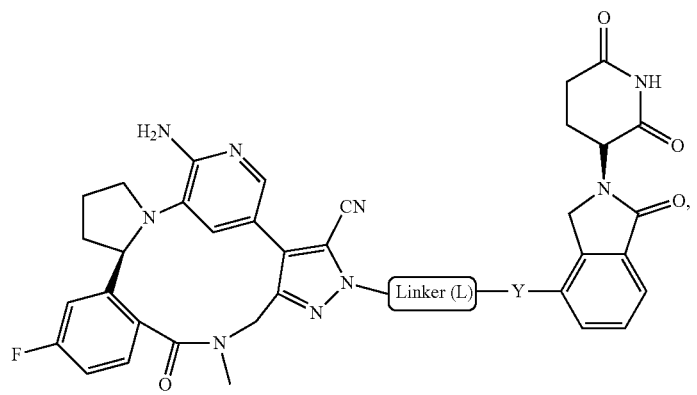
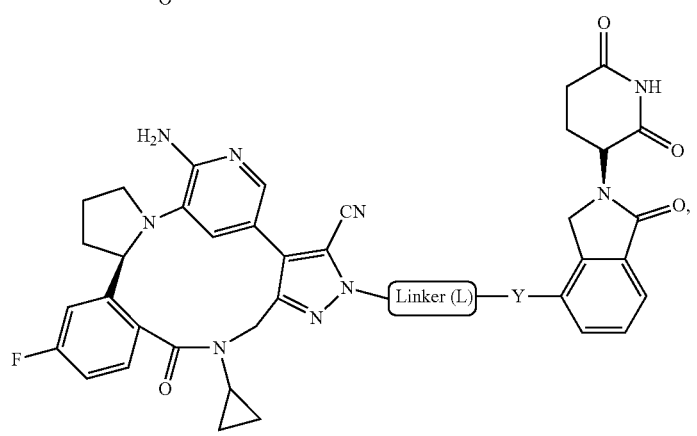

-continued
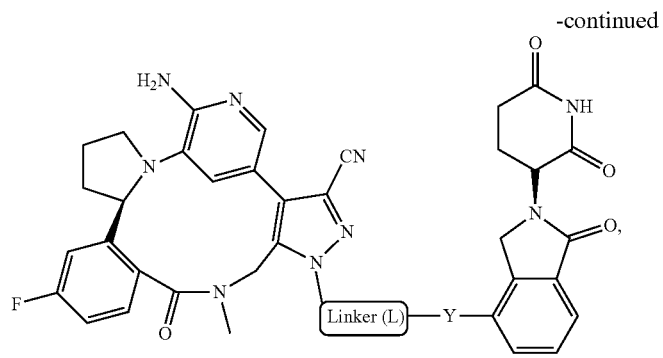
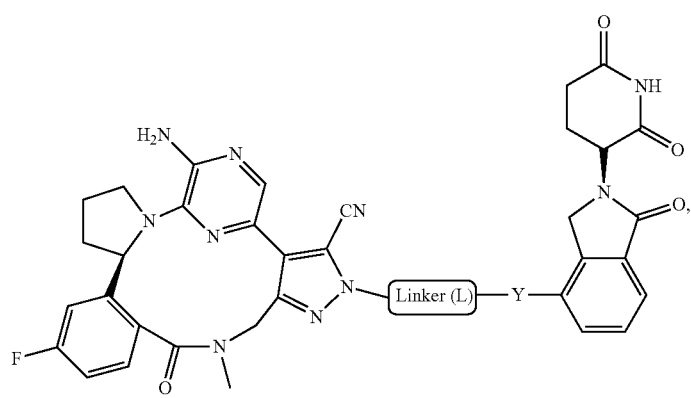
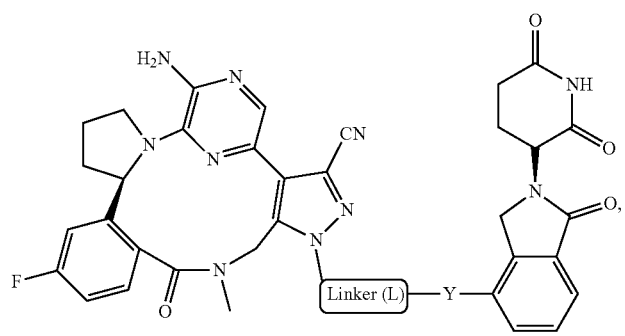
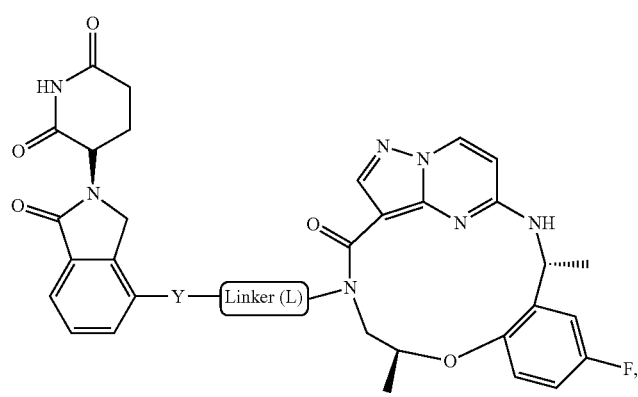

-continued
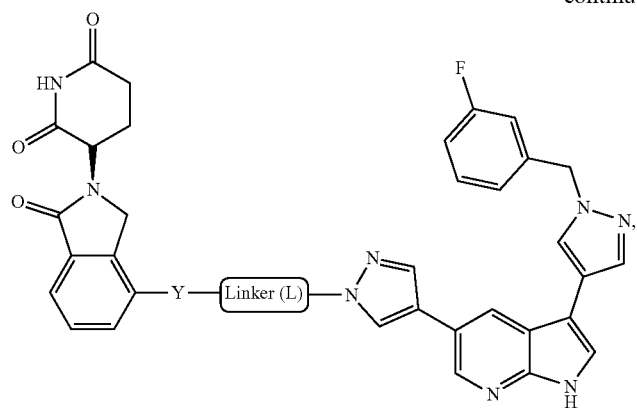
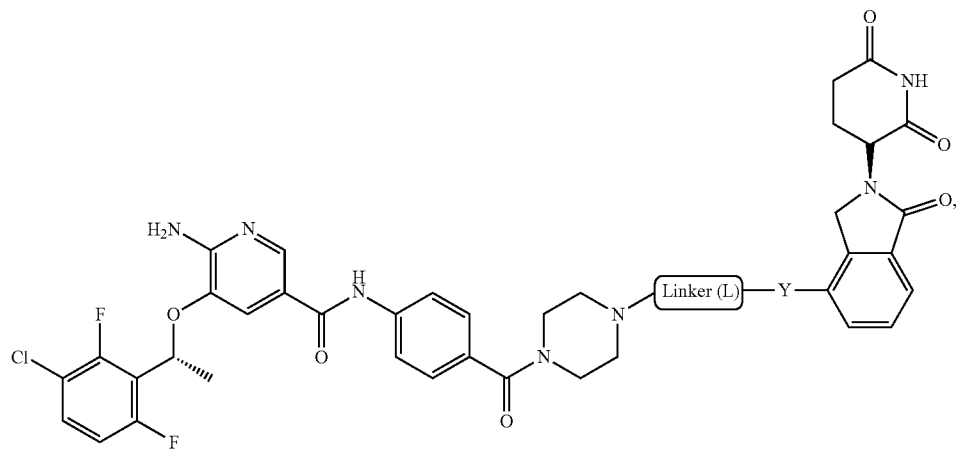
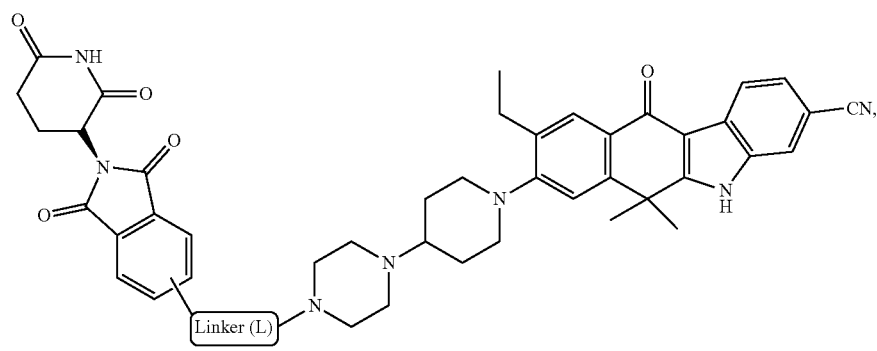
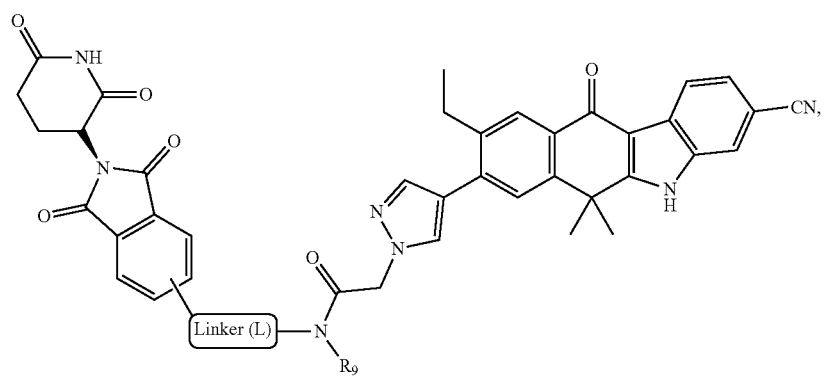

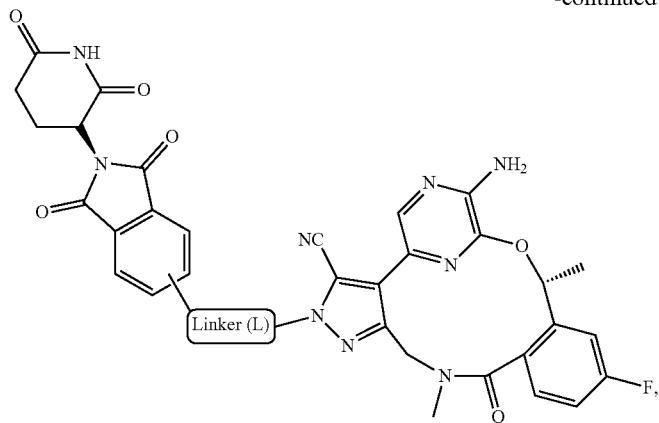
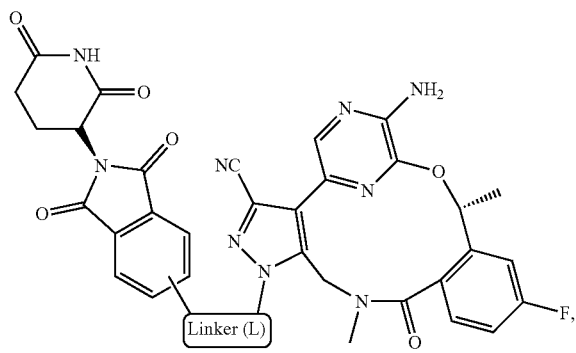
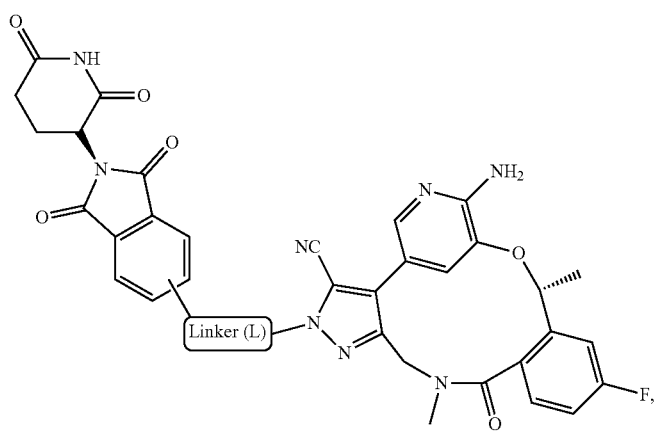
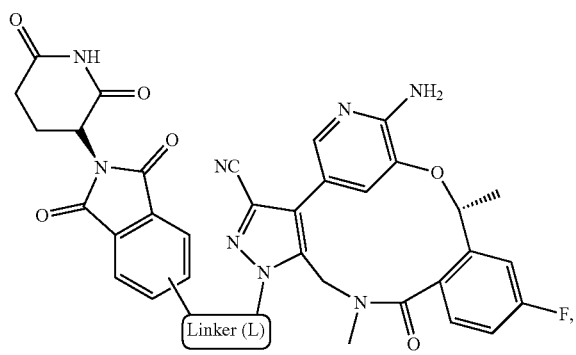

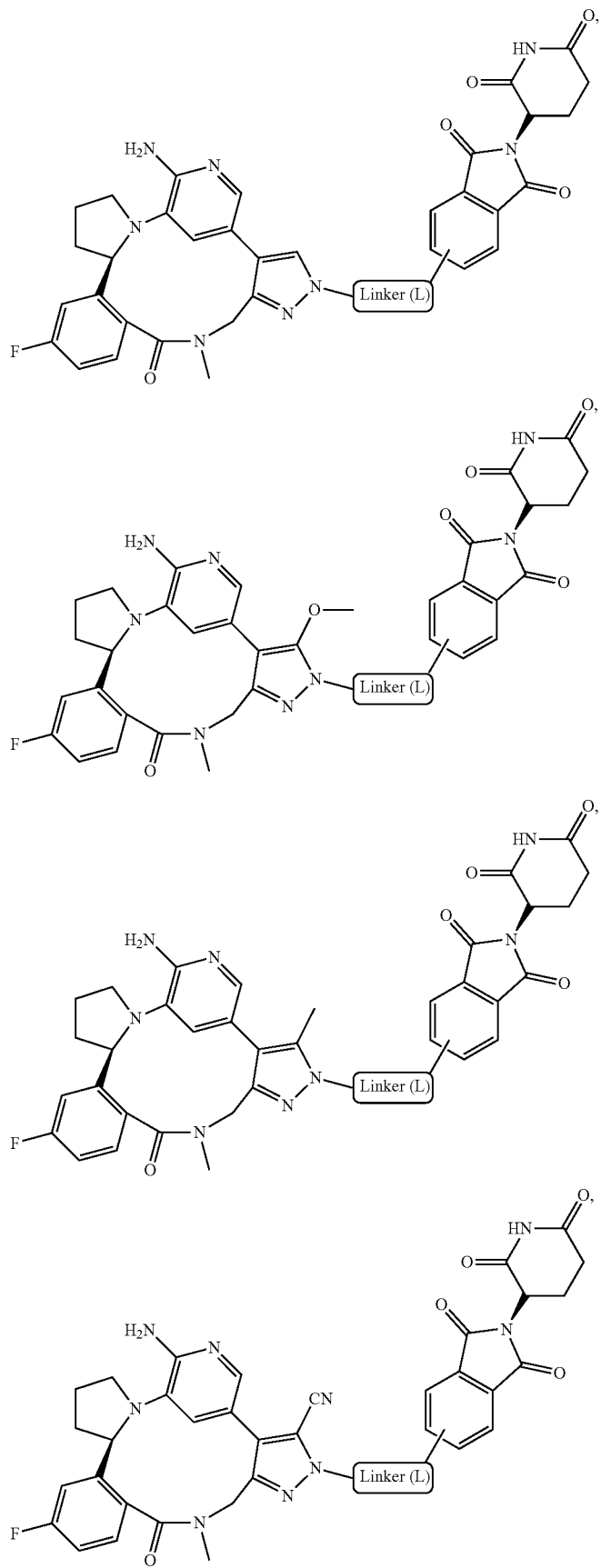

-continued
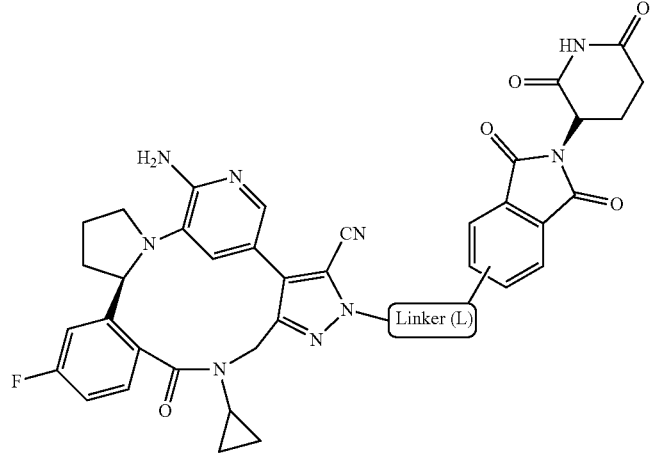
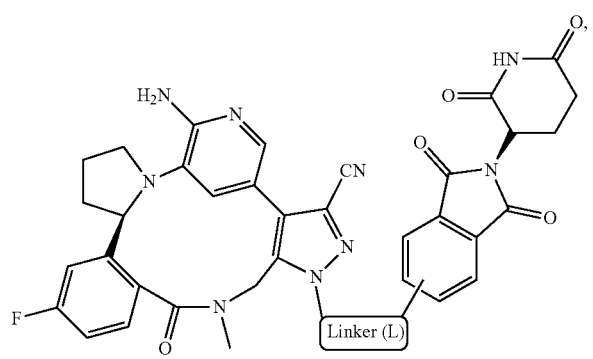
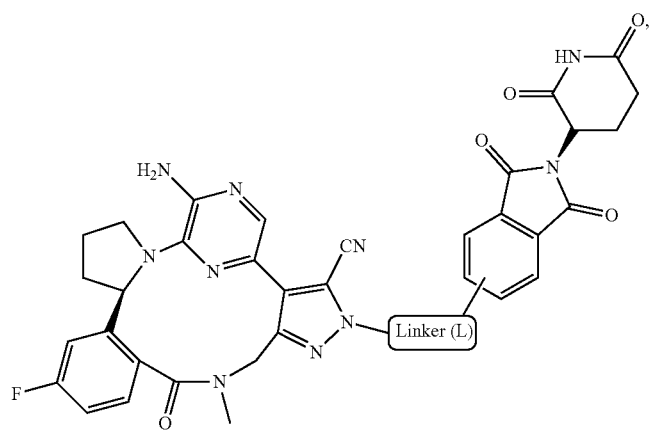
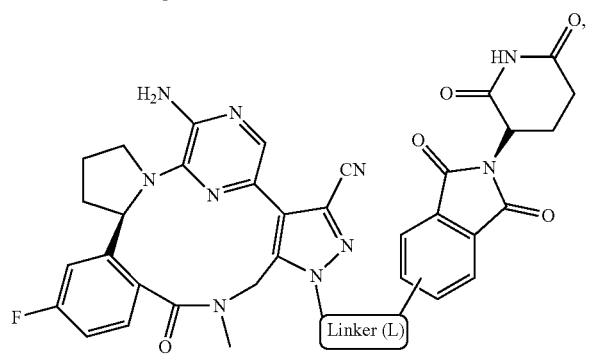

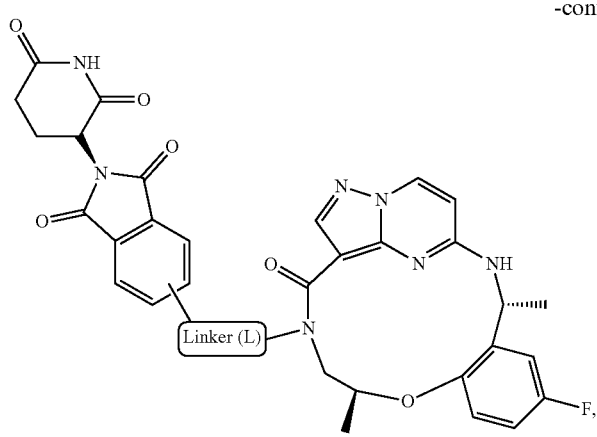
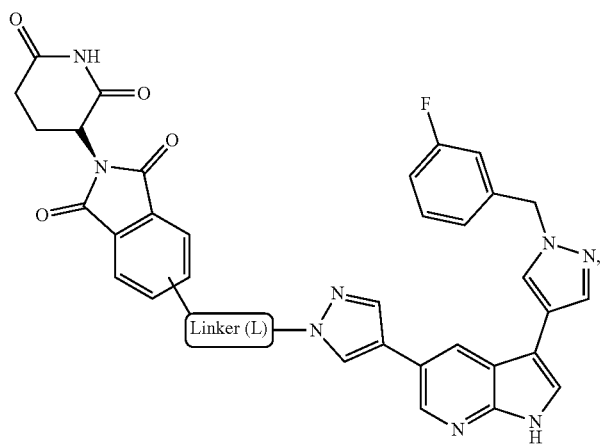
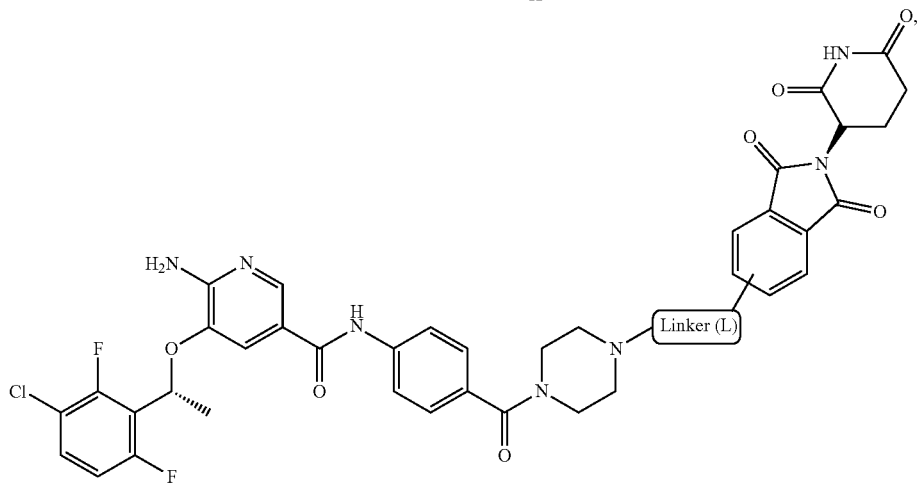
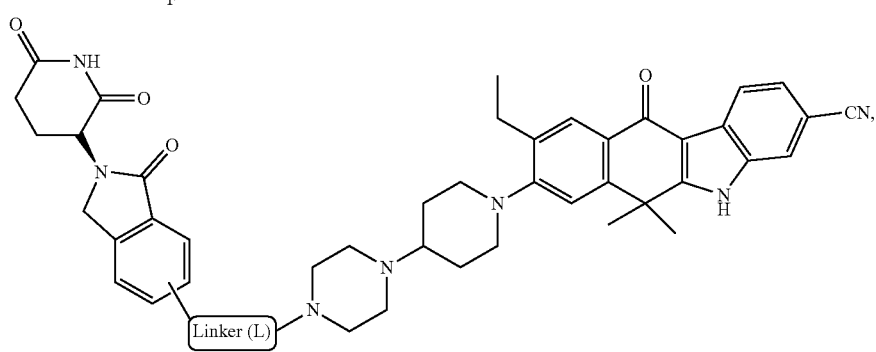

-continued
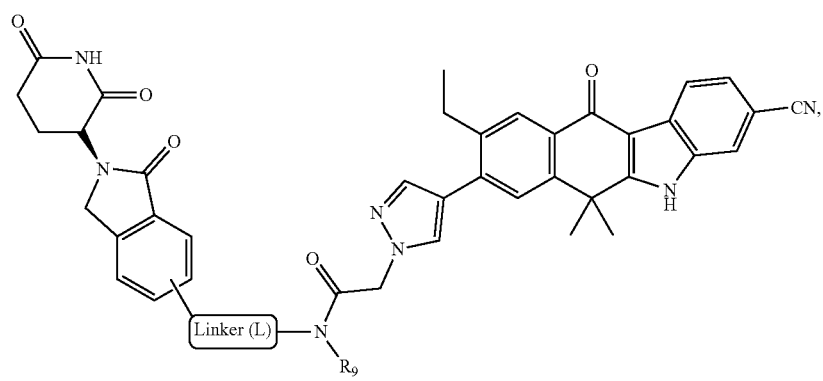
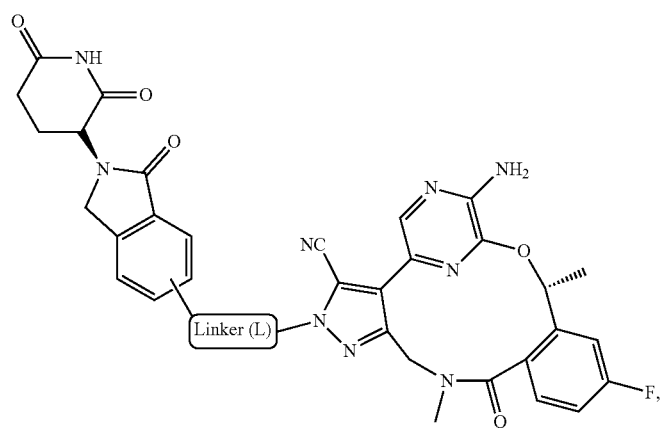
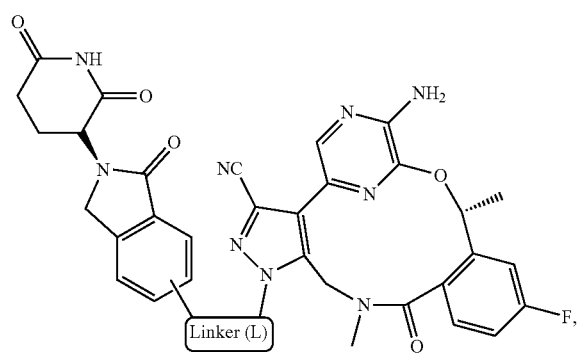
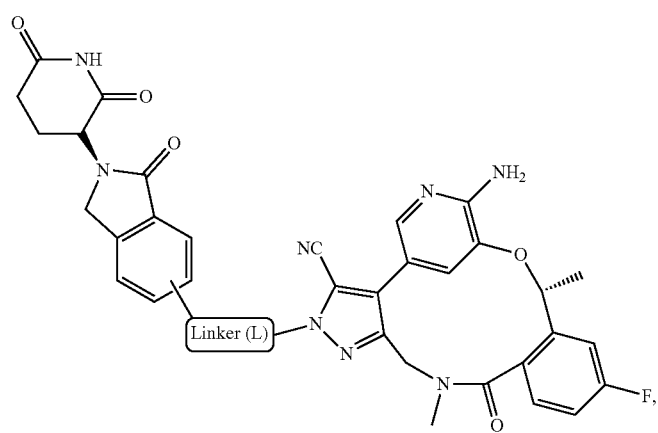

-continued
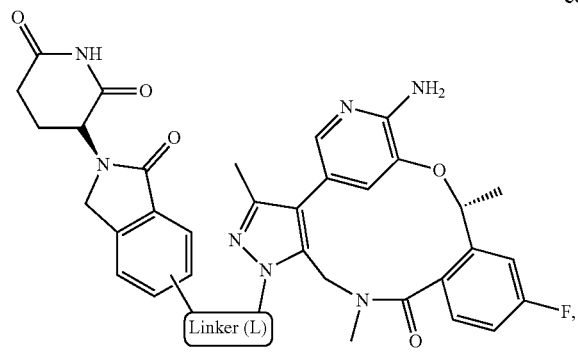
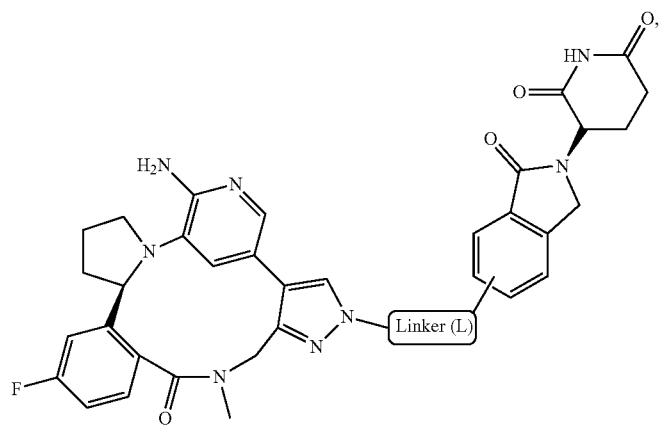
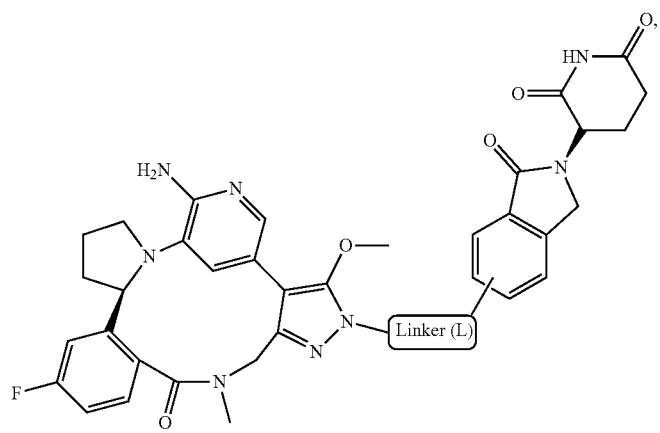
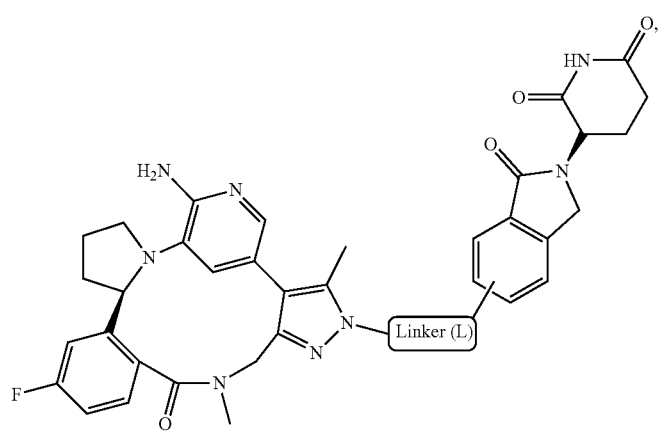

-continued
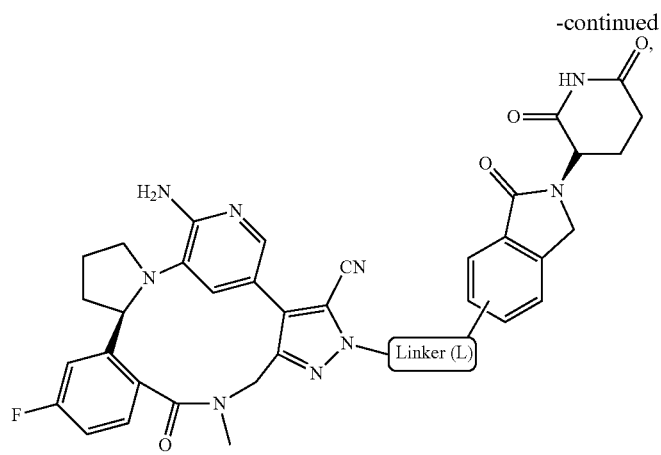
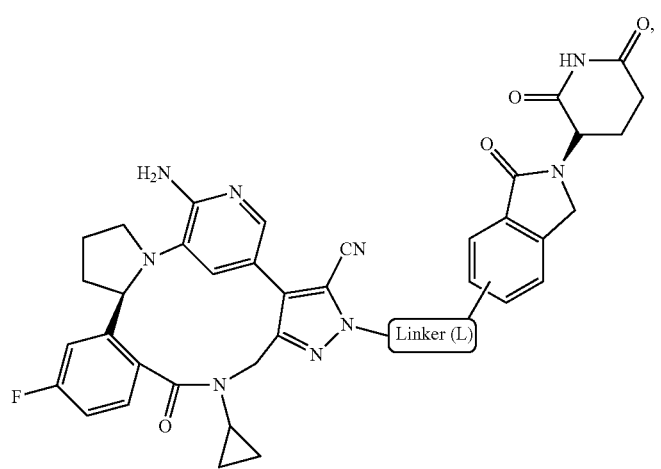
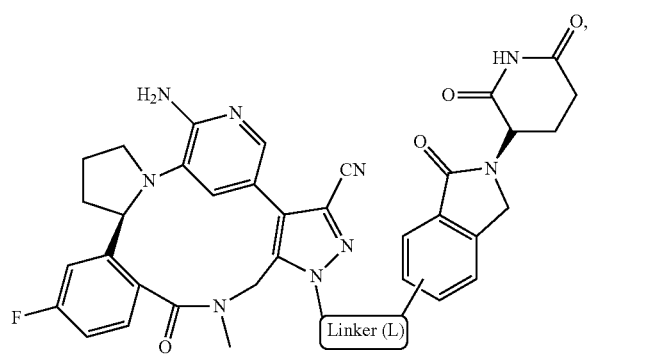
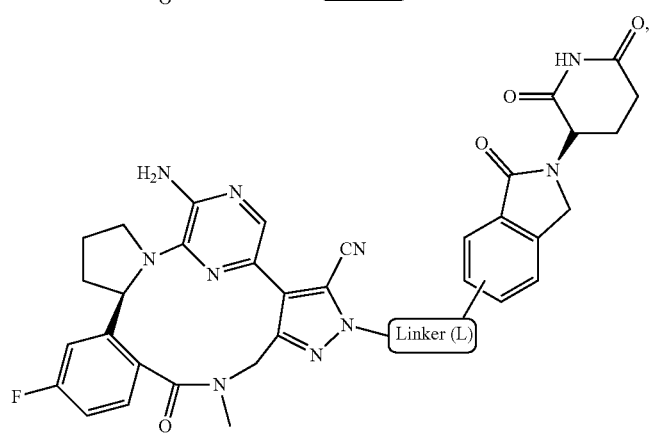

-continued
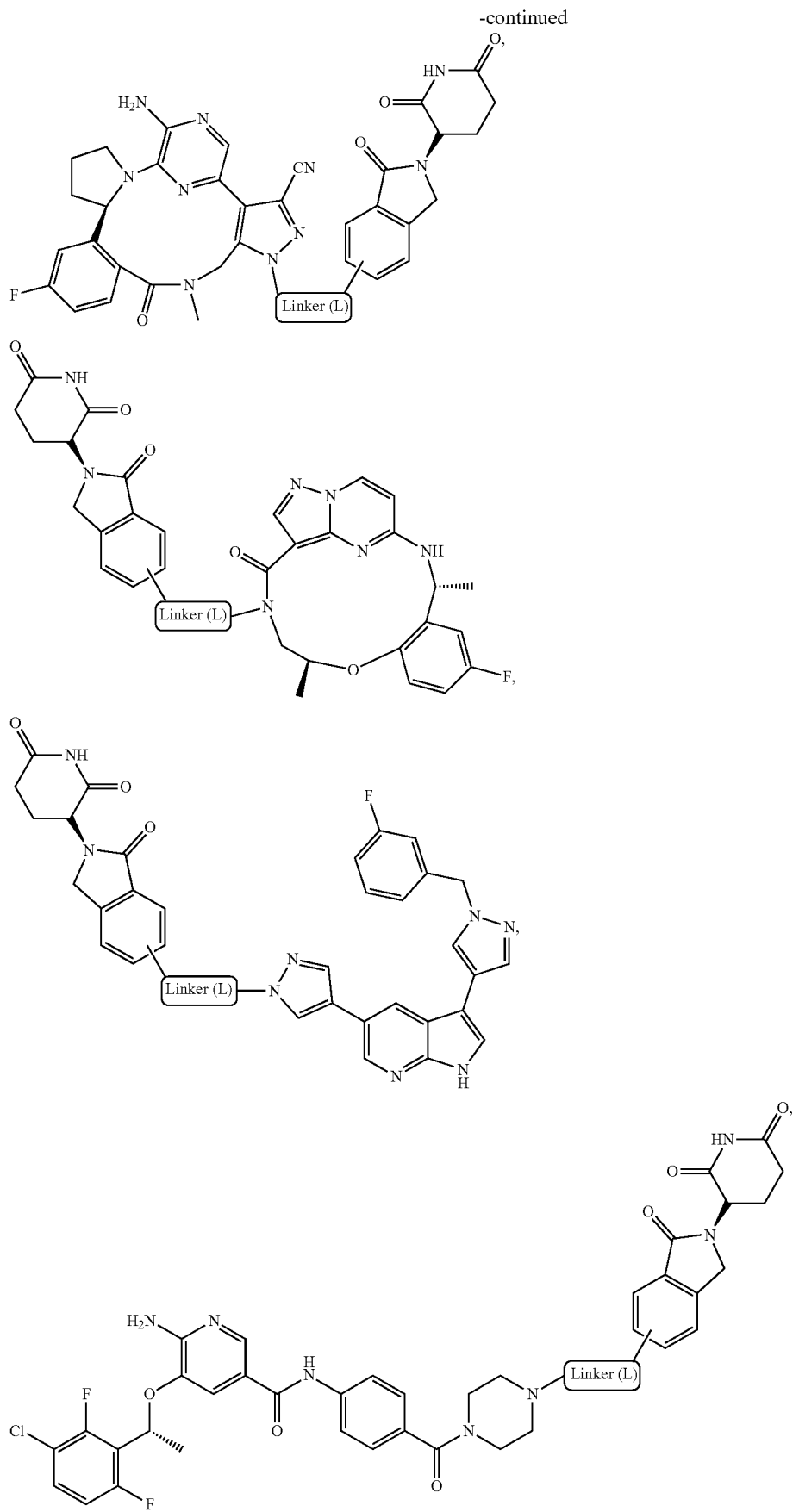

-continued
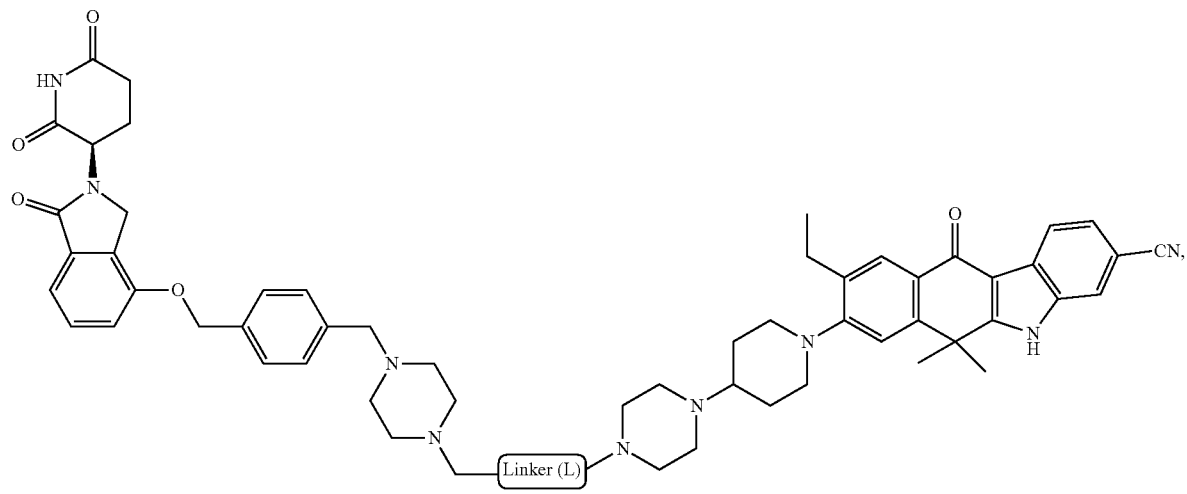
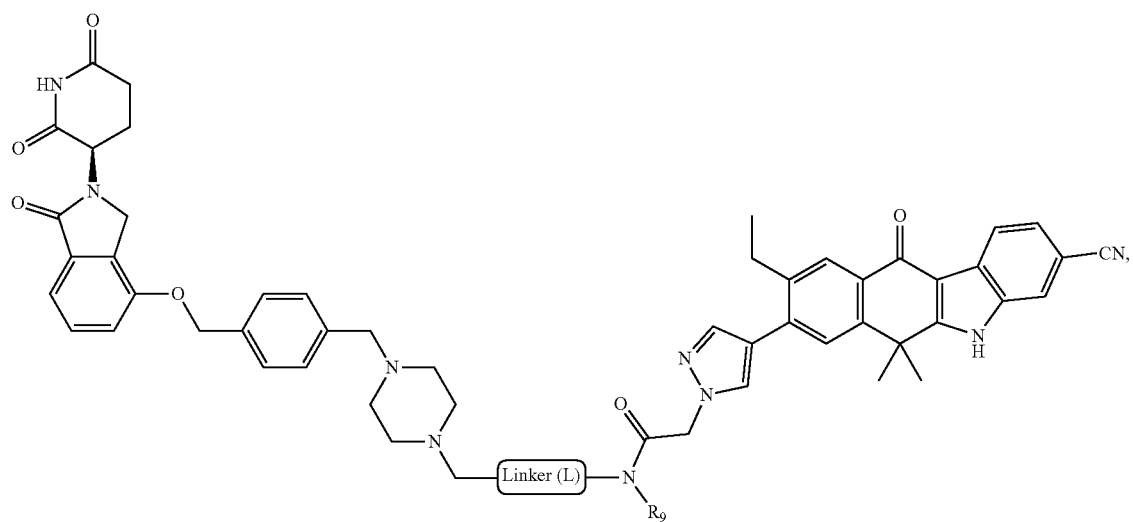
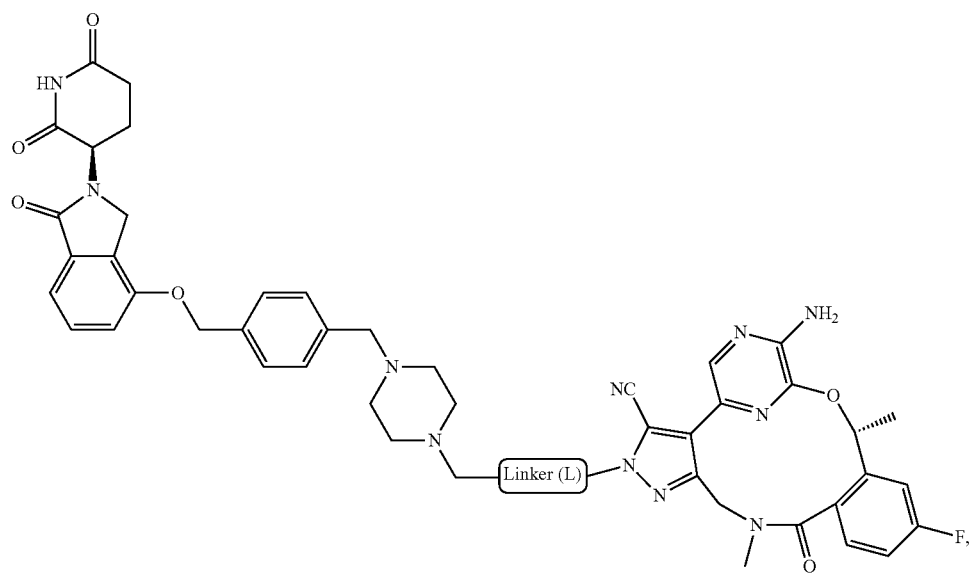

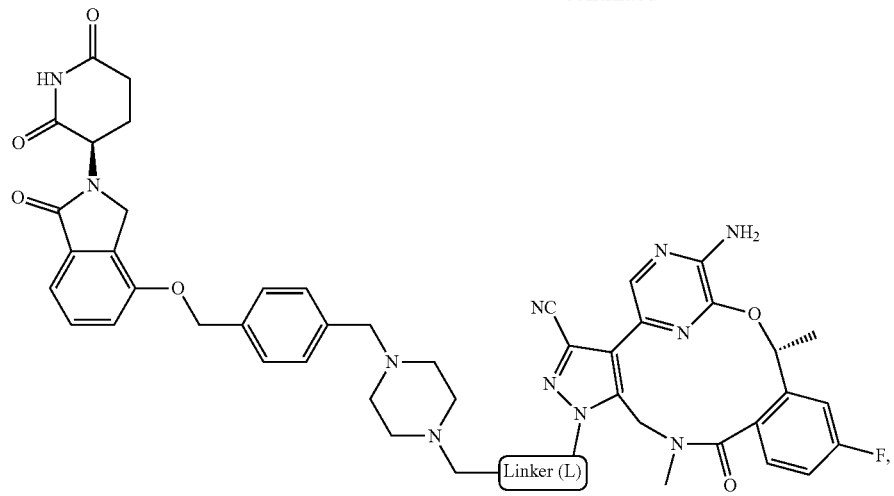
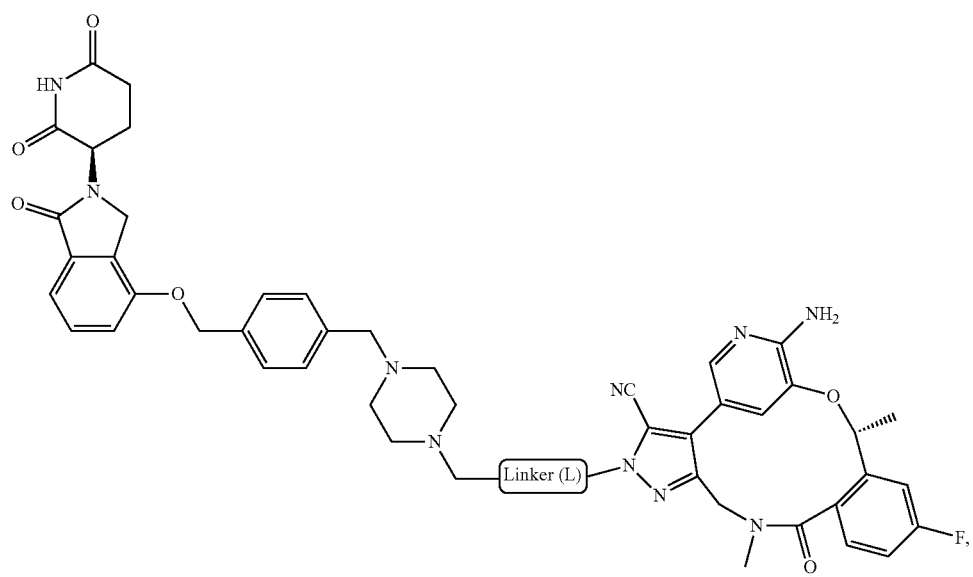
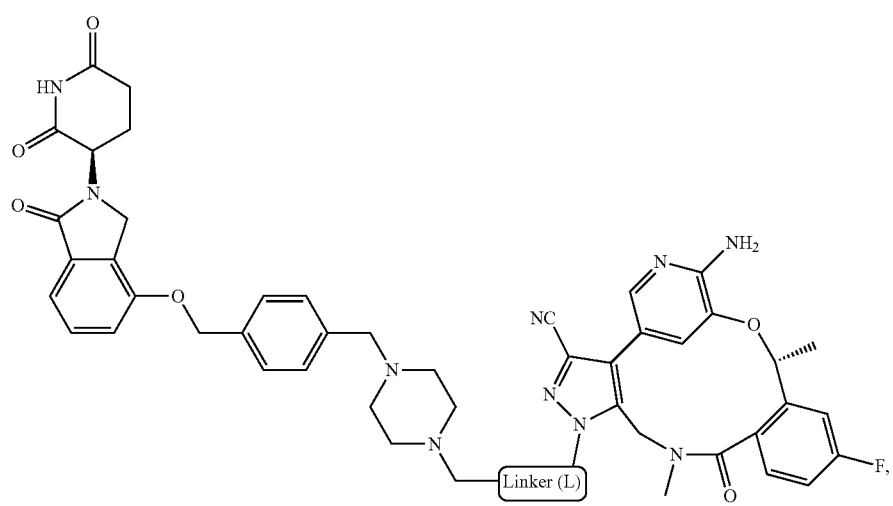

-continued
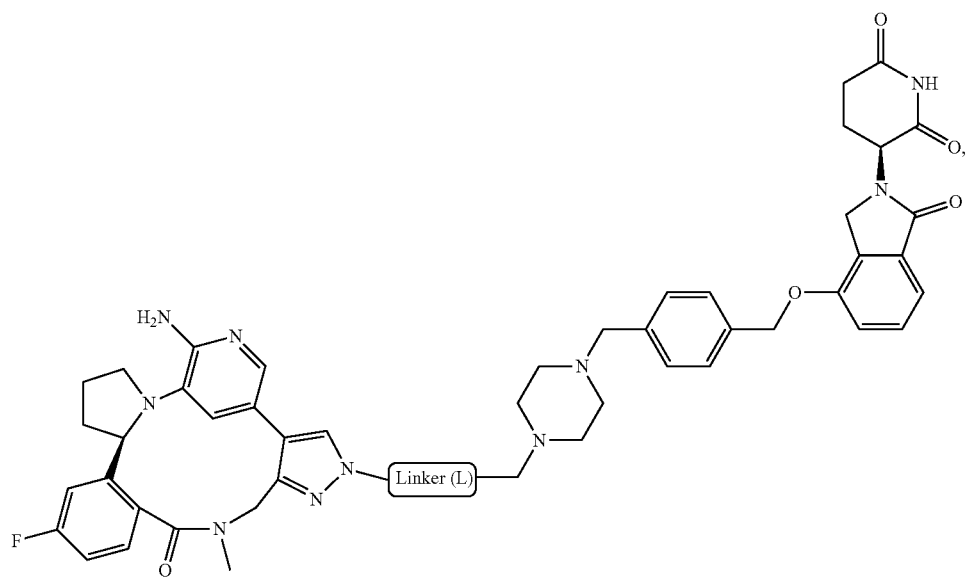
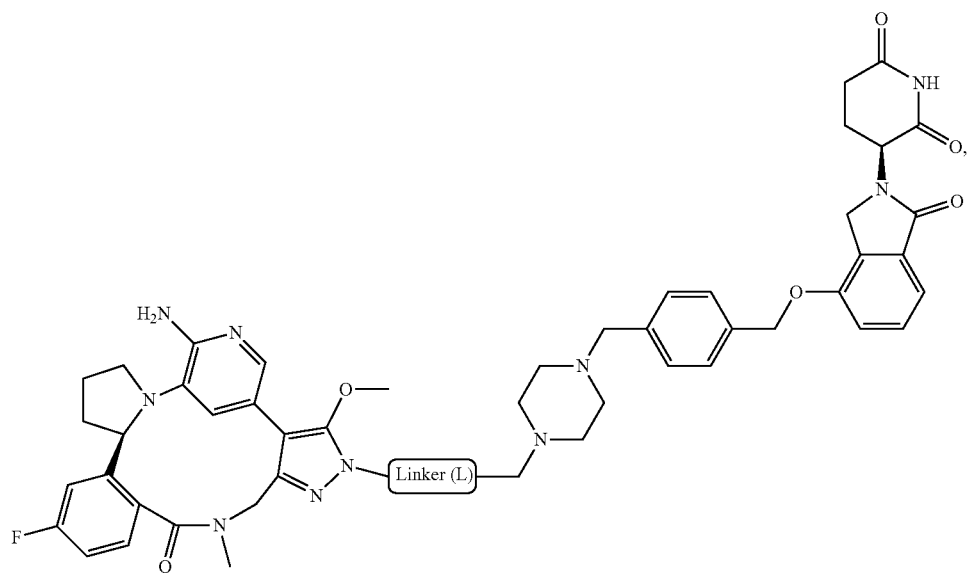

-continued
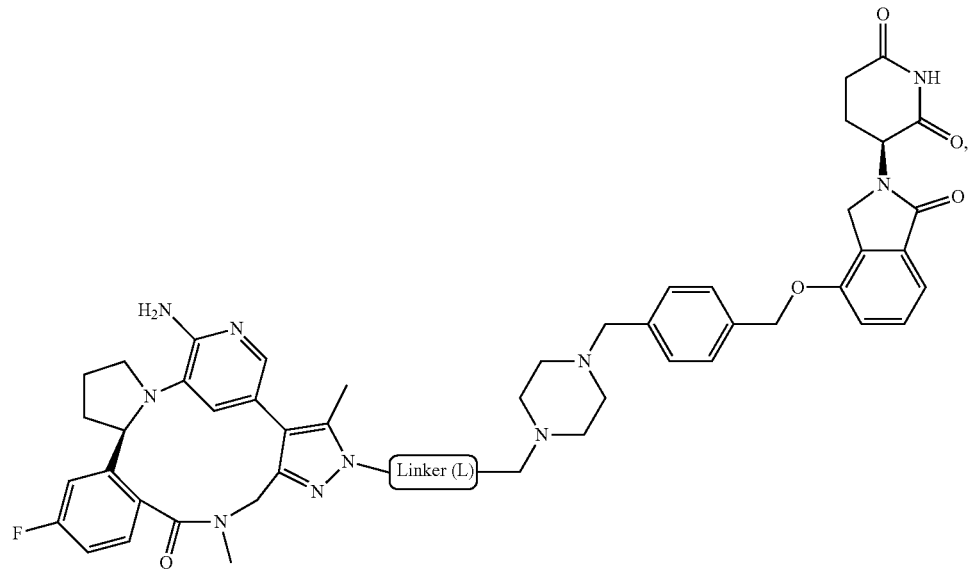
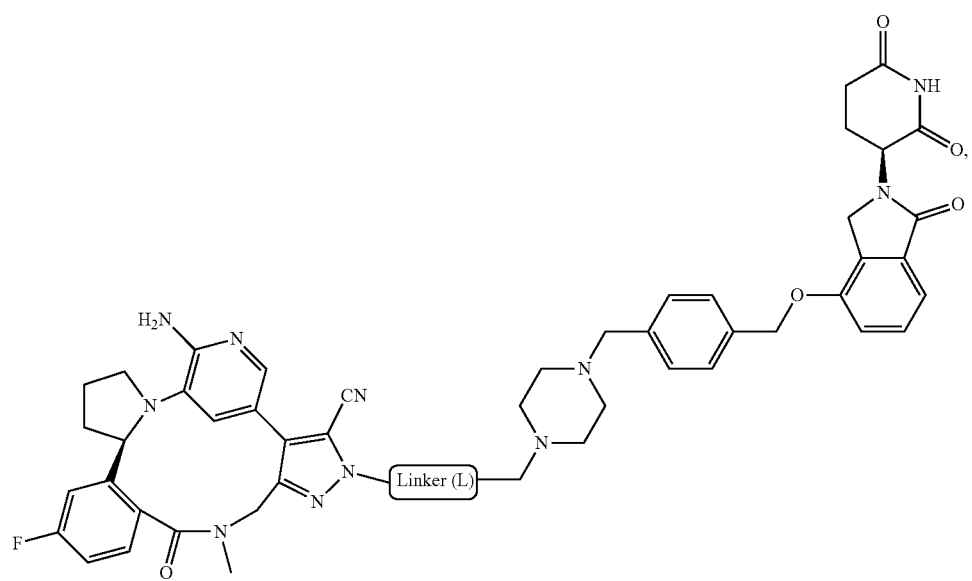

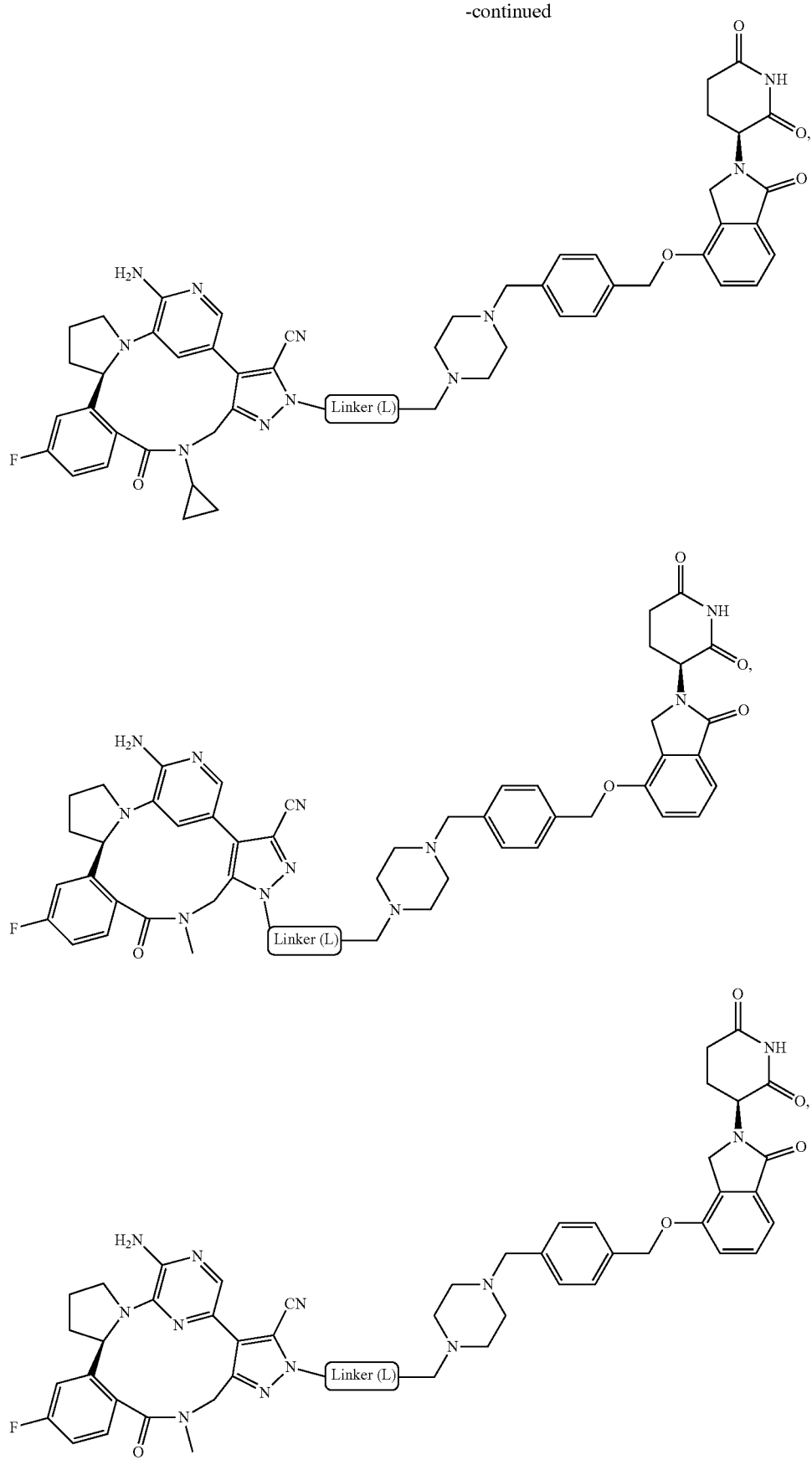

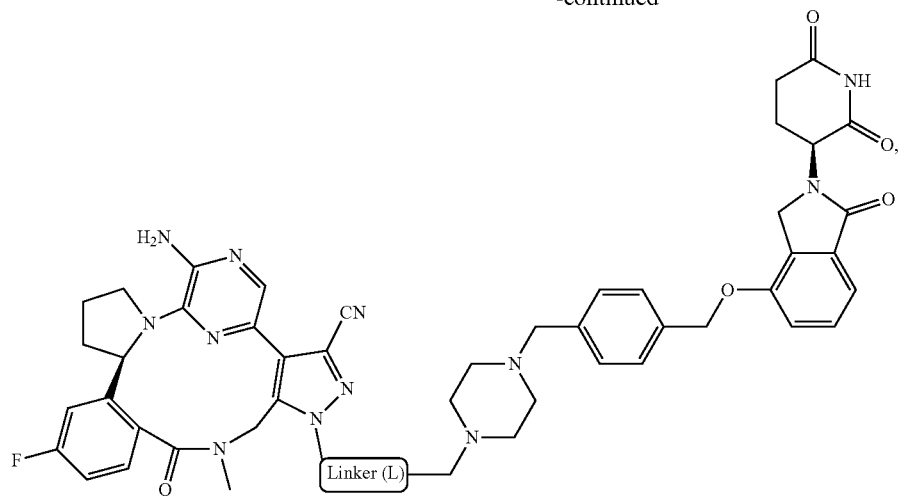
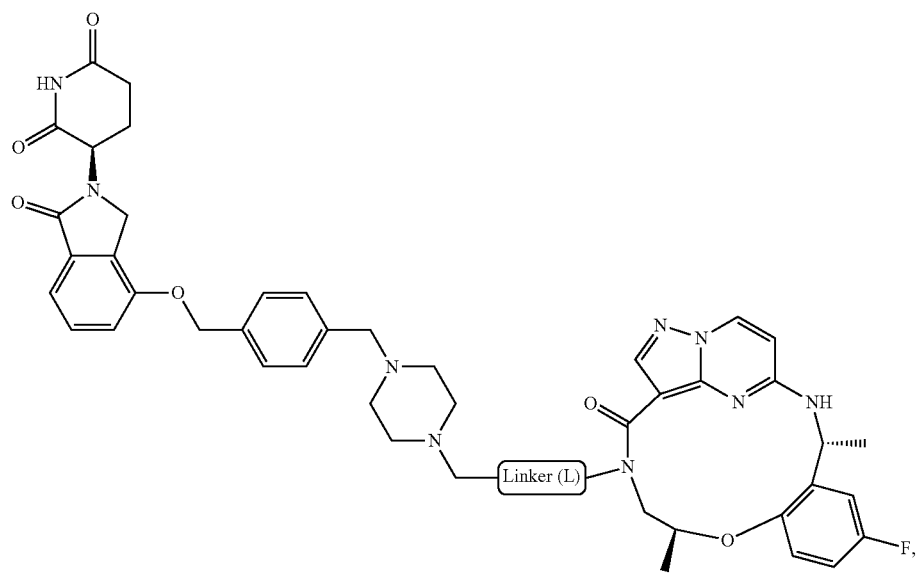
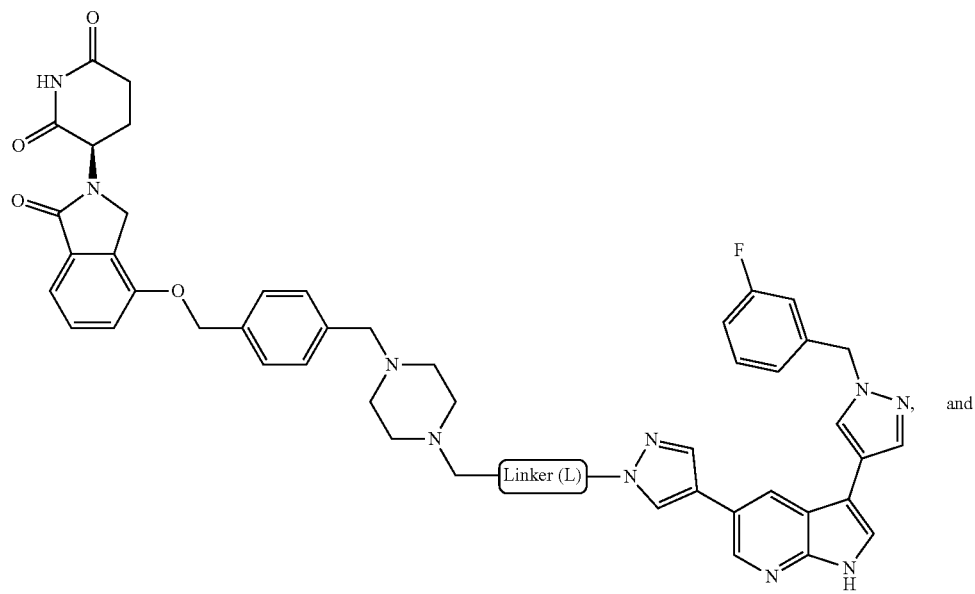

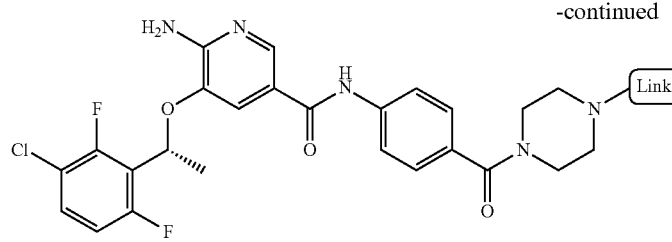

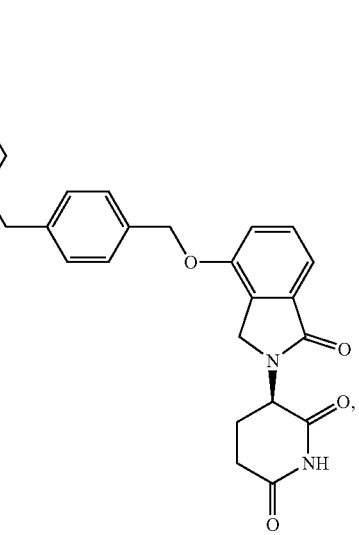

wherein $R_9$ is H or Me

X is alkyl, halo, CN, $CF_3$, $OCHF_2$ or $OCF_3$;

Y is NH or O;

or a pharmaceutically acceptable salt or stereoisomer thereof.

Yet other degrons that bind cereblon and which may be suitable for use in the present invention are disclosed in U.S. Patent Application Publication 2018/0015085 (e.g., the indolinones such as isoindolinones and isoindoline-1,3-diones embraced by formulae IA ad IA' therein, and the bridged cycloalkyl compounds embraced by formulae IB and IB' therein).

In some embodiments, the E3 ubiquitin ligase that is bound by the degron is the von Hippel-Lindau (VHL) tumor suppressor. See, Iwai et al., Proc. Nat'l. Acad. Sci. USA 96:12436-41(1999).

Representative examples of degrons that bind VHL are as follows:

(D2-a)

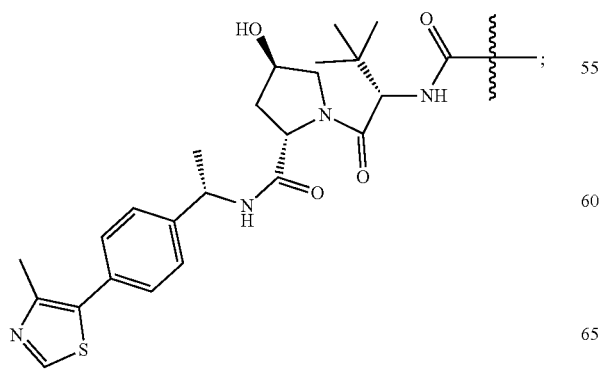

-continued (D2-b)

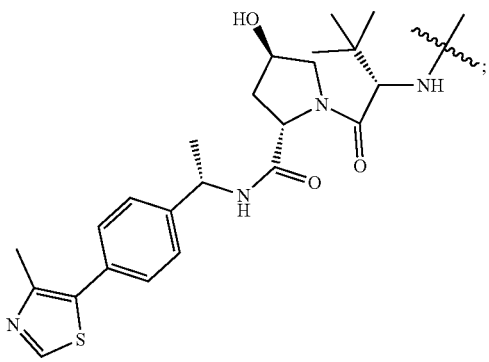

(D2-c)

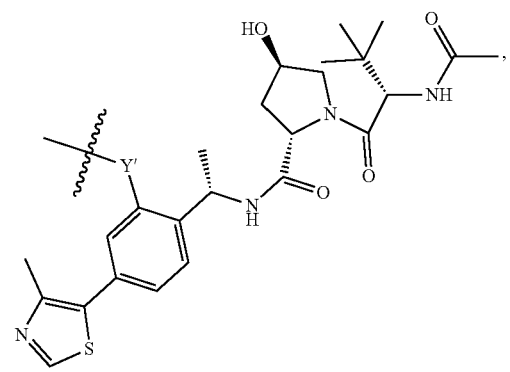

wherein Y' is a bond, N, O or C;

(D2-d)
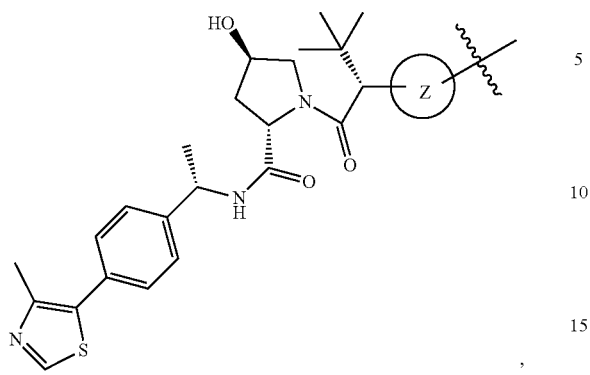
wherein Z is a cyclic group, e.g., a C5-6 carbocyclic or heterocyclic group, and
(D2-e)
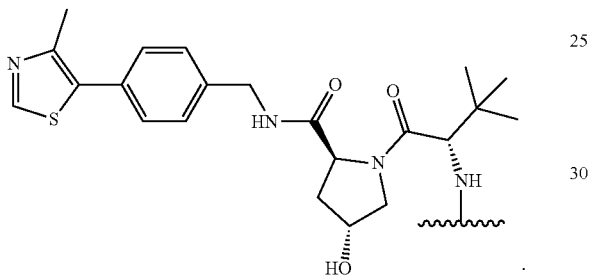
In certain embodiments, Z is a cyclic group selected from the group consisting of:
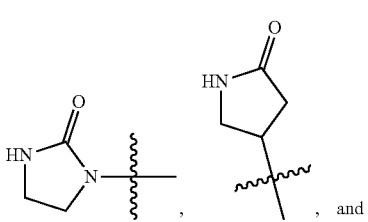, and
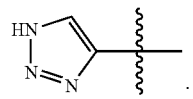.
Thus, in some embodiments, the bispecific compounds of the present invention are represented by any one of the following structures:
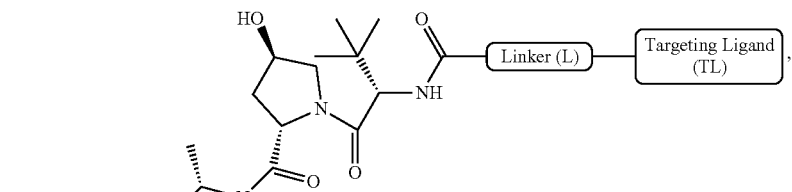
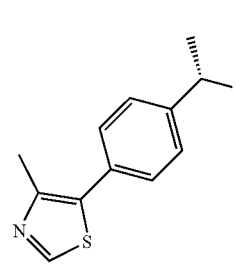
,
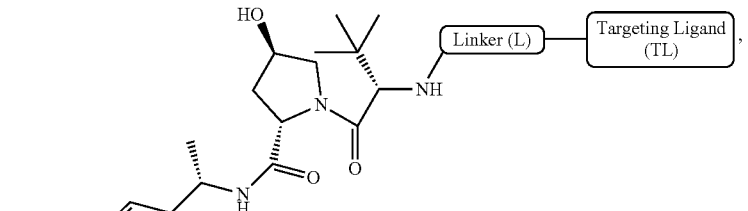
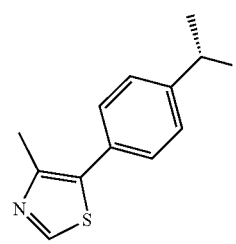
,

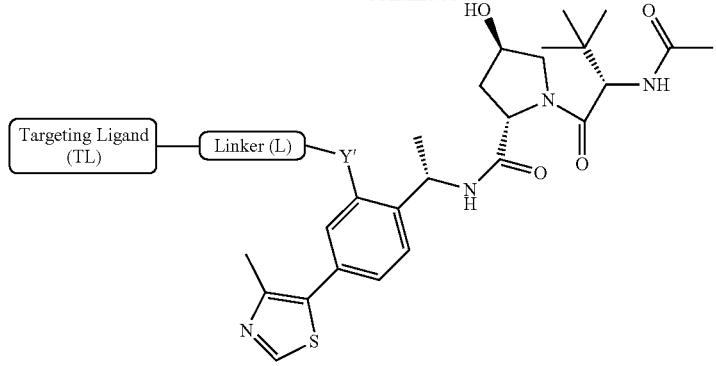
wherein Y' is a bond, N, O or C,
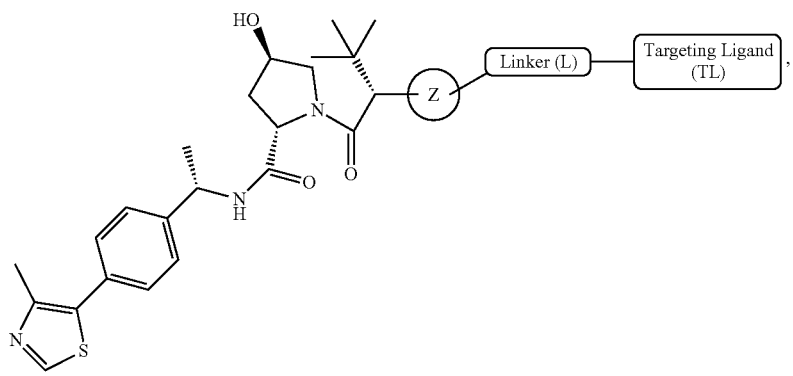
wherein Z is a cyclic group, e.g., a C5-6 carbocyclic or heterocyclic group, and
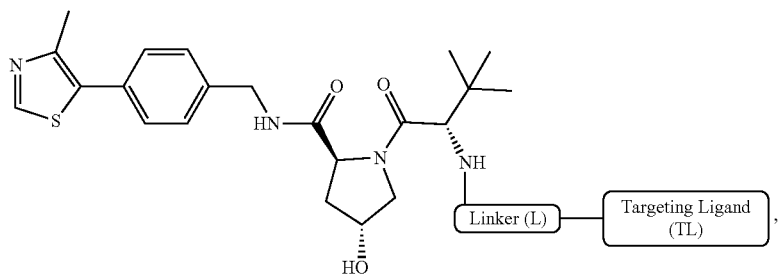
or a pharmaceutically acceptable salt or stereoisomer thereof.
In some embodiments, the bispecific compounds of the present invention are represented by any one of the following structures:

173 174
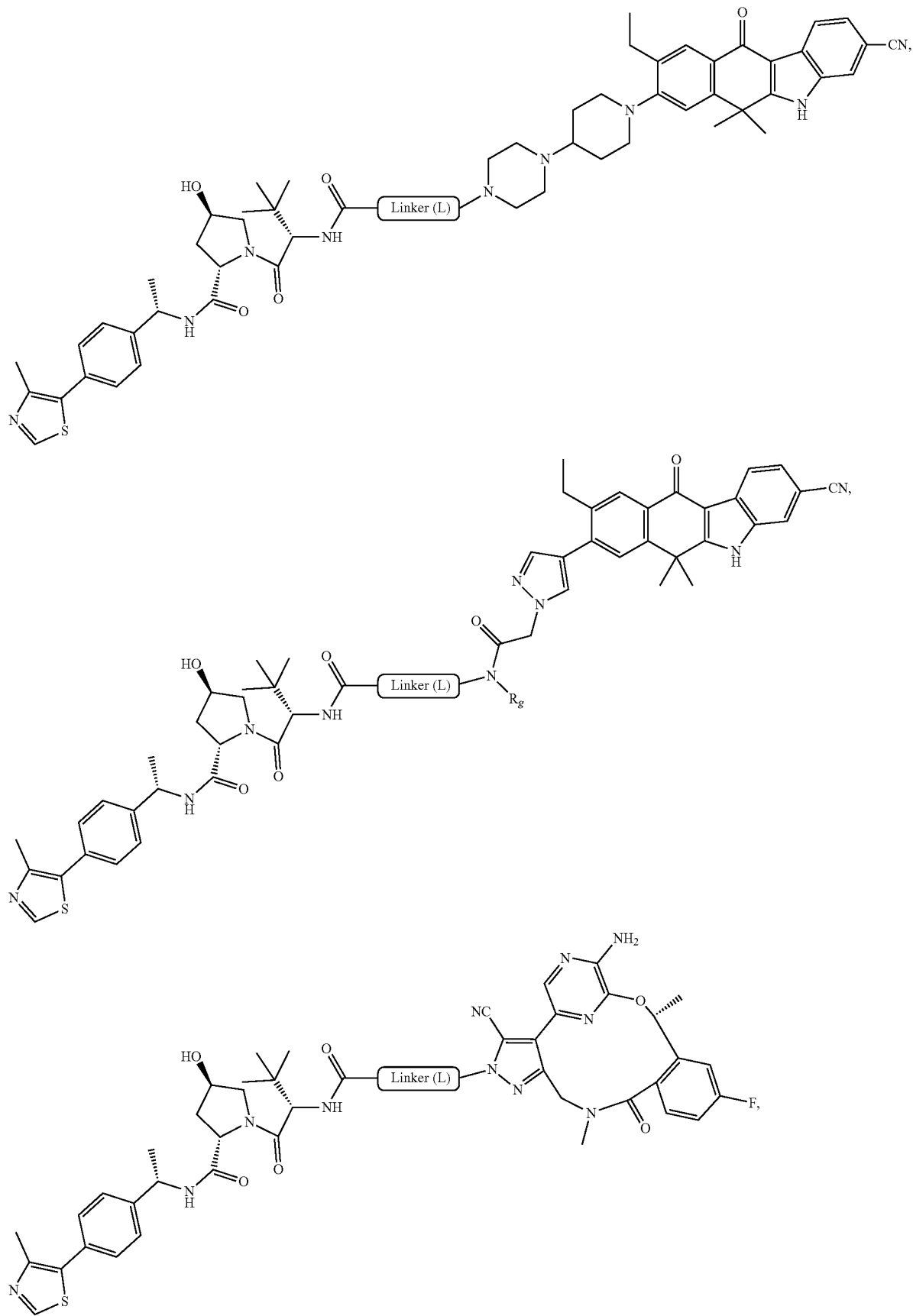

-continued
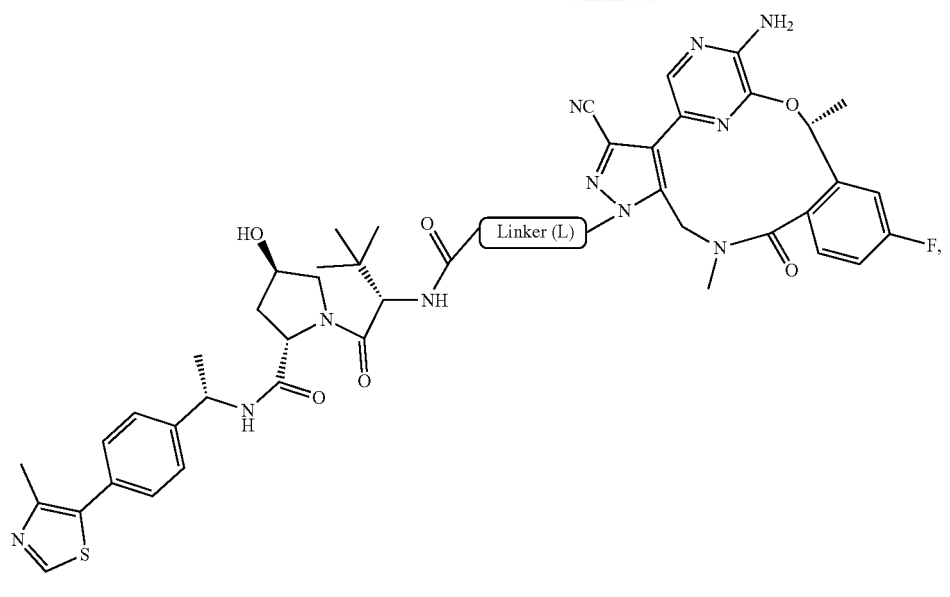
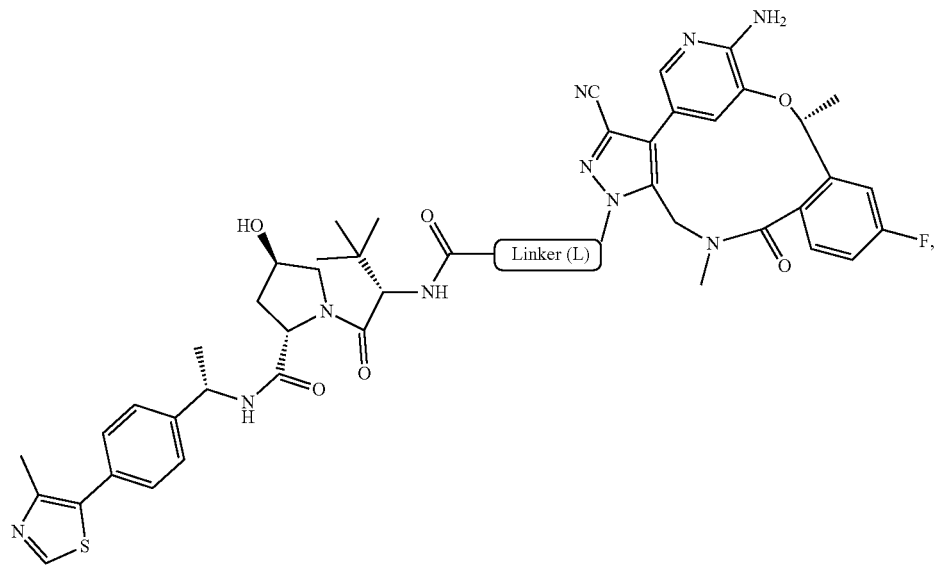
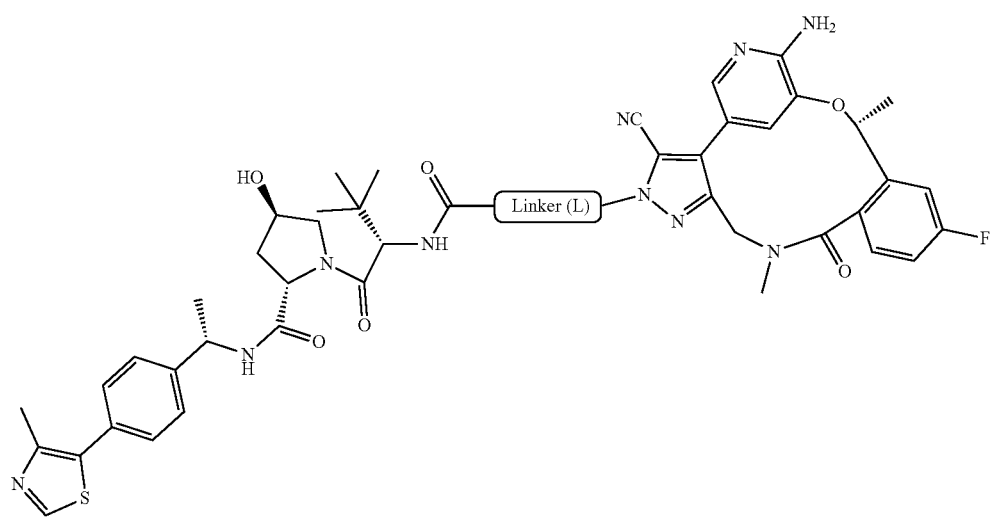

-continued
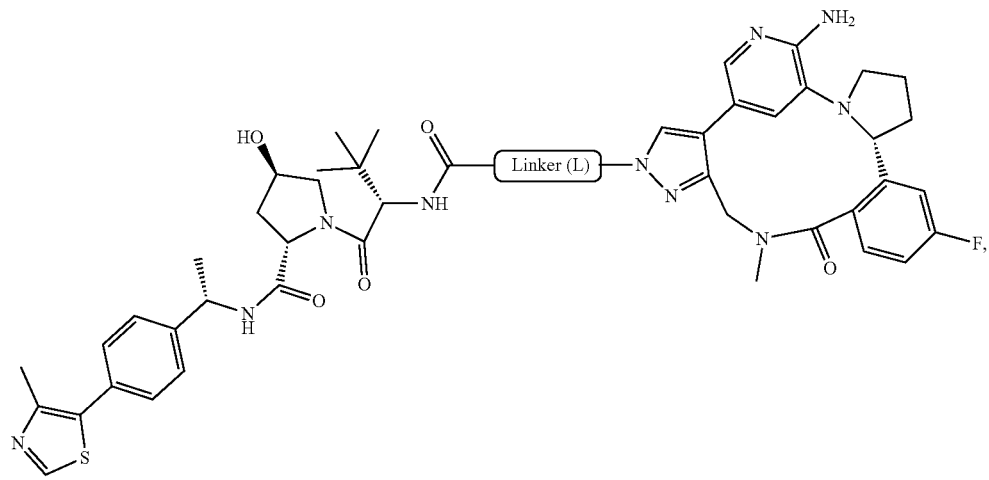
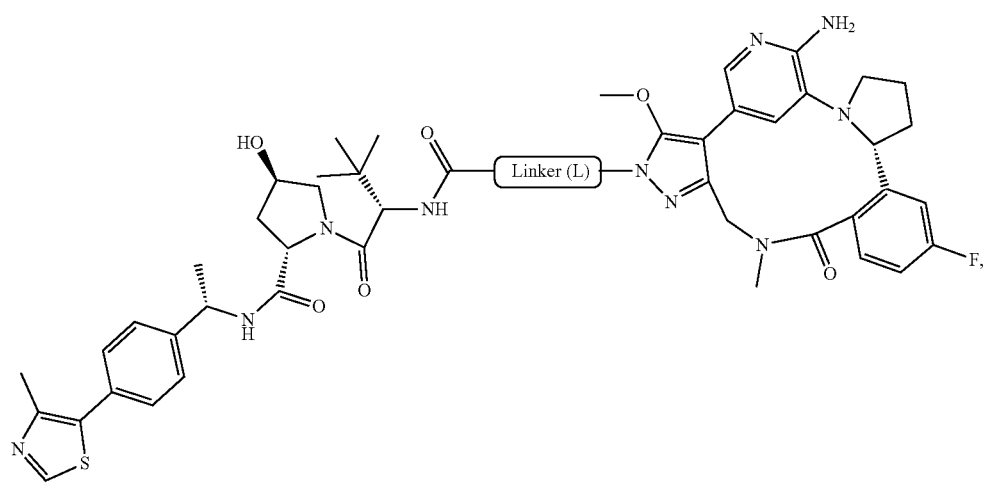
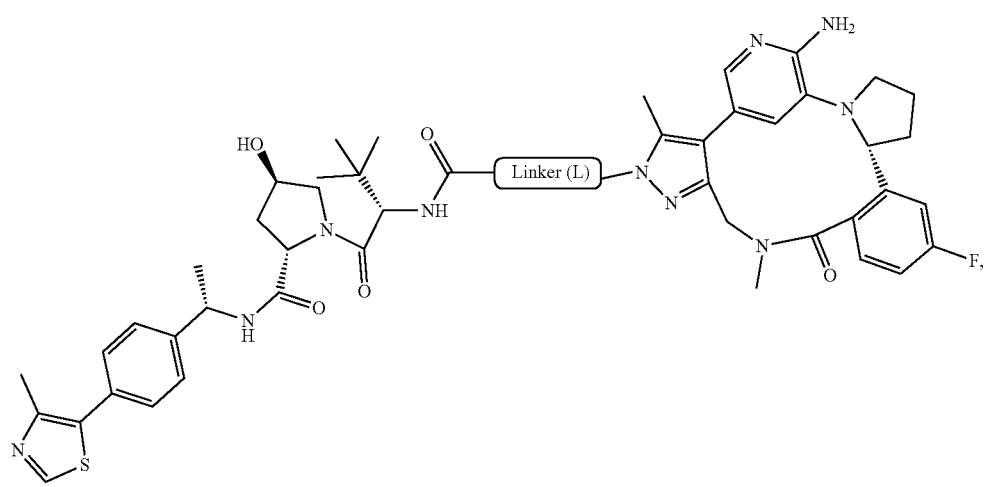

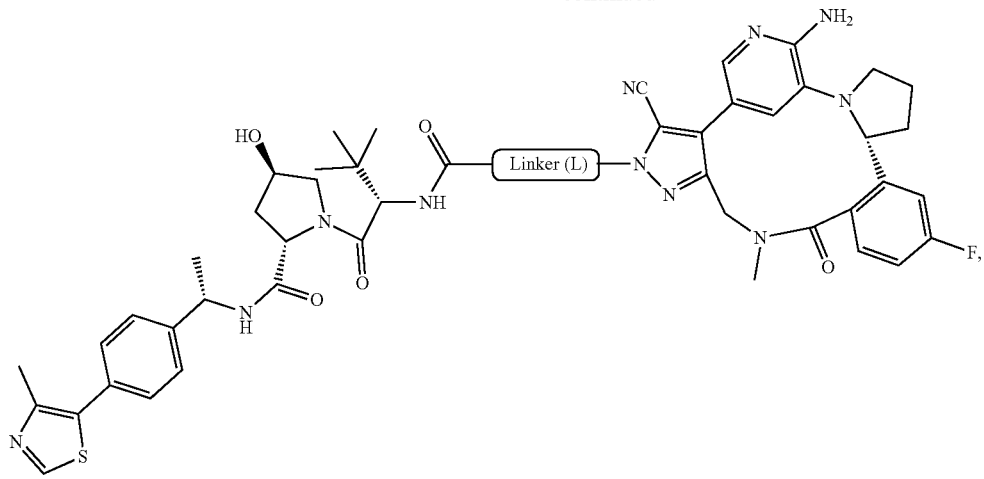
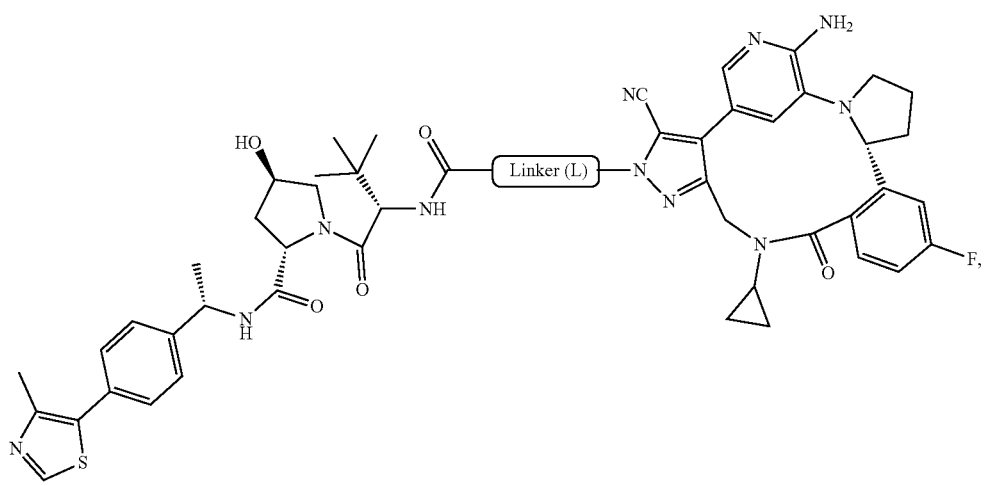
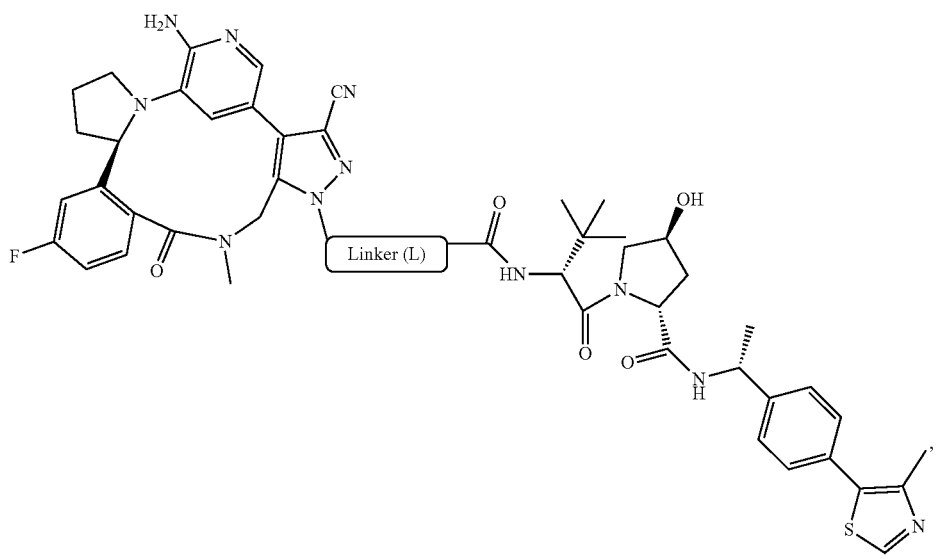

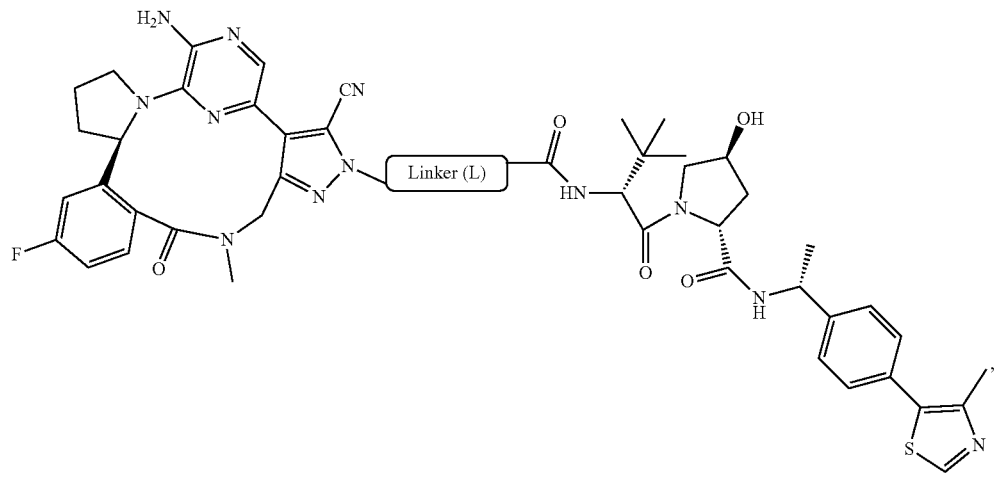
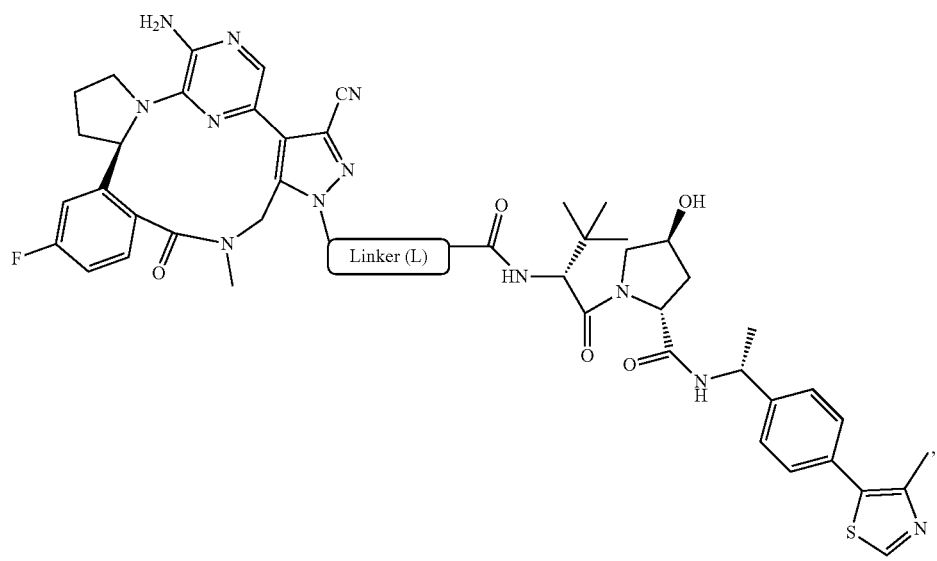
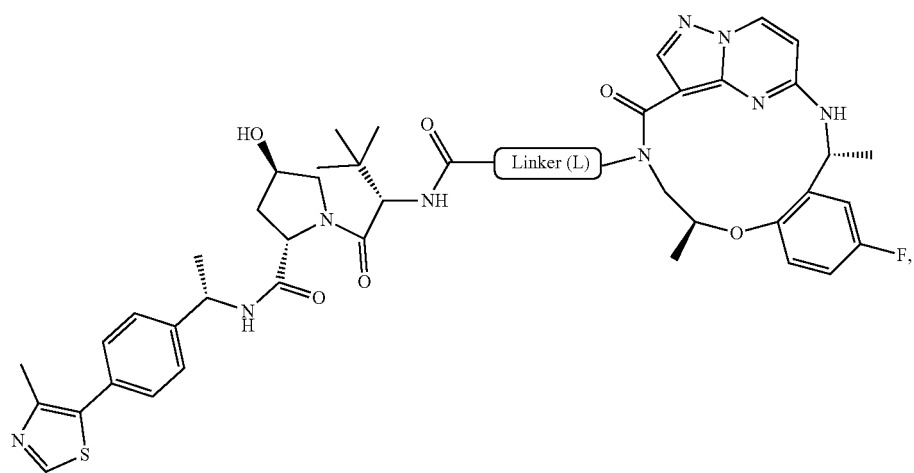

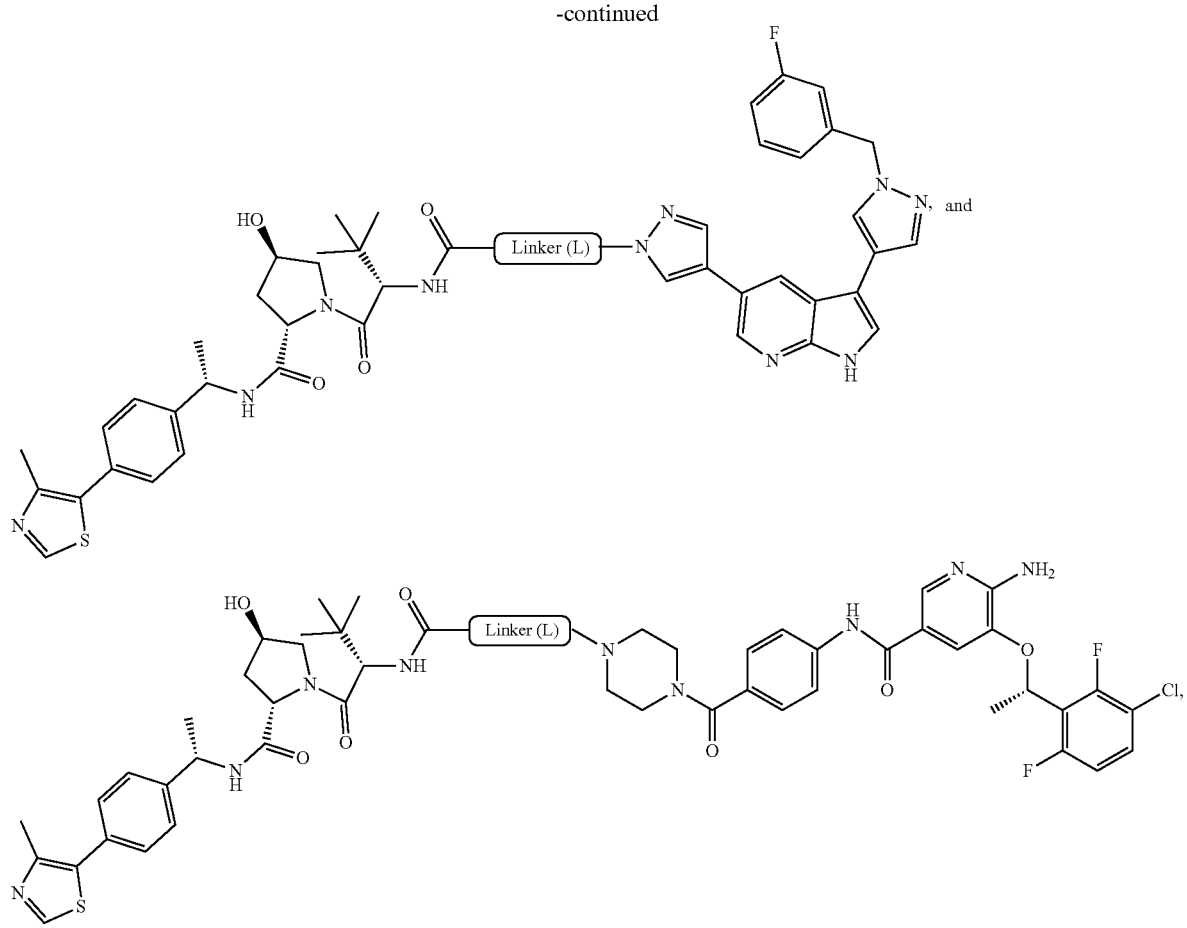

or a pharmaceutically acceptable salt or stereoisomer thereof.

Yet other degrons that bind VHL and which may be suitable for use in the present invention are disclosed in U.S. Patent Application Publication 2017/0121321 A1.

In some embodiments, the E3 ubiquitin ligase that is bound by the degron is an inhibitor of apoptosis protein (IAP). Representative examples of degrons that bind IAP and may be suitable for use in the present invention are represented by any one of the following structures:

(D3-a)

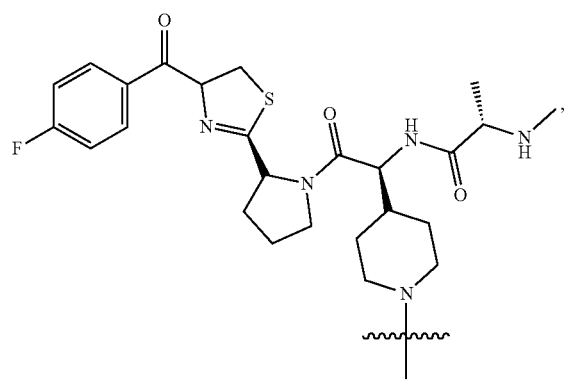

-continued (D3-b)

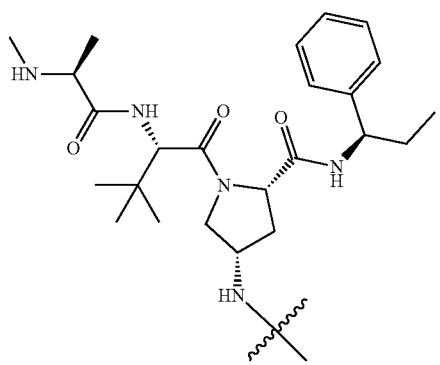

(D3-c)

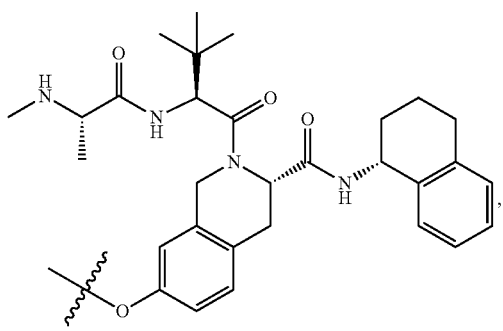

-continued (D3-d)
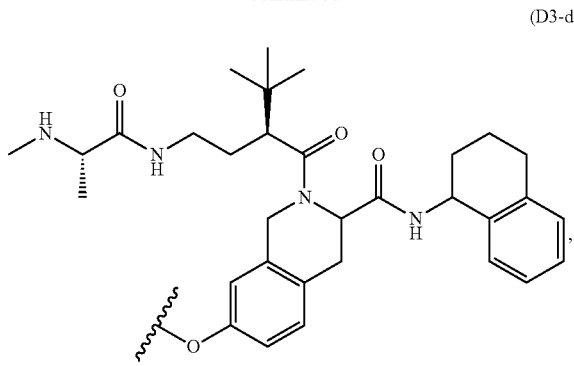

(D3-e)
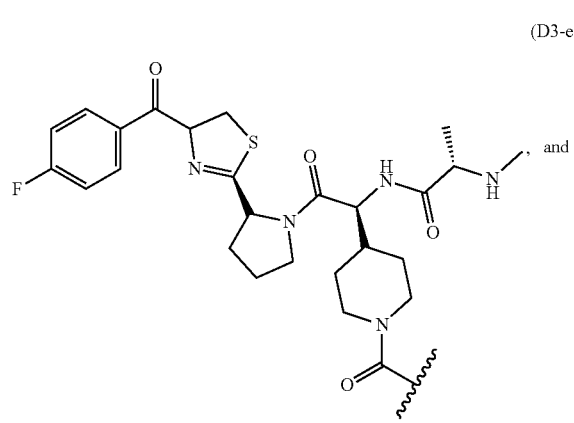, and (D3-f)
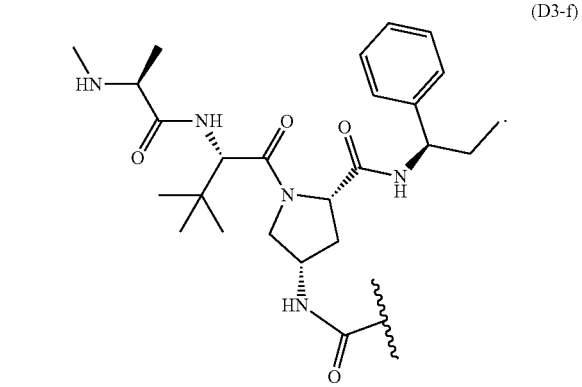

Thus, in some embodiments, the bispecific compounds of the present invention are represented by any one of the following structures:

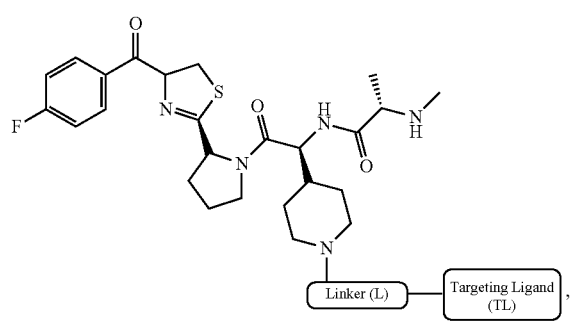,

-continued

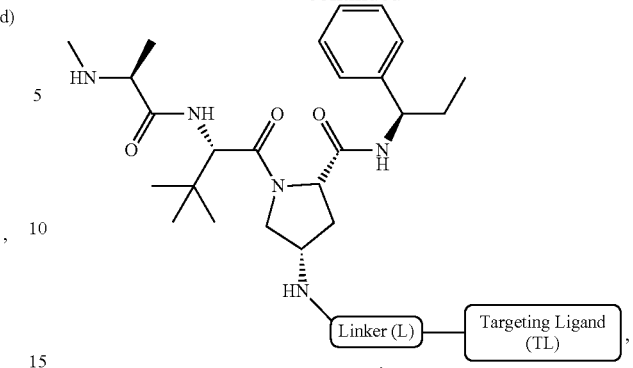,

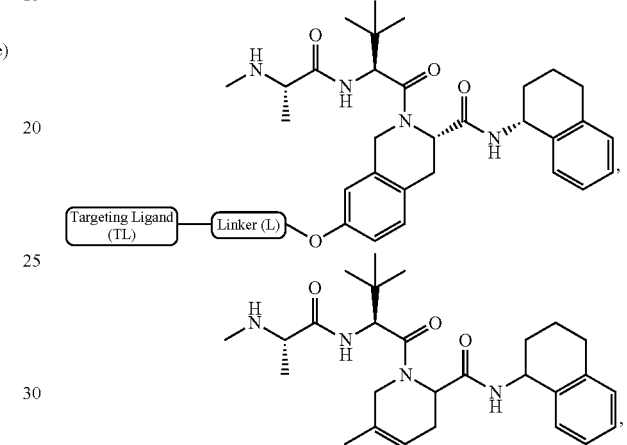,

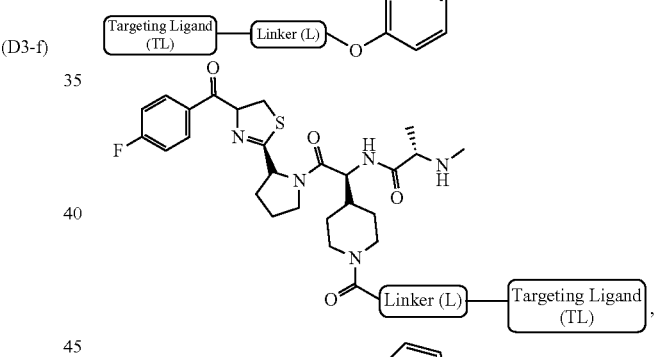, and
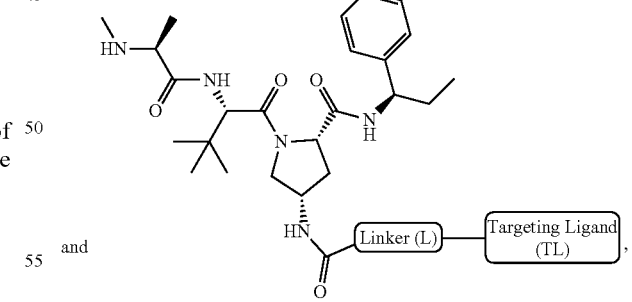, or a pharmaceutically acceptable salt or stereoisomer thereof.

Yet other degrons that bind IAPs and which may be suitable for use as degrons in the present invention are disclosed in International Patent Application Publication Nos. WO 2008128171, WO 2008/016893, WO 2014/060768, WO 2014/060767, and WO 15092420.

In some embodiments, the E3 ubiquitin ligase that is bound by the degron is murine double minute 2 (MDM2).

Representative examples of degrons that bind IAP and may be suitable for use in the present invention are represented by any one of the following structures:
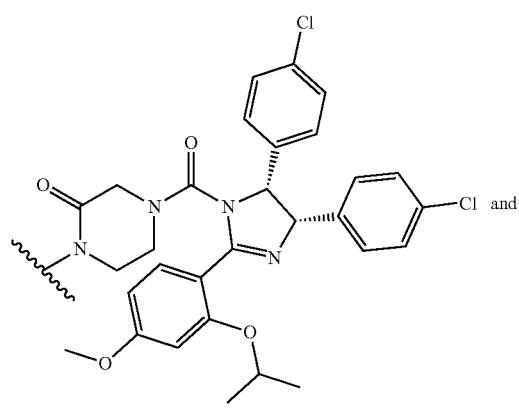
(D4-a)
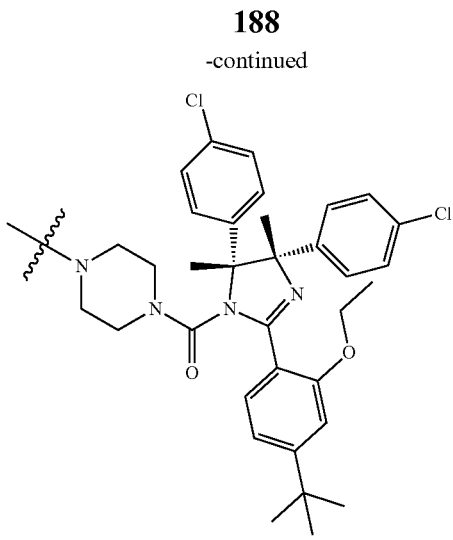
(D4-b)
Thus, in some embodiments, the bispecific compounds of the present invention are represented by any one of the following structures:
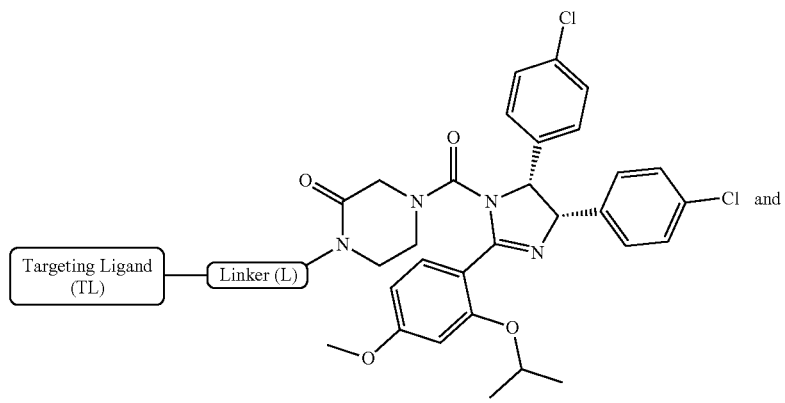
and
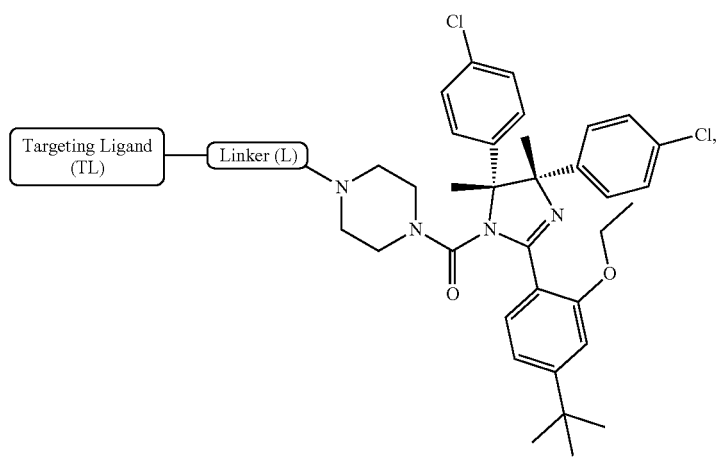

or a pharmaceutically acceptable salt or stereoisomer thereof.

Yet other degrons that bind MDM2 and which may be suitable for use as degrons in the present invention are disclosed in U.S. Pat. No. 9,993,472 B2. MDM2 is known in the art to function as an ubiquitin-E3 ligase.

Thus, in some embodiments, the compounds of this invention are represented by any structures generated by the combination of structures TL1 to TL5, L1 to L11, and the structures of the degrons described herein, including D1 to D4, or a pharmaceutically acceptable salt or stereoisomer thereof.

In some embodiments, the compound of the present invention is represented by any one of the following structures:

(1)
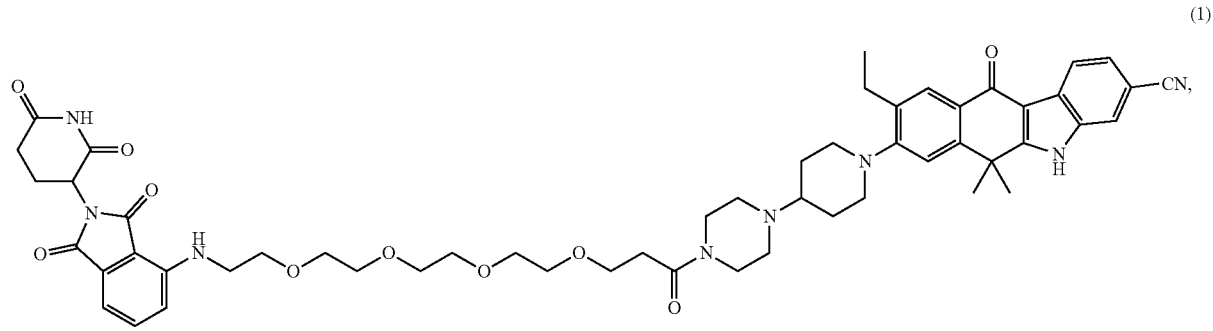

(2)
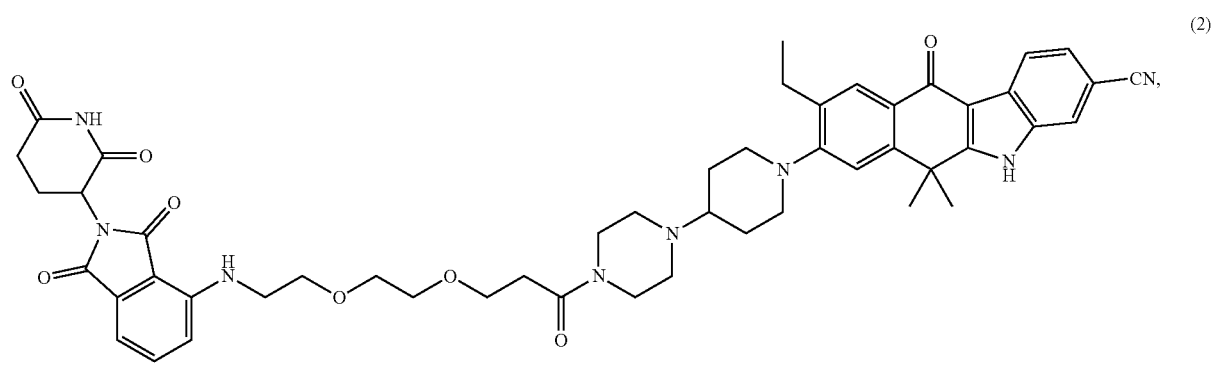

(3)
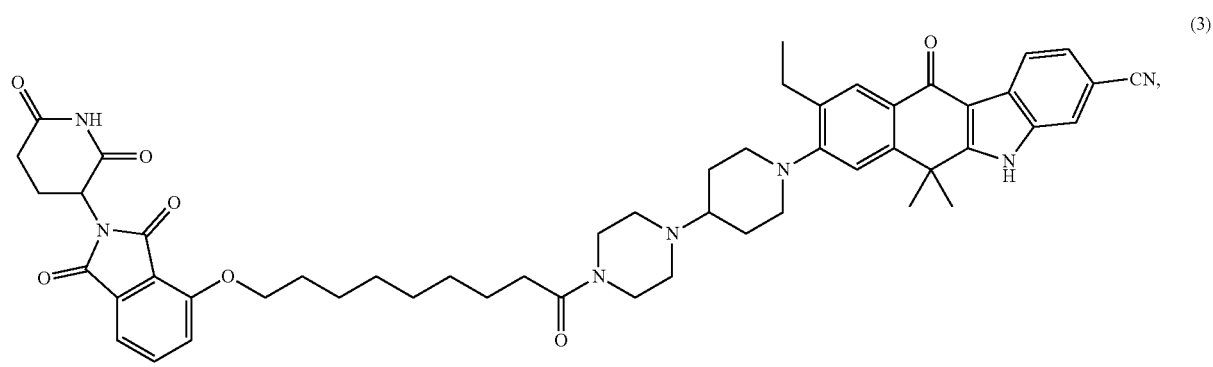

(4)
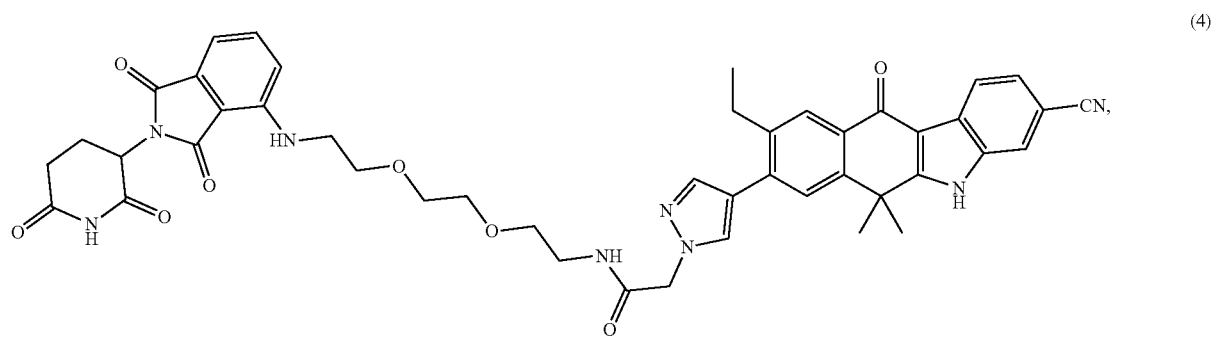

(5)
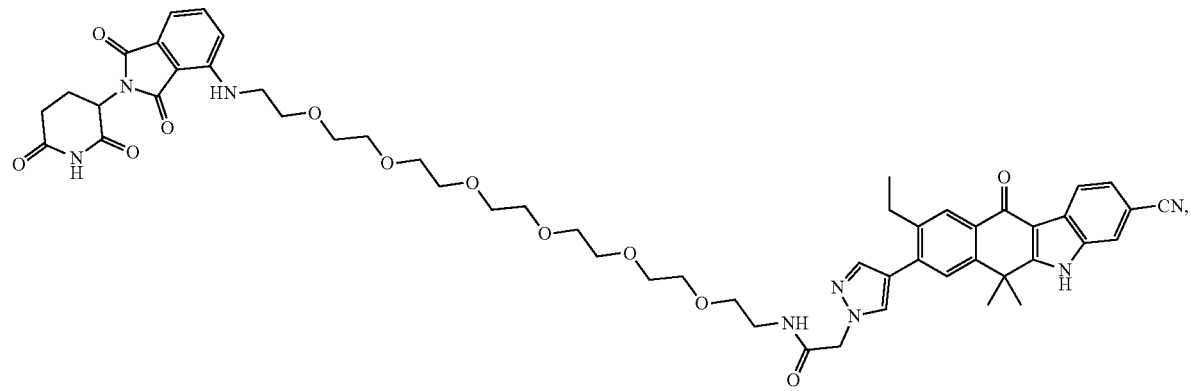
(6)
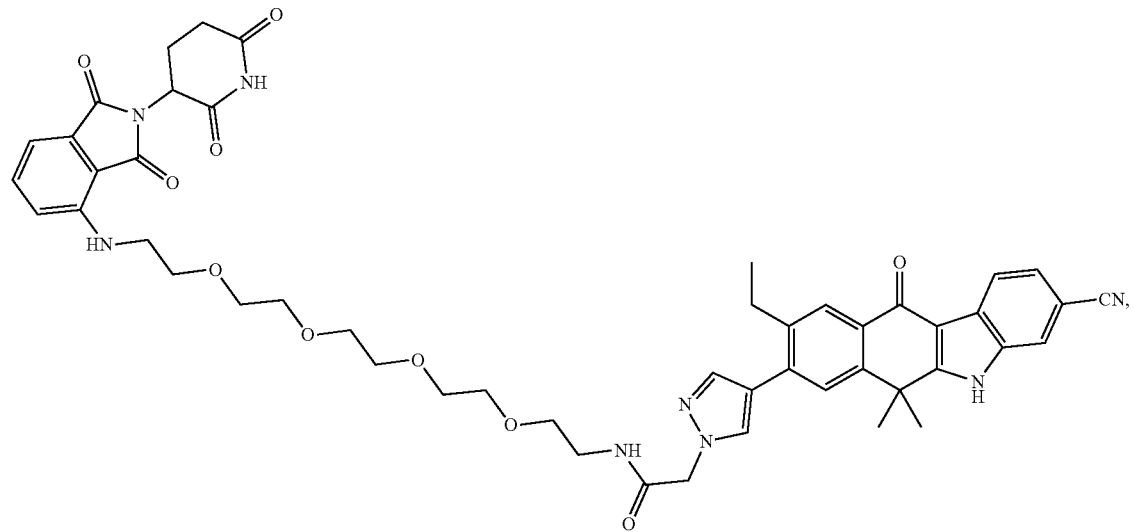
(7)
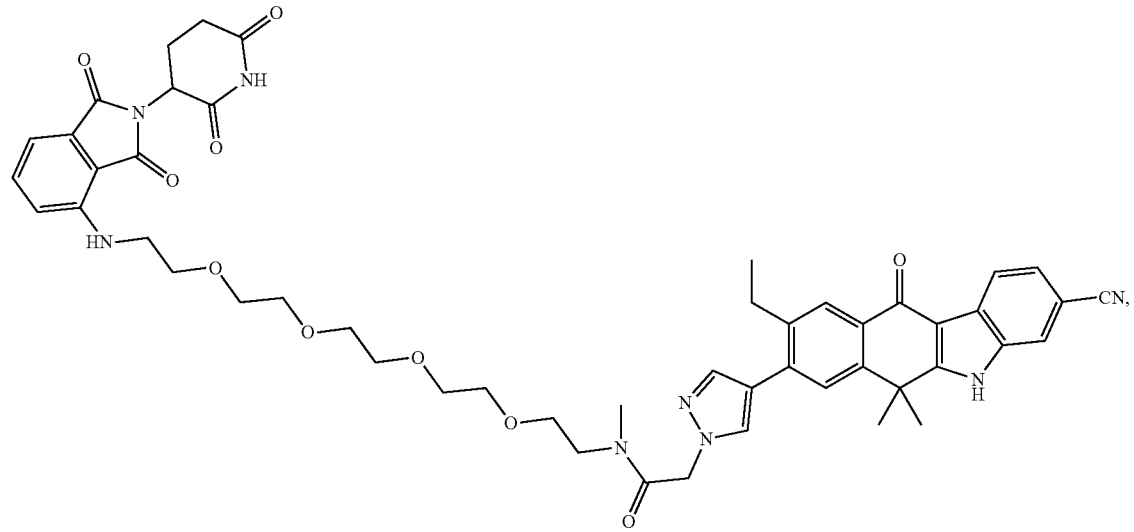

(8)
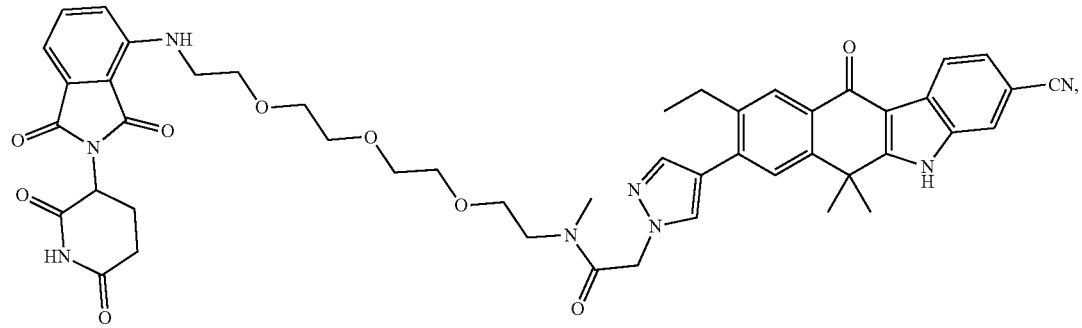
(9)
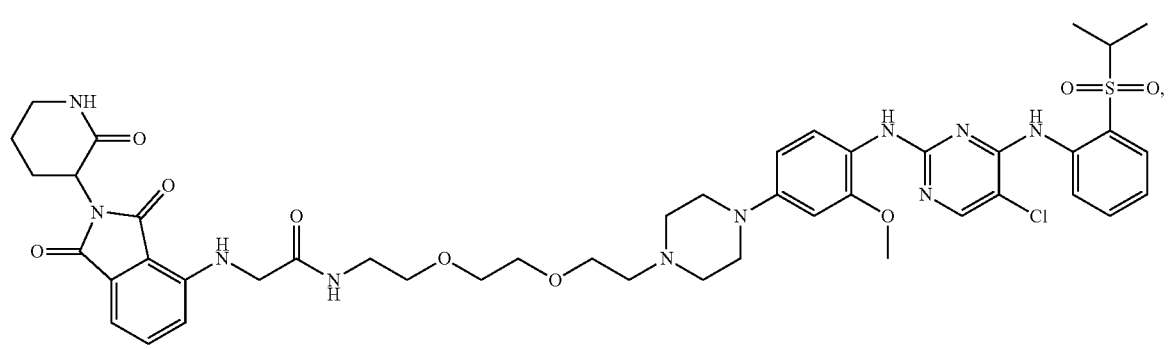
(10)
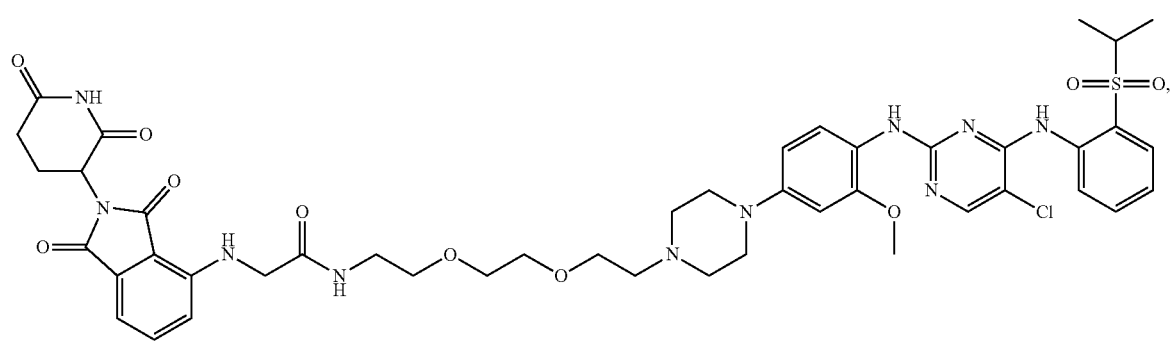
(11)
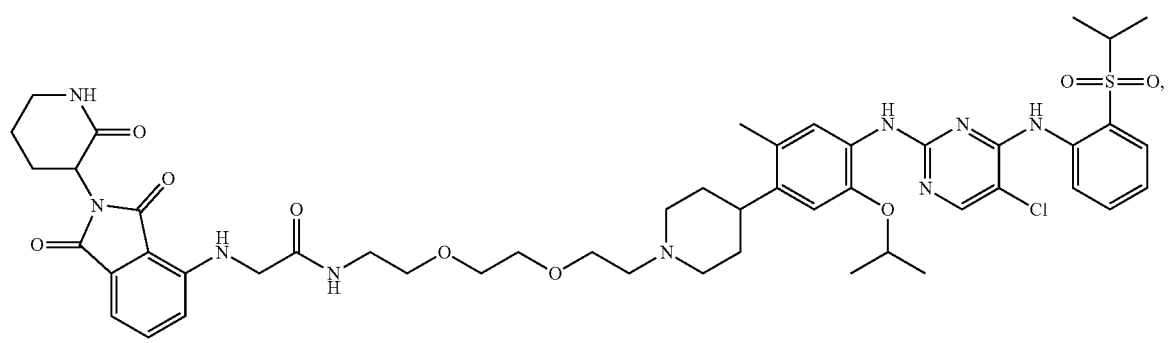

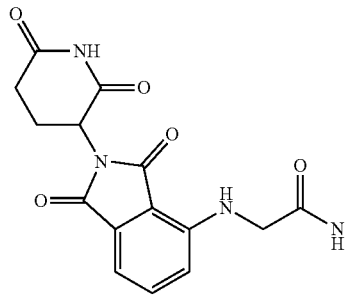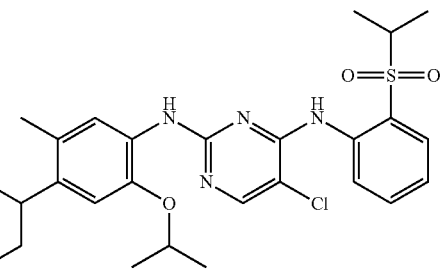
(12)
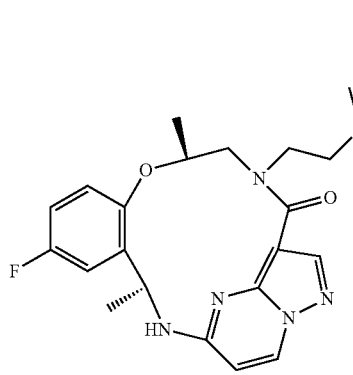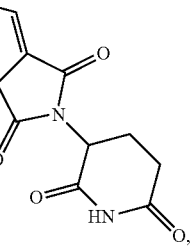
(14)
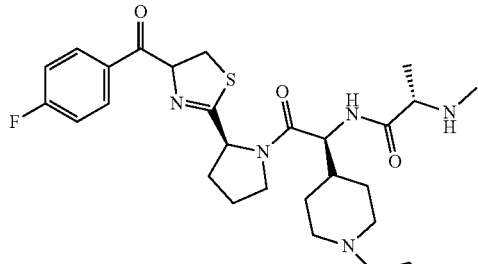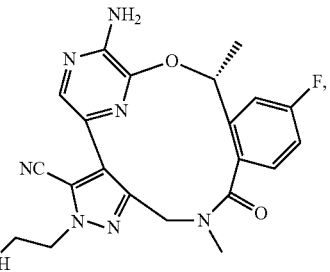
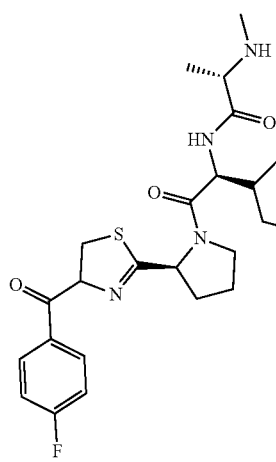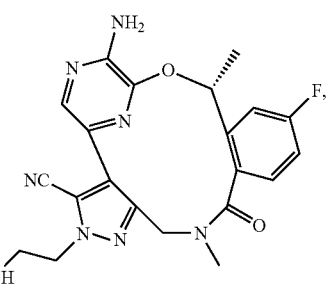

-continued
197
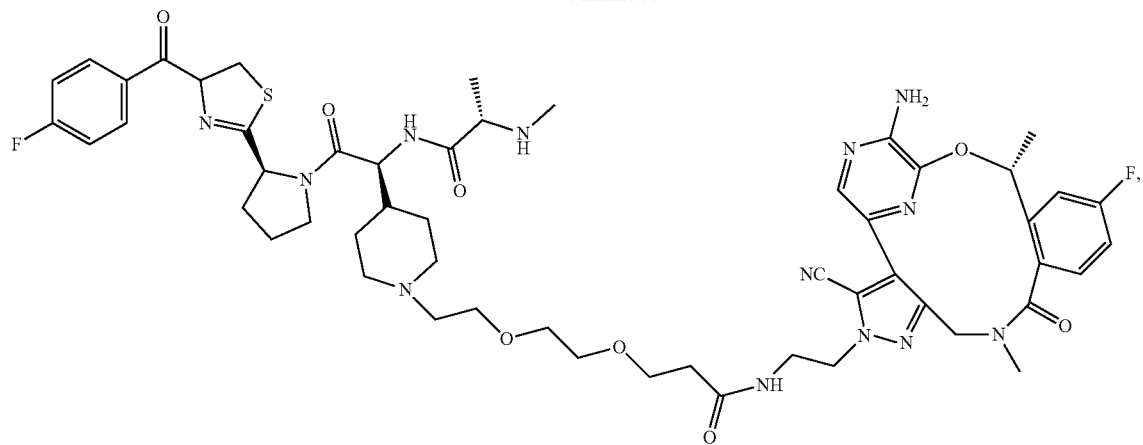
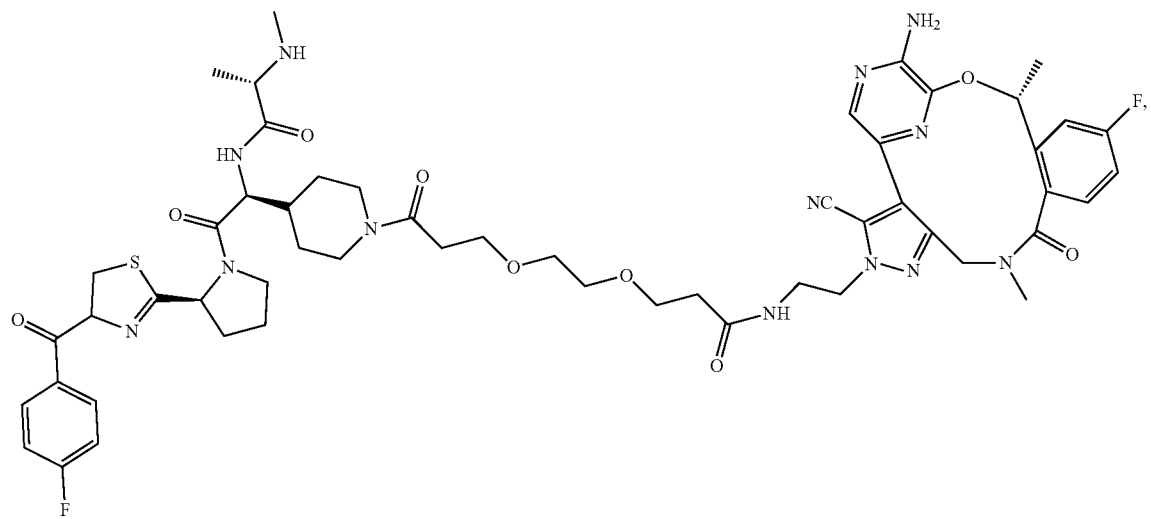
198
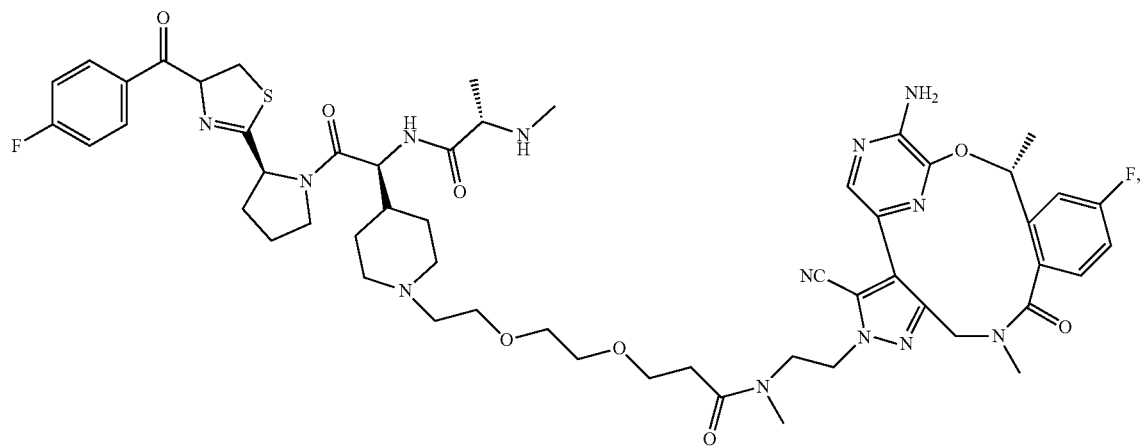

199 200
-continued
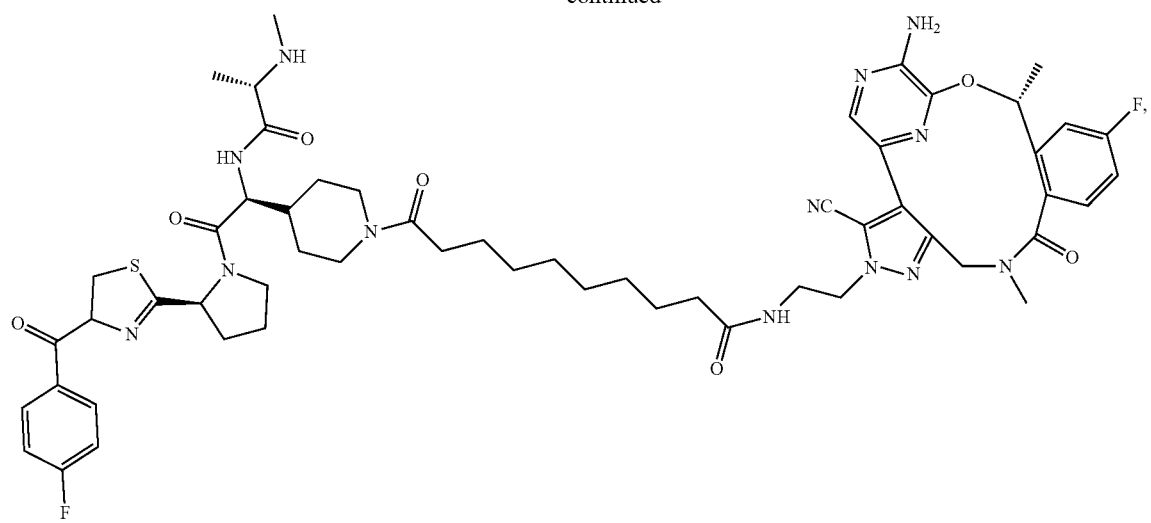
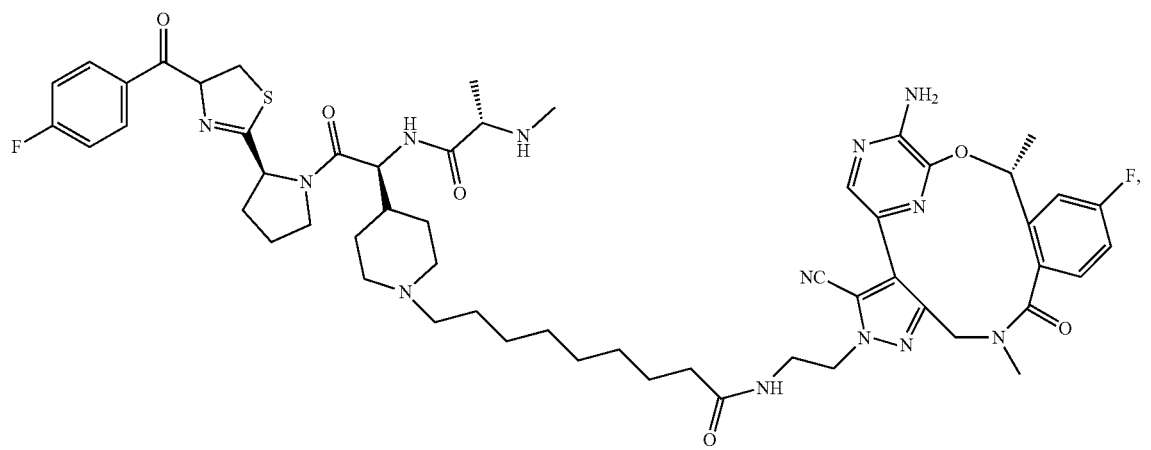
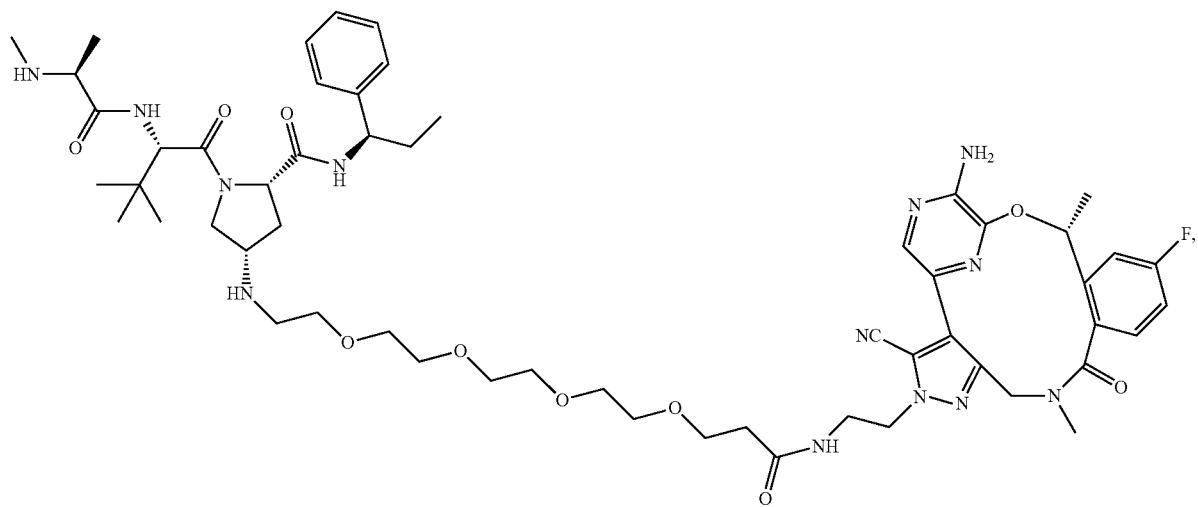

201
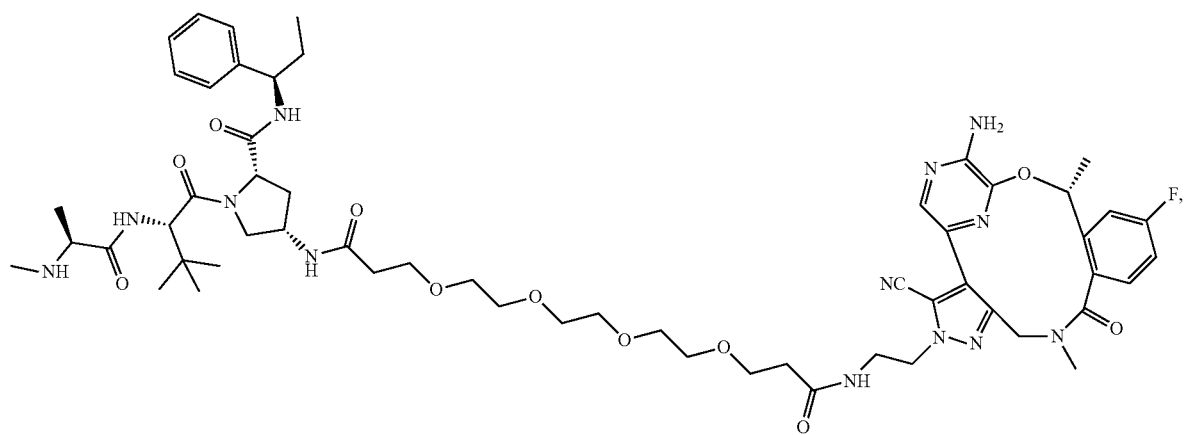
202
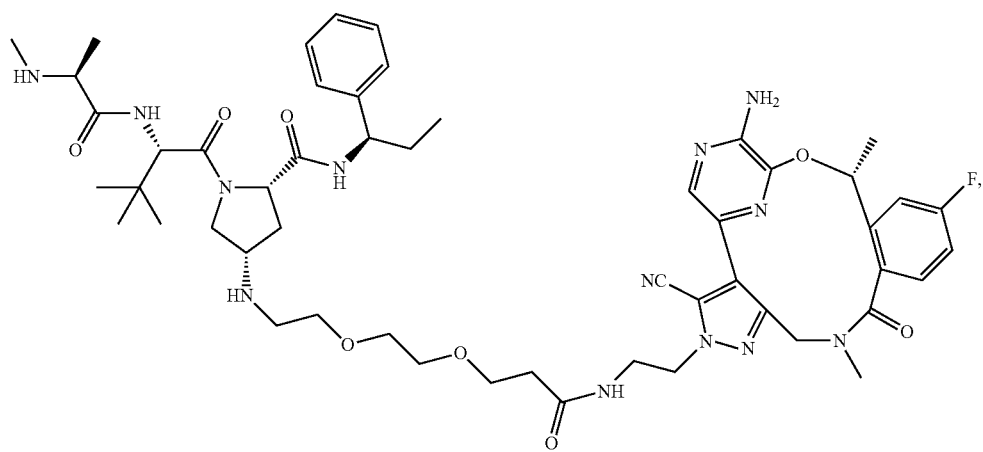
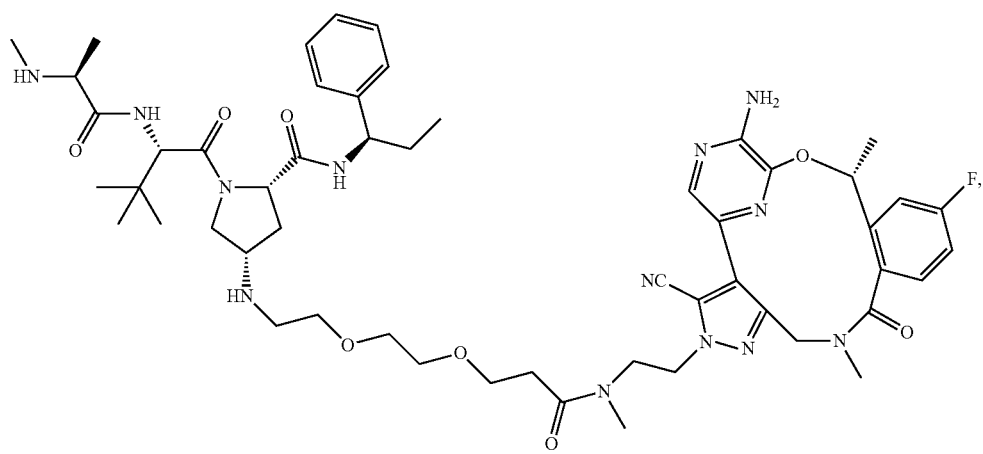

203
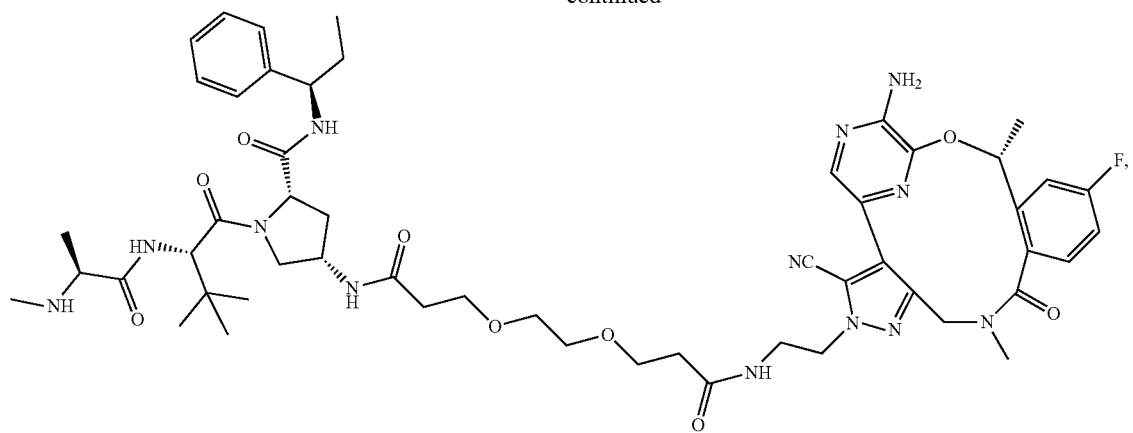
204
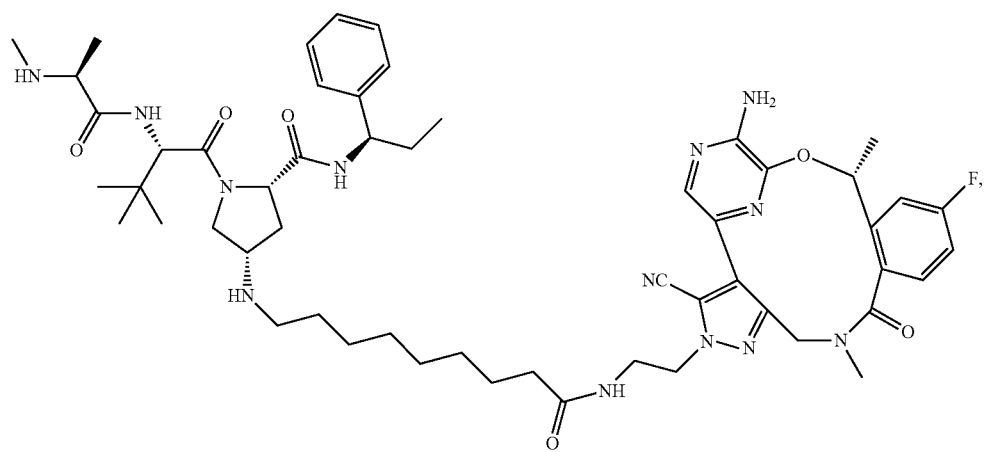
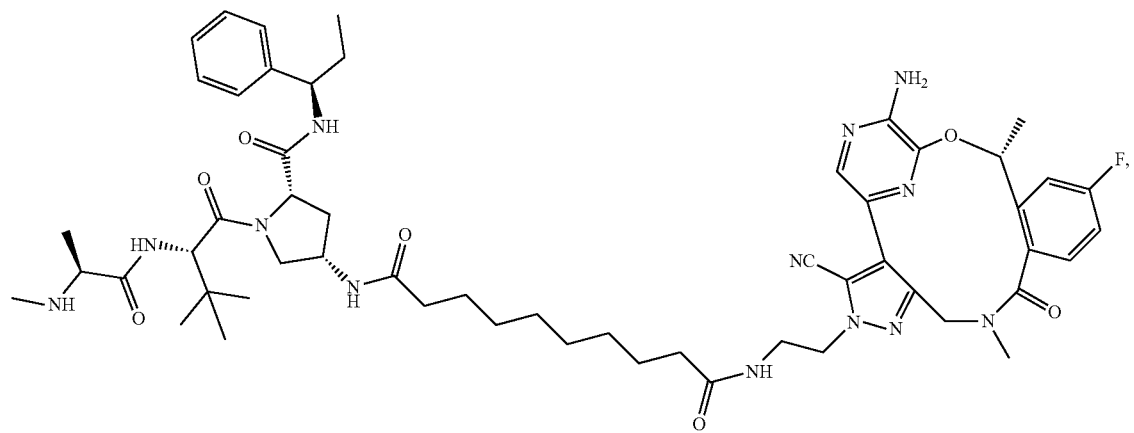

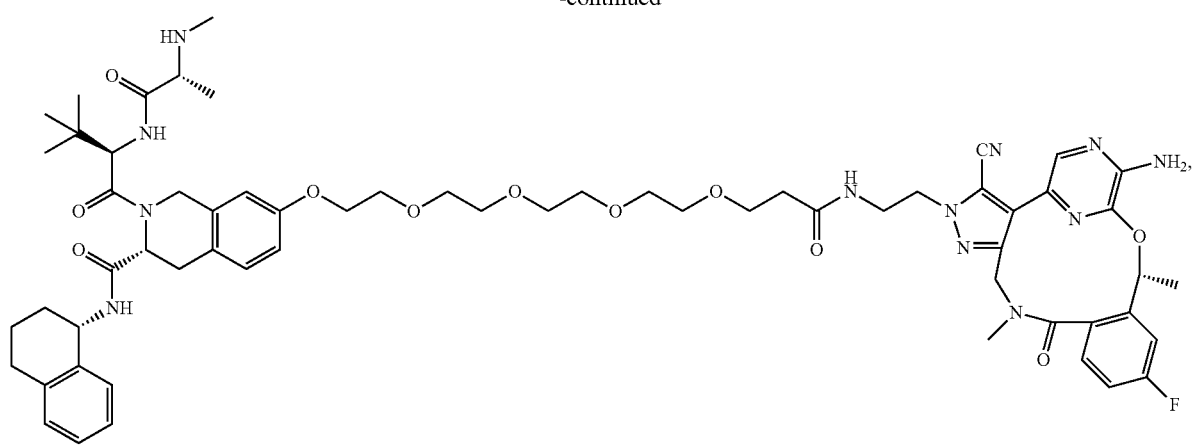
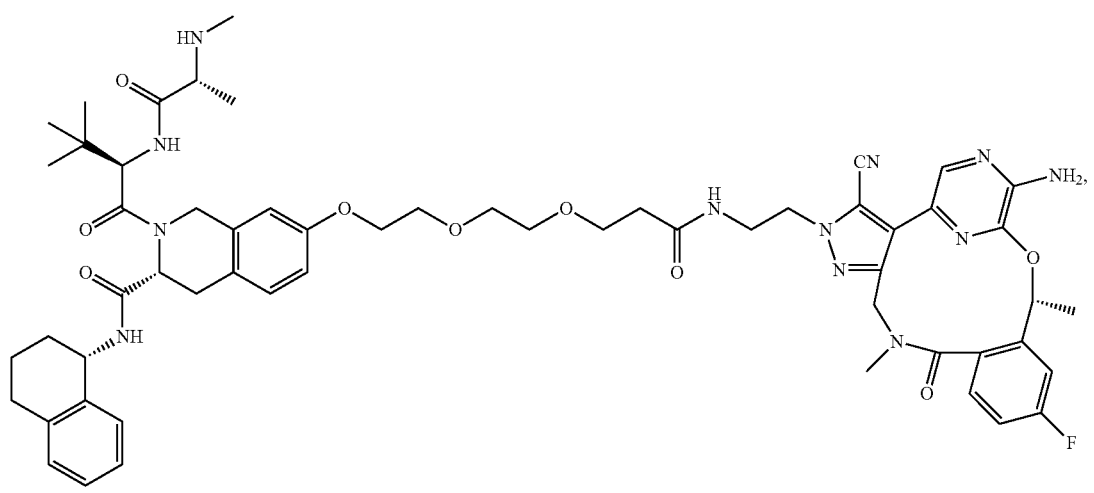
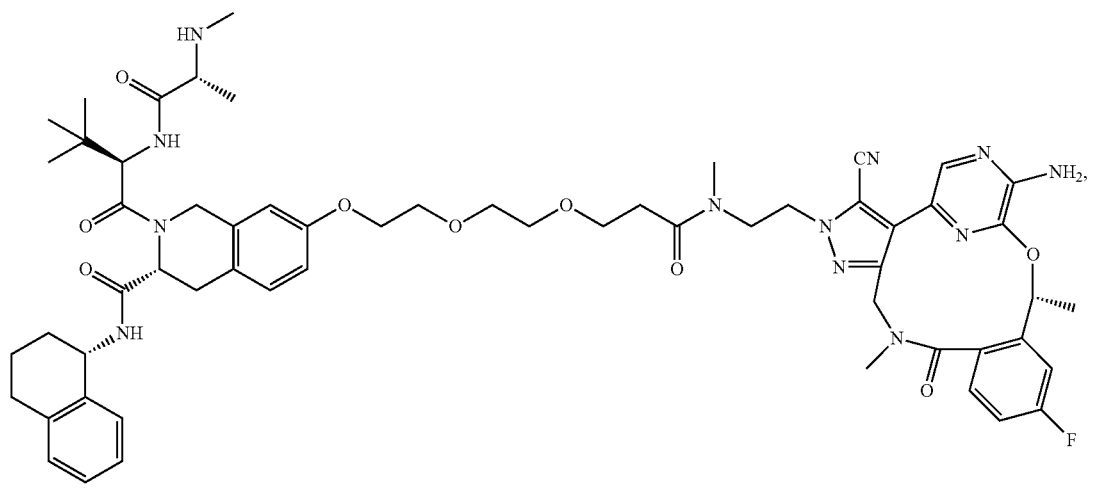

207
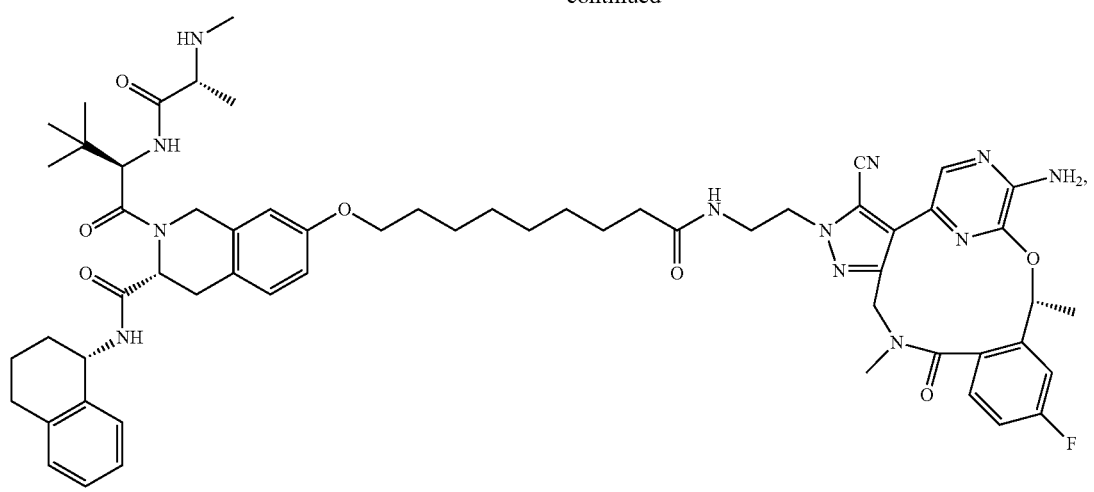
-continued
208
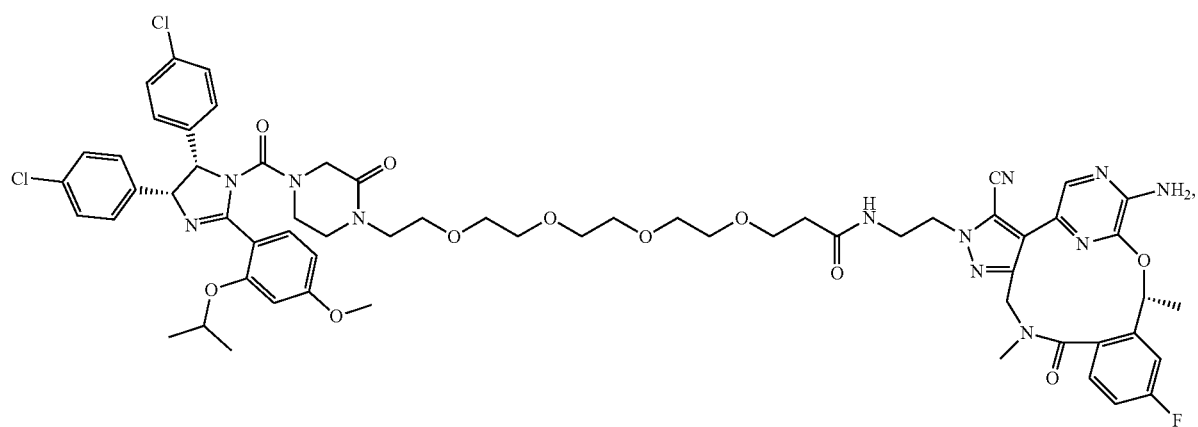
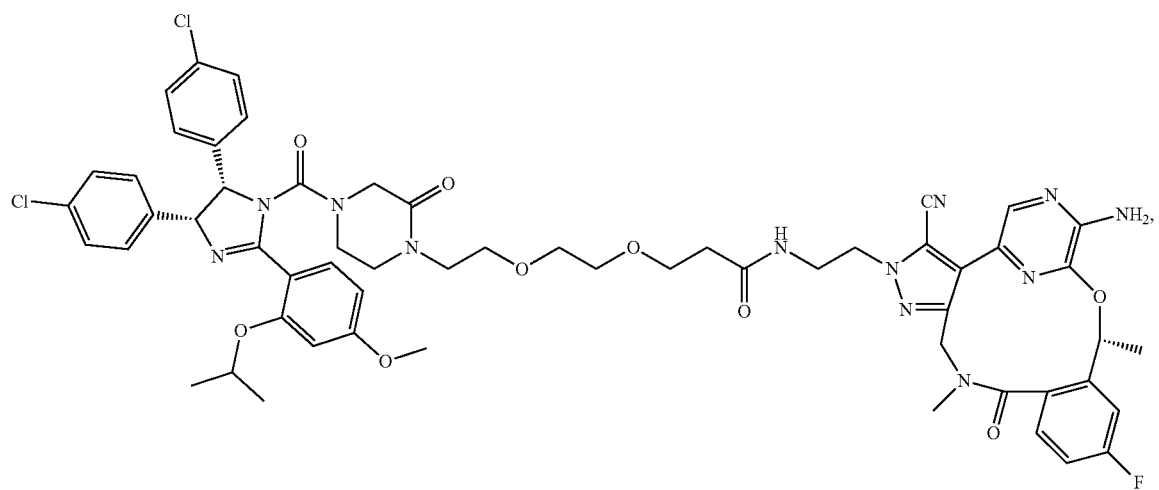

209
210
-continued
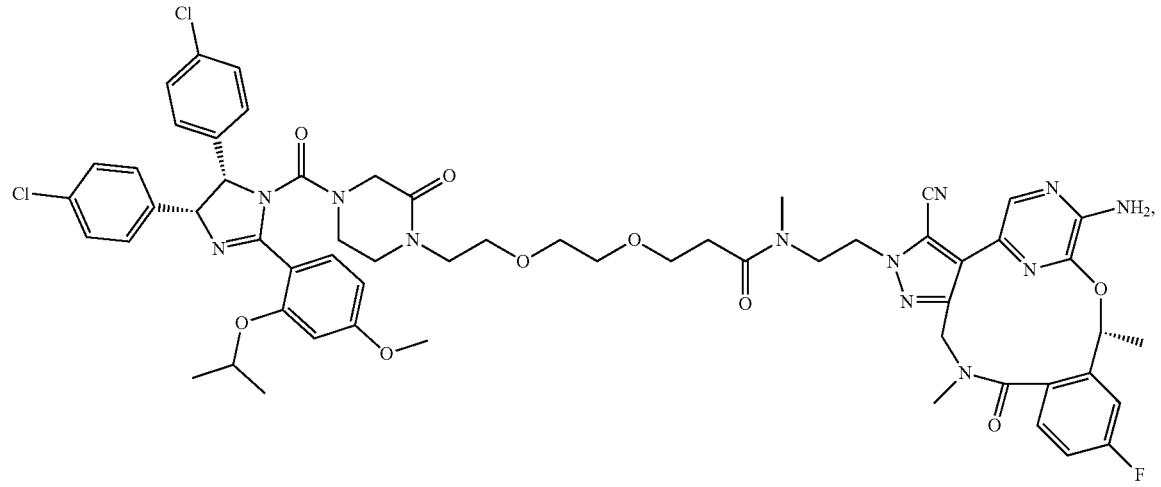
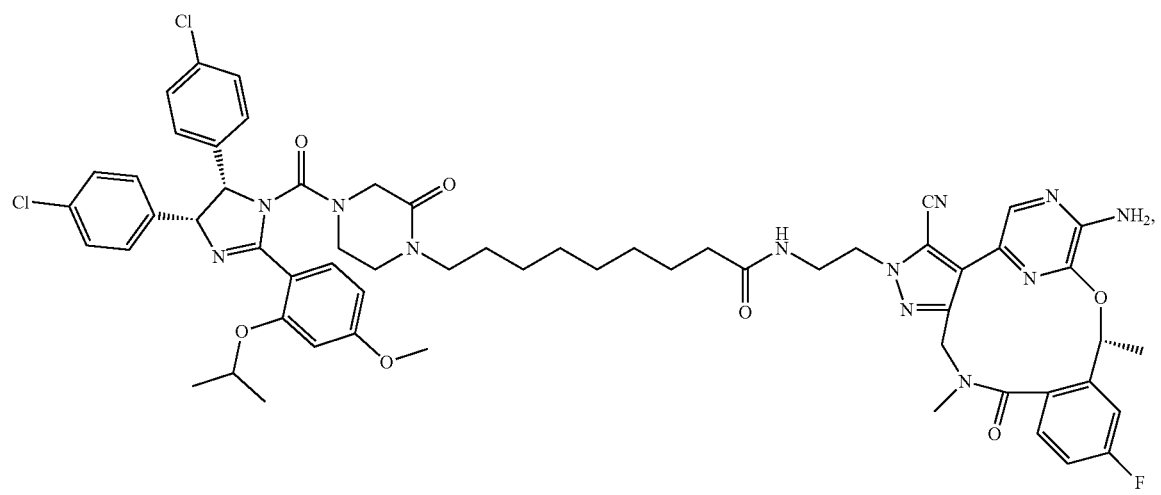
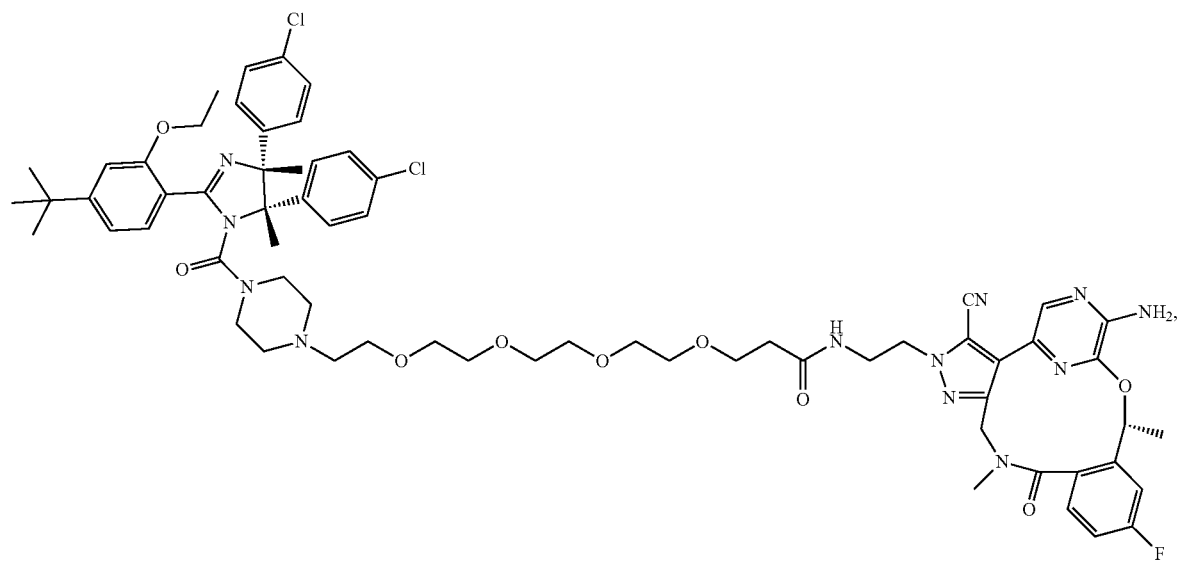

211
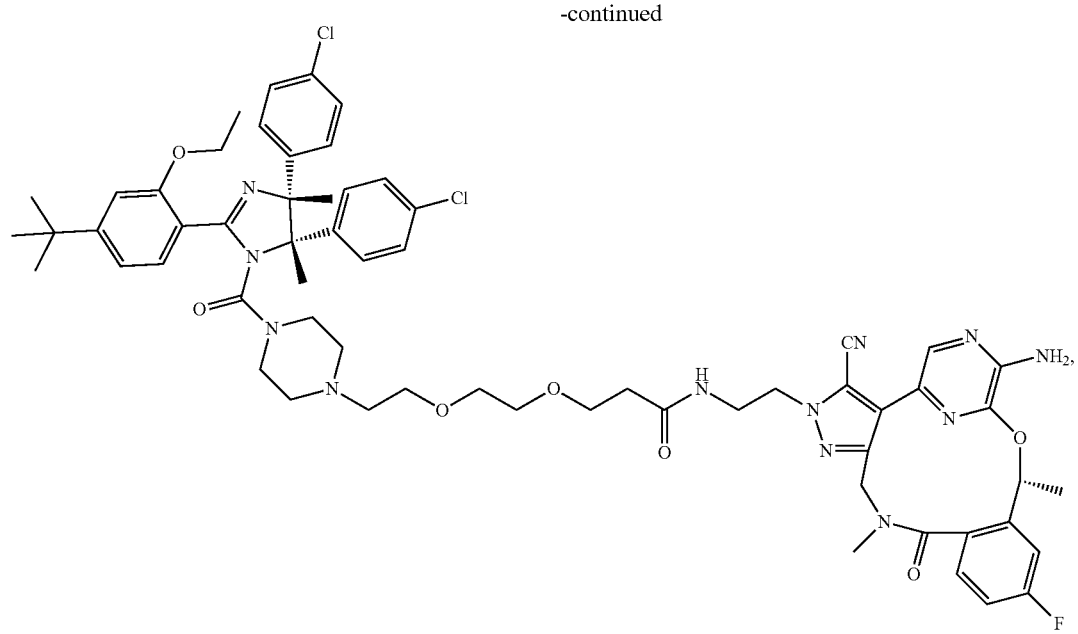
212
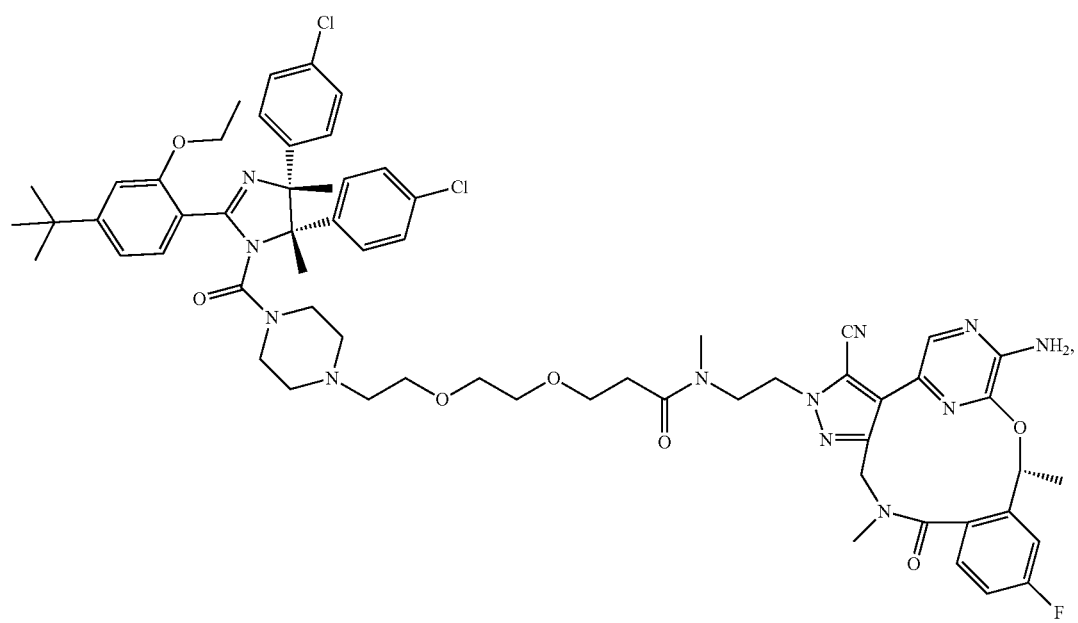

213
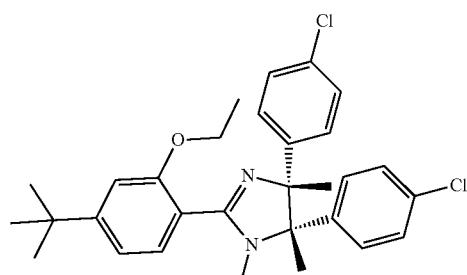
214
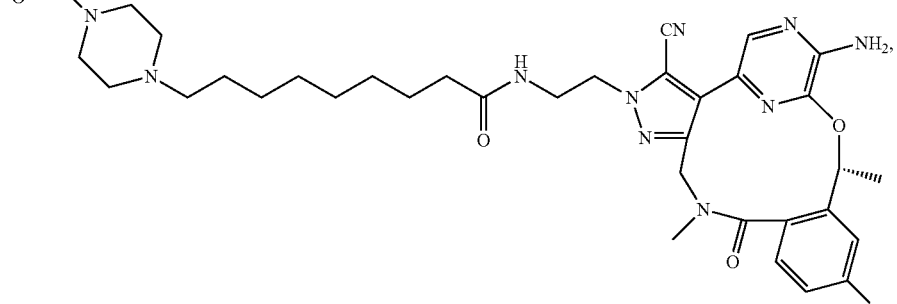
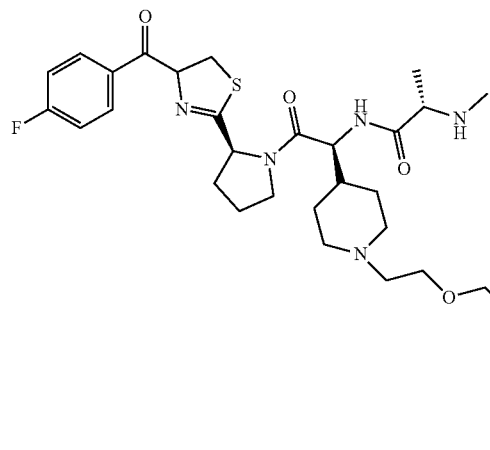
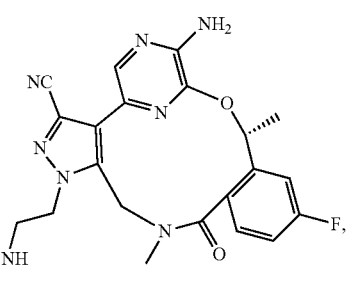
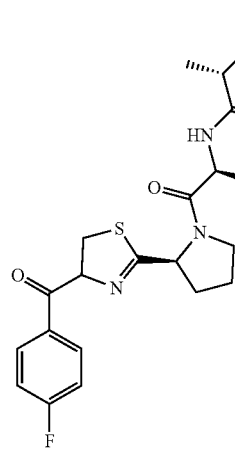
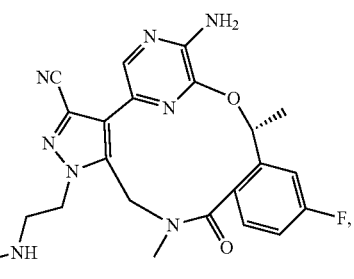

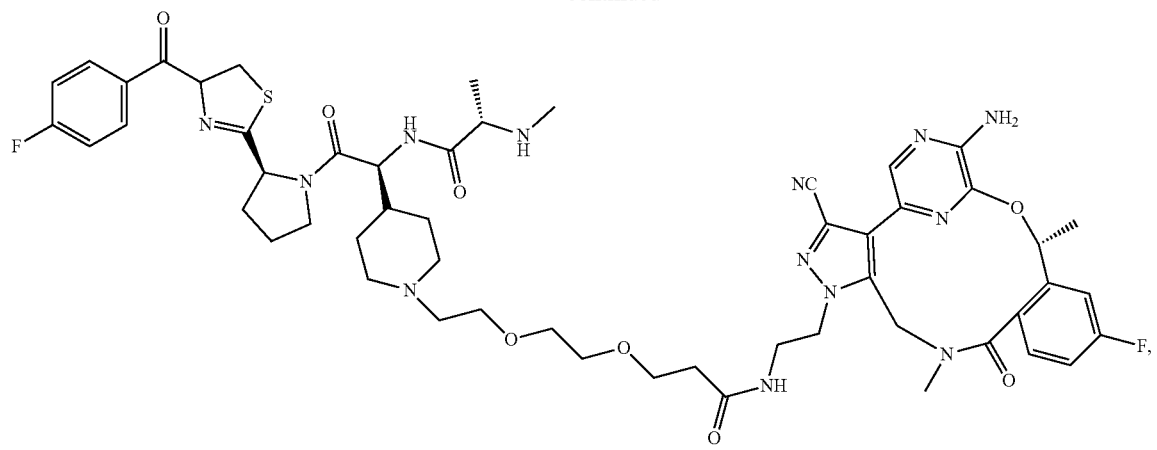
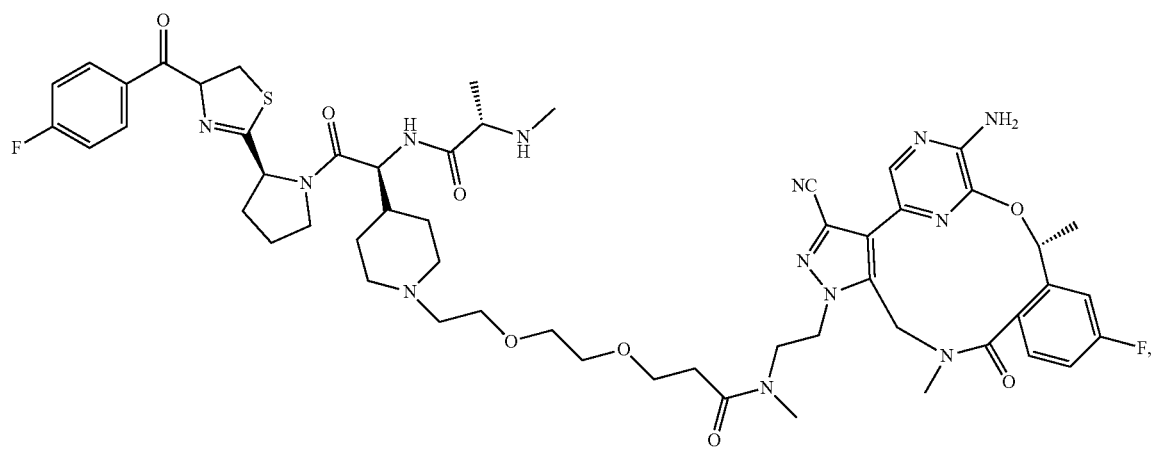
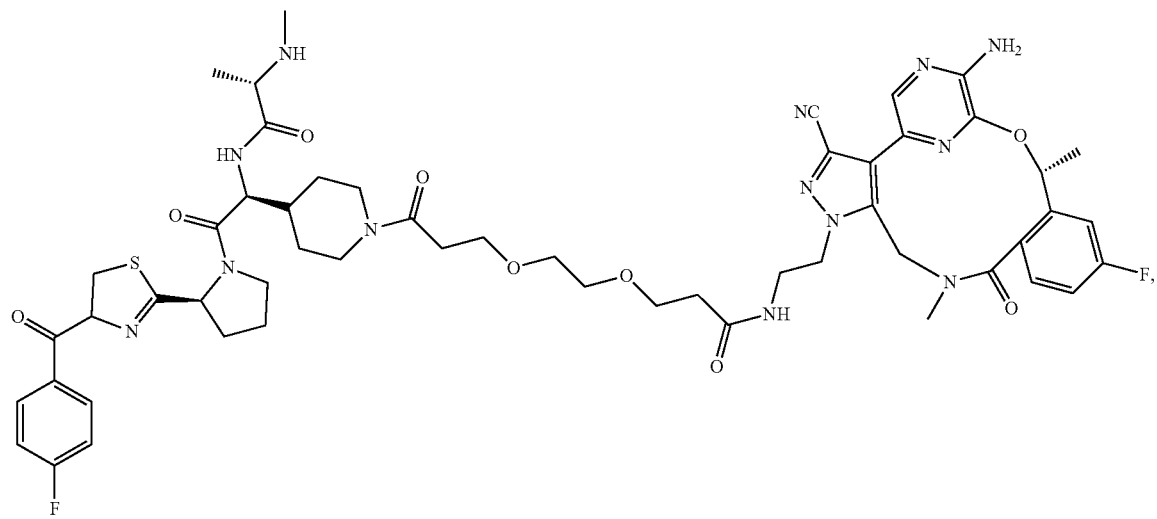

217
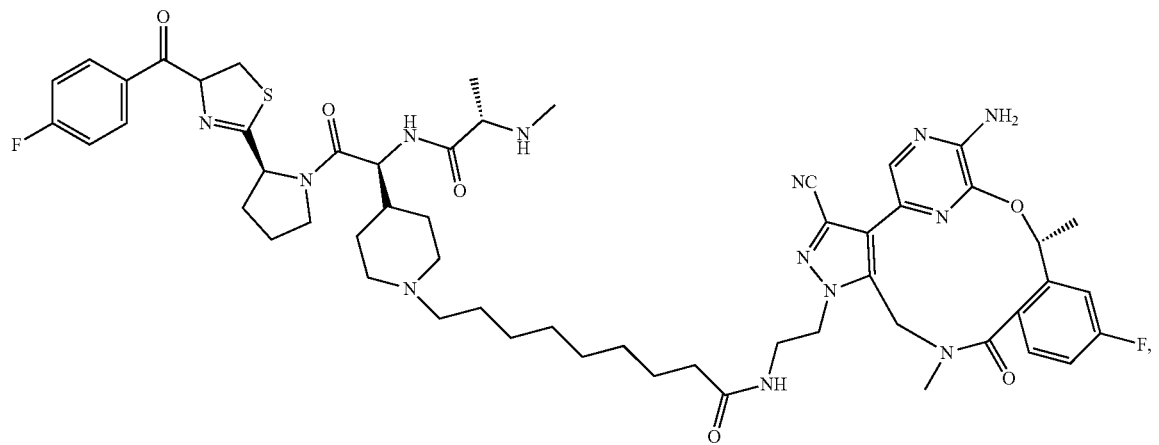
218
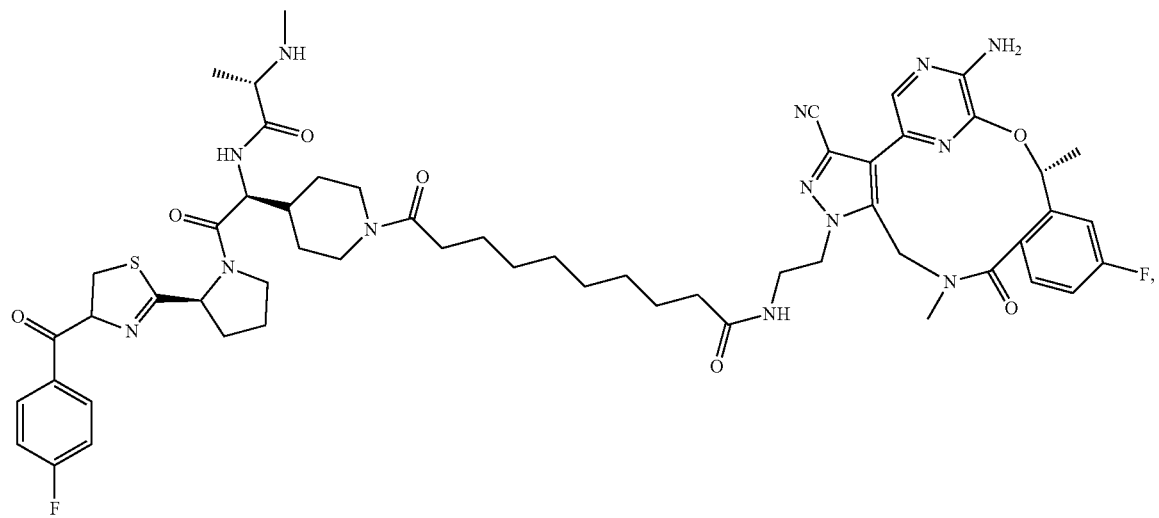
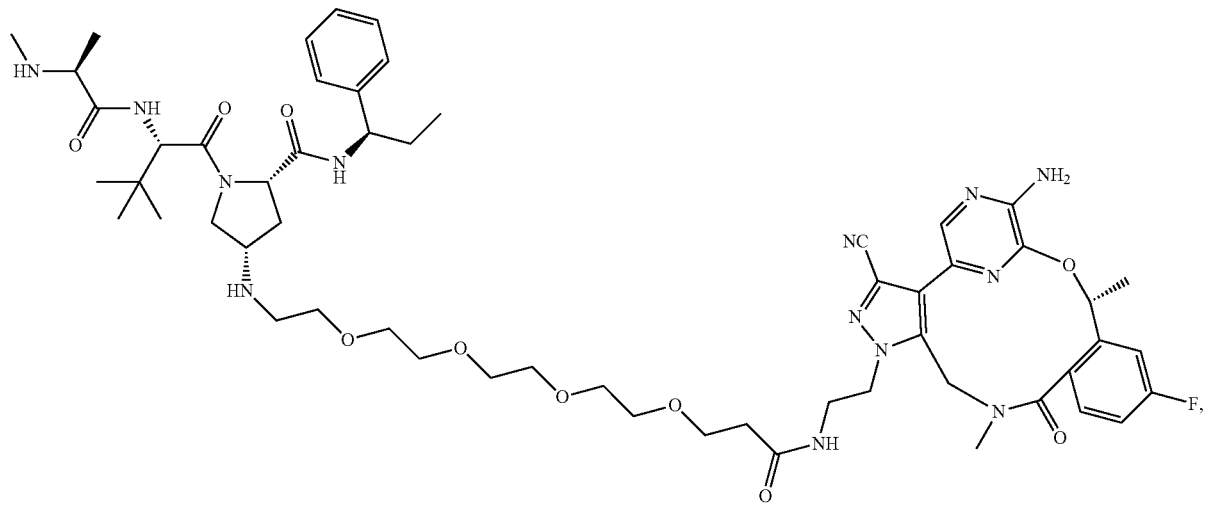

-continued
219
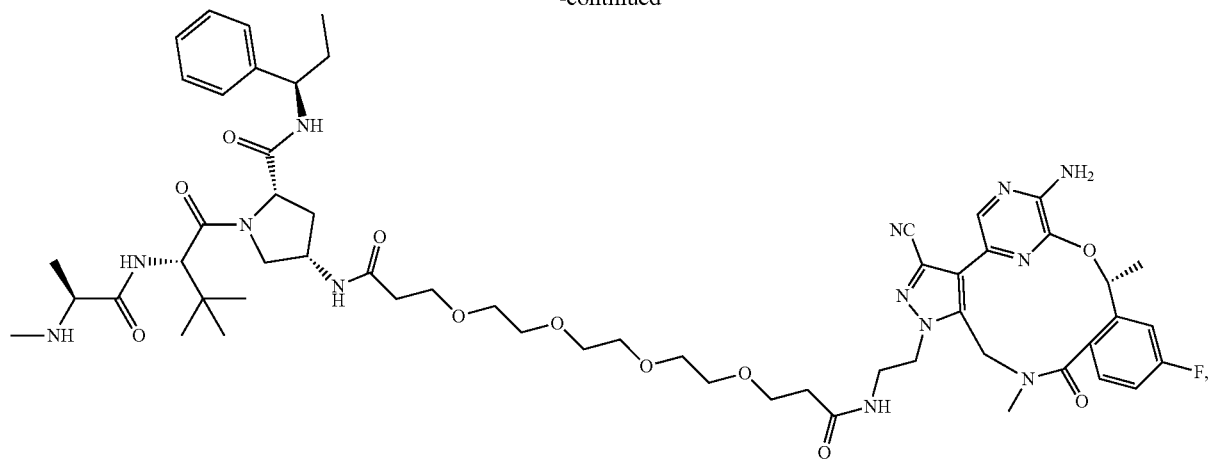
220
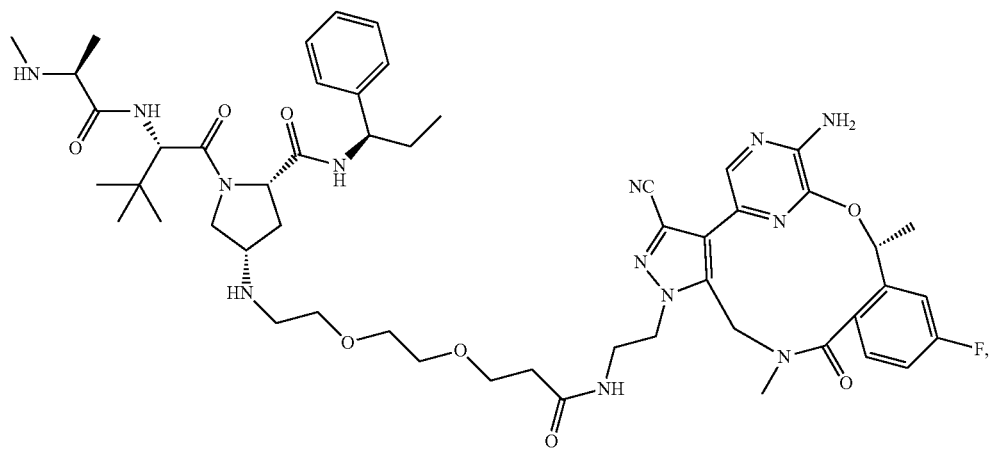
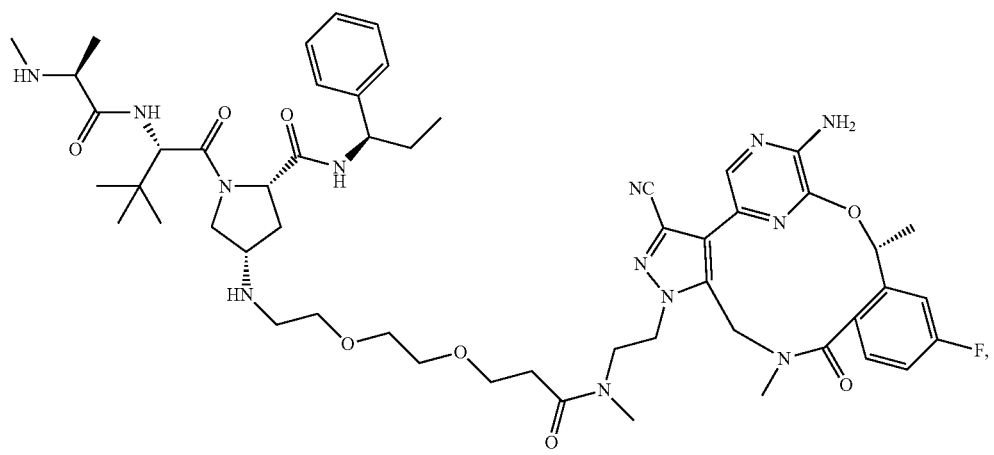

221
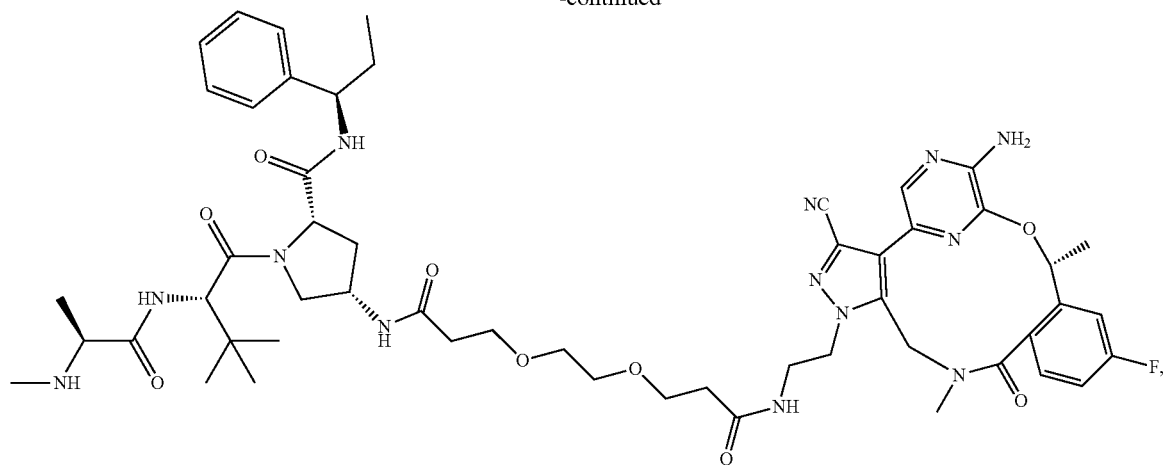
222
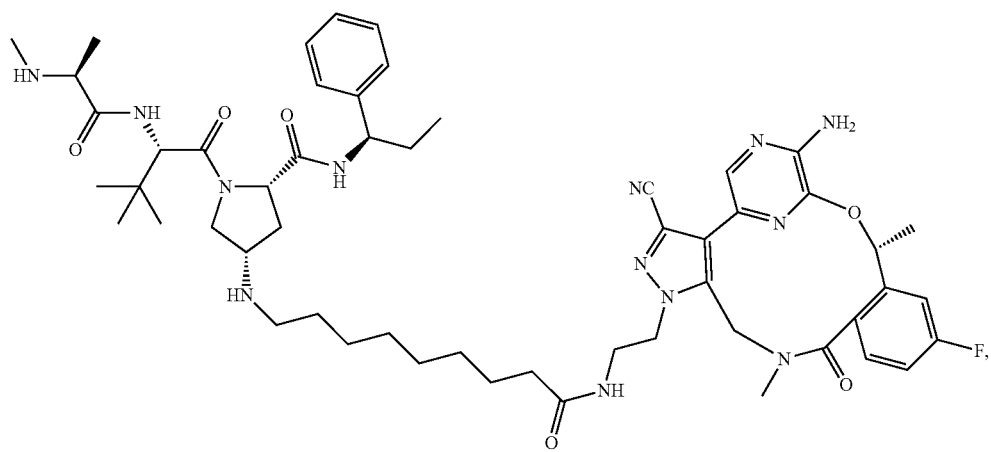
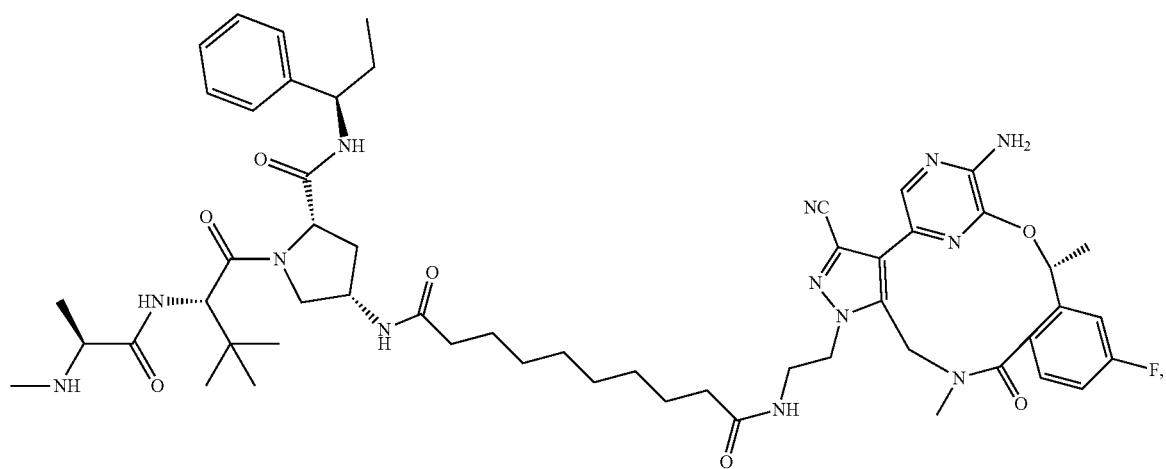

223
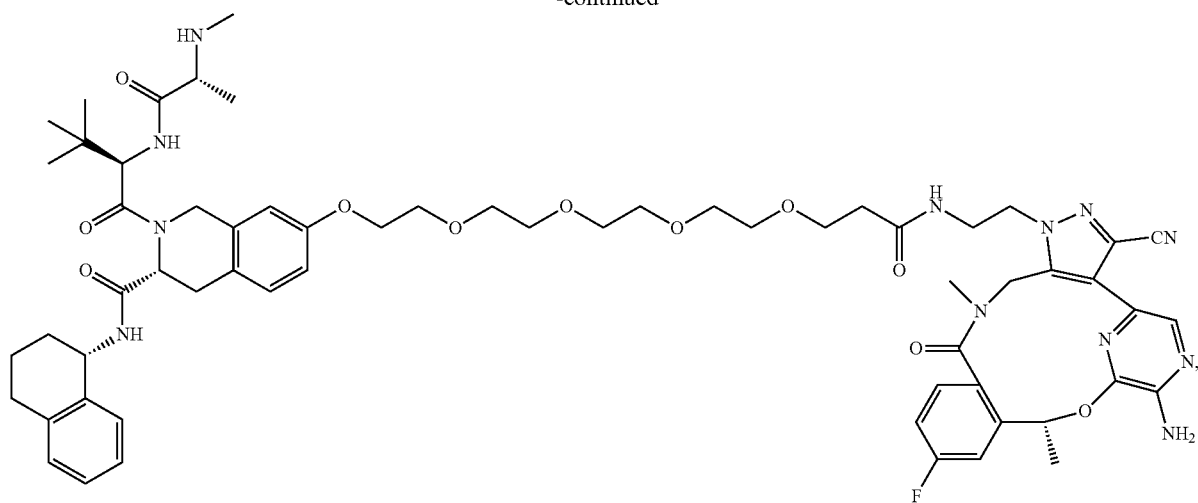
224
-continued
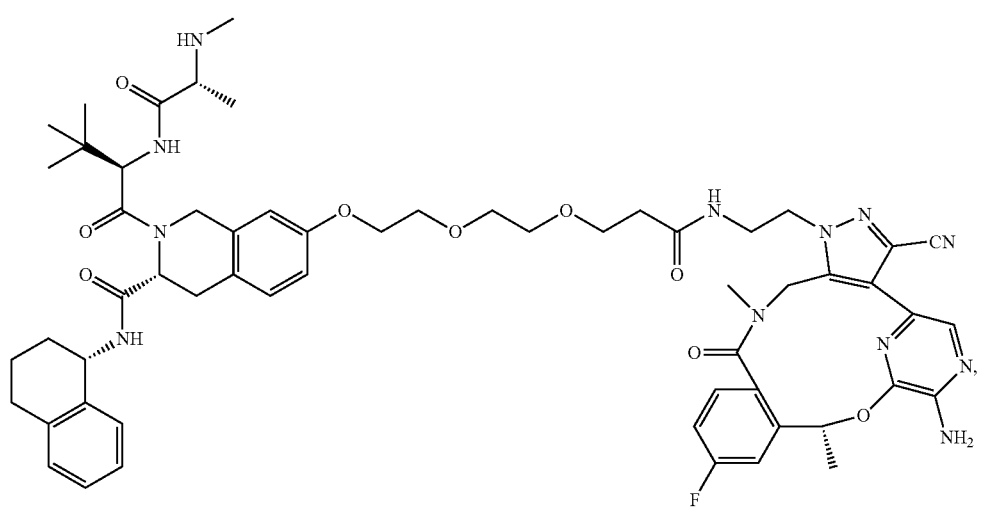
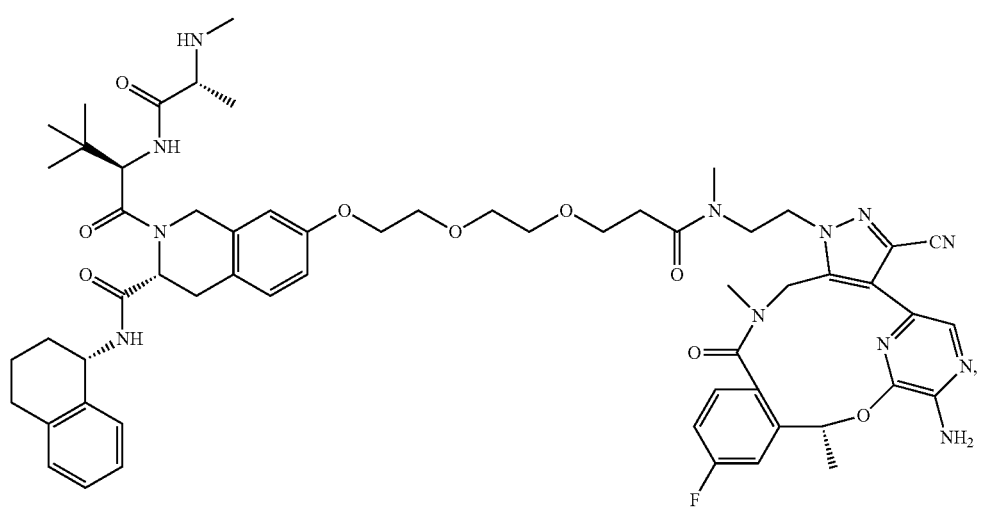

225
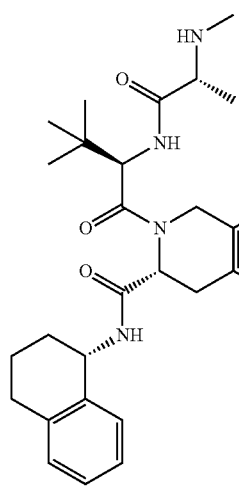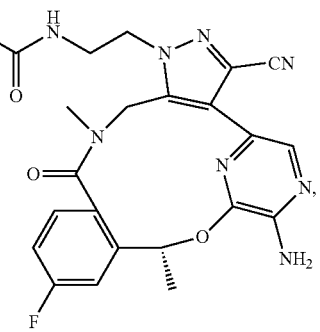
226
-continued
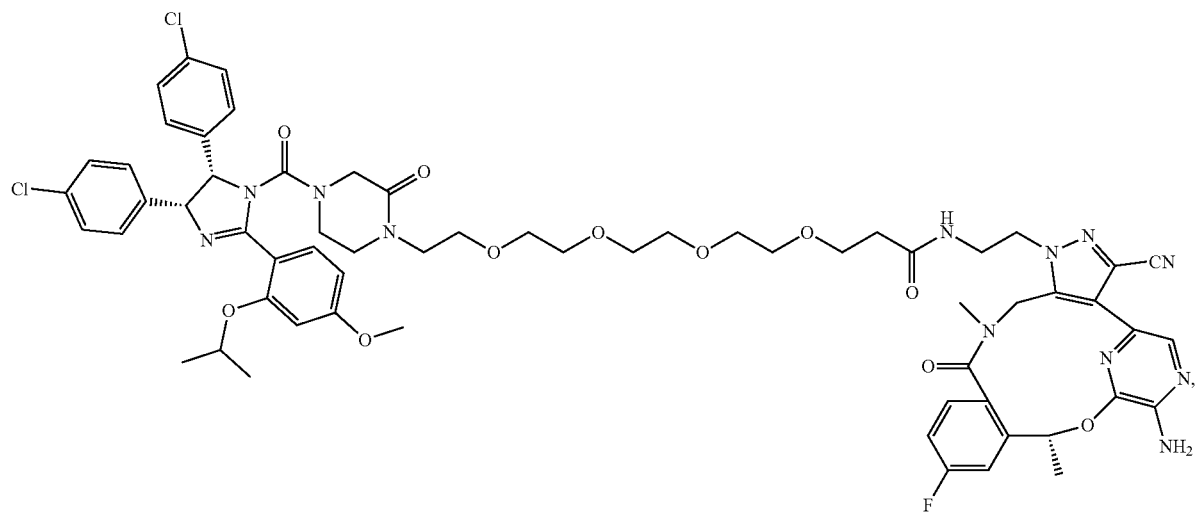
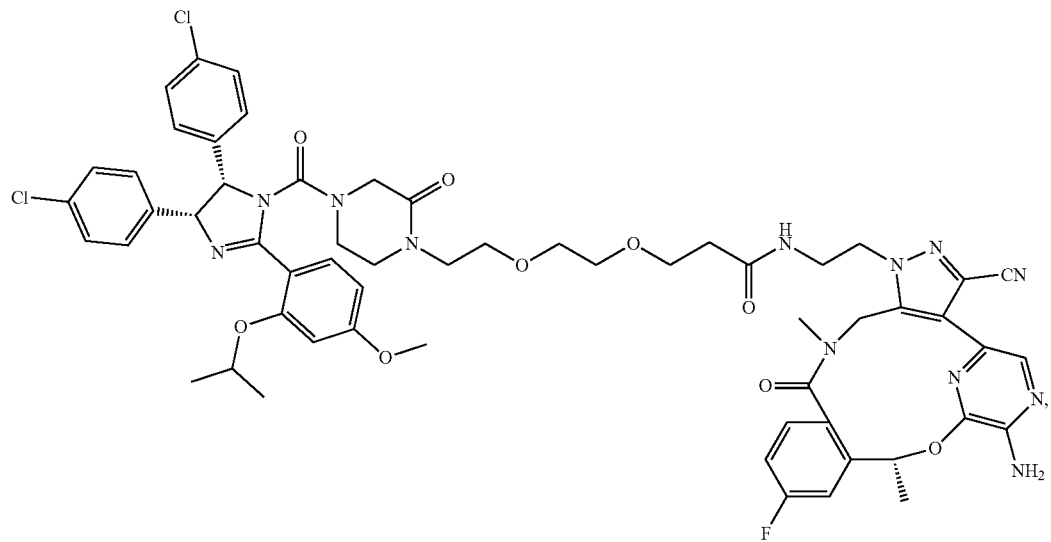

227
228
-continued
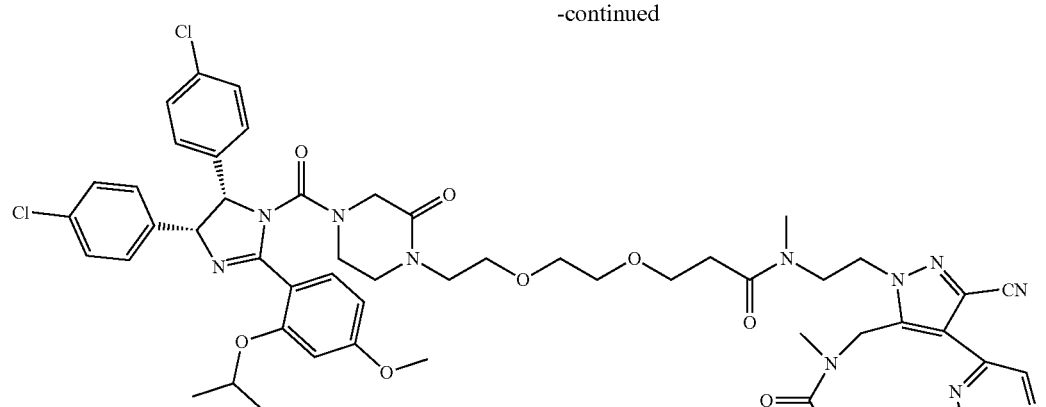
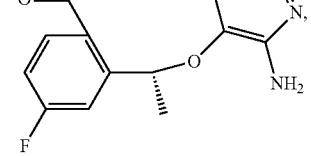
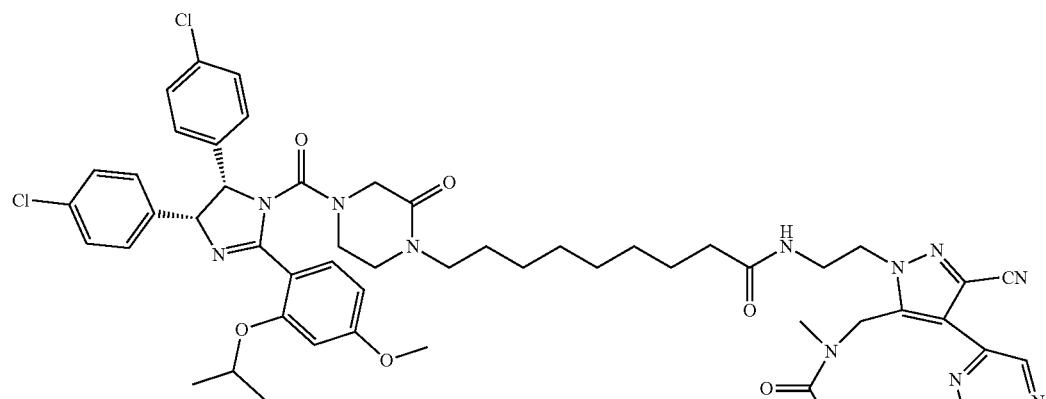
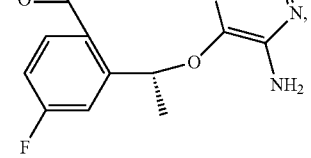
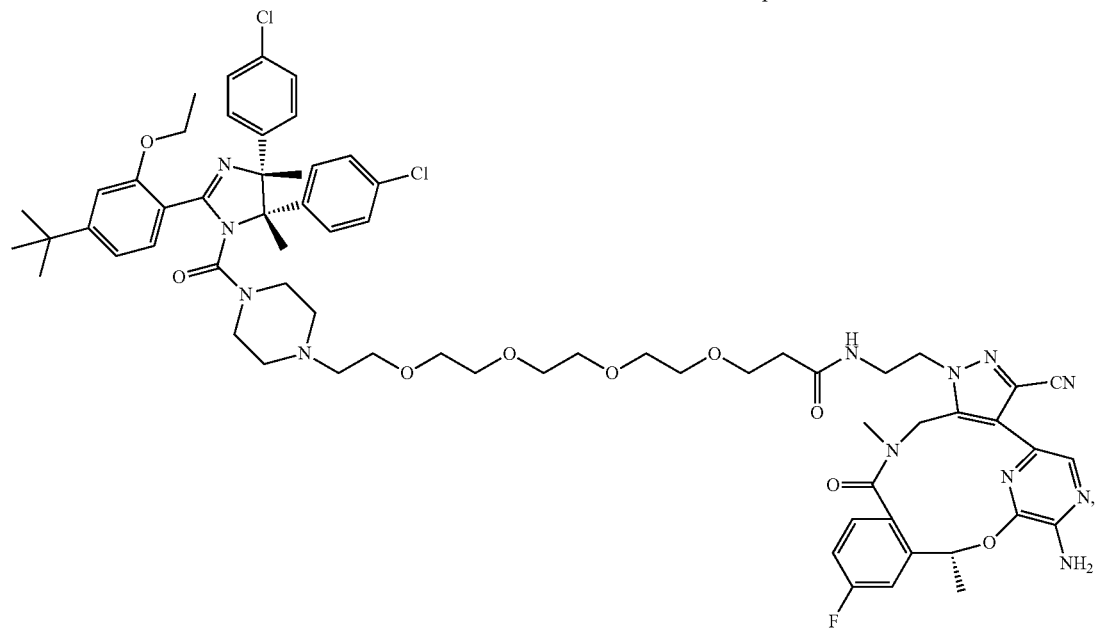
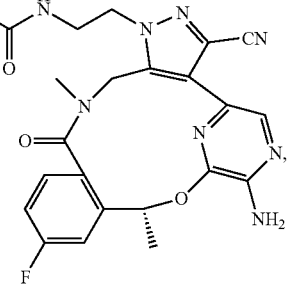

-continued
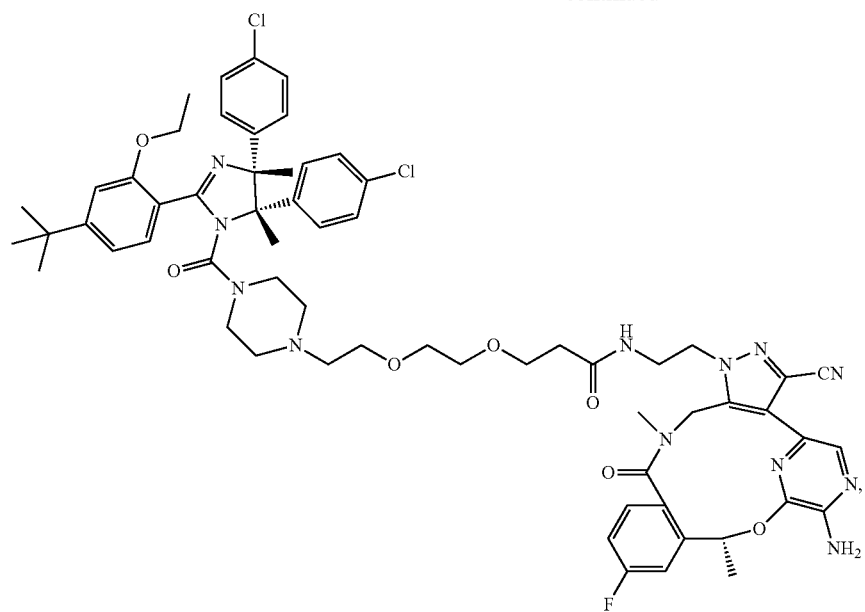
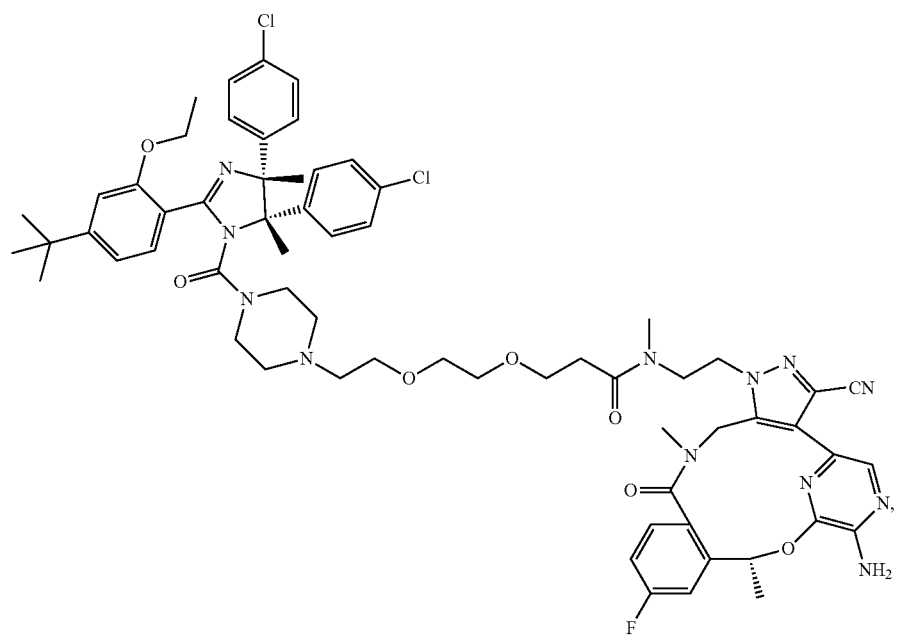

231
232
-continued
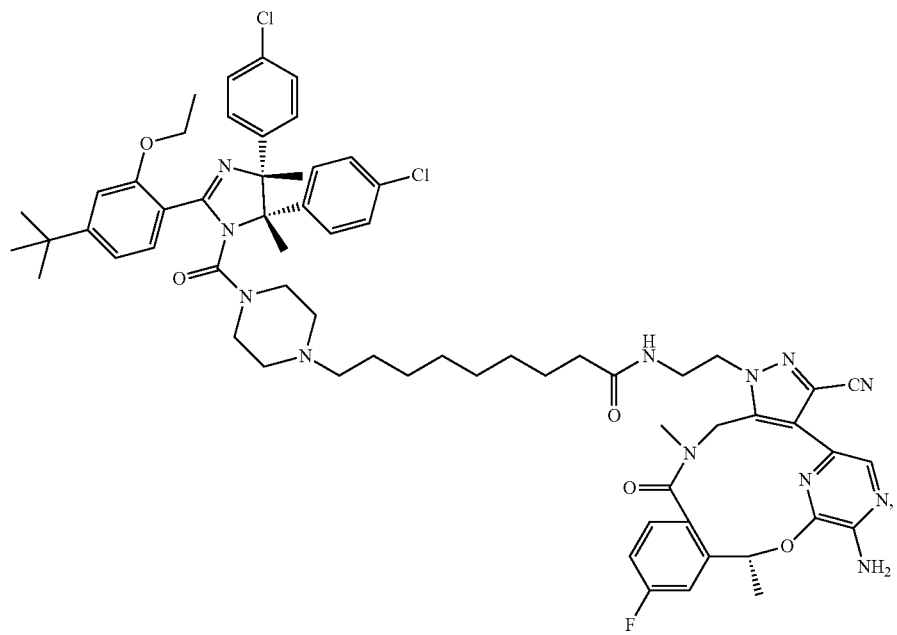
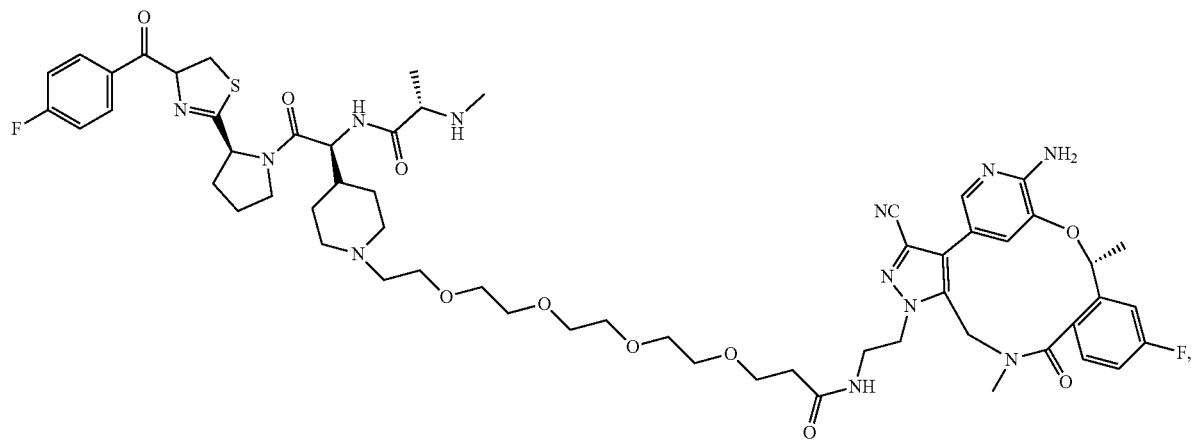
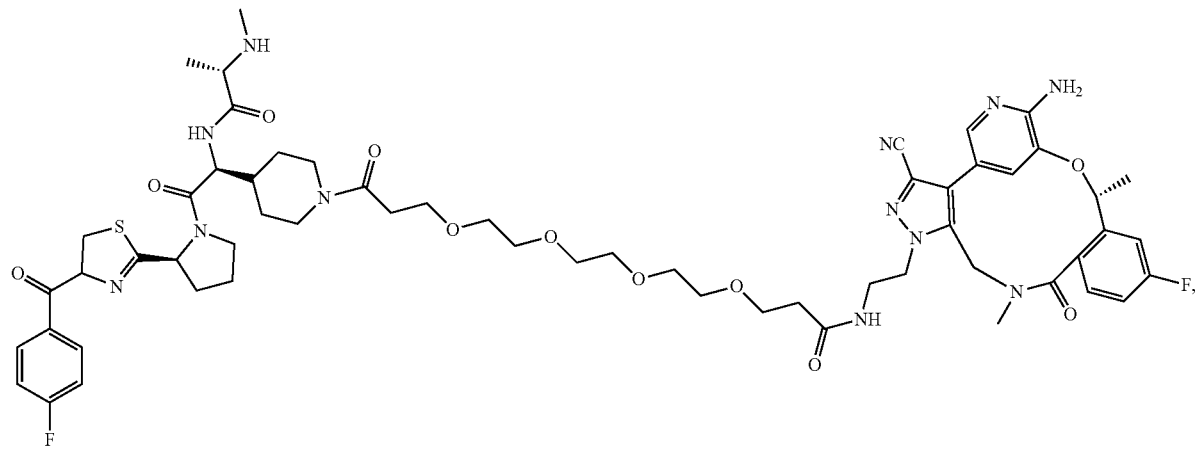

233
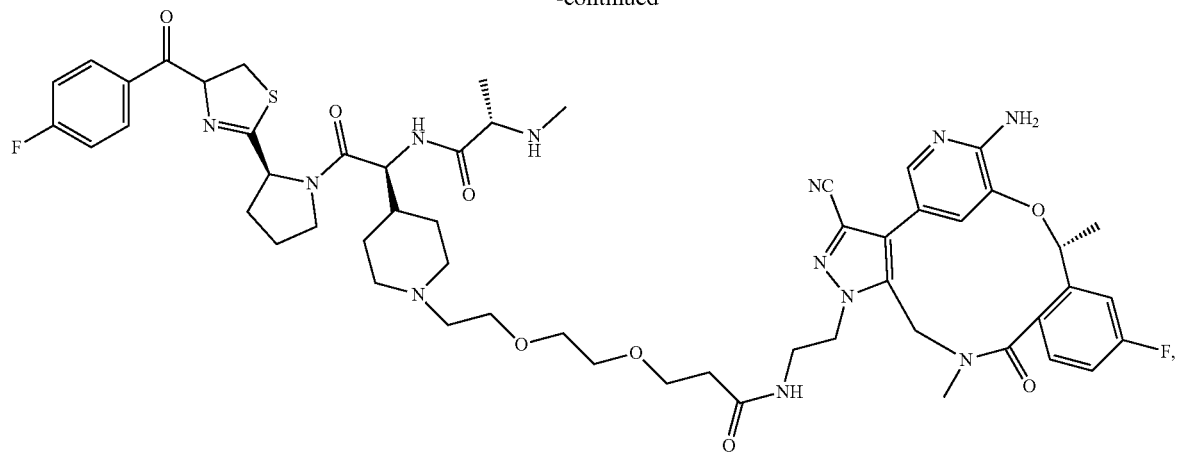
234
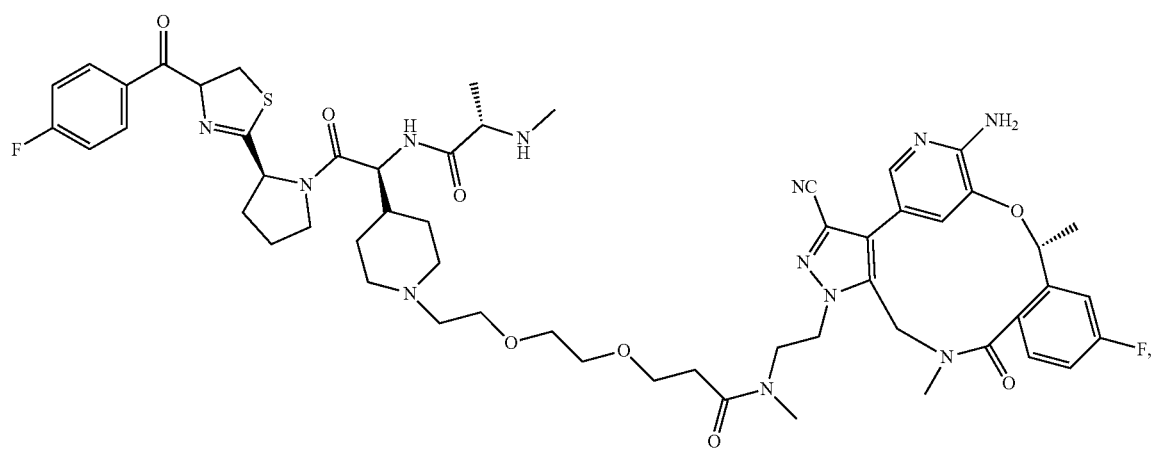
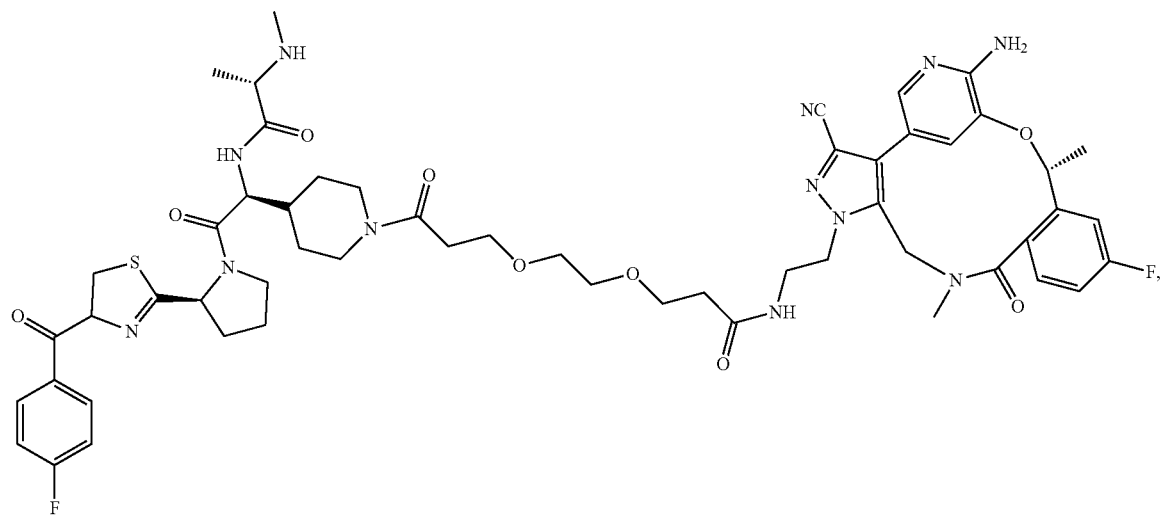

235
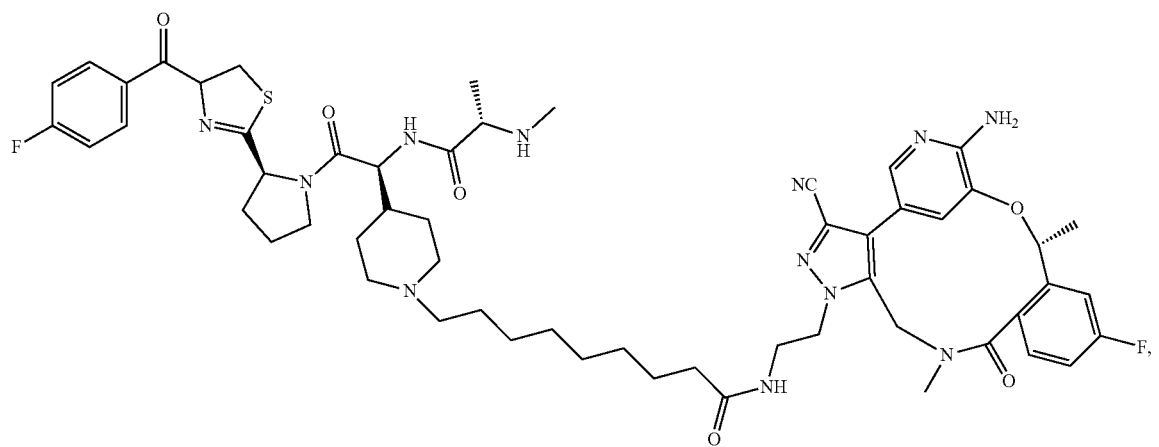
236
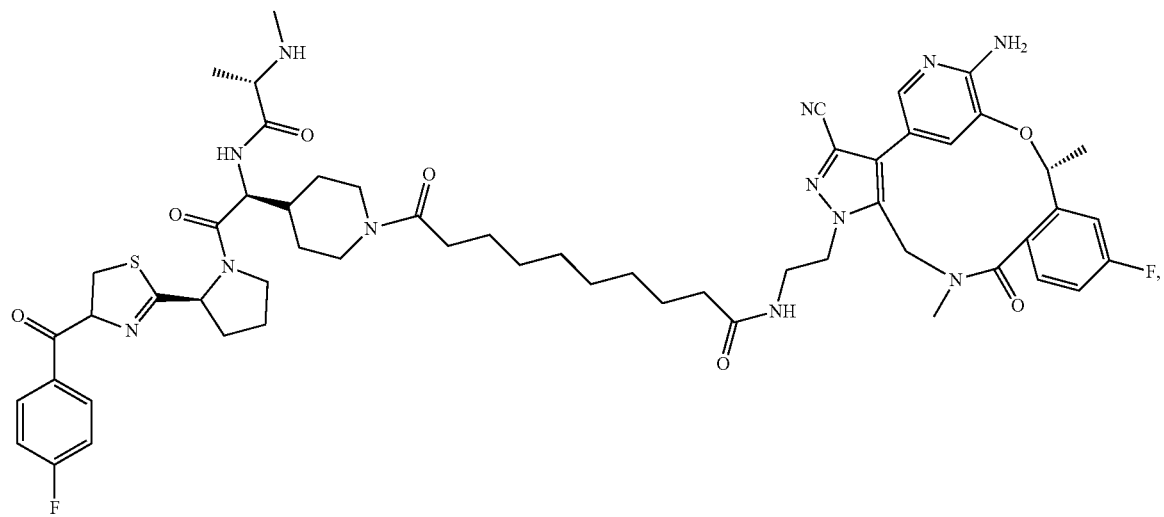
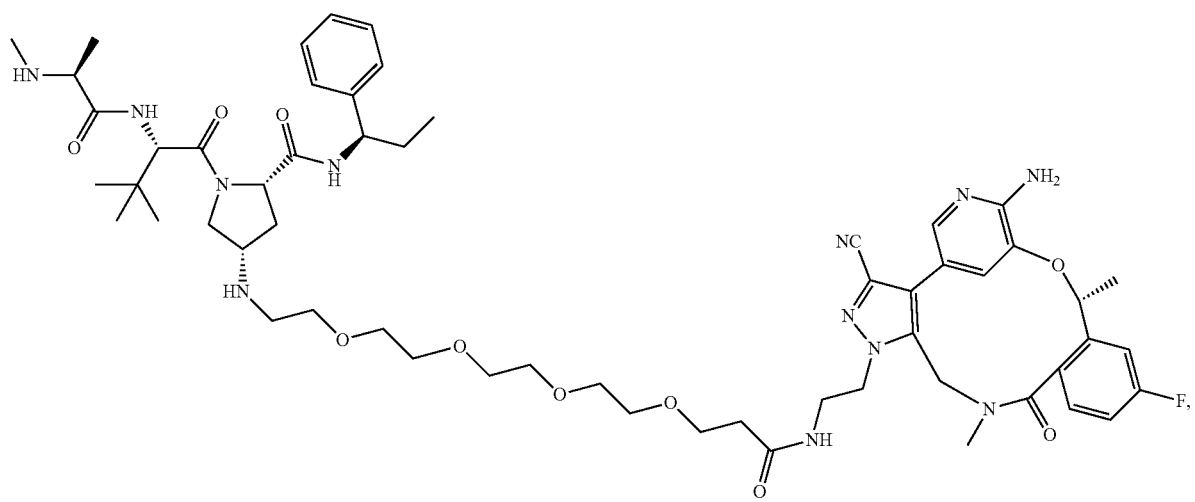

237
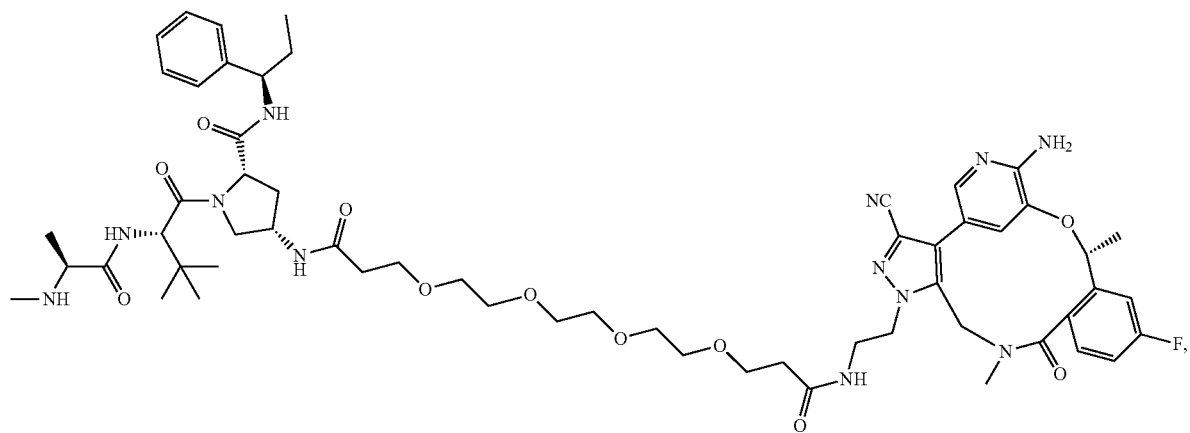
238
-continued
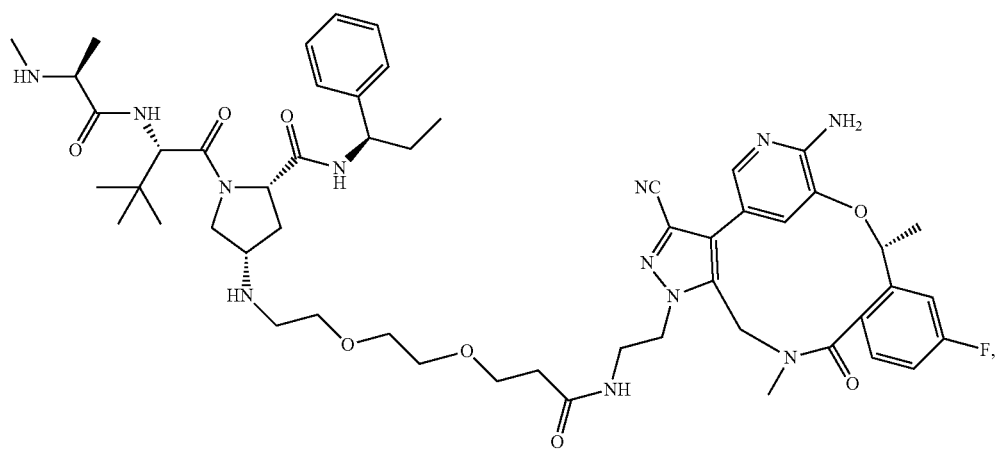
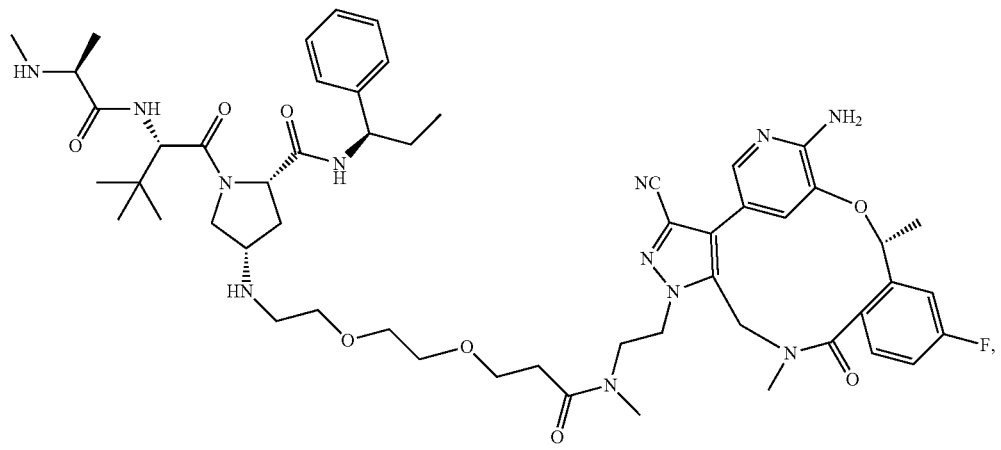

-continued
239
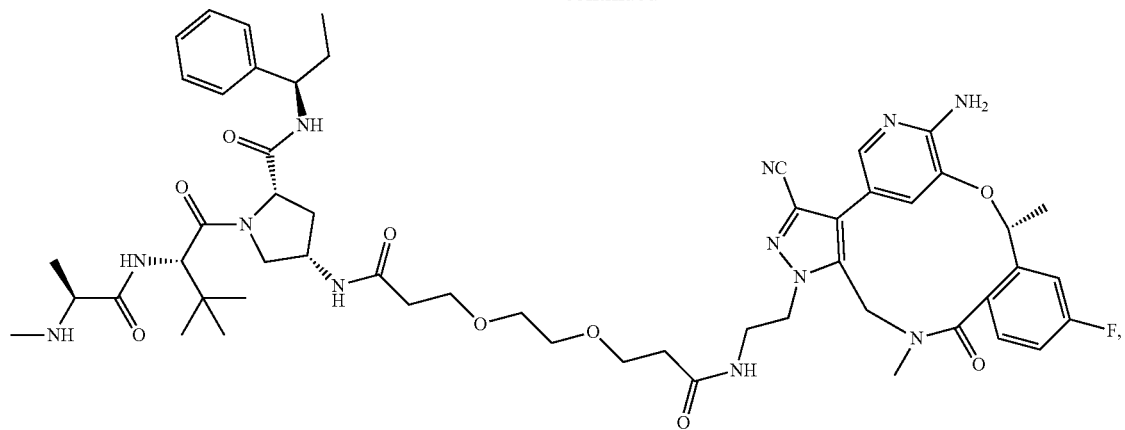
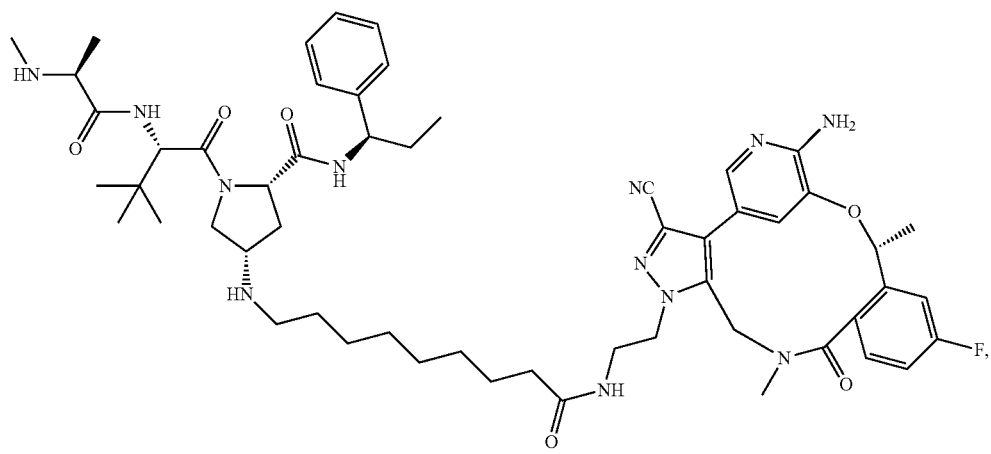
240
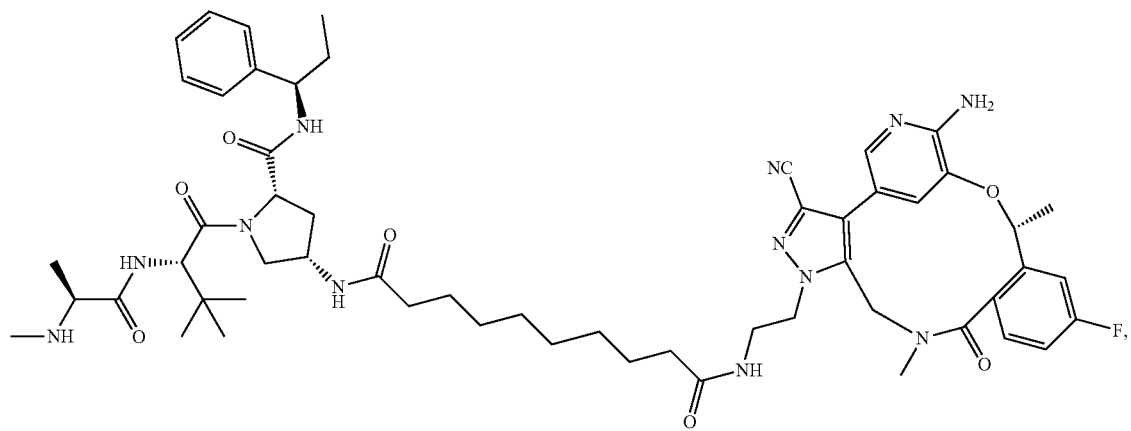

241
242
-continued
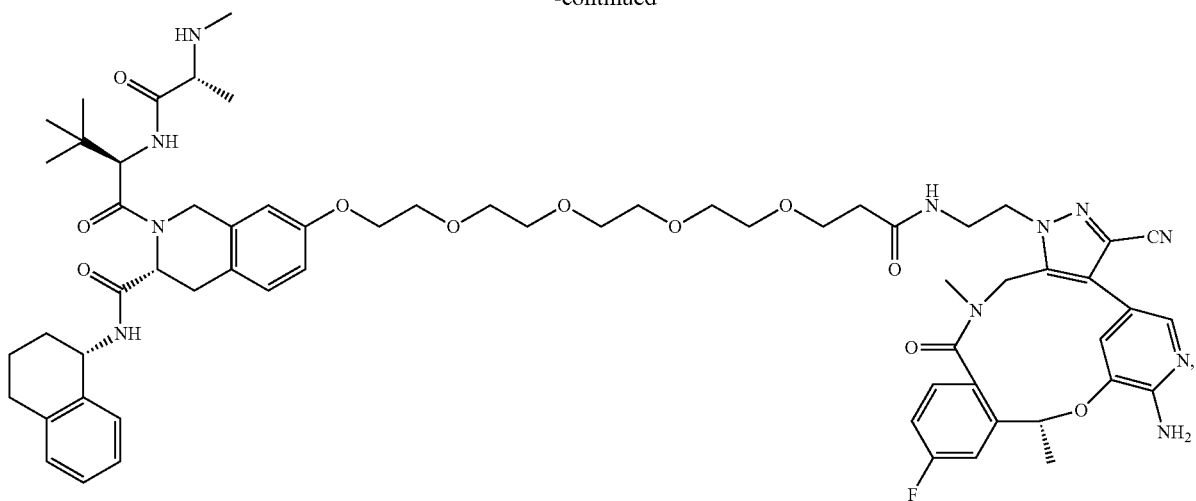
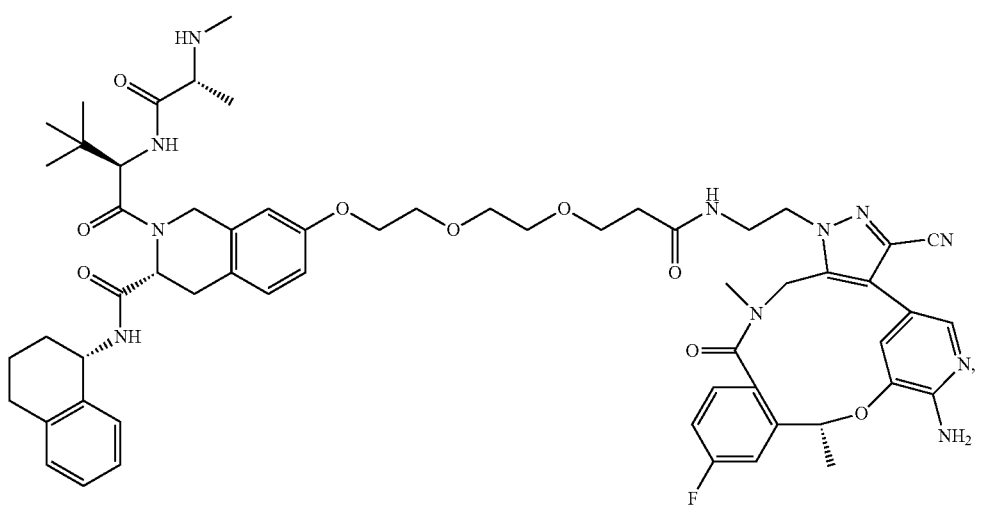
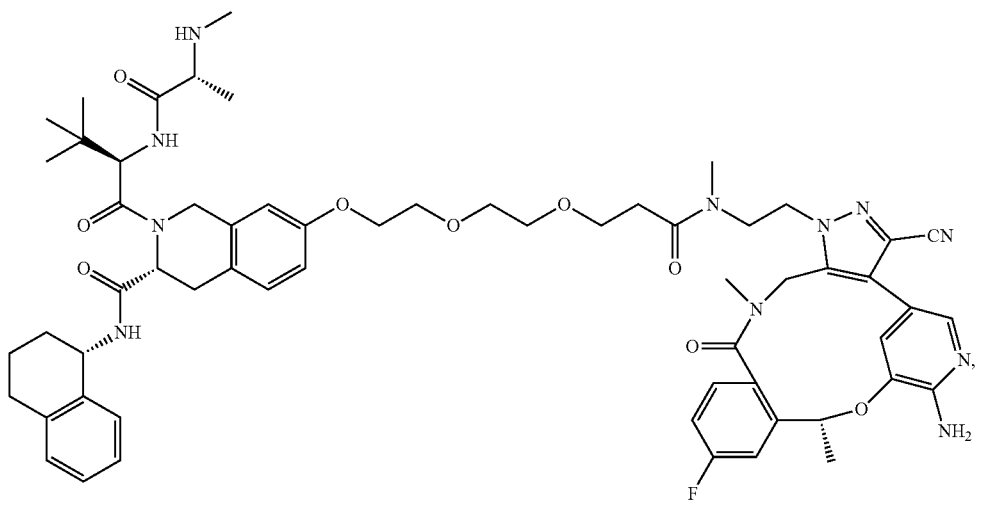

243
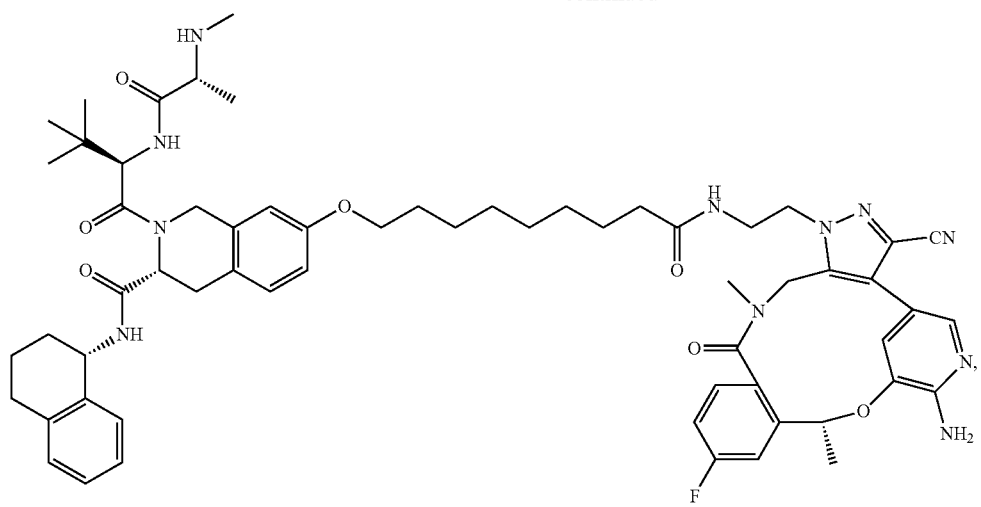
244
-continued
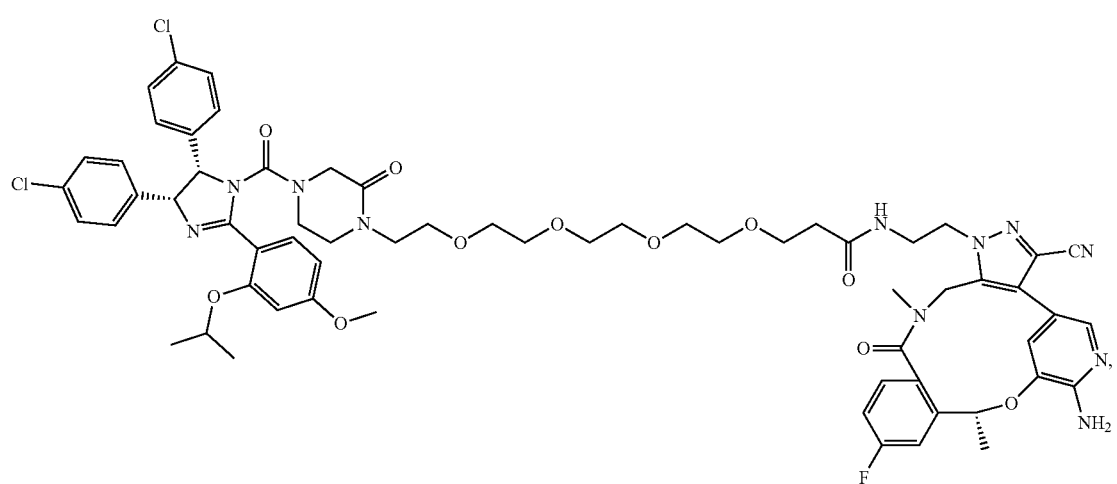
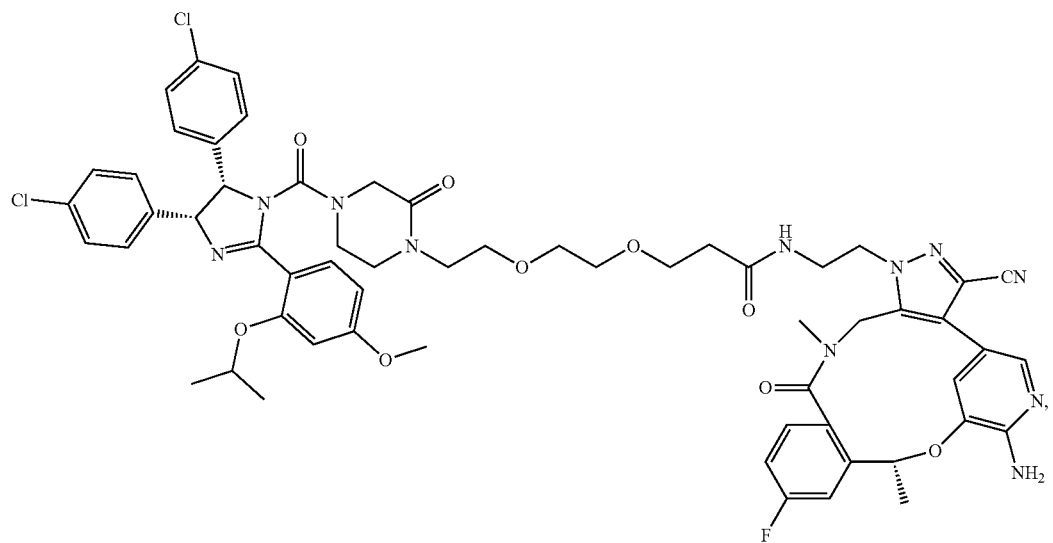

245
246
-continued
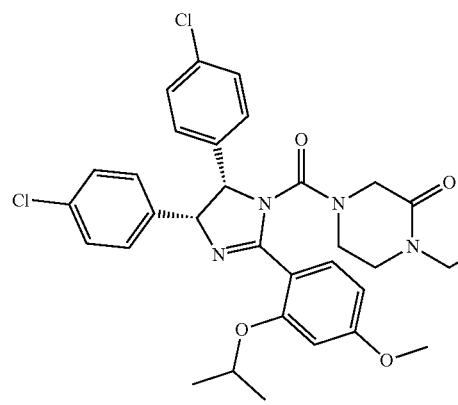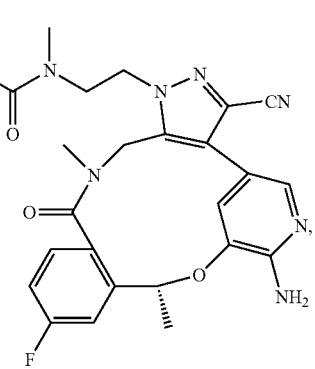
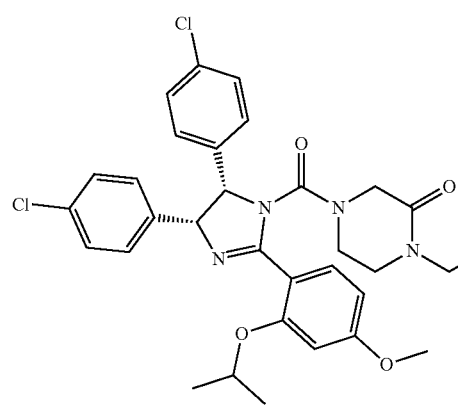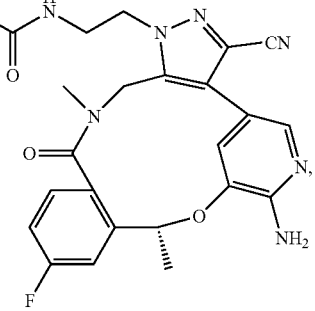
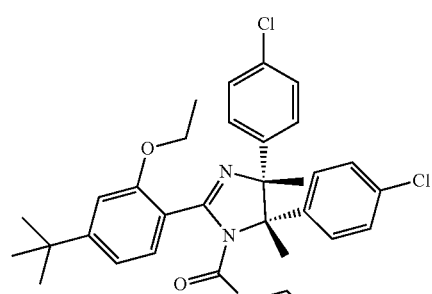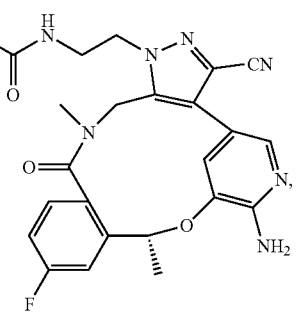

-continued
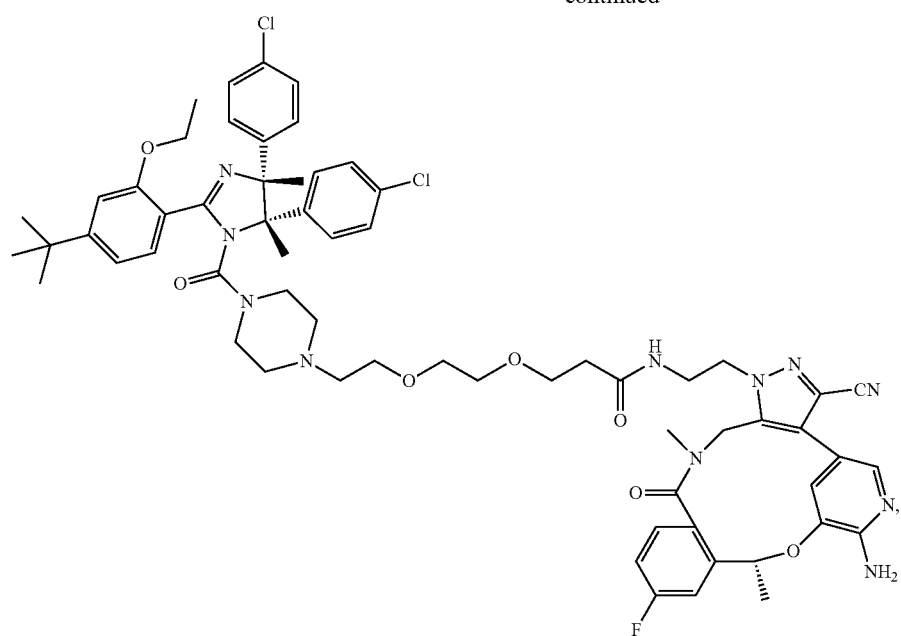
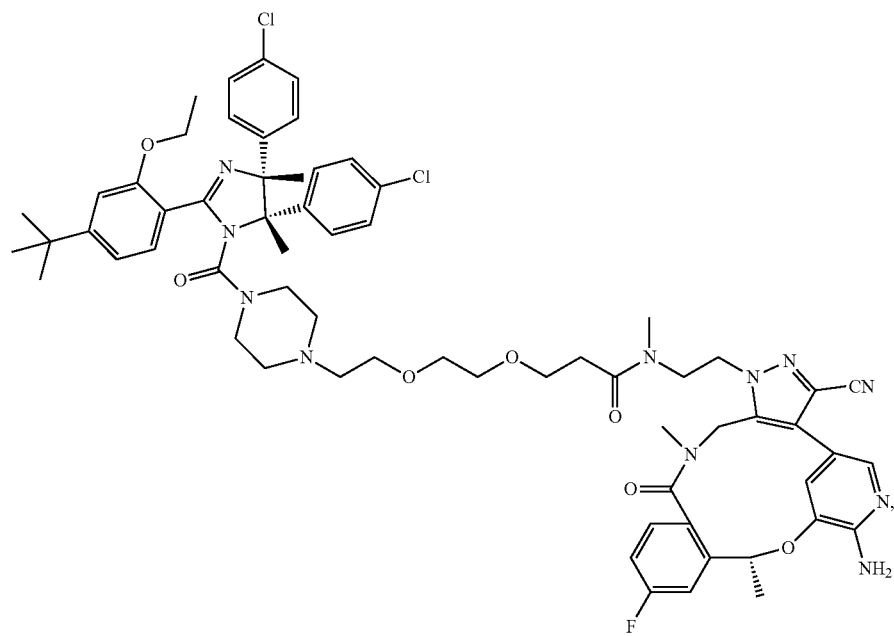

249 250
-continued
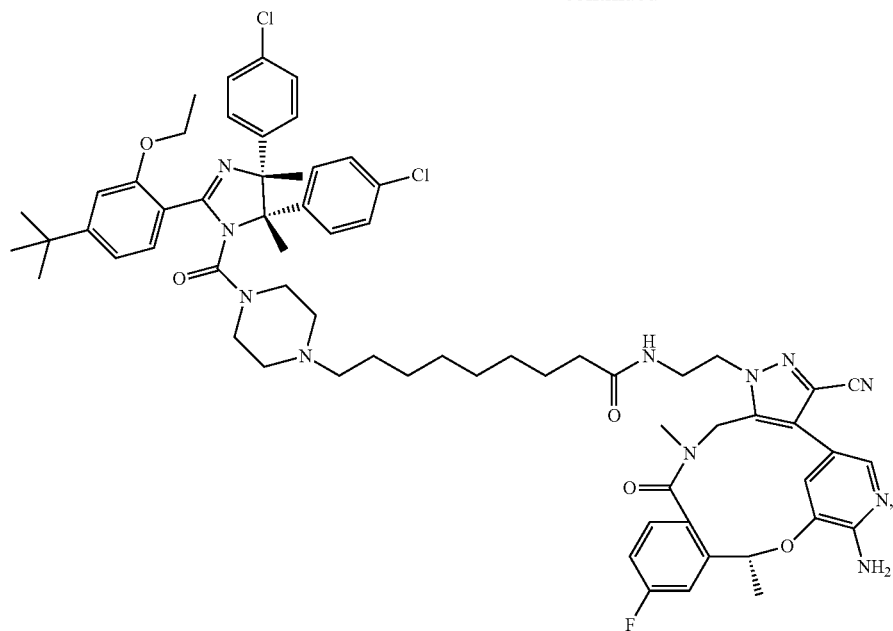
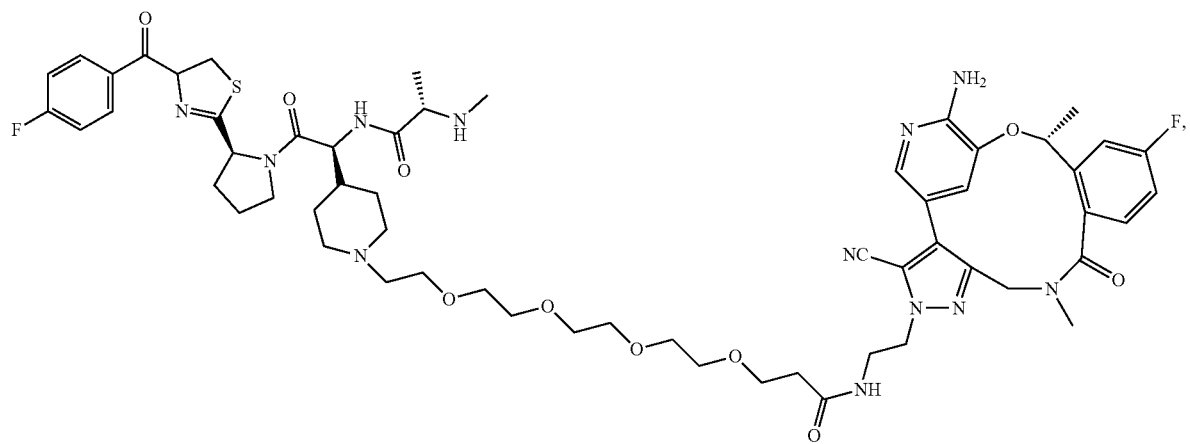
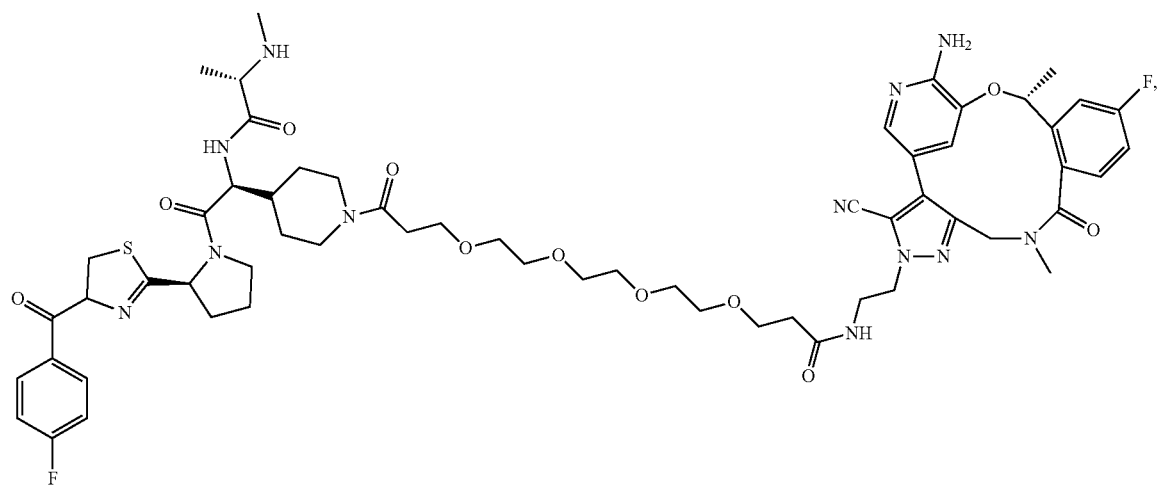

251
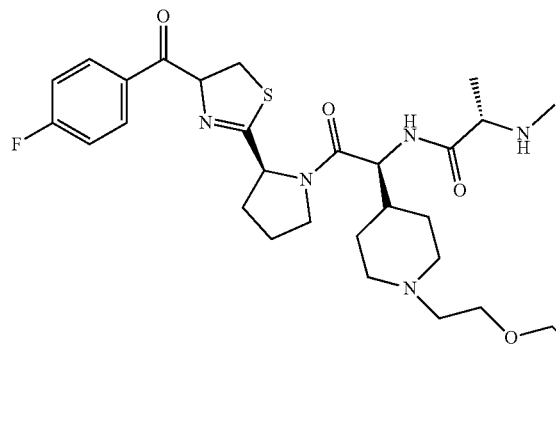
252
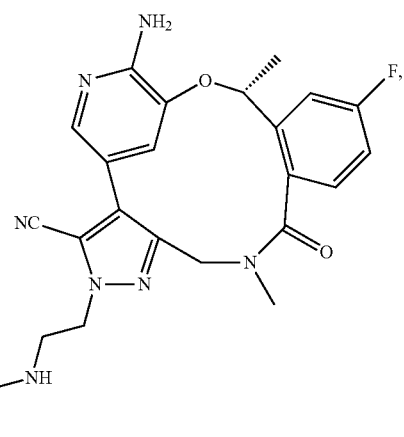
-continued
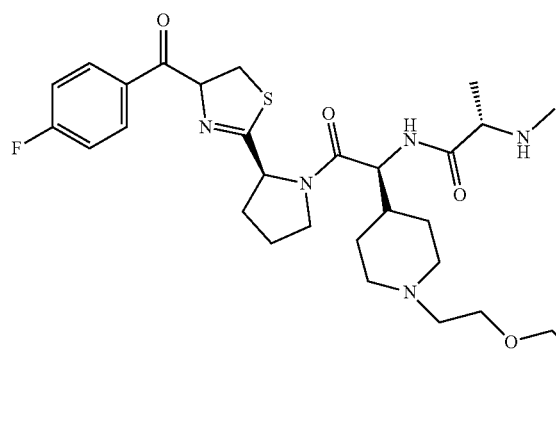
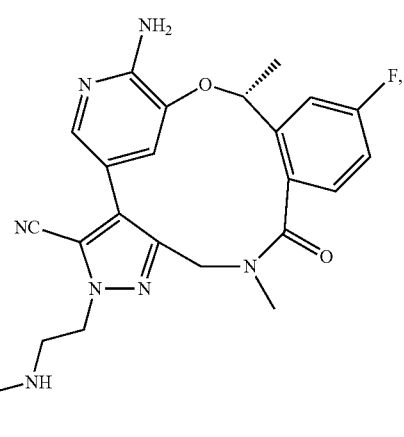
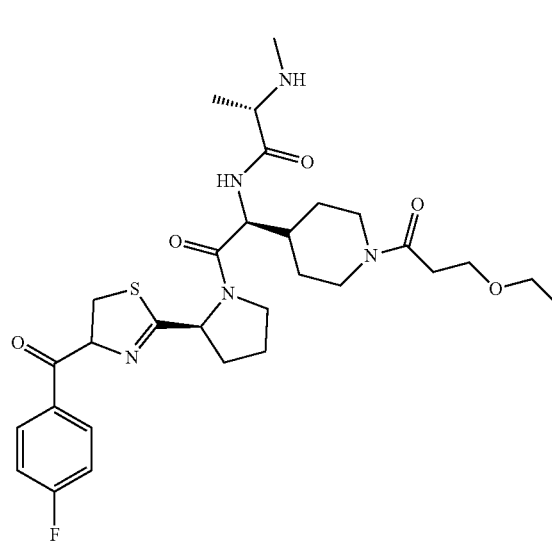
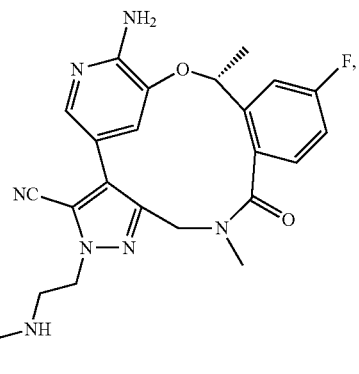

253
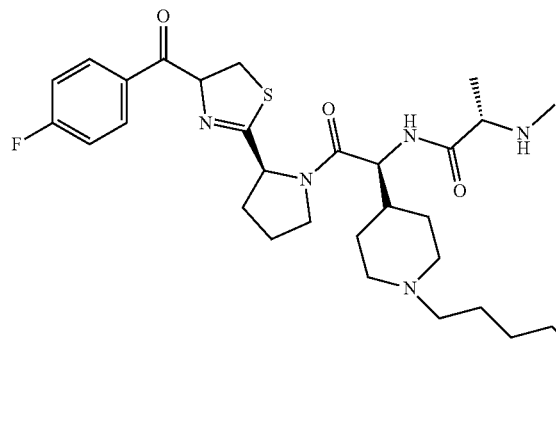
254
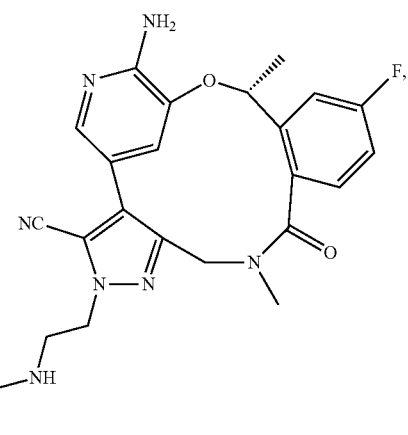
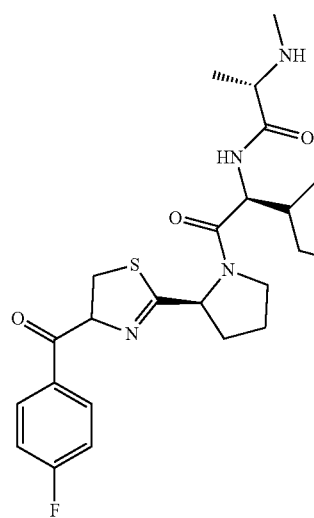
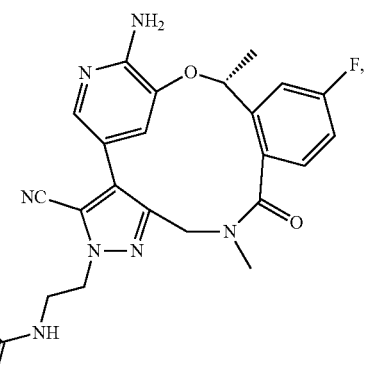
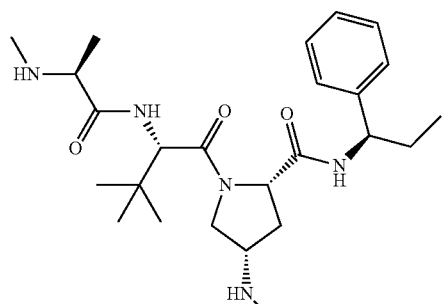
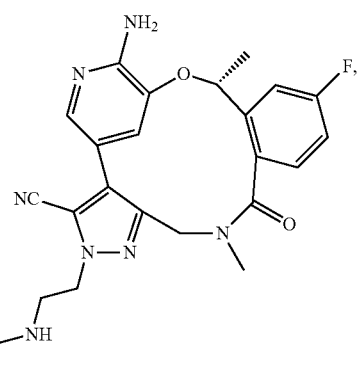

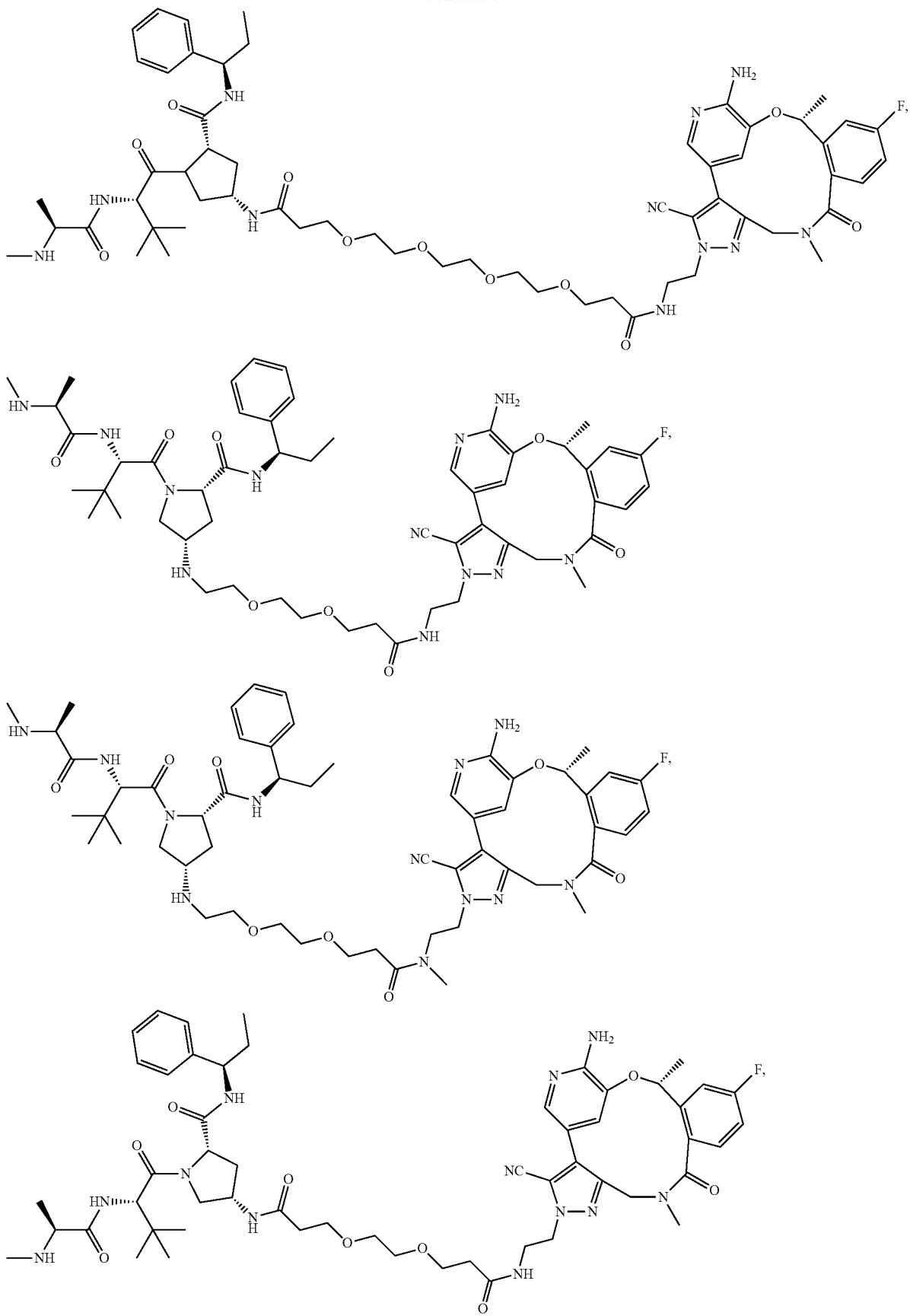

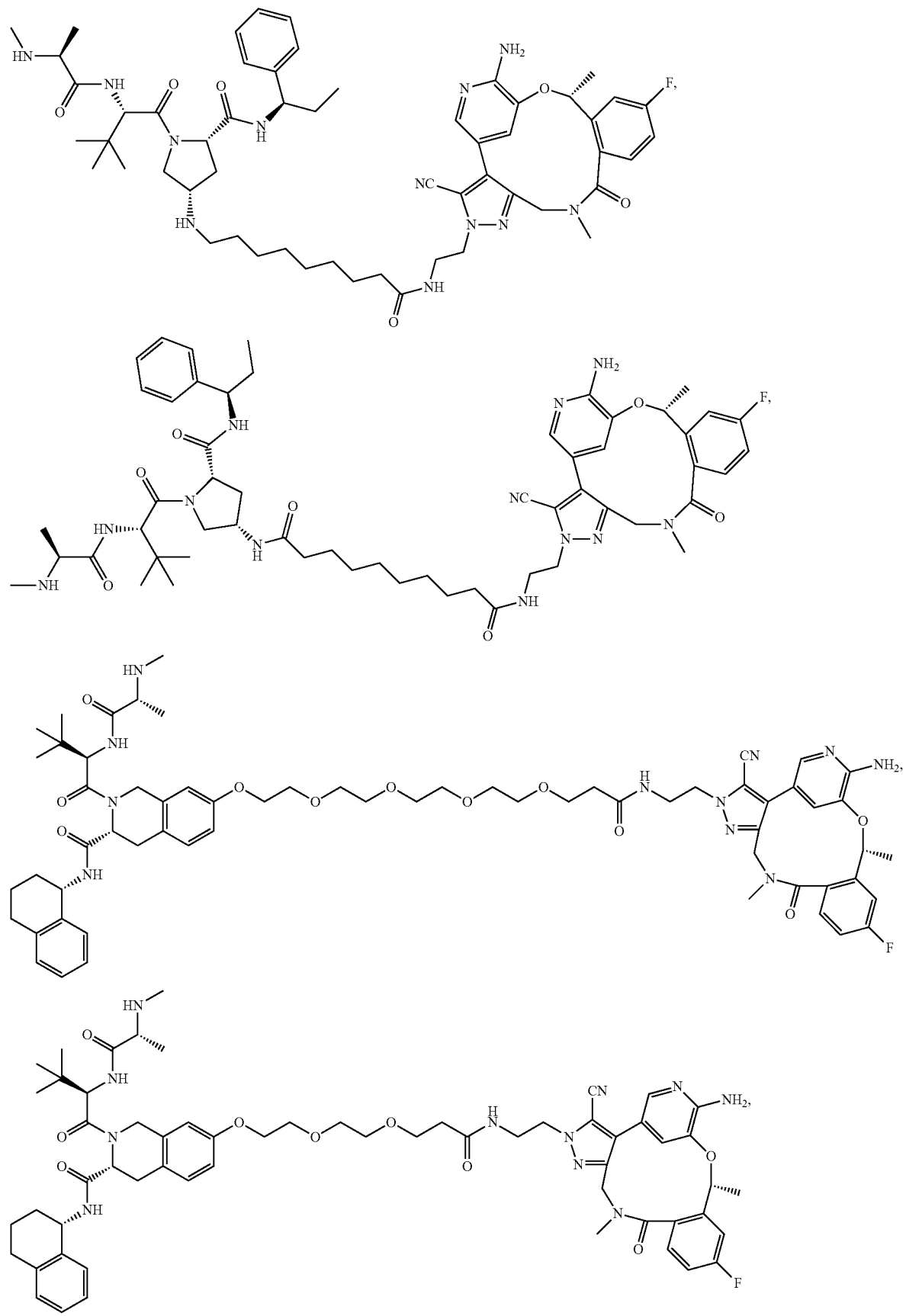

259 260
-continued
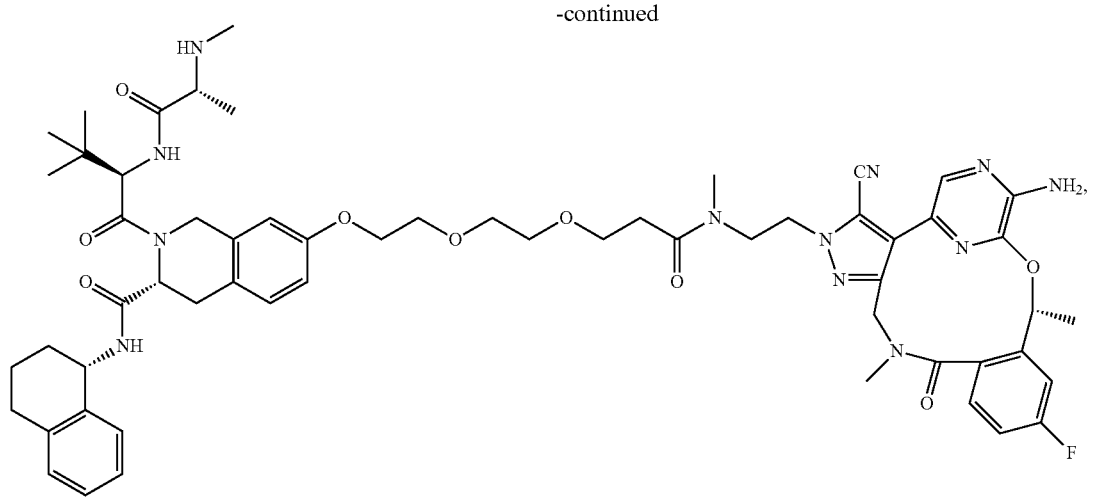
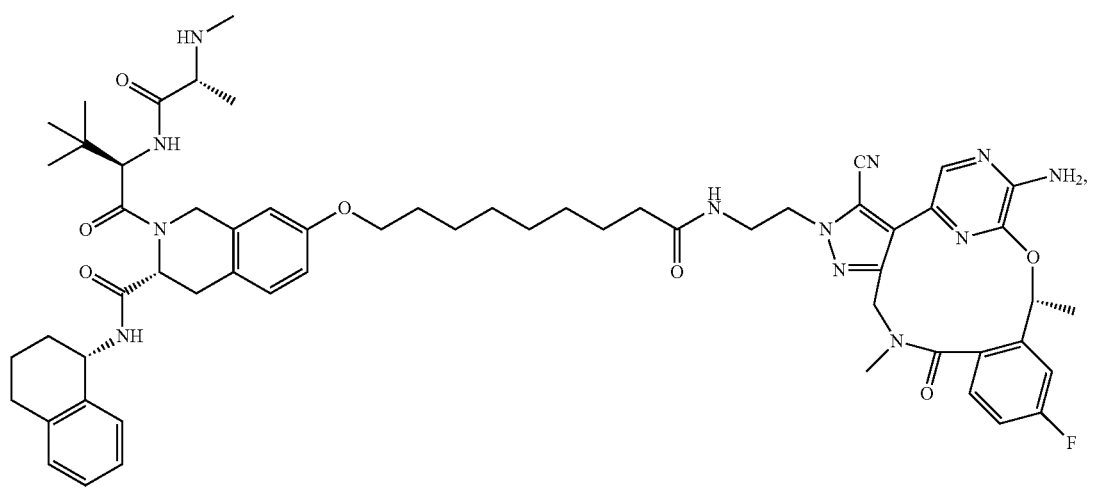
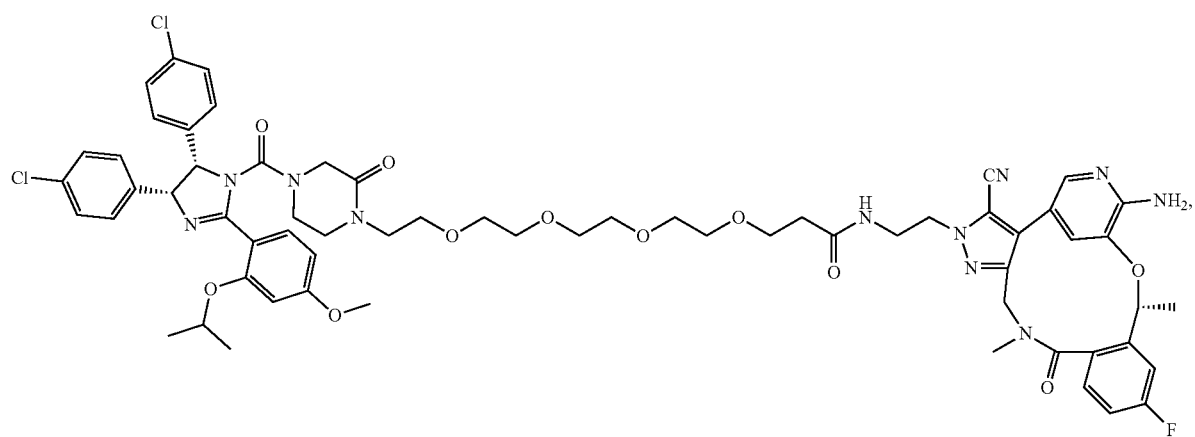

261
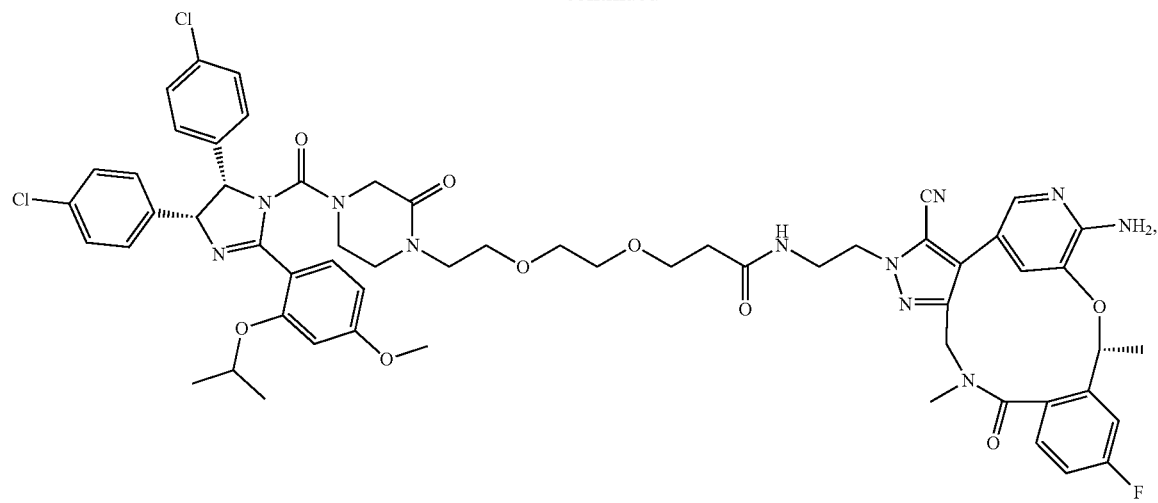
-continued
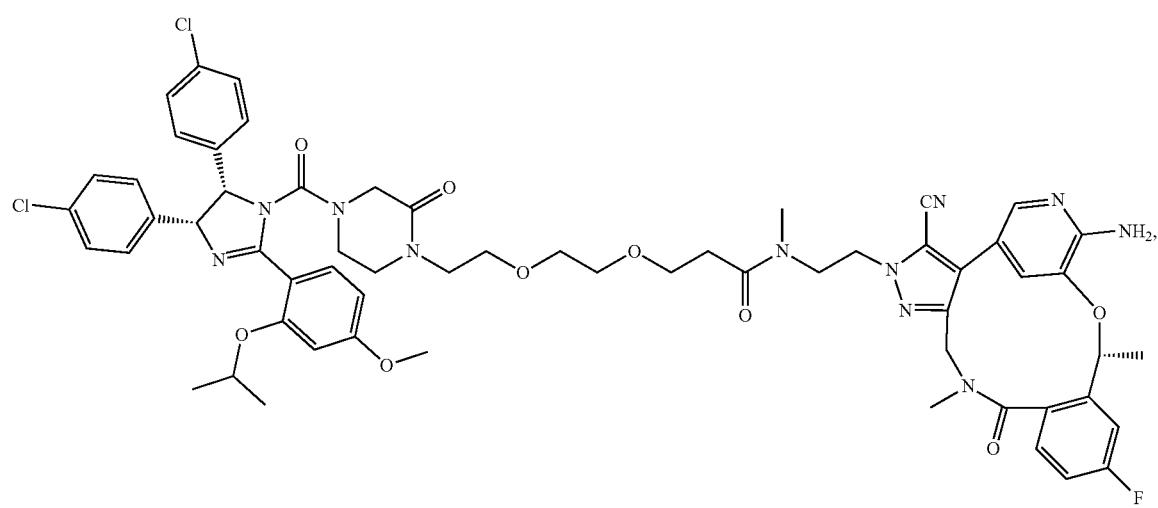
262
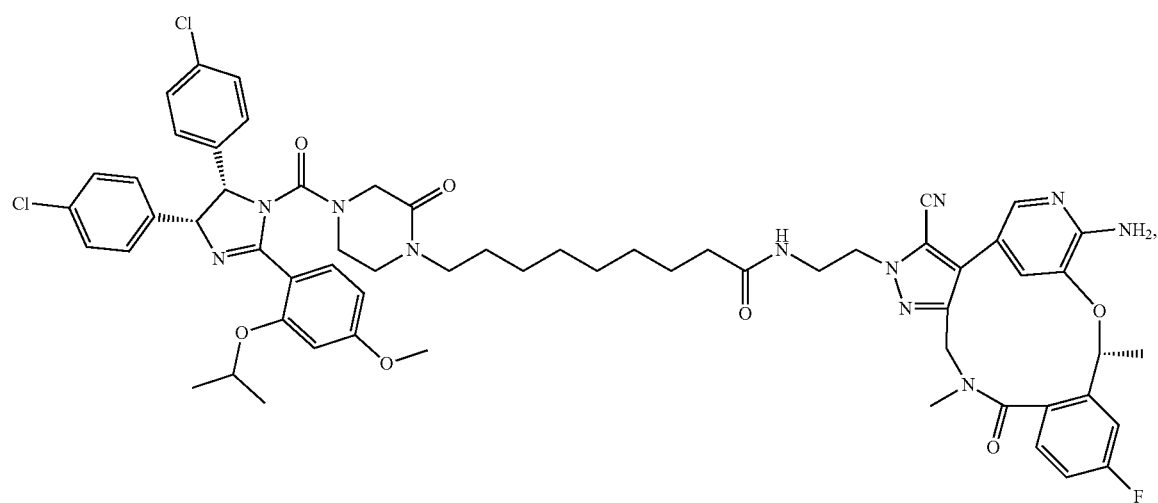

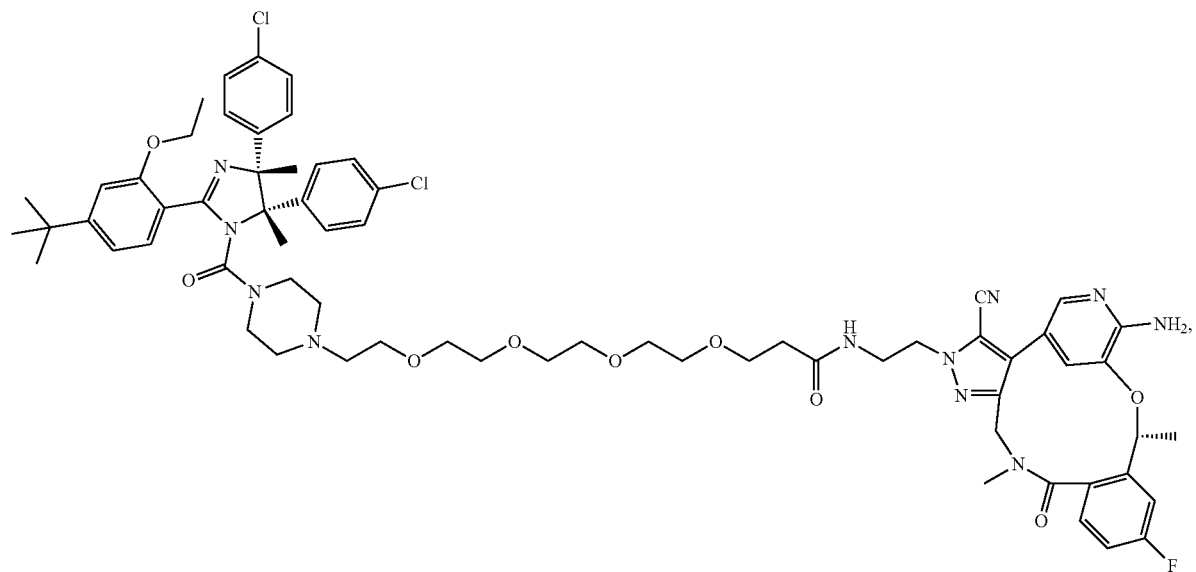
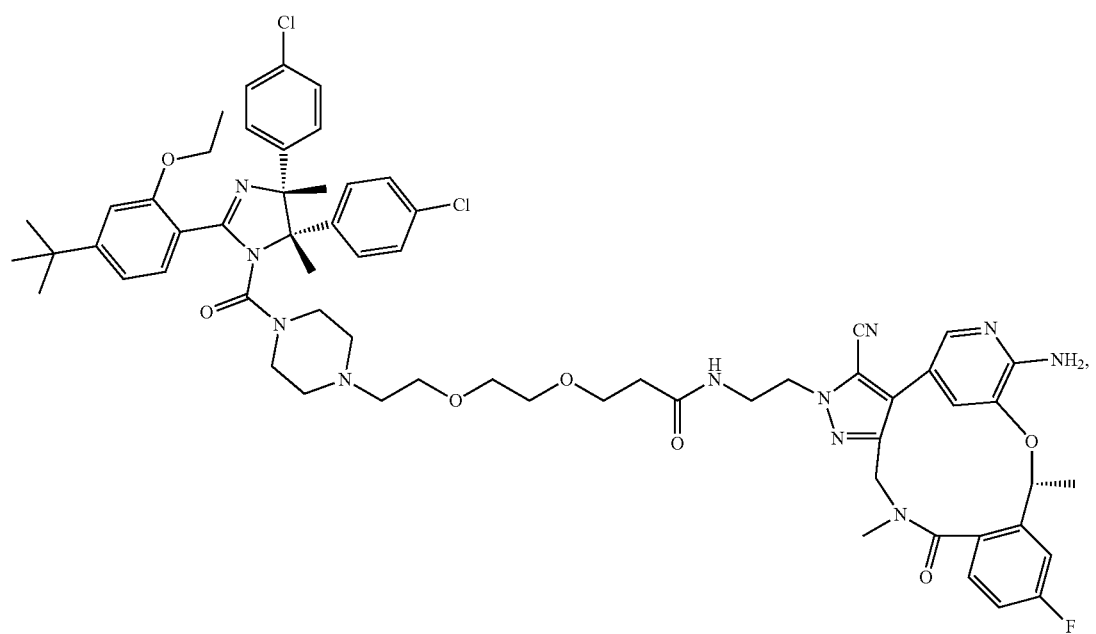

265
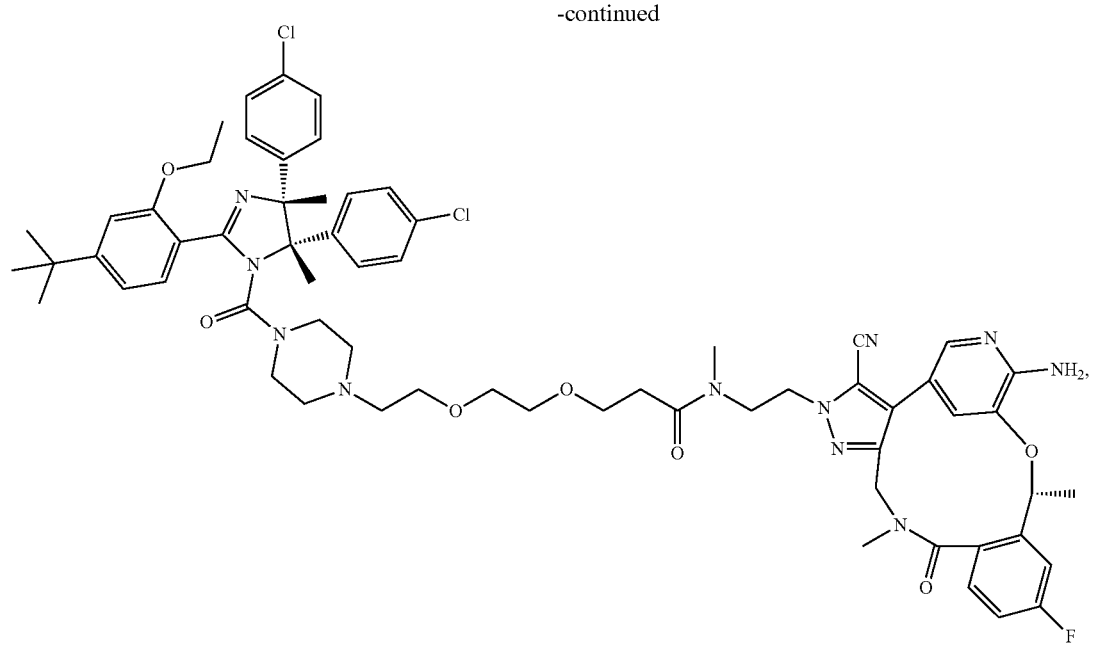
-continued
266
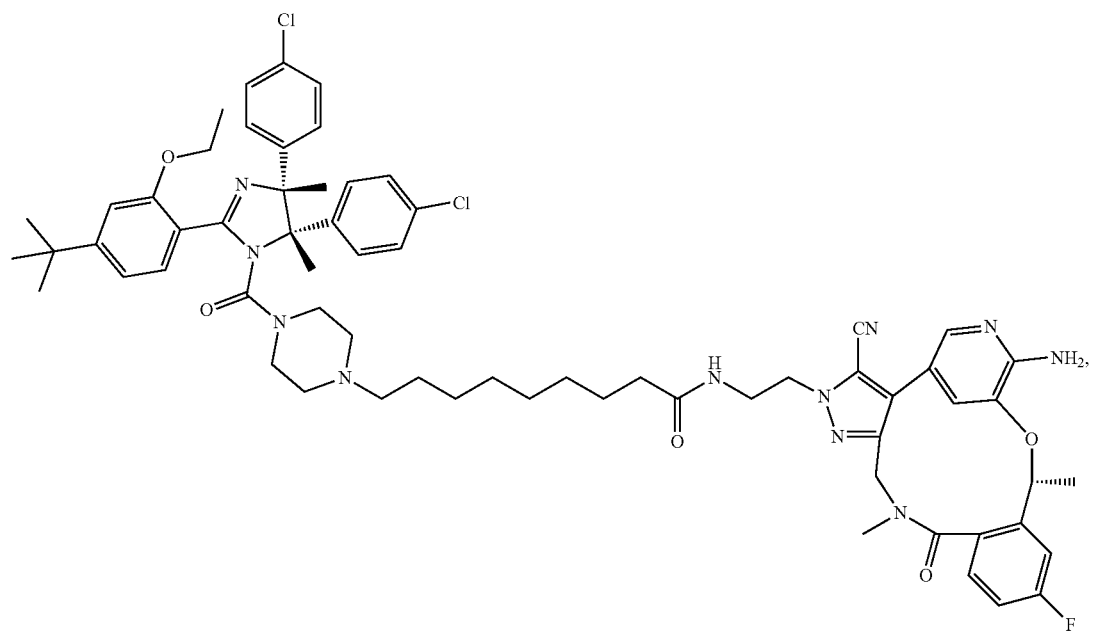

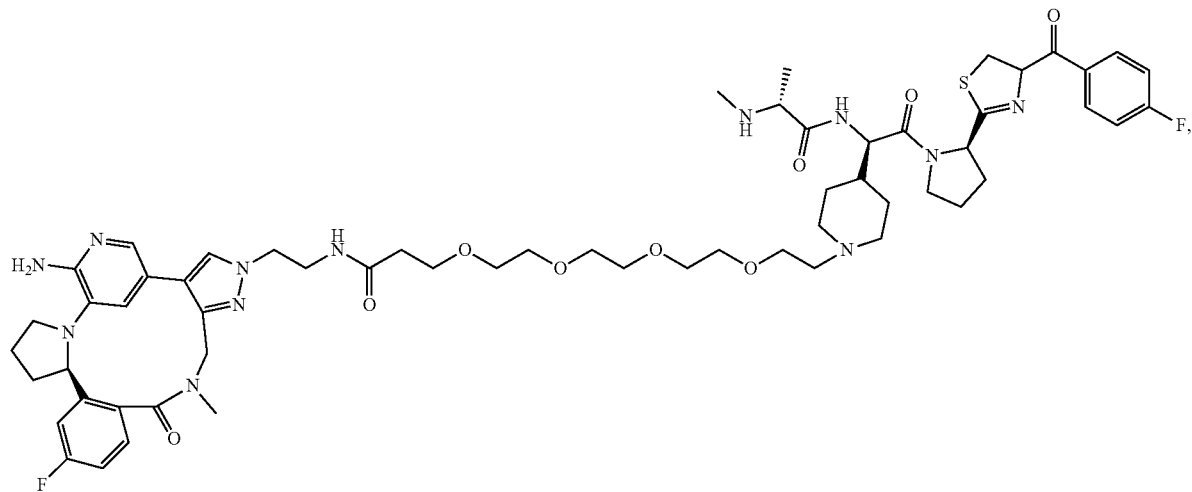
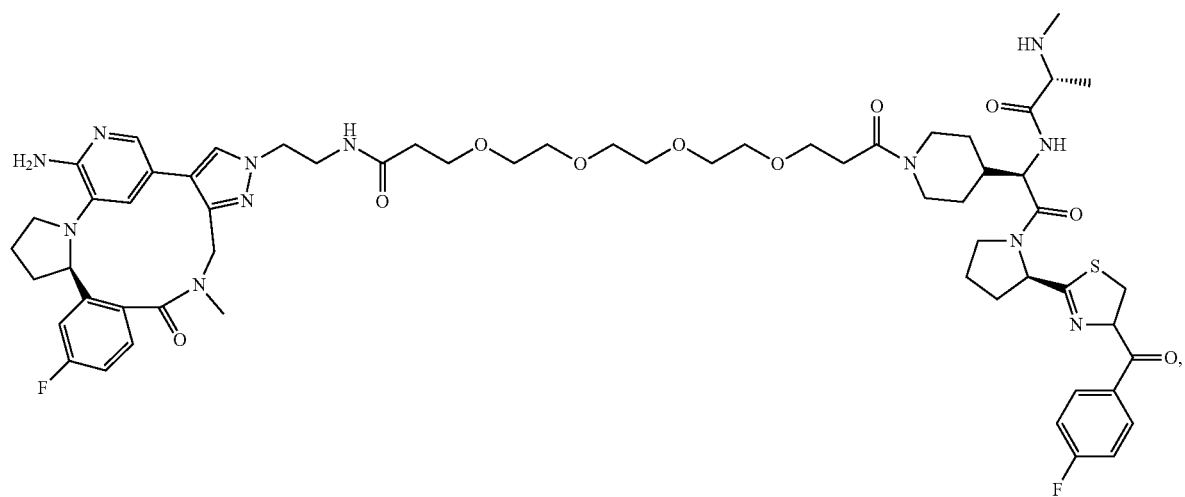
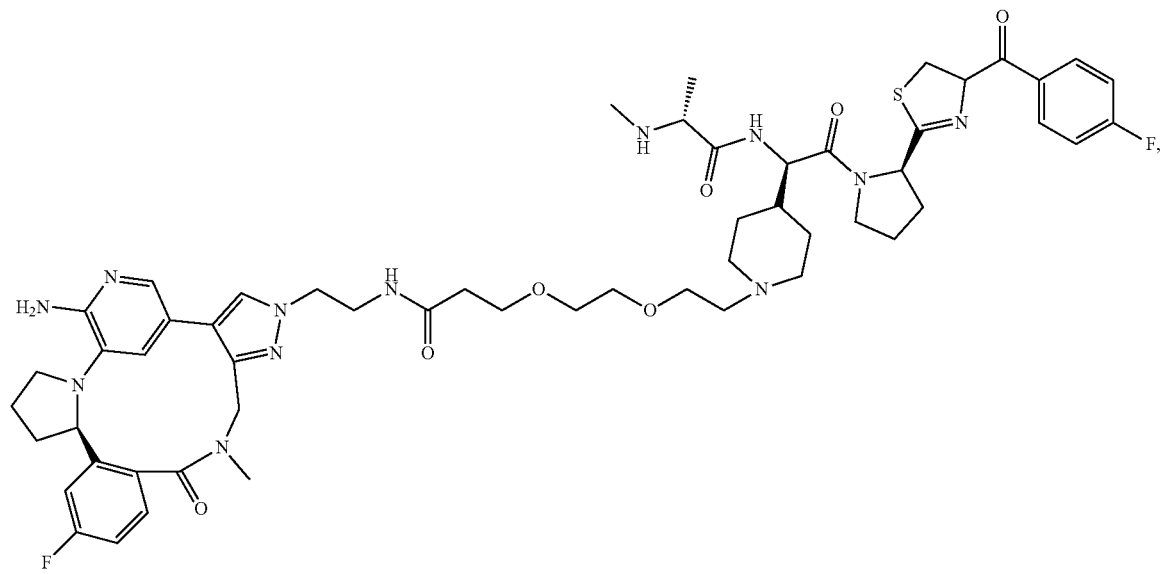

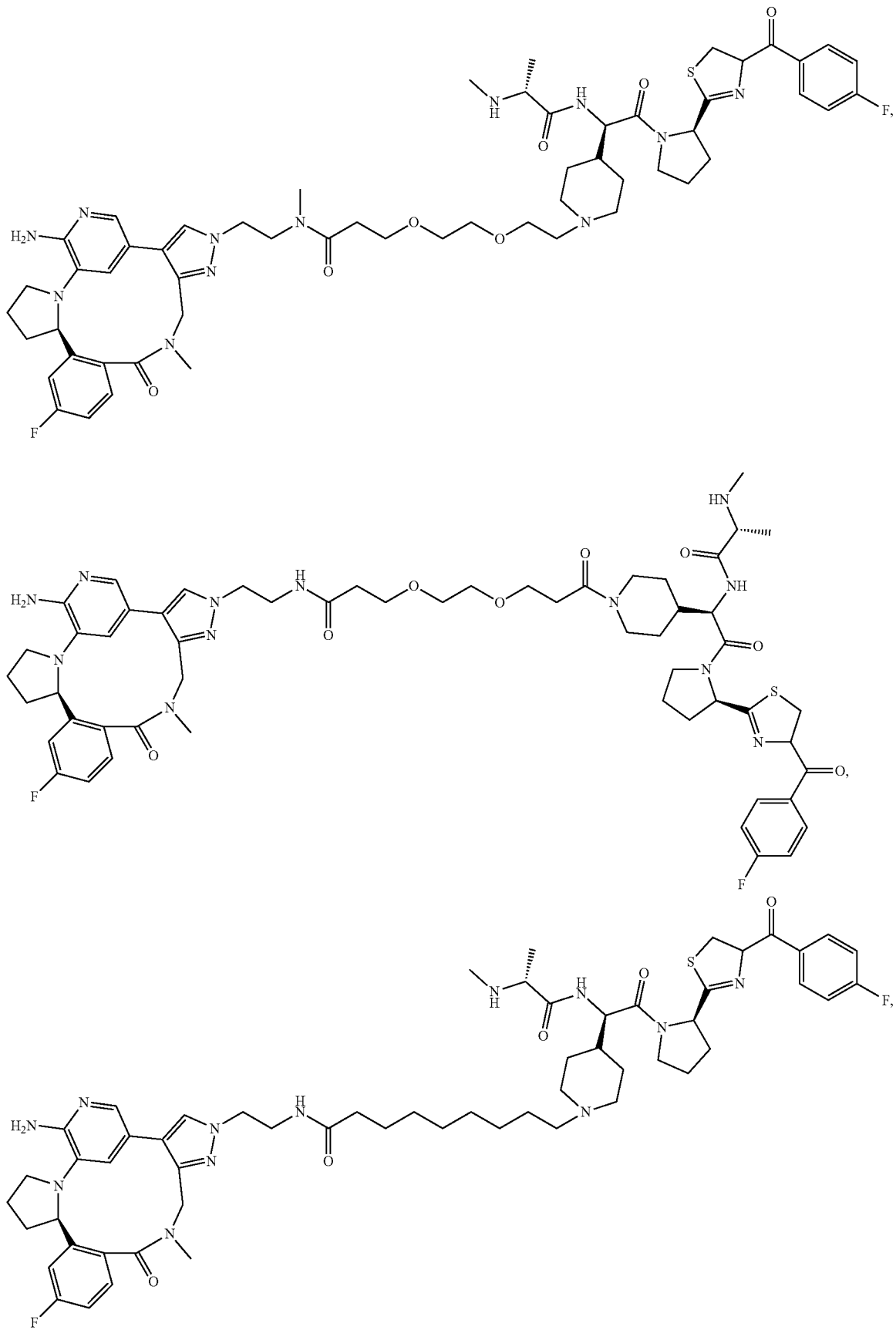

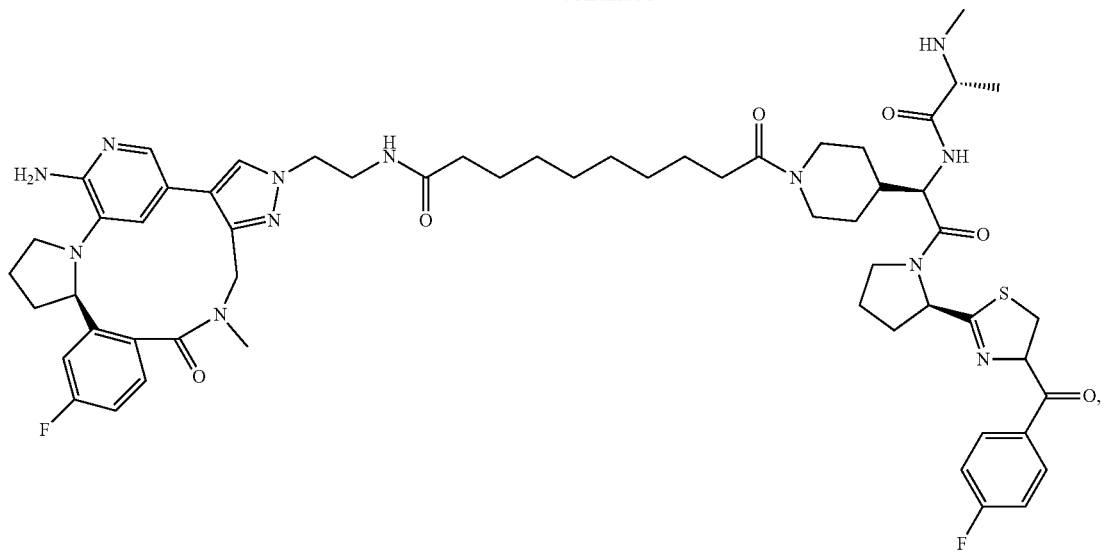
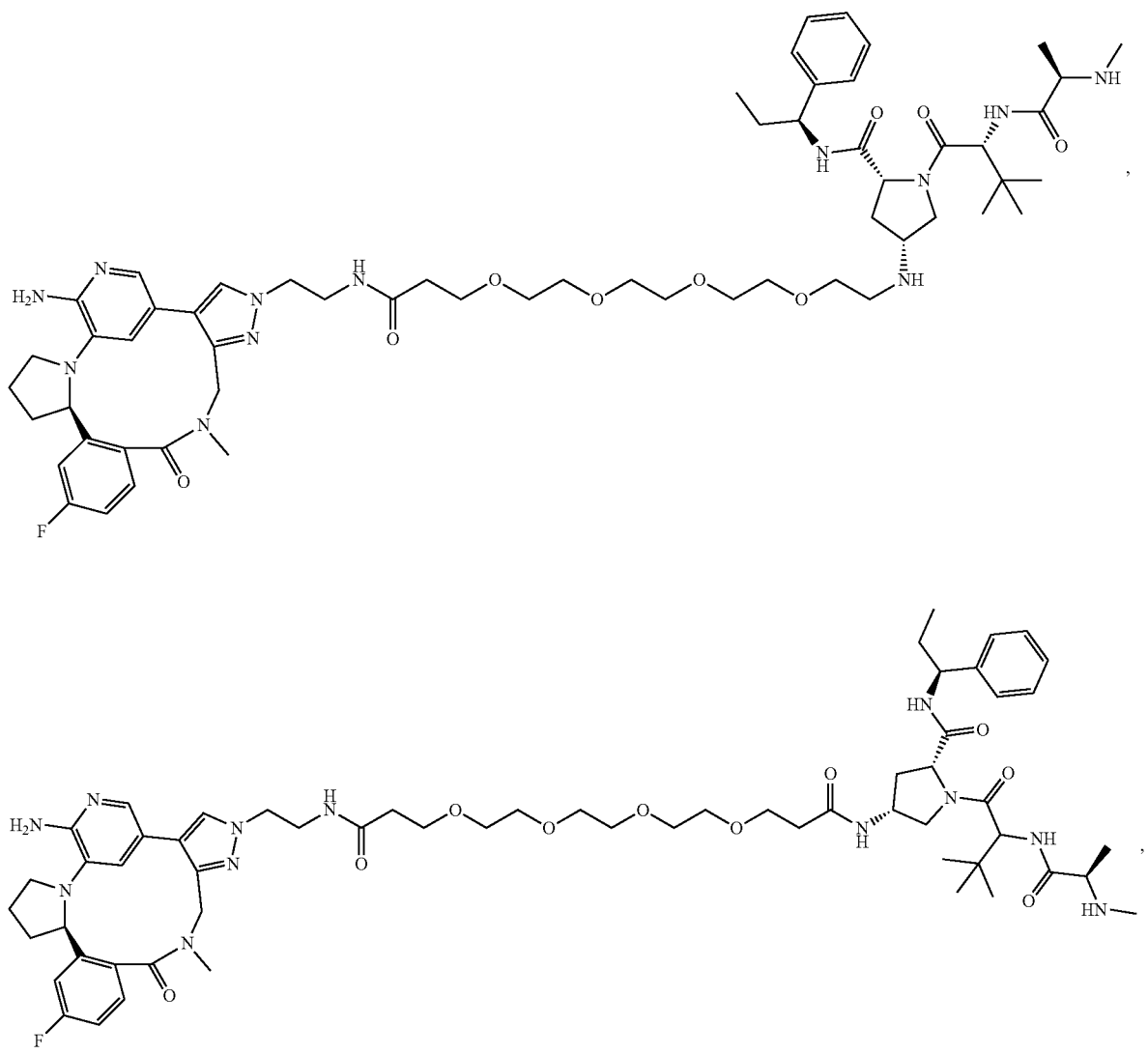

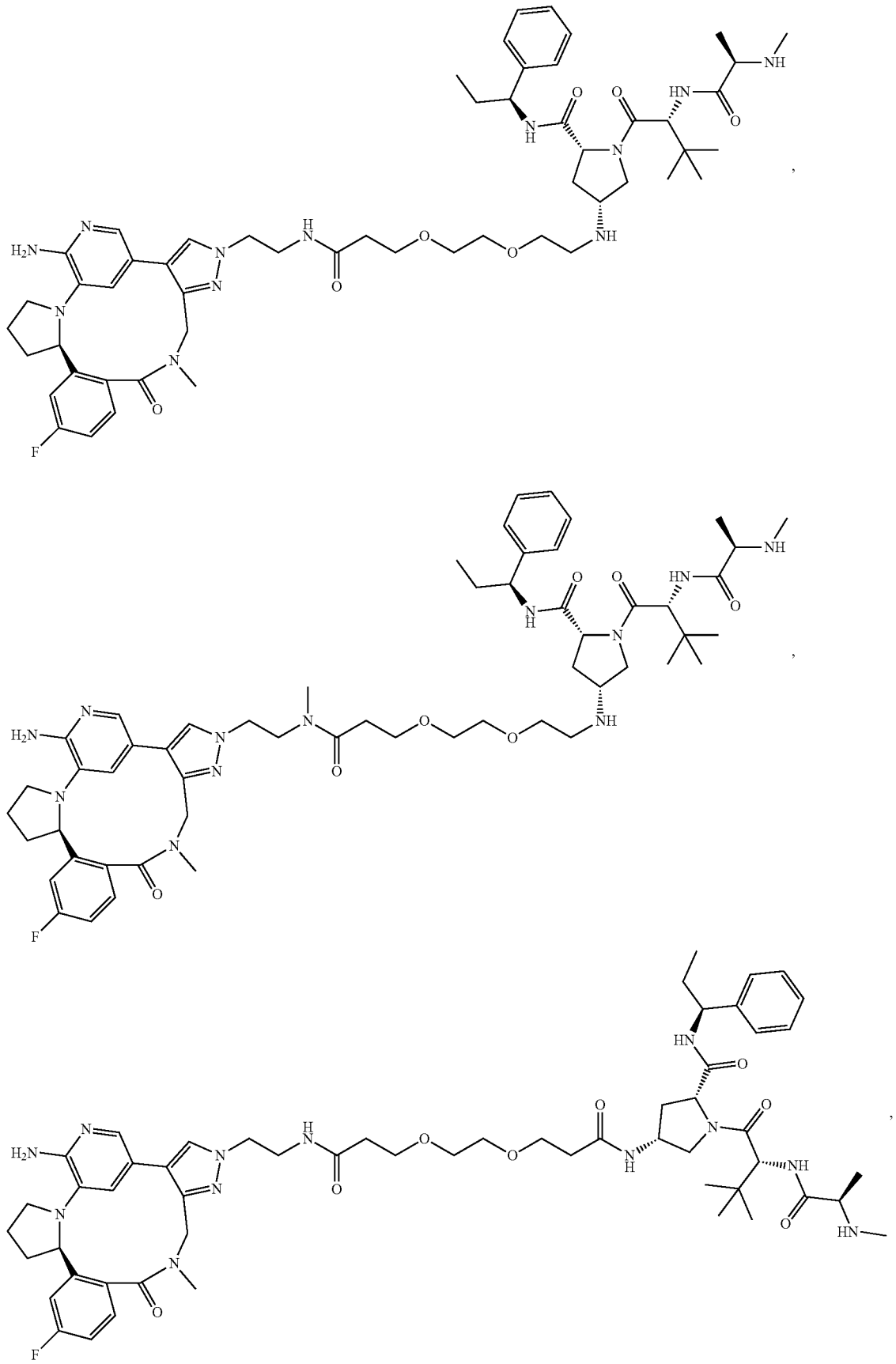

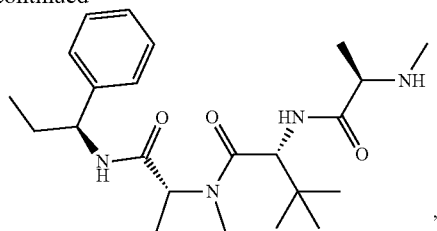
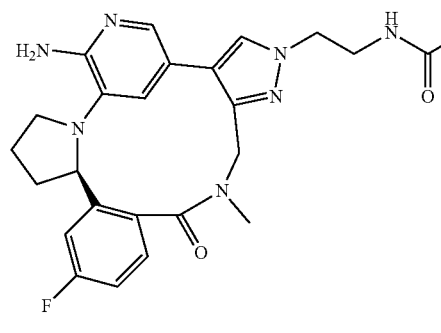
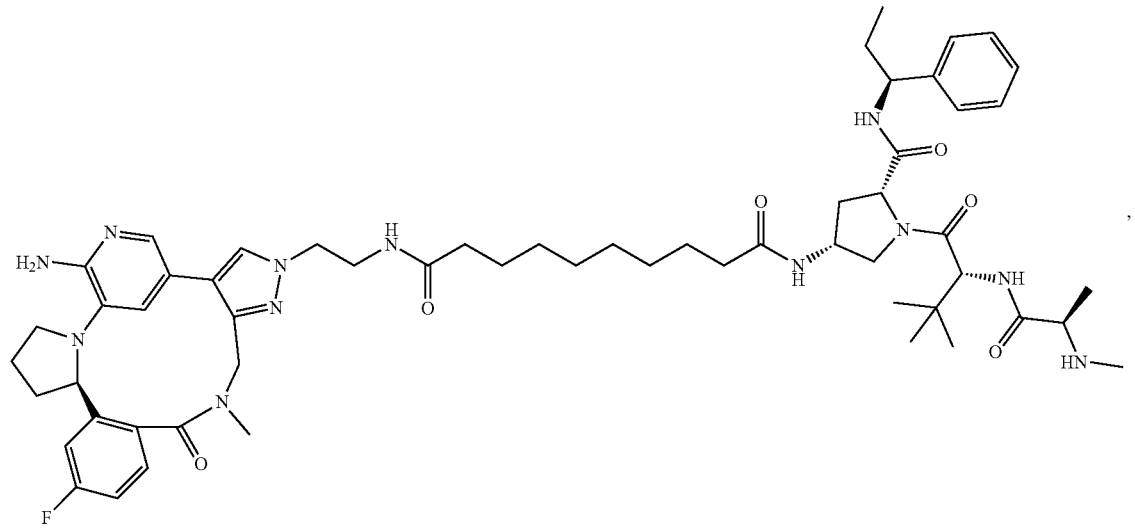
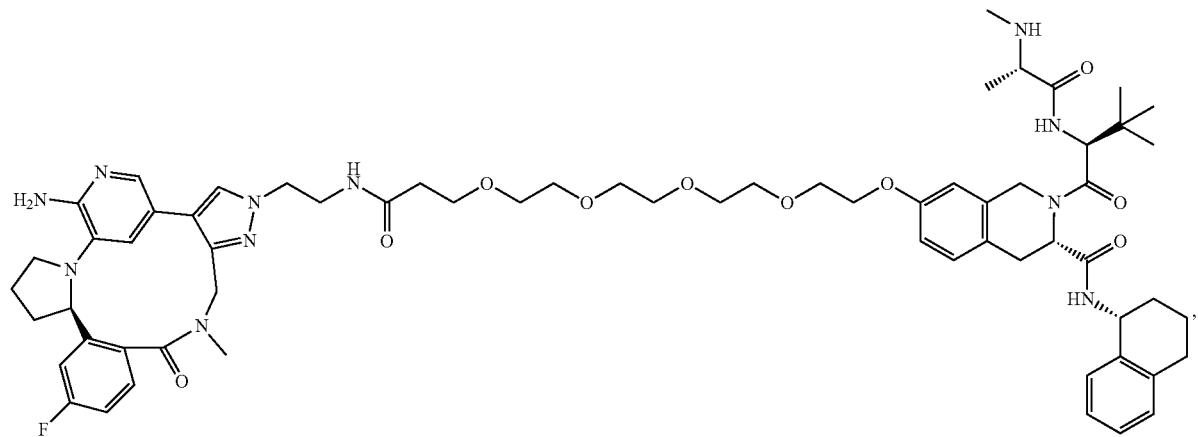

277 278
-continued
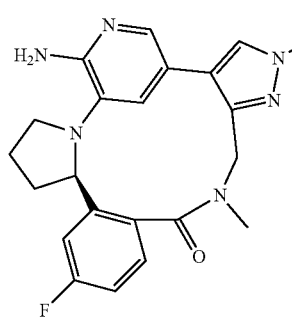 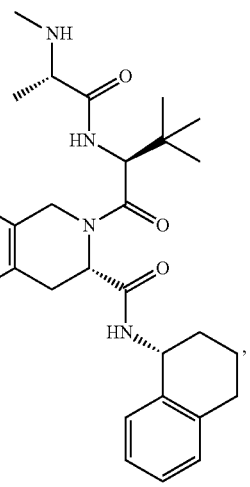
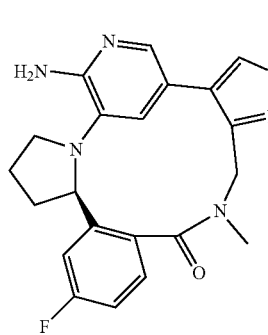 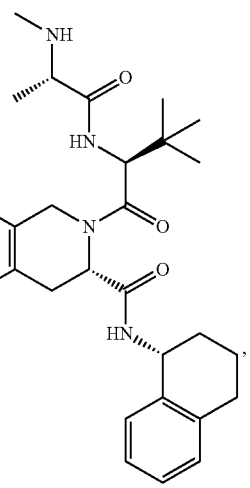
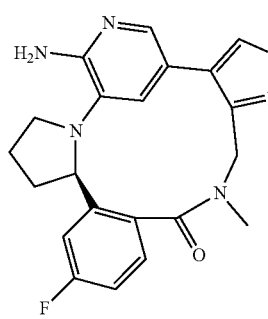 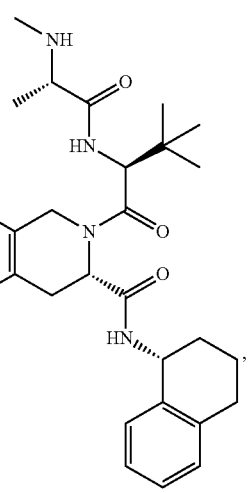

-continued
279
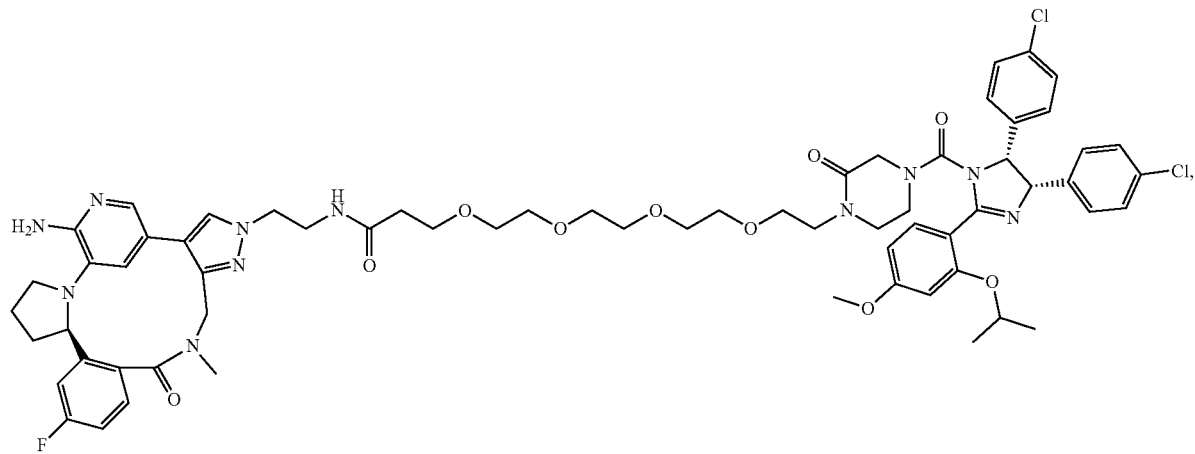
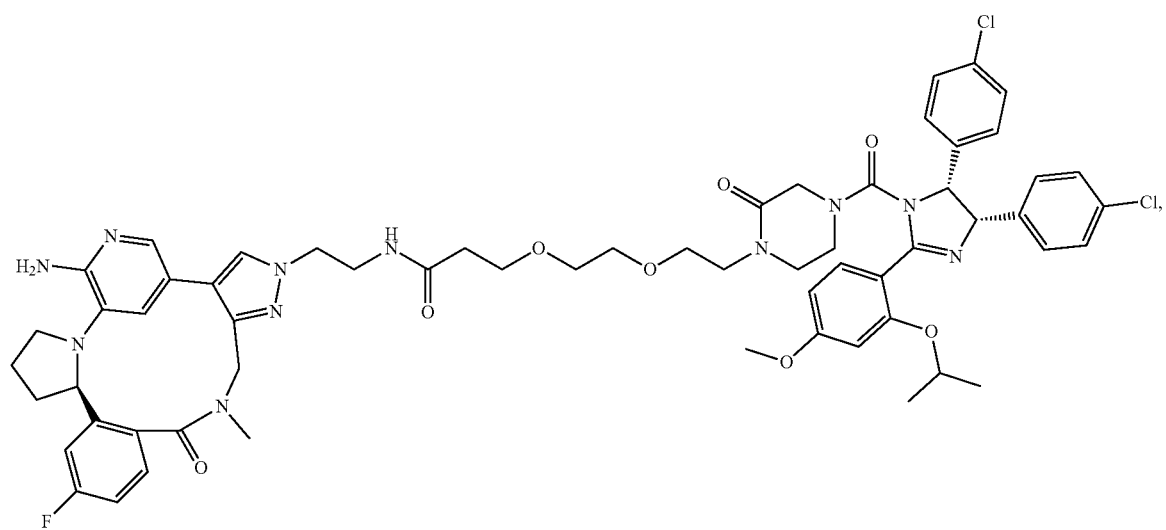
280
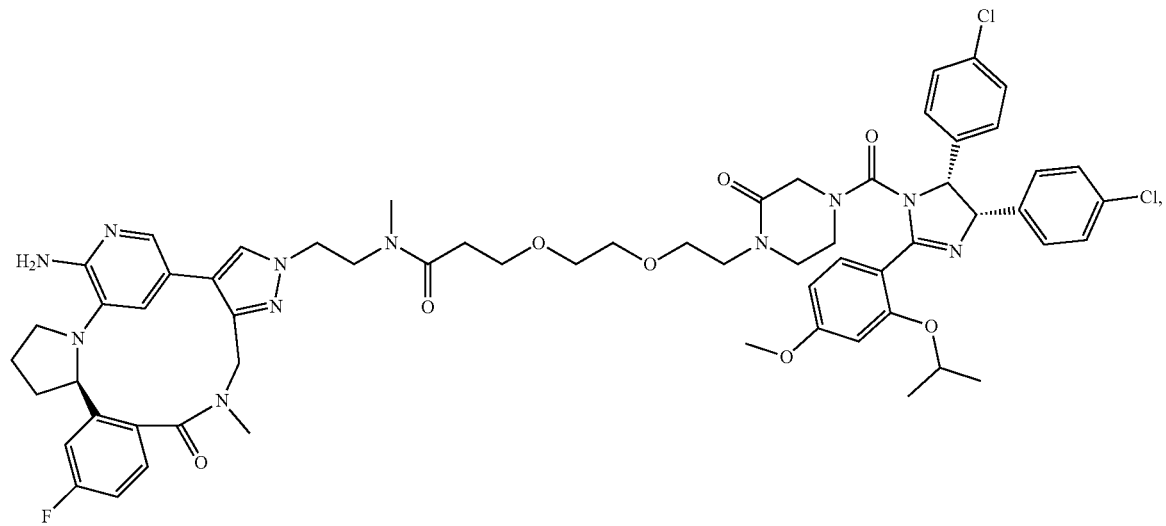

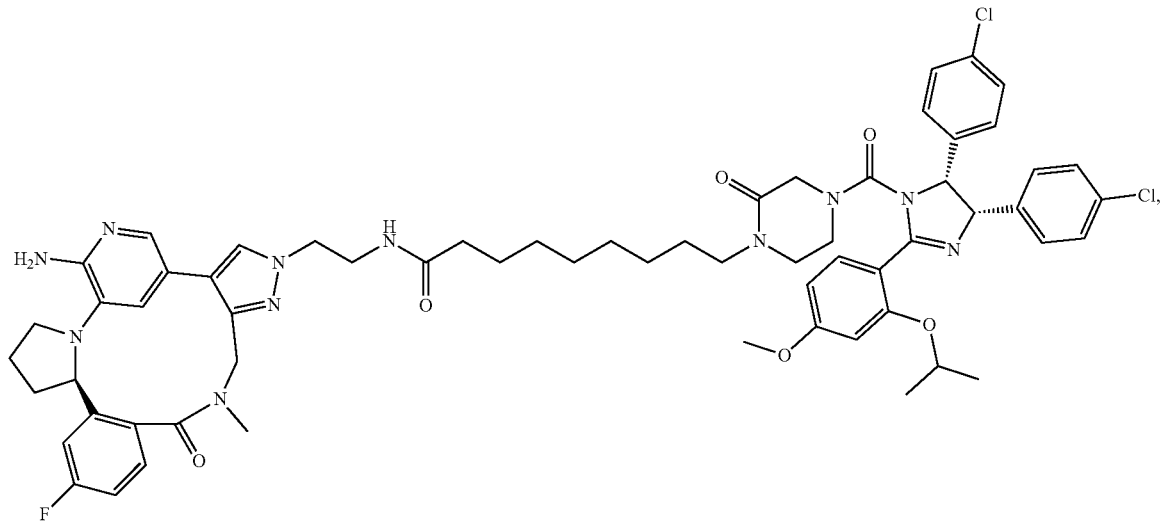
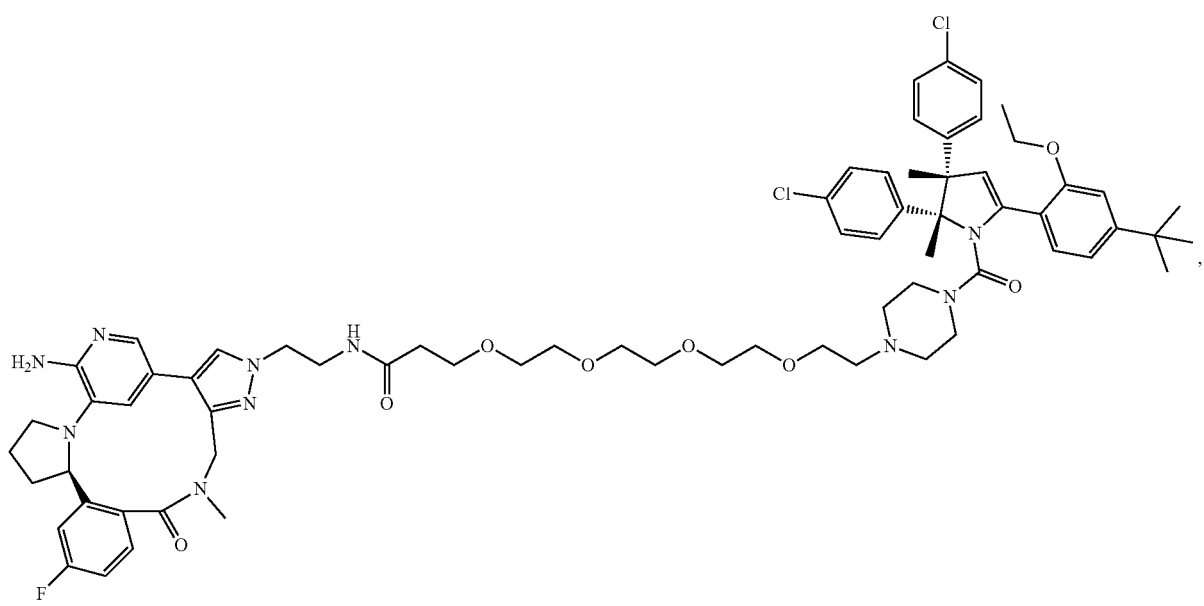

283
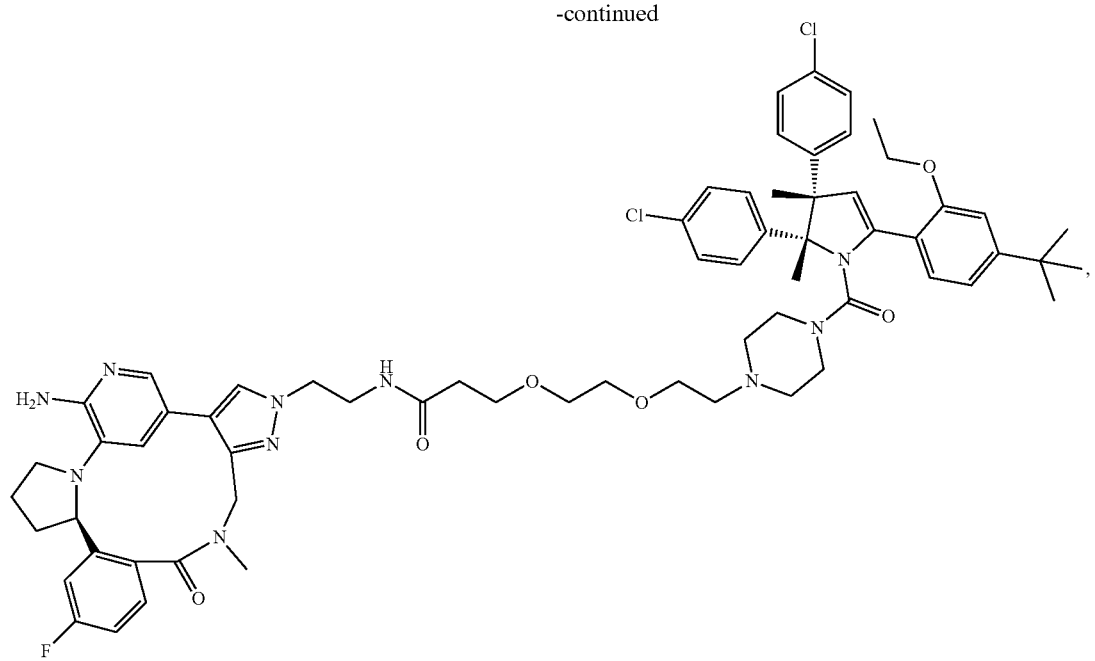
284
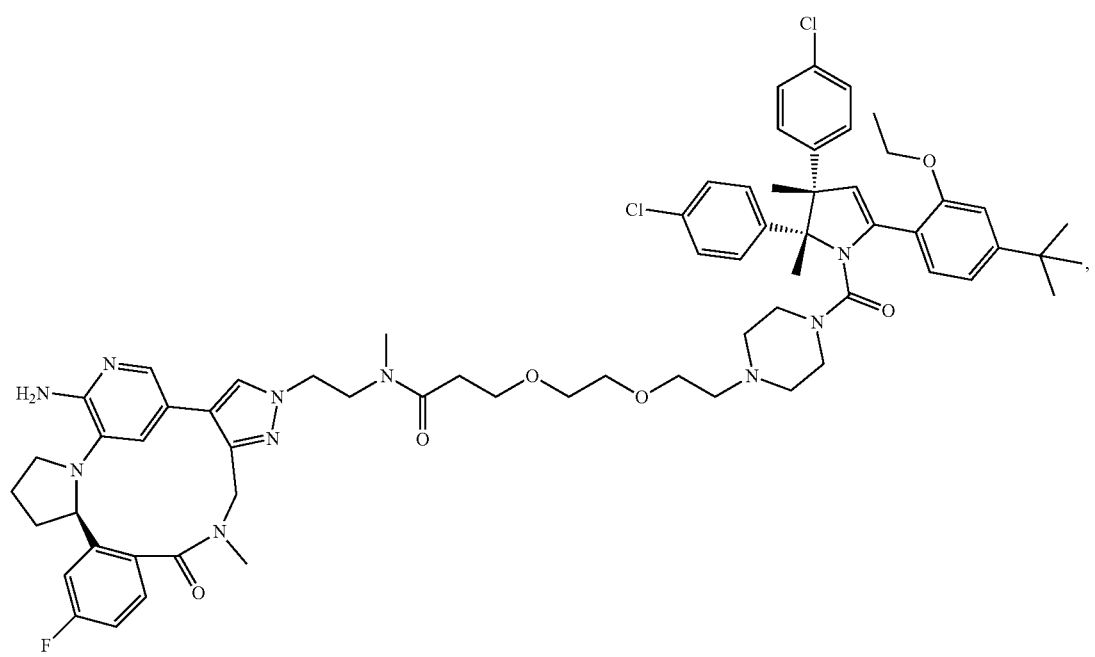

285 286
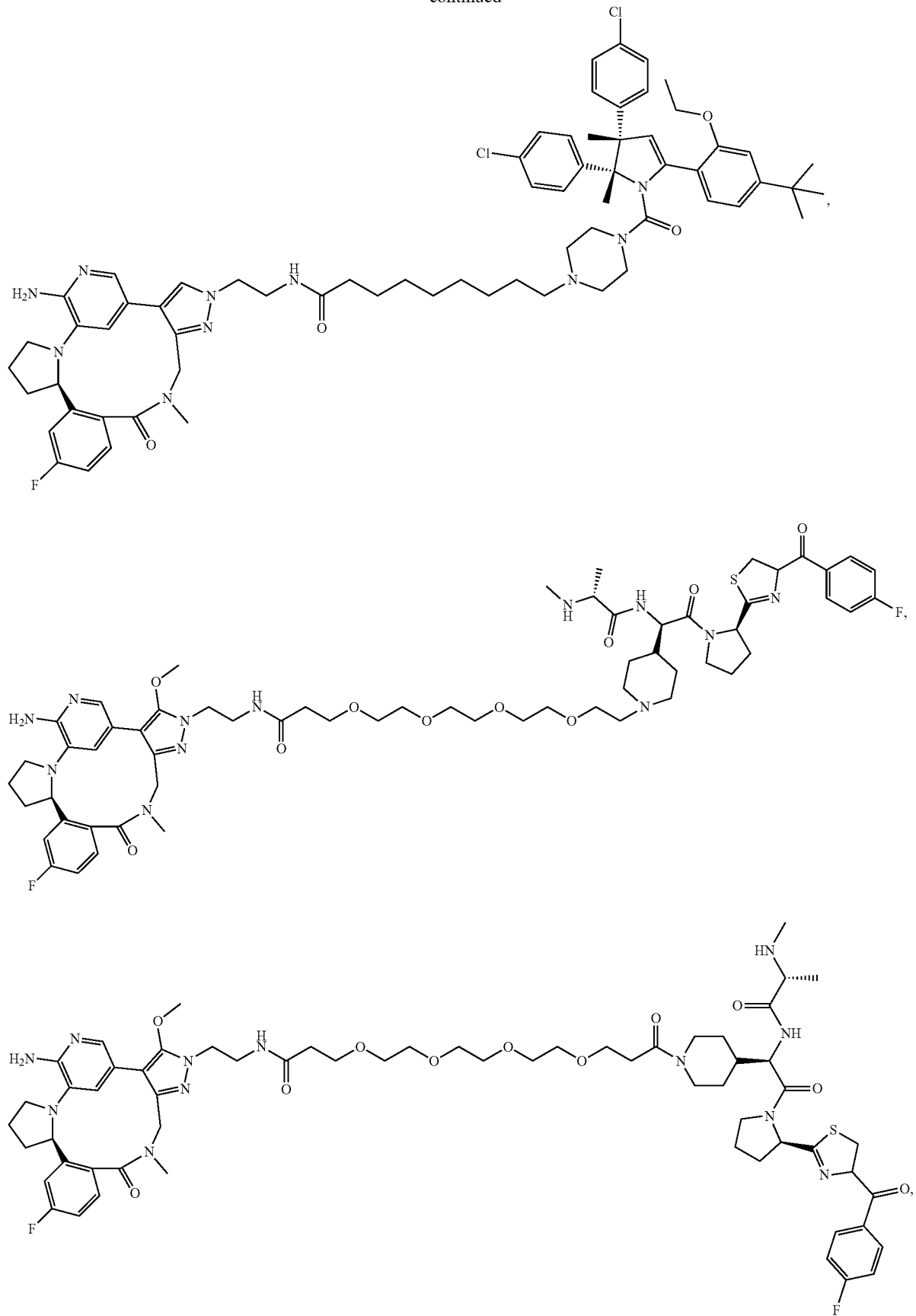

287
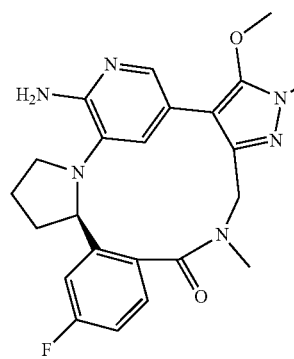
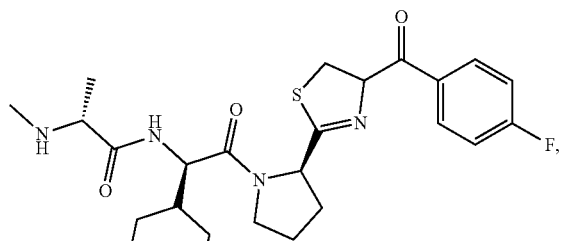
288
-continued
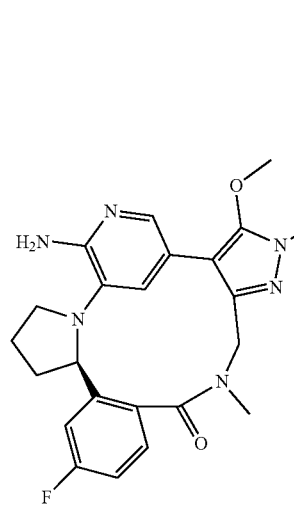
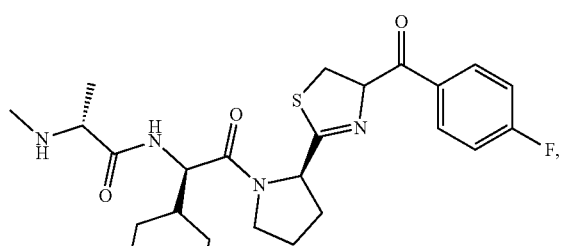

289
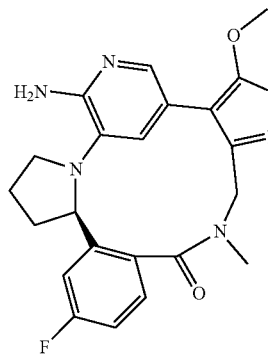
290
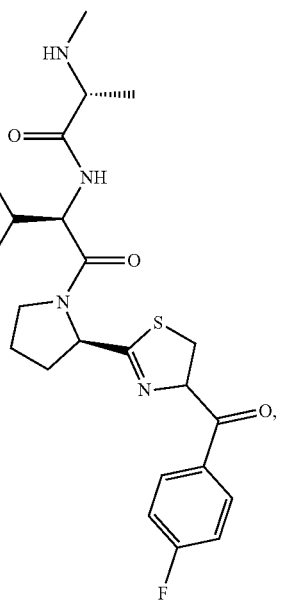
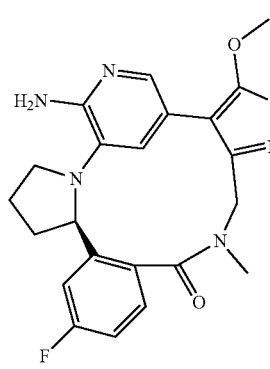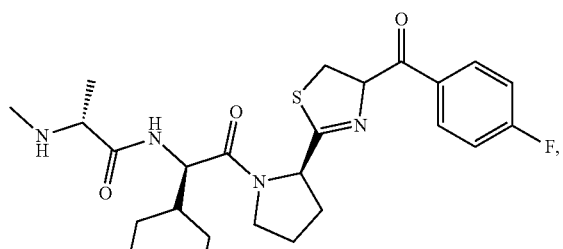

291
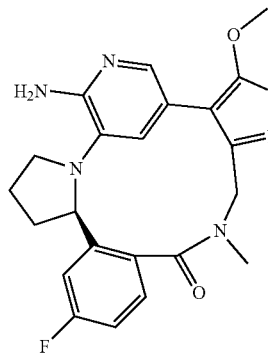
292
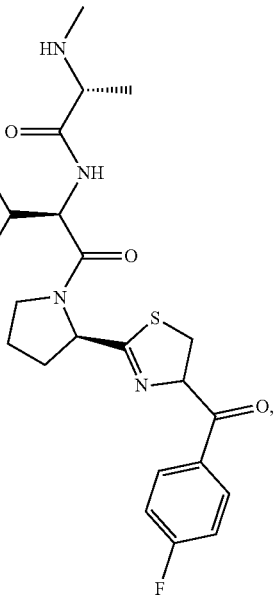
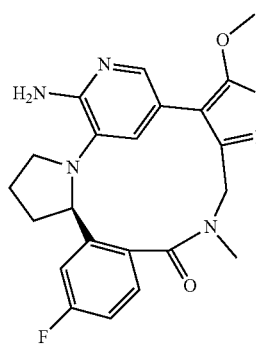
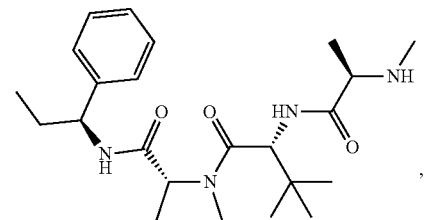
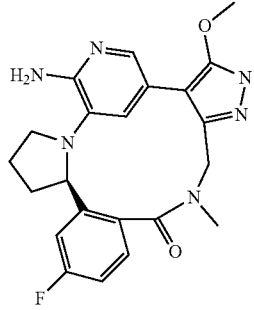
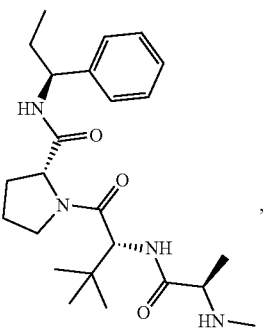

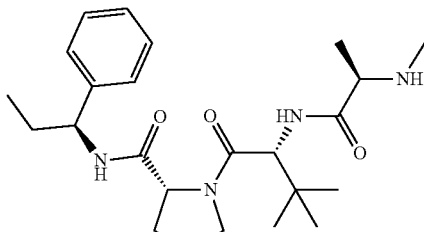
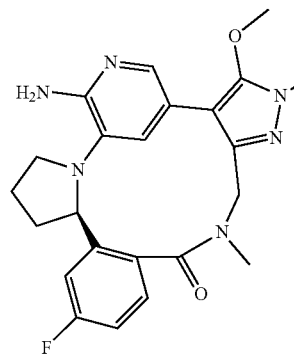
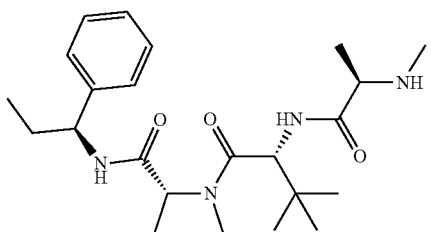
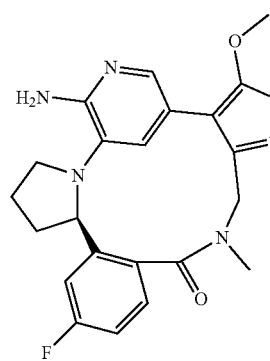
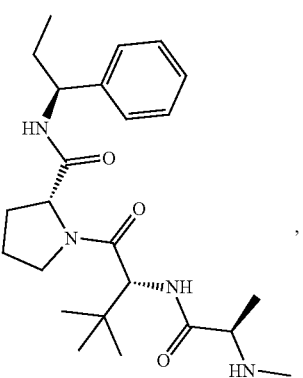
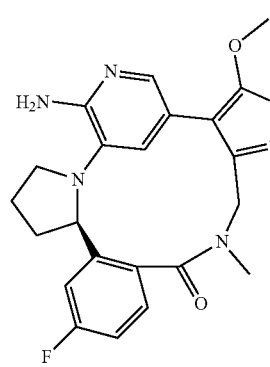

-continued
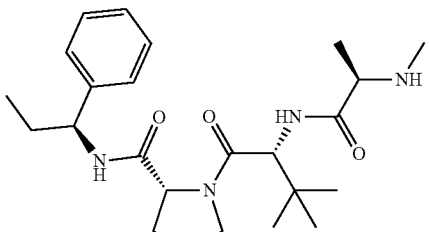
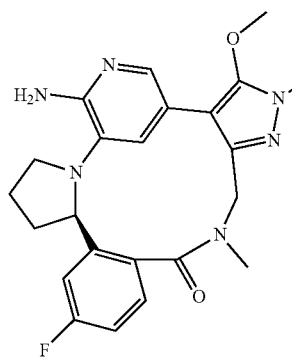
,
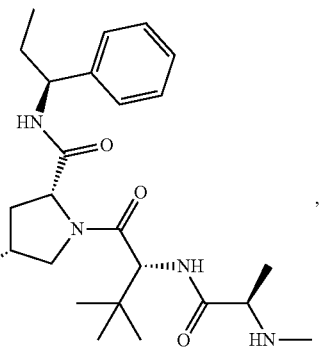
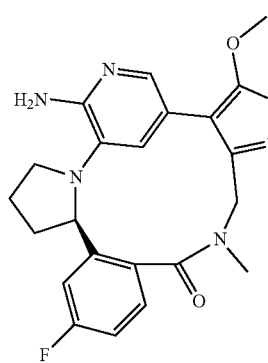
,
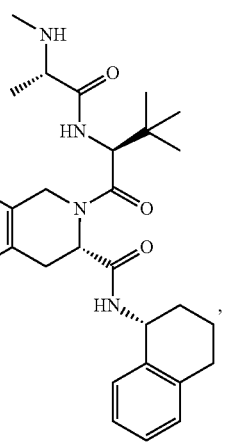
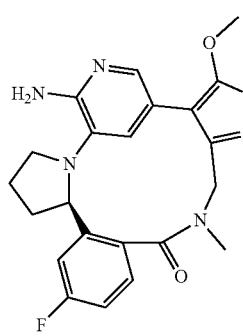
, 297 298
-continued
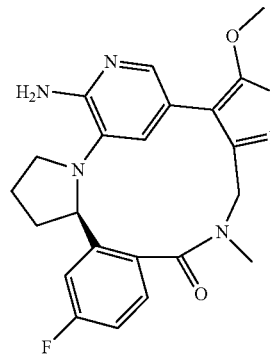 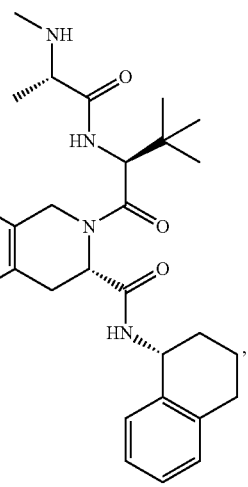
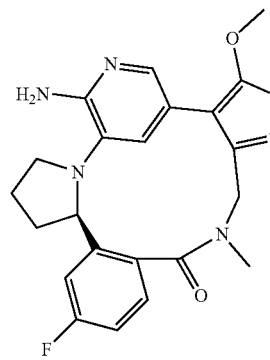 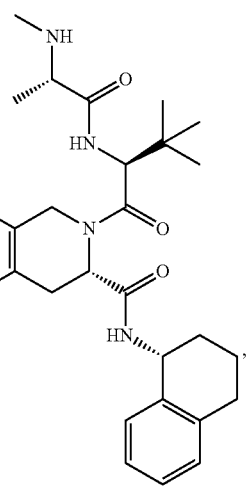
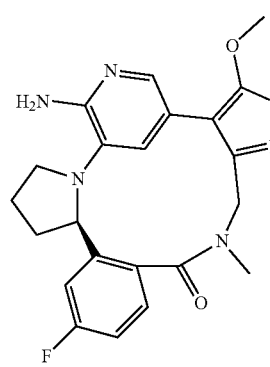 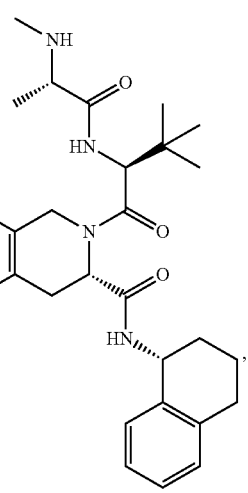

299
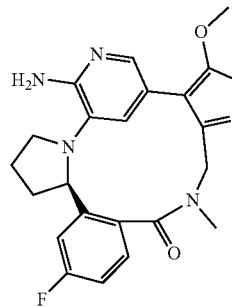
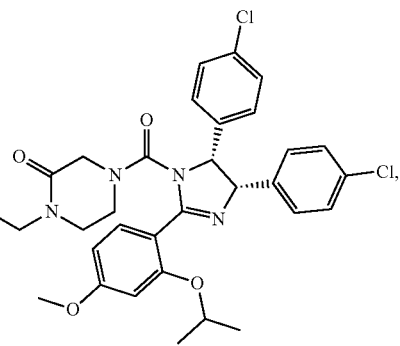
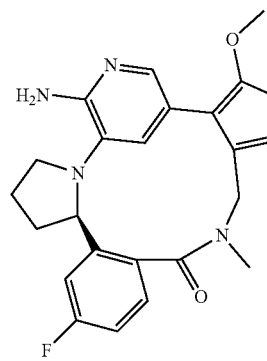
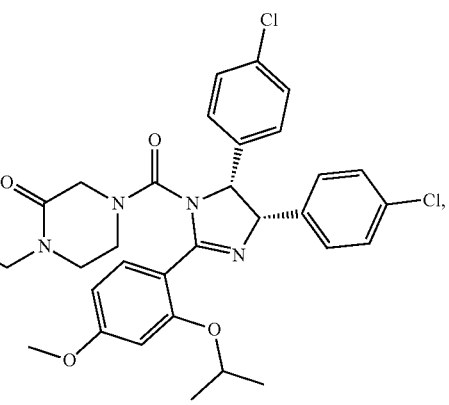
300
-continued
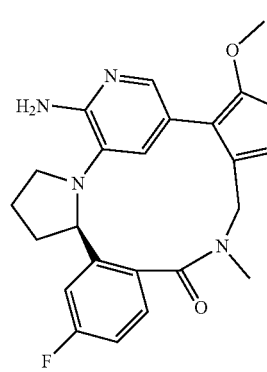
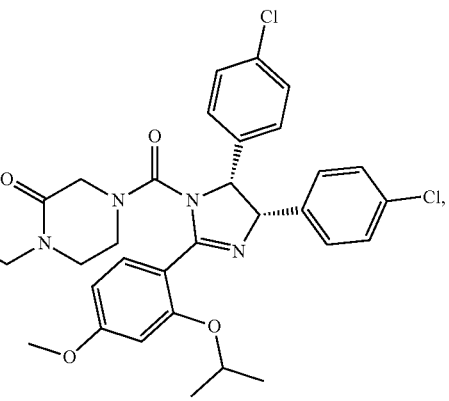

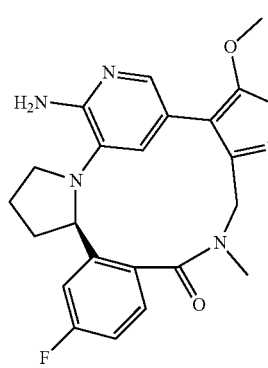
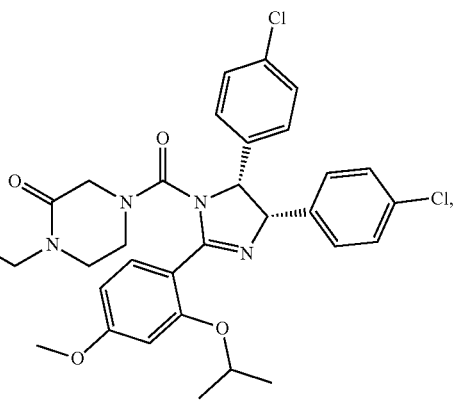
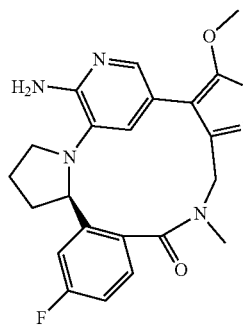
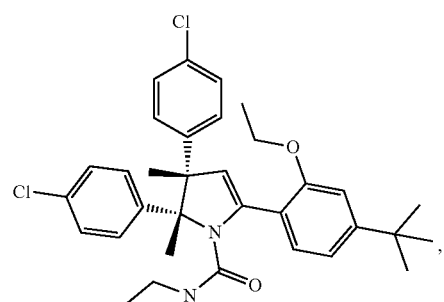
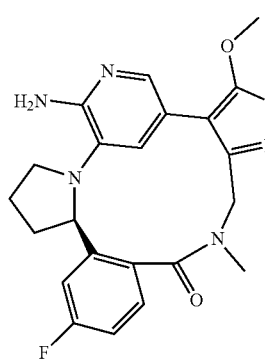
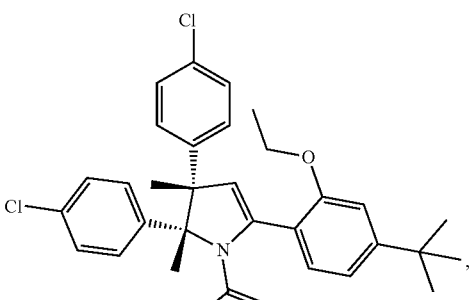

303
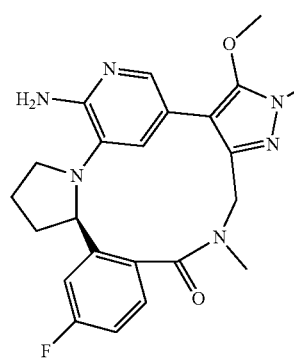
304
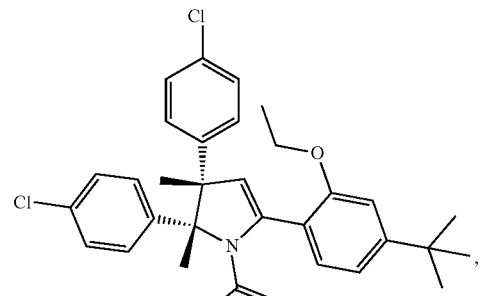
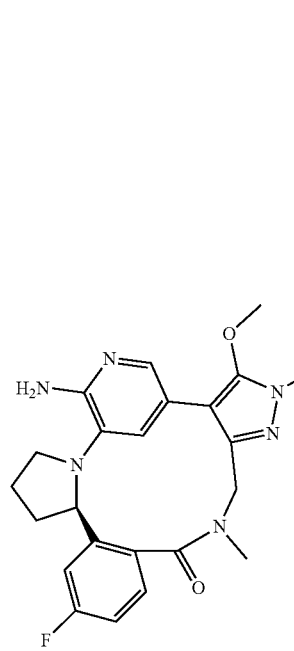
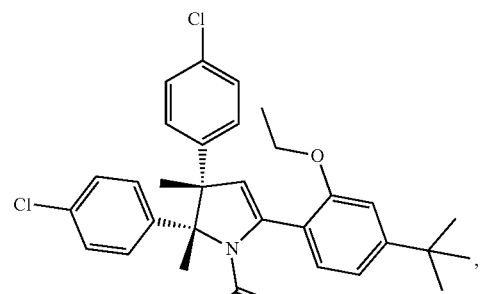

305
306
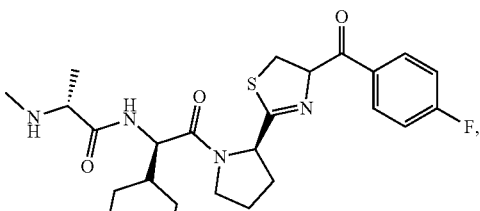
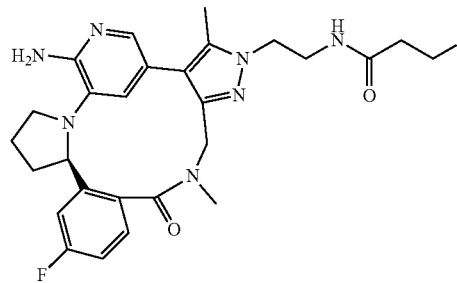
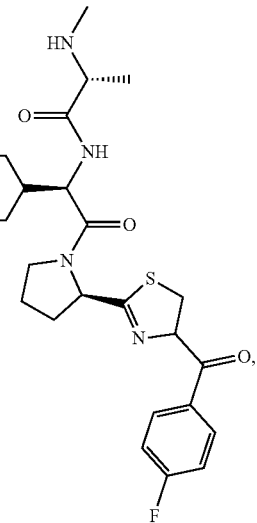
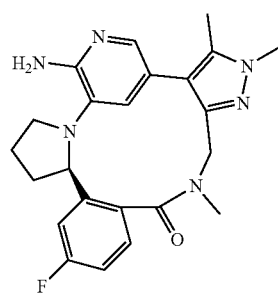
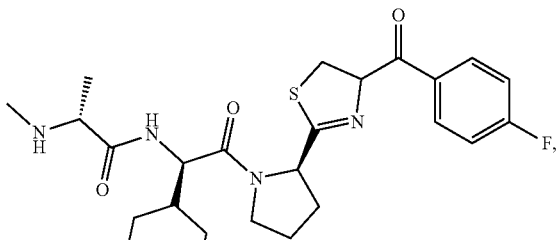
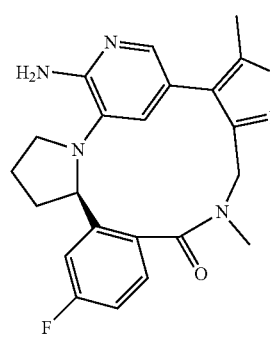

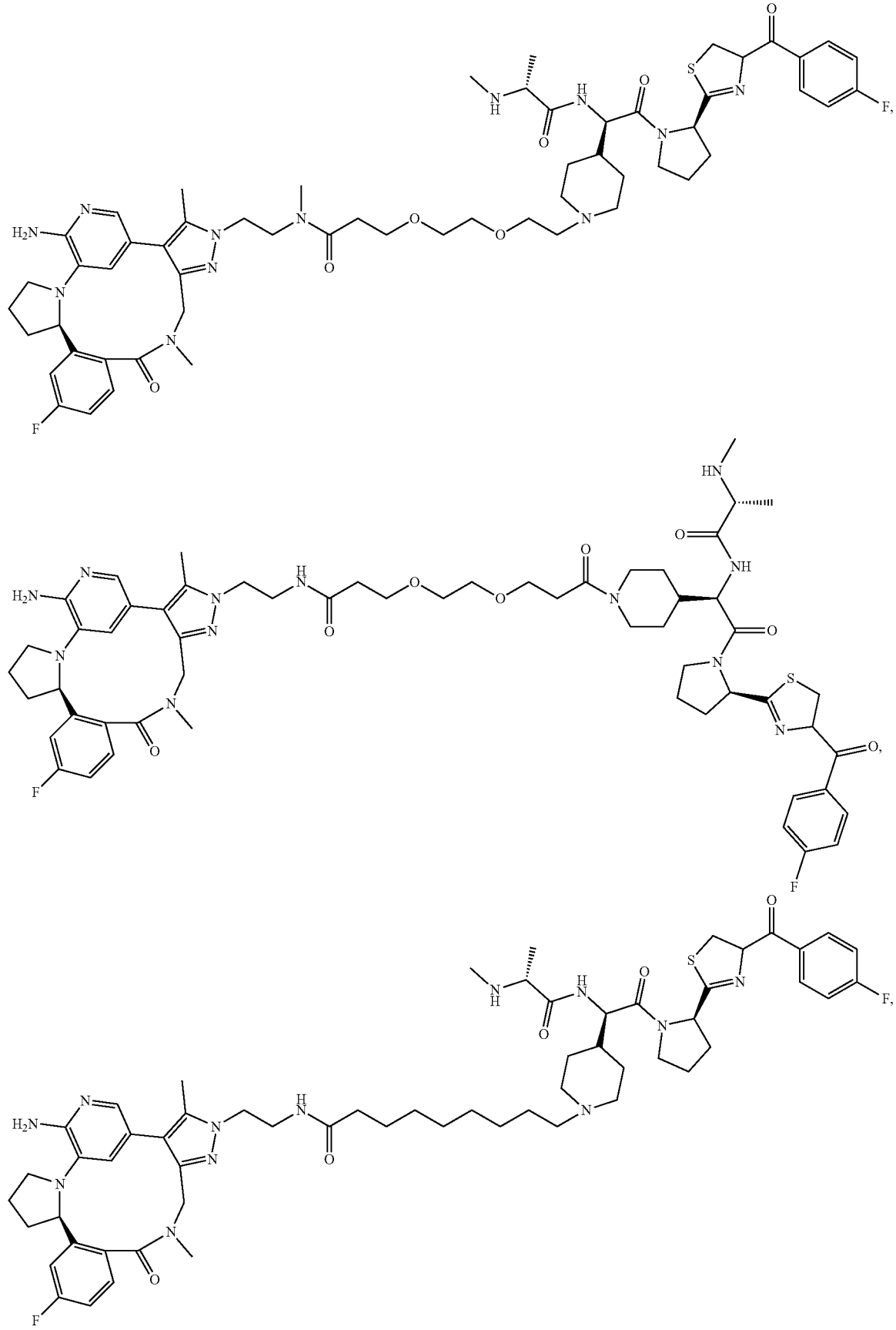

309
310
-continued
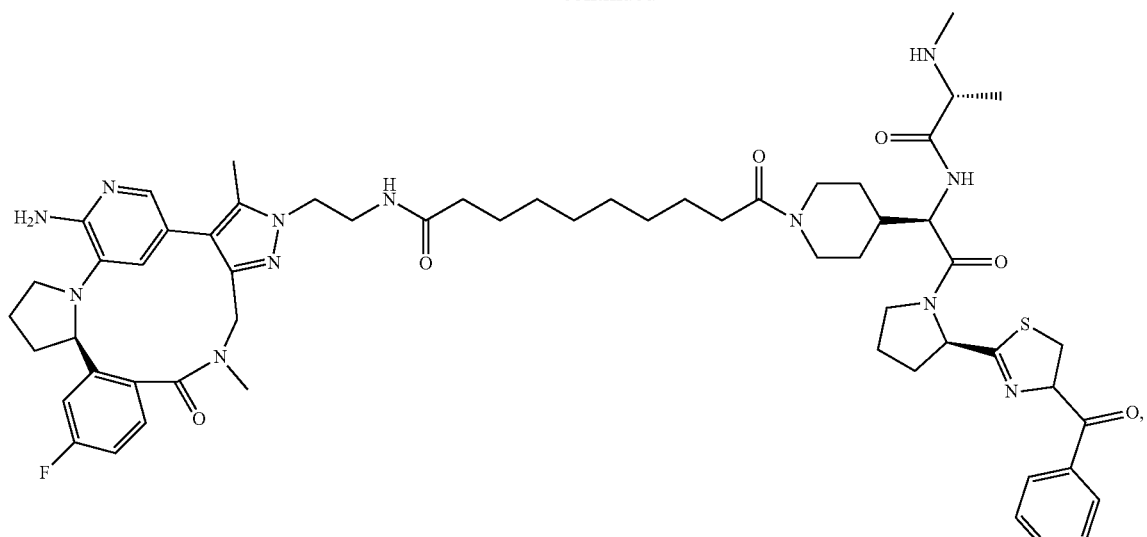
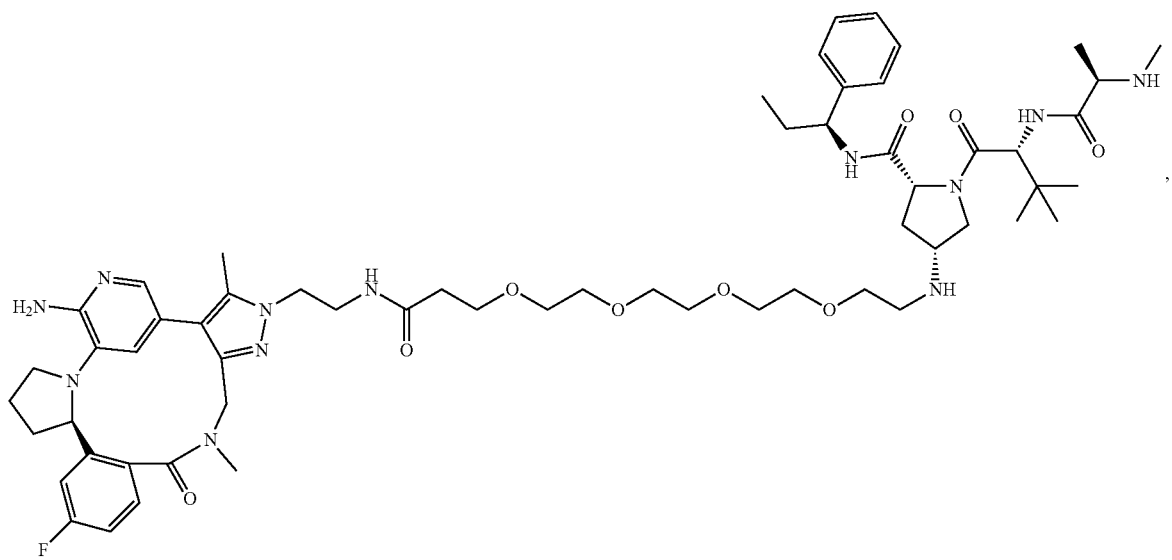
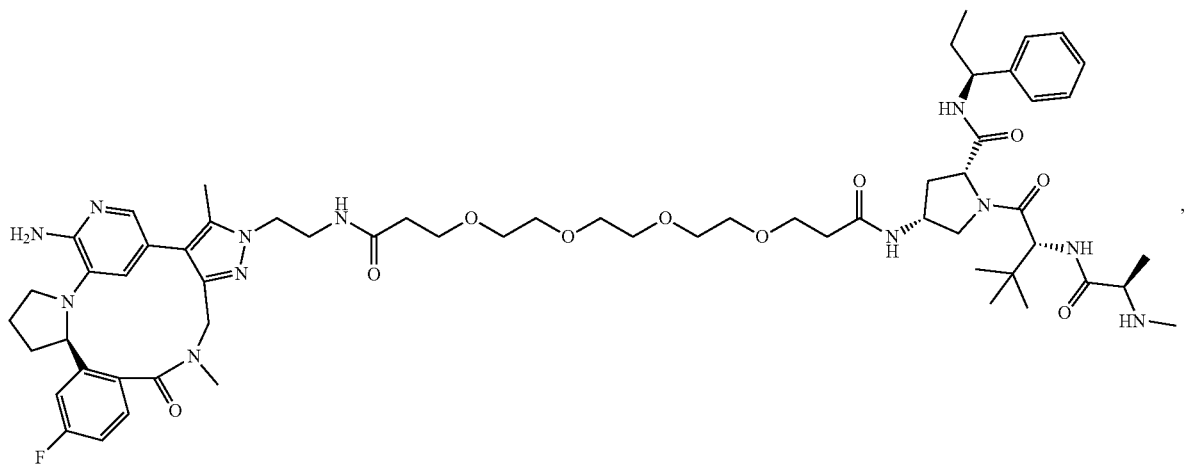

311 312
-continued
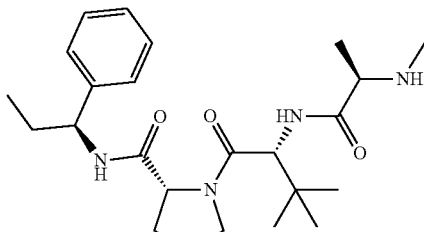
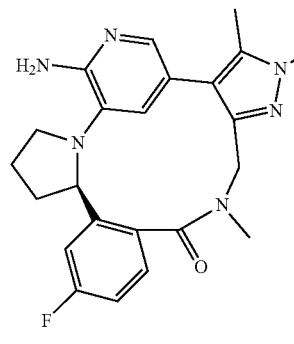
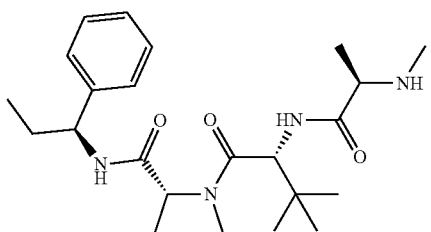
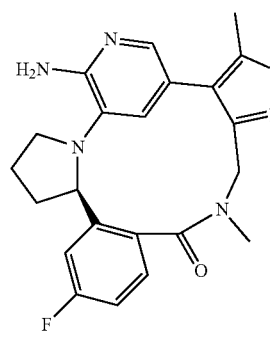
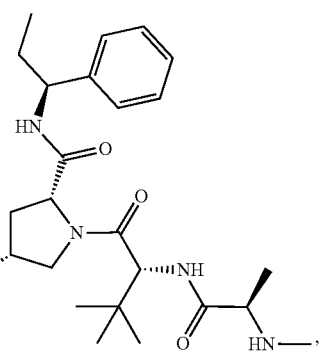
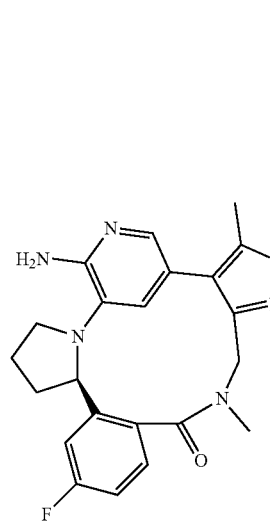

313                                                314
-continued
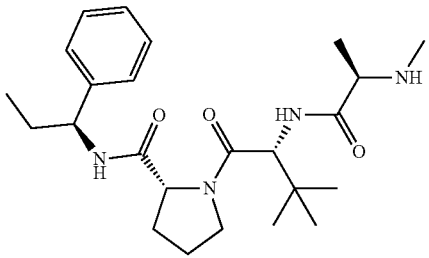
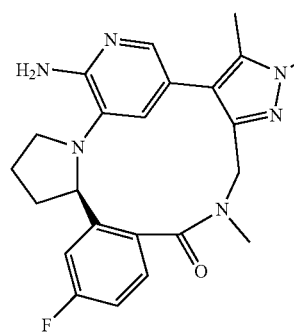
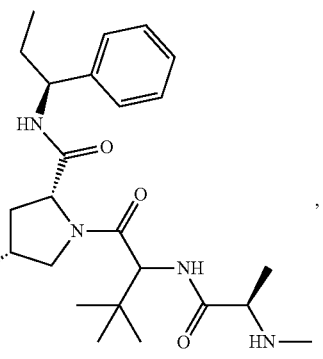
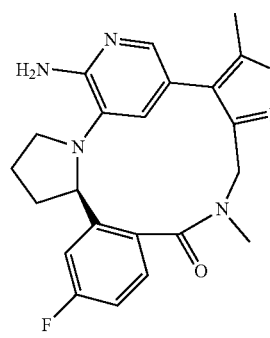
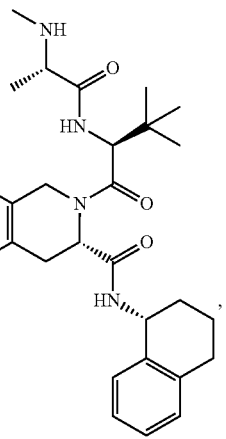
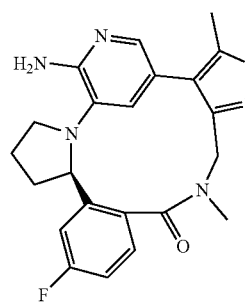

315
316
-continued
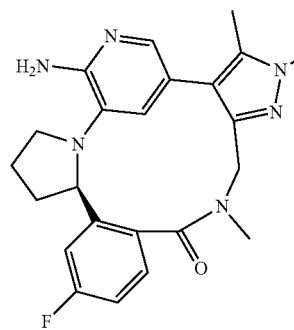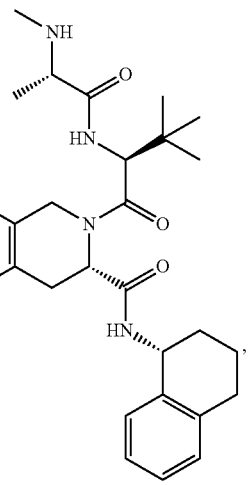
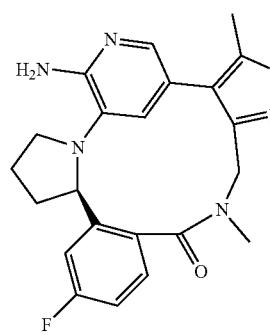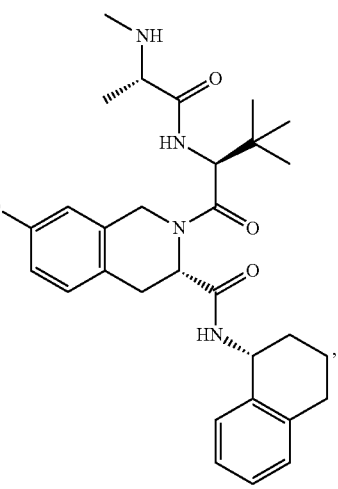
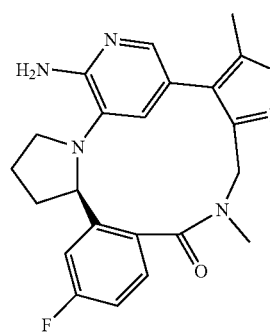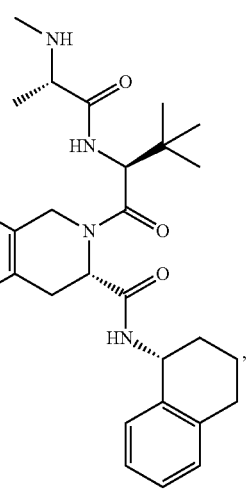

317
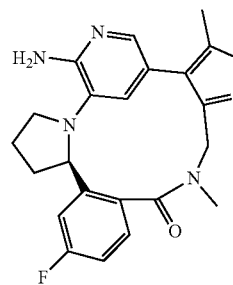
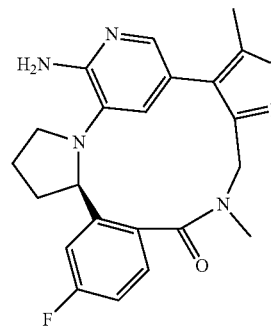
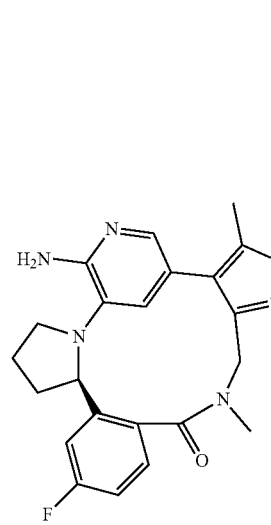
318
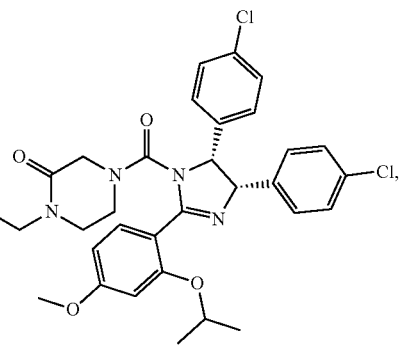
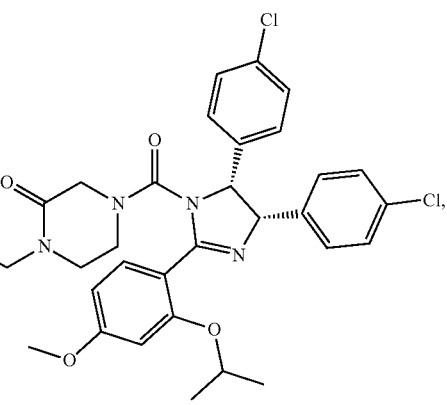
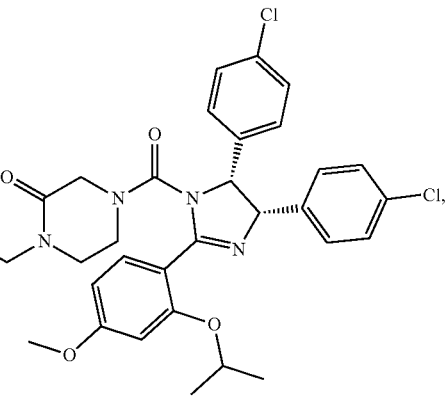

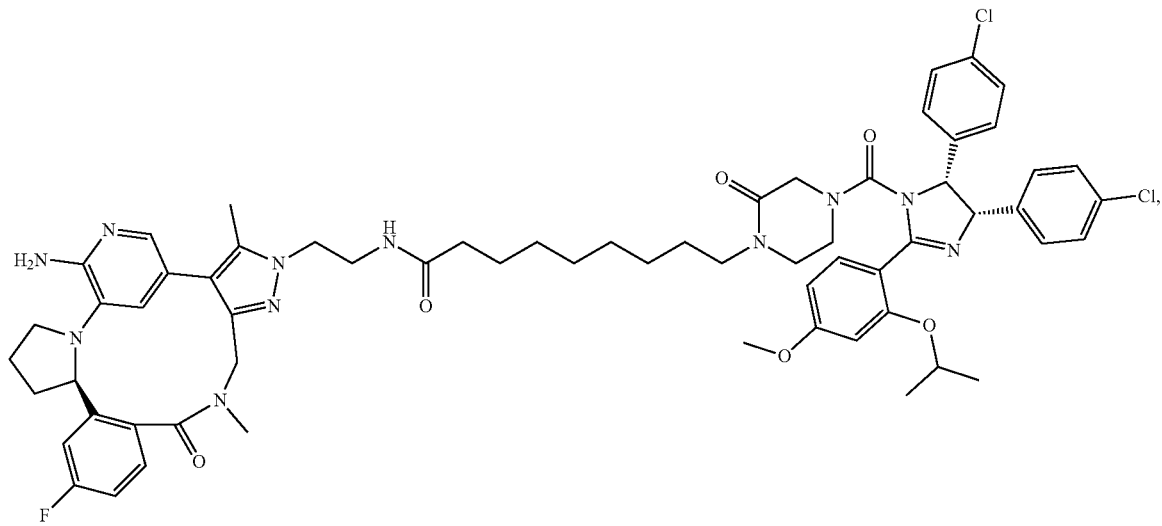
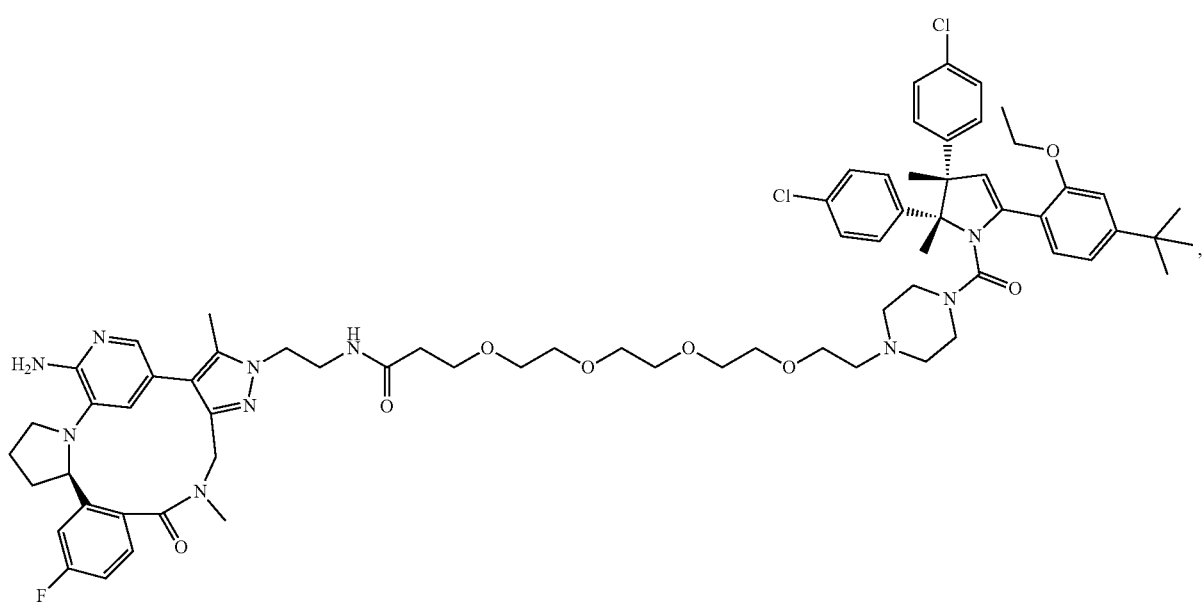

321
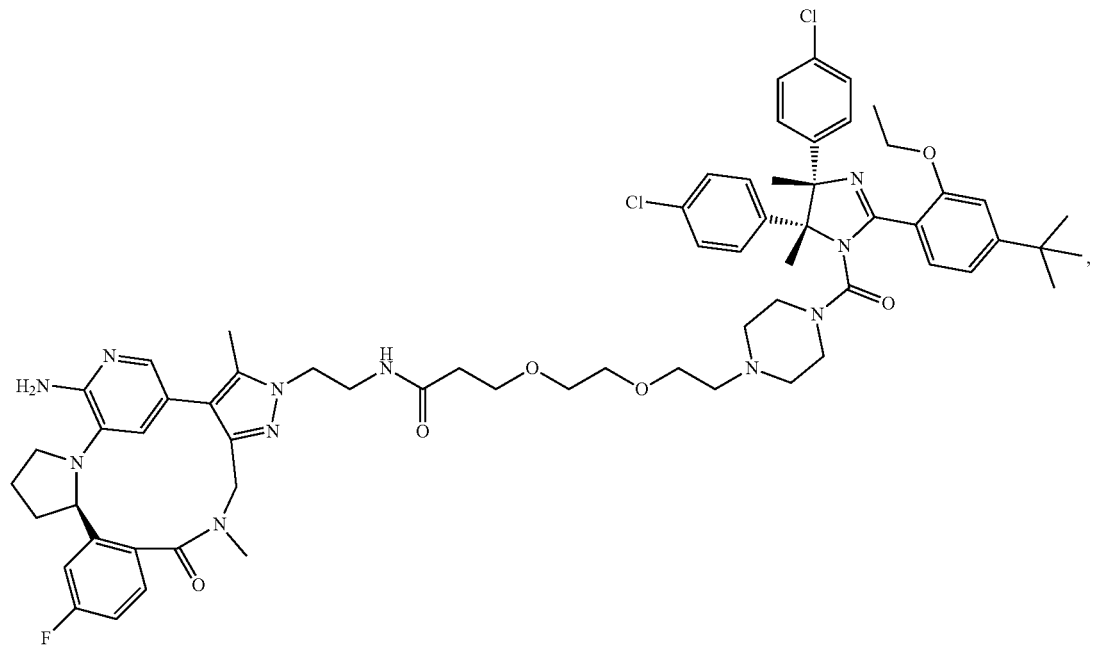
322
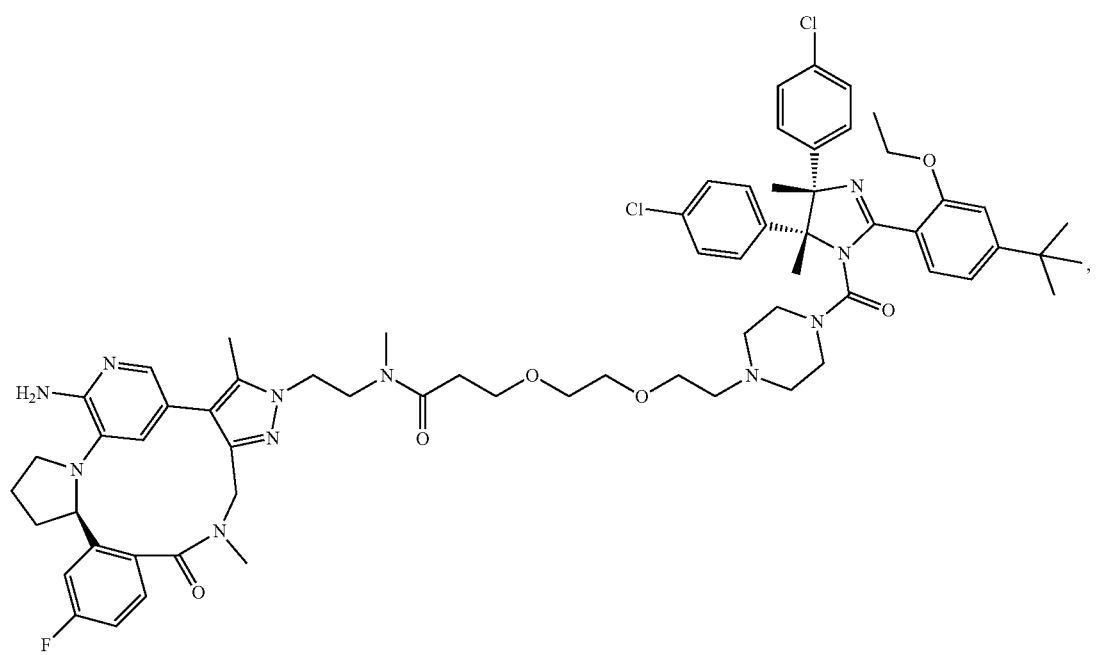

323
324
-continued
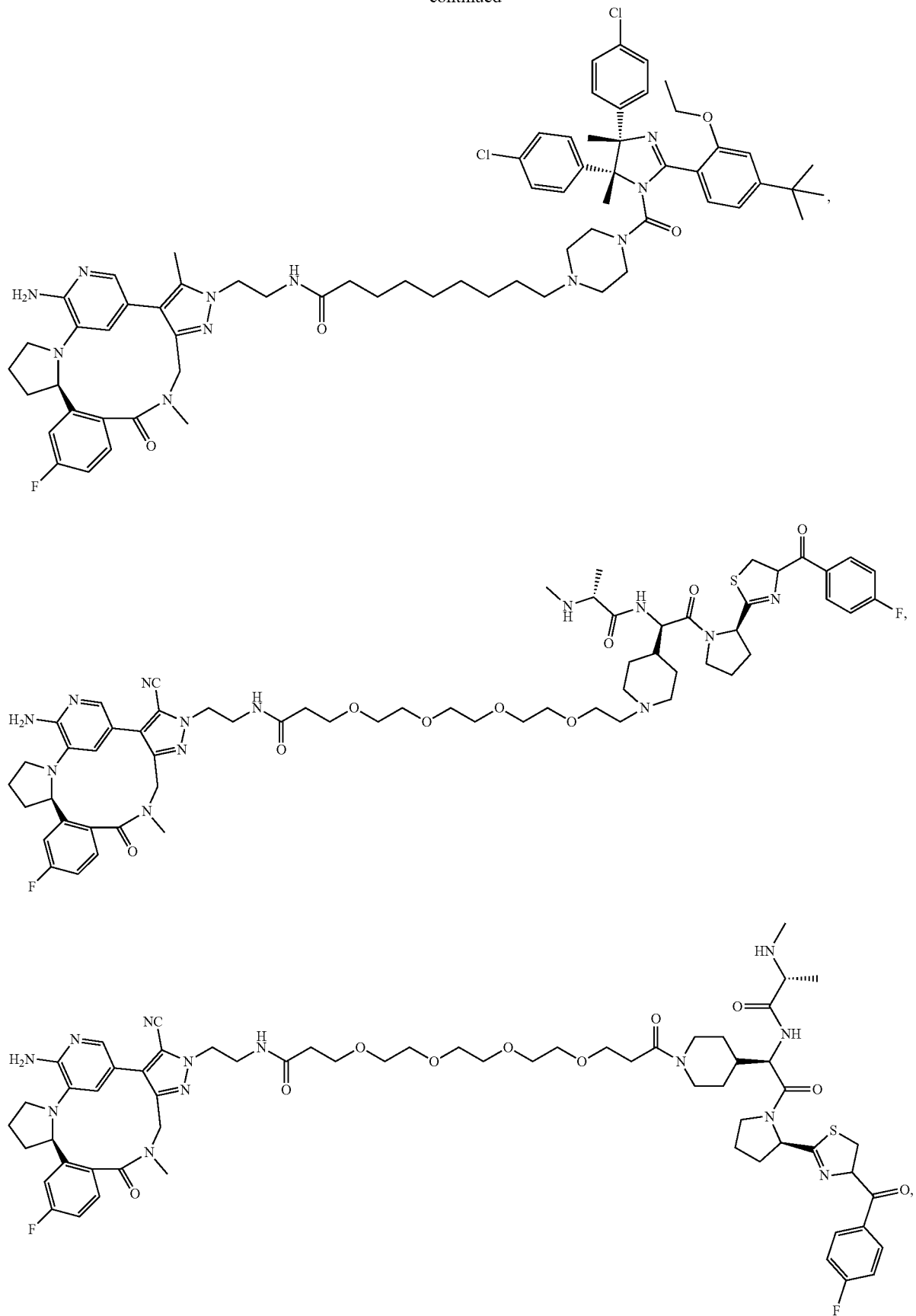

325
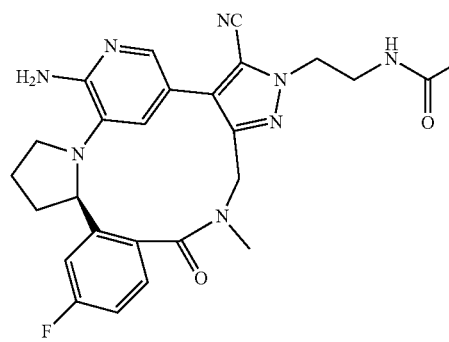
-continued
326
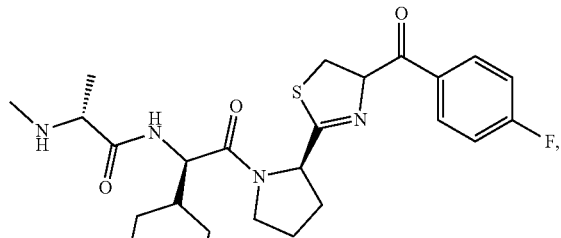
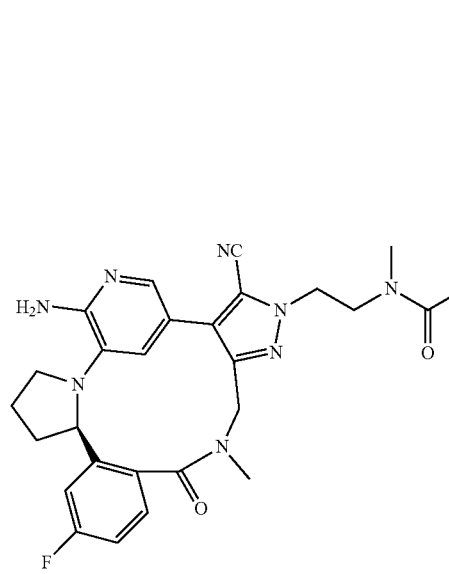
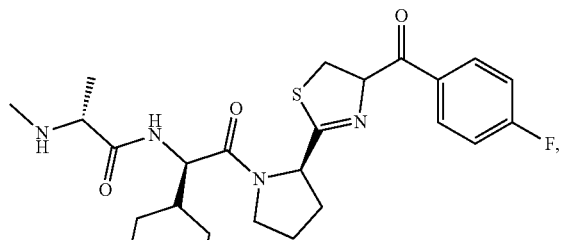

327
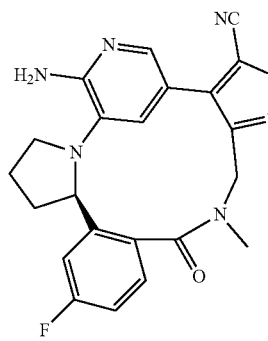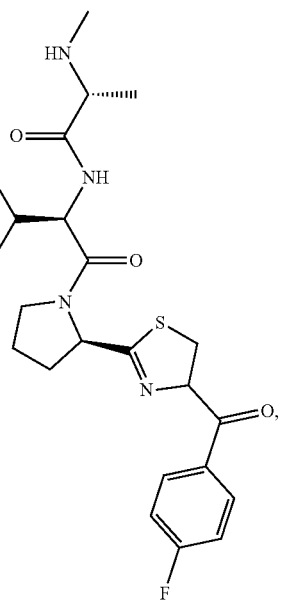
328
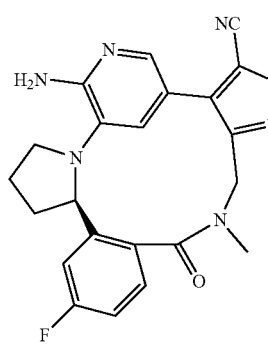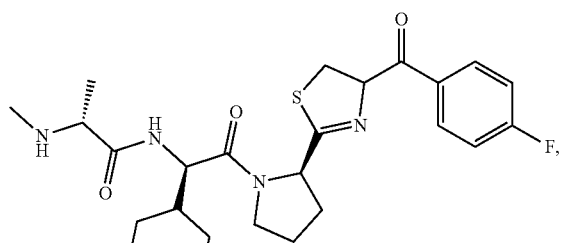

329
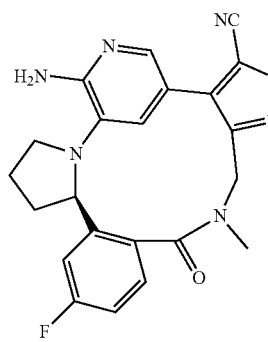
330
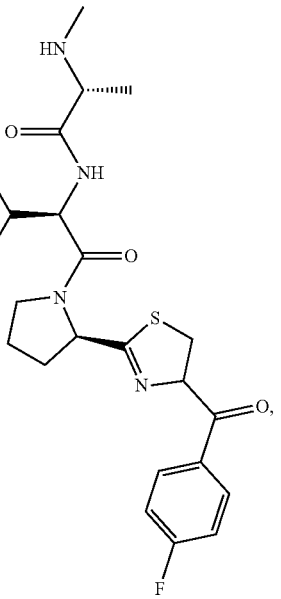
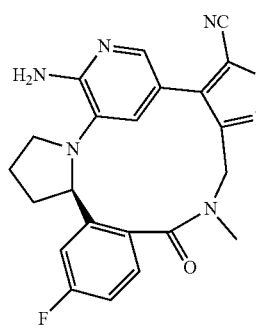
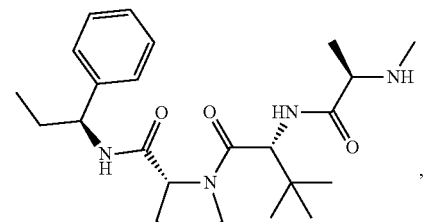
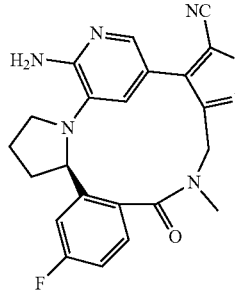
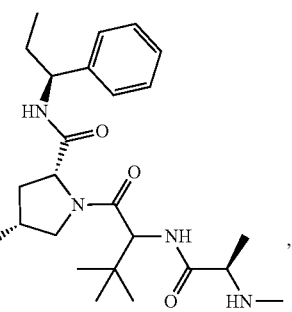

331 332
-continued
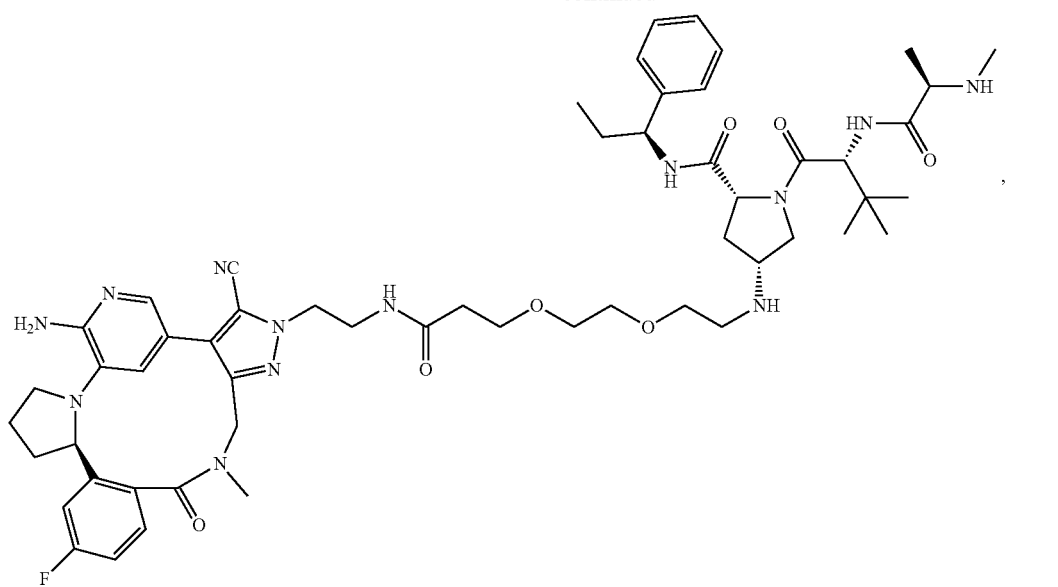
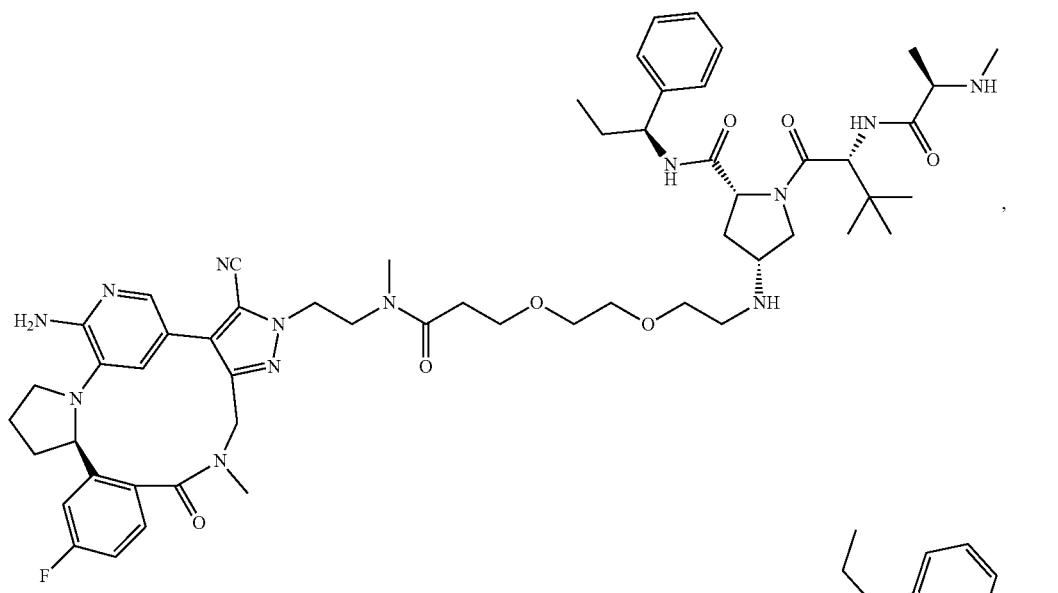
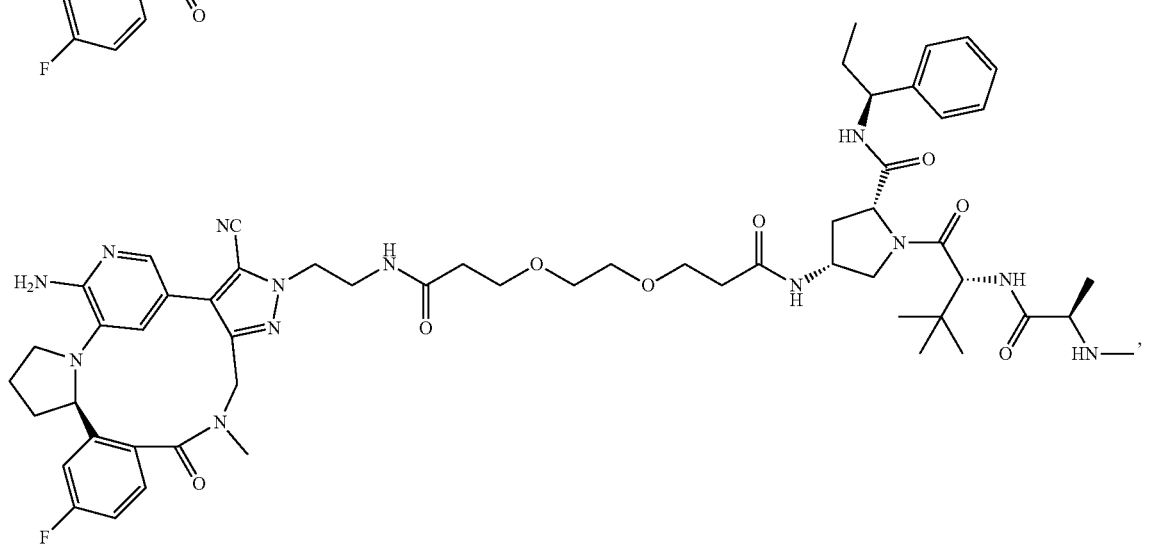

-continued
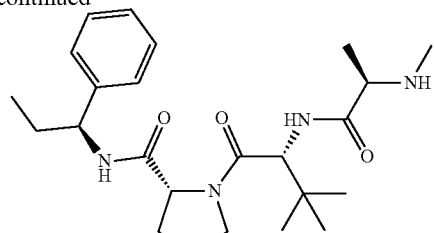
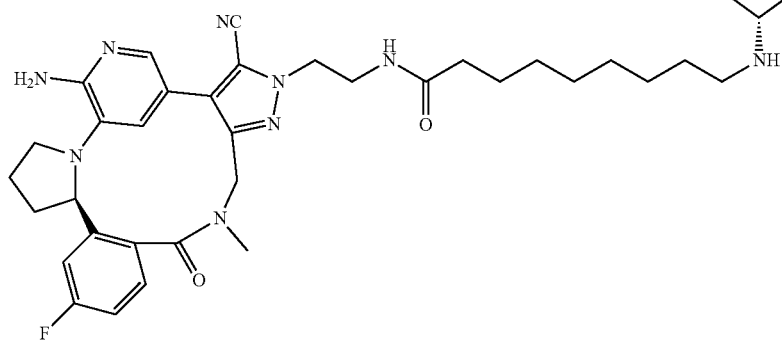
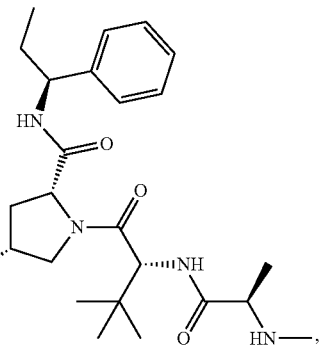
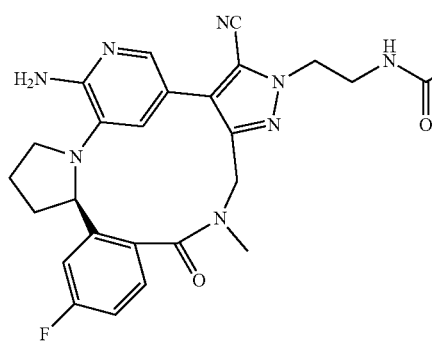
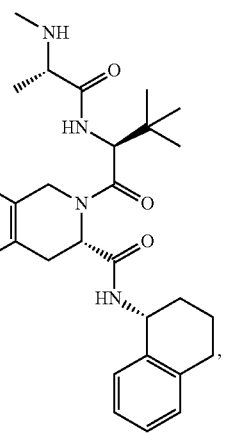
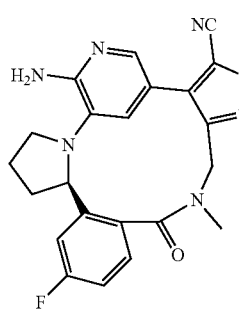

-continued
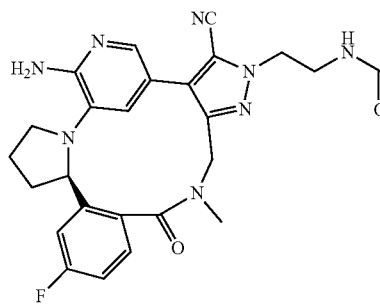 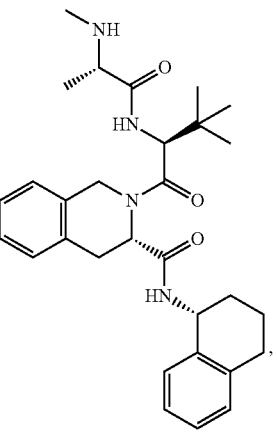
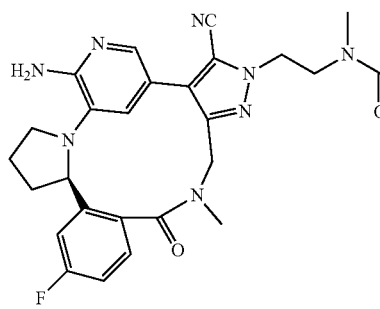 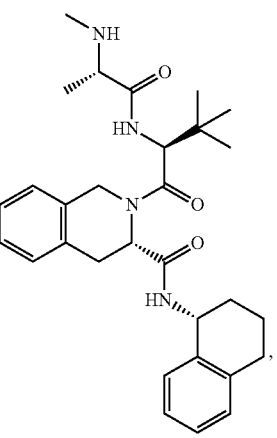
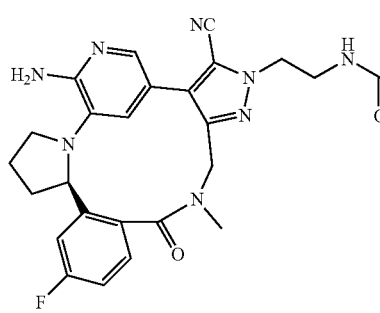 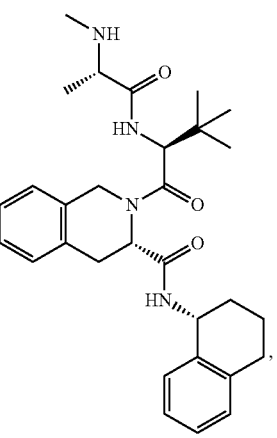

337
338
-continued
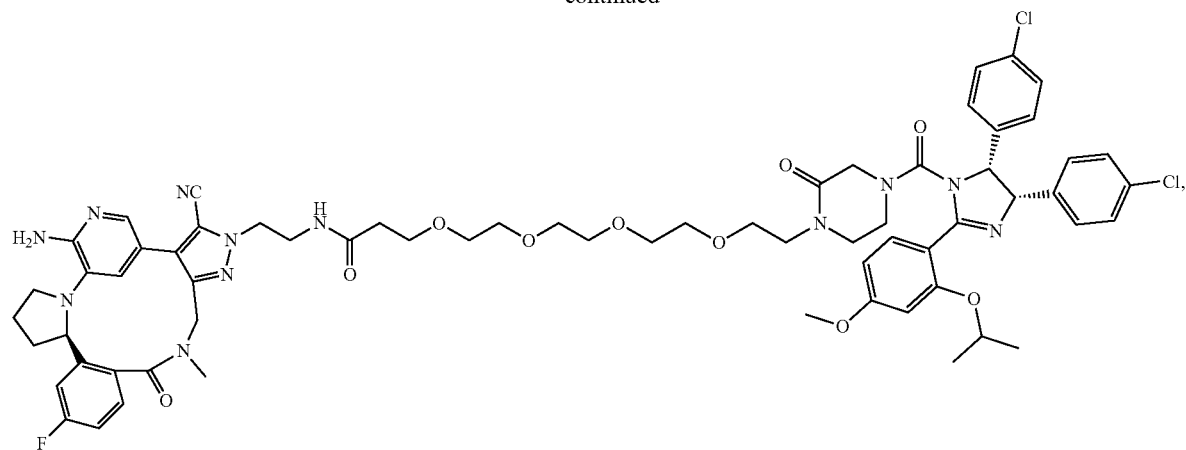
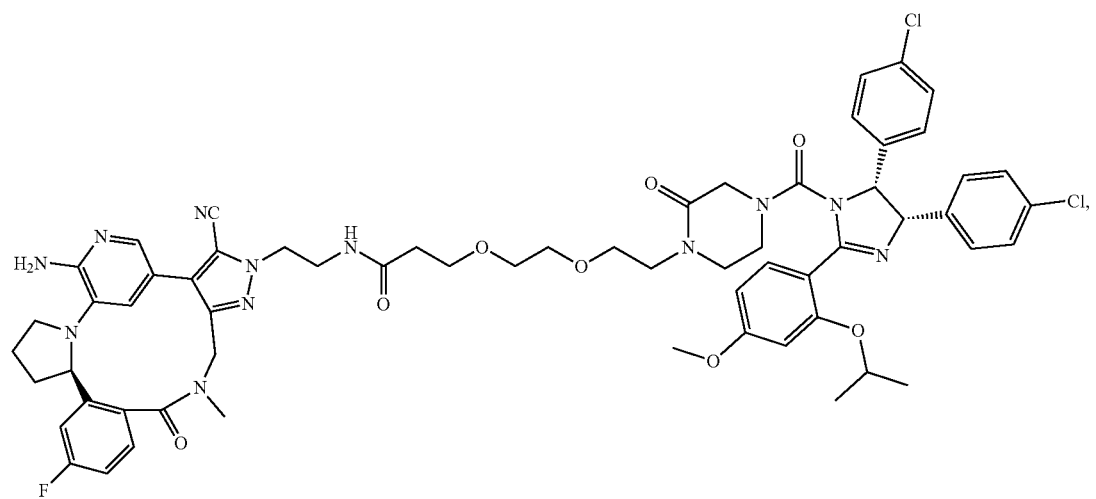
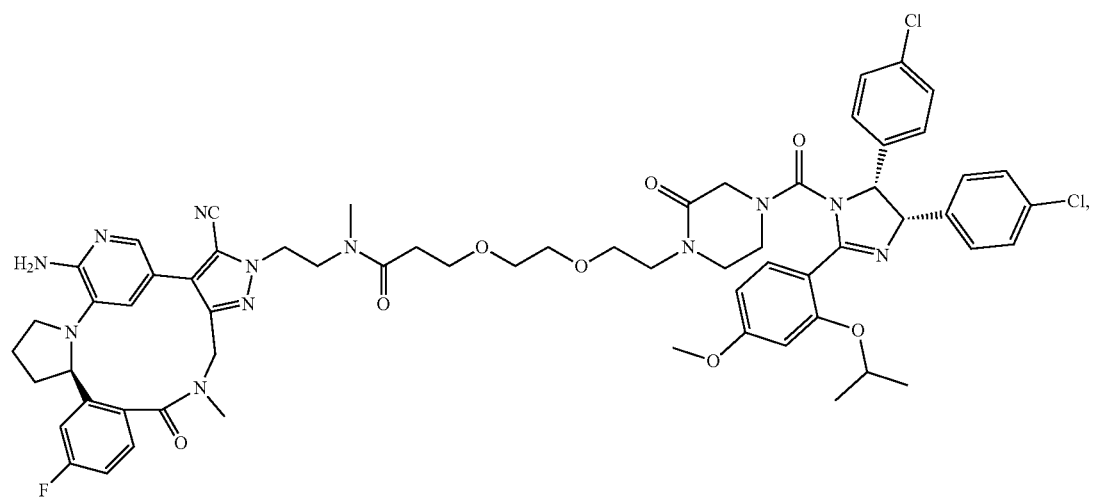

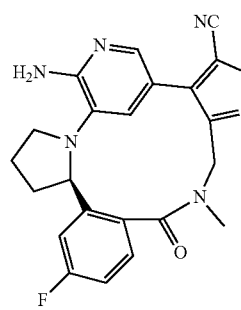
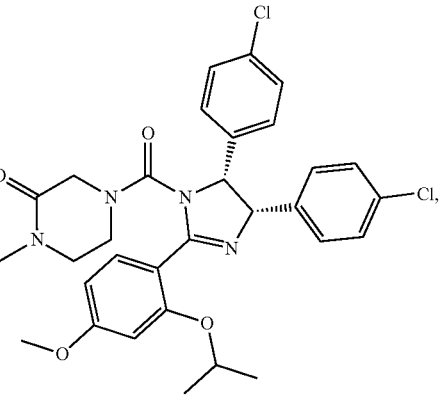
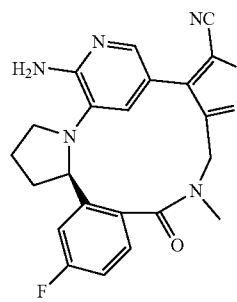
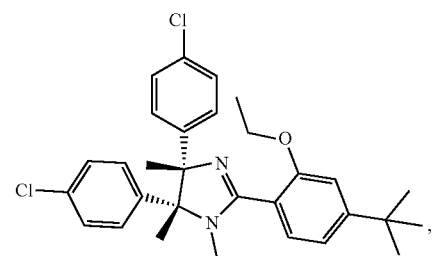
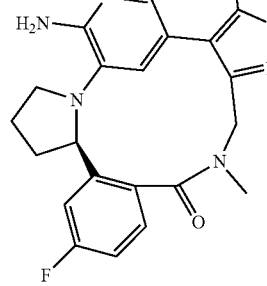
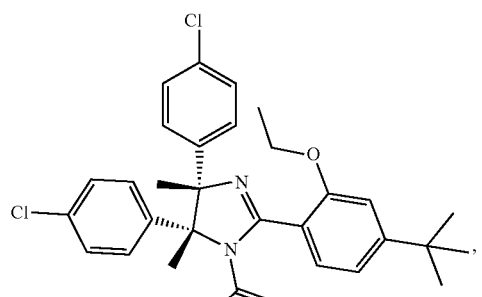

341
342
-continued
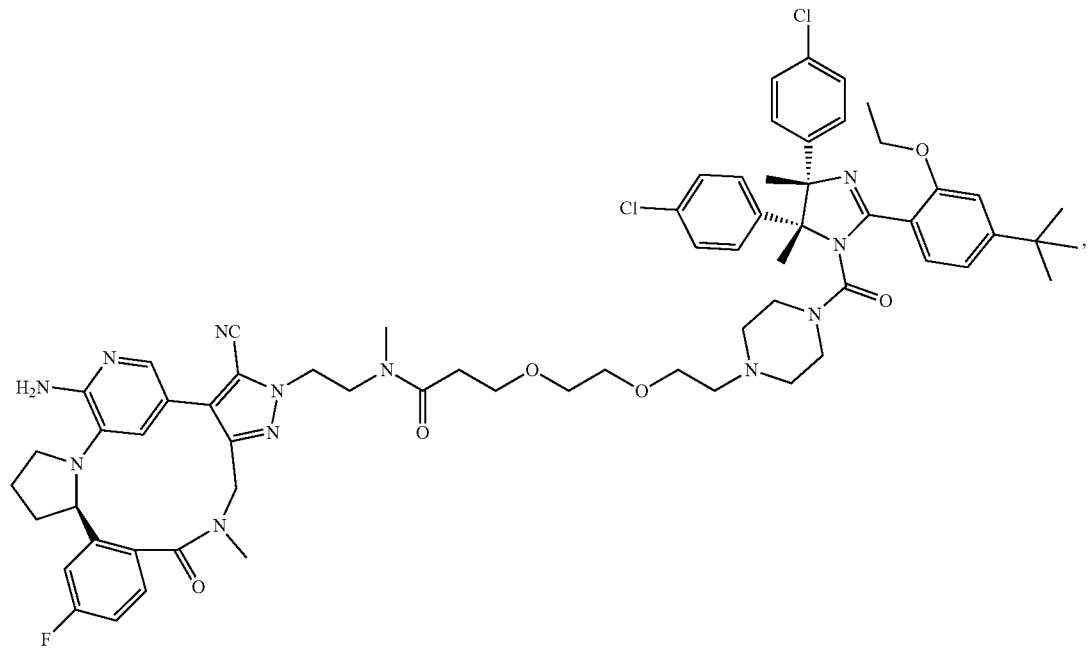
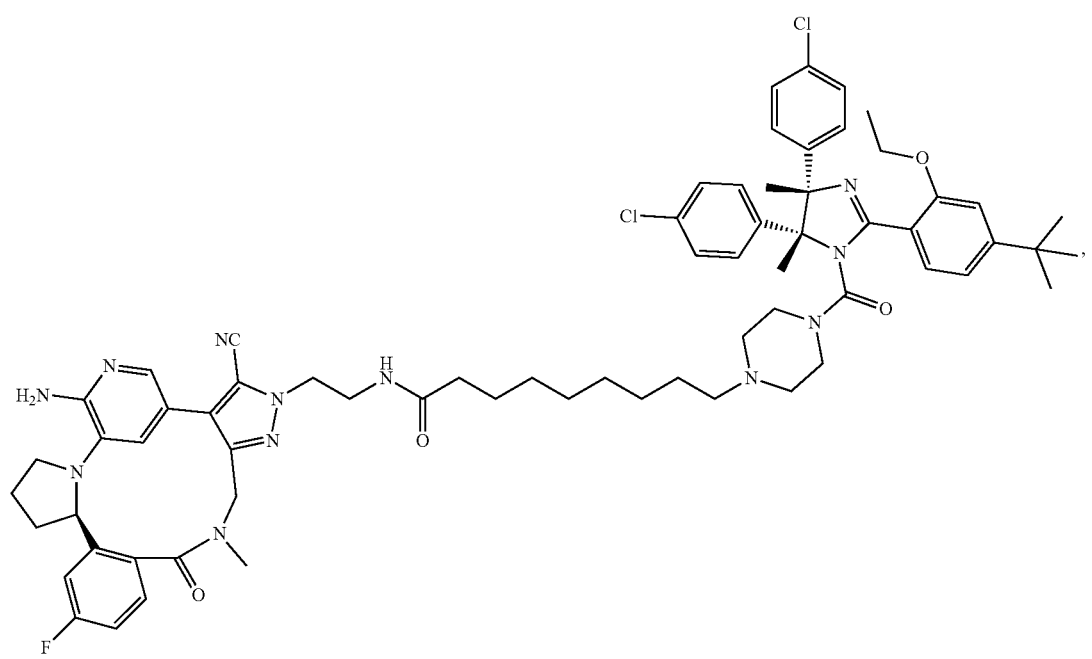

343
344
-continued
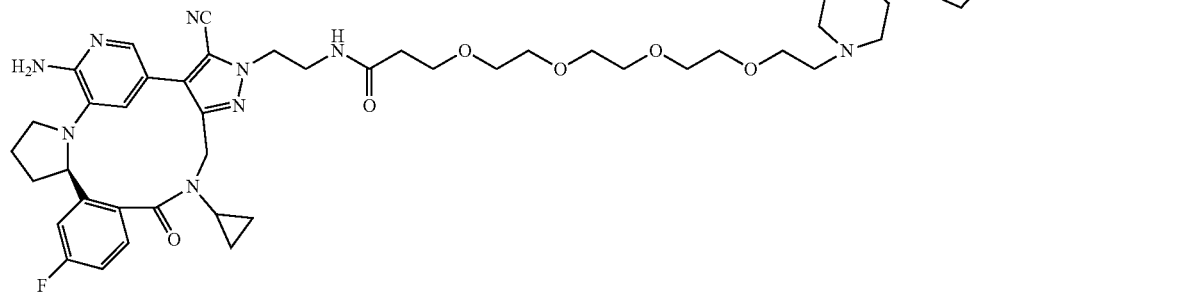
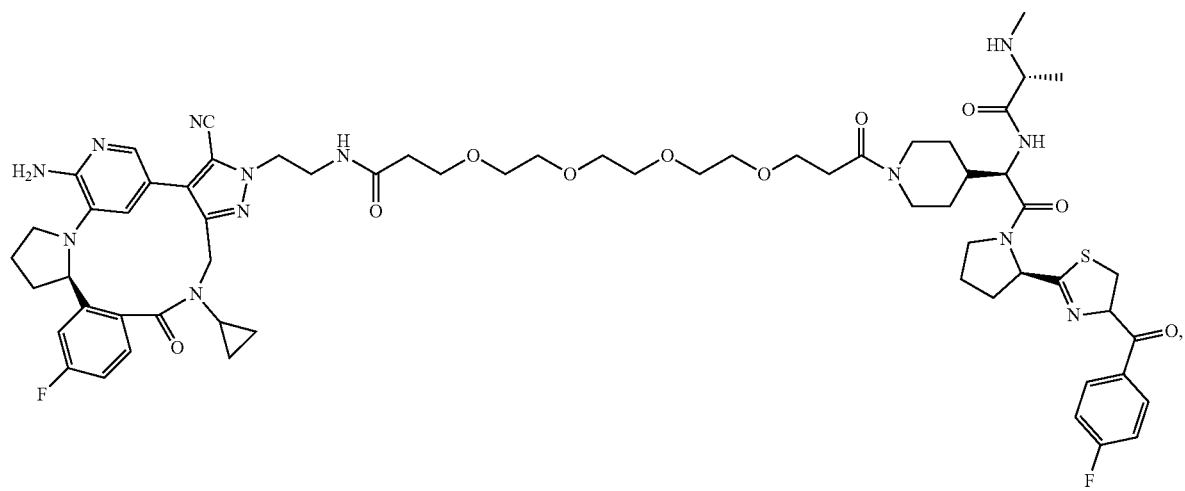
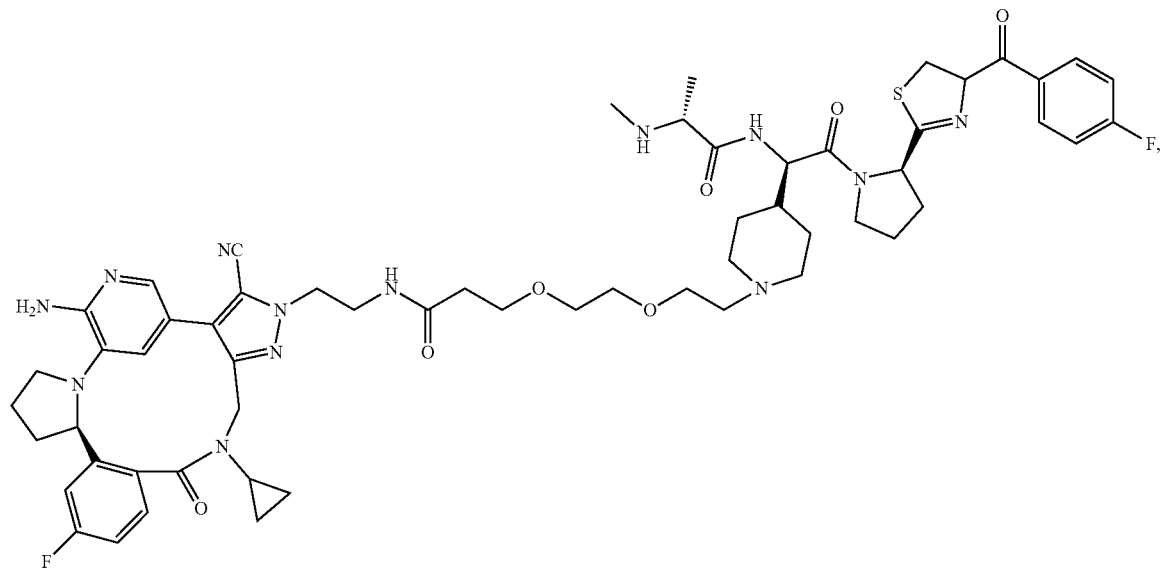

345
346
-continued
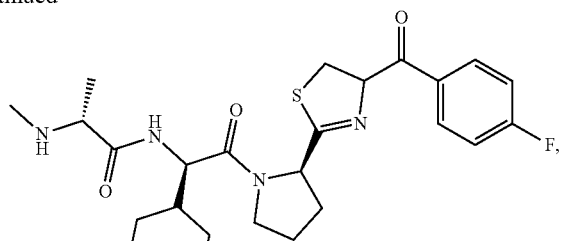
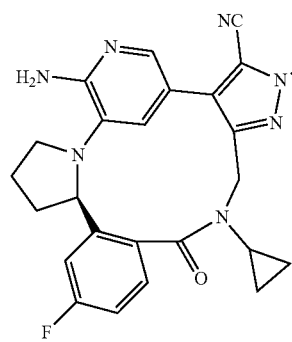
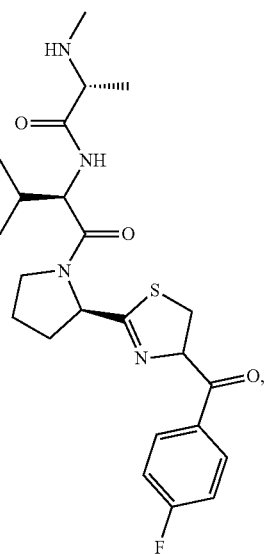
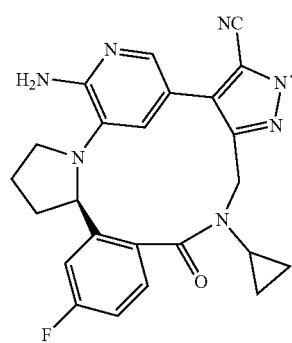
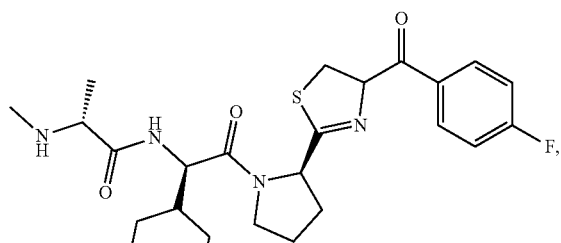
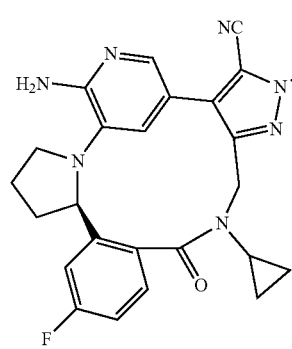

347 348
-continued
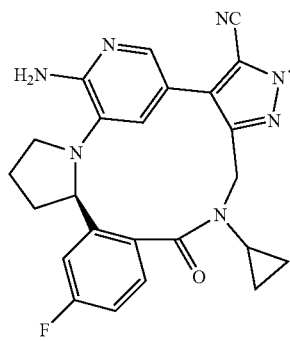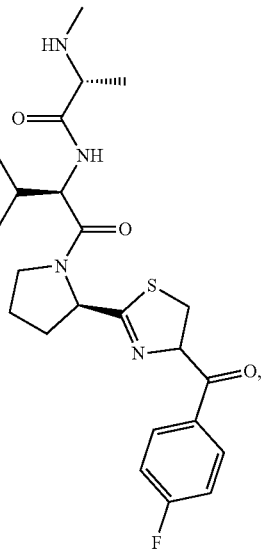
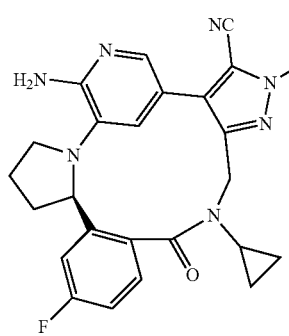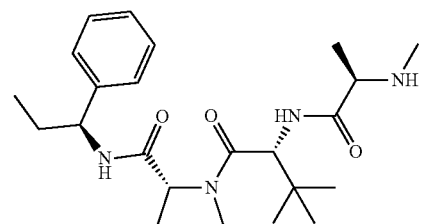
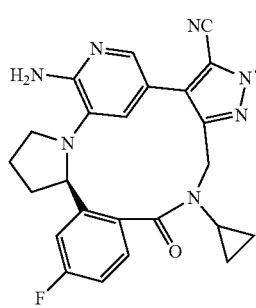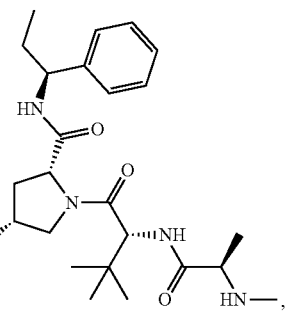

-continued
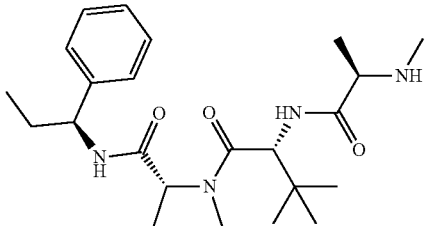
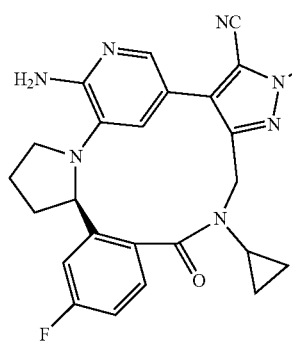
,
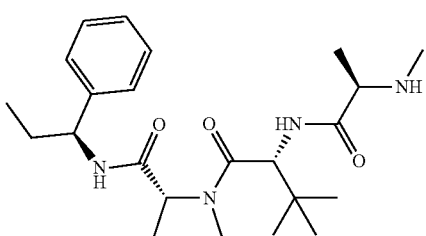
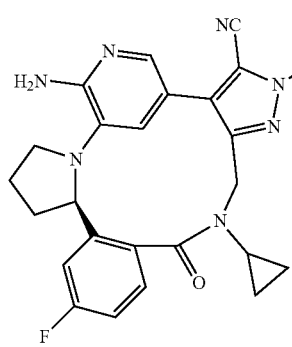
,
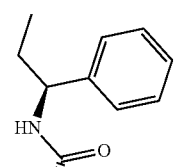
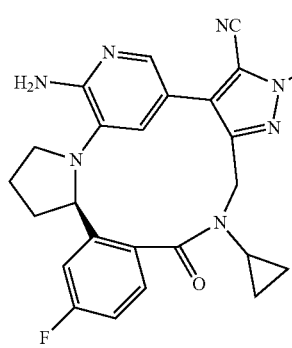
, -continued
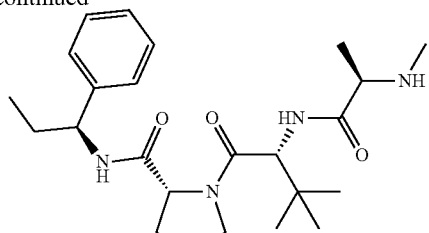
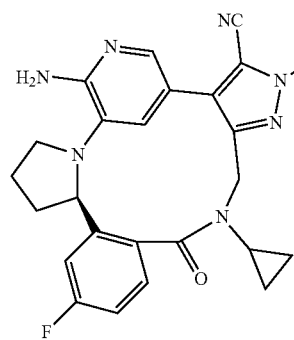
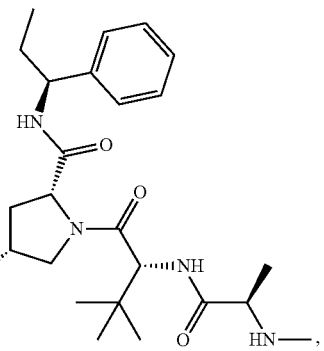
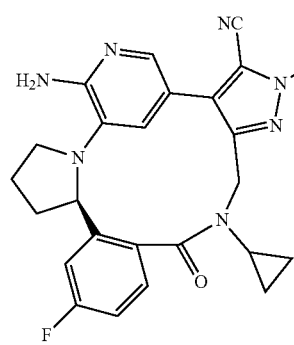
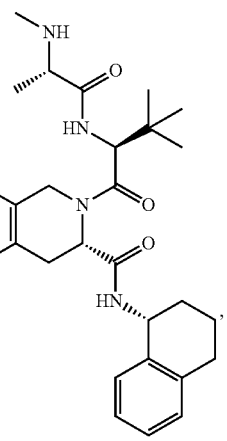
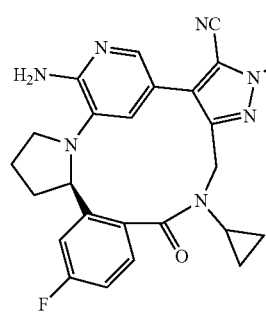

353
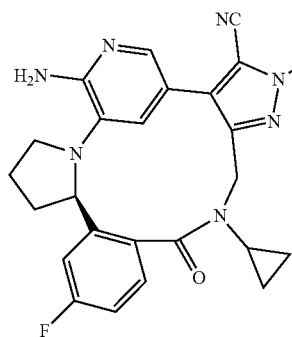
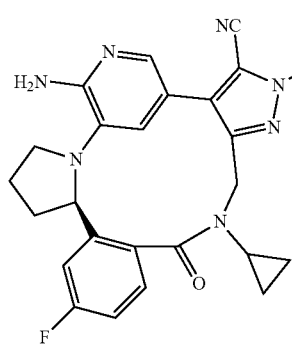
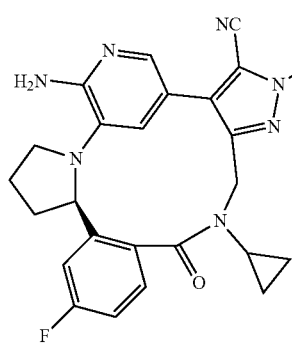
-continued
354
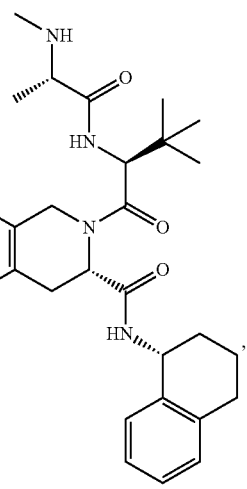
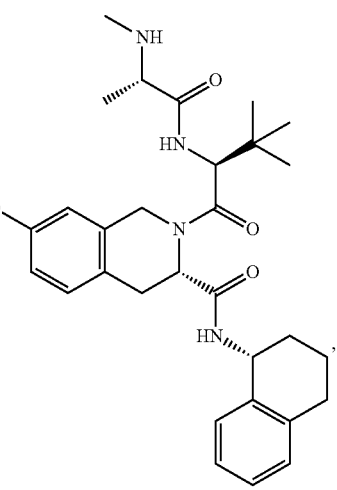
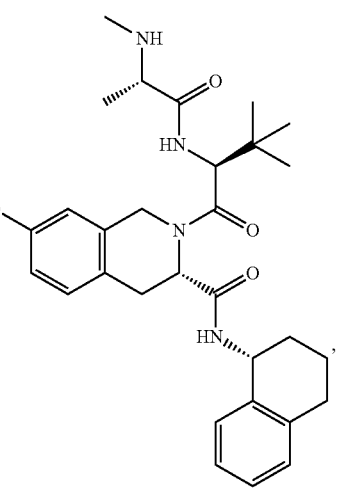

355 356
-continued
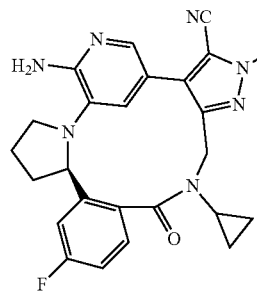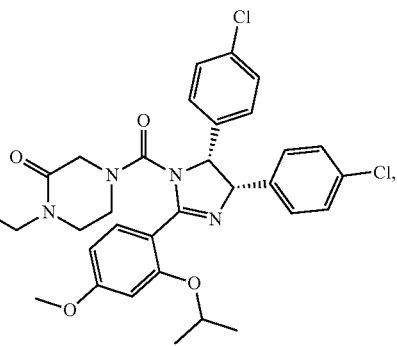
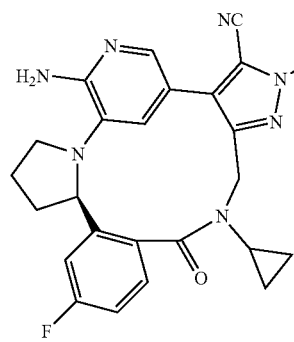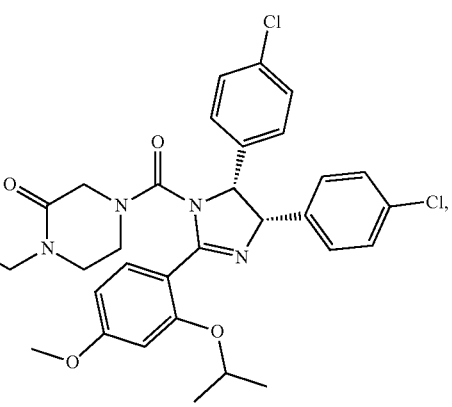
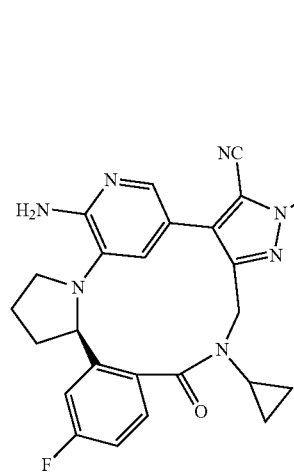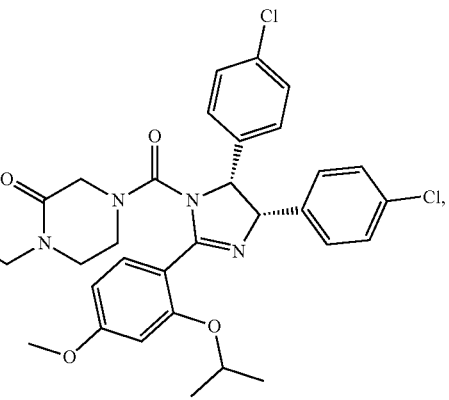

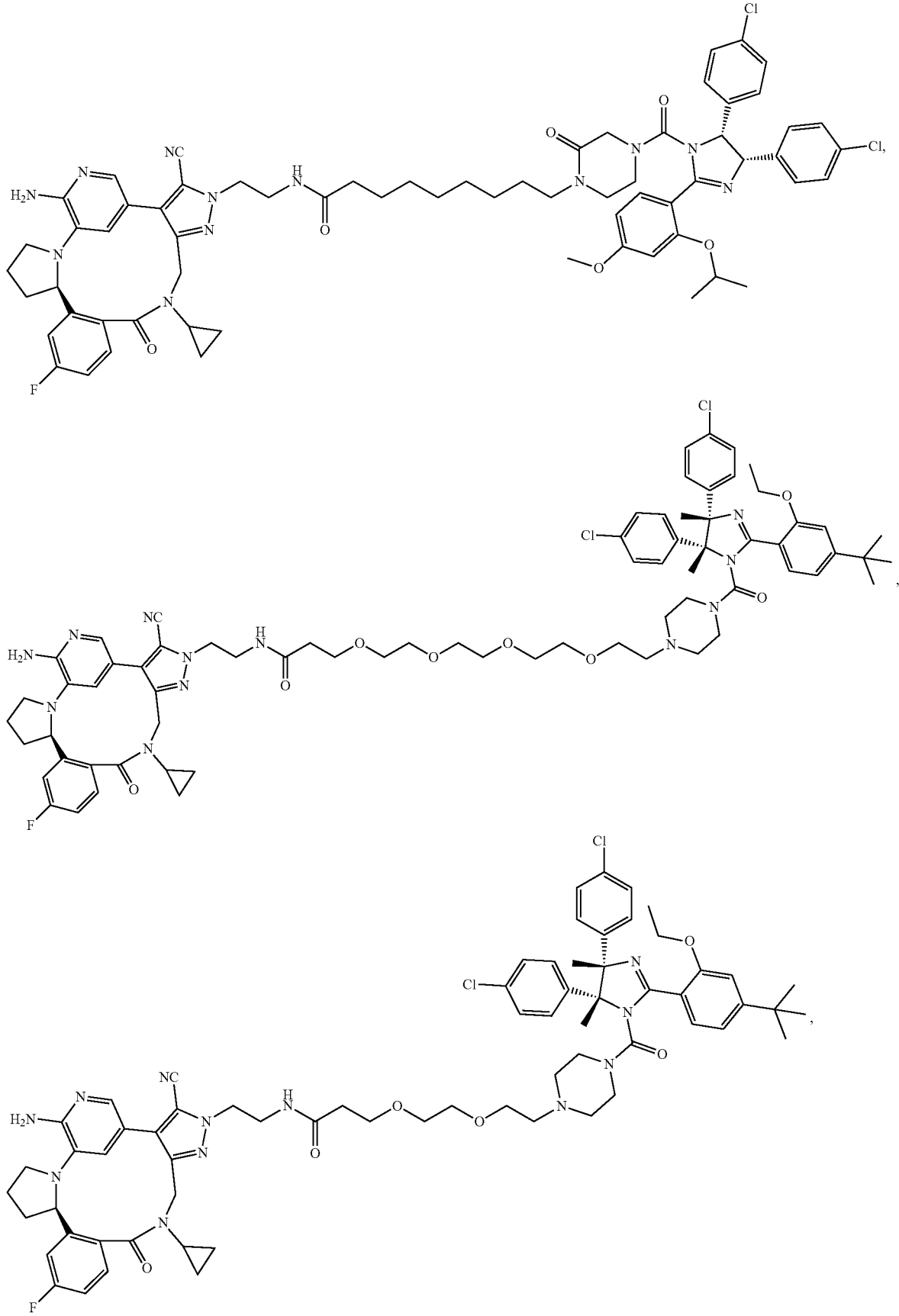

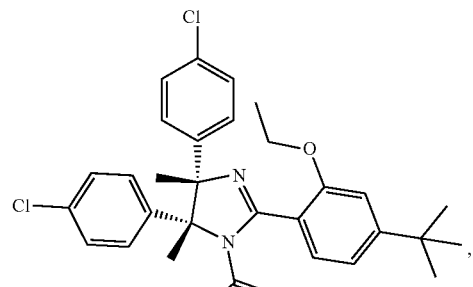
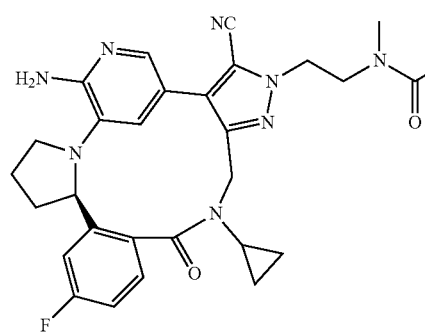
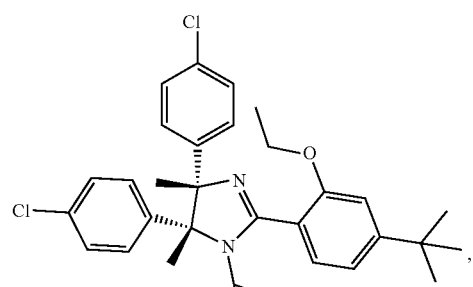
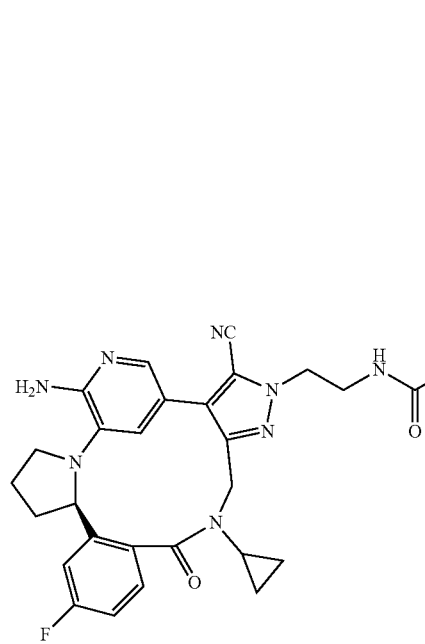

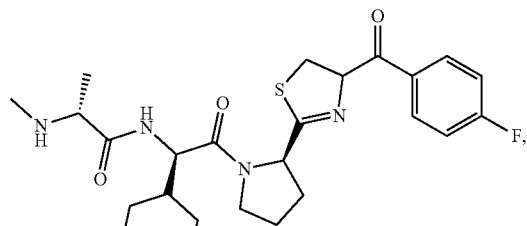
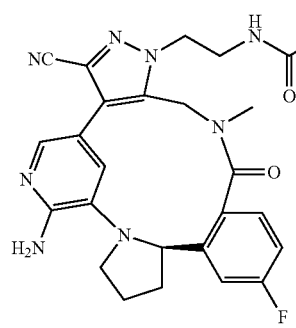
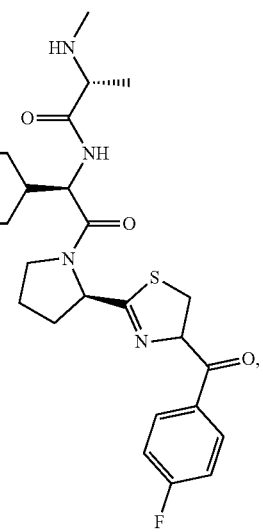
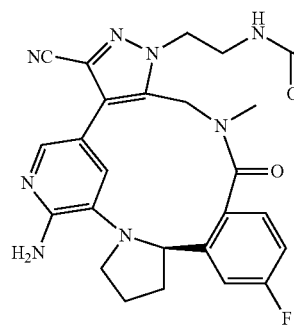
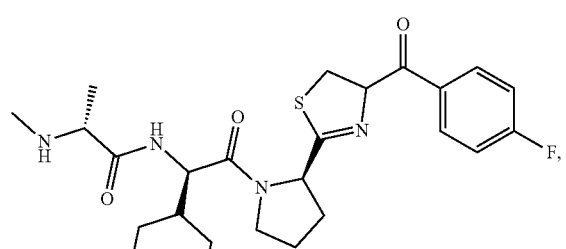
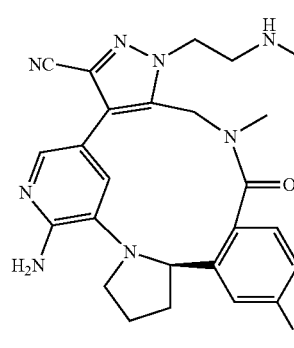

-continued
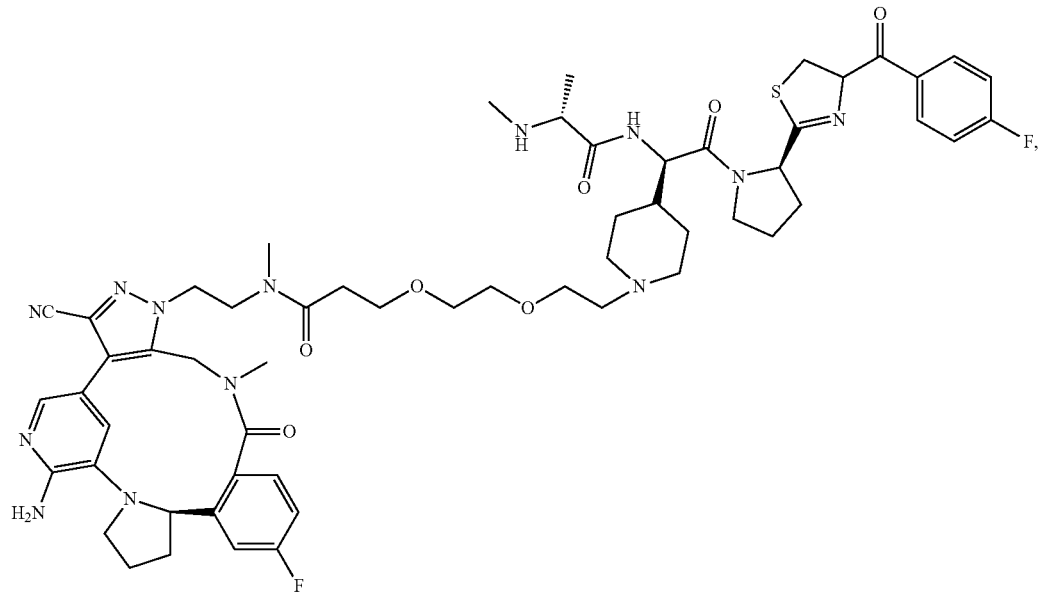
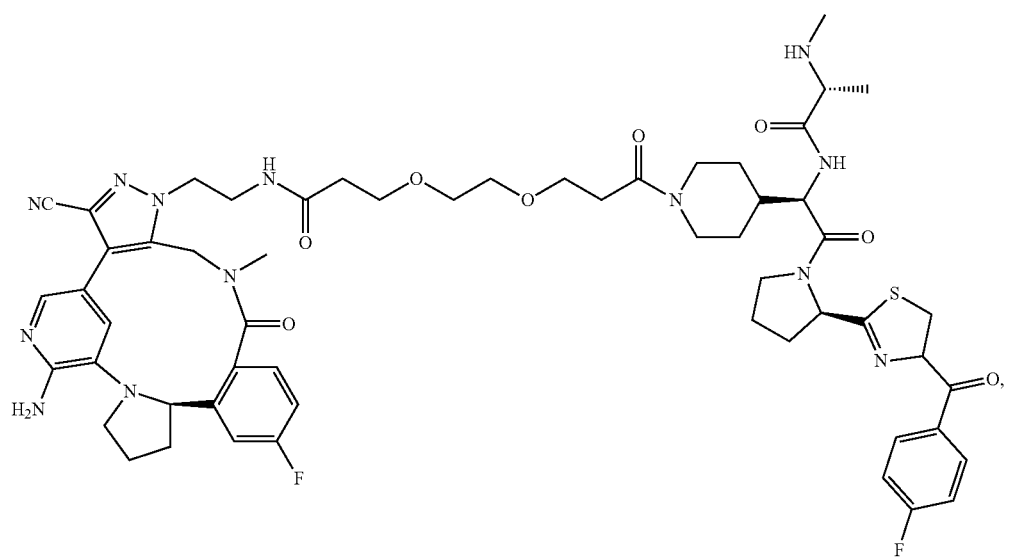

365
366
-continued
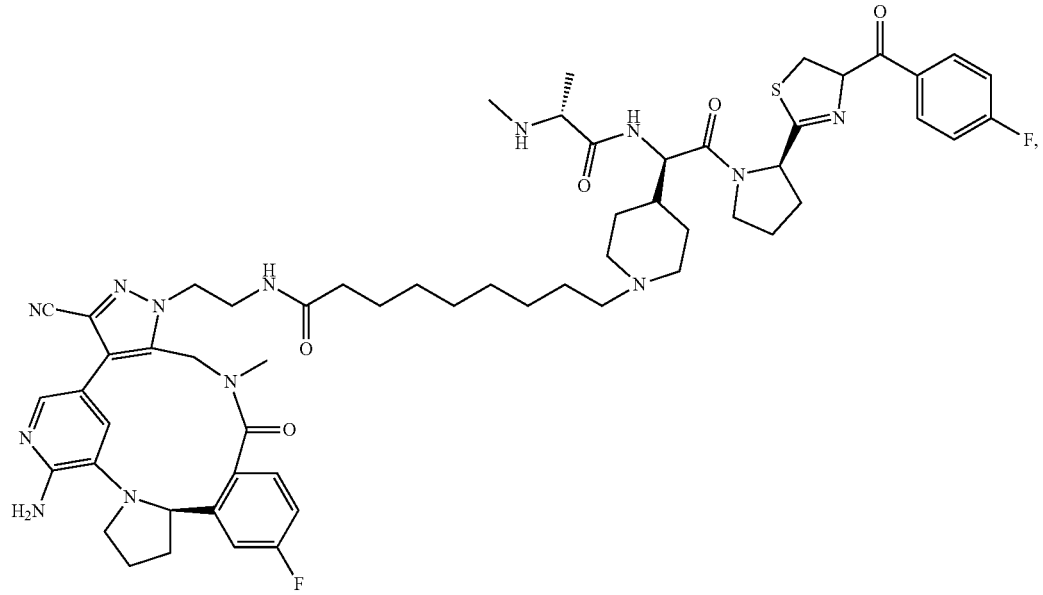
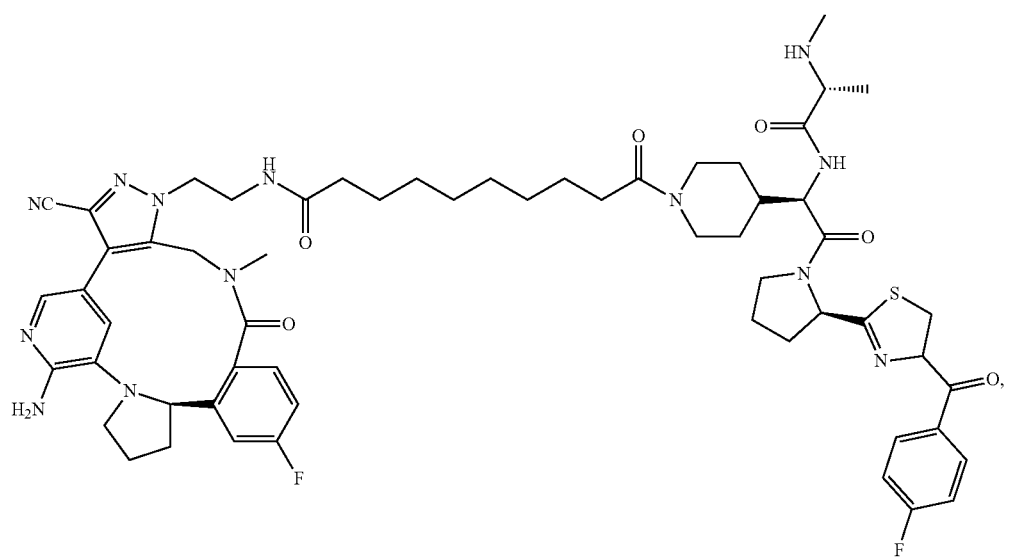

367
368
-continued
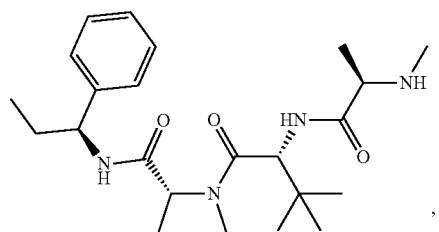
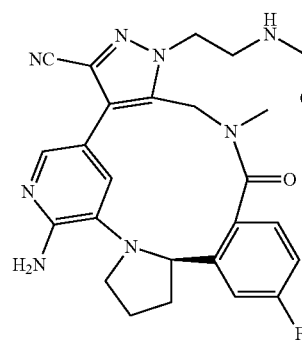
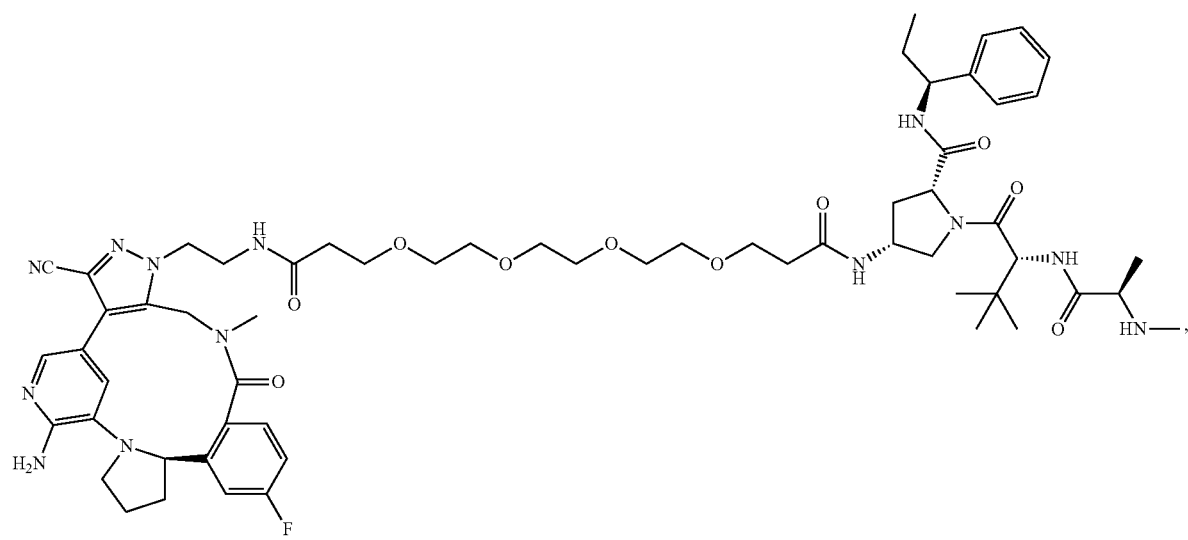

-continued
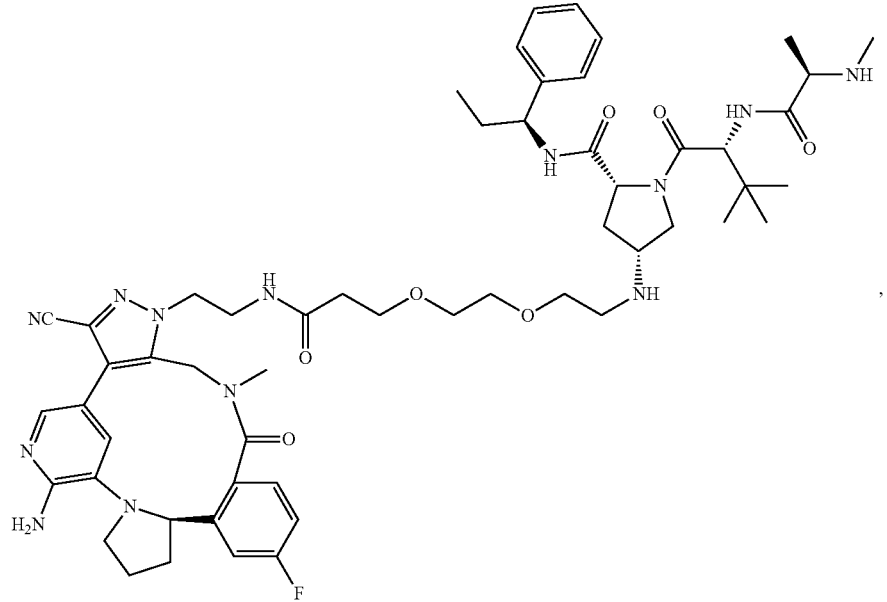
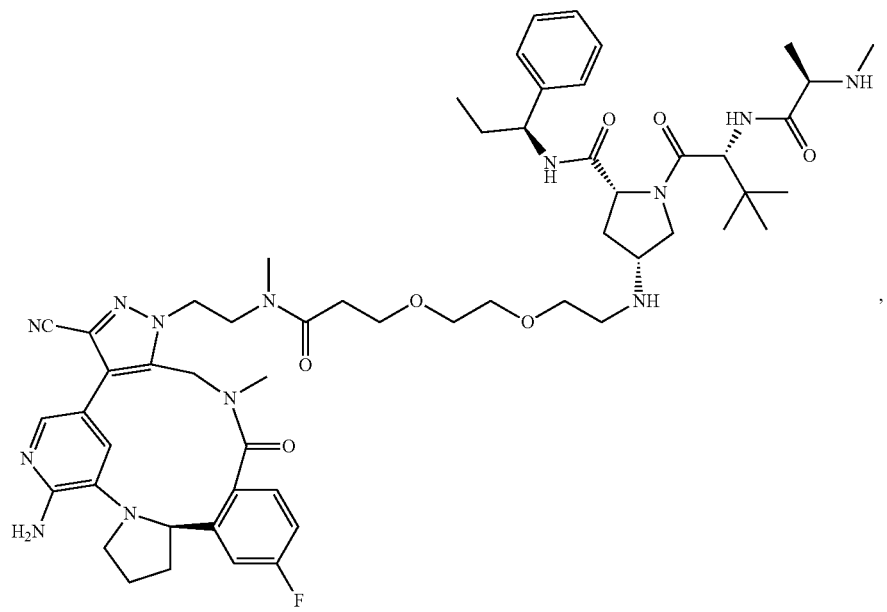

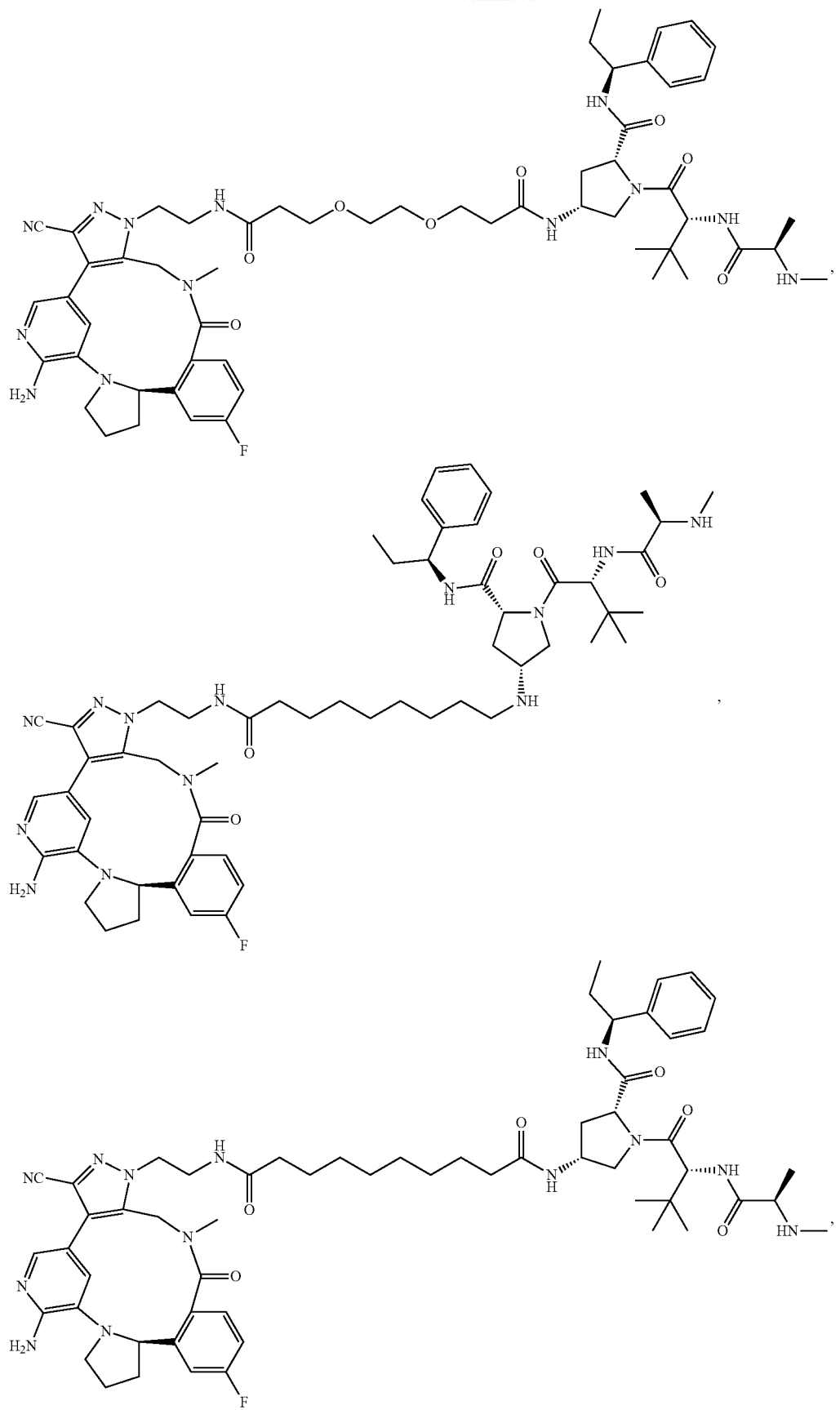

373 374
-continued
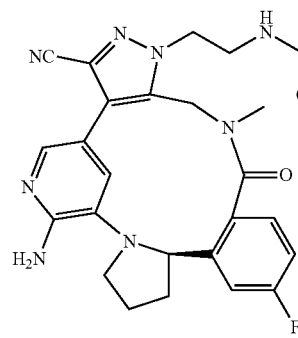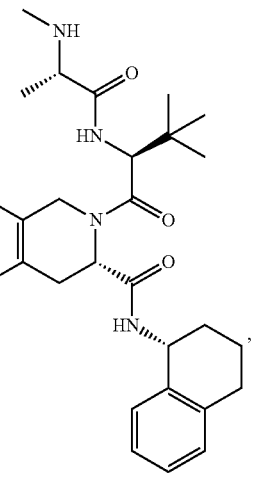
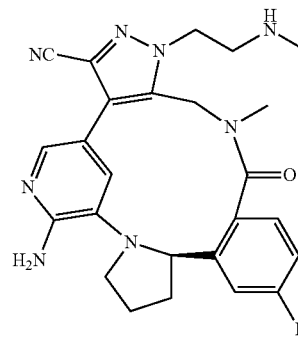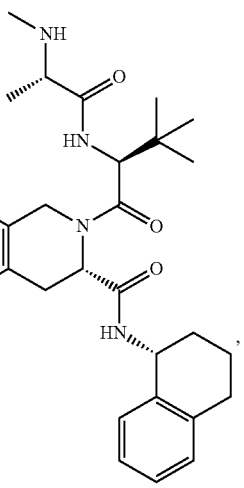
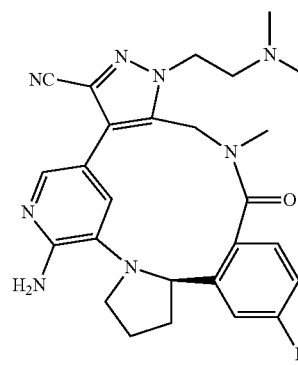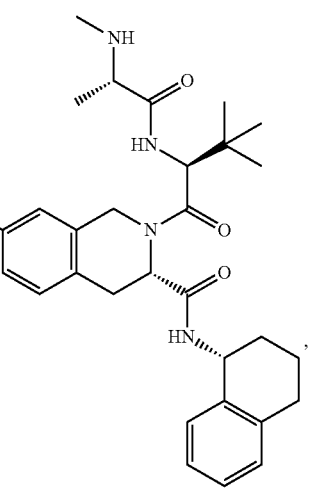

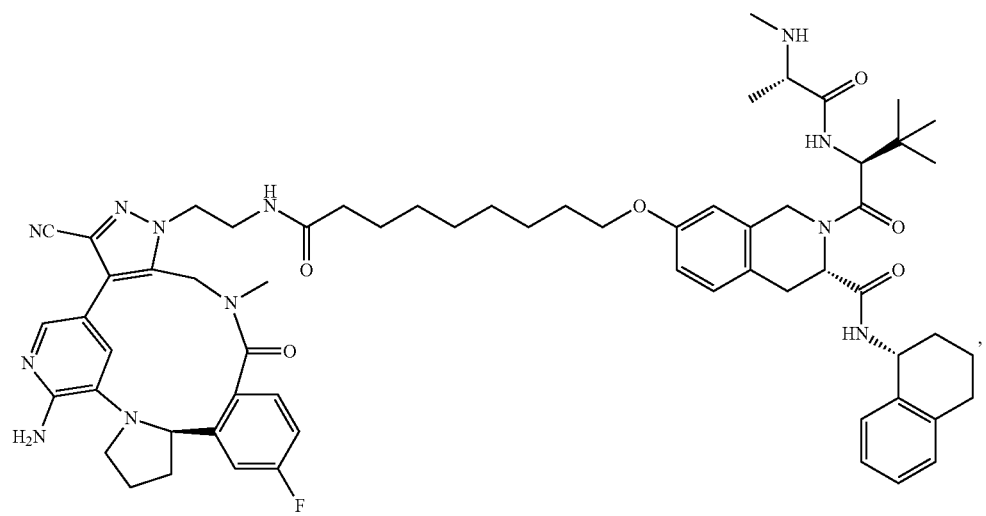 [SMILES: CN[C@@H](C)C(=O)N[C@H](C(=O)N1Cc2cc(OCCCCCCCCC(=O)NCCn3nc(C#N)c4c3CN(C)C(=O)c3ccc(F)cc3[C@H]3CCCN3c3cc-4cnc3N)ccc2C[C@H]1C(=O)N[C@@H]1CCCc2ccccc21)C(C)(C)C]
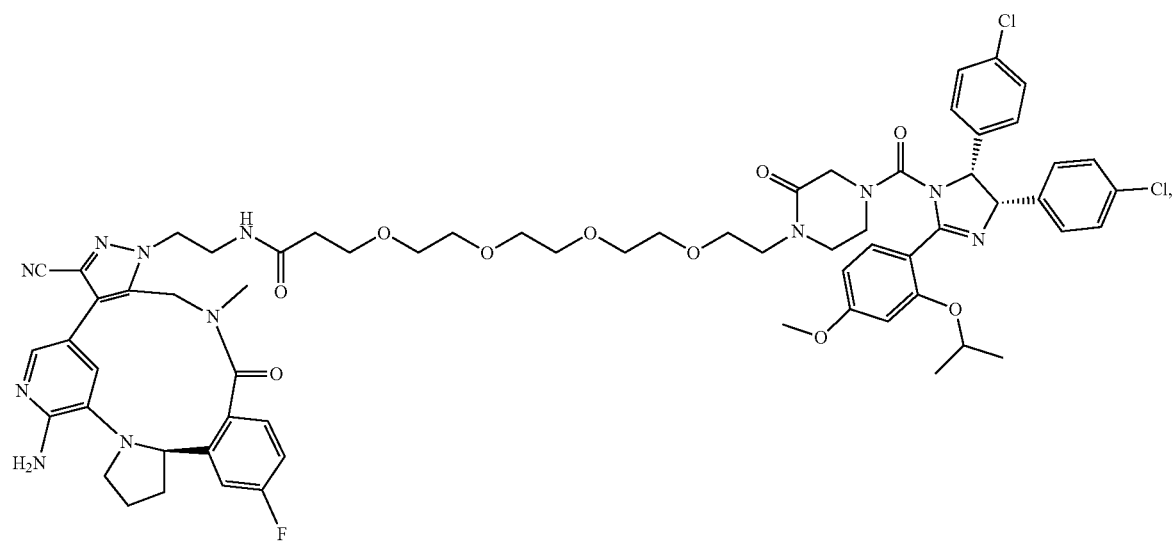
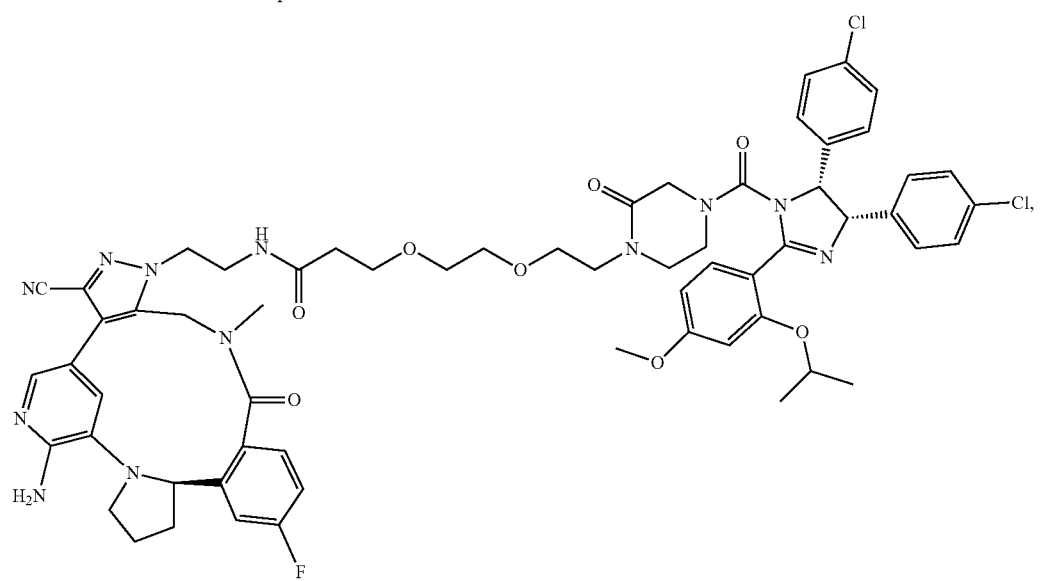

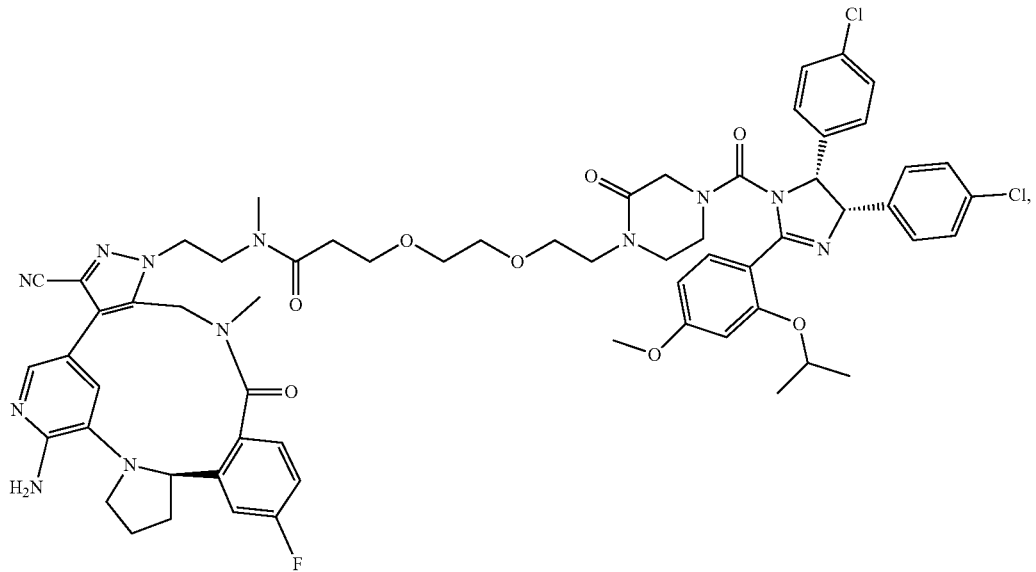
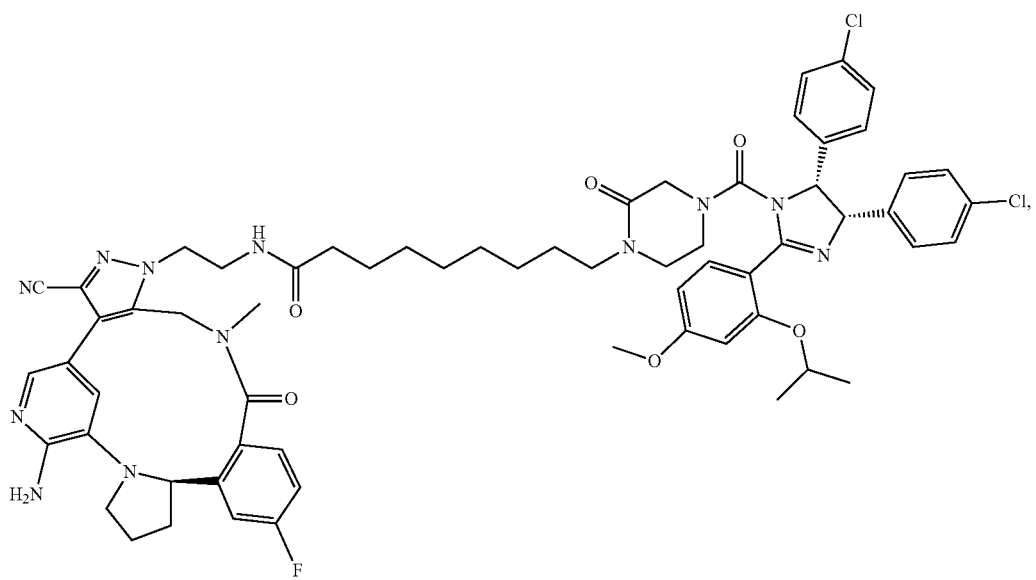

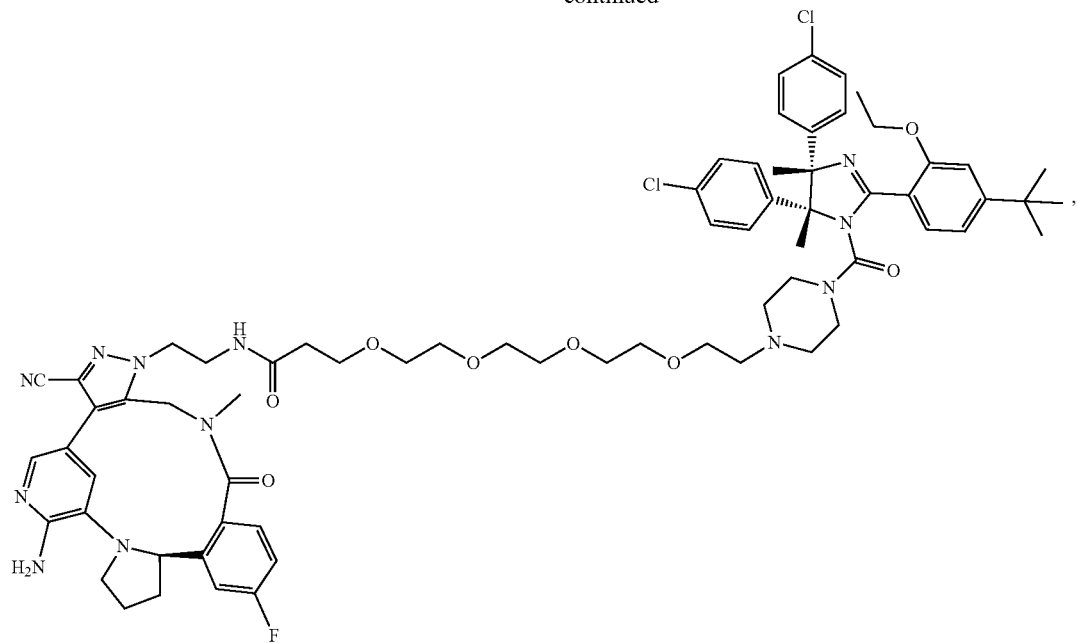
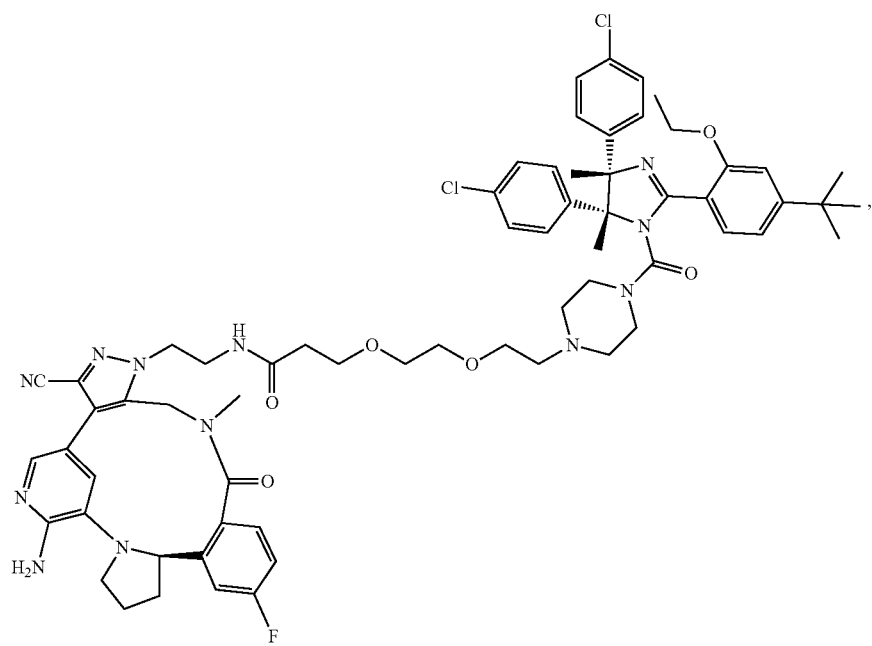

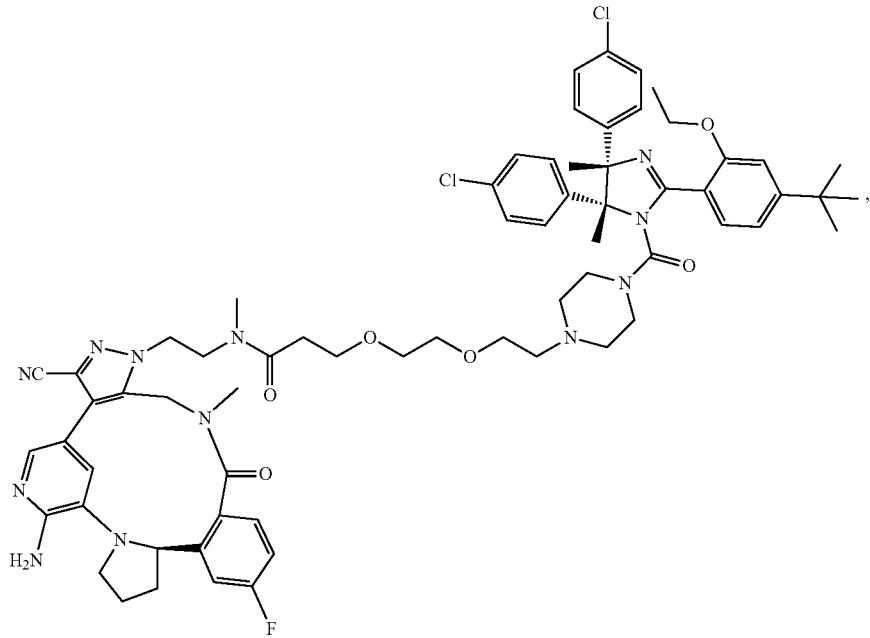
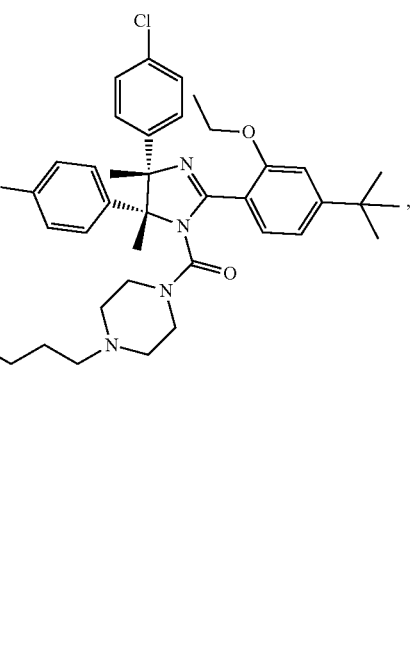

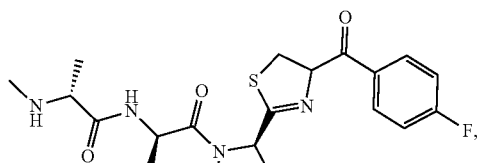
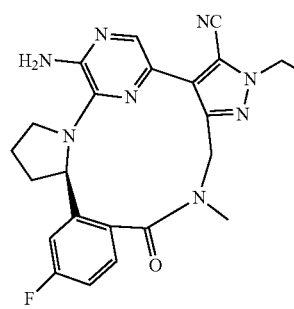
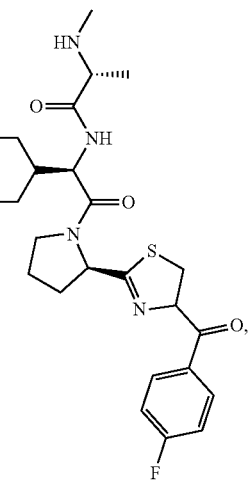
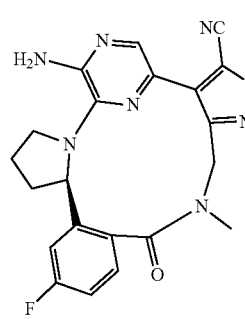
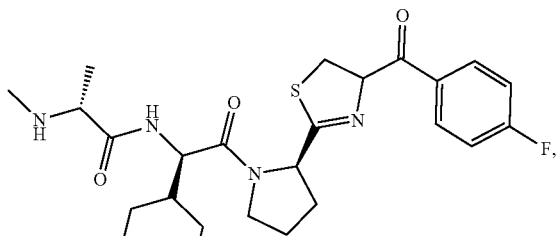
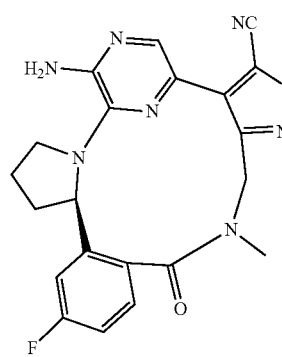

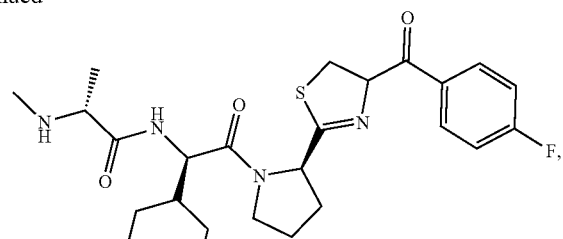
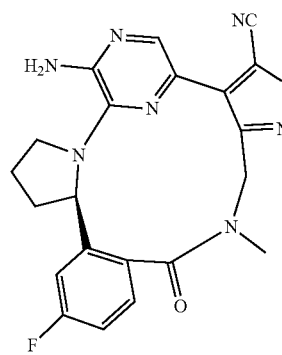
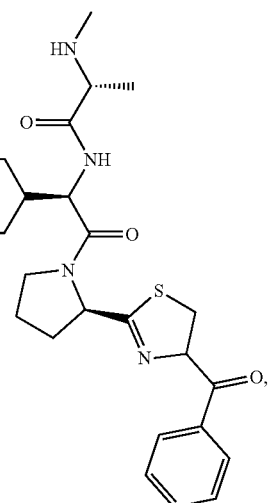
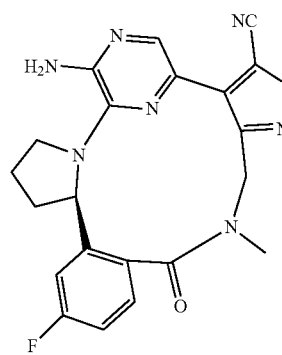
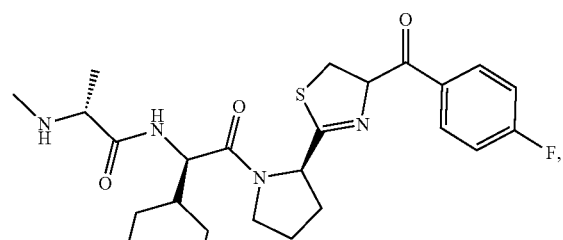
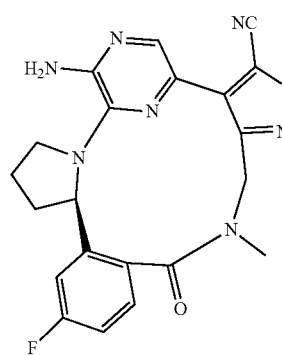

387
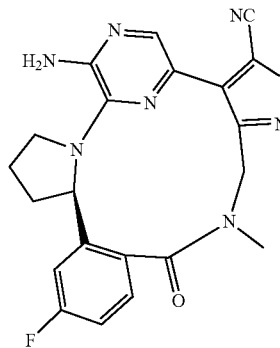
388
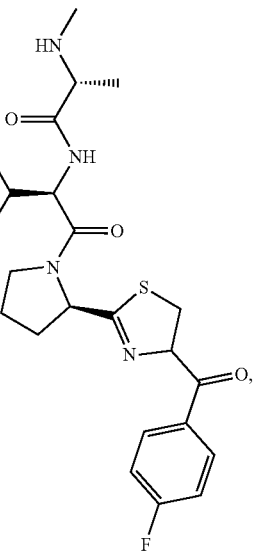
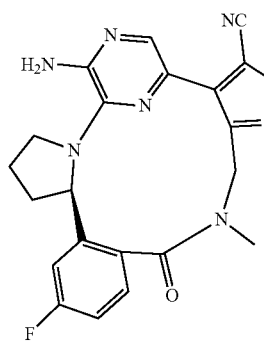
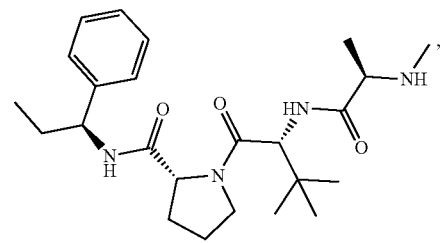
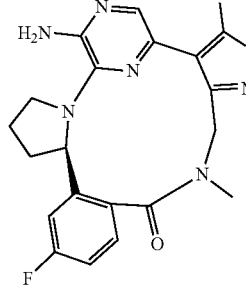
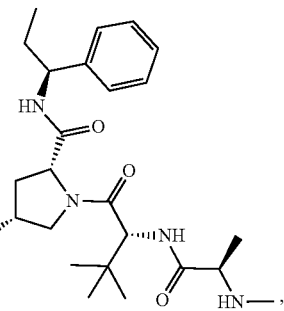

-continued
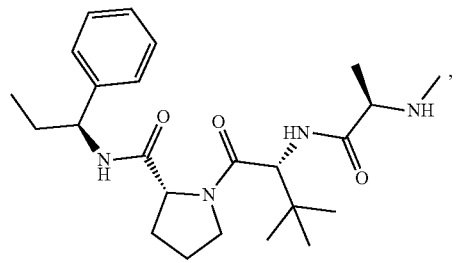
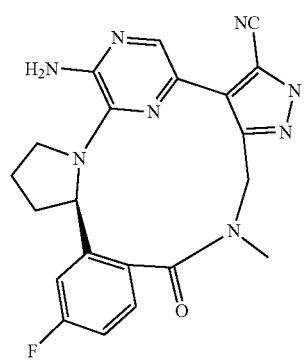
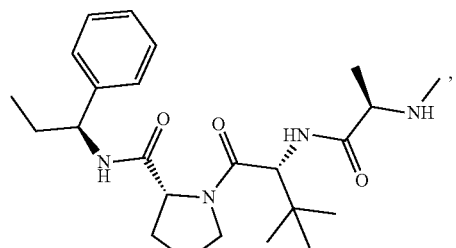
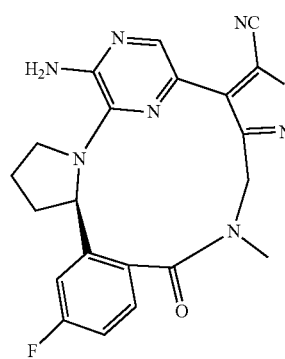
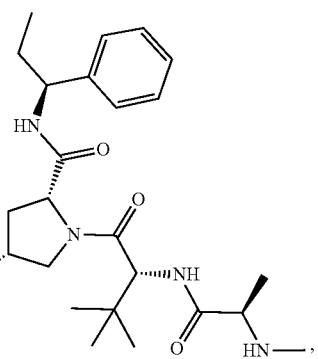
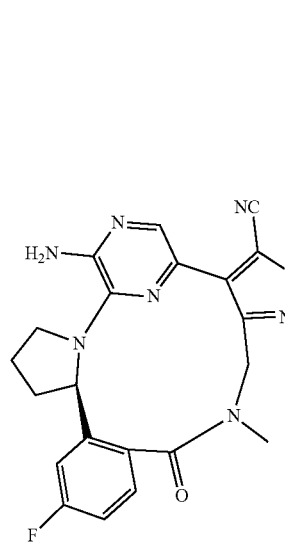

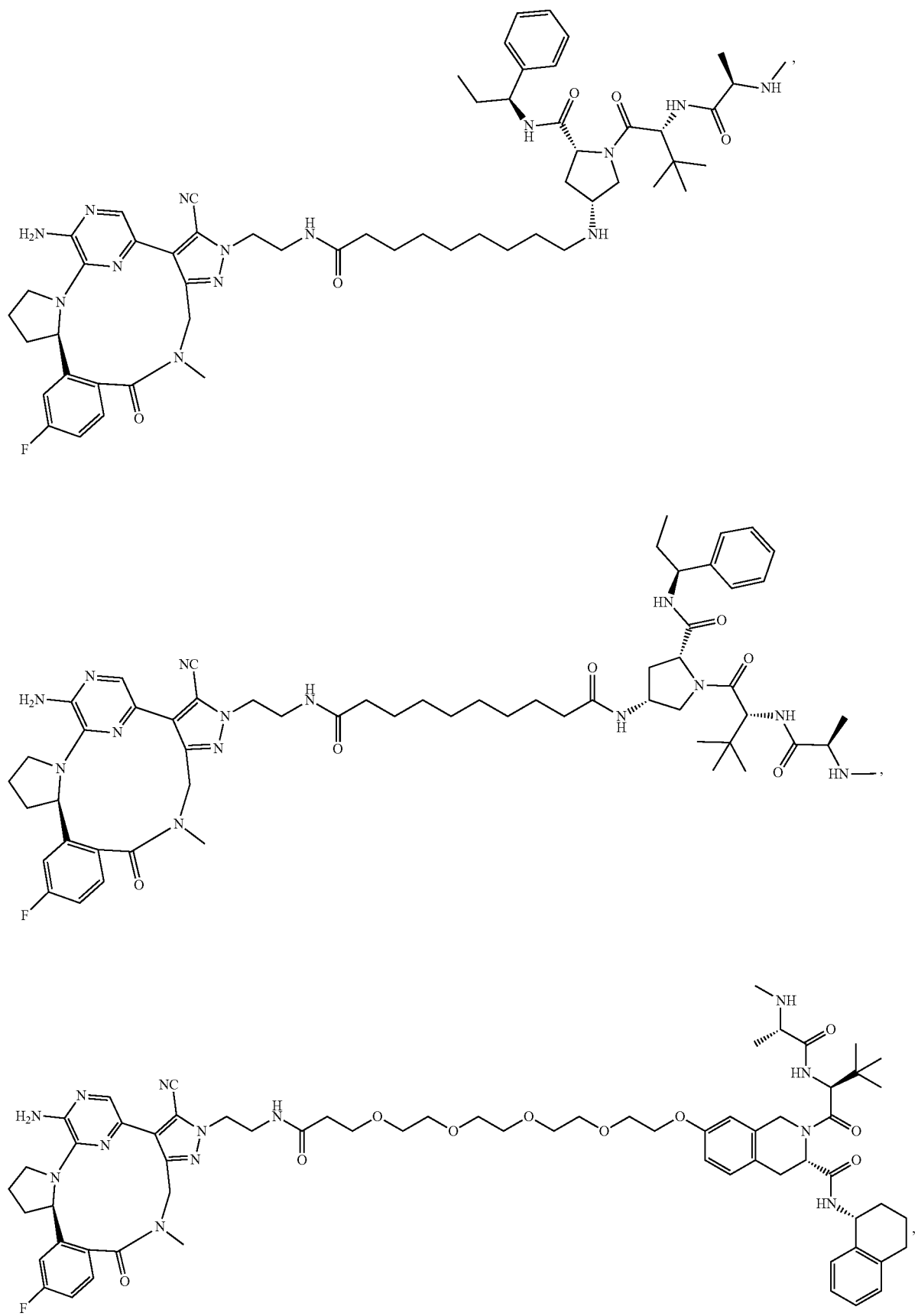

393
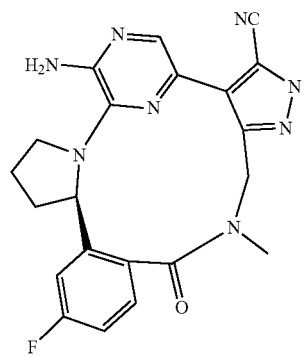
394
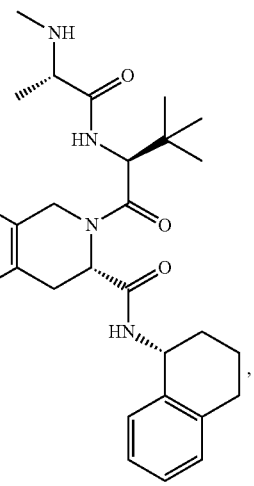
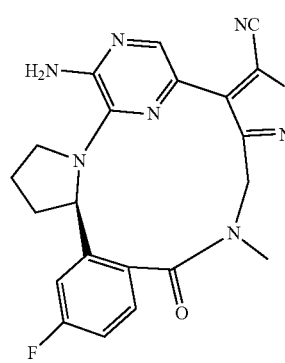
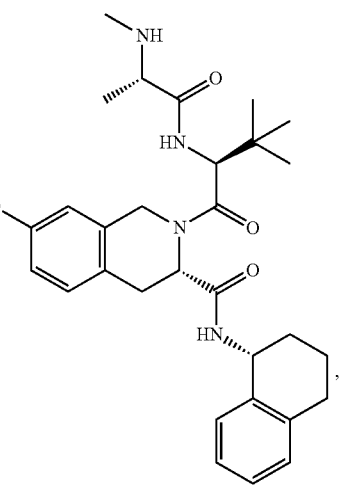
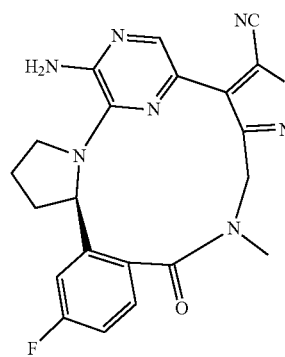
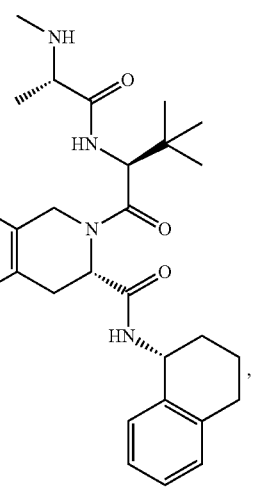

395
396
-continued
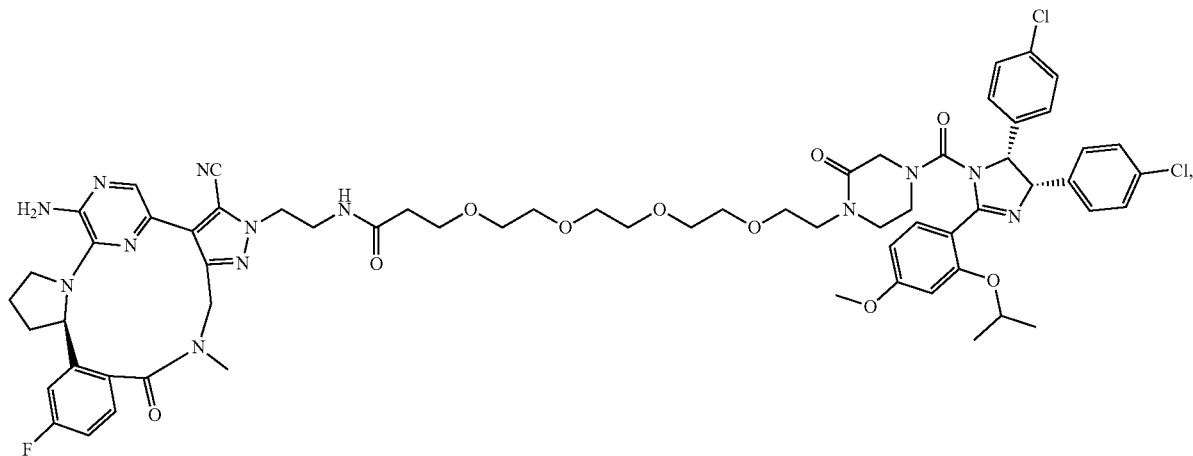
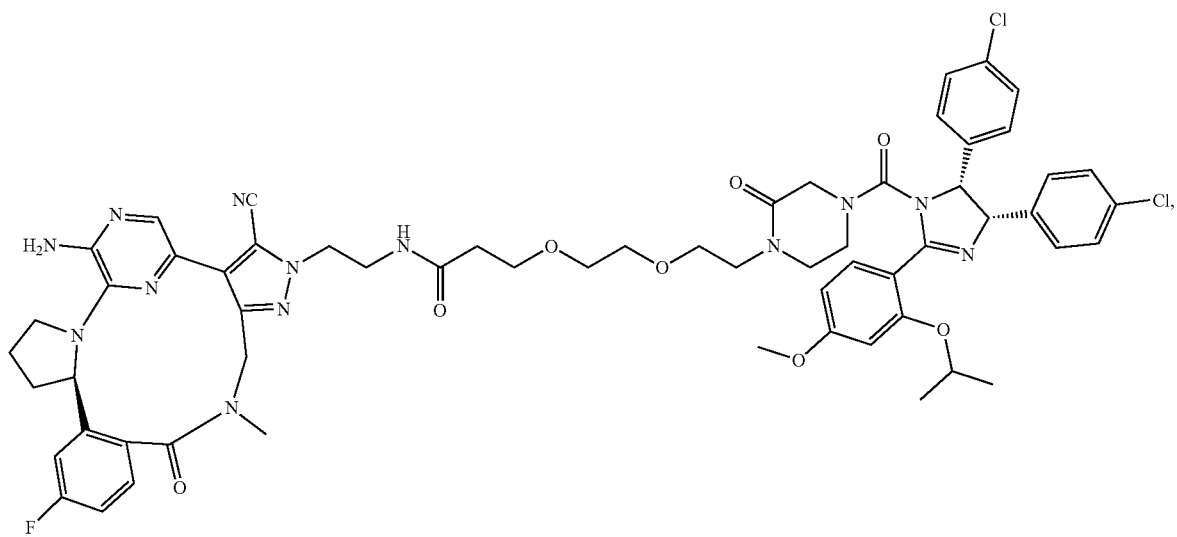
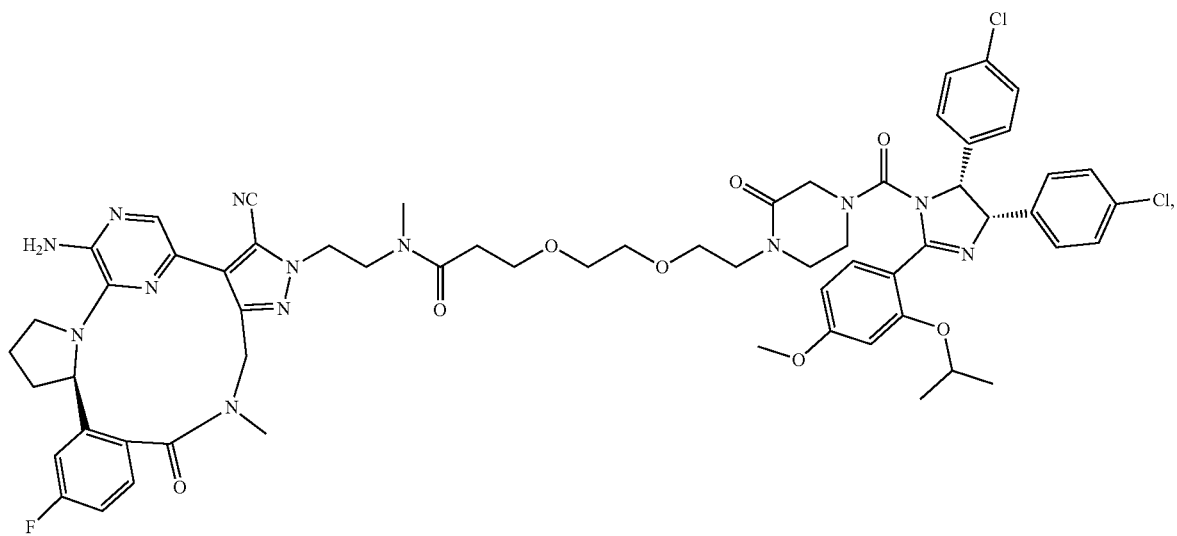

397
398
-continued
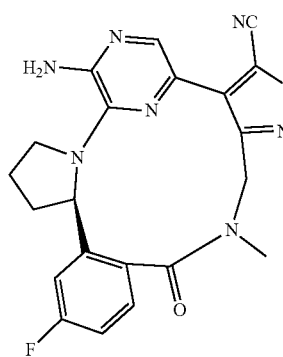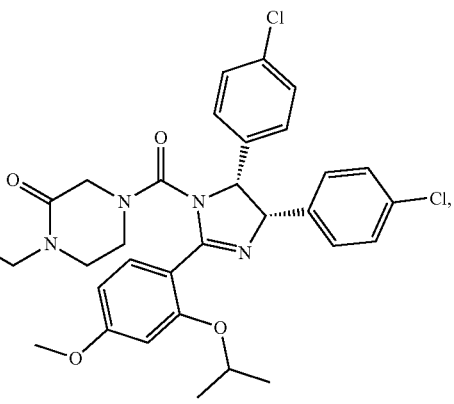
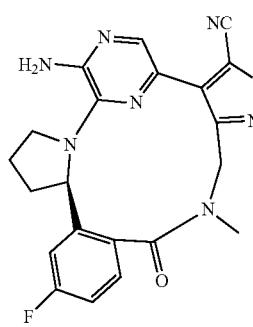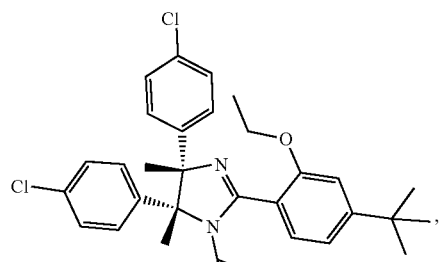

-continued
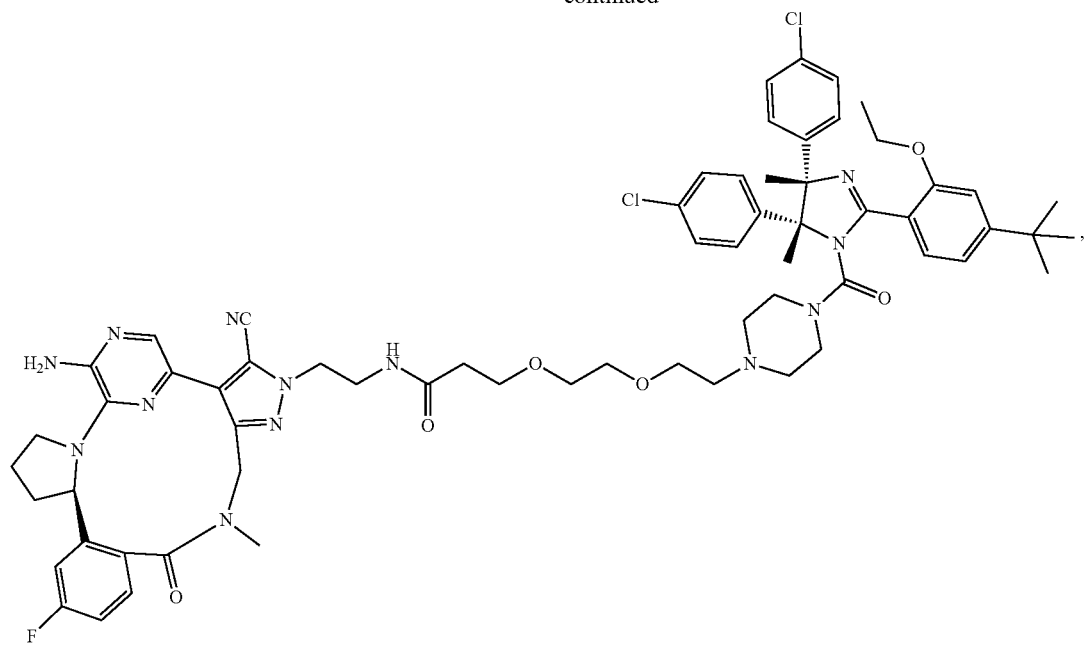
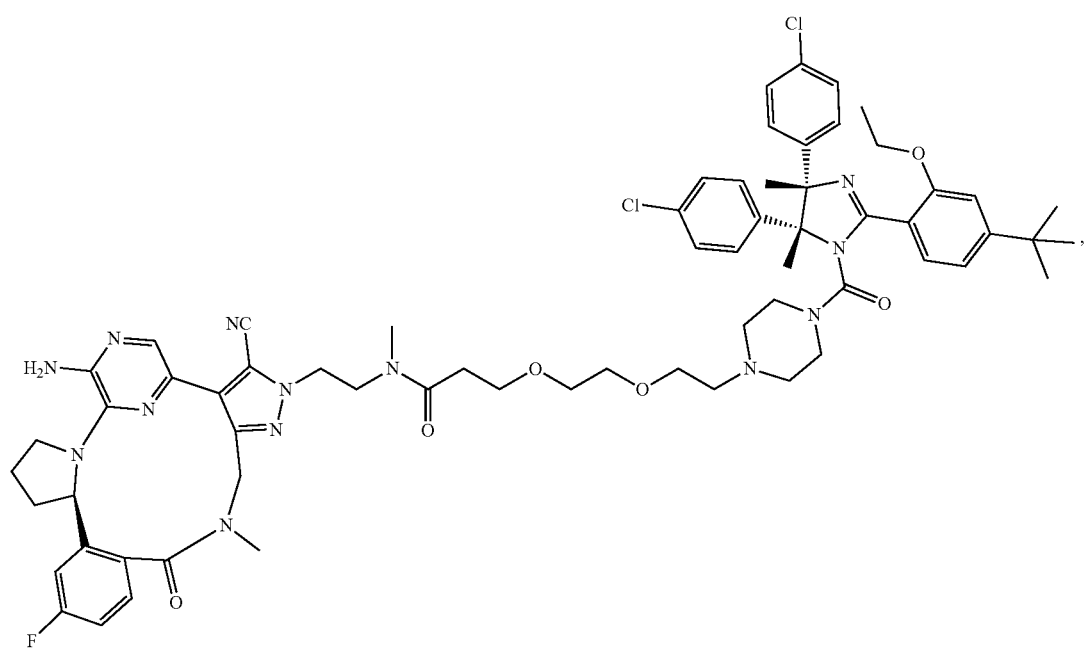

401
402
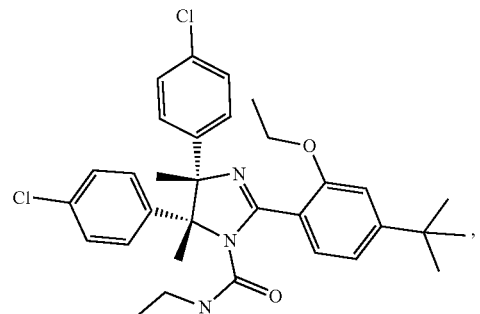
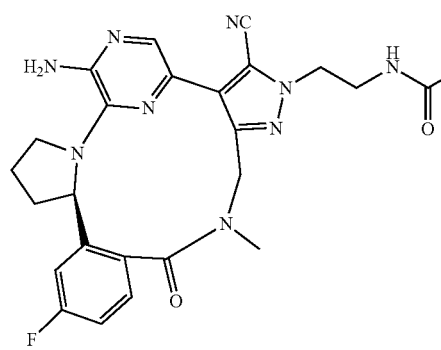
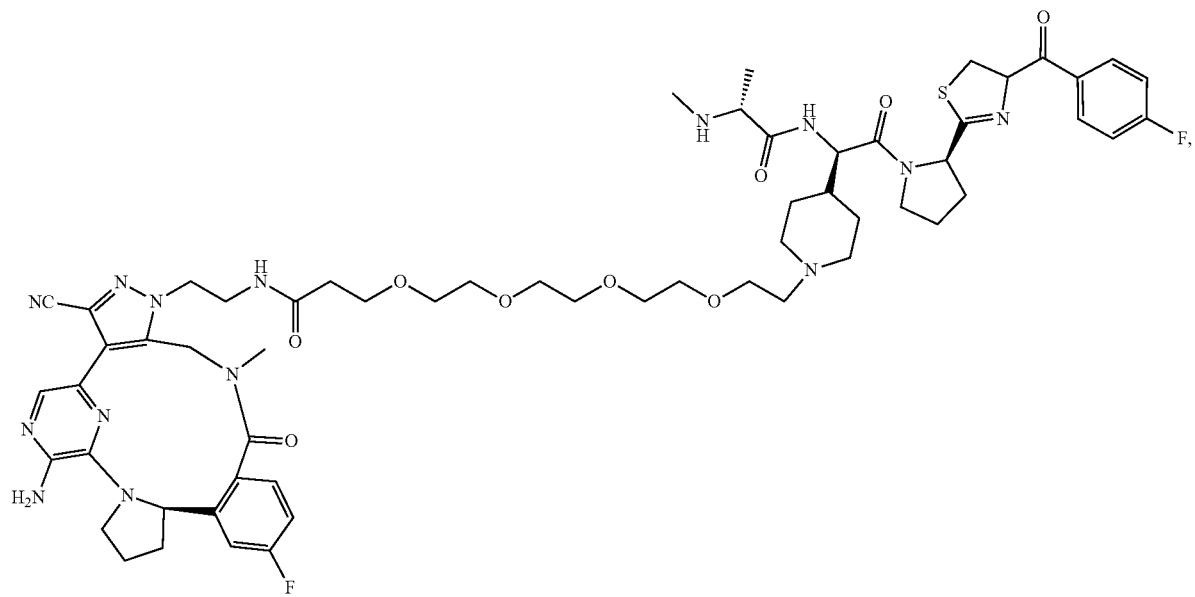

403
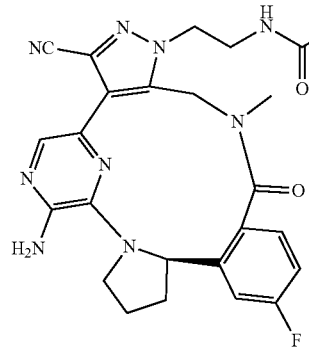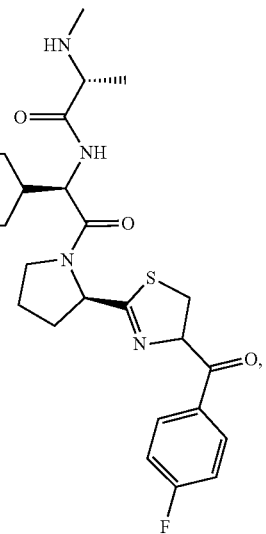
404
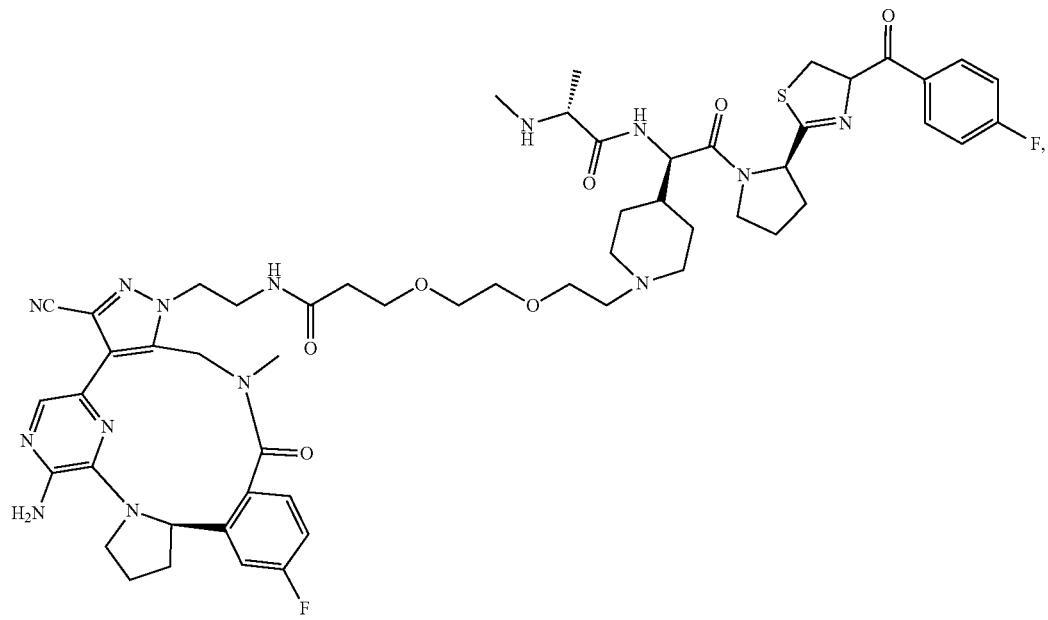

405
406
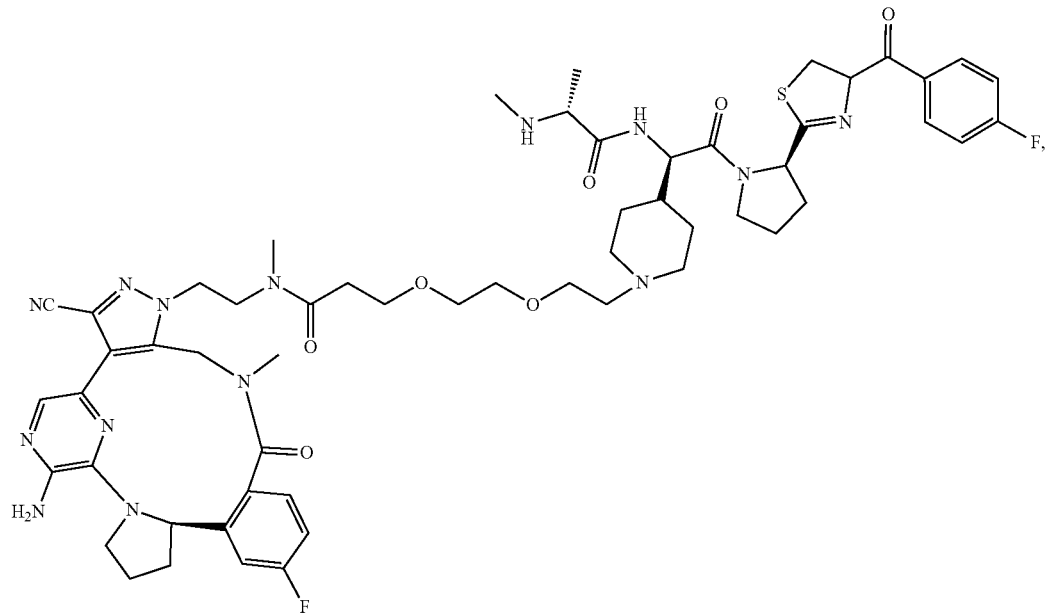
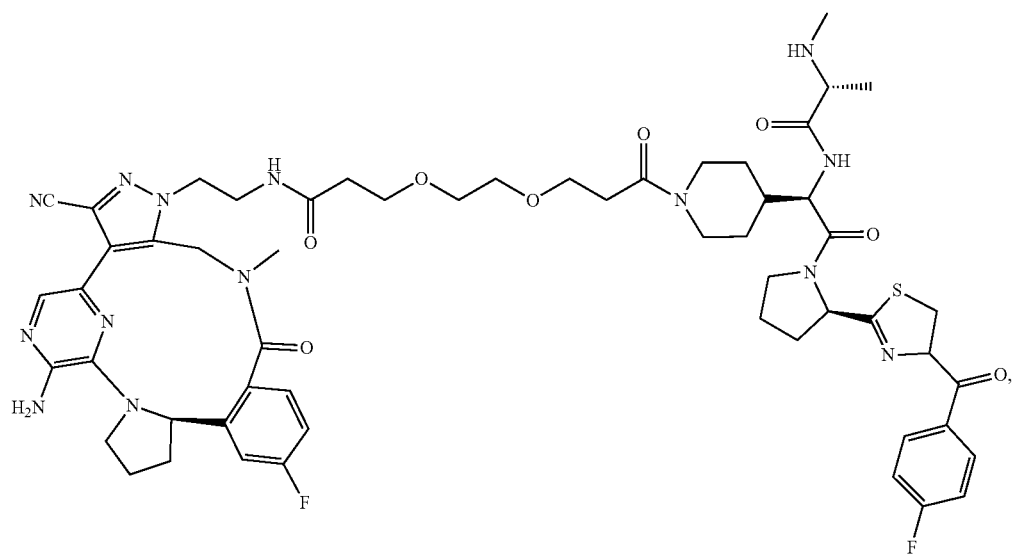

407
408
-continued
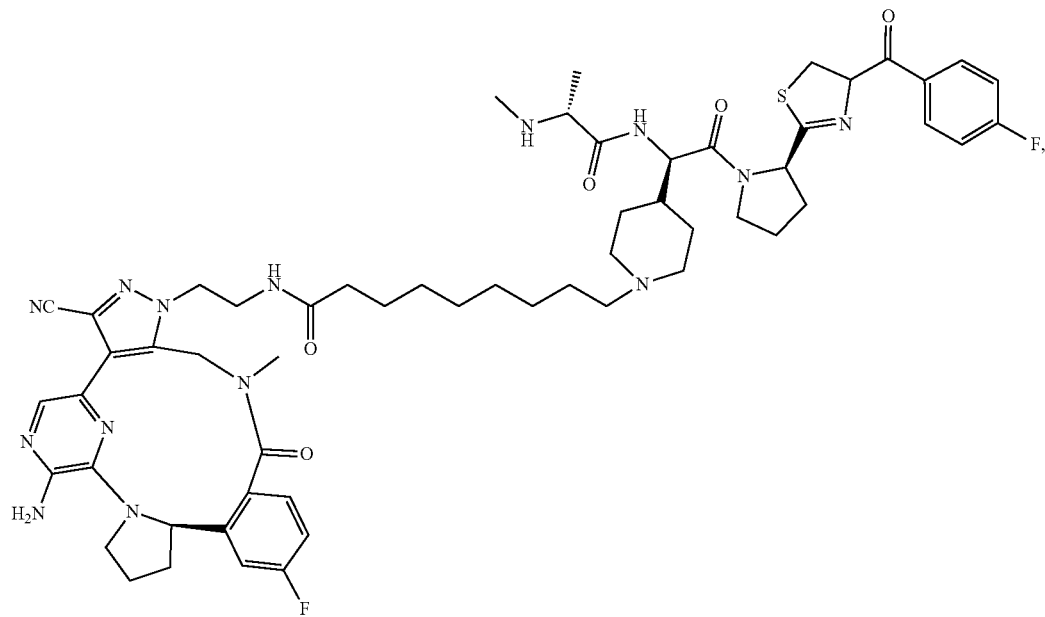
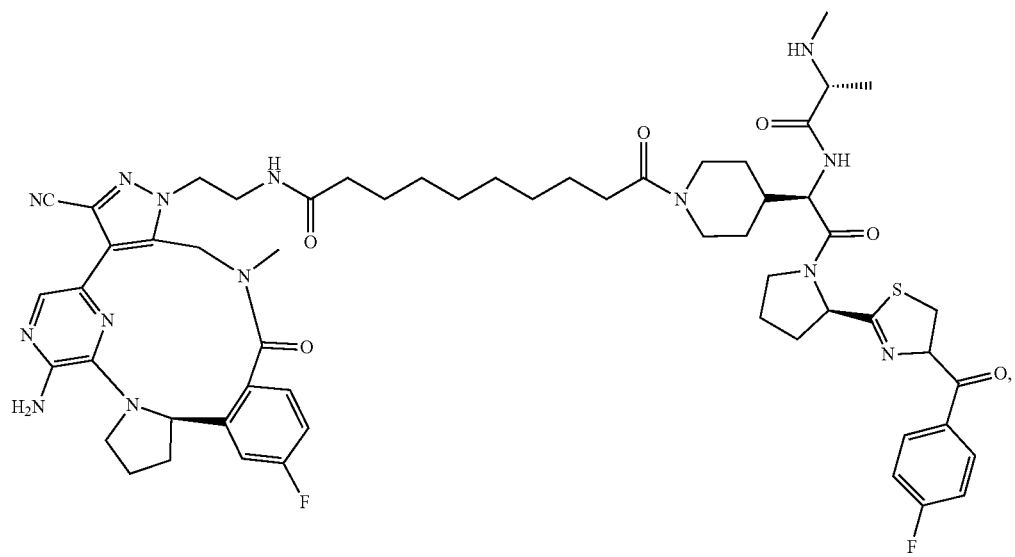

409
410
-continued
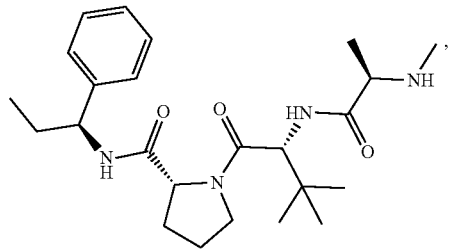
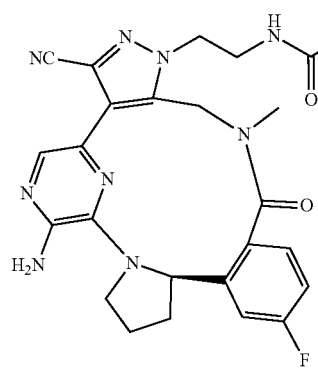
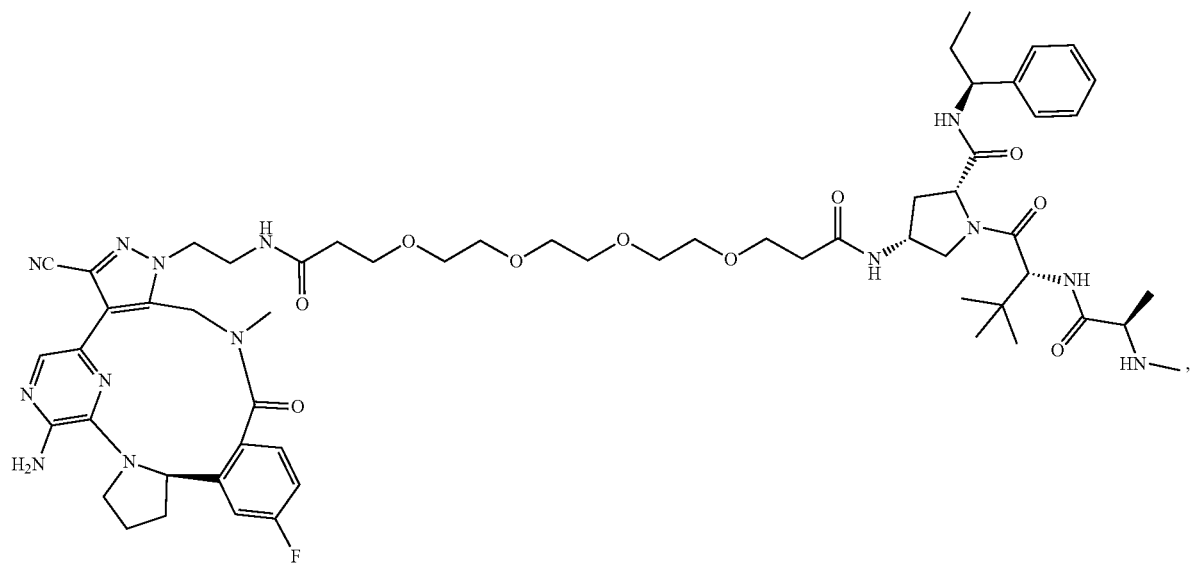

411
-continued
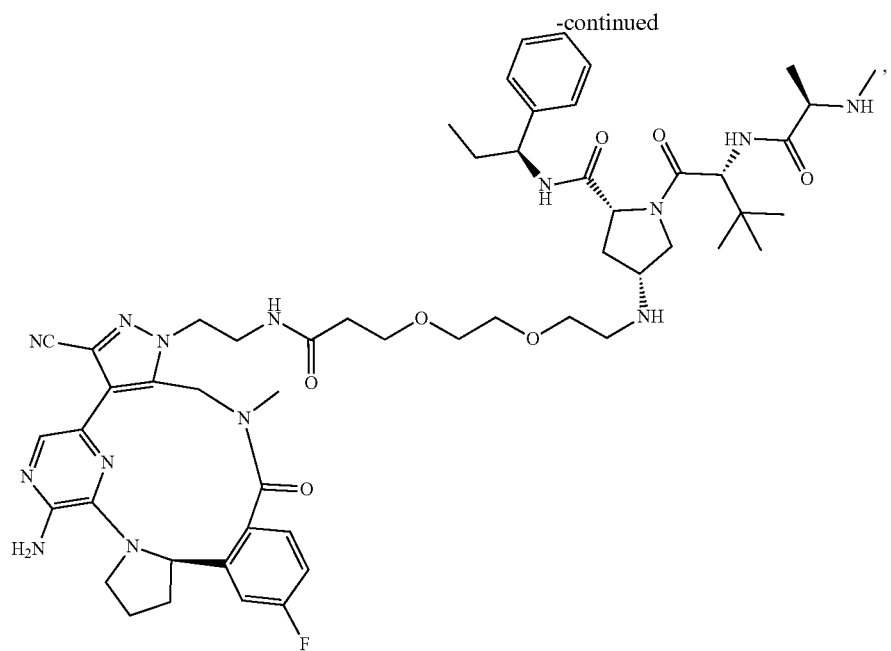
412
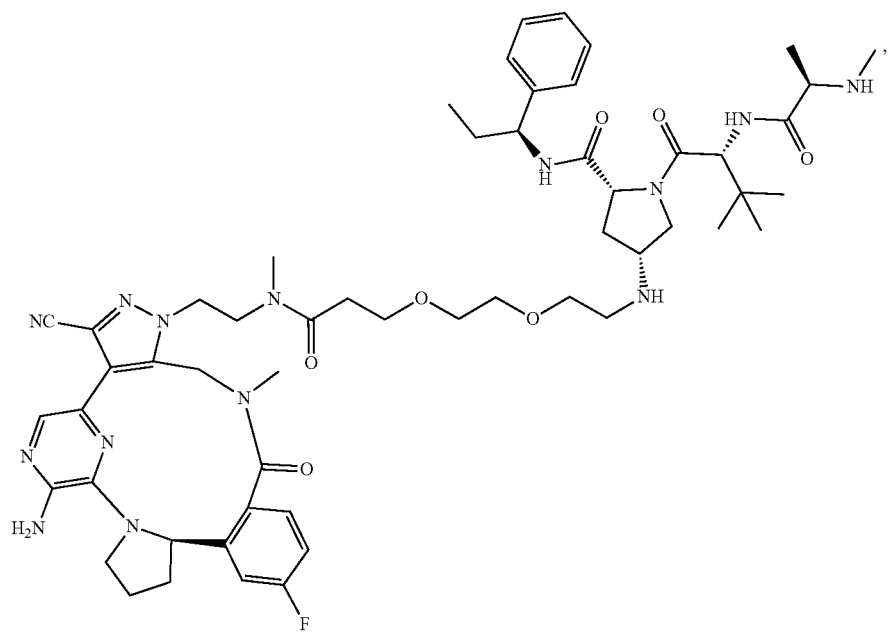

413
414
-continued
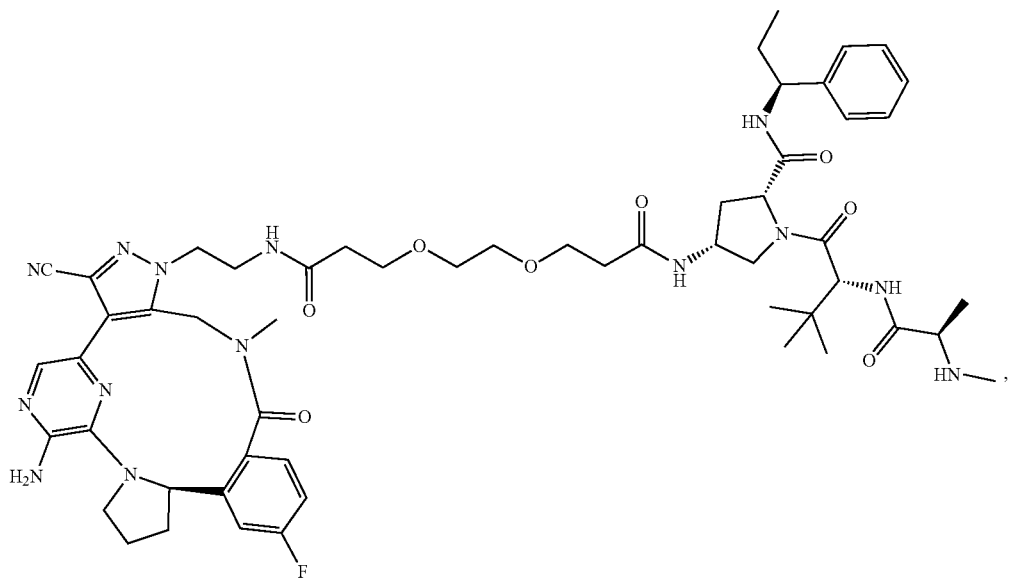
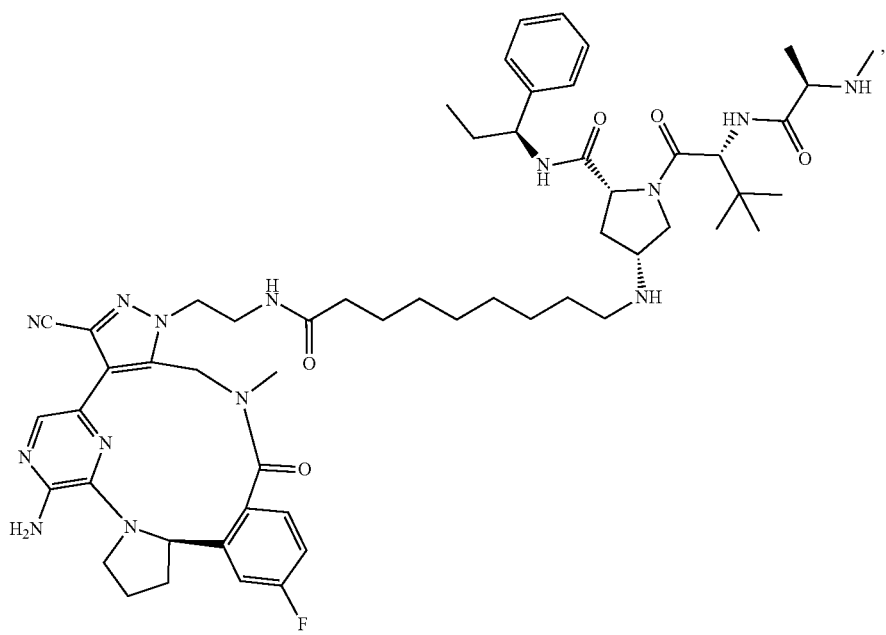

415
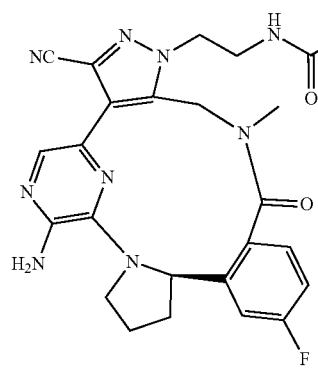
416
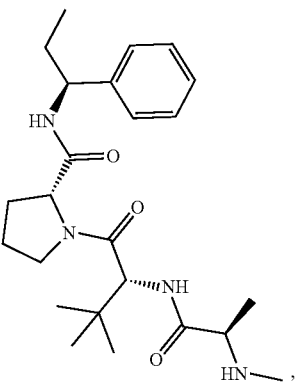
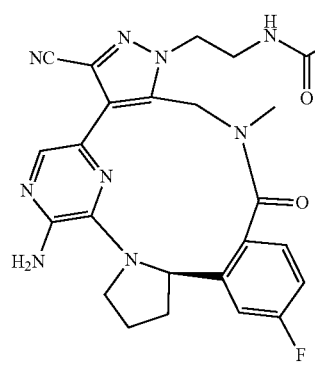
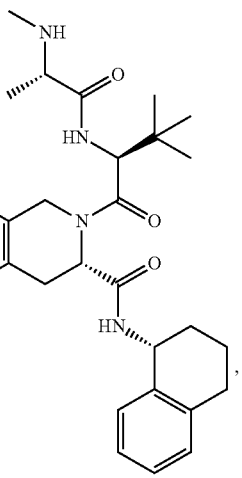
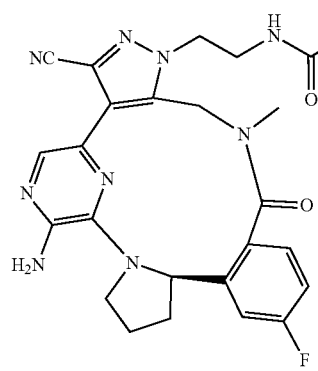
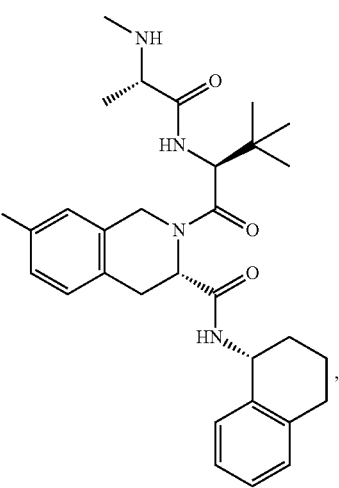

-continued
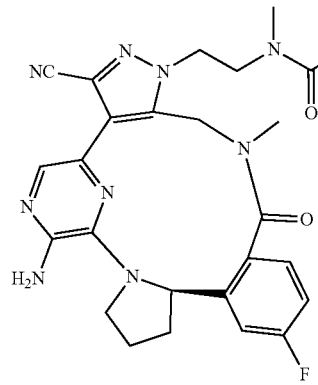 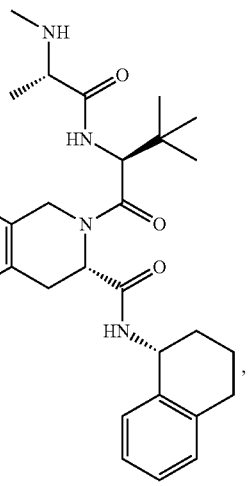
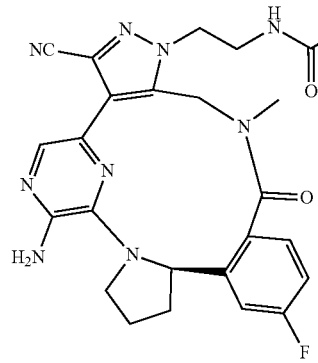 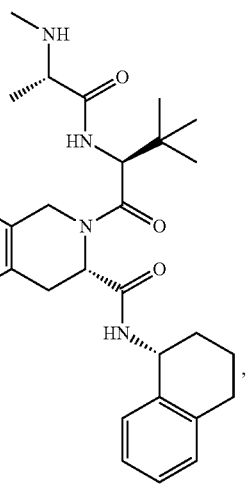
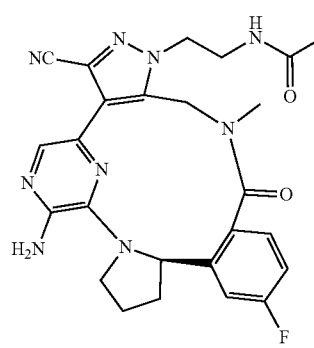 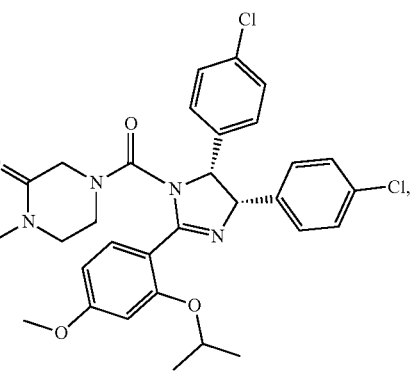

-continued
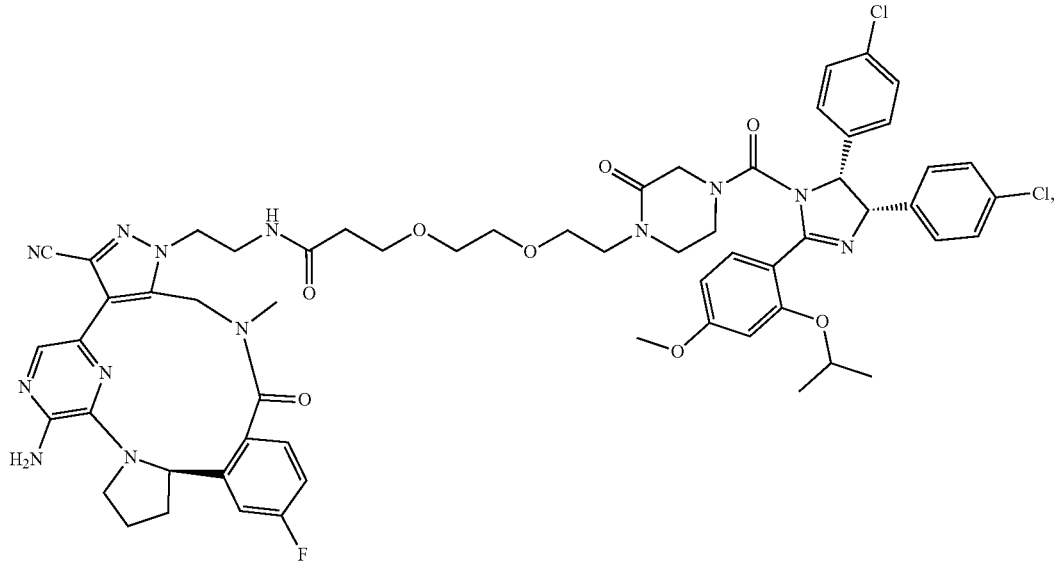
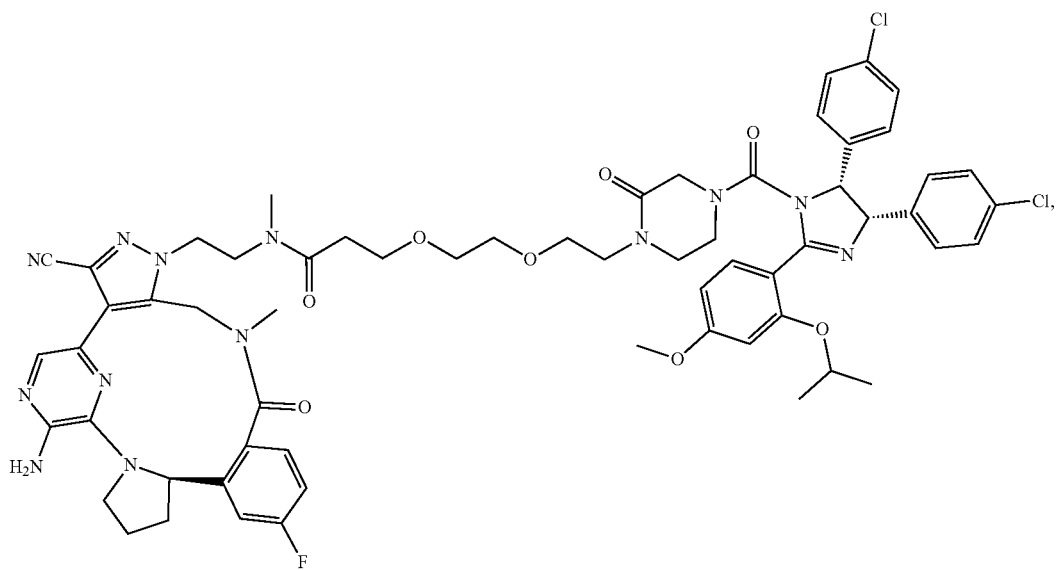
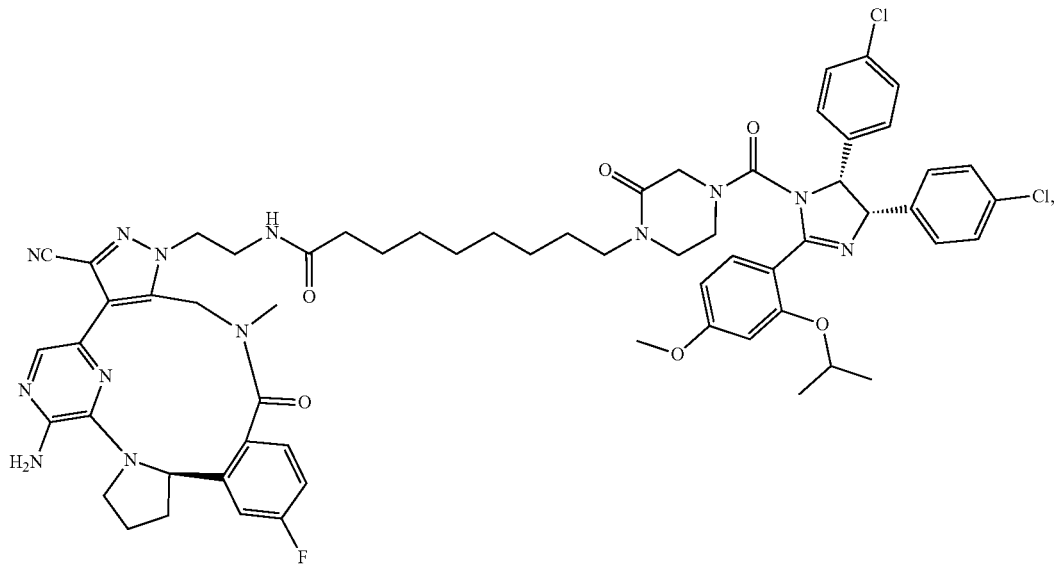

421
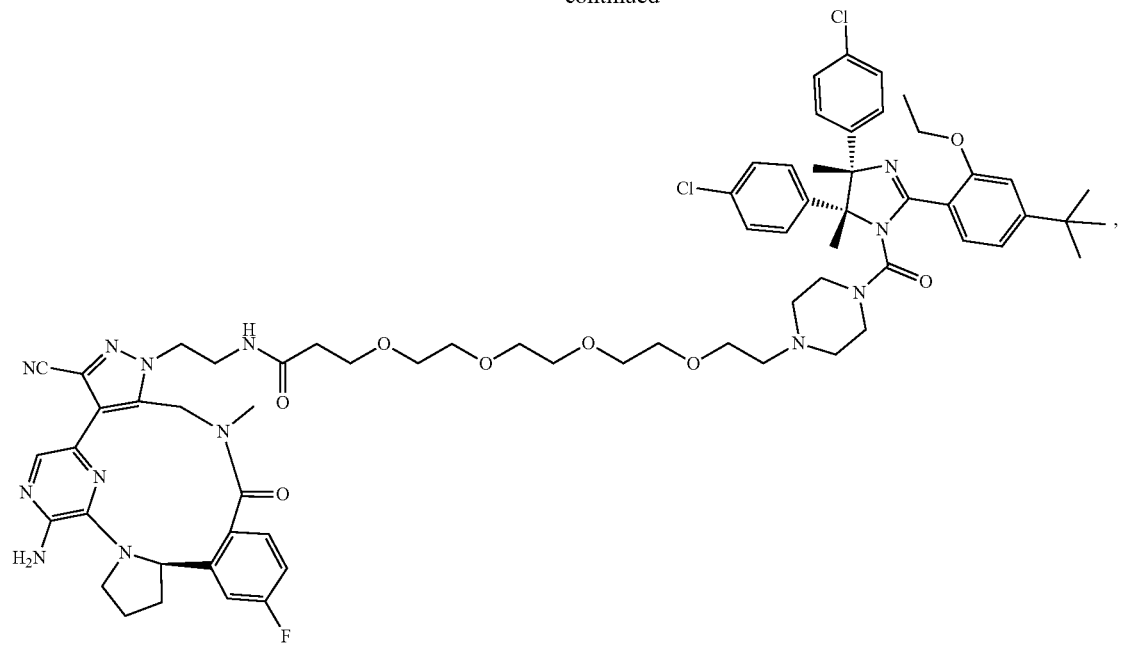
422
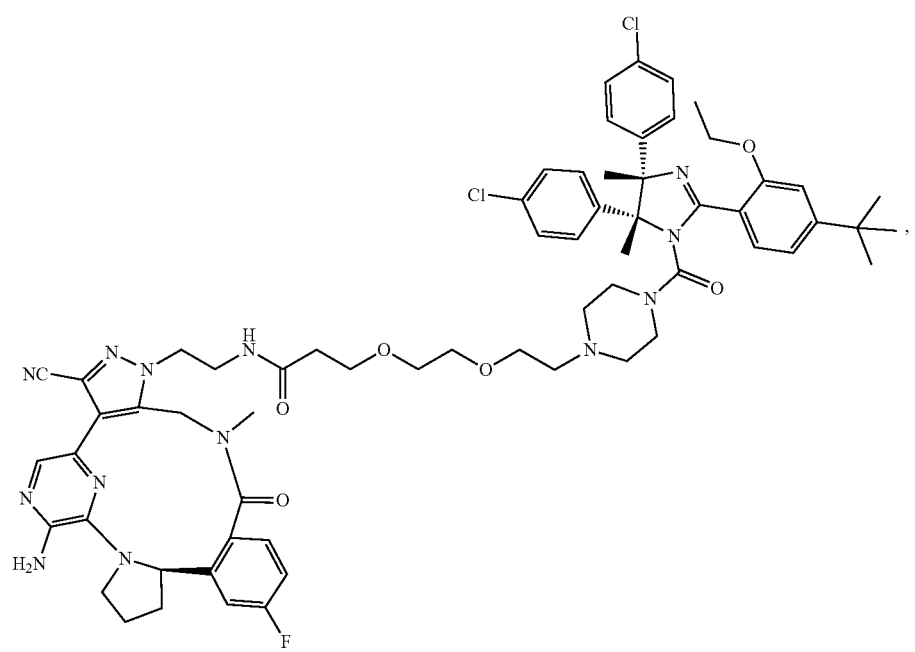

423
424
-continued
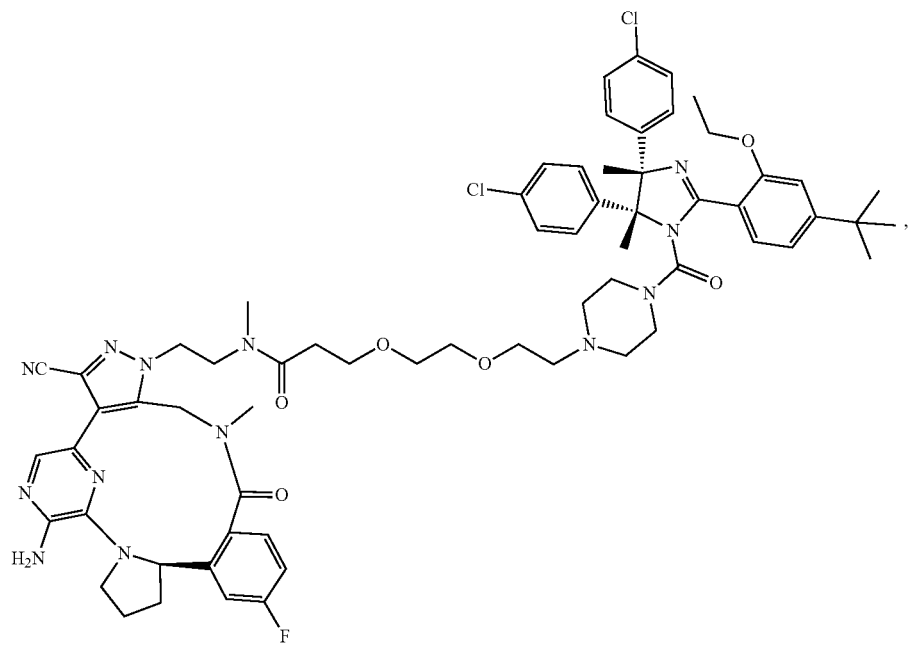
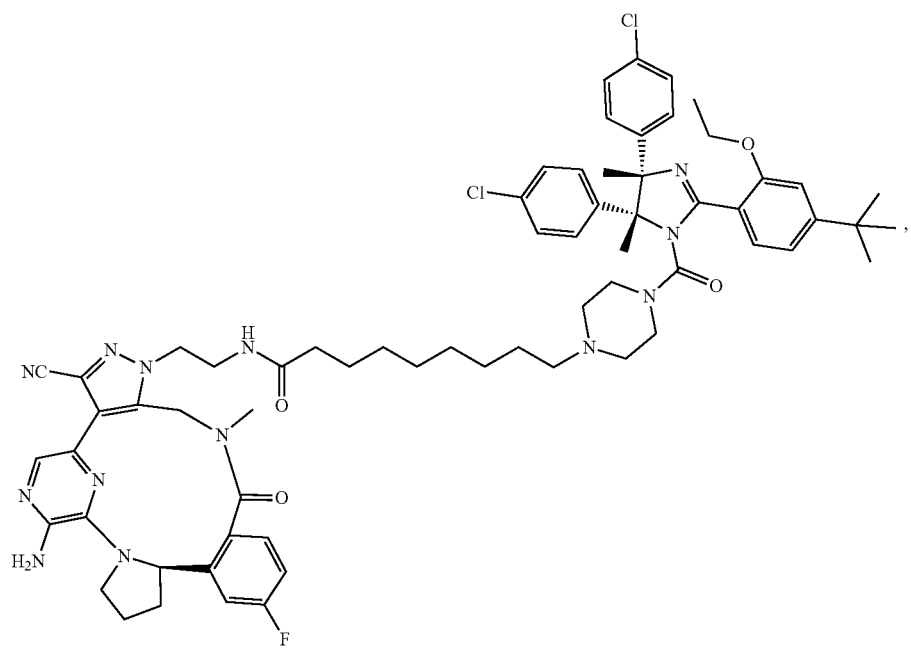
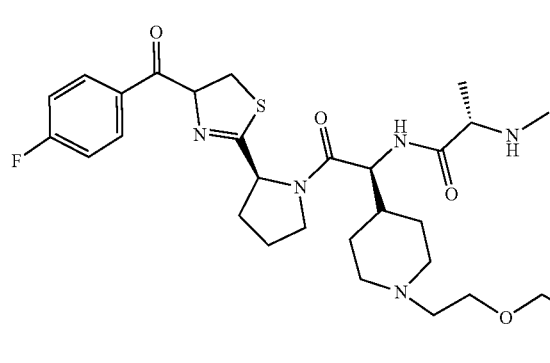
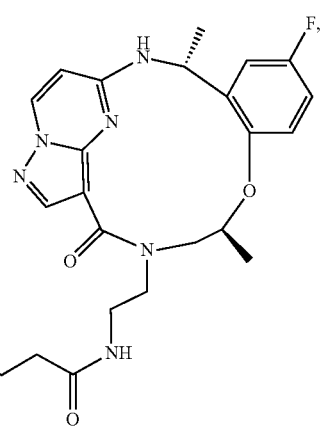

425
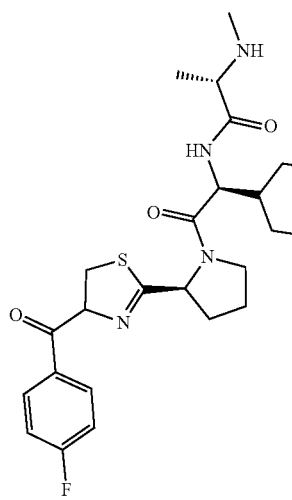
426
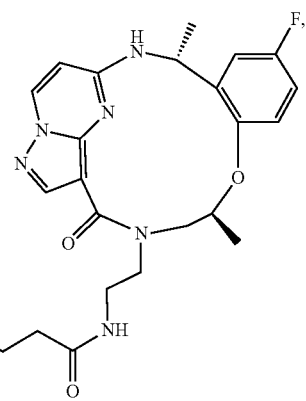
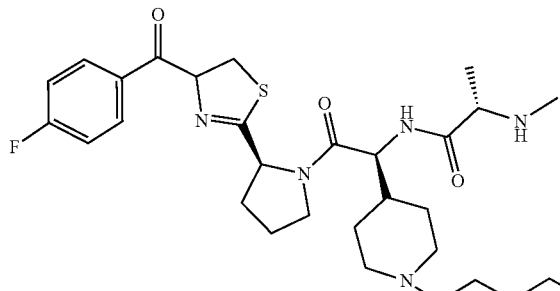
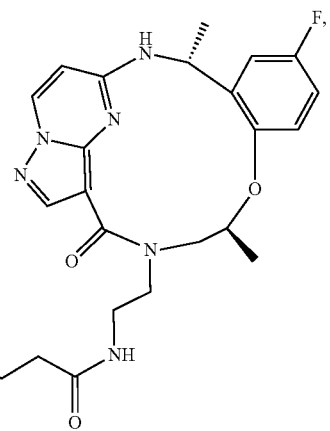
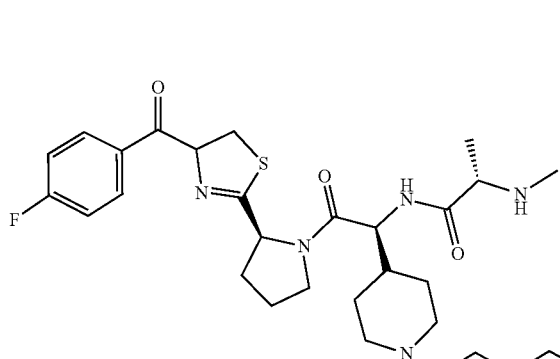
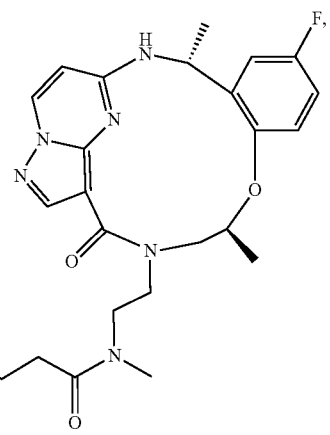

427 428
-continued
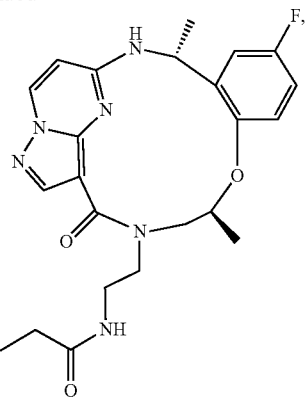
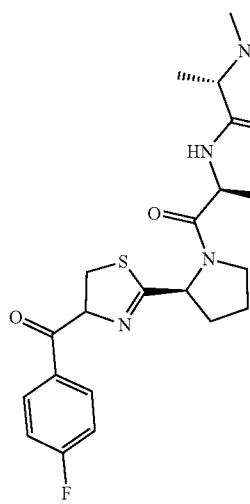
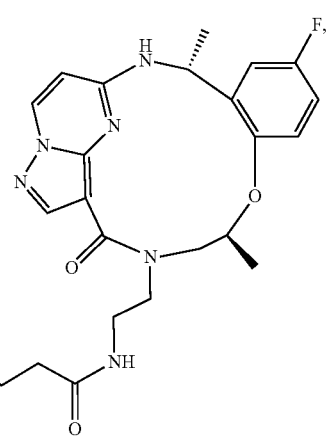
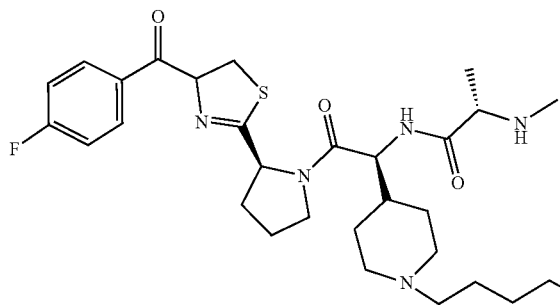
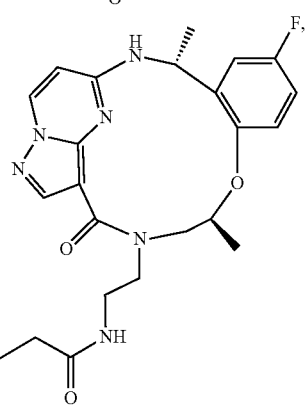
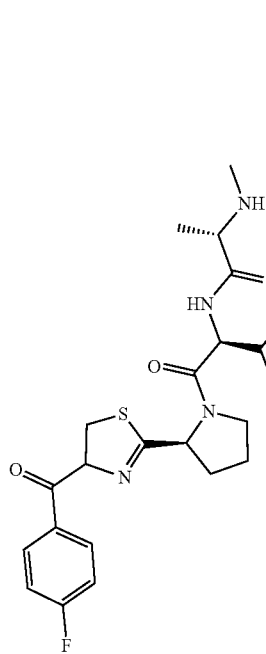

429
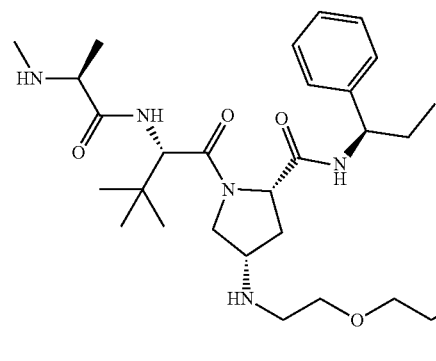
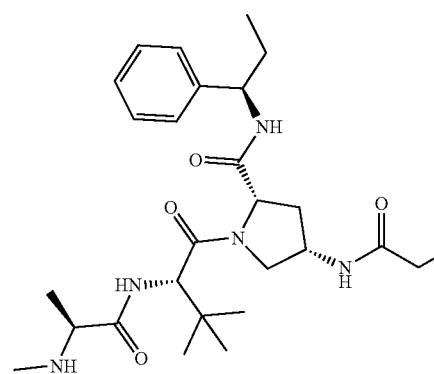
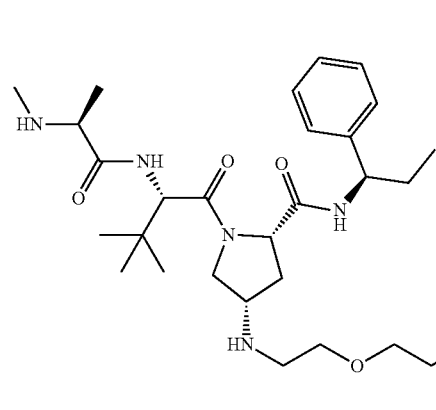
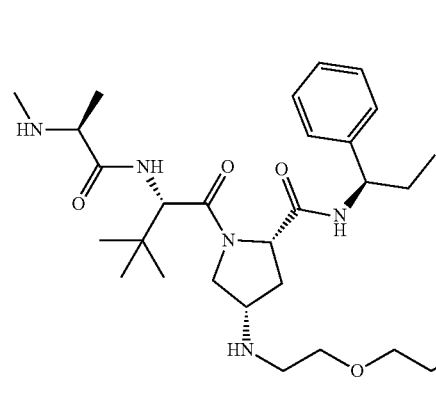
430
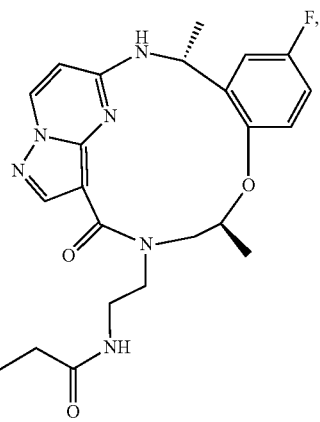
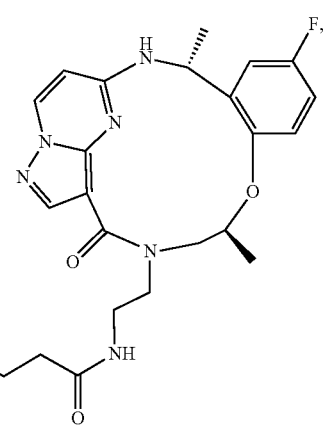
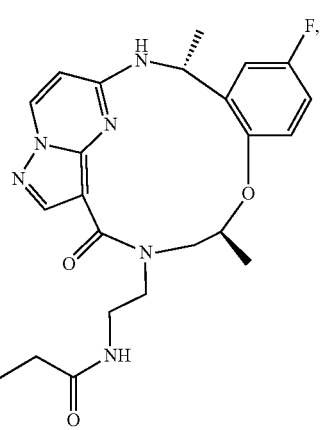
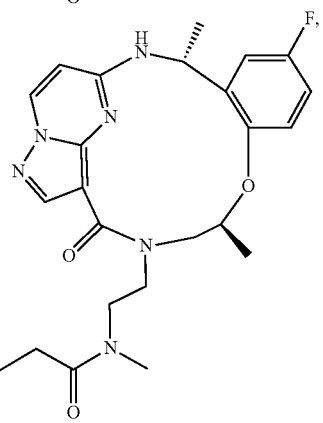

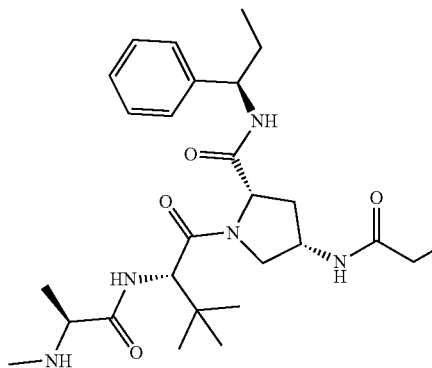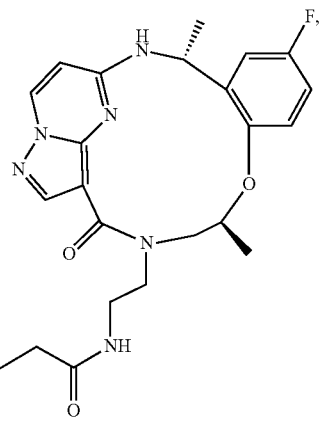
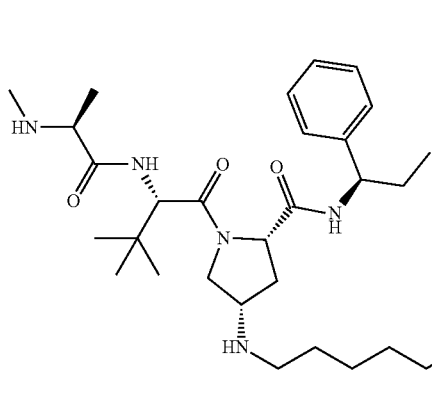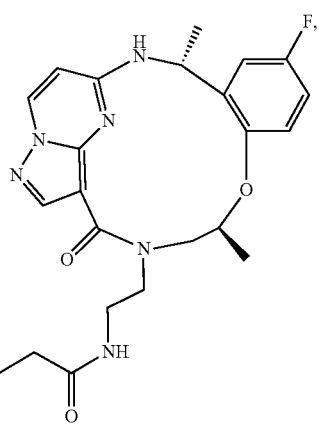
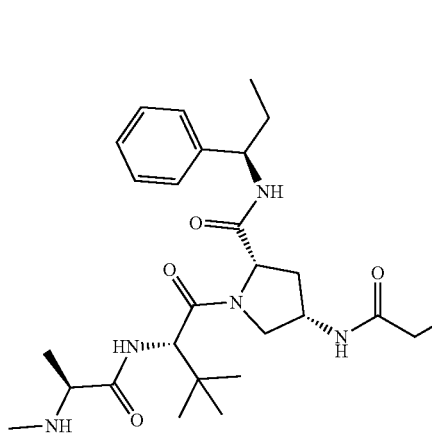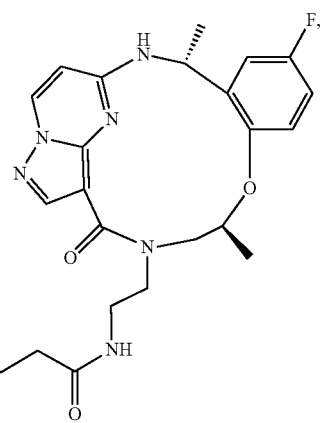

433
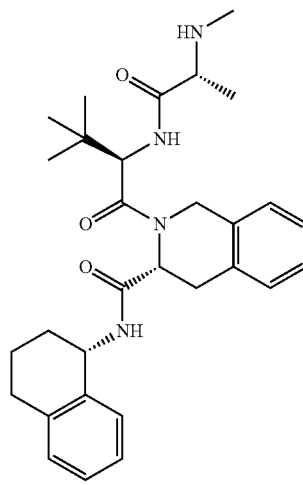 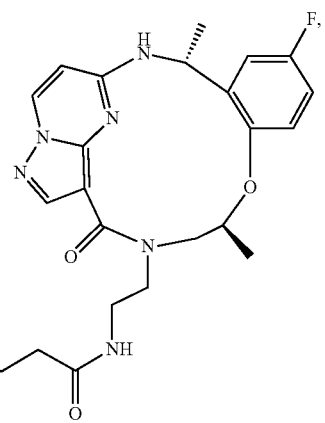
434
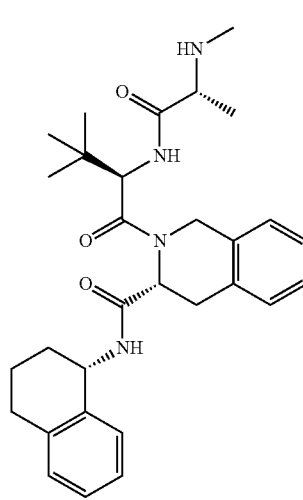 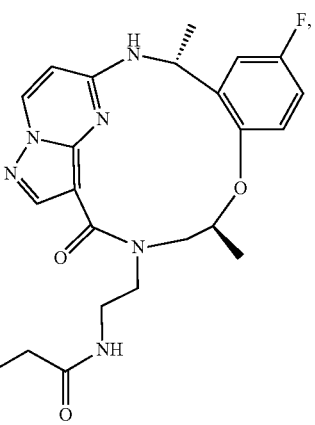

435
436
-continued
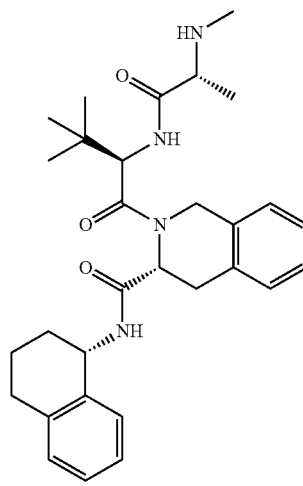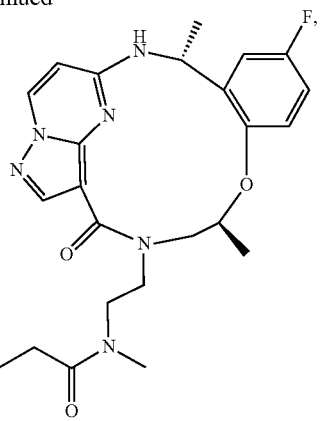
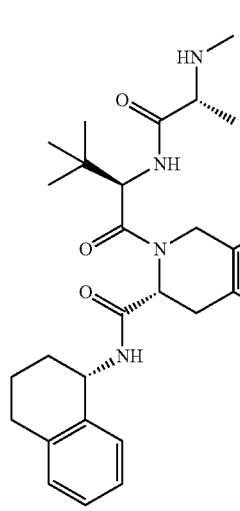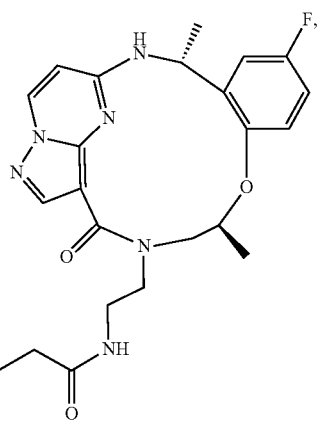

437
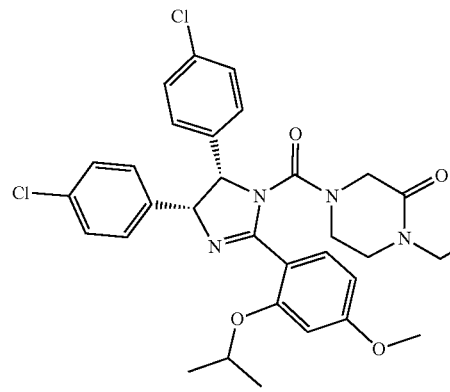
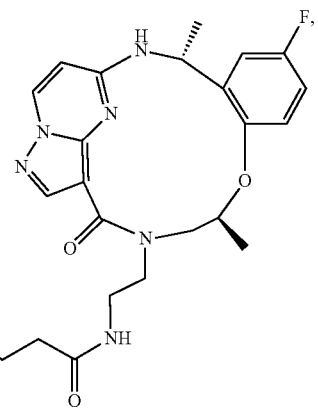
438
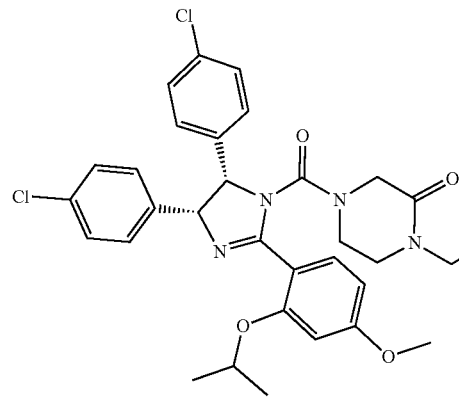
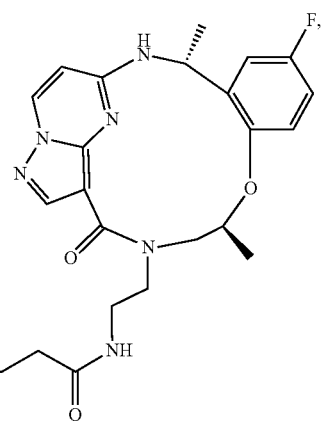
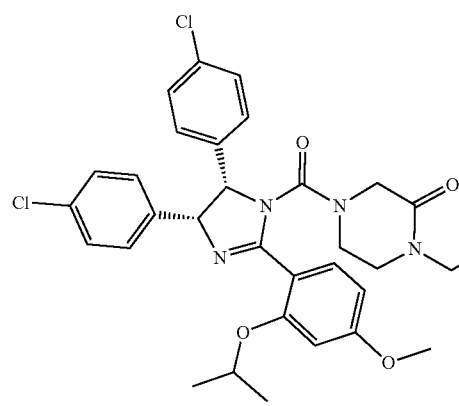
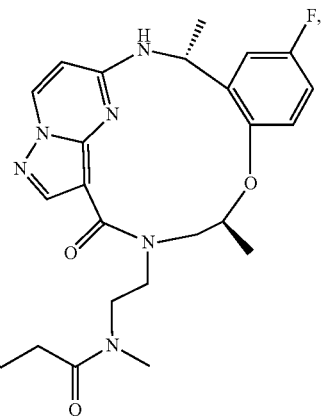

439
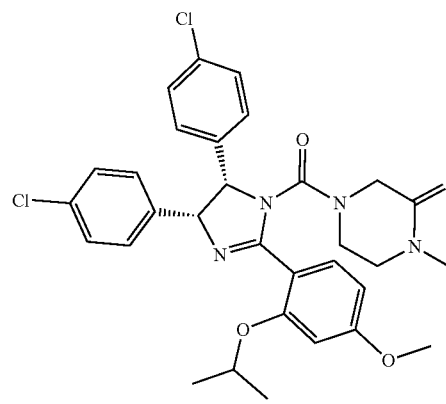
440
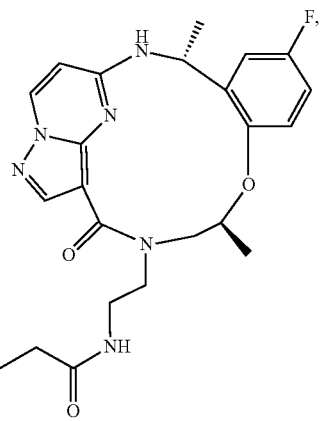
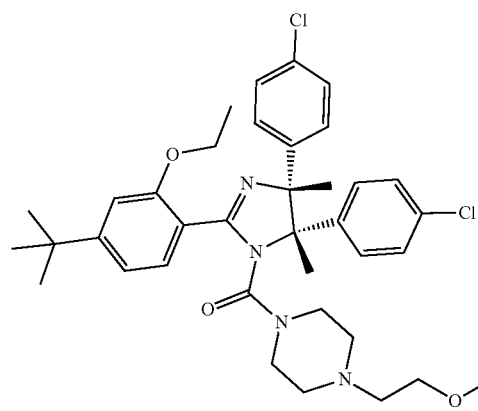
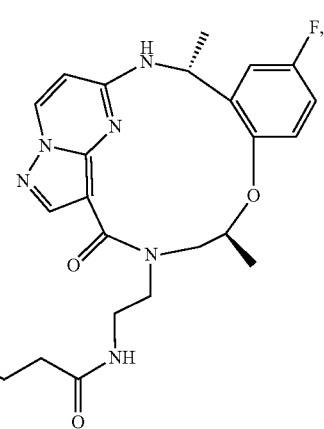
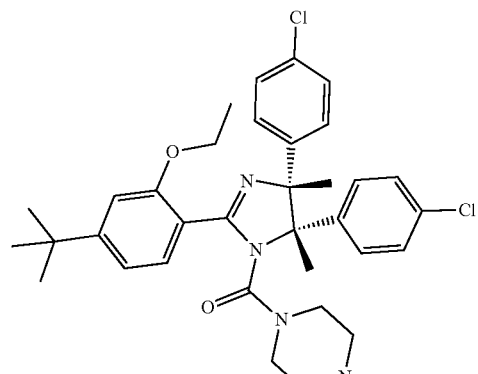
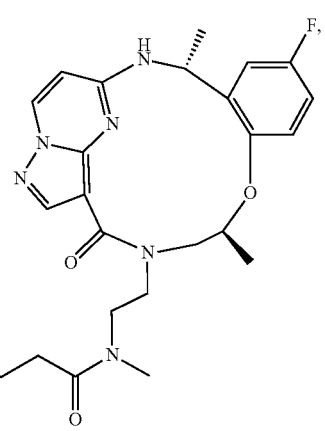

-continued
441 442
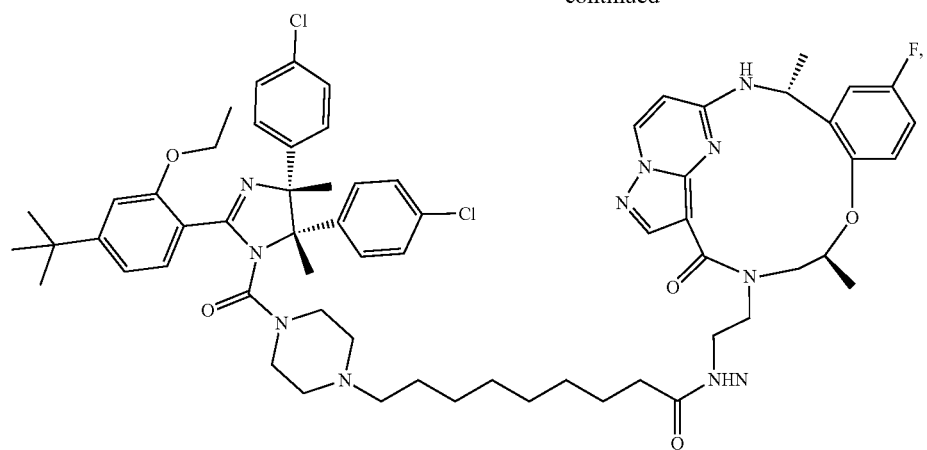
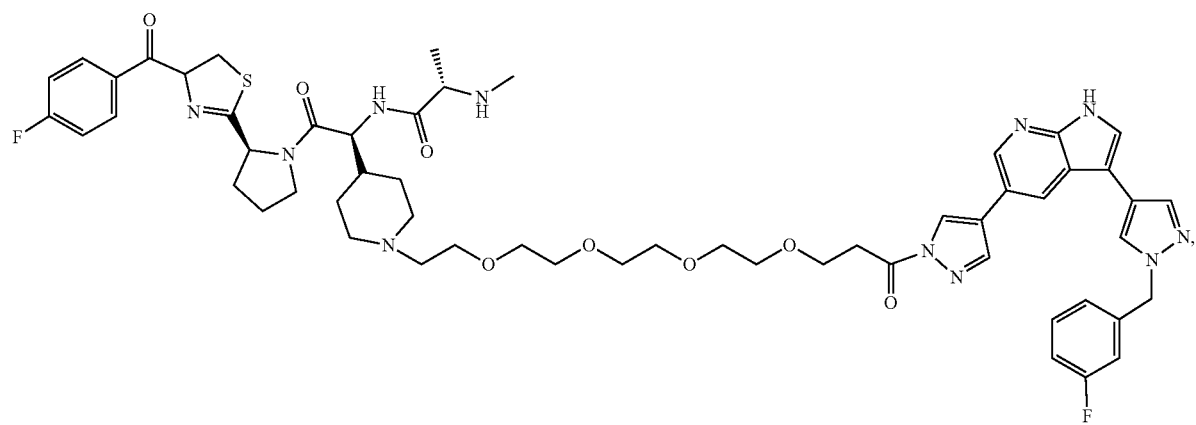
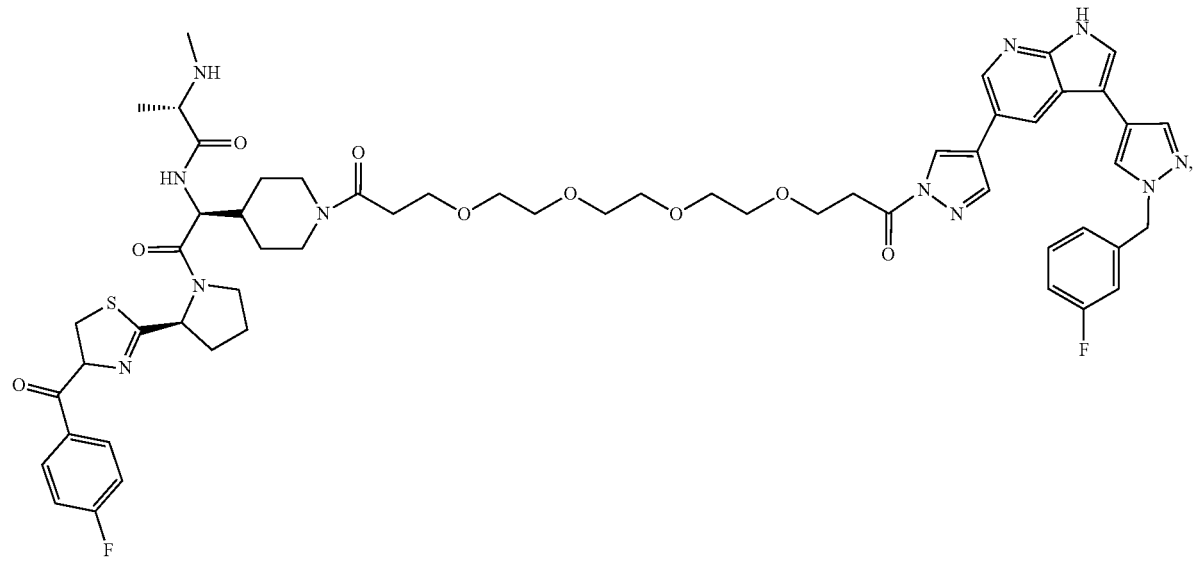

443
-continued
444
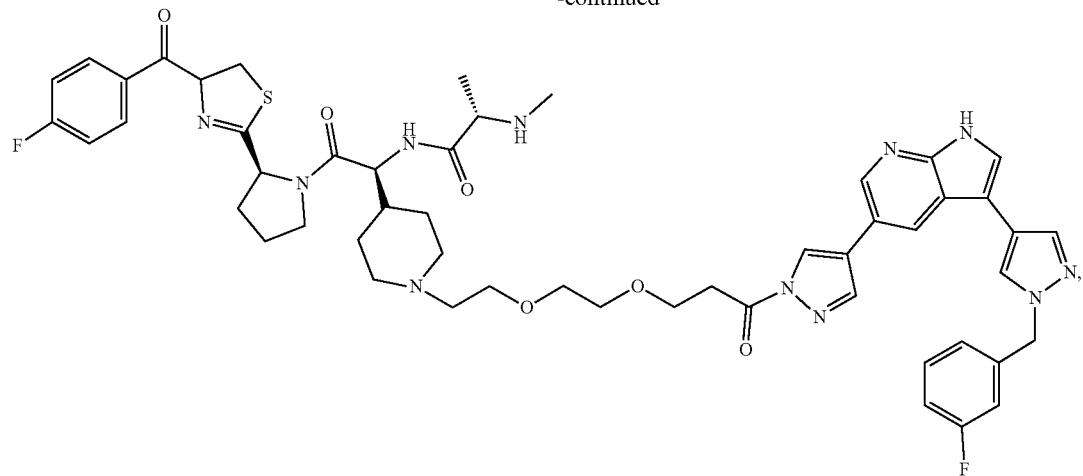
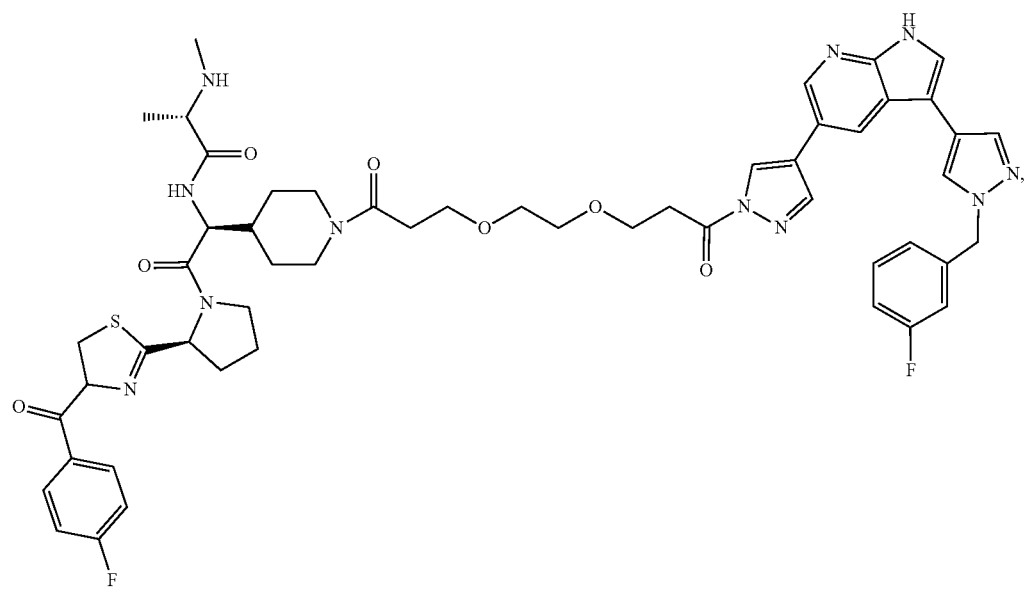
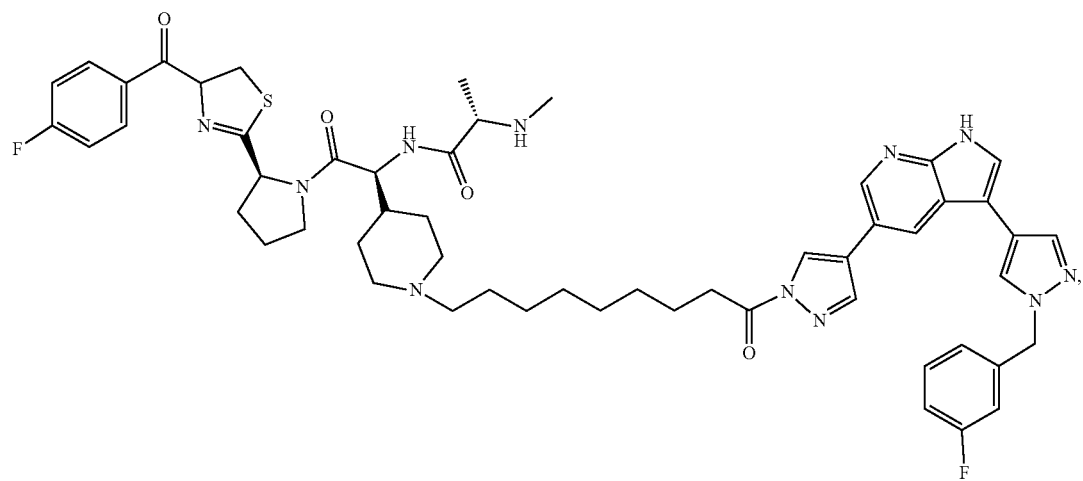

-continued
445
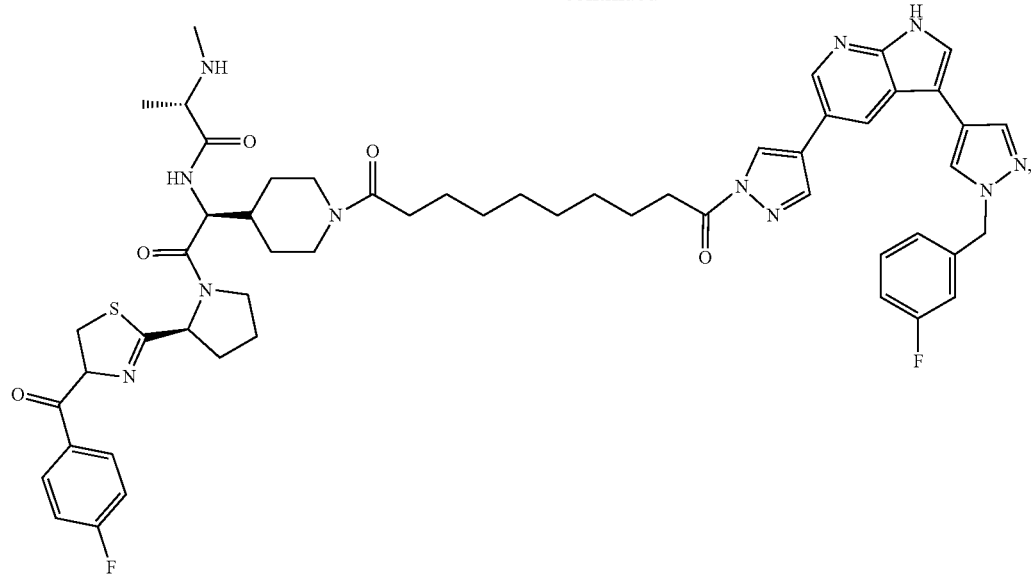
446
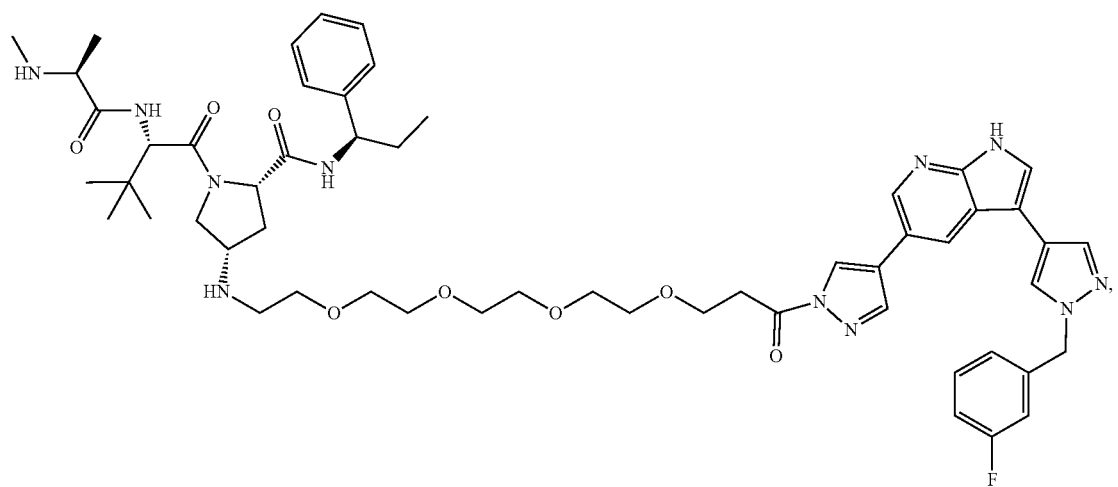
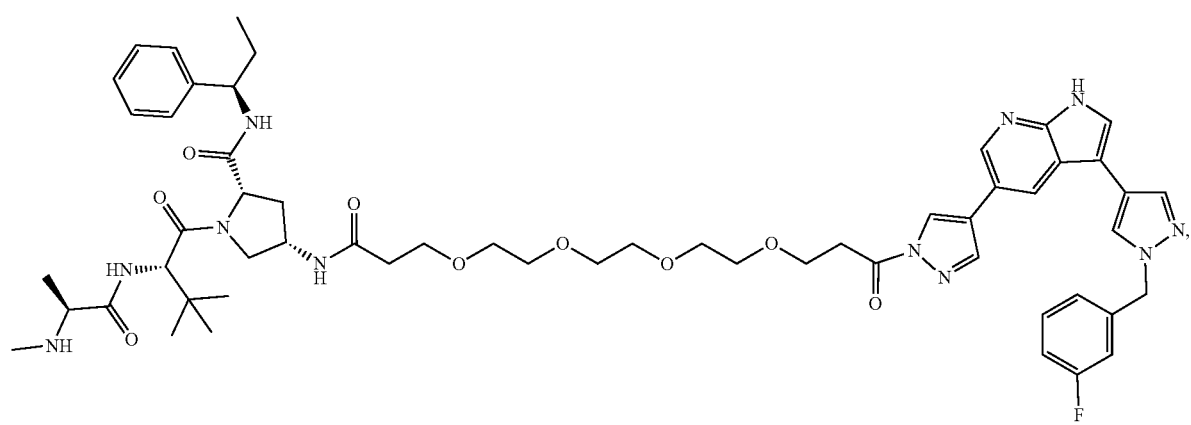

447
-continued
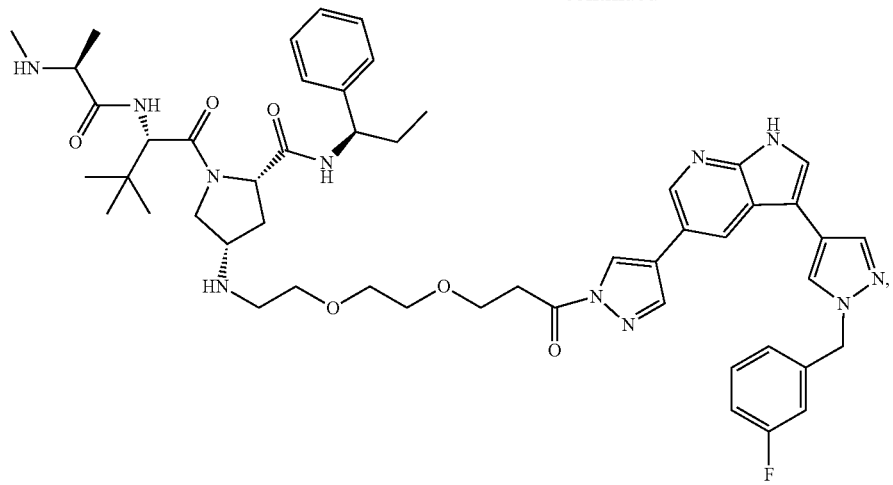
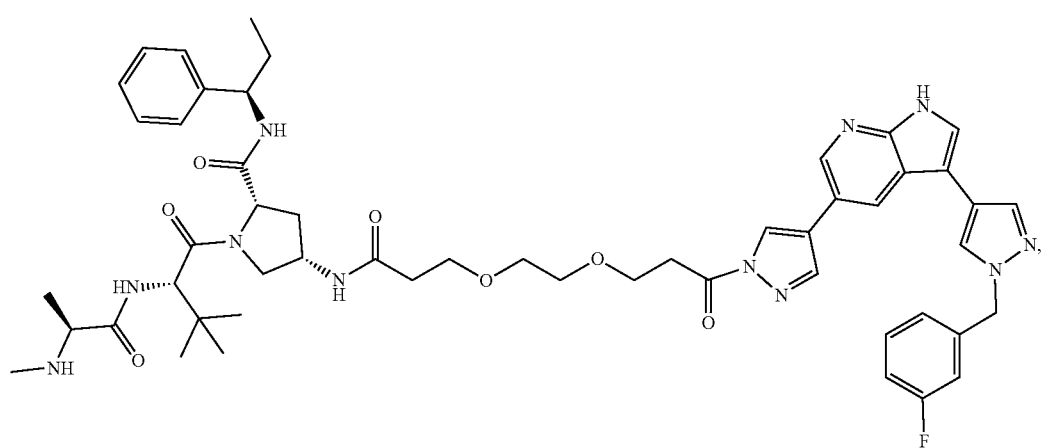
448
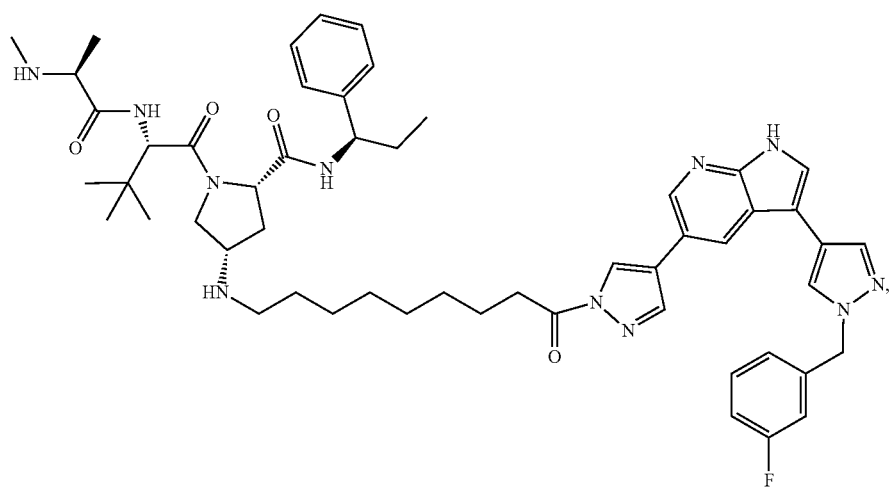

449
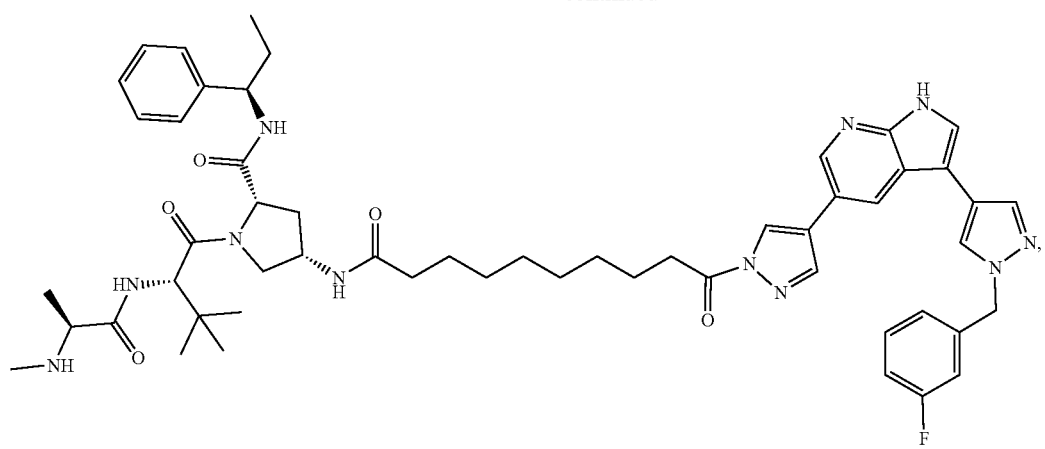
450
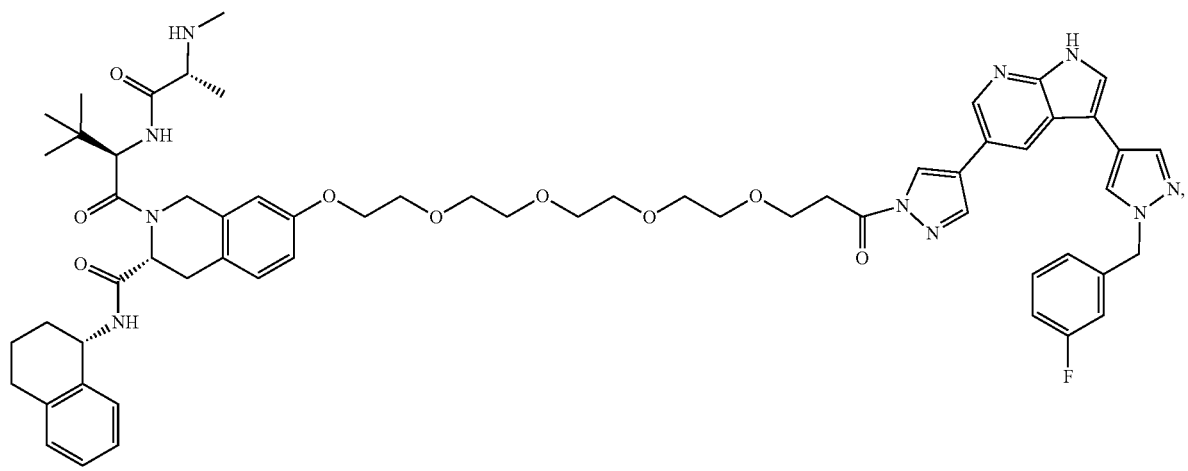
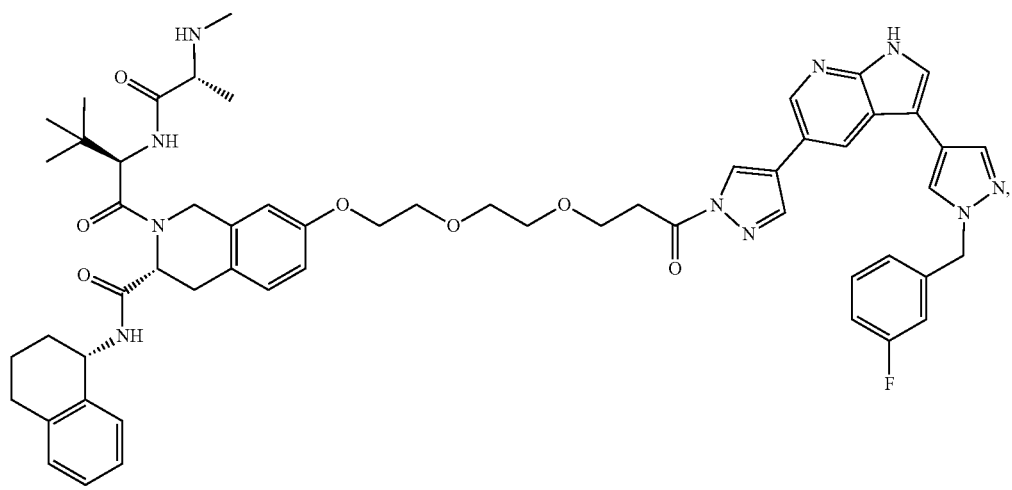

-continued
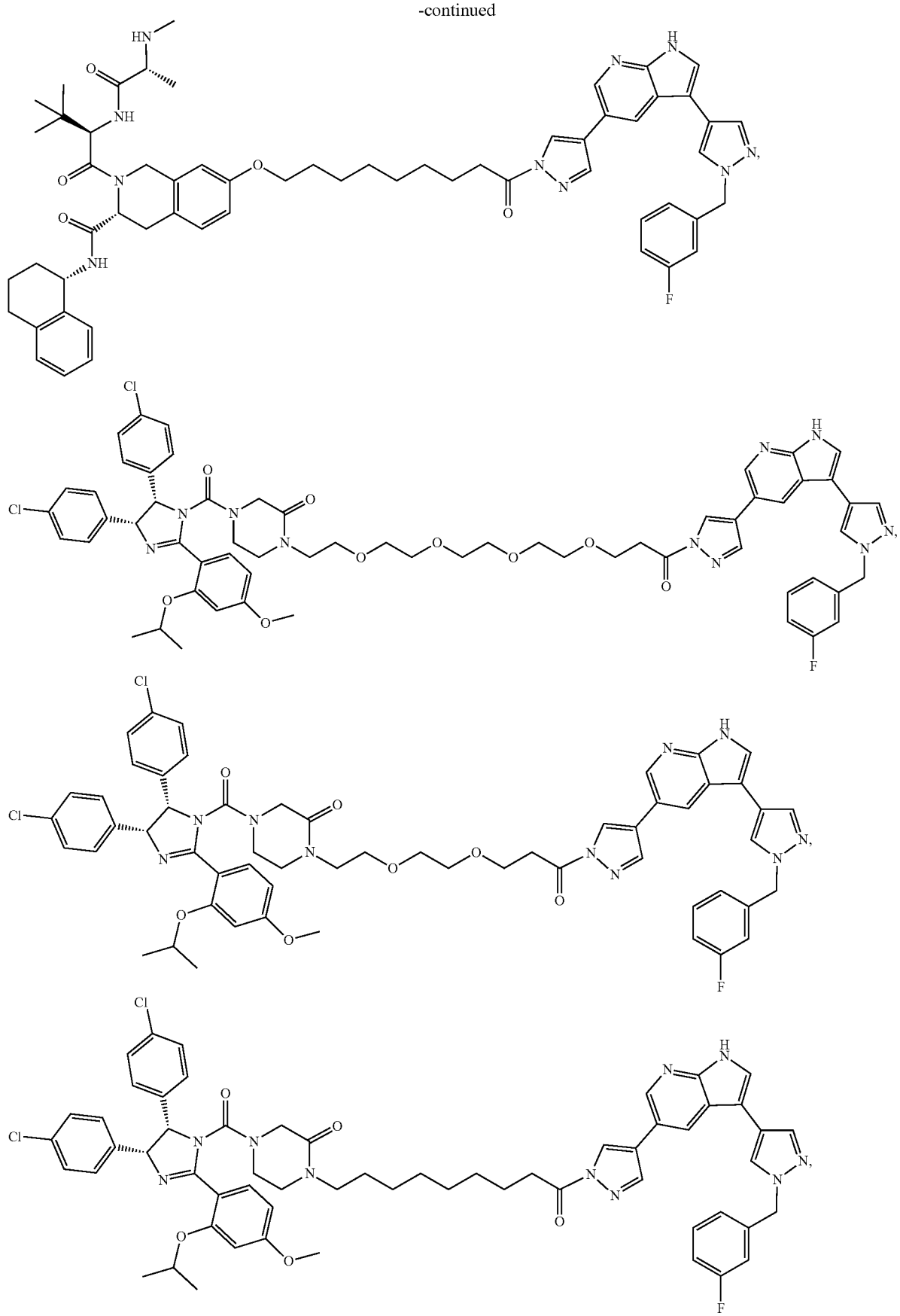

453
454
-continued
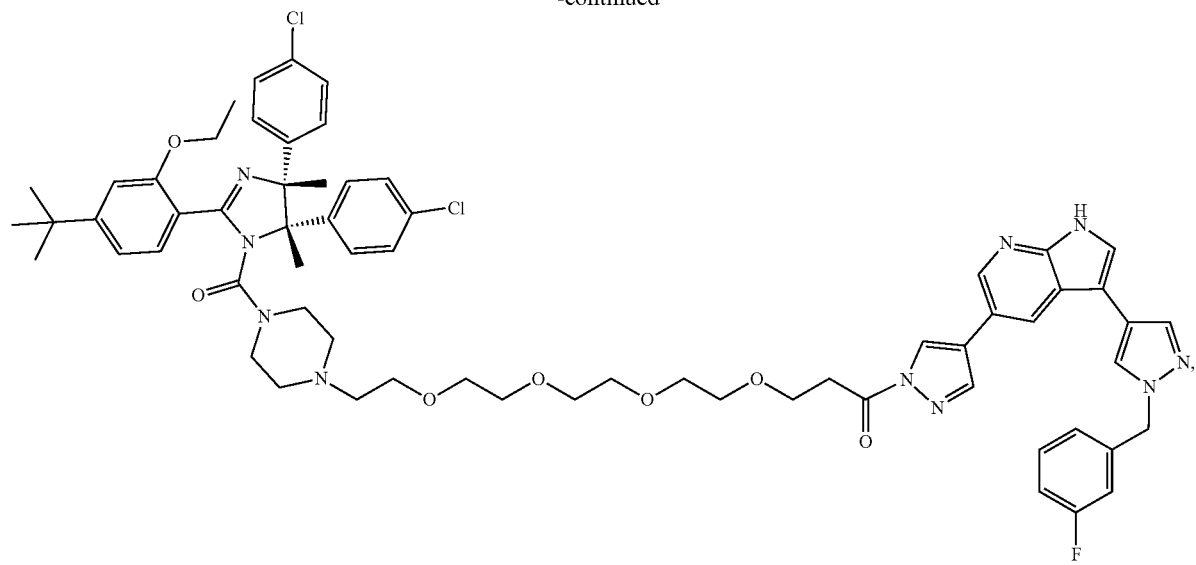
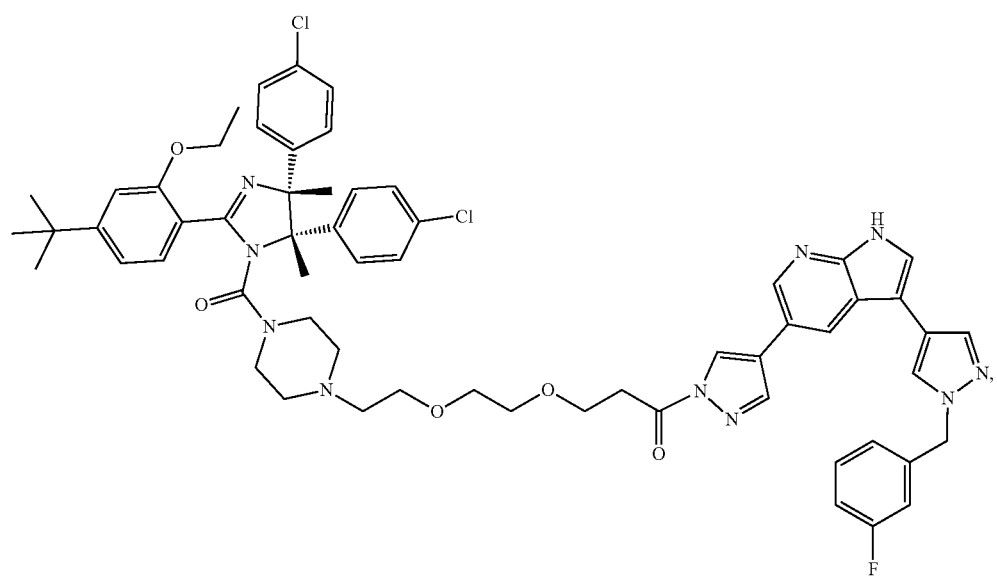
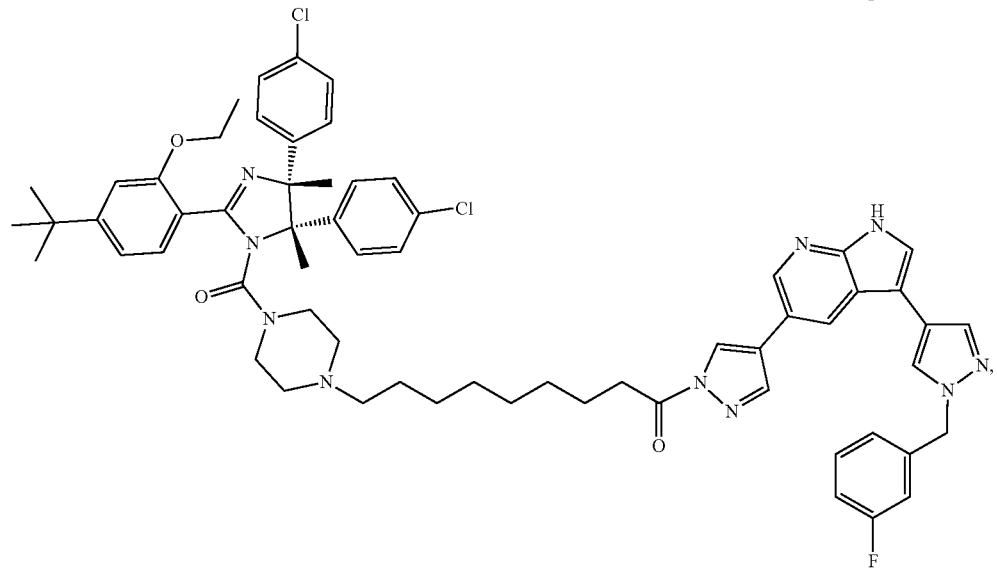

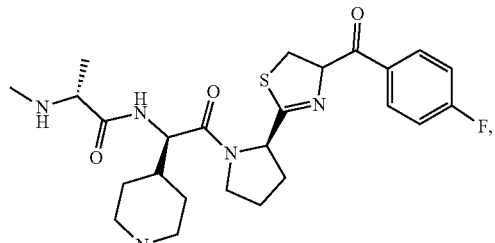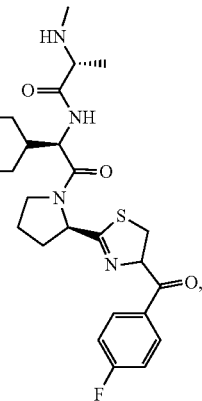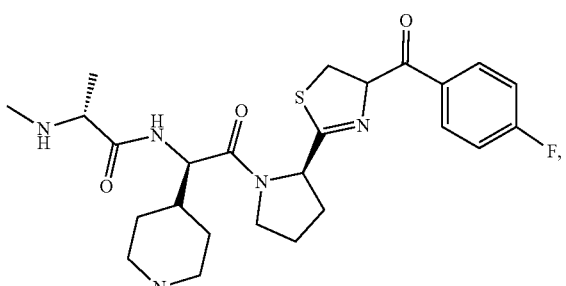

-continued
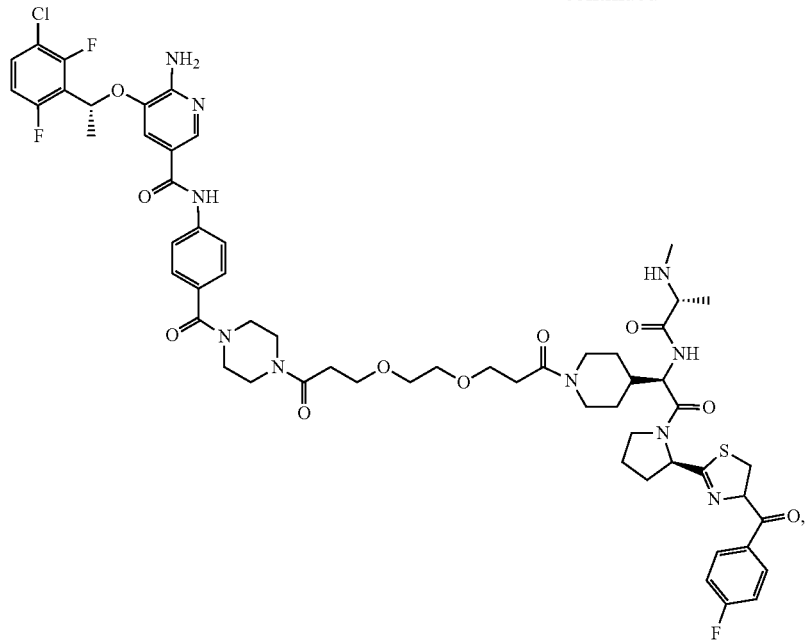
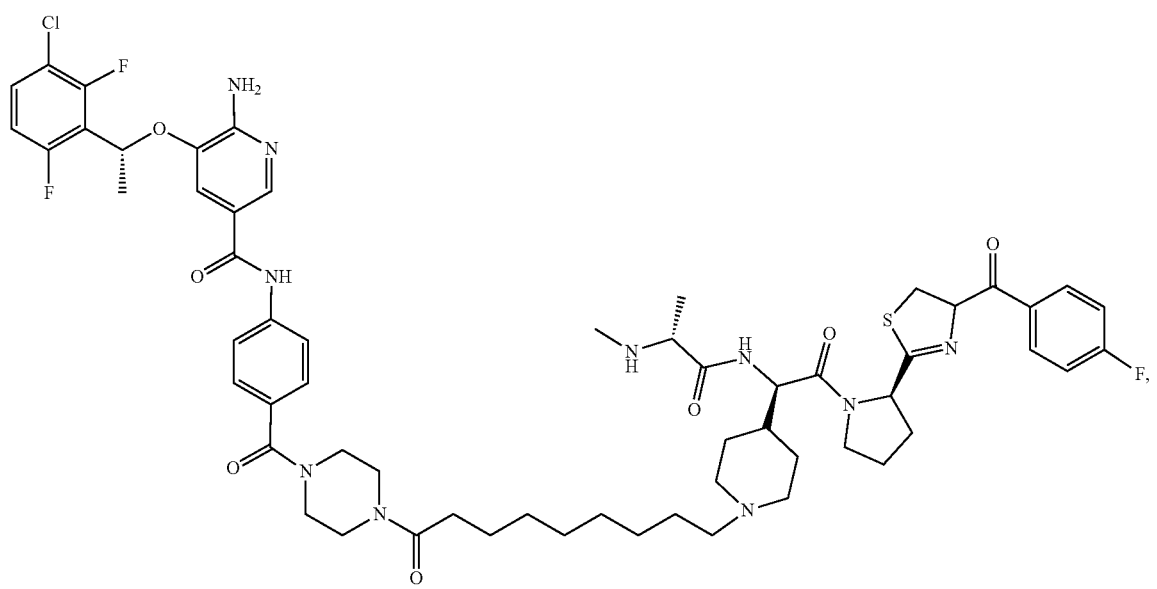

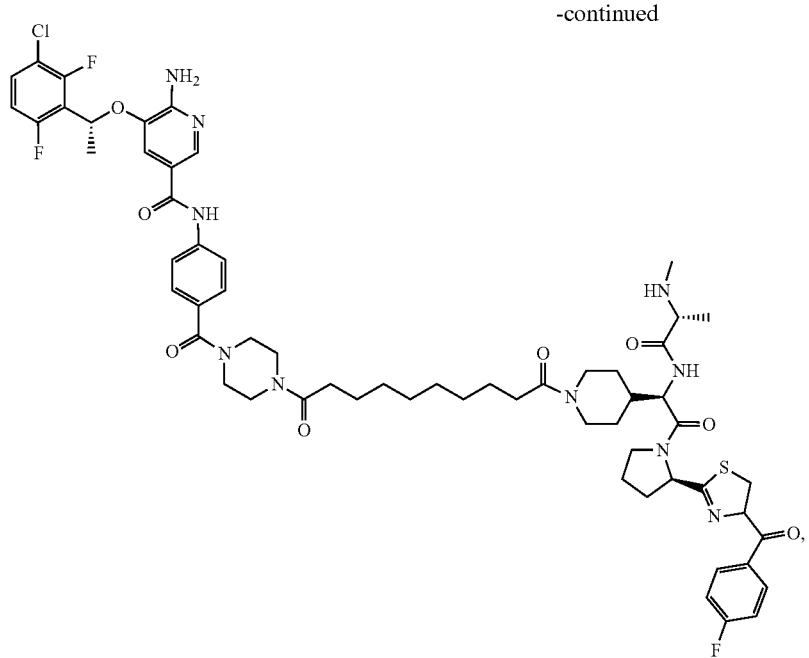
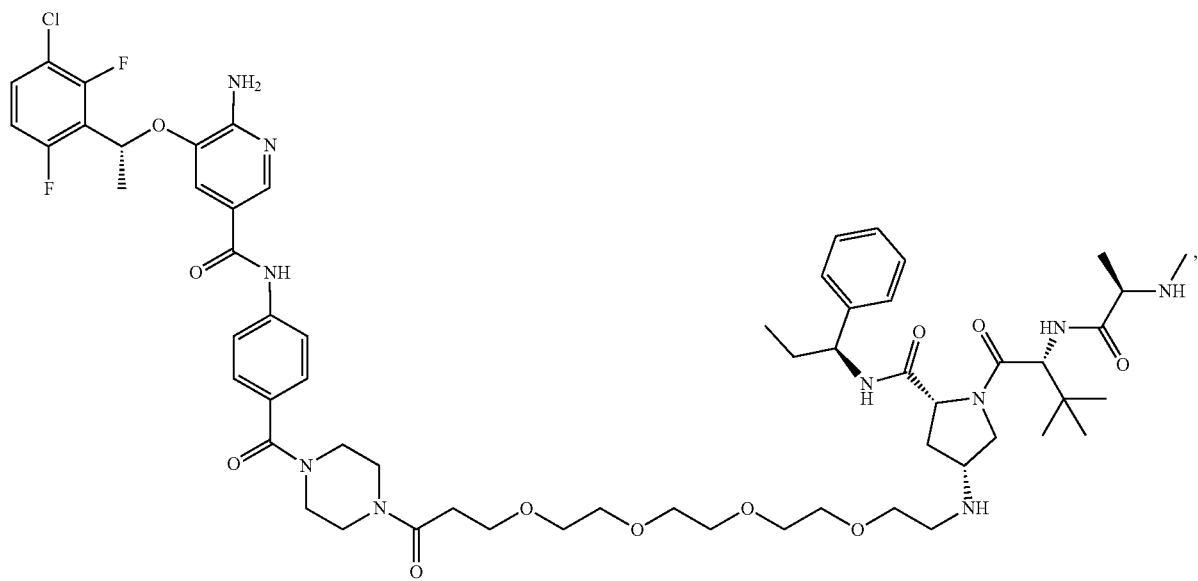

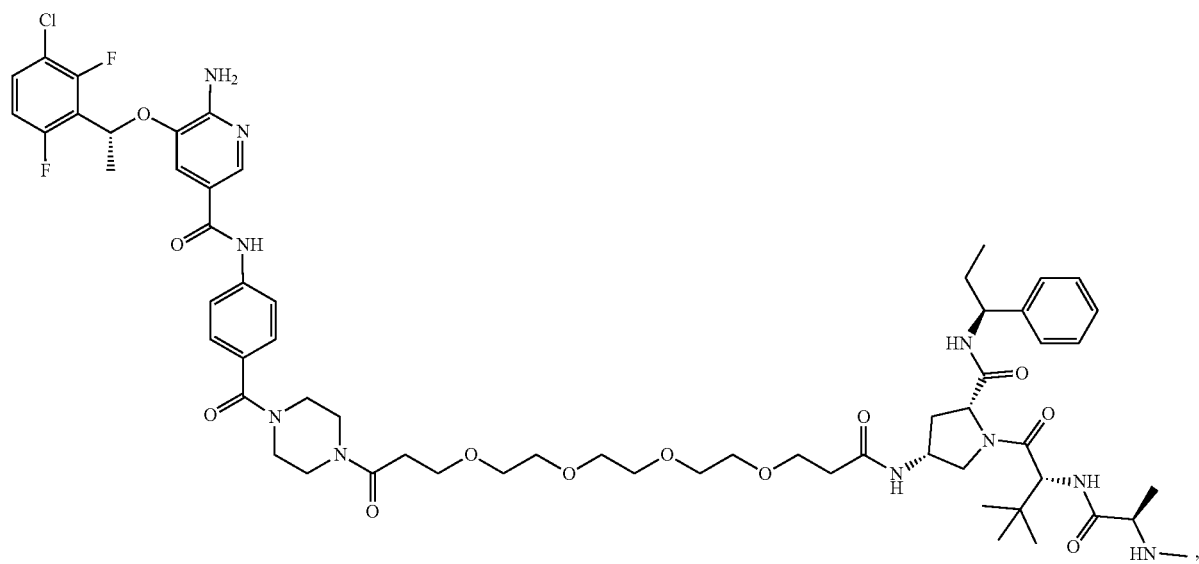
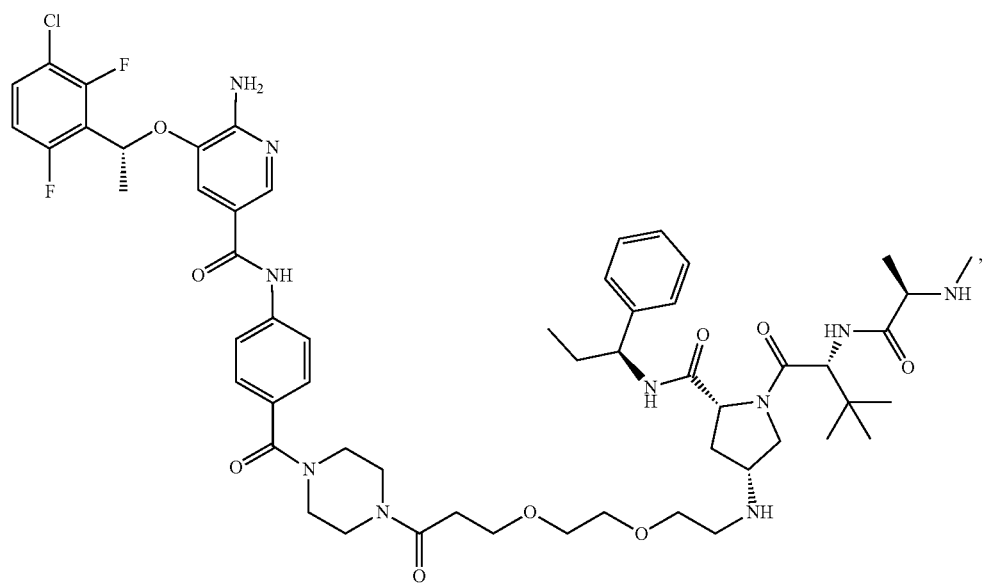

463
464
-continued
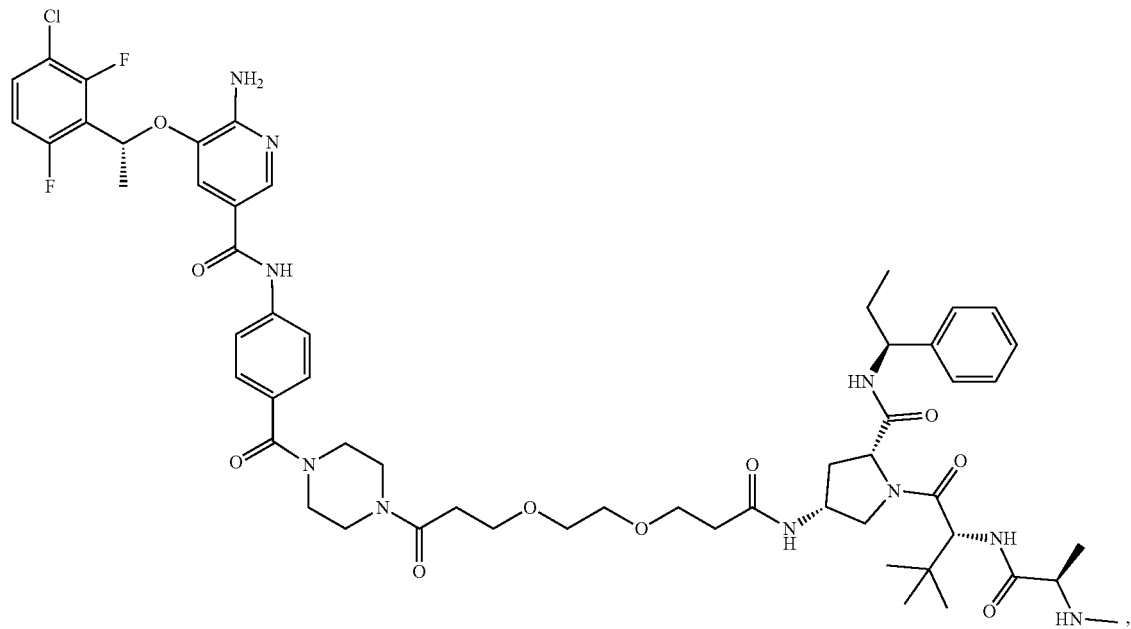
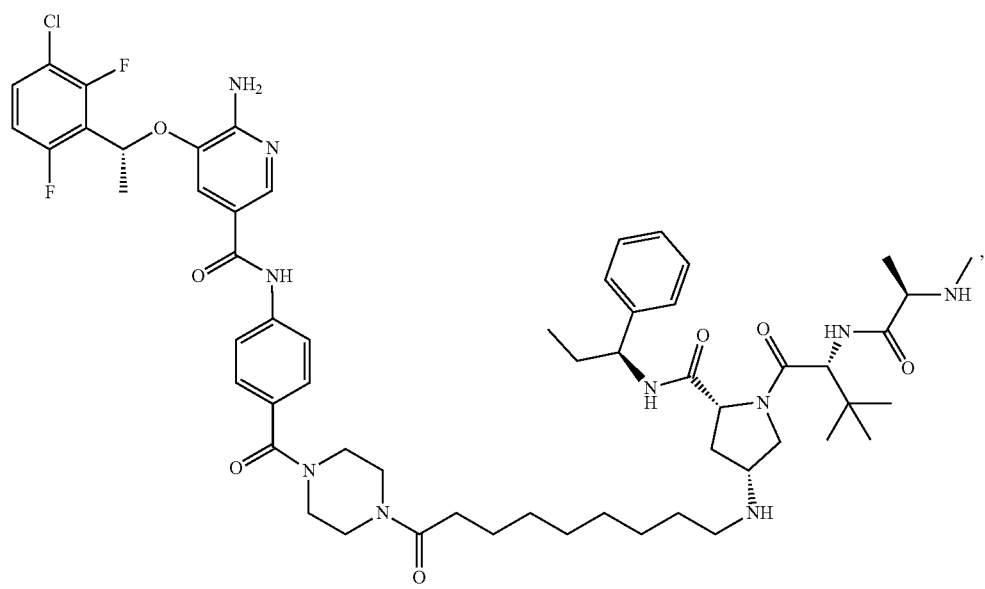

-continued
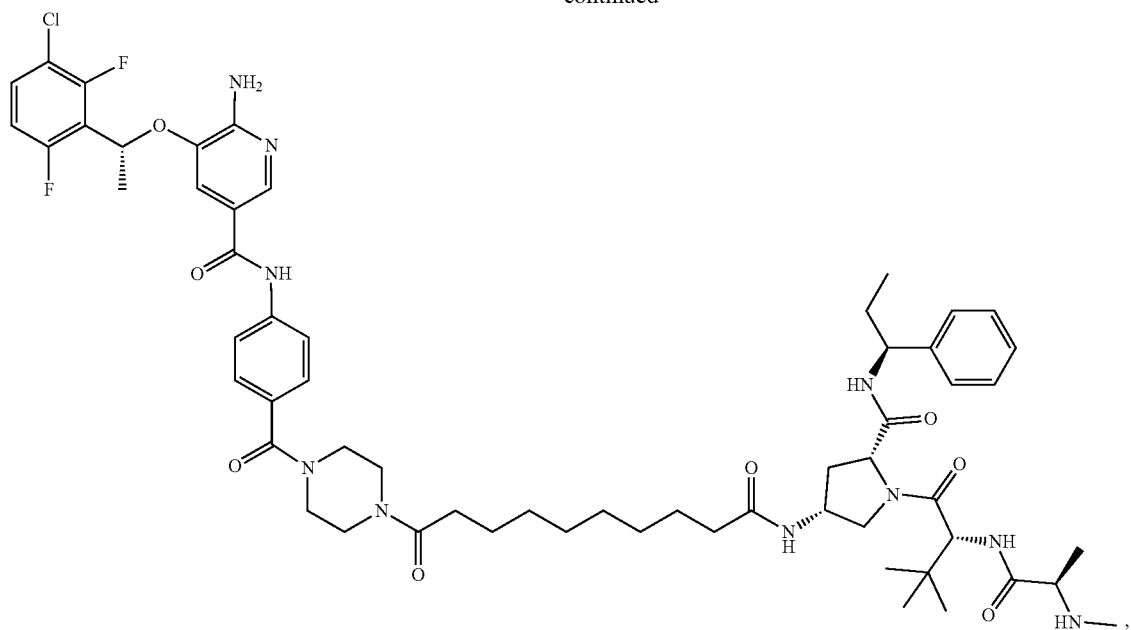
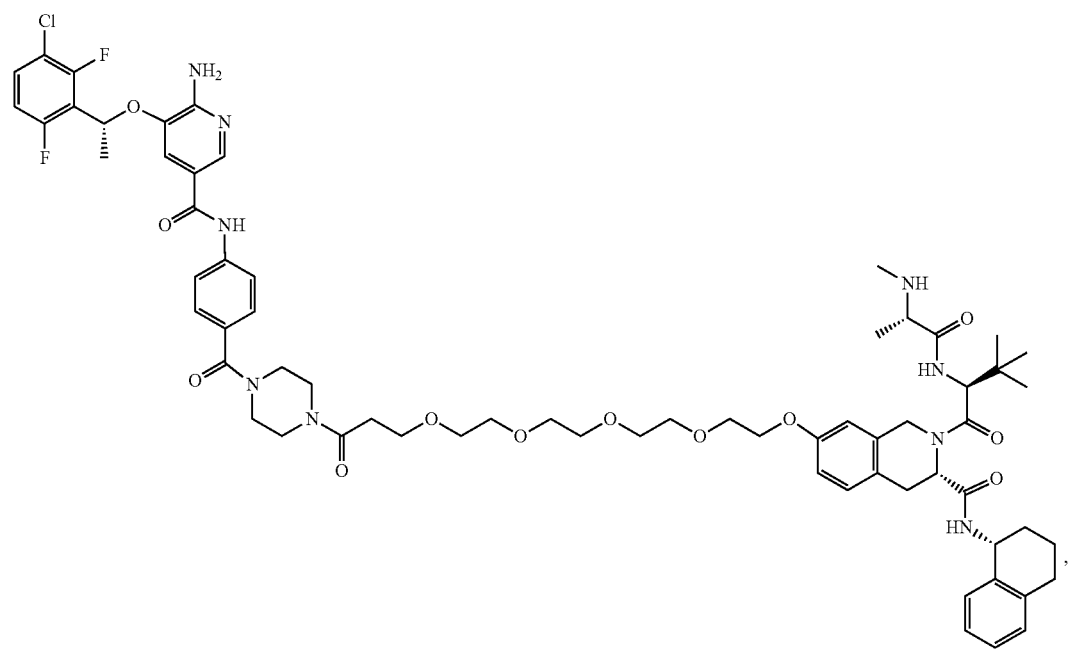

-continued
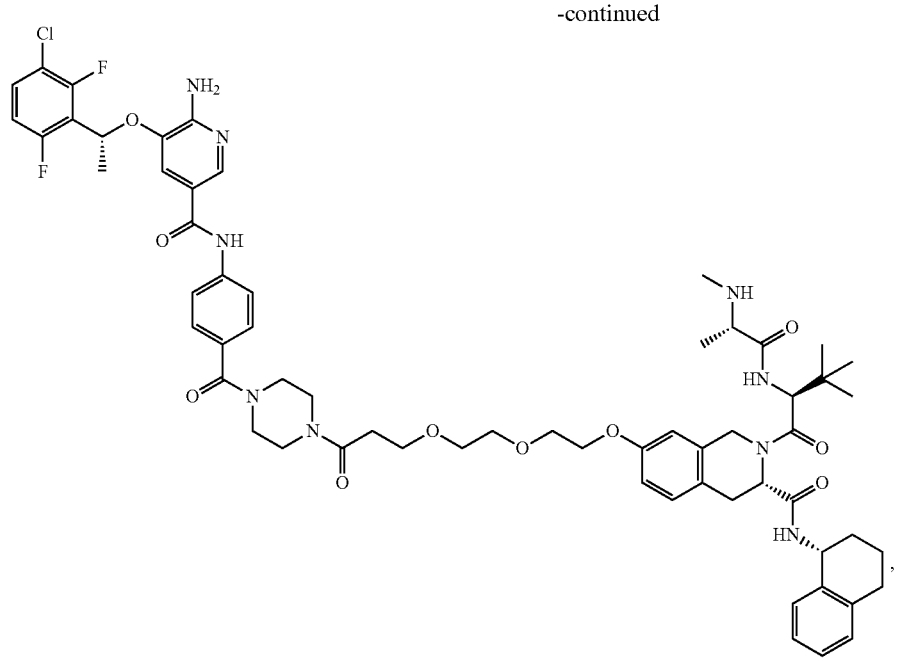
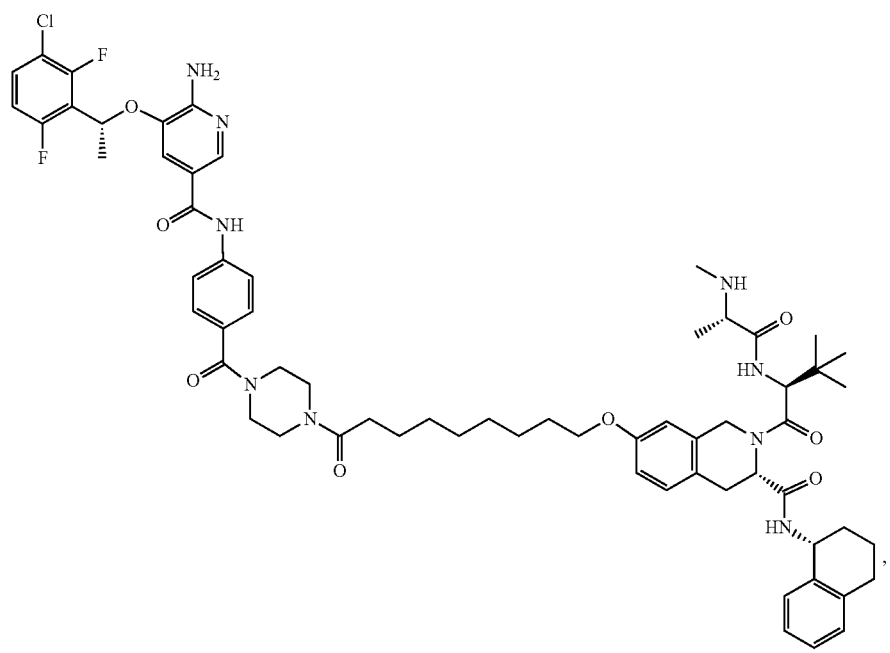

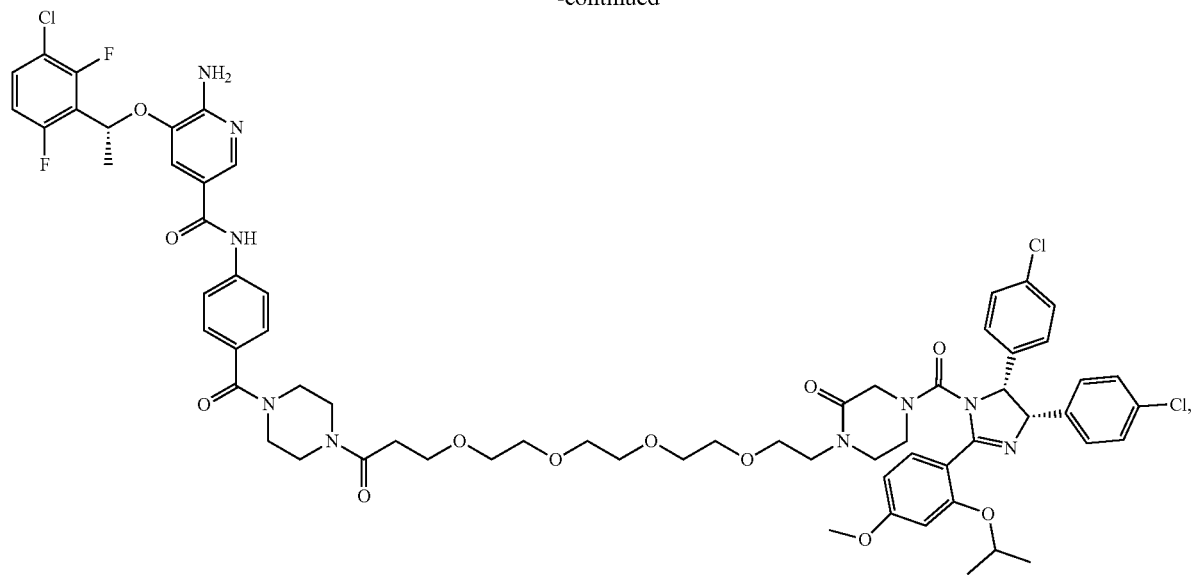
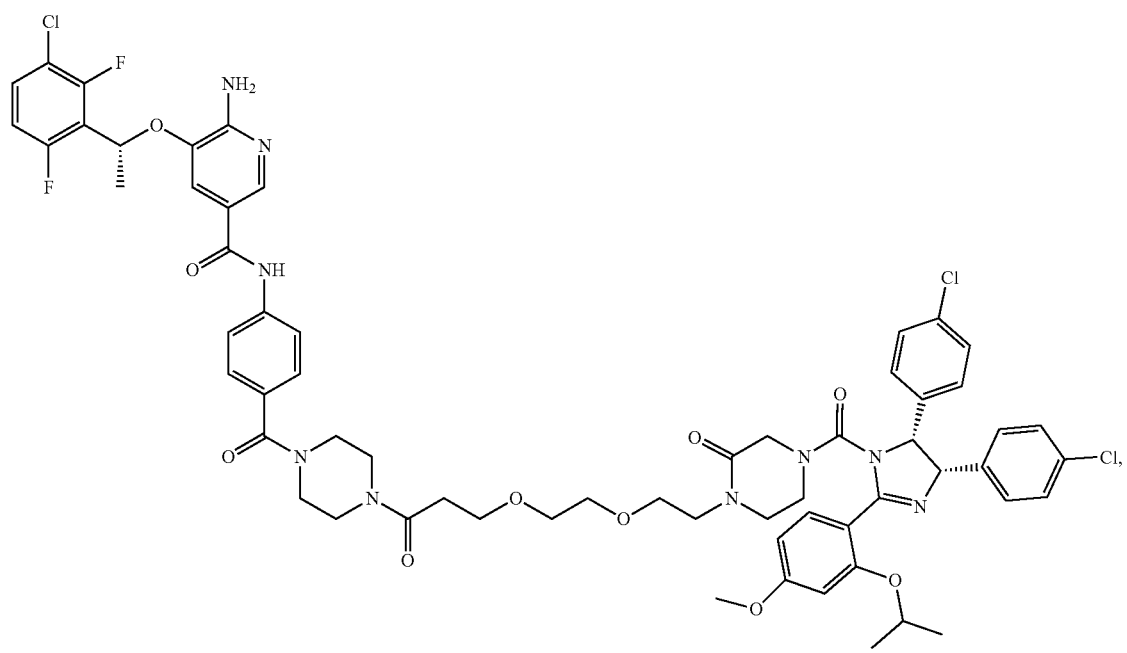

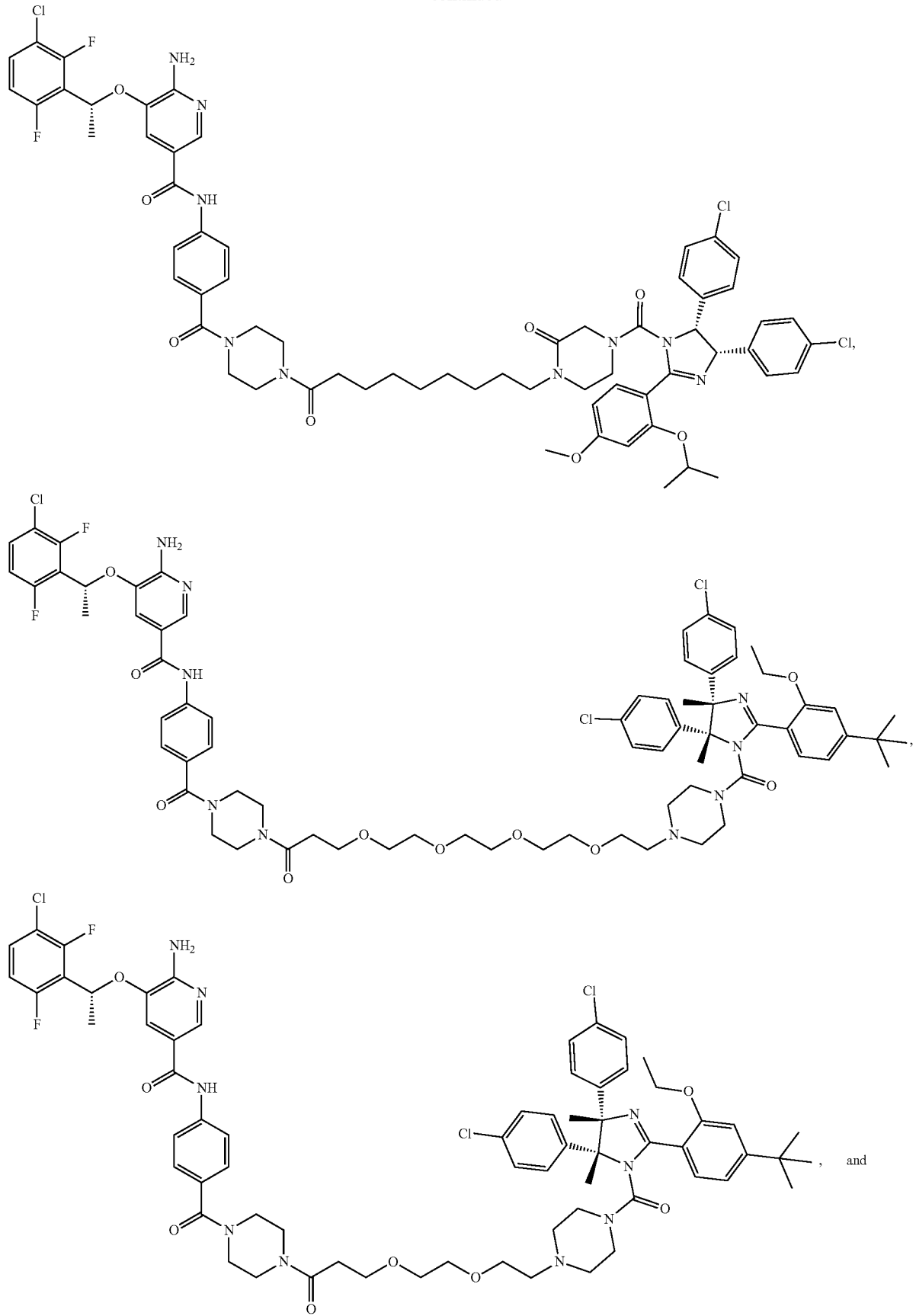

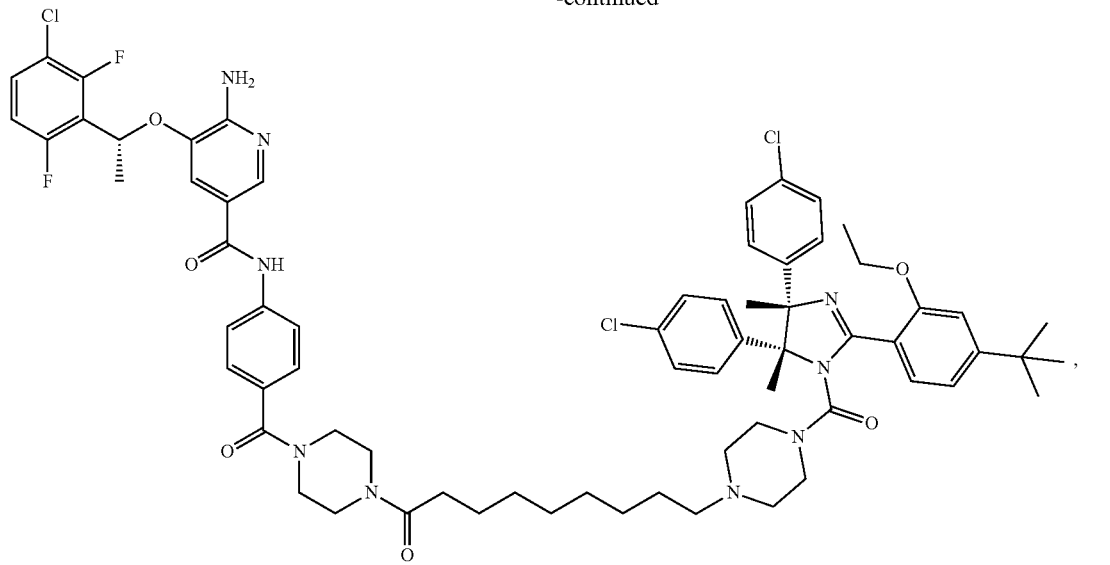

or a pharmaceutically acceptable salts and stereoisomers thereof.

Bispecific compounds of the present invention may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin. Suitable base salts include aluminum, calcium, lithium, magnesium, potassium, sodium, or zinc, salts.

Bispecific compounds of the present invention or a pharmaceutically acceptable salt thereof may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In some embodiments, the bispecific compound or a pharmaceutically acceptable salt or stereoisomer thereof is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

In addition, bispecific compounds of formula (I) and their pharmaceutically acceptable salts and stereoisomers embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In another aspect, the present invention is directed to a method for making a bispecific compound of formula I. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of the bispecific compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bispecific compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., *Remington: The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the bispecific compounds are formulated for oral or intravenous administration (e.g., systemic intravenous injection).

Accordingly, bispecific compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the bispecific compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bispecific compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the bispecific compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bispecific compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The bispecific compounds may be formulated for buccal or sublingual administration, examples of which include tablets, lozenges and gels.

The bispecific compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bispecific compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bispecific compound of formula I or a pharmaceutically acceptable salt or a stereoisomer thereof that is effective in producing the desired therapeutic response in a particular patient suffering from a disease or disorder mediated by aberrant ALK activity. The term "therapeutically effective amount" thus includes the amount of the bispecific compound or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of ALK in diseased cells.

The total daily dosage of the compounds and usage thereof may be decided in accordance with standard medical practice, e.g., by the attending physician using sound medical judgment. The specific therapeutically effective dose for any particular subject will depend upon a variety of factors including the disease or disorder being treated and the severity thereof (e.g., its present status); the activity of the bispecific compound employed; the specific composition employed; the age, body weight, general health, sex and diet of the subject; the time of administration, route of administration, and rate of excretion of the bispecific compound employed; the duration of the treatment; drugs used in combination or coincidental with the specific compound employed; and like factors well known in the medical arts (see, for example, *Goodman and Gilman's The Pharmacological Basis of Therapeutics,* 10th Edition, A. Gilman, J. Hardman and L. Limbird, eds., McGraw-Hill Press, 155-173, 2001).

The bispecific compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g., from 1 to 30 mg/kg per day in one or more dosages per day may be effective. By way of example, a suitable dose for oral administration may be in the range of 1-30 mg/kg of body weight per day, and a suitable dose for intravenous administration may be in the range of −10 mg/kg of body weight per day.

In some embodiments, the bispecific compound is administered in a dose between 100 mg per day and 250 mg per day. In other embodiments the bispecific compound is administered in a dose between 200 mg per day and 400 mg per day, e.g., 250-350 mg per day.

METHODS OF USE

In some aspects, the present invention is directed to treating diseases or disorders, cancerous and non-cancerous alike, characterized or mediated by aberrant (e.g., elevated levels of ALK or otherwise functionally abnormal e.g., deregulated ALK activity relative to a non-pathological state. A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" the treatment may be suffering from or suspected of suffering from a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, the inventive compounds may be useful in the treatment of cell proliferative diseases and disorders (e.g., cancer or benign neoplasms). As used herein, the term "cell proliferative disease or disorder" refers to the conditions characterized by aberrant cell growth, or both, including noncancerous conditions such as neoplasms, precancerous conditions, benign tumors, and cancer.

Exemplary types of non-cancerous (e.g., cell proliferative) diseases or disorders that may be amenable to treatment with bispecific compounds of formula (I) include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In some embodiments, the bispecific compounds may be useful in the treatment of non-cancerous neurodegenerative diseases and disorders. As used herein, the term "neurodegenerative diseases and disorders" refers to the conditions characterized by progressive degeneration or death of nerve cells, or both, including problems with movement (ataxias), or mental functioning (dementias). Representative examples of such diseases and disorders include Alzheimer's disease (AD) and AD-related dementias, Parkinson's disease (PD) and PD-related dementias, prion disease, motor neuron diseases (MND), Huntington's disease (HD), Pick's syndrome, spinocerebellar ataxia (SCA), spinal muscular atrophy (SMA), primary progressive aphasia (PPA), amyotrophic lateral sclerosis (ALS), traumatic brain injury (TBI), multiple sclerosis (MS), dementias (e.g., vascular dementia (VaD), Lewy body dementia (LBD), semantic dementia, and frontotemporal lobar dementia (FTD).

In some embodiments, the bispecific compounds may be useful in the treatment of autoimmune diseases and disorders. As used herein, the term "autoimmune disease" refers to the condition where the immune system produces antibodies that attack normal body tissues. Representative examples of such diseases include Sjogren's syndrome, Hashimoto thyroiditis, rheumatoid arthritis, juvenile (type 1) diabetes, polymyositis, scleroderna, Addison disease, lupus including systemic lupus erythematosus, vitiligo, pernicious anemia, glomerulonephritis, pulmonary fibrosis, celiac disease, polymyalgia rheumatica, multiple sclerosis, ankylosing spondylitis, alopecia areata, vasculitis, and temporal arteritis.

In some embodiments, the methods are directed to treating subjects having cancer. Broadly, the bispecific compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), polycythemia vera, lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, head and neck cancer, Hodgkin's lymphoma, leukemia, lymphoma, multiple myeloma, hepatocellular carcinoma, hypopharyngeal cancer, intraocular melanoma, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, essential thrombocythemia, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present invention entail treatment of subjects having cell proliferative diseases or disorders of the hematological system, liver (hepatocellular), brain, lung, colorectal (e.g., colon), pancreas, prostate, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver (hepatocellular)" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

The bispecific compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but who became intolerant to the particular treatment. Therapy may also be given as an adjuvant treatment, i.e., to prevent reoccurrence of cancer in patients with no currently detectable disease or after surgical removal of a tumor. Thus, in some embodiments, the bifunctional compounds may be administered to a patient who has received another therapy, such as chemotherapy, radioimmunotherapy, surgical therapy, immunotherapy, radiation therapy, targeted therapy or any combination thereof.

The methods of the present invention may entail administration of compounds of the invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the bispecific compound may be dosed twice a day (BID) over the course of two and a half days (for a total of 5 doses) or once a day (QD) over the course of two days (for a total of 2 doses). In other embodiments, the bispecific compound may be dosed once a day (QD) over the course of five days.

Combination Therapy

The bispecific compounds of formula I and their pharmaceutically acceptable salts and stereoisomers may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bispecific compound of formula I or a pharmaceutically acceptable salt or stereoisomer in combination with one or more additional therapeutics known for use in treating the disease or disorder (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; *Physician's Desk Reference* 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the bispecific compound of formula I and the additional agent or therapeutic (e.g., an anti-cancer therapeutic) are cyclically administered. By way of example in the context of cancer treatment, cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, a bispecific compound of the present invention may be used in combination other anti-cancer agents, examples of which include Durvalumab (e.g., for NSCLC), LEE011 (e.g., for NSCLC), Cisplatin, Gemcitabine Hydrochloride, or Paclitaxel Albumin-Stabilized Nanoparticle Formulation (e.g., for advanced malignant solid neoplasm, metastatic pancreatic adenocarcinoma, and Stage III and Stage IV pancreatic cancer), Trametinib (e.g., for NSCLC and neuroblastoma), Axitinib (e.g., for advanced solid tumors), Cobimetinib (e.g., for NSCLC), Brentuximab Vedotin (e.g., for ALK-Positive anaplastic large cell lymphoma, CD30-Positive neoplastic cells, and systemic anaplastic large cell lymphoma), Nivolumab (e.g., for ALK-positive NSCLC), Everolimus (e.g., for head and neck cancer), Pemetrexed, Cisplatin, and Carboplatin (e.g., for NSCLC), Pemetrexed, Cisplatin, and Docetaxel (e.g., for NSCLC), Pemetrexed and Docetaxel (e.g., for NSCLC), Bevacizumab (e.g., for NSCLC), and with Atezolizumab and Erlotinib (e.g., for NSCLC). In some embodiments, a bispecific compound of the present invention may be used alone or in combination with any one or more of Alectinib, Brigatinib, Crizotinib, and Ceritinib (e.g. for non-metastatic or metastatic lung cancer, NSCLC, ALK-positive NSCLC, NSCLC harboring ROS1 Rearrangement, Lung Adenocarcinoma, and Squamous Cell Lung Carcinoma).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the compound of the present invention or a pharmaceutical composition. The kits or pharmaceutical systems of the invention may also include printed instructions for using the bispecific compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of 8-(4-(4-(1-((2-(2,6-dioxopiperidin-3-yl)-1,3-dioxoisoindolin-4-yl)amino)-3,6,9,12-tetraoxapentadecan-15-oyl)piperazin-1-yl)piperidin-1-yl)-9-ethyl-6,6-dimethyl-11-oxo-6,11-dihydro-5H-benzo[b]carbazole-3-carbonitrile (1)

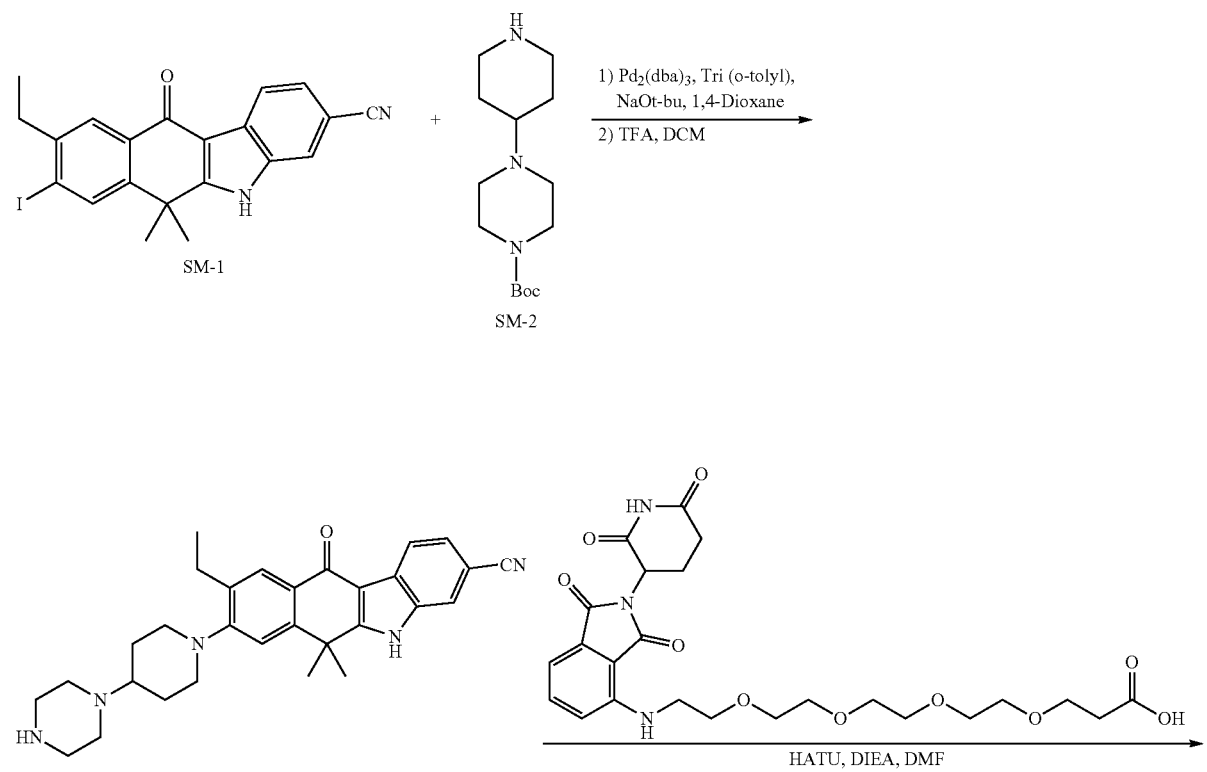

-continued

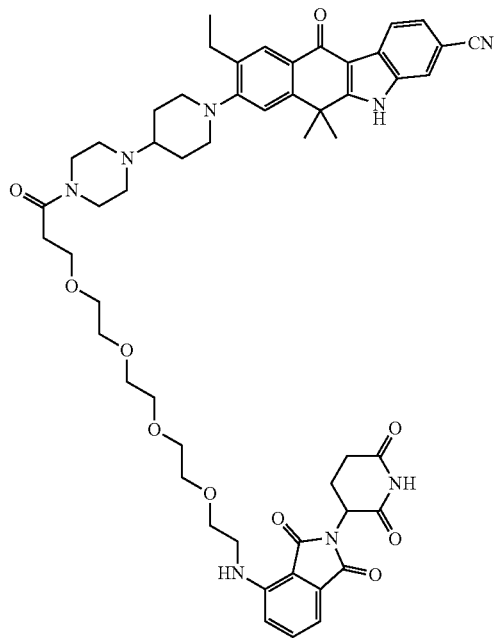

Compounds SM-1 and SM-2 are commercially available.

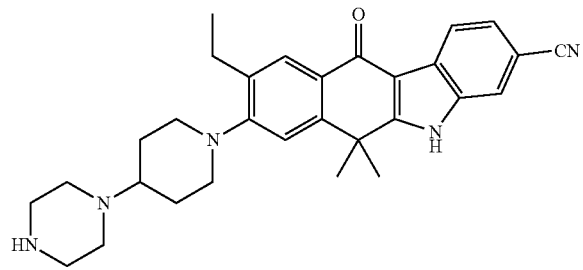 [SMILES: CCc1cc2c(cc1N1CCC(N3CCNCC3)CC1)C(C)(C)c1[nH]c3cc(C#N)ccc3c1C2=O]

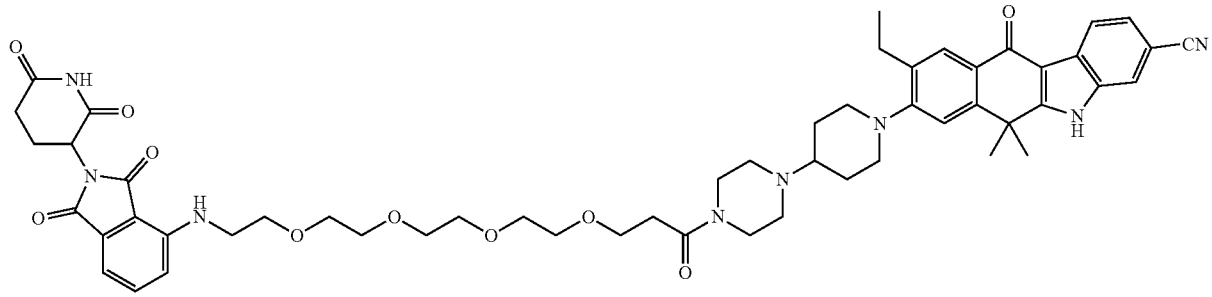 [SMILES: CCc1cc2c(cc1N1CCC(N3CCN(C(=O)CCOCCOCCOCCOCCNc4cccc5c4C(=O)N(C4CCC(=O)NC4=O)C5=O)CC3)CC1)C(C)(C)c1[nH]c3cc(C#N)ccc3c1C2=O]

9-ethyl-6,6-dimethyl-11-oxo-8-(4-(piperazin-1-yl)
piperidin-1-yl)-6,11-dihydro-5H-benzo[b]carbazole-
3-carbonitrile 9-ethyl-6,6-dimethyl-11-oxo-8-(4-(piperazin-1-yl)piperidin-1-yl)-6,11-dihydro-5H-benzo[b]carbazole-3-carbonitrile was prepared according to the procedure described in Hatcher et al., J. Med. Chem. 58(23):9296-9308 (2015), followed by treatment with 10% TFA in DCM (10 mL) for 1 hour. The solvent was then removed under vacuum and the product was used without further purification. MS (ESI) m/z 482.47 (M+H)$^+$.

To a stirred solution of 9-ethyl-6,6-dimethyl-11-oxo-8-(4-(piperazin-1-yl)piperidin-1-yl)-6,11-dihydro-5H-benzo[b]carbazole-3-carbonitrile (20 mg, 0.04 mmol), 1-((2-(2,6-dioxopiperidin-3-yl)-1,3-dioxoisoindolin-4-yl)amino)-3,6,9,12-tetraoxapentadecan-15-oic acid (22 mg, 0.04 mmol), and HATU (30 mg, 0.08 mmol) was added DIEA (35 µL, 0.2 mmol). The mixture was stirred for 15 minutes and then purified by reverse phase HPLC using a gradient of 1% to 70% ACN in H$_2$O to give the title compound as a yellow solid (22 mg, 56% yield). MS (ESI) m/z 986.38 (M+H)$^+$.

Example 2: Synthesis of 8-(4-(4-(3-(2-(2-((2-(2,6-dioxopiperidin-3-yl)-1,3-dioxoisoindolin-4-yl)amino)ethoxy)ethoxy)propanol)piperazin-1-yl)piperidin-1-yl)-9-ethyl-6,6-dimethyl-11-oxo-6,11-dihydro-5H-benzo[b]carbazole-3-carbonitrile (2)

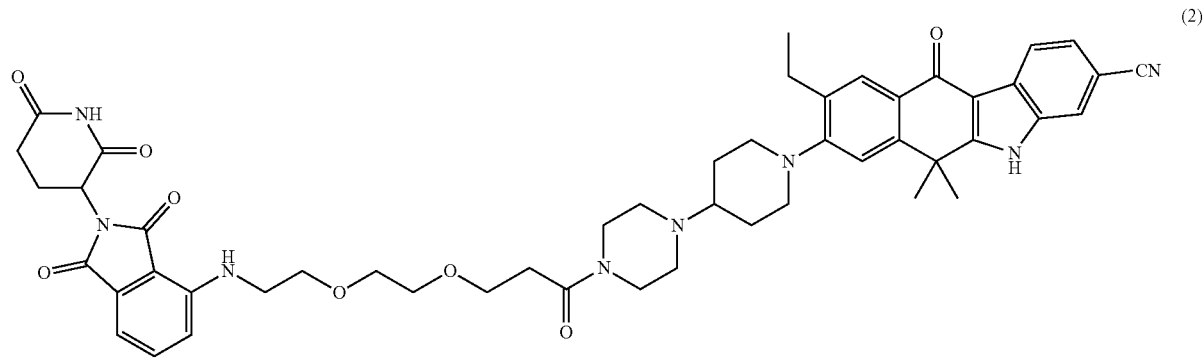 [SMILES: CCc1cc2c(cc1N1CCC(N3CCN(C(=O)CCOCCOCCNc4cccc5c4C(=O)N(C4CCC(=O)NC4=O)C5=O)CC3)CC1)C(C)(C)c1[nH]c3cc(C#N)ccc3c1C2=O]

Compound 2 was prepared in an analogous manner to compound 1 in example 1 with 3-(2-(2-((2-(2,6-dioxopiperidin-3-yl)-1,3-dioxoisoindolin-4-yl)amino)ethoxy)ethoxy)propanoic acid. MS (ESI) m/z 898.29 (M+H)$^+$.

Example 3: Synthesis of 8-(4-(4-(9-((2-(2,6-dioxopiperidin-3-yl)-1,3-dioxoisoindolin-4-yl)amino)nonanoyl)piperazin-1-yl)piperidin-1-yl)-9-ethyl-6,6-dimethyl-11-oxo-6,11-dihydro-5H-benzo[b]carbazole-3-carbonitrile (3)

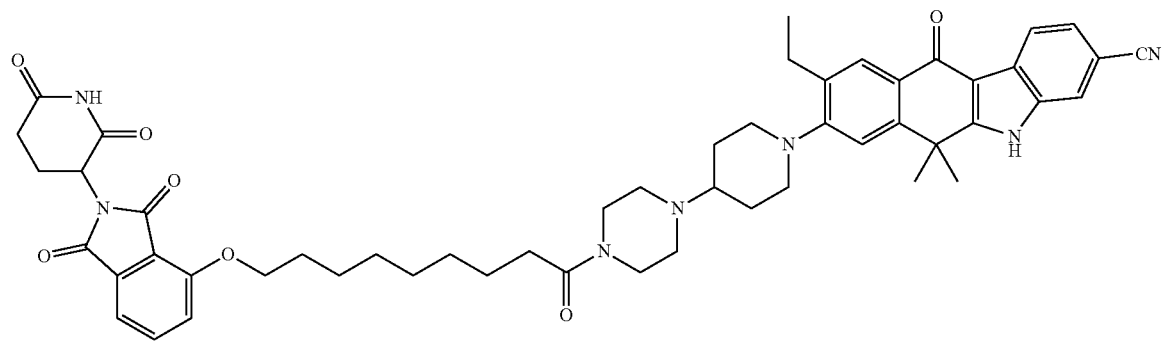 [SMILES: CCc1cc2c(cc1N1CCC(N3CCN(C(=O)CCCCCCCCOc4cccc5c4C(=O)N(C4CCC(=O)NC4=O)C5=O)CC3)CC1)C(C)(C)c1[nH]c3cc(C#N)ccc3c1C2=O]

Compound 3 was prepared in an analogous manner to compound 1 in example 1 with 9-((2-(2,6-dioxopiperidin-3-yl)-1,3-dioxoisoindolin-4-yl)amino)nonanoic acid. MS (ESI) m/z 894.09 (M+H)$^+$.

Example 4: Synthesis of 2-(4-(3-cyano-9-ethyl-6,6-dimethyl-11-oxo-6,11-dihydro-5H-benzo[b]carbazol-8-yl)-1H-pyrazol-1-yl)-N-(14-((2-(2,6-dioxopiperidin-3-yl)-1,3-dioxoisoindolin-4-yl)amino)-3,6,9,12-tetraoxatetradecyl)-N-methylacetamide (7)

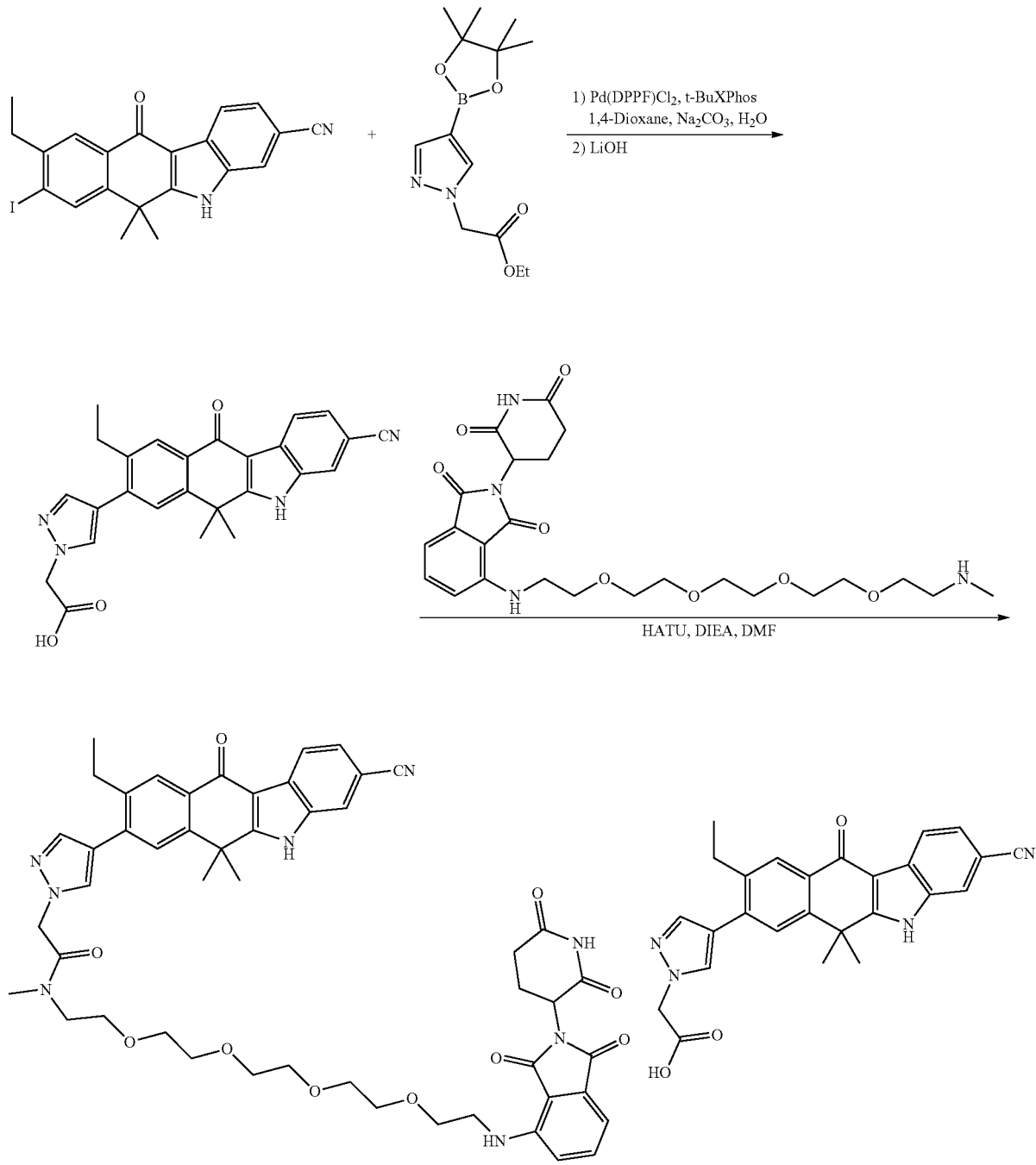

2-(4-(3-cyano-9-ethyl-6,6-dimethyl-11-oxo-6,11-dihydro-5H-benzo[b]carbazol-8-yl)-1H-pyrazol-1-yl)acetic acid 2-(4-(3-cyano-9-ethyl-6,6-dimethyl-11-oxo-6,11-dihydro-5H-benzo[b]carbazol-8-yl)-1H-pyrazol-1-yl)acetic acid was prepared according to the procedure described in Hatcher et al., J. Med. Chem. 58(23):9296-9308 (2015).

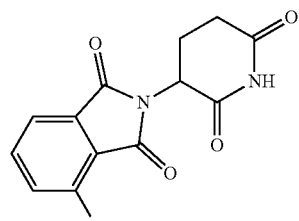
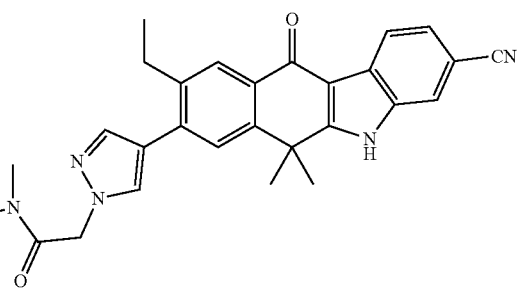

(7)

To a stirred solution of 2-(4-(3-cyano-9-ethyl-6,6-dimethyl-11-oxo-6,11-dihydro-5H-benzo[b]carbazol-8-yl)-1H-pyrazol-1-yl)acetic acid (7) (15 mg, 0.034 mmol), 4-((5,8,11,14-tetraoxa-2-azahexadecan-16-yl)amino)-2-(2,6-dioxopiperidin-3-yl)isoindoline-1,3-dione (8) (17 mg, 0.034 mmol) and HATU (26 mg, 0.068 mmol) was added DIEA (30 μL, 0.17 mmol). The mixture was stirred for 15 minutes and then purified by reverse phase HPLC using a gradient of 1% to 70% ACN in H$_2$O to give the title compound as a yellow solid (14 mg, 41% yield). MS (ESI) m/z 928.61 (M+H)$^+$.

Example 5: Synthesis of 2-(4-(3-cyano-9-ethyl-6,6-dimethyl-11-oxo-6,11-dihydro-5H-benzo[b]carbazol-8-yl)-1H-pyrazol-1-yl)-N-(2-(2-(2-((2-(2,6-dioxopiperidin-3-yl)-1,3-dioxoisoindolin-4-yl)amino)ethoxy)ethoxy)ethyl)acetamide (4)

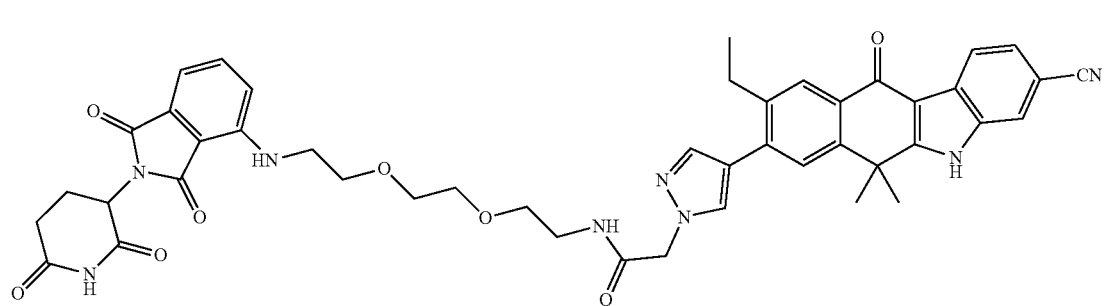

(4)

Compound 4 was prepared in an analogous manner to compound 7 in example 4 with 4-((2-(2-(2-aminoethoxy)ethoxy)ethyl)amino)-2-(2,6-dioxopiperidin-3-yl)isoindoline-1,3-dione. MS (ESI) m/z 825.73 (M+H)$^+$.

Example 6: Synthesis of 2-(4-(3-cyano-9-ethyl-6,6-dimethyl-11-oxo-6,11-dihydro-5H-benzo[b]carbazol-8-yl)-1H-pyrazol-1-yl)-N-(20-((2-(2,6-dioxopiperidin-3-yl)-1,3-dioxoisoindolin-4-yl)amino)-3,6,9,12,15,18-hexaoxaicosyl)acetamide (5)

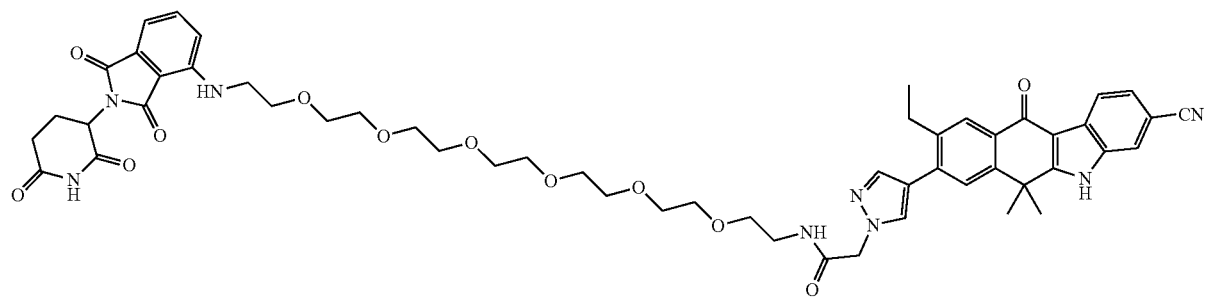

(5)

Compound 5 was prepared in an analogous manner to compound 7 in example 4 with 4-((20-amino-3,6,9,12,15,18-hexaoxaicosyl)amino)-2-(2,6-dioxopiperidin-3-yl)isoindoline-1,3-dione. MS (ESI) m/z 1002.46 (M+H)$^+$.

Example 7: Synthesis of 2-(4-(3-cyano-9-ethyl-6,6-dimethyl-11-oxo-6,11-dihydro-5H-benzo[b]carbazol-8-yl)-1H-pyrazol-1-yl)-N-(14-((2-(2,6-dioxopiperidin-3-yl)-1,3-dioxoisoindolin-4-yl)amino)-3,6,9,12-tetraoxatetradecyl)acetamide (6)

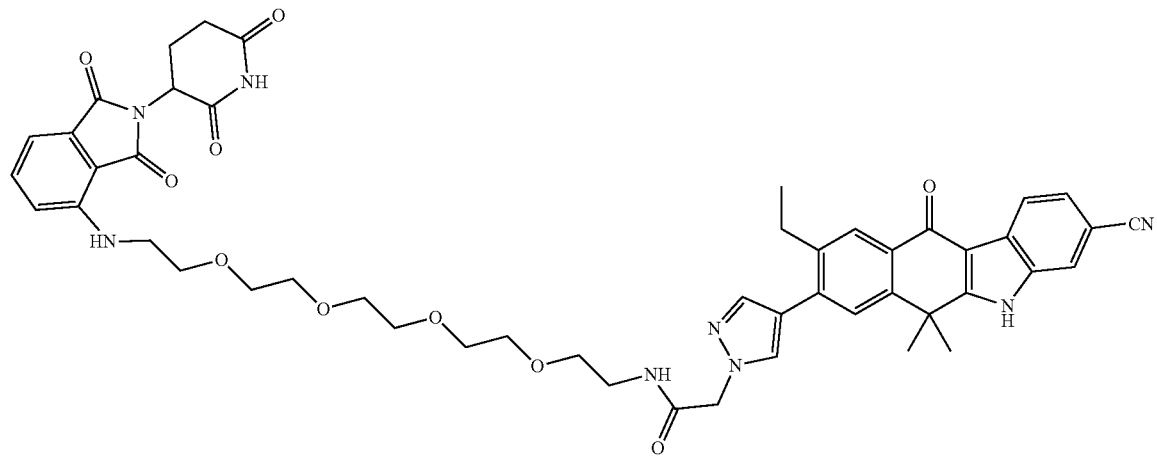

(6)

Compound 6 was prepared in an analogous manner to compound 7 in example 4 with 4-((14-amino-3,6,9,12-tetraoxatetradecyl)amino)-2-(2,6-dioxopiperidin-3-yl)isoindoline-1,3-dione. MS (ESI) m/z 913.79 (M+H)$^+$.

Example 8: Synthesis of 2-(4-(3-cyano-9-ethyl-6,6-dimethyl-11-oxo-6,11-dihydro-5H-benzo[b]carbazol-8-yl)-1H-pyrazol-1-yl)-N-(2-(2-(2-(2-((2-(2,6-dioxopiperidin-3-yl)-1,3-dioxoisoindolin-4-yl)amino)ethoxy)ethoxy)ethoxy)ethyl)-N-methylacetamide (8)

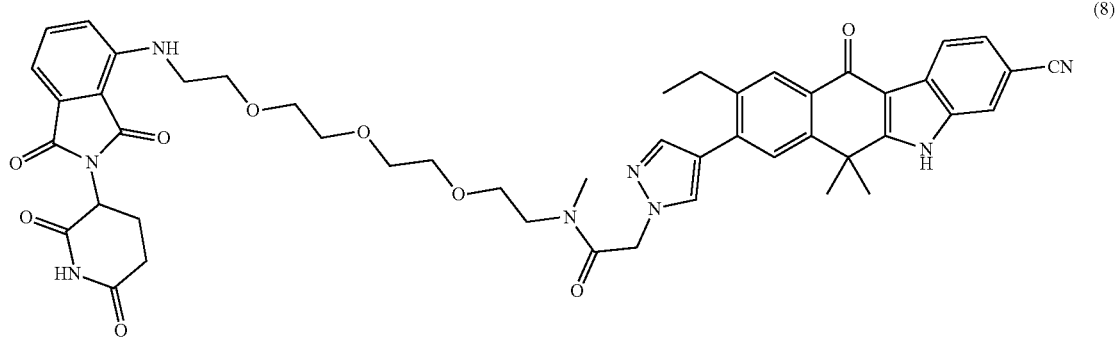 [SMILES: CCc1cc2c(cc1-c1cnn(CC(=O)N(C)CCOCCOCCOCCNc3cccc4c3C(=O)N(C3CCC(=O)NC3=O)C4=O)c1)C(C)(C)c1[nH]c3cc(C#N)ccc3c1C2=O]

Compound 8 was prepared in an analogous manner to compound 7 in example 4 with 4-((5,8,11-trioxa-2-azatridecan-13-yl)amino)-2-(2,6-dioxopiperidin-3-yl)isoindoline-1,3-dione. MS (ESI) m/z 883.62 (M+H)⁺.

Example 9: Synthesis of Non-Inventive Compound 13

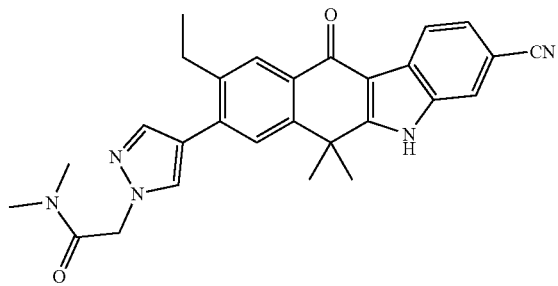

Compound 13 was prepared according to the procedure described in Hatcher et al., J. Med. Chem. 58(23):9296-9308 (2015).

Example 10: Synthesis of N-(2-(2-(2-(4-(4-((5-Chloro-4-((2-(isopropylsulfonyl)phenyl)-amino)pyrimidin-2-yl)amino)-3-methoxyphenyl)piperazin-1-yl)ethoxy)ethoxy)ethyl)-2-((1,3-dioxo-2-(2-oxopiperidin-3-yl)-isoindolin-4-yl)amino)acetamide (9)

Compound 9 was prepared in an analogous manner to compound 10 in example 11. ¹H NMR (500 MHz, DMSO-d₆) δ 9.78 (br, 1H), 9.59 (s, 1H), 8.55 (br, 1H), 8.44 (s, 1H), 8.20 (s, 1H), 8.18 (dd, J=6.0, 5.5 Hz, 1H), 7.82 (s, 1H), 7.81 (d, J=8.0 Hz, 1H), 7.60 (m, 1H), 7.55 (dd, J=8.0, 7.5 Hz, 1H), 7.40 (d, J=8.5 Hz, 1H), 7.31 (dd, J=7.5, 7.5 Hz, 1H), 7.04 (d, J=7.0 Hz, 1H), 6.95 (m, 1H), 6.82 (d, J=8.5 Hz, 1H), 6.71 (d, J=2.5 Hz, 1H), 6.53 (dd, J=8.5, 2.5 Hz, 1H), 4.52 (dd, J=12.0, 6.5 Hz, 1H), 3.93 (d, J=4.5 Hz, 2H), 3.85 (m, 2H), 3.80 (m, 2H), 3.77 (s, 3H), 3.60 (m, 4H), 3.57 (m, 2H), 3.46 (m, 4H), 3.40 (m, 2H), 3.30 (m, 2H), 3.22 (m, 2H), 3.03 (m, 2H), 2.20 (m, 1H), 1.96 (m, 1H), 1.89 (m, 2H), 1.16 (d, J=6.5 Hz, 6H). MS (ESI) m/z 947 (M+H)⁺.

Example 11: Synthesis of N-(2-(2-(2-(4-(4-((5-Chloro-4-((2-(isopropylsulfonyl)phenyl)-amino)pyrimidin-2-yl)amino)-3-methoxyphenyl)piperazin-1-yl)ethoxy)ethoxy)ethyl)-2-((2-(2,6-dioxopiperidin-3-yl)-1,3-dioxoisoindolin-4-yl)amino)acetamide (10)

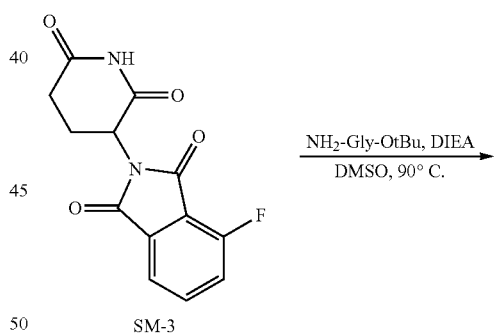

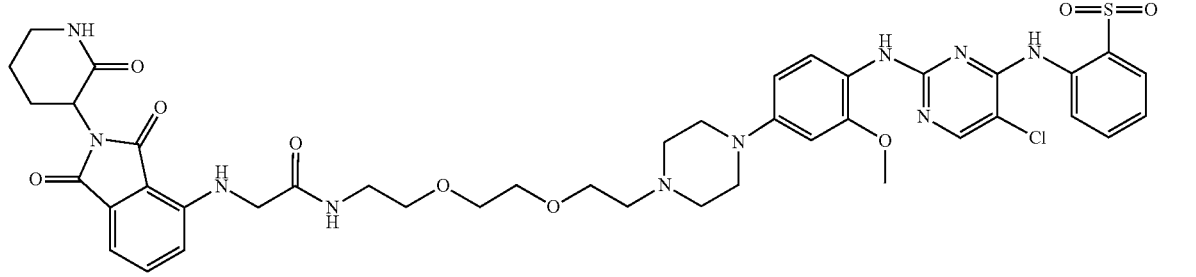

501
-continued

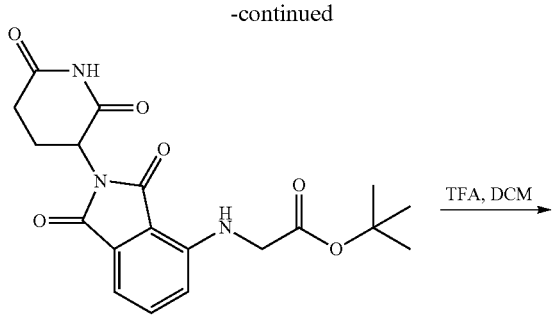

502
tert-Butyl (2-(2,6-Dioxopiperidin-3-yl)-1,3-dioxoisoindolin-4-yl)glycinate

SM-3 was prepared according to Lu et al., Chem. Biol. 22:755-763 (2015). To SM-3 (550 mg, 2.0 mmol) and glycine tert-butyl ester (260 mg, 2.0 mmol) in anhydrous DMSO (20 mL) was added N,N-diisopropylethylamine (DIEA) (700 μL, 4.0 mmol). The reaction mixture was stirred under 90° C. for 1 day, then cooled down. The mixture was diluted with ethyl acetate (200 mL), washed with water and brine, dried with Na2SO4, then filtered and concentrated, purified by column chromatography (dichloromethane/ethyl acetate=2:1) to give the title compound as a yellow oil (530 mg, 68%). $^1$H NMR (400 MHz, CDCl$_3$) δ 8.06 (s, 1H), 7.51 (dd, J=8.4, 7.2 Hz, 1H), 7.15 (d, J=7.6 Hz, 1H), 6.76 (d, J=6.76 Hz, 1H), 4.93 (dd, J=12.0, 6.4 Hz, 1H), 3.94 (s, 2H), 2.67-2.92 (m, 2H), 2.12 (m, 1H), 1.93 (m, 1H), 1.50 (s, 9H). MS (ESI) m/z 388 (M+H)$^+$.

(2-(2,6-Dioxopiperidin-3-yl)-1,3-dioxoisoindolin-4-yl)glycine

TFA (1.8 mL) was added to a solution of tert-Butyl (2-(2,6-Dioxopiperidin-3-yl)-1,3-dioxoisoindolin-4-yl)glycinate (390 mg, 1.0 mmol) in dichloromethane (18 mL). The mixture was stirred at rt overnight, then was concentrated and dried under vacuum to give the title compound as a yellow solid, which was used in next step without purification. MS (ESI) m/z 330 (M−H)$^−$.

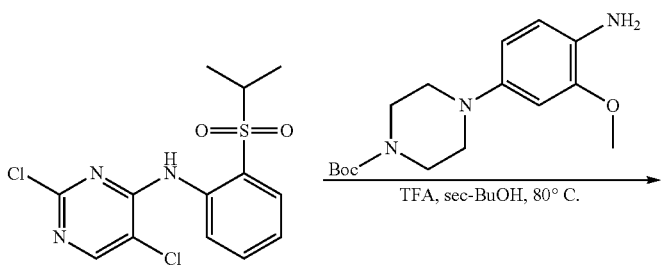

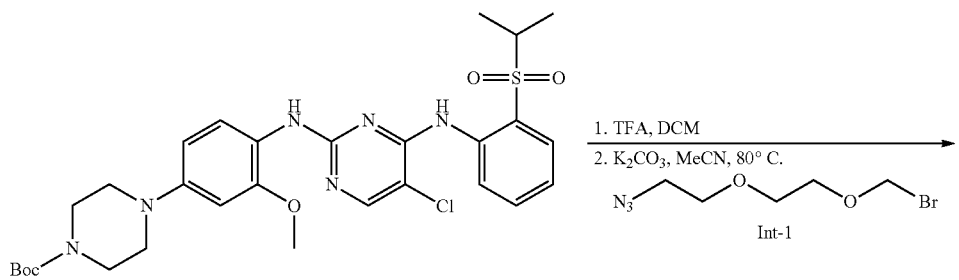

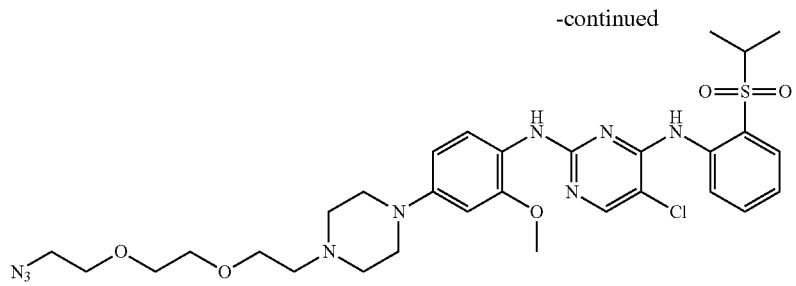

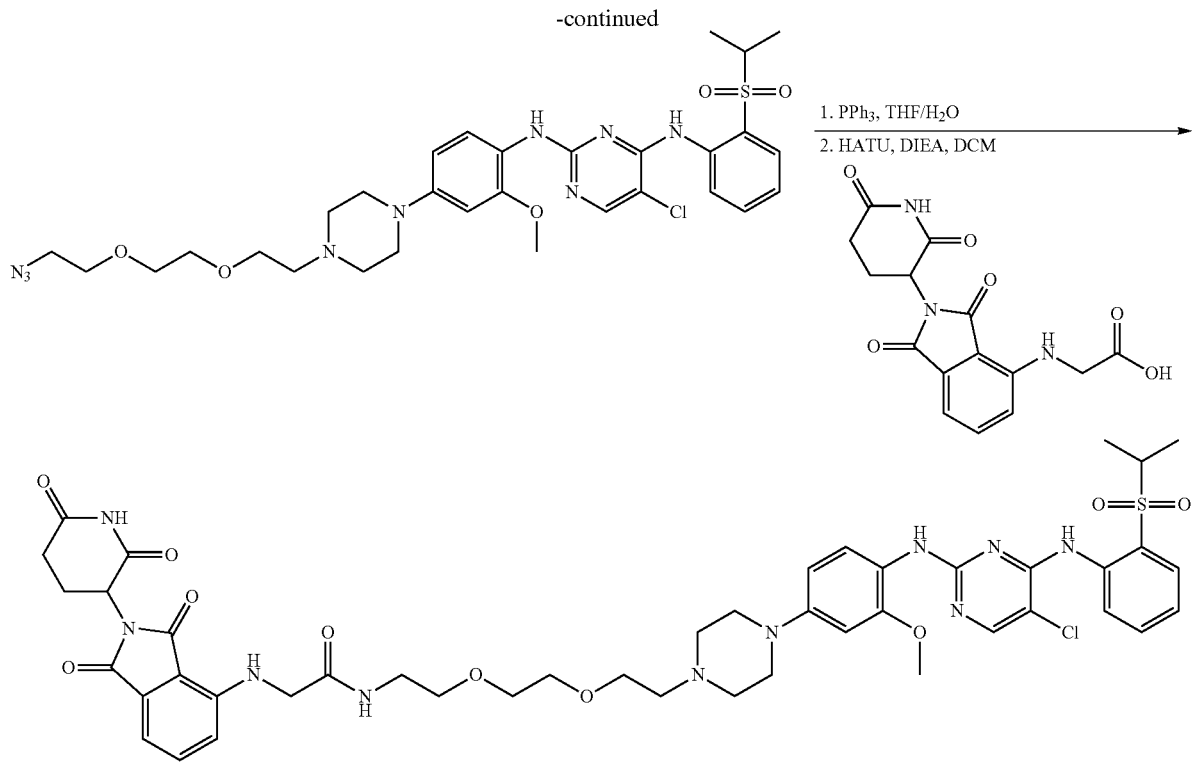

tert-Butyl 4-(4-((5-Chloro-4-((2(isopropylsulfonyl)phenyl)-amino)pyrimidin-2yl)amino)-3-methoxyphenyl)piperazine-1-carboxylate SM-4 was prepared according to Galkin et al., Proc. Natl. Acad. Sci. USA 104:270-275 (2007). TFA (185 µL, 2.4 mmol) was added to a solution of SM-4 (693 mg, 2.0 mmol) and tert-butyl 4-(4-amino-3-methoxyphenyl)piperazine-1-carboxylate (740 mg, 2.4 mmol) in sec-butanol (4 mL), and the mixture was stirred overnight at 80° C. The mixture was then concentrated and purified by column chromatography (dichloromethane/methanol=20:1) to give the title compound as a white solid (925 mg, 75%). $^1$H NMR (400 MHz, CDCl$_3$) δ 9.54 (s, 1H), 8.60 (d, J=8.4 Hz, 1H), 8.13 (s, 1H), 8.06 (d, J=7.2 Hz, 1H), 7.91 (d, J 8.0 Hz, 1H), 7.62 (dd, J=8.8, 8.4 Hz, 1H), 7.33 (s, 1H), 7.25 (dd, J=8.4, 8.4 Hz, 1H), 6.55 (s, 1H), 6.47 (d, J=8.8 Hz, 1H), 3.88 (s, 3H), 3.60 (m, 4H), 3.24 (m, 1H), 3.09 (m, 4H), 1.49 (s, 9H), 1.30 (d, J=7.2 Hz, 6H). MS (ESI) m/z 617 (M+H)$^+$.

N$^2$-(4-(4-(2-(2-(2-Azidoethoxy)ethoxy)ethyl)piperazin-1-yl)-2-methoxyphenyl)-5-chloro-N$^4$-(2-(isopropylsulfonyl)phenyl)-pyrimidine-2,4-diamine TFA was added (1.8 mL) to a solution of tert-Butyl 4-(4-((5-Chloro-4-((2(isopropylsulfonyl)phenyl)-amino)pyrimidin-2yl)amino)-3-methoxyphenyl)piperazine-1-carboxylate (620 mg, 1.0 mmol) in dichloromethane (18 mL), and the mixture was stirred at rt for 2 h, then was concentrated and dried under vacuum. To the obtained crude intermediate in acetonitrile (5 mL) were added commercially available Int-1 (300 mg, 1.2 mmol) and potassium carbonate (414 mg, 3.0 mmol). The resulting mixture was stirred under 80° C. overnight, then cooled to rt and diluted with 50 mL of dichloromethane. The precipitated was filtered, and the filtrate was concentrated and purified by column chromatography (dichloromethane/methanol=10:1) to give the title compound as a colorless oil (524 mg, 78%). $^1$H NMR (400 MHz, DMSO-d$_6$) δ 9.54 (s, 1H), 8.62 (d, J=8.4 Hz, 1H), 8.13 (s, 1H), 8.02 (d, J=8.4 Hz, 1H), 7.91 (d, J=8.0 Hz, 1H), 7.62 (dd, J=8.0, 8.0 Hz, 1H), 7.30 (m, 2H), 6.56 (s, 1H), 6.48 (d, J=8.4 Hz, 1H), 3.88 (s, 3H), 3.70 (m, 10H), 3.25 (m, 1H), 3.41 (t, J=5.2 Hz, 2H), 3.20 (m, 4H), 2.70 (m, 4H), 1.32 (d, J=7.2 Hz, 6H). MS (ESI) m/z 674 (M+H)$^+$.

N-(2-(2-(2-(4-(4-((5-Chloro-4-((2-(isopropylsulfonyl)phenyl)-amino)pyrimidin-2-yl)amino)-3-methoxyphenyl)piperazin-1-yl)ethoxy)ethoxy)ethyl)-2-((2-(2,6-dioxopiperidin-3-yl)-1,3-dioxoisoindolin-4-yl)amino)acetamide Under a nitrogen atmosphere, triphenylphosphine (63 mg, 0.24 mmol) was added to a solution of N$^2$-(4-(4-(2-(2-(2-Azidoethoxy)ethoxy)ethyl)piperazin-1-yl)-2-methoxyphenyl)-5-chloro-N$^4$-(2-(isopropylsulfonyl)phenyl)-pyrimidine-2,4-diamine (135 mg, 0.2 mmol) in tetrahydrofuran (18 mL) and water (1.8 mL). The reaction mixture was stirred overnight, then concentrated and dried under vacuum. To the obtained crude oil in anhydrous dichloromethane (3 mL) were added (2-(2,6-Dioxopiperidin-3-yl)-1,3-dioxoisoindolin-4-yl)glycine (73 mg, 0.22 mmol) and (1-[bis(dimethylamino)methylene]-1H-1,2,3-triazolo[4,5-b]pyridinium 3-oxide hexafluorophosphate) (HATU) and DIEA (110 µL, 0.6 mmol). The reaction mixture was stirred for 2 h, then concentrated and purified by column chromatography (dichloromethane/methanol=10:1) to give the title compound a yellow foam (136 mg, 71%). $^1$H NMR (500 MHz, DMSO-d$_6$) δ 11.10 (s, 1H), 9.76 (br, 1H), 9.57 (s, 1H), 8.56 (br, 1H), 8.41 (H, 1H), 8.19 (s, 1H), 8.18 (m, 1H), 7.81 (d, J=8.0 Hz, 1H), 7.60 (m, 1H), 7.57 (dd, J=8.0, 7.5 Hz, 1H), 7.41 (d, J=8.5 Hz, 1H), 7.30 (dd, J=8.0, 7.5 Hz, 1H), 7.07 (d, J=7.0 Hz, 1H), 6.95 (m, 1H), 6.85 (d, J=8.5 Hz, 1H), 6.71 (d, J=2.5 Hz, 1H), 6.53 (dd, J=8.5, 2.5 Hz, 1H), 5.07 (dd, J=13.0, 5.5 Hz, 1H), 3.94 (d, J=5.0 Hz, 2H), 3.85 (m, 2H), 3.80 (m, 2H), 3.76 (s, 3H), 3.58 (m, 4H), 3.45 (m, 4H), 3.40 (m, 4H), 3.30 (m, 2H), 3.24 (m, 2H), 3.03 (m, 2H), 2.53-2.63 (m, 2H), 1.16 (d, J=7.0 Hz, 6H). MS (ESI) m/z 961 (M+H)$^+$.

Example 12: Synthesis of N-(2-(2-(2-(4-(4-((5-Chloro-4-((2-(isopropylsulfonyl)phenyl)-amino)pyrimidin-2-yl)amino)-5-isopropoxy-2-methylphenyl)-piperidin-1-yl)ethoxy)ethoxy)ethyl)-2-((1,3-dioxo-2-(2-oxopiperidin-3-yl)isoindolin-4-yl)amino)acetamide (11)

Compound 12 was prepared in an analogous manner to compound 10 in example 11. $^1$H NMR (500 MHz, DMSO-d$_6$) δ 11.09 (s, 1H), 9.59 (s, 1H), 9.46 (s, 1H), 8.44 (d, J=8.5 Hz, 1H), 8.38 (br, 1H), 8.25 (s, 1H), 8.18 (dd, J=6.0, 5.5 Hz, 1H), 8.09 (s, 1H), 7.83 (d, J=8.0 Hz, 1H), 7.60 (dd, J=8.5, 8.0 Hz, 1H), 7.57 (dd, J=8.0, 7.5 Hz, 1H), 7.34 (dd, J=8.5, 8.0 Hz, 1H), 7.06 (d, J=6.0 Hz, 1H), 6.93 (dd, J=5.5, 5.5 Hz, 1H), 6.84 (d, J=9.0 Hz, 1H), 6.75 (s, 1H), 5.06 (dd, J=13.0, 5.5 Hz, 1H), 4.48 (m, J=6.0 Hz, 1H), 3.93 (d, J=5.5 Hz, 2H), 3.78 (m, 2H), 3.59 (m, 4H), 3.56 (m, 2H), 3.44 (m, 4H), 3.28 (m, 2H), 3.13 (m, 4H), 2.83-2.99 (m, 2H), 2.52-2.61 (m, 1H), 2.13 (s, 3H), 1.85-2.04 (m, 4H), 1.22 (d, J=6.0 Hz, 6H), 1.15 (d, J=7.0 Hz, 6H). MS (ESI) m/z 1002 (M+H)$^+$.

(11)

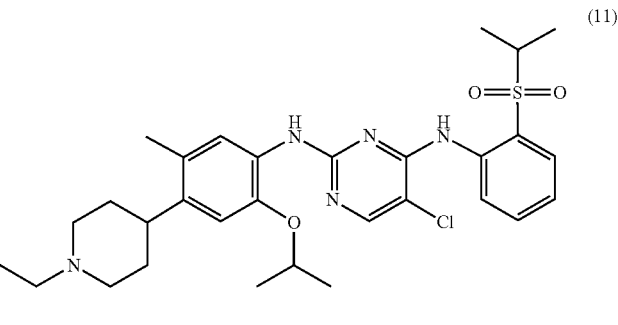

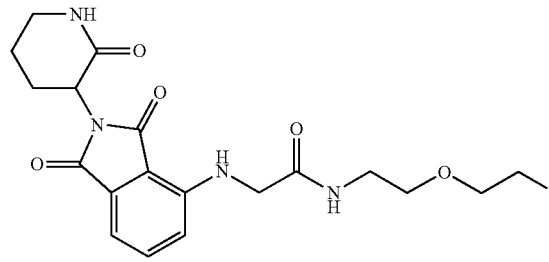

Compound 11 was prepared in an analogous manner to compound 10 in example 11. $^1$H NMR (500 MHz, DMSO-d$_6$) δ 9.46 (s, 1H), 8.46 (d, J=8.5 Hz, 1H), 8.25 (s, 1H), 8.16 (dd, J=5.5, 5.0 Hz, 1H), 8.07 (s, 1H), 7.84 (d, J=8.0 Hz, 1H), 7.81 (s, 1H), 7.61 (dd, J=8.5, 8.0 Hz, 1H), 7.55 (dd, J=8.0, 7.5 Hz, 1H), 7.52 (s, 1H), 7.35 (dd, J=8.5, 8.0 Hz, 1H), 7.03 (d, J=6.0 Hz, 1H), 6.93 (dd, J=6.0, 5.5 Hz, 1H), 6.83 (d, J=8.5 Hz, 1H), 6.78 (br, 1H), 4.52 (dd, J=12.0, 6.0 Hz, 1H), 3.92 (d, J=5.5 Hz, 2H), 3.54 (m, 6H), 3.45 (m, 4H), 3.29 (m, 4H), 3.21 (m, 4H), 2.20 (m, 3H), 2.12 (s, 3H), 1.81-2.00 (m, 6H), 1.22 (d, J=6.0 Hz, 6H), 1.16 (d, J=6.5 Hz, 6H). MS (ESI) m/z 988 (M+H)$^+$.

Example 13: Synthesis of N-(2-(2-(2-(4-(4-((5-Chloro-4-((2-(isopropylsulfonyl)phenyl)-amino)pyrimidin-2-yl)amino)-5-isopropoxy-2-methylphenyl)-piperidin-1yl)ethoxy)ethoxy)ethyl)-2-((2-(2,6-dioxopiperidin-3-yl)-1,3-dioxoisoindolin-4-yl)amino)acetamide (12)

Example 14: Synthesis of 4-((2-(2,6-Dioxopiperidin-3-yl)-1,3-dioxoisoindolin-4-yl)amino)-N-(2-((1$^3$E,1$^4$E,3R,6S)-4$^5$-fluoro-3,6-dimethyl-9-oxo-5-oxa-2,8-diaza-1(5,3)-pyrazolo[1,5-a]pyrimidina-4(1,2)-benzenacyclononaphane-8-yl)ethyl)-N-methylbutanamide (14)

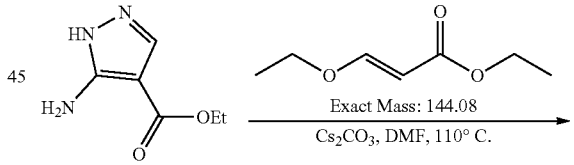

(12)

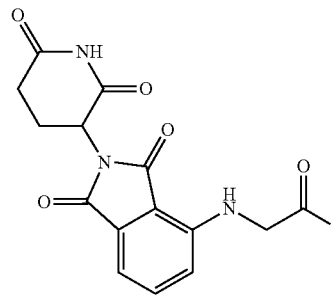

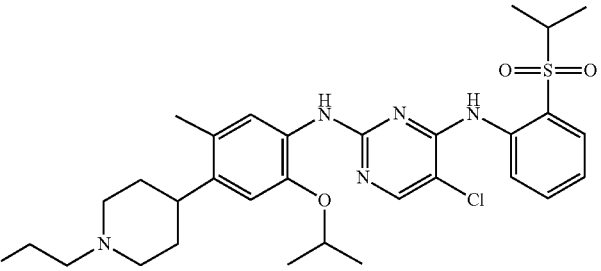

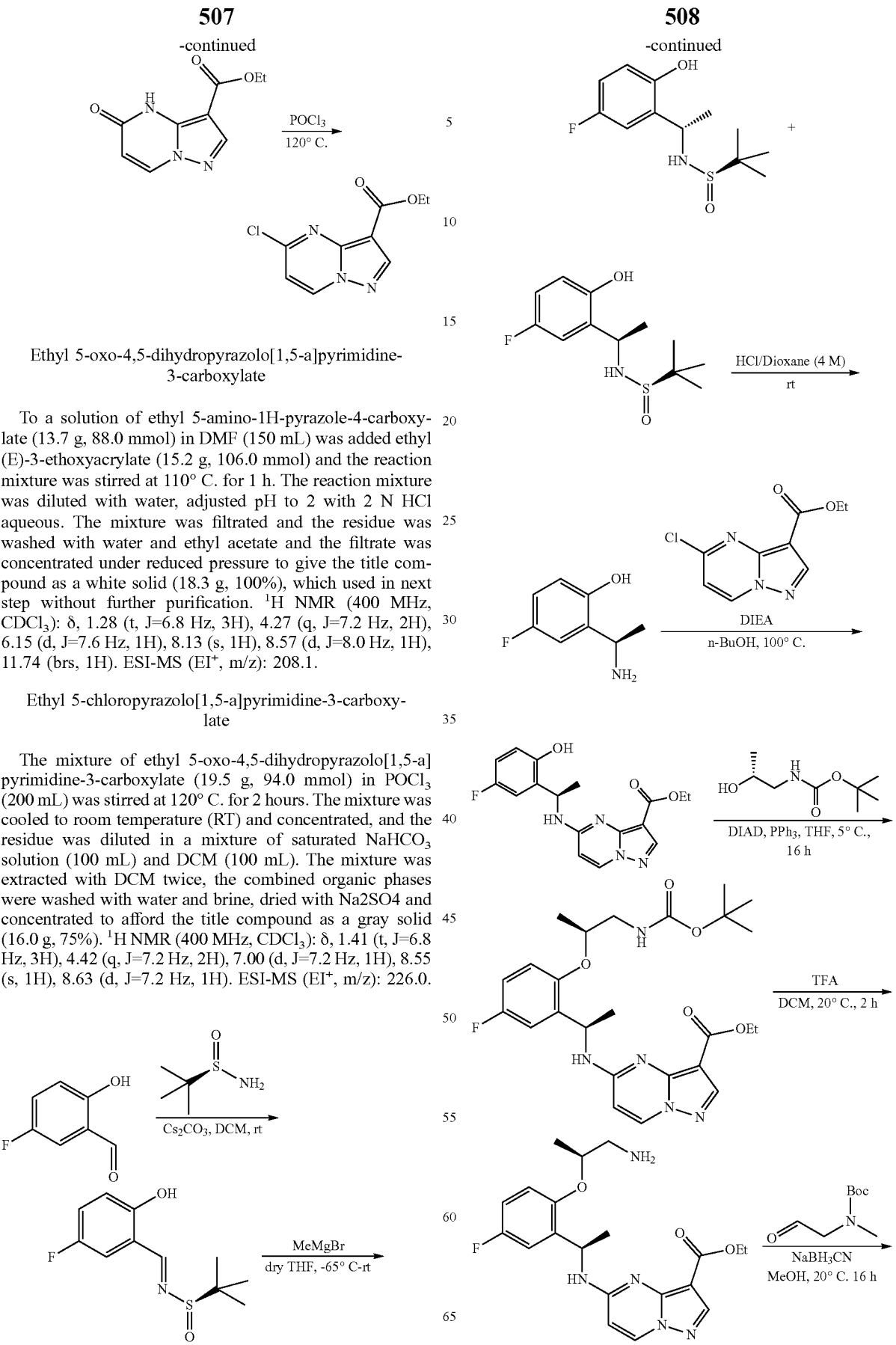

Ethyl 5-oxo-4,5-dihydropyrazolo[1,5-a]pyrimidine-3-carboxylate

To a solution of ethyl 5-amino-1H-pyrazole-4-carboxylate (13.7 g, 88.0 mmol) in DMF (150 mL) was added ethyl (E)-3-ethoxyacrylate (15.2 g, 106.0 mmol) and the reaction mixture was stirred at 110° C. for 1 h. The reaction mixture was diluted with water, adjusted pH to 2 with 2 N HCl aqueous. The mixture was filtrated and the residue was washed with water and ethyl acetate and the filtrate was concentrated under reduced pressure to give the title compound as a white solid (18.3 g, 100%), which used in next step without further purification. $^1$H NMR (400 MHz, CDCl$_3$): δ, 1.28 (t, J=6.8 Hz, 3H), 4.27 (q, J=7.2 Hz, 2H), 6.15 (d, J=7.6 Hz, 1H), 8.13 (s, 1H), 8.57 (d, J=8.0 Hz, 1H), 11.74 (brs, 1H). ESI-MS (EI$^+$, m/z): 208.1.

Ethyl 5-chloropyrazolo[1,5-a]pyrimidine-3-carboxylate

The mixture of ethyl 5-oxo-4,5-dihydropyrazolo[1,5-a]pyrimidine-3-carboxylate (19.5 g, 94.0 mmol) in POCl$_3$ (200 mL) was stirred at 120° C. for 2 hours. The mixture was cooled to room temperature (RT) and concentrated, and the residue was diluted in a mixture of saturated NaHCO$_3$ solution (100 mL) and DCM (100 mL). The mixture was extracted with DCM twice, the combined organic phases were washed with water and brine, dried with Na2SO4 and concentrated to afford the title compound as a gray solid (16.0 g, 75%). $^1$H NMR (400 MHz, CDCl$_3$): δ, 1.41 (t, J=6.8 Hz, 3H), 4.42 (q, J=7.2 Hz, 2H), 7.00 (d, J=7.2 Hz, 1H), 8.55 (s, 1H), 8.63 (d, J=7.2 Hz, 1H). ESI-MS (EI$^+$, m/z): 226.0.

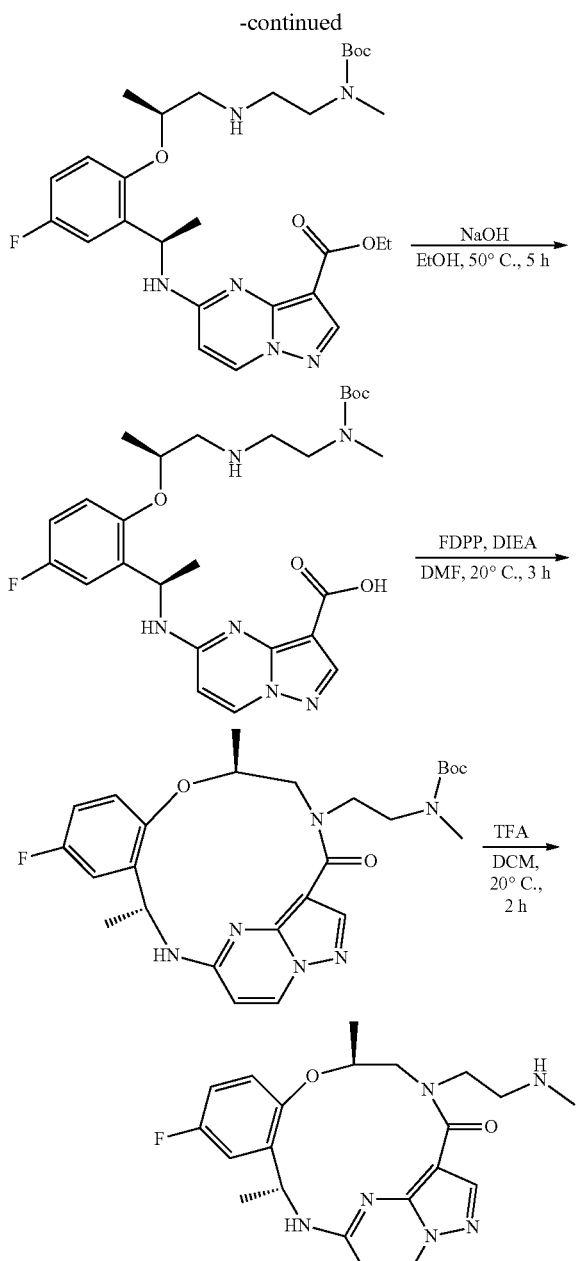

(R)—N-(5-Fluoro-2-hydroxybenzylidene)-2-methyl-propane-2-sulfinamide

To a solution of 2-hydroxybenzaldehyde (20.0 g, 143 mmol) and (R)-2-methylpropane-2-sulfinamide (17.3 g, 143 mmol) in DCM (300 mL) was added $Cs_2CO_3$ (93 g, 286 mmol). After being stirred at room temperature overnight, the mixture was quenched with water at 0° C. and extracted with ethyl acetate ×3, the combined organic phases were dried with $Na_2SO_4$ and concentrated. The residue was purified by column chromatography eluted with DCM/MeOH=100/1 to afford the title compound as a white solid (41.1 g, 83.3%). $^1$H NMR (400 MHz, CDCl$_3$): δ 1.26 (s, 9H), 6.95-7.01 (m, 1H), 7.14-7.20 (m, 2H), 8.62 (s, 1H), 10.84 (s, 1H). ESI-MS (EI, m/z): 244.1.

(R)—N—((R)-1-(5-Fluoro-2-hydroxyphenyl)ethyl)-2-methylpropane-2-sulfinamide

To a solution of (R)—N-(5-Fluoro-2-hydroxybenzylidene)-2-methylpropane-2-sulfinamide (40 g, 164.0 mmol) in THF (240 mL) was added MeMgBr (3 M in 2-methy-THF, 272 mL, 206.0 mmol) at −65° C. under nitrogen. After stirring at room temperature overnight, the mixture was quenched with water at 0° C., and the mixture was extracted with EtOAc×2. The combined organic phases was dried and concentrated, and the residue was purified by column chromatography eluted with Pet. ether/ethyl acetate=5/1 to afford the title compound as a light yellow solid (22.3 g, 52.4%) and the S-enantiomer as a light yellow solid (3.0 g, 7%). (R)-enantiomer: $^1$H NMR (400 MHz, DMSO-d$_6$): δ1.26 (s, 9H), 1.50 (d, J=8 Hz, 3H), 4.36 (quint, J=7.2 Hz, 1H), 5.09 (d, J=7.6 Hz, 4H), 6.41 (dd, J=4.8, 9.2 Hz, 1H), 6.56 (dt, J=2.8, 8.4 Hz, 1H), 6.76 (dd, J=2.8, 8.8 Hz, 1H), 9.13 (s, 1H). ESI-MS (EI, m/z): 260.1. (S)-enantiomer: $^1$H NMR (400 MHz, DMSO-d$_6$): δ1.20 (s, 9H), 1.60 (d, J=6.8 Hz, 3H), 3.80 (d, J=6.0 Hz, 1H), 4.65 (quint, J=6.4 Hz, 1H), 7.31 (dd, J=4.8, 8.8 Hz, 1H), 7.38 (dt, J=2.8, 8.4 Hz, 1H), 8.41 (d, J=2.8, 1H).

(R)-2-(1-Aminoethyl)-4-fluorophenol hydrochloride

To the solid of (R)—N—((R)-1-(5-Fluoro-2-hydroxyphenyl)ethyl)-2-methylpropane-2-sulfinamide (21.2 g, 82.0 mmol) was added HCl/Dioxane (4 M in dioxane, 40 mL). After stirring at room temperature for 3 h, the reaction mixture was concentrated to give the title compound as the HCl salt as a while solid (15.7 g, 100%), which was used directly in the next step without further purification. ESI-MS (EI, m/z): 156.1

Ethyl (R)-5-((1-(5-fluoro-2-hydroxyphenyl)ethyl)amino)pyrazolo[1,5-a]pyrimidine-3-carboxylate To a solution of (R)-2-(1-Aminoethyl)-4-fluorophenol hydrochloride (15.7 g, 82.0 mmol) and DIEA (63.5 g, 491.0 mmol) in n-BuOH (150 mL) was added ethyl 5-chloropyrazolo[1,5-a]pyrimidine-3-carboxylate (15.1 g, 66 mmol). After stirring at 100° C. overnight, the reaction mixture was diluted with ethyl acetate and washed with water and brine. The organic phase was dried with $Na_2SO_4$ and concentrated, and the residue was purified by column chromatography eluted with DCM/MeOH=50/1 to afford the title compound as a yellow solid (22.7 g, 100%). $^1$H NMR (400 MHz, DMSO-d$_6$): δ 1.27 (t, J=7.2 Hz, 3H), 1.45 (d, J=6.8 hz, 3H), 4.17 (q, J=7.2 Hz, 1H), 5.48-5.59 (m, 1H), 6.46 (d, J=8.0 Hz, 1H), 6.77-6.90 (m, 2H), 7.07 (dd, J=3.2, 9.6 Hz, 1H), 8.12 (s, 1H), 8.24 (d, J=8.0 Hz, 1H), 8.52 (d, J=7.6 Hz, 1H), 9.58 (brs, 1H). ESI-MS (EI$^+$, m/z): 345.1.

Ethyl 5-(((R)-1-(2-(((R)-1-((tert-butoxycarbonyl)amino)propan-2-yl)oxy)-5-fluorophenyl)ethyl)amino)pyrazolo[1,5-a]pyrimidine-3-carboxylate A solution of ethyl (R)-5-((1-(5-fluoro-2-hydroxyphenyl)ethyl)amino)pyrazolo[1,5-a]pyrimidine-3-carboxylate (10.0 g, 29.1 mmol), tert-butyl (R)-(2-hydroxypropyl)carbamate (5.1 g, 29.1 mmol) and PPh$_3$ (7.62 g, 29.1 mmol) in THF (100 mL) was stirred in ice bath (−5° C.). After dropwise addition of DIAD (5.87 g, 29.1 mmol), the reaction mixture was stirred in an ice bath for 16 h and the mixture was partitioned between ethyl acetate and water. The combined organic phases were washed with water and brine, dried over Na₂SO₄ and concentrated. The crude product was purified by column chromatography eluted with hexanes/ethyl acetate=1/1 to afford the title compound as a yellow solid (6.5 g, 45%). ESI-MS (EI⁺, m/z): 502.2.

Ethyl 5-(((R)-1-(2-(((R)-1-aminopropan-2-yl)oxy)-5-fluorophenyl)ethyl)amino)pyrazolo[,5-a]pyrimidine-3-carboxylate TFA salt To a mixture of ethyl 5-(((R)-1-(2-(((R)-1-((tert-butoxycarbonyl)amino)propan-2-yl)oxy)-5-fluorophenyl)ethyl)amino)pyrazolo[1,5-a]pyrimidine-3-carboxylate (6.5 g, 13.0 mmol) in DCM (30 mL) was added TFA (10 mL) and the mixture was stirred at room temperature for 2 h. The mixture was evaporated in vacuo and the residue was partitioned between ethyl acetate and water. The combined organic phases were washed with water and brine, dried over Na₂SO₄ and concentrated obtain the title compound as a yellow solid (5.2 g, 100%), which was used without further purification. ESI-MS (EI, m/z): 402.2.

Ethyl 5-(((R)-1-(2-(((R)-1-((2-((tert-butoxycarbonyl)(methyl)amino)ethyl)amino)propan-2-yl)oxy)-5-fluorophenyl)ethyl)amino)pyrazolo[1,5-a]pyrimidine-3-carboxylate A solution of ethyl 5-(((R)-1-(2-(((R)-1-aminopropan-2-yl)oxy)-5-fluorophenyl)ethyl)amino)pyrazolo[1,5-a]pyrimidine-3-carboxylate TFA salt (5.2 g, 13.0 mmol) and tert-butyl methyl(2-oxoethyl)carbamate (2.28 g, 13.0 mmol) in MeOH (50 mL) was stirred at RT. After addition of NaBH₃CN (2.42 g, 39.0 mmol), the reaction mixture was stirred in an ice bath for 16 h. The mixture was partitioned between ethyl acetate and water and extracted with ethyl acetate. The combined organic phases were washed with water and brine, dried over Na₂SO₄ and concentrated. The crude product was purified by column chromatography eluted with DCM/MeOH=10/1 to afford the title compound as a yellow solid (2.2 g, 30%). ESI-MS (EI, m/z): 559.3.

5-(((R)-1-(2-(((R)-1-((2-((tert-butoxycarbonyl)(methyl)amino)ethyl)amino)propan-2-yl)oxy)-5-fluorophenyl)ethyl)amino)pyrazolo[1,5-a]pyrimidine-3-carboxylic acid A solution of NaOH aqueous (2 N, 8 mL) was added to a mixture of ethyl 5-(((R)-1-(2-(((R)-1-((2-((tert-butoxycarbonyl)(methyl)amino)ethyl)amino)propan-2-yl)oxy)-5-fluorophenyl)ethyl)amino)pyrazolo[1,5-a]pyrimidine-3-carboxylate (2.2 g, 3.94 mmol) in EtOH (16 mL) and the resulting mixture was stirred at 50° C. for 3 h. The mixture was concentrated and the residue was diluted with water (48 mL). The mixture was adjusted pH to 3 and filtered, the solid was dried to afford the title compound as yellow solid (1.5 g, 71.7%). ESI-MS (EI, m/z): 531.3 tert-Butyl (2-((1³E,1⁴E,3R,6S)-4⁵-fluoro-3,6-dimethyl-9-oxo-5-oxa-2,8-diaza-1(5,3)-pyrazolo[1,5-a]pyrimidina-4(1,2)-benzenacyclononaphane-8-yl)ethyl)(methyl)carbamate The solution of 5-(((R)-1-(2-(((R)-1-((2-((tert-butoxycarbonyl)(methyl)amino)ethyl)amino)propan-2-yl)oxy)-5-fluorophenyl)ethyl)amino)pyrazolo[1,5-a]pyrimidine-3-carboxylic acid (1.5 g, 2.83 mmol) and DIEA (1.1 g, 8.49 mmol) in DMF (45 mL) and DCM (90 mL) was stirred at RT. After addition of FDPP (1.63 g, 4.25 mmol), the reaction mixture was stirred at room temperature for 3 h. The mixture was partitioned between ethyl acetate and water. The combined organic phases were washed with water and brine, dried over Na₂SO₄ and concentrated. The crude product was purified by column chromatography eluted with PE/EA=1/1 to afford the title compound as a white solid (800 mg, 55%). ESI-MS (EI, m/z): 513.1.

(1³E,1⁴E,3R,6S)-4⁵-fluoro-3,6-dimethyl-8-(2-(methylamino)ethyl)-5-oxa-2,8-diaza-1(5,3)-pyrazolo[1,5-a]pyrimidina-4(1,2)-benzenacyclononaphan-9-one TFA salt To a mixture of tert-Butyl (2-((1³E,1⁴E,3R,6S)-4⁵-fluoro-3,6-dimethyl-9-oxo-5-oxa-2,8-diaza-1(5,3)-pyrazolo[1,5-a]pyrimidina-4(1,2)-benzenacyclononaphane-8-yl)ethyl)(methyl)carbamate (512 mg, 1.0 mmol) in DCM (9 mL) was treated with TFA (3 mL) and the mixture was stirred at room temperature for 2 h. The mixture was concentrated to give the title compound as a yellow solid (526 mg, 100%), which was used in the next step without further purification. ESI-MS (EI, m/z): 413.2.

4-((2-(2,6-Dioxopiperidin-3-yl)-1,3-dioxoisoindolin-4-yl)amino)-N-(2-((1³E,1⁴E,3R,6S)-4⁵-fluoro-3,6-dimethyl-9-oxo-5-oxa-2,8-diaza-1(5,3)-pyrazolo[1,5-a]pyrimidina-4(1,2)-benzenacyclononaphane-8-yl)ethyl)-N-methylbutanamide

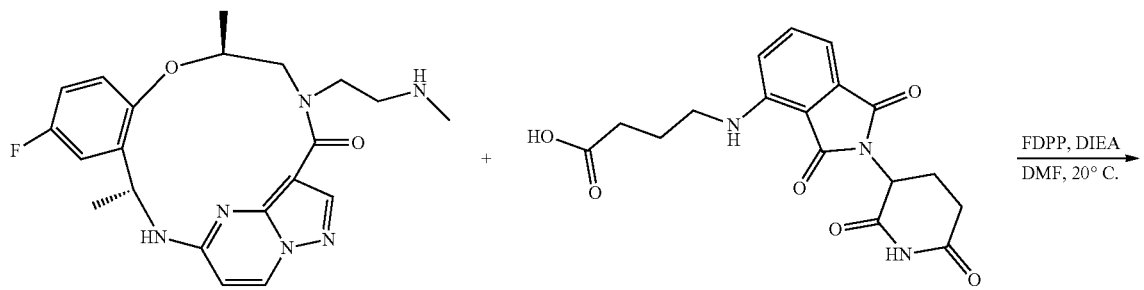

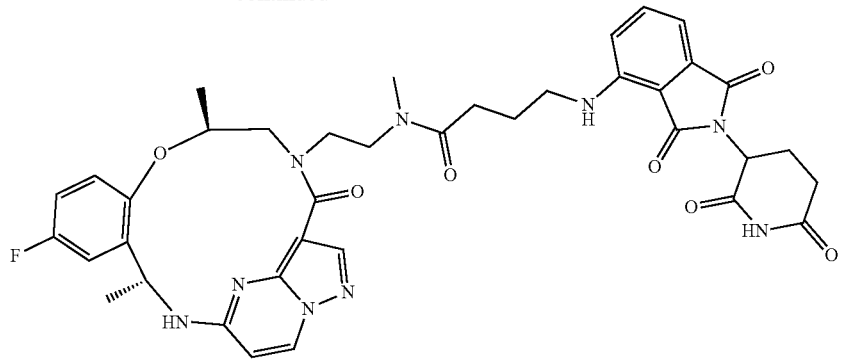

A solution of ethyl (1$^3$E,1$^4$E,3R,6S)-4$^5$-fluoro-3,6-dimethyl-8-(2-(methylamino)ethyl)-5-oxa-2,8-diaza-1(5,3)-pyrazolo[1,5-a]pyrimidina-4(1,2)-benzenacyclononaphan-9-one (TFA salt) (105 mg, 0.2 mmol) and 4-((2-(2,6-dioxopiperidin-3-yl)-1,3-dioxoisoindolin-4-yl)amino)butanoic acid (72 mg, 0.2 mmol) in DMF (5 mL) was stirred at RT. After the addition of HATU (114 mg, 0.3 mmol), the reaction mixture was stirred at room temperature for 3 h. The mixture was partitioned between ethyl acetate and water. The combined organic phase was washed with water and brine, dried over Na$_2$SO$_4$ and concentrated. The crude product was purified by prep-HPLC with ACN/water=60/40 to afford the title compound as a yellow solid (49.6 mg, 33%). $^1$H NMR (400 MHz, DMSO-d$_6$): δ 11.09 (s, 1H), 8.43-8.36 (m, 2H), 7.94-7.79 (m, 1H), 7.60-7.56 (m, 1H), 7.18-7.01 (m, 3H), 6.84-6.75 (m, 2H), 6.75-6.64 (m, 1H), 6.23-6.22 (s, 1H), 5.49 (t, J=8.0 Hz, 1H), 5.07-5.04 (m, 1H), 4.53-4.50 (m, 1H), 4.03-4.00 (m, 1H), 3.73-3.46 (m, 3H), 3.25-3.14 (m, 4H), 2.90-2.78 (m, 3H), 2.61-2.56 (m, 3H), 2.30-2.03 (m, 3H), 1.70-1.68 (m, 2H), 1.44-1.38 (m, 6H). ESI-MS (EI$^+$, m/z): 754.3.

Example 15: Cellular Degradation of ALK with Inventive Compounds 1-3 and 12

CellTiter-Glo®: Cell viability was evaluated using the CellTiter-Glo® Luminescent Cell Viability Assay (Promega™) following the manufacturer's standards. 12-point dose titrations were tested in triplicate from 10000 nM to 0.056 nM over 72 hours. Anti-proliferative best fit EC$_{50}$ values with 95% CI are shown as calculated by Graphpad Prism™ 7 software.

As shown in FIG. 1A, compounds 1 and 2, with PEG linkers, displayed anti-proliferative activity in H3122 cells that is comparable to compound 12. Compound 3, with a carbon linker, displayed 10-fold lower activity than compound 12. Additionally, compounds 1 and 2, with PEG linkers, showed activity against EML4-ALK with secondary mutations L1196M, C1156Y, or G1202R that is comparable to the parental inhibitor alectinib.

Blotting: Cells were washed with PBS before being lysed with Cell Lysis Buffer (Cell Signaling Technology®) supplemented with protease and phosphatase inhibitor cocktails (Roche™) at 4° C. for 15 minutes. The cell lysate was vortexed every 5 minutes over a 30-minute period before being centrifuged at 14,000×g for 20 min at 4° C. Protein in cell lysate was quantified by BCA assay (Pierce™). Primary antibodies used in this study include ALK (Cell Signaling Technology®, D5F3), Aurora A (Cell Signaling Technology®, 1F8), FAK (PTK2) (Cell Signaling Technology®, #3285), and GAPDH (Cell Signaling Technology®, 14C10). Blot quantification was performed using Image Studio™ 4.0 software, normalizing to loading control (GAPDH).

Figure 1B:
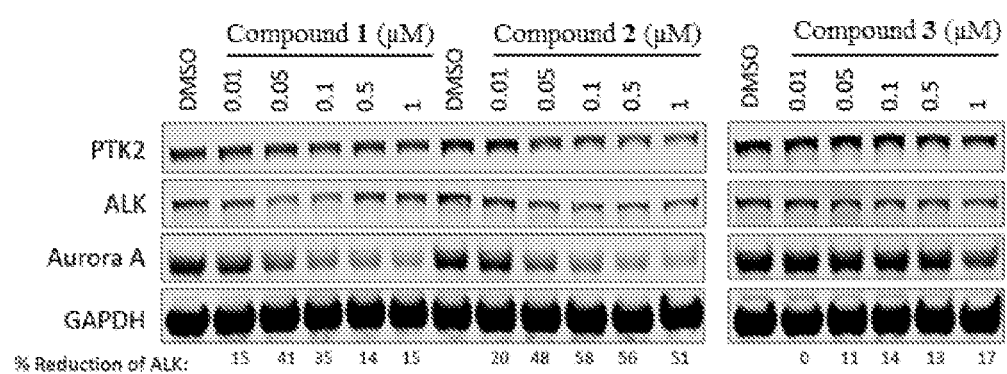
FIG. 1B is a collection of Western blots that show the degradation of ALK in H3122 cells at 16 hours following treatment with 0.01-1 µM of inventive compounds 1-3.

As shown in FIG. 1B, compounds 1 and 2, with PEG linkers, displayed the ability to degrade ALK in a dose dependent manner in H3122 cells after 16-hour treatments. Off target degradation of Aurora A was also seen. Notably, off target degradation of PTK2 was very low, unlike the previously reported compounds 10 and 12. Compound 3, with a carbon linker, induced only minimal ALK degradation; this complements the differences in anti-proliferative activity seen with compounds 1-3 in EML4-ALK expressing cell lines (FIG. 1A).

Figure 1C:
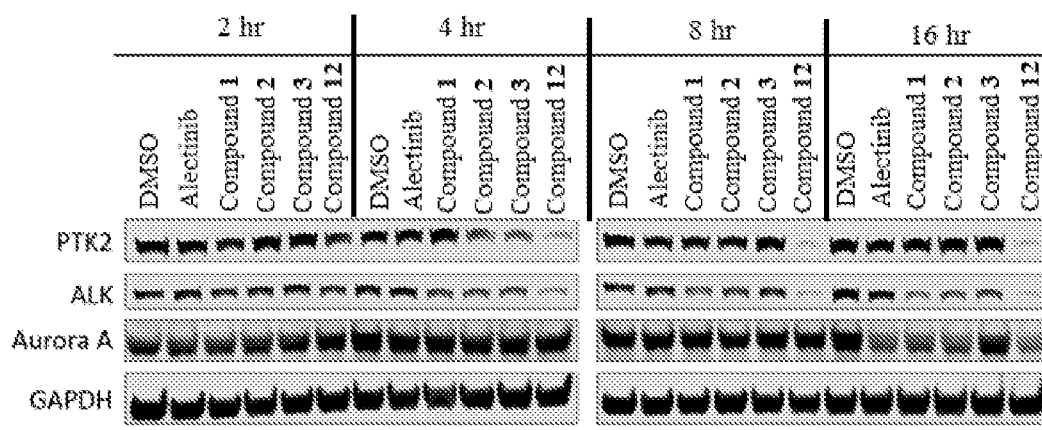
FIG. 1C is a collection of Western blots that show the degradation of ALK in H3122 cells in a time course study following treatment with 100 nM of inventive compounds 1-3 and 12 and Alectinib.

FIG. 1C shows a time course in H3122 cells with 100 nM doses of the compounds 1-3, compound 12, and alectinib. Compounds 1-3 were able to degrade ALK around 4 hours with maximum degradation seen around 16 hours. Compound 12 was also able to degrade ALK around 4 hours with maximum degradation seen around 8 hours. FIG. 1C confirms that compounds 1-3 lost the off target degradation activity against PTK2 that was seen with compound 12, but maintained the off target degradation of Aurora A.

Example 16: Cellular Degradation of ALK with Inventive Compounds 4-6

The experimental protocol was as in Example 15.

Figure 2A:
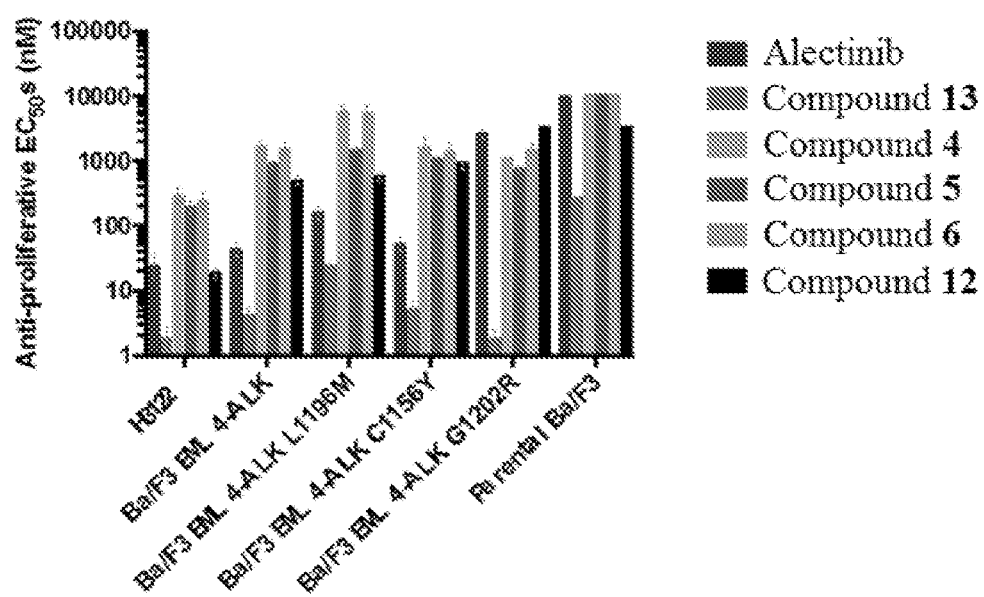
FIG. 2A is graph that shows the anti-proliferative activities of inventive compounds 4-6, 12, non-inventive compound 13, and Alectinib on H3122 cells, ALK-positive Ba/F3 cells, and parental Ba/F3 cells after 72 hours by CellTiter-Glo®.

FIG. 2A shows the anti-proliferative activity of compounds 4-6 in EML4-ALK expressing cell lines. Although some anti-proliferative effects were seen with these compounds, their activity was less than that of the previous ALK degrader compound 12 by an order of magnitude.

Figure 2B:
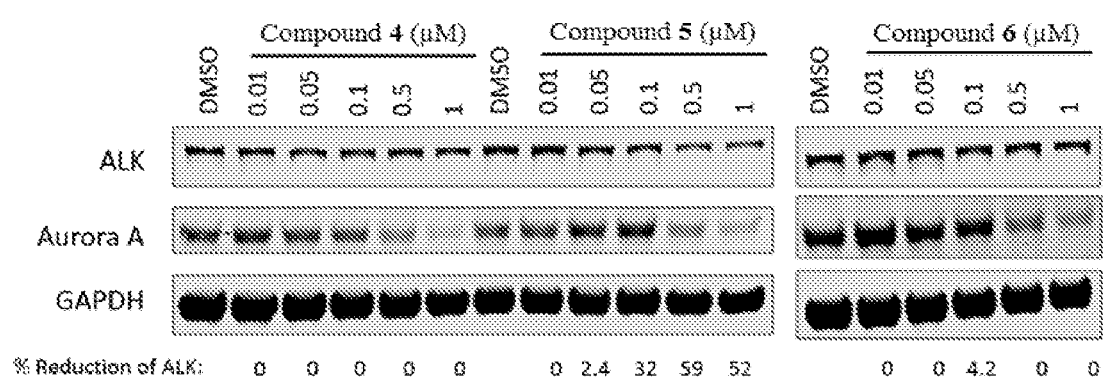
FIG. 2B is a collection of Western blots that show the degradation of ALK in H3122 cells at 16 hours following treatment with 0.01-1 µM of inventive compounds 4-6.

In FIG. 2B shows ALK and aurora A degradation in H3122 cells after 16 hour treatments with compounds 4-6. Only the compound with the longest linker, compound 5, demonstrated significant degradation of ALK. Compound 4 and 6 did not degrade ALK to a significant extent. This data complements the anti-proliferative activity seen in FIG. 2A, where compounds 4-6 showed low anti-proliferative effects compared to previous ALK degraders, with compound 5 showing slightly better activity than the other members of this group. Compounds 4-6 still induced off target degradation of aurora A.

Example 17: Cellular Degradation of ALK with Inventive Compound 8

The experimental protocol was as in Example 15.

Figure 3A:
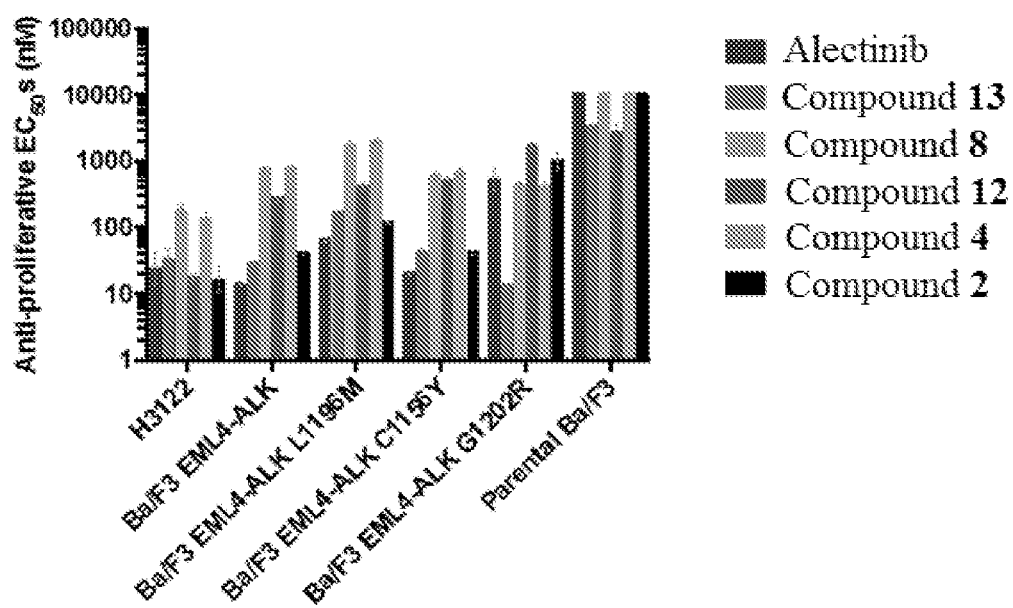
FIG. 3A is graph that shows the anti-proliferative activities of inventive compounds 2, 4, 8, 12, non-inventive compound 13, and Alectinib on H3122 cells, ALK-positive Ba/F3 cells, and parental Ba/F3 cells after 72 hours by CellTiter-Glo®.

Compound 8 has the same warhead as compounds 4-6 for engaging ALK and CRBN. However, compounds 4-6 have an N—H amide that could form an intramolecular hydrogen bond with the pyrazole, which could change the trajectory of the warhead. Compound 8 has an N-methyl amide, instead of the N—H amide, with the goal of improving on the activities of compound 4-6 by preventing the intramolecular hydrogen bond with the pyrazole. However, the anti-proliferative activity as seen in FIG. 3A showed that compound 8 has similar activity as compound 4 and has lower antiproliferative activity than compound 2 and compound 12 in EML4-ALK expressing cells.

Figure 3B:
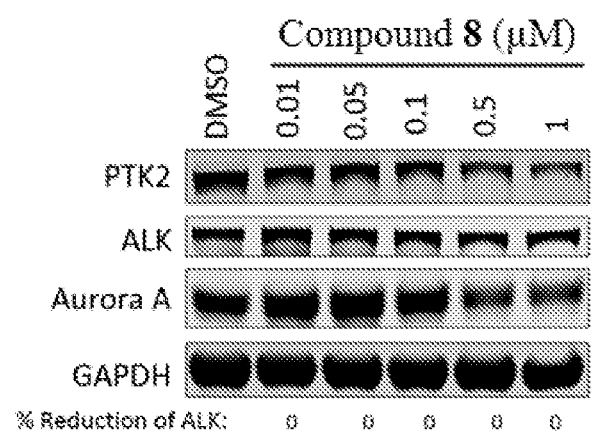
FIG. 3B is a Western blot that shows the degradation of ALK in H3122 cells at 16 hours following treatment with 0.01-1 µM of inventive compound 8.

In FIG. 3B the degradation of ALK, aurora A, and PTK2 is shown after 16-hour treatments with compound 8 in H3122 cells. Similar to compounds 4-6, no ALK degradation was seen with this compound, but off target degradation of aurora A was still seen at higher doses. Some slight degradation of PTK2 was also seen a 1 µM of compound 8.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound, which is:

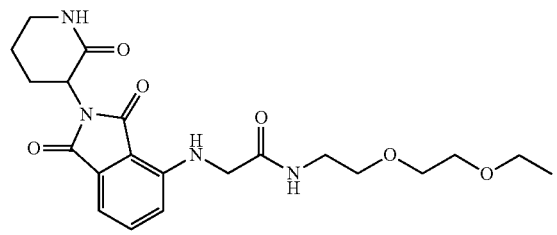

(9)

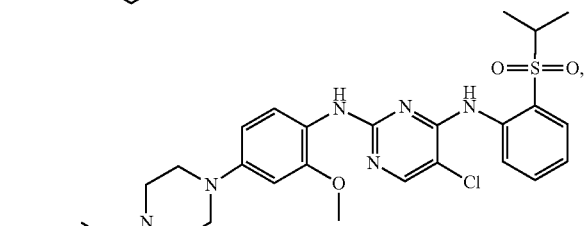

(10)

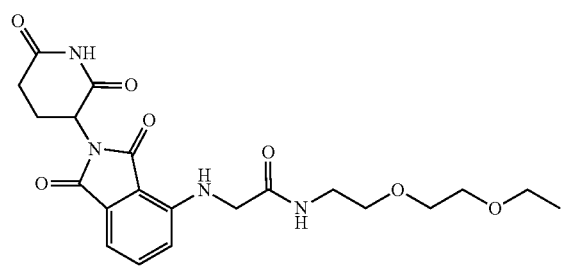

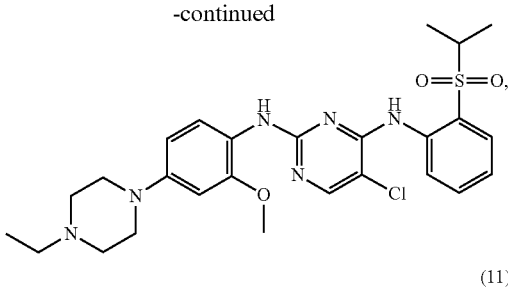

(11)

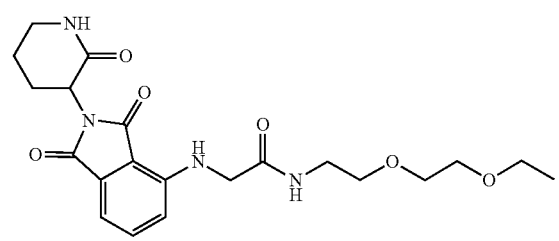

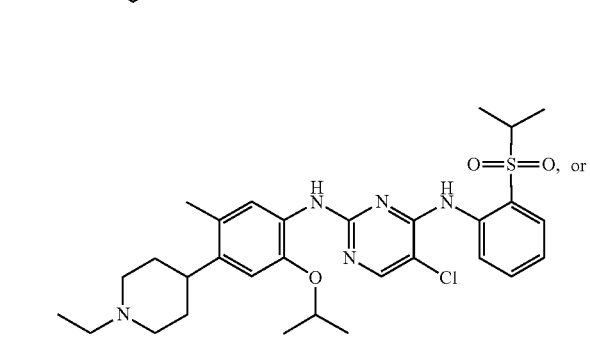

(12)

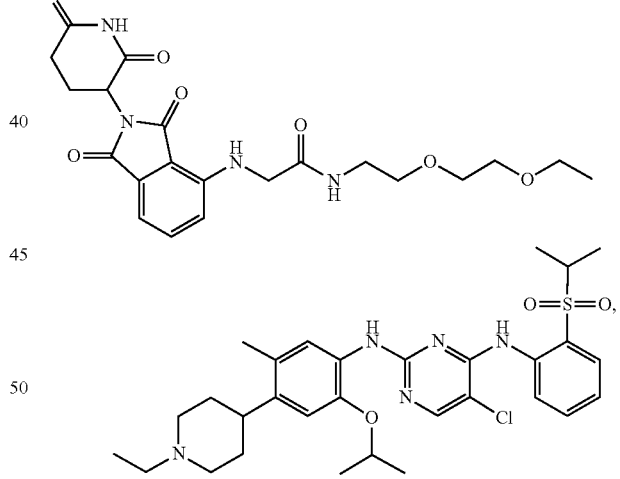

or a pharmaceutically acceptable salt or stereoisomer thereof.

2. A pharmaceutical composition comprising a therapeutically effective amount of the bispecific compound of claim 1 or a pharmaceutically acceptable salt or stereoisomer thereof, and a pharmaceutically acceptable carrier.

3. A method of treating a disease or disorder characterized or mediated by aberrant ALK activity, comprising administering a therapeutically effective amount of the bispecific compound of claim 1 or a pharmaceutically acceptable salt or stereoisomer thereof, to a subject in need thereof.

4. The compound of claim 1, which is
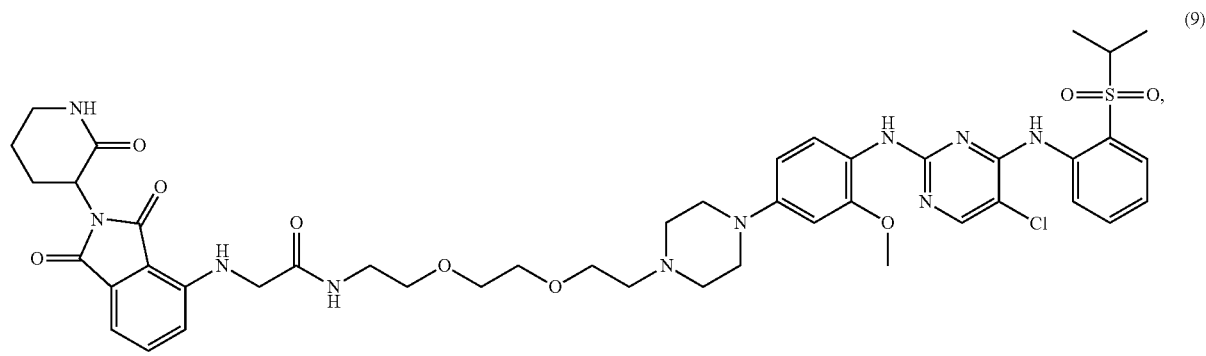
(9)
or a pharmaceutically acceptable salt thereof.
5. The compound of claim 1, which is
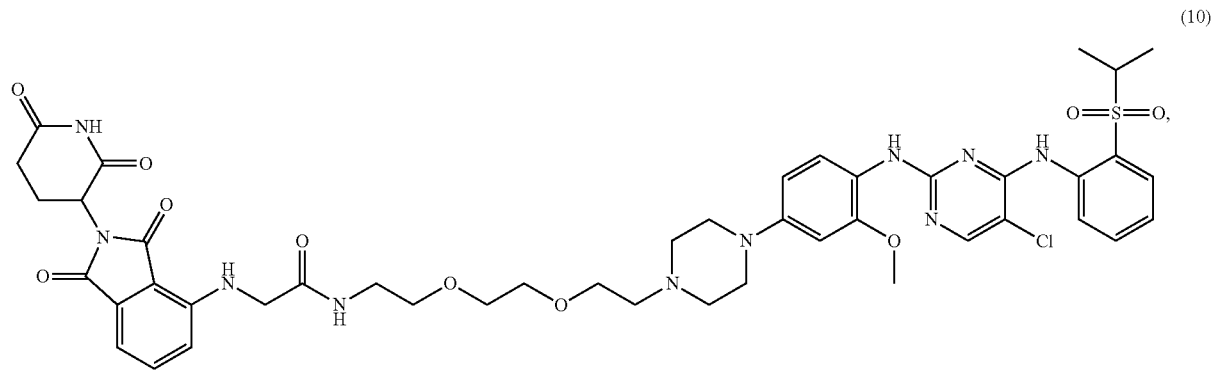 [SMILES: COc1cc(N2CCN(CCOCCOCCNC(=O)CNc3cccc4c3C(=O)N(C3CCC(=O)NC3=O)C4=O)CC2)ccc1Nc1ncc(Cl)c(Nc2ccccc2S(=O)(=O)C(C)C)n1]
(10)
or a pharmaceutically acceptable salt thereof.
6. The compound of claim 1, which is
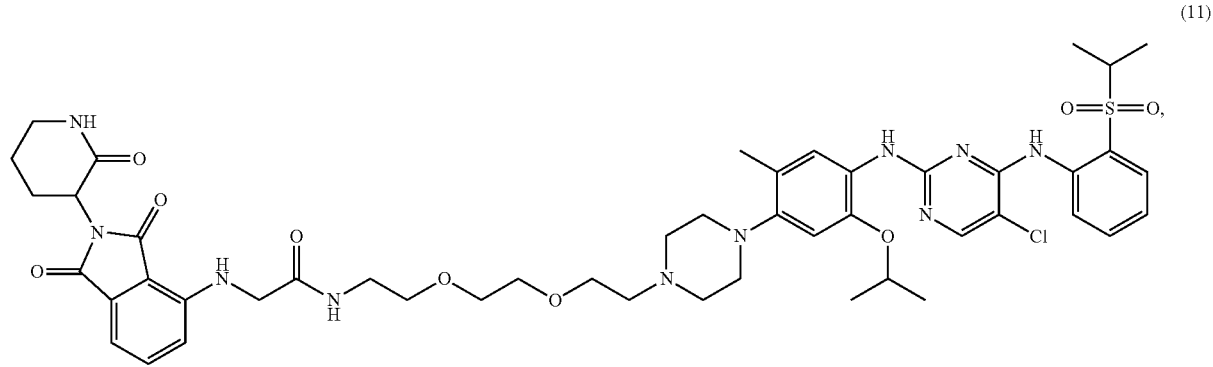 [SMILES: Cc1cc(Nc2ncc(Cl)c(Nc3ccccc3S(=O)(=O)C(C)C)n2)c(OC(C)C)cc1N1CCN(CCOCCOCCNC(=O)CNc2cccc3c2C(=O)N(C2CCCNC2=O)C3=O)CC1]
(11)
or a pharmaceutically acceptable salt thereof.

7. The compound of claim 1, which is or a pharmaceutically acceptable salt thereof.

UNITED STATES PATENT AND TRADEMARK OFFICE
CERTIFICATE OF CORRECTION

PATENT NO. : 12,233,128 B2
APPLICATION NO. : 17/278093
DATED : February 25, 2025
INVENTOR(S) : Nathanael S. Gray et al.

Page 1 of 2

It is certified that error appears in the above-identified patent and that said Letters Patent is hereby corrected as shown below:

In the Claims

In Columns 517-518, Claim 6, bottom of page:
Delete the following structure:

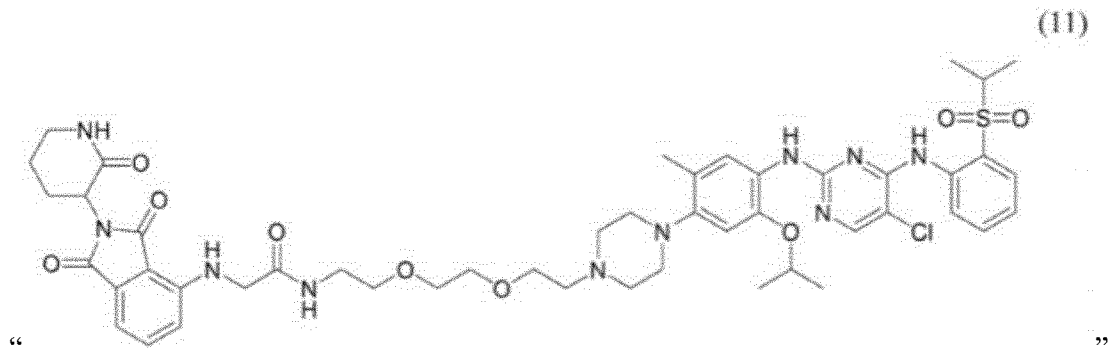

"                                                                                              "

Replace with the following structure:

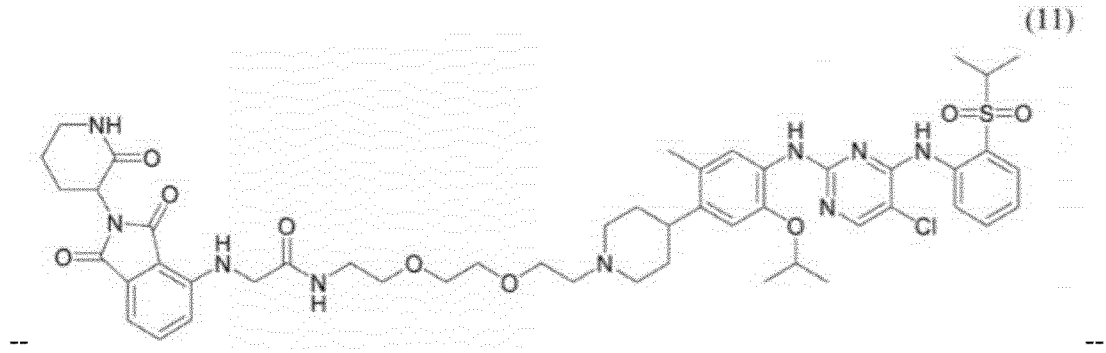

--                                                                                              --

Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 12,233,128 B2

Page 2 of 2

In Columns 519-520, Claim 7, top of page:
Delete the following structure:

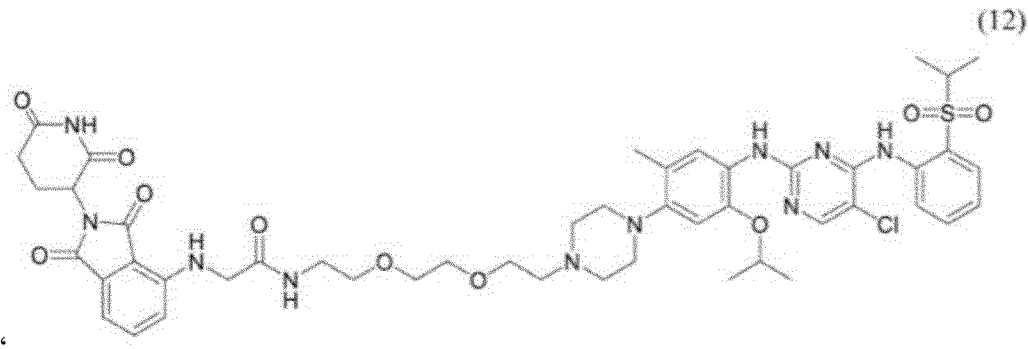

"                                                                              "

Replace with the following structure:

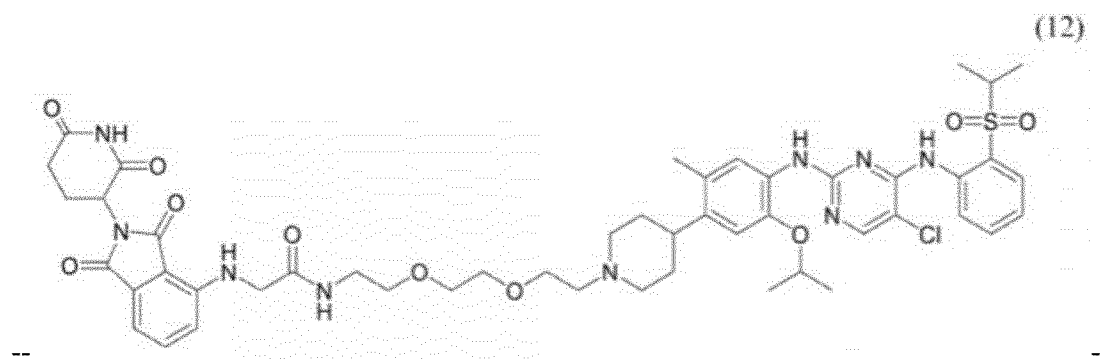

--                                                                             --